US012715857B2

(12) United States Patent
Dai et al.

(10) Patent No.: US 12,715,857 B2
(45) Date of Patent: Aug. 25, 2026

(54) TRICYCLIC COMPOUNDS AND USES THEREOF

(71) Applicant: HUTCHMED LIMITED, Shanghai (CN)

(72) Inventors: Guangxiu Dai, Shanghai (CN); Kun Xiao, Shanghai (CN); Wei Deng, Shanghai (CN)

(73) Assignee: HUTCHMED LIMITED, Shanghai (CN)

( * ) Notice: Subject to any disclaimer, the term of this patent is extended or adjusted under 35 U.S.C. 154(b) by 445 days.

(21) Appl. No.: 18/264,386

(22) PCT Filed: Jan. 28, 2022

(86) PCT No.: PCT/CN2022/074753
§ 371 (c)(1),
(2) Date: Aug. 4, 2023

(87) PCT Pub. No.: WO2022/166844
PCT Pub. Date: Aug. 11, 2022

(65) Prior Publication Data

US 2024/0140931 A1 May 2, 2024

(30) Foreign Application Priority Data

Feb. 5, 2021 (CN) ......................... 202110166021.0
Jan. 21, 2022 (CN) ......................... 202210069346.1

(51) Int. Cl.
*C07D 401/14* (2006.01)
*C07D 401/04* (2006.01)
*C07D 413/14* (2006.01)
*C07D 519/00* (2006.01)

(52) U.S. Cl.
CPC ......... *C07D 401/14* (2013.01); *C07D 401/04* (2013.01); *C07D 413/14* (2013.01); *C07D 519/00* (2013.01); *C07B 2200/07* (2013.01)

(58) Field of Classification Search
CPC .. C07D 401/14; C07D 401/04; C07D 413/14; C07D 519/00; C07B 2200/07
See application file for complete search history.

(56) References Cited

U.S. PATENT DOCUMENTS

2017/0015680 A1 1/2017 Chen et al.
2018/0186770 A1 7/2018 Chen et al.
2019/0127378 A1 5/2019 Ma et al.
2019/0210977 A1 7/2019 Jogalekar et al.
2019/0290649 A1 9/2019 Xie et al.
2020/0048249 A1 2/2020 Jones et al.
2020/0108071 A1 4/2020 Chin et al.
2020/0281926 A1 9/2020 Jorand-Lebrun et al.
2020/0317665 A1 10/2020 Blake et al.
2020/0339552 A1 10/2020 Li et al.
2020/0392128 A1 12/2020 Ma et al.
2020/0407372 A1 12/2020 Koltun et al.
2021/0053989 A1 2/2021 Zou et al.
2021/0179565 A1 6/2021 Jorand-Lebrun et al.
2021/0355105 A1 11/2021 Liu et al.
2021/0393623 A1 12/2021 Han et al.
2022/0388977 A1 12/2022 Wang et al.
2023/0134869 A1 5/2023 Zhan et al.
2023/0212180 A1 7/2023 Yi et al.
2023/0339882 A1 10/2023 Wu et al.

FOREIGN PATENT DOCUMENTS

CN 110143949 A 8/2019
CN 111138412 A 5/2020
CN 111704611 A 9/2020
CN 112166110 A 1/2021
CN 113493440 A 10/2021
CN 113754683 A 12/2021
EP 3712151 A1 9/2020
WO WO 2012077655 A1 6/2012
WO WO-2018172984 A1 * 9/2018 ............. A61P 35/00
WO 2019/183367 A1 9/2019
WO WO 2020/094104 A1 5/2020
WO WO 2020/108590 A1 6/2020
WO WO 2020156242 A1 8/2020
WO WO 2020156243 A1 8/2020
WO WO 2020/259679 A1 12/2020
WO WO 2021147879 A1 7/2021
WO WO 2021218755 A1 11/2021
WO WO 2021249057 A1 12/2021
WO 2020/249079 A1 12/2023

OTHER PUBLICATIONS

Huang, W-Q. et al., "Structure, Function, and Pathogenesis of SHP2 in Developmental Disorders and Tumorigenesis," Current Cancer Drug Targets, vol. 14, pp. 567-588, 23 pages, (2014).

(Continued)

*Primary Examiner* — Jeffrey H Murray
*Assistant Examiner* — Kristen W Romero
(74) *Attorney, Agent, or Firm* — Hoxie & Associates LLC

(57) ABSTRACT

Tricyclic compounds of formula (I), pharmaceutical compositions comprising same, methods for preparing same, and uses thereof, wherein each variable is as defined in the description.

(I)

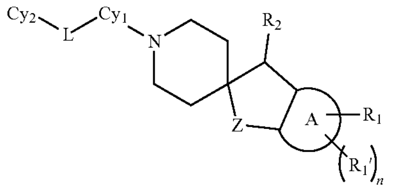

20 Claims, No Drawings

(56) References Cited

OTHER PUBLICATIONS

Muenst, S. et al., "SHP2 expression is an independent negative prognostic factor in human breast cancer," NIH Public Access, Author manuscript, available in PMC 2014, 16 pages, front page states: Published in final edited form as: Histopathology. Jul. 2013 ; 63(1): 74-82. doi:10.1111/his.12140.

Nichols, R. et al., "RAS nucleotide cycling underlies the SHP2 phosphatase dependence of mutant BRAF-, NF1- and RAS-driven cancers," Nature Cell Biology, vol. 20, pp. 1064-1073, 16 pages, (2018).

Ruess, D. et al., "Mutant KRAS-driven cancers depend on PTPN11/SHP2 phosphatase," Nature Medicine, vol. 24, pp. 954-960, 13 pages, (2018).

Song, Z. et al., "Tyrosine phosphatase SHP2 inhibitors in tumor-targeted therapies," Acta Pharmaceutica Sinica B, vol. 11, Issue 1, pp. 13-29, 17 pages, (2021).

Zhang, J. et al., "Functions of Shp2 in cancer," J. Cell. Mol. Med., vol. 19, No. 9, pp. 2075-2083, 9 pages, (2015).

* cited by examiner

TRICYCLIC COMPOUNDS AND USES THEREOF

CROSS-REFERENCE TO RELATED APPLICATIONS

This application is a United States Application under 35 U.S.C. § 371 claiming priority to, and the benefit of, International Application No. PCT/CN2022/074753, filed on Jan. 28, 2022, which claims priority to Chinese patent application No. CN202110166021.0, filed on Feb. 5, 2021, and Chinese Application No. CN202210069346.1, filed on Jan. 21, 2022, the contents of each of which is hereby incorporated by reference in their entireties.

TECHNICAL FIELD

The present invention relates to tricyclic compounds, pharmaceutical compositions comprising same, methods for preparing same, and uses thereof.

BACKGROUND ART

SHP2 (Src homology-2 domain-containing protein tyrosine phosphatase-2) is a non-receptor protein tyrosine phosphohydrolase encoded by a PTPN11 gene. SHP2 contains two SH2 domains (N-terminal SH2 domain and C-terminal SH2 domain), a catalytic domain and a C-terminal sequence containing two tyrosine phosphorylation sites. The non-receptor protein tyrosine phosphohydrolase subfamily contains two members, SHP1 and SHP2. The SHP1 and SHP2 proteins have 61% similarity in amino acid sequences, and have up to 75% amino acid identity in the catalytic domains (PTP). SHP1 is mainly expressed in hematopoietic cells and some epithelial cells, and is mainly involved in the negative regulation of intracellular signaling. SHP2 is widely expressed in various organs of the human body, and plays an important physiological role in the growth and development and homeostasis of the human body. After being stimulated by growth factors or hormones, SHP2 participates in the signal regulation and transduction of many signaling pathways, including RAS-ERK, JAK-STAT, PI3K-AKT, and PD1-PD-L1, thereby promoting many biological functions, such as cell proliferation, differentiation and migration.

Mutation or overexpression of SHP2 would lead to hereditary developmental diseases and tumors. It is reported that in the hereditary developmental diseases, 90% of the LEOPARD Syndrome cases and 50% of the Noonan Syndrome cases have been found to have gain-of-function (GOF) mutations in the PTPN11 gene. Mutations in the PTPN11 gene have also been reported in hematologic malignancies, such as myelodysplastic syndrome (10%), B-cell acute lymphocytic leukemia (7%), and juvenile acute myelogenous leukemia (5%). Mutations in SHP2 are rarely found in solid tumors, but overexpression/activation of SHP2 is closely related to the occurrence of a variety of tumors. SHP2 expression in invasive ductal breast cancer has increased by 70%; overexpression of the SHP2 binding protein, GAB2 has also been detected in 10%-15% of breast cancers; and overexpression of SHP2 in melanoma is often closely related to poor prognosis.

SHP2 is closely related to tumors, making it becoming an attractive anti-tumor drug target. Currently, several selective SHP2 inhibitors such as TNO155 (Novartis), RMC-4630 (Revolution Medicines/Sanofi), JAB-3068 (Jacobio), and RLY-1971 (Relay Therapeutics) have entered clinical studies; however, no SHP2 inhibitor has been approved for marketing.

Therefore, SHP2 inhibitors stand for the development of an attractive therapy for related diseases, especially cancer, Noonan Syndrome and LEOPARD Syndrome.

SUMMARY OF THE INVENTION

The present invention provides a compound of formula (I):

(I)

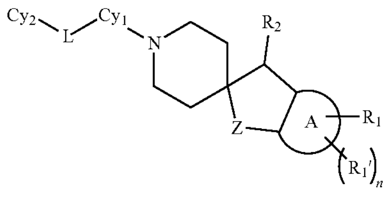

or a pharmaceutically acceptable salt thereof, or a solvate, a racemic mixture, an enantiomer, a diastereomer or a tautomer thereof, wherein ring A is a benzene ring or a pyridine ring;

Z is $CH_2$, O, S or NH;

$R_1$ is chosen from $C_{2-6}$ alkynyl, —$NR_3R_4$, —$SR_5$ and —$SR_6$, wherein the $C_{2-6}$ alkynyl is optionally substituted with one or more groups independently chosen from: halogen, —CN, —OH, —$NH_2$, $C_{3-8}$ cycloalkyl, 4-8 membered heterocyclyl, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —S($C_{3-8}$ cycloalkyl), —S(4-8 membered heterocyclyl), —NH($C_{1-6}$ alkyl), —N($C_{1-6}$ alkyl)$_2$, —NH—CN, —$NHCONH_2$, —NHCO($C_{1-6}$alkyl), —$CONR_aR_b$, —$COOR_c$ and —$COR_d$, wherein $R_a$, $R_b$, $R_c$ and $R_d$ are each independently chosen from hydrogen, $C_{1-6}$ alkyl, $C_{1-6}$ haloalkyl, —($C_{1-6}$ alkyl)-O—($C_{1-6}$ alkyl), —($C_{1-6}$ alkyl)-OH, —($C_{1-6}$ alkyl)-CN, $C_{3-8}$ cycloalkyl and 4-8 membered heterocyclyl; $R_3$ is independently chosen from hydrogen, $C_{1-6}$ alkyl, $C_{1-6}$ haloalkyl, —($C_{1-6}$ alkyl)-OH, —($C_{1-6}$ alkyl)-O—($C_{1-6}$ alkyl) and —($C_{1-6}$ alkyl)-CN; $R_4$ and $R_5$ are each independently chosen from $C_{3-8}$ cycloalkyl, phenyl, 4-8 membered heterocyclyl and 5-12 membered heteroaryl; $R_6$ is chosen from —CO($C_{1-6}$ alkyl), —CO($C_{3-8}$ cycloalkyl), —CO(4-8 membered heterocyclyl), —$CONH_2$, —CONH($C_{1-6}$ alkyl), —CONH($C_{3-8}$ cycloalkyl), —CONH(4-8 membered heterocyclyl), —CON($C_{1-6}$ alkyl)$_2$, —($C_{1-6}$ alkyl)-O—($C_{1-6}$ alkyl), —($C_{1-6}$ alkyl)-OH, —($C_{1-6}$ alkyl)-NH($C_{1-6}$ alkyl), —($C_{1-6}$ alkyl)-N($C_{1-6}$ alkyl)$_2$ and —($C_{1-6}$ alkyl)-NHCO($C_{1-6}$ alkyl), wherein the $C_{1-6}$ alkyl of $R_6$ is optionally substituted with one or more groups independently chosen from: halogen, —CN, —OH and —O($C_{1-6}$ alkyl); and the above-mentioned $C_{3-8}$ cycloalkyl, phenyl, 4-8 membered heterocyclyl and 5-12 membered heteroaryl are each optionally substituted with one or more groups independently chosen from: halogen, —CN, —$CONH_2$, —OH, oxo, —$NH_2$, $C_{1-6}$ alkyl, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —S($C_{1-6}$alkyl), —NH($C_{1-6}$ alkyl) and —N($C_{1-6}$ alkyl)$_2$;

$R_1'$ is independently chosen from halogen, —CN, —$CONH_2$, —OH, —$NH_2$, $C_{1-6}$ alkyl, $C_{1-6}$ haloalkyl, $C_{3-8}$ cycloalkyl, 4-8 membered heterocyclyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —NH($C_{1-6}$ alkyl) and —N($C_{1-6}$ alkyl)$_2$, wherein the $C_{3-8}$ cycloalkyl and 4-8 membered heterocyclyl are each optionally substituted with one or more halogen;

n is 0, 1, 2 or 3;

$R_2$ is chosen from —$NH_2$, —NH($C_{1-6}$ alkyl), —N($C_{1-6}$ alkyl)$_2$, oxo and —OH;

$Cy_1$ is 5-12 membered heterocyclyl or 5-12 membered heteroaryl, each of which is optionally substituted with one or more groups independently chosen from: halogen, —CN, —$CONH_2$, —OH, oxo, —$NH_2$, $C_{1-6}$ alkyl, $C_{2-6}$ alkenyl, $C_{2-6}$ alkynyl, $C_{1-6}$ haloalkyl, $C_{3-8}$ cycloalkyl, 4-8 membered heterocyclyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —NH($C_{1-6}$ alkyl), —N($C_{1-6}$ alkyl)$_2$, —NHCO($C_{1-6}$ alkyl), —CONH($C_{1-6}$ alkyl) and —CON($C_{1-6}$ alkyl)$_2$, wherein the $C_{3-8}$ cycloalkyl and 4-8 membered heterocyclyl are each optionally substituted with one or more halogen;

$Cy_2$ is phenyl or 5-14 membered heteroaryl, each of which is optionally substituted with one or more groups independently chosen from: halogen, —CN, —$CONH_2$, —OH, oxo, $C_{1-6}$ alkyl, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —$NR_7R_8$, —NHCO($C_{1-6}$ alkyl), —CONH($C_{1-6}$ alkyl) and —CON($C_{1-6}$ alkyl)$_2$, wherein $R_7$ and $R_8$ are each independently chosen from hydrogen, $C_{1-6}$ alkyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-CN, $C_{3-8}$ cycloalkyl, phenyl, 3-8 membered heterocyclyl and 5-6 membered heteroaryl; and L is absent, or L is S, O, NH, $C_{1-6}$ alkyl, $C_{2-6}$ alkenyl or $C_{2-6}$ alkynyl.

The above-mentioned compounds and the active compounds (including compounds of general formula and specific compounds) disclosed in the context of the present invention, and pharmaceutically acceptable salts thereof, or solvates, racemic mixtures, enantiomers, diastereomers or tautomers thereof are collectively referred to herein as "compounds of the present invention".

The prevent invention also provides a pharmaceutical composition, comprising the compounds of the present invention, and optionally comprising a pharmaceutically acceptable excipient.

The prevent invention also provides a method of in vivo or in vitro inhibiting the activity of SHP2, comprising contacting SHP2 with an effective amount of the compounds of the present invention.

The prevent invention also provides a method of treating or preventing a disease mediated by SHP2 or at least in part by SHP2, comprising administering to the subject in need thereof an effective amount of the compounds of the present invention.

The prevent invention also provides a method of treating or preventing cancer, Noonan Syndrome or LEOPARD Syndrome, comprising administering to the subject in need thereof an effective amount of the compounds of the present invention.

The prevent invention also provides the use of the compounds of the present invention in the treatment or prevention of a disease mediated by SHP2 or at least in part by SHP2.

The prevent invention also provides the use of the compounds of the present invention in the treatment or prevention of cancer, Noonan Syndrome or LEOPARD Syndrome.

The prevent invention also provides the use of the compounds of the present invention in the manufacture of a medicament for treating or preventing a disease mediated by SHP2 or at least in part by SHP2.

The prevent invention also provides the use of the compounds of the present invention in the manufacture of a medicament for treating or preventing cancer, Noonan Syndrome or LEOPARD Syndrome.

The prevent invention also provides the compounds of the present invention for in vivo or in vitro inhibiting the activity of SHP2.

The prevent invention also provides the compounds of the present invention for use as a medicament.

The prevent invention also provides the compounds of the present invention for use as a medicament for treating or preventing a disease mediated by SHP2 or at least in part by SHP2, especially for treating or preventing cancer, Noonan Syndrome or LEOPARD Syndrome.

The prevent invention also provides a pharmaceutical combination, comprising the compounds of the present invention and at least one additional therapeutic agent, wherein the additional therapeutic agent is preferably chosen from: an anti-neoplastic active agent, an anti-inflammatory agent or an immunomodulator, wherein the anti-neoplastic active agent includes a chemotherapeutic agent, an immune checkpoint inhibitor or agonist, and a targeted therapeutic agent.

The prevent invention also provides a kit for treating or preventing a disease mediated by SHP2 or at least in part by SHP2. The kit can comprise the pharmaceutical composition of the present invention and instructions for use, and the pharmaceutical composition comprises the compounds of the present invention.

DETAILED DESCRIPTION OF THE INVENTION

Definitions

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$OR_6$ refers to the attachment of $R_6$ to the rest of the molecule through an oxygen atom.

The term "alkyl" as used herein refers to a straight or branched saturated hydrocarbon radical containing 1-18 carbon atoms ($C_{1-18}$) preferably 1-10 carbon atoms ($C_{1-10}$), more preferably 1-6 carbon atoms ($C_{1-6}$), and further more preferably 1-4 carbon atoms ($C_{1-4}$) or 1-3 carbon atoms ($C_{1-3}$). When the term "alkyl" is prefixed with "$C_a$-b", it means the number of carbon atoms in the alkyl, where a is the minimum number of carbons in the alkyl and b is the maximum number of carbons in the alkyl. For example, "$C_{1-6}$ alkyl" refers to an alkyl containing 1-6 carbon atoms.

"$C_{1-3}$ alkyl" refers to an alkyl containing 1-3 carbon atoms. Examples of $C_{1-6}$ alkyl include, but are not limited to, methyl, ethyl, propyl (e.g. n-propyl, i-propyl), butyl (e.g. n-butyl, i-butyl, s-butyl and t-butyl), pentyl (e.g. n-pentyl, i-pentyl, neo-pentyl), hexyl, and the like. When used as a linker (e.g., in the definition of L) or between two dashes ("-") (e.g., —($C_{1-6}$ alkyl)-OH), the alkyl refers to an alkylene.

The term "alkenyl" as used herein refers to a straight or branched unsaturated hydrocarbon radical containing one or more, for example 1, 2, or 3 carbon-carbon double bonds (C═C) and 2-18 carbon atoms ($C_{2-18}$), preferably 2-10 carbon atoms ($C_{2-10}$), more preferably 2-6 carbon atoms ($C_{2-6}$), and further more preferably 2-4 carbon atoms ($C_{2-4}$). When the term "alkenyl" is prefixed with "$C_{a-b}$", it means the number of carbon atoms in the alkenyl, where a is the minimum number of carbons in the alkenyl and b is the maximum number of carbons in the alkenyl. For example, "$C_{2-6}$ alkenyl" refers to an alkenyl containing 2-6 carbon atoms. "$C_{2-4}$ alkenyl" refers to an alkenyl containing 2-4 carbon atoms. Examples of $C_{2-6}$ alkenyl include, but are not limited to, vinyl, propenyl (e.g. 2-propenyl), and butenyl (e.g. 2-butenyl), and the like. The point of attachment for the alkenyl can be on or not on the double bonds. When used as a linker (e.g., in the definition of L), the alkenyl refers to an alkenylene.

The term "alkynyl" as used herein refers to a straight or branched unsaturated hydrocarbon radical containing one or more, for example 1, 2, or 3, carbon-carbon triple bonds (C≡C) and 2-18 carbon atoms ($C_{2-18}$), preferably 2-10 carbon atoms ($C_{2-10}$), more preferably 2-6 carbon atoms ($C_{2-6}$), and further more preferably 2-4 carbon atoms ($C_{2-4}$). When the term "alkynyl" is prefixed with "$C_{a-b}$", it means the number of carbon atoms in the alkynyl, where a is the minimum number of carbons in the alkynyl and b is the maximum number of carbons in the alkynyl. For example, "$C_{2-6}$ alkynyl" refers to an alkynyl containing 2-6 carbon atoms. "$C_{2-4}$ alkynyl" refers to an alkynyl containing 2-4 carbon atoms. Examples of $C_{2-6}$ alkynyl include, but are not limited to, ethynyl, propynyl (e.g. 2-propynyl), and butynyl (e.g. 2-butynyl), and the like. The point of attachment for the alkynyl can be on or not on the triple bonds. When used as a linker (e.g., in the definition of L), the alkynyl refers to an alkynylene.

The term "halogen" or "halo" as used herein means fluoro, chloro, bromo, and iodo, preferably fluoro, chloro and bromo, more preferably fluoro and chloro.

The term "haloalkyl" as used herein refers to an alkyl radical, as defined herein, in which one or more, for example 1, 2, 3, 4, or 5, or all hydrogen atoms are replaced with halogen atoms, and when more than one hydrogen atoms are replaced with halogen atoms, the halogen atoms may be the same or different from each other. In one embodiment, the term "haloalkyl" as used herein refers to an alkyl radical, as defined herein, in which two or more, such as 2, 3, 4, or 5, or all hydrogen atoms are replaced with halogen atoms, wherein the halogen atoms are identical to each other. In another embodiment, the term "haloalkyl" as used herein refers to an alkyl radical, as defined herein, in which two or more hydrogen atoms, such as 2, 3, 4, or 5, or all hydrogen atoms are replaced with halogen atoms, wherein the halogen atoms are different from each other. When the term "haloalkyl" is prefixed with "$C_a$-b", it means the number of carbon atoms in the haloalkyl, where a is the minimum number of carbons in the haloalkyl and b is the maximum number of carbons in the haloalkyl. For example, "$C_{1-6}$ haloalkyl" refers to a haloalkyl as defined herein containing 1-6 carbon atoms. "$C_{1-4}$ haloalkyl" refers to a haloalkyl as defined herein containing 1-4 carbon atoms. Examples of $C_{1-6}$ haloalkyl include, but are not limited to —$CF_3$, —$CHF_2$, —$CH_2F$, —$CH_2CF_3$, —$CH(CF_3)_2$, and the like.

The term "cycloalkyl" as used herein refers to saturated or partially unsaturated cyclic hydrocarbon radical having 3-12 ring carbon atoms ($C_{3-12}$), such as 3-8 ring carbon atoms ($C_{3-8}$), 5-7 ring carbon atoms ($C_{5-7}$), 4-7 ring carbon atoms ($C_{4-7}$) or 3-6 ring carbon atoms ($C_{3-6}$), which may have one or more rings, such as 1, 2, or 3 rings, preferably 1 or 2 rings. When the term "cycloalkyl" is prefixed with "$C_{a-b}$", it means the number of carbon atoms in the cycloalkyl, where a is the minimum number of carbons in the cycloalkyl and b is the maximum number of carbons in the cycloalkyl. For example, "$C_{3-8}$ cycloalkyl" or "3-8 membered cycloalkyl" refers to a cycloalkyl containing 3-8 ring carbon atoms; "$C_{3-6}$ cycloalkyl" or "3-6 membered cycloalkyl" refers to a cycloalkyl containing 3-6 ring carbon atoms. The cycloalkyl may include a fused or bridged ring, or a spirocyclic ring. The rings of the cycloalkyl may be saturated or have one or more, for example, one or two double bonds (i.e. partially unsaturated), but not fully conjugated, and not an aryl as defined herein. Examples of $C_{3-8}$ cycloalkyl include, but are not limited to cyclopropyl, cyclobutyl, cyclopentyl, cyclohexyl, spiro[2.2]pentyl, cyclopropenyl, cyclobutenyl, cyclopentenyl, cyclopentadienyl, cyclohexenyl, etc.

The term "heterocyclyl" or "heterocycle" as used herein can be used interchangeably and each refers to saturated or partially unsaturated cyclic radicals having 3-12 ring atoms, such as 5-12 ring atoms (5-12 membered heterocyclyl), 3-8 ring atoms (3-8 membered heterocyclyl), 4-8 ring atoms (4-8 membered heterocyclyl), 4-6 ring atoms (4-6 membered heterocyclyl) or 4-5 ring atoms (4-5 membered heterocyclyl), and containing one or more, for example 1, 2 or 3, preferably 1 or 2 heteroatoms independently chosen from N, O and S in the rings, with the remaining ring atoms being carbon; it may have one or more rings, for example 1, 2 or 3, preferably 1 or 2 rings. The heterocyclyl also includes those wherein the N or S heteroatom are optionally oxidized to various oxidation states. The point of attachment of heterocyclyl can be on the N heteroatom or carbon. For example, "4-8 membered heterocyclyl" represents a heterocyclyl having 4-8 (4, 5, 6, 7 or 8) ring atoms comprising at least one, such as 1, 2 or 3, preferably 1 or 2 heteroatoms independently chosen from N, O and S; "4-6 membered heterocyclyl" represents a heterocyclyl having 4-6 (4, 5 or 6) ring atoms comprising at least one, preferably 1 or 2 heteroatoms independently chosen from N, O and S (preferably N and O), which is preferably a monocyclic ring; and "4-5 membered heterocyclyl" represents a heterocyclyl having 4-5 ring atoms comprising at least one, preferably 1 or 2 heteroatoms independently chosen from N, O and S (preferably N and O), which is a monocyclic ring. The heterocyclyl also includes a fused or bridged ring, or a spirocyclic ring. The rings of the heterocyclyl may be saturated or have one or more, for example, one or two double bonds (i.e. partially unsaturated), but not fully conjugated, and not a heteroaryl as defined herein. Examples of heterocyclyl include, but are not limited to: 3-8 membered heterocyclyl, 4-8 membered heterocyclyl, 4-6 membered heterocyclyl and 4-5 membered heterocyclyl, such as oxetanyl, azetidinyl, pyrrolidyl, tetrahydrofuranyl, dioxolanyl, tetrahydropyranyl, morpholinyl, thiomorpholinyl, piperidyl, piperazinyl, tetrahydropyridyl, dihydropyrimidyl, dihydropyrazinyl, pyrazolidinyl and oxaspiro[3.3]heptyl, preferably oxetanyl (such as oxetan-3-yl), azetidinyl, tetrahydropyranyl, morpholinyl (such as morpholino), piperazinyl (such as piperazin-1-yl), tetrahydropyridyl (such as 1,2,3,6-tetrahydropyridyl), dihydropyrimidyl (such as 1,6-dihydropyrimidyl).

The term “aryl” or “aromatic ring” as used herein can be used interchangeably and each refers to carbocyclic hydrocarbon radical of 6 to 14 carbon atoms consisting of one ring or more fused rings, wherein at least one ring is an aromatic ring. Examples of aryl include, but are not limited to phenyl, naphthalenyl, 1,2,3,4-tetrahydronaphthalenyl, phenanthryl, indenyl, indanyl, azulenyl, preferably phenyl and naphthalenyl.

The term “heteroaryl” or “heteroaromatic ring” as used herein can be used interchangeably and each refers to: mono-, bi-, or tri-ring system having 5-15 ring atoms, preferably 5-14 ring atoms, more preferably 5-12 ring atoms, further preferably 5-10 ring atoms, and most preferably 5-6 or 8-10 ring atoms, wherein at least one ring is 5- or 6-membered aromatic ring containing one or more, for example 1 to 4, heteroatoms independently chosen from N, O, and S, wherein S and N may be optionally oxidized to various oxidation states. When the total number of S and O atoms in the heteroaryl group exceeds 1, said S and O heteroatoms are not adjacent to one another. Preferably, the heteroaryl is 5-12 membered heteroaryl. For example, the heteroaryl includes:

- a 5-6 membered monocyclic heteroaryl, i.e., a monocyclic ring aromatic hydrocarbyl having 5 or 6 ring atoms, wherein the ring atoms include one or more, such as 1, 2 or 3 heteroatoms independently chosen from N, O and S (preferably N), and the remaining ring atoms are carbon atoms; and the heteroaryl is preferably triazolyl, pyridyl, pyrazinyl, pyrimidyl, pyrazolyl, imidazolyl, isoxazolyl, triazinyl, oxazolyl, thiadiazolyl, and pyridazinyl, more preferably pyridyl (such as pyridin-4-yl, pyridin-3-yl), pyrazinyl, pyrimidyl, and triazinyl (such as 1,2,4-triazinyl), and
- a 8-10 membered bicyclic heteroaryl, i.e., a bicycle aromatic hydrocarbyl having 8, 9 or 10 ring atoms, wherein the ring atoms include one or more, such as 1, 2, 3 or 4, preferably 1, 2 or 3 heteroatoms independently chosen from N, O and S (preferably N), and the remaining ring atoms are carbon atoms, wherein at least one ring is an aromatic ring; which is preferably imidazo[1,2-c]pyrimidyl, 1H-pyrrolo[2,3-b]pyridyl, indazolyl, imidazo[1,2-a]pyrazinyl, imidazo[1,5-a]pyrazinyl, pyrrolo[1,2-a]pyrazinyl, pyrazolo[1,5-a]pyrazinyl, [1,2,4]triazolo[1,5-a]pyrazinyl, [1,2,4]triazolo[4,3-c]pyrimidyl, [1,2,4]triazolo[1,5-c]pyrimidyl, and 1,2,3,4-tetrahydro-1,5-naphthyridinyl.

Examples of heteroaryl include, but are not limited to: 5-6 membered monocyclic heteroaryl, such as pyridyl, N-oxide pyridyl, pyrazinyl, pyrimidyl, triazinyl (such as 1,2,4-triazinyl, 1,3,5-triazinyl), pyrazolyl, imidazolyl, oxazolyl, isoxazolyl, oxadiazolyl (such as 1,2,4-oxadiazolyl, 1,2,5-oxadiazolyl and 1,3,4-oxadiazolyl), thiazolyl, isothiazolyl, thiadiazolyl, tetrazolyl, triazolyl, thienyl, furanyl, pyranyl, pyrrolyl, and pyridazinyl; and a 8-10 membered bicyclic heteroaryl, such as benzoxazolyl, benzoisoxazolyl, benzothienyl, benzothiazolyl, benzoisothiazolyl, imidazopyrimidyl (such as imidazo[1,2-c]pyrimidyl), imidazopyrazinyl (such as imidazo[1,2-a]pyrazinyl and imidazo[1,5-a]pyrazinyl), imidazopyridyl (such as imidazo[1,2-a]pyridyl), imidazopyridazinyl (such as imidazo[1,2-b]pyridazinyl), pyrrolopyrazinyl (such as pyrrolo[1,2-a]pyrazinyl), pyrrolopyridyl (such as 1H-pyrrolo[2,3-b]pyridyl), pyrrolopyrimidyl (such as pyrrolo[3,4-d]pyrimidyl), pyrazolopyrazinyl (such as pyrazolo[1,5-a]pyrazinyl), pyrazolopyridyl (such as 1H-pyrazolo[3,4-b]pyridyl), pyrazolopyrimidyl (such as pyrazolo[1,5-a]pyrimidyl), triazolopyrimidyl (such as [1,2,4]triazolo[4,3-c]pyrimidyl and [1,2,4]triazolo[1,5-c]pyrimidyl), triazolopyrazinyl (such as [1,2,4]triazolo[1,5-a]pyrazinyl), triazolopyridyl (such as [1,2,4]triazolo[4,3-a]pyridyl and [1,2,4]triazolo[1,5-a]pyridyl), tetrazolopyridyl (such as tetrazolo[1,5-a]pyridyl), benzofuranyl, indolyl, indazolyl, purinyl, quinolinyl, isoquinolinyl, 6,7-dihydro-4H-pyrazolo[5,1-c][1,4]oxazinyl, and 1,2,3,4-tetrahydro-1,5-naphthyridinyl.

The term “—OH” as used herein refers to hydroxyl radical.

The term “—CN” as used herein refers to cyano radical.

The term “oxo” as used herein refers to =O.

The term “optional” or “optionally” as used herein means that the subsequently described event or circumstance may or may not occur, and the description includes instances wherein the event or circumstance occur and instances in which it does not occur. For example, “optionally substituted with one or more” includes unsubstituted and substituted with 1, 2, 3 or more substituents as described. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

The term “substituted” or “substituted with . . . ”, as used herein, means that one or more (such as, 1, 2, 3 or 4) hydrogens on the designated atom or group are replaced with one or more (such as 1, 2, 3 or 4) substituents, preferably the substituents chosen from the indicated group of substituents or radicals, provided that the designated atom’s normal valence is not exceeded. The said substituents may be the same or different from each other. The term “substituted with one or more groups chosen from” or “substituted with one or more” as used herein means that one or more hydrogens on the designated atom or group are independently replaced with one or more radicals from the indicated group of substituents or radicals, wherein the said radicals may be the same or different from each other. Preferably, “substituted with one or more groups chosen from” or “substituted with one or more” means that the designated atom or group is substituted with 1, 2, 3, or 4 radicals independently chosen from the indicated group of substituents or radicals, wherein the said radicals may be the same or different from each other. In some embodiments, when a substituent is oxo (i.e., =O), then 2 hydrogens on a single atom are replaced by the oxo. An optional substituent can be any radicals, provided that combinations of substituents and/or variables result in a chemically correct and stable compound. A chemically correct and stable compound is meant to imply a compound that is sufficiently robust to survive sufficient isolation from a reaction mixture to be able to identify the chemical structure of the compound. Preferably, substituents are those exemplified in the compounds of the examples of the present application.

Unless otherwise specified, substituents are named into the core structure. For example, it is to be understood that when (cycloalkyl)alkyl is listed as a possible substituent, the point of attachment of this substituent to the core structure is in the alkyl portion.

When a structural formula herein contains an asterisk “*”, it means that the chiral center (or chiral axis) at the “*” mark in the compound is a single configuration of (R) configuration or (S) configuration; wherein the content of the single-configuration compound marked with “*” is at least 90% (e.g., 90%, 91%, 92%, 93%, 94%, 95%, 96%, 97%, 98%, 99%, 99.5%, 99.9%, 100%, or any value between these listed values). For example, some compounds of the present invention are axially chiral compounds, such as the following compound of formula (a), and its structural formula contains an asterisk "*", which means that the compound is a compound of formula (b) or compound of formula (c) in a single configuration.

a

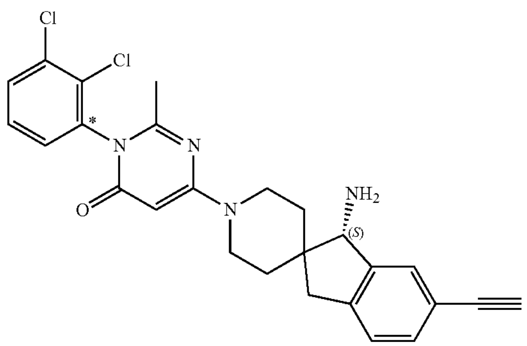

b

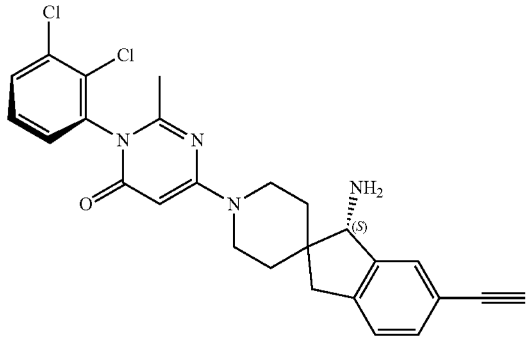

c

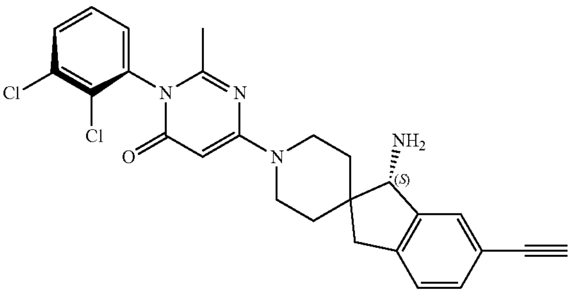

It will be appreciated by the person of ordinary skill in the art ("POSITA") that some of the compounds of formula (I) may contain one or more chiral centers (or chiral axes) and therefore exist in two or more stereoisomeric forms. The racemates of these isomers, the individual isomers and mixtures enriched in one enantiomer, as well as diastereomers when there are two chiral centers (or chiral axes), and mixtures partially enriched with specific diastereomers are within the scope of the present invention. It will be further appreciated by the POSITA that the present invention includes all the individual stereoisomers (e.g. enantiomers, diastereomers), racemic mixtures or partially resolved mixtures of the compounds of formula (I) and, where appropriate, the individual tautomeric forms thereof.

The term "axial chirality" as used herein is a special case of chirality. The molecule has a chiral axis, with multiple groups arranged around the axis, and their arrangement makes the molecule unable to superimpose with its mirror image. Axial chirality is most commonly found in asymmetric biaromatic ring (e.g. biphenyl) compounds with limited rotation, such as 1,1'-bi-(2-naphthol).

The term "stereoisomers" as used herein refers to compounds that have the same chemical constitution but differ in the arrangement of atoms or groups in space. Stereoisomers include enantiomers, diastereomers and the like.

The terms "enantiomers" and "enantiomeric forms" as used herein can be used interchangeably and refer to two stereoisomers of a compound that are non-superimposable mirror images of each other.

The terms "diastereomers" and "diastereomeric forms" as used herein can be used interchangeably and refer to stereoisomers that have two or more chiral centers (or chiral axes) and whose molecules are not mirror images of each other. Diastereomers have different physical properties, such as melting points, boiling points, spectral properties, or biological activities. A mixture of diastereomers can be separated by high-resolution analytical methods such as electrophoresis and chromatography such as HPLC.

In some embodiments, the present invention provides compounds of various stereoisomeric purities, that is, enantiomeric or diastereomeric purity expressed in different "ee" or "de" values. In some embodiments, the compound of formula (I) described herein has an enantiomeric purity of at least 60% ee (e.g., 60%, 65%, 70%, 75%, 80%, 85%, 90%, 91%, 92%, 93%, 94%, 95%, 96%, 97%, 98%, 99%, 99.5%, 99.9%, 100% ee, or any value between these listed values). In some embodiments, the compound of formula (I) described herein has an enantiomeric purity of greater than 99.9% ee. In some embodiments, the compound of formula (I) described herein has a diastereomeric purity of at least 60% de (e.g., 60%, 65%, 70%, 75%, 80%, 85%, 90%, 91%, 92%, 93%, 94%, 95%, 96%, 97%, 98%, 99%, 99.5%, 99.9%, 100% de, or any value between these listed values). In some embodiments, the compound of formula (I) described herein has a diastereomeric purity of greater than 99.9% de.

The term "enantiomeric excess" or "ee" refers to the amount of one enantiomer relative to the other. For a mixture of R and S enantiomers, the percentage of enantiomeric excess is defined as $|R-S|*100$, where R and S are the mole or weight fractions of the respective enantiomers in the mixture, $R+S=1$. If the optical rotation of a chiral substance is known, the percentage of enantiomeric excess is defined as ([a]obs/[a]max)*100, wherein [a]obs is the optical rotation of the enantiomeric mixture, and [a]max is the optical rotation of the pure enantiomer.

The term "diastereomeric excess" or "de" refers to the amount of one diastereomer relative to the other, and is defined by analogy based on the enantiomeric excess. Therefore, for a mixture of diastereomers D1 and D2, the percentage of diastereomeric excess is defined as $|D1-D2|*100$, wherein D1 and D2 are the mole or weight fractions of the respective diastereomers in the mixture, $D1+D2=1$.

The diastereomeric excess and enantiomeric excess can be measured by a number of analytical techniques (including nuclear magnetic resonance spectroscopy, chiral column chromatography and/or optical polarimetry) according to conventional protocols well known to a person skilled in the art.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively, individual isomers can be separated chemically from a mixture by: forming diastereomeric salts with a chiral acid (such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like), fractionally crystallizing the salts, and then freeing one or both of the resolved bases, optionally repeating the process, so as obtain either or both substantially free of the other; i.e., in a form having an optical purity of >95%. Alternatively, the racemates can be covalently linked to a chiral compound (auxiliary) to produce diastereomers which can be separated by chromatography or by fractional crystallization after which time the chiral auxiliary is chemically removed to afford the pure enantiomers.

The term "tautomer" as used herein refers to constitutional isomers of compounds generated by rapid movement of an atom in two positions in a molecule. Tautomers readily interconvert into each other, e.g., enol form and ketone form are tipical tautomers.

A "pharmaceutically acceptable salt" is intended to mean a salt of a free acid or base of a compound of Formula (I) that is non-toxic, biologically tolerable, or otherwise biologically suitable for administration to the subject to be treated or prevented. For example, an acid addition salt includes such as a salt derived from an inorganic acid and an organic acid. For examples, see, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002.

In addition, if a compound described herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. The POSITA will recognize various synthetic methodologies that may be used without undue experimentation to prepare non-toxic pharmaceutically acceptable acid addition salts or base addition salts.

The term "solvates" means solvent addition forms that contain either stoichiometric or non-stoichiometric amounts of solvent. Some compounds have a tendency to trap a fixed molar ratio of solvent molecules in the solid state, thus forming a solvate. If the solvent is water, the solvate formed is a hydrate, when the solvent is alcohol, the solvate formed is an alcoholate. Hydrates are formed by the combination of one or more molecules of water, or less than one molecule of water, with one molecule of the substances in which the water retains its molecular state as $H_2O$, such combination being able to form one or more hydrates, for example, hemihydrate, monohydrate, and dihydrate.

As used herein, the terms "group(s)" and "radical(s)" are synonymous and are intended to indicate functional groups or fragments of molecules attachable to other fragments of molecules.

The term "active ingredient" is used to indicate a chemical substance which has biological activity. In some embodiments, an "active ingredient" is a chemical substance having pharmaceutical utility.

The term "pharmaceutical combination" as used herein means a product obtained by mixing or combining two or more active ingredients, including fixed and non-fixed combinations of active ingredients, such as a kit, and a pharmaceutical composition. The term "fixed combination" means that two or more active ingredients (such as compounds of the present invention and additional therapeutic agents) are administered simultaneously to a patient in the form of a single entity or dose. The term "non-fixed combination" means that two or more active ingredients (such as compounds of the present invention and additional therapeutic agents) are administered simultaneously, in parallel or successively to a patient in separate entities, wherein the administration provides the patient with a therapeutically effective level of the compound.

The terms "treating" or "treatment" or "prevention" of a disease or disorder, in the context of achieving therapeutic benefit, refer to administering one or more pharmaceutical substances, especially compounds of the present invention to a subject that has the disease or disorder, or has a symptom of a disease or disorder, or has a predisposition toward a disease or disorder, with the purpose to cure, heal, alleviate, relieve, alter, remedy, ameliorate, improve, or affect the disease or disorder, the symptoms of the disease or disorder, or the predisposition toward the disease or disorder. In some embodiments, the disease or disorder is cancer, such as solid tumors or hematologic malignancies, including leukemia, lymphoma and myeloma. In another embodiment, the disease or disorder is Noonan Syndrome or LEOPARD Syndrome.

The terms "treating", "contacting" and "reacting," in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount or dose of a SHP2 inhibitor sufficient to generally bring about a therapeutic benefit in patients in need of treatment or prevention for a disease or disorder mediated by SHP2 or at least in part by SHP2. Effective amounts or doses of the active ingredient of the present disclosure may be ascertained by methods such as modeling, dose escalation studies or clinical trials, and by taking into consideration factors, e.g., the mode or route of administration or drug delivery, the pharmacokinetics of the agent, the severity and course of the disease or disorder, the subject's previous or ongoing therapy, the subject's health status and response to drugs, and the judgment of the attending physician.

An exemplary dose is in the range of from about 0.0001 to about 200 mg of active agent per kg of subject's body weight per day, such as from about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease or disorder has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

The term "inhibition" or "inhibiting" indicates a decrease in the baseline activity of a biological activity or process. The term "inhibition of SHP2 activity" is a practical pharmaceutical activity for purposes of this disclosure and refers to a decrease in the activity of SHP2 as a direct or indirect response to the presence of the compound of the present invention, relative to the activity of SHP2 in the absence of the compound of the present invention. The decrease in activity may be due to the direct interaction of the compound of the present invention with SHP2, or due to the interaction of the compound of the present invention, with one or more other factors that in turn affect the SHP2 activity. For example, the presence of the compound of the present invention may decrease the SHP2 activity by directly binding to the SHP2, by causing (directly or indirectly) another factor to decrease the SHP2 activity, or by (directly or indirectly) decreasing the amount of SHP2 present in the cell or organism.

The term "subject" or "patient" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" or "patient" does not denote a particular age or sex. In some embodiments, the subject or patient is a human.

In general, the term "about" is used herein to modify a numerical value above or below the stated value by a variance of 20%.

Technical and scientific terms used herein and not specifically defined have the meaning commonly understood by the POSITA to which the present disclosure pertains.

All numerical ranges herein shall be interpreted as disclosing each numerical value and subset of numerical values within the range, regardless of whether they are specifically otherwise disclosed. For example, when referring to any range of values, it should be regarded as referring to every value within the range of values, for example, every integer within the range of values. For example, $C_{1-6}$ as used herein represents the inclusion of 1, 2, 3, 4, 5 or 6 C. The invention relates to all values falling within the ranges, all smaller ranges and the upper or lower limits of the numerical range.

DETAILED DESCRIPTION OF EMBODIMENTS

Embodiment 1. A compound of formula (I):

(I)

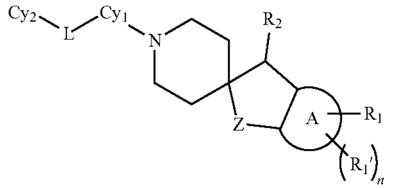

or a pharmaceutically acceptable salt thereof, or a solvate, a racemic mixture, an enantiomer, a diastereomer or a tautomer thereof, wherein ring A is a benzene ring or a pyridine ring;

Z is $CH_2$, O, S or NH;

$R_1$ is chosen from $C_{2-6}$ alkynyl, —$NR_3R_4$, —$SR_5$ and —$SR_6$, wherein the $C_{2-6}$ alkynyl is optionally substituted with one or more groups independently chosen from: halogen, —CN, —OH, —$NH_2$, $C_{3-8}$ cycloalkyl, 4-8 membered heterocyclyl, —O($C_{1-6}$ alkyl), —O($C_{1-6}$ haloalkyl), —O($C_{3-18}$ cycloalkyl), —O(4-8 membered heterocyclyl), —S($C_{1-6}$ alkyl), —S($C_{3-8}$ cycloalkyl), —S(4-8 membered heterocyclyl), —NH($C_{1-6}$ alkyl), —N($C_{1-6}$ alkyl)$_2$, —NH—CN, —$NHCONH_2$, —NHCO($C_{1-6}$ alkyl), —$CONR_aR_b$, —$COOR_c$ and —$COR_d$, wherein $R_a$, $R_b$, $R_c$ and $R_d$ are each independently chosen from hydrogen, $C_{1-6}$ alkyl, $C_{1-6}$ haloalkyl, —($C_{1-6}$ alkyl)-O—($C_{1-6}$ alkyl), —($C_{1-6}$ alkyl)-OH, —($C_{1-6}$ alkyl)-CN, $C_{3-8}$ cycloalkyl and 4-8 membered heterocyclyl; $R_3$ is independently chosen from hydrogen, $C_{1-6}$ alkyl, $C_{1-6}$ haloalkyl, —($C_{1-6}$ alkyl)-OH, —($C_{1-6}$ alkyl)-O—($C_{1-6}$ alkyl) and —($C_{1-6}$ alkyl)-CN; $R_4$ and $R_5$ are each independently chosen from $C_{3-8}$ cycloalkyl, phenyl, 4-8 membered heterocyclyl and 5-12 membered heteroaryl; $R_6$ is chosen from —CO($C_{1-6}$ alkyl), —CO($C_{3-8}$ cycloalkyl), —CO(4-8 membered heterocyclyl), —$CONH_2$, —CONH($C_{1-6}$ alkyl), —CONH($C_{3-8}$ cycloalkyl), —CONH(4-8 membered heterocyclyl), —CON($C_{1-6}$ alkyl)$_2$, —($C_{1-6}$ alkyl)-O—($C_{1-6}$ alkyl), —($C_{1-6}$ alkyl)-OH, —($C_{1-6}$ alkyl)-NH($C_{1-6}$ alkyl), —($C_{1-6}$ alkyl)-N($C_{1-6}$ alkyl)$_2$ and —($C_{1-6}$ alkyl)-NHCO($C_{1-6}$ alkyl), wherein the $C_{1-6}$ alkyl of $R_6$ is optionally substituted with one or more groups independently chosen from: halogen, —CN, —OH and —O($C_{1-6}$ alkyl); and the above-mentioned $C_{3-8}$ cycloalkyl, phenyl, 4-8 membered heterocyclyl and 5-12 membered heteroaryl are each optionally substituted with one or more groups independently chosen from: halogen, —CN, —$CONH_2$, —OH, oxo, —$NH_2$, $C_{1-6}$ alkyl, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —S($C_{1-6}$ alkyl), —NH($C_{1-6}$ alkyl) and —N($C_{1-6}$ alkyl)$_2$;

$R_1'$ is independently chosen from halogen, —CN, —$CONH_2$, —OH, —$NH_2$, $C_{1-6}$ alkyl, $C_{1-6}$ haloalkyl, $C_{3-8}$ cycloalkyl, 4-8 membered heterocyclyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —NH($C_{1-6}$ alkyl) and —N($C_{1-6}$ alkyl)$_2$, wherein the $C_{3-8}$ cycloalkyl and 4-8 membered heterocyclyl are each optionally substituted with one or more halogen;

n is 0, 1, 2 or 3;

$R_2$ is chosen from —$NH_2$, —NH($C_{1-6}$ alkyl), —N($C_{1-6}$ alkyl)$_2$, oxo and —OH;

$Cy_1$ is 5-12 membered heterocyclyl or 5-12 membered heteroaryl, each of which is optionally substituted with one or more groups independently chosen from: halogen, —CN, —$CONH_2$, —OH, oxo, —$NH_2$, $C_{1-6}$ alkyl, $C_{2-6}$ alkenyl, $C_{2-6}$ alkynyl, $C_{1-6}$ haloalkyl, $C_{3-8}$ cycloalkyl, 4-8 membered heterocyclyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —NH($C_{1-6}$ alkyl), —N($C_{1-6}$ alkyl)$_2$, —NHCO($C_{1-6}$ alkyl), —CONH($C_{1-6}$ alkyl) and —CON($C_{1-6}$ alkyl)$_2$, wherein the $C_{3-8}$ cycloalkyl and 4-8 membered heterocyclyl are each optionally substituted with one or more halogen;

$Cy_2$ is phenyl or 5-14 membered heteroaryl, each of which is optionally substituted with one or more groups independently chosen from: halogen, —CN, —CONH$_2$, —OH, oxo, $C_{1-6}$ alkyl, $C_{2-6}$ alkenyl, $C_{2-6}$ alkynyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-CN, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —NR$_7$R$_8$, —NHCO($C_{1-6}$ alkyl), —CONH($C_{1-6}$ alkyl) and —CON($C_{1-6}$ alkyl)$_2$, wherein $R_7$ and $R_8$ are each independently chosen from hydrogen, $C_{1-6}$ alkyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-CN, $C_{3-8}$ cycloalkyl, phenyl, 3-8 membered heterocyclyl and 5-6 membered heteroaryl; and L is absent, or L is S, O, NH, $C_{1-6}$ alkyl, $C_{2-6}$ alkenyl or $C_{2-6}$ alkynyl.

Embodiment 2. The compound or the pharmaceutically acceptable salt thereof, or the solvate, the racemic mixture, the enantiomer, the diastereomer or the tautomer thereof according to embodiment 1, wherein the compound is a compound of formula (IA):

(IA)

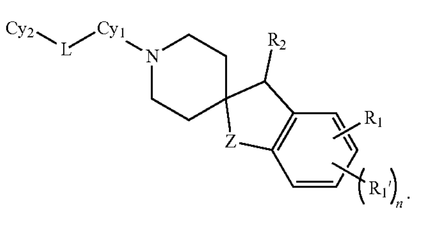

Embodiment 3. The compound or the pharmaceutically acceptable salt thereof, or the solvate, the racemic mixture, the enantiomer, the diastereomer or the tautomer thereof according to embodiment 1 or 2, wherein Z is CH$_2$ or O; and preferably, Z is CH$_2$.

Embodiment 4. The compound or the pharmaceutically acceptable salt thereof, or the solvate, the racemic mixture, the enantiomer, the diastereomer or the tautomer thereof according to any one of embodiments 1-3, wherein $R_1$ is chosen from $C_{2-6}$ alkynyl, —NR$_3$R$_4$ and —SR$_5$, wherein the $C_{2-6}$ alkynyl is optionally substituted with one or more groups independently chosen from: halogen, —CN, —OH, —NH$_2$, $C_{3-8}$ cycloalkyl, 4-8 membered heterocyclyl, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —S($C_{3-8}$ cycloalkyl), —S(4-8 membered heterocyclyl), —NH($C_{1-6}$ alkyl), —N($C_{1-6}$ alkyl)$_2$, —NHCONH$_2$, —NHCO($C_{1-6}$ alkyl), —CONR$_a$R$_b$, —COOR$_c$ and —COR$_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), —($C_{1-6}$ alkyl)-OH, $C_{3-8}$ cycloalkyl and 4-8 membered heterocyclyl; $R_3$ is independently chosen from hydrogen and $C_{1-6}$ alkyl; $R_4$ and $R_5$ are each independently chosen from $C_{3-8}$ cycloalkyl, 4-8 membered heterocyclyl and 5-12 membered heteroaryl; and the above-mentioned $C_{3-8}$ cycloalkyl, 4-8 membered heterocyclyl and 5-12 membered heteroaryl are each optionally substituted with one or more groups independently chosen from: halogen, —CN, —CONH$_2$, —OH, oxo, —NH$_2$, $C_{1-6}$ alkyl and —O($C_{1-6}$ alkyl).

Embodiment 5. The compound or the pharmaceutically acceptable salt thereof, or the solvate, the racemic mixture, the enantiomer, the diastereomer or the tautomer thereof according to embodiment 4, wherein $R_1$ is $C_{2-6}$ alkynyl, wherein the $C_{2-6}$ alkynyl is optionally substituted with one or more groups independently chosen from: —OH, —O($C_{1-6}$ alkyl), —NH($C_{1-6}$ alkyl), —N($C_{1-6}$ alkyl)$_2$, —NHCONH$_2$, —CONR$_a$R$_b$, —COOR$_c$ and —COR$_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), $C_{3-8}$ cycloalkyl and 4-8 membered heterocyclyl, wherein the $C_{3-8}$ cycloalkyl and 4-8 membered heterocyclyl are each optionally substituted with one or more groups independently chosen from: $C_{1-6}$ alkyl and —O($C_{1-6}$ alkyl); preferably, $R_1$ is $C_{2-6}$ alkynyl, wherein the $C_{2-6}$ alkynyl is optionally substituted with one or more groups independently chosen from: —OH, —CONH$_2$, —O($C_{1-6}$ alkyl), —NH($C_{1-6}$ alkyl), —N($C_{1-6}$ alkyl)$_2$, —NHCONH$_2$, —CONH($C_{1-6}$ alkyl), —CONH($C_{1-6}$ alkyl)-O—($C_{1-6}$ alkyl), —CON($C_{1-6}$ alkyl)$_2$, —CON($C_{1-6}$ alkyl)($C_{1-6}$ alkyl-O—$C_{1-6}$ alkyl), —CONH($C_{3-8}$ cycloalkyl), —COOH, —COO($C_{1-6}$ alkyl), —CO($C_{1-6}$ alkyl), —CO(4-8 membered heterocyclyl) and —CO(4-8 membered heterocyclyl)-O—($C_{1-6}$ alkyl); more preferably, $R_1$ is ethynyl, propynyl or butynyl, each of which is unsubstituted or substituted with —OH, —CONH$_2$, —OCH$_3$, —NH(CH$_3$), —N(CH$_3$)$_2$, —NHCONH$_2$, —CONH($C_{1-3}$ alkyl), —CONH(CH$_2$CH$_2$)—O—(CH$_3$), —CON(CH$_3$)$_2$, —CON(CH$_3$)(CH$_2$CH$_2$—O—CH$_3$), —CONH(cyclopropyl), —COOH, —COO(CH$_3$), —CO(CH$_3$), —CO(azetidinyl) or —CO(azetidinyl)-O—(CH$_3$); and most preferably, $R_1$ is ethynyl, or ethynyl substituted with —CONH($C_{1-3}$ alkyl).

Embodiment 6. The compound or the pharmaceutically acceptable salt thereof, or the solvate, the racemic mixture, the enantiomer, the diastereomer or the tautomer thereof according to embodiment 4, wherein $R_1$ is chosen from —NR$_3$R$_4$ and —SR$_5$, wherein the $R_3$ is independently chosen from hydrogen and $C_{1-6}$ alkyl; and $R_4$ and $R_5$ are each independently chosen from $C_{3-8}$ cycloalkyl, 4-8 membered heterocyclyl and 5-6 membered heteroaryl, wherein the $C_{3-8}$ cycloalkyl, 4-8 membered heterocyclyl and 5-6 membered heteroaryl are each optionally substituted with one or more groups independently chosen from: $C_{1-6}$ alkyl.

Embodiment 7. The compound or the pharmaceutically acceptable salt thereof, or the solvate, the racemic mixture, the enantiomer, the diastereomer or the tautomer thereof according to any one of embodiments 1-6, wherein $R_1'$ is chosen from halogen, —CN, —O($C_{1-6}$ alkyl) and —S($C_{1-6}$ alkyl), and n is 0 or 1; preferably, $R_1'$ is halogen, and n is 0 or 1; and more preferably, n is 0.

Embodiment 8. The compound or the pharmaceutically acceptable salt thereof, or the solvate, the racemic mixture, the enantiomer, the diastereomer or the tautomer thereof according to any one of embodiments 1-7, wherein $R_2$ is chosen from —NH$_2$ and oxo; and preferably, $R_2$ is —NH$_2$.

Embodiment 9. The compound or the pharmaceutically acceptable salt thereof, or the solvate, the racemic mixture, the enantiomer, the diastereomer or the tautomer thereof according to any one of embodiments 1-8, wherein $Cy_1$ is 5-12 membered heterocyclyl or 5-12 membered heteroaryl, preferably 5-10 membered heterocyclyl or 5-10 membered heteroaryl, and more preferably 5-6 membered heterocyclyl or 5-9 membered heteroaryl, which is optionally substituted with one or more groups independently chosen from: oxo, —NH$_2$, —CN, halogen, $C_{1-6}$ alkyl, $C_{1-6}$ haloalkyl and —($C_{1-6}$ alkyl)-OH.

Embodiment 10. The compound or the pharmaceutically acceptable salt thereof, or the solvate, the racemic mixture, the enantiomer, the diastereomer or the tautomer thereof according to embodiment 9, wherein $Cy_1$ is chosen from 1,6-dihydropyrimidyl, pyrazinyl, pyrimidyl, 1,2,4-triazinyl, imidazopyrimidyl, triazolopyrimidyl, imidazopyrazinyl, pyrrolopyrazinyl, pyrazolopyrazinyl and triazolopyrazinyl, each of which is optionally substituted with one or more groups independently chosen from: oxo, —$NH_2$, —CN, halogen, $C_{1-6}$ alkyl, $C_{1-6}$ haloalkyl and —($C_{1-6}$ alkyl)-OH.

Embodiment 11. The compound or the pharmaceutically acceptable salt thereof, or the solvate, the racemic mixture, the enantiomer, the diastereomer or the tautomer thereof according to embodiment 10, wherein $Cy_1$ is chosen from

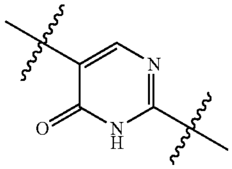 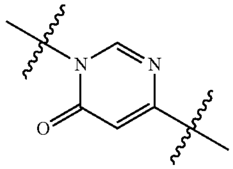
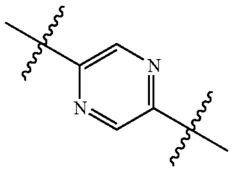 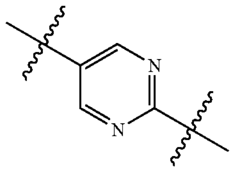
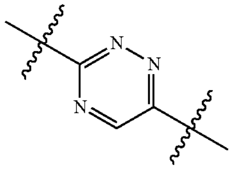 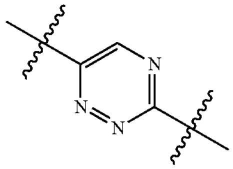
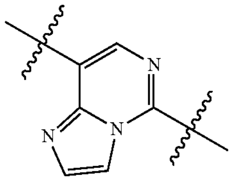 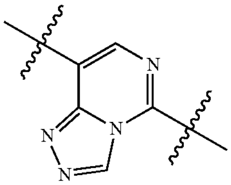
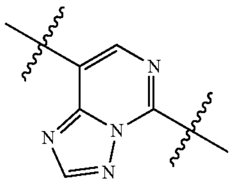 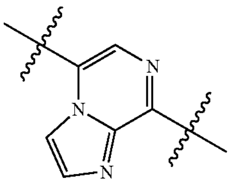
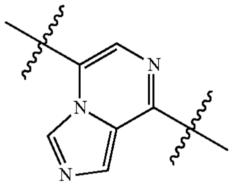 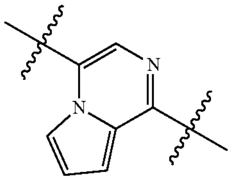
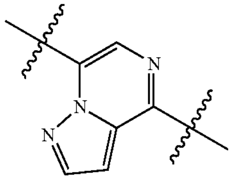 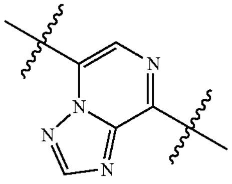, each of which is optionally substituted with one or more groups independently chosen from: —$NH_2$, —CN, halogen, $C_{1-6}$ alkyl, $C_{1-6}$ haloalkyl and —($C_{1-6}$ alkyl)-OH; preferably, $Cy_1$ is chosen from

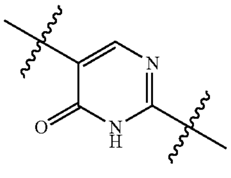 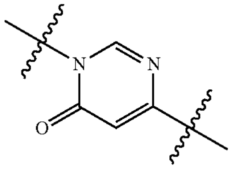
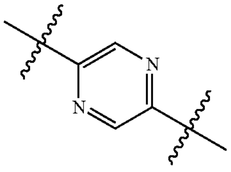 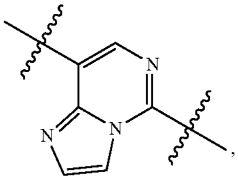, each of which is optionally substituted with one or more groups independently chosen from: —$NH_2$, —CN, halogen, $C_{1-6}$ alkyl, $C_{1-6}$ haloalkyl and —($C_{1-6}$ alkyl)-OH;

more preferably, $Cy_1$ is chosen from

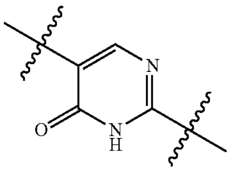 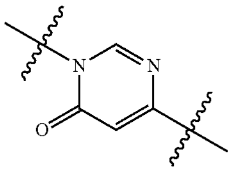
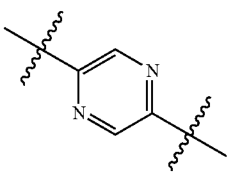 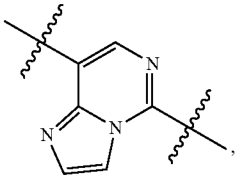, each of which is optionally substituted with one or more groups independently chosen from: —$NH_2$, $C_{1-6}$ alkyl and —($C_{1-6}$ alkyl)-OH;

further preferably, $Cy_1$ is

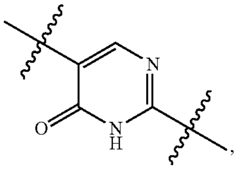 [SMILES: *c1ncc(*)c(=O)[nH]1], which is optionally substituted with one or more groups independently chosen from: —$NH_2$ and $C_{1-6}$ alkyl; or $Cy_1$ is

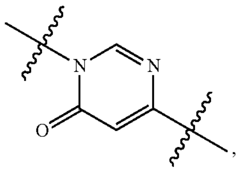 [SMILES: *c1cc(=O)n(*)cn1]

which is optionally substituted with one or more groups independently chosen from: $C_{1-6}$ alkyl; or $Cy_1$ is

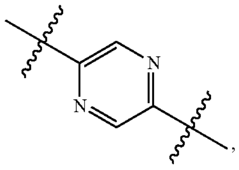 [SMILES: *c1cnc(*)cn1]

which is optionally substituted with one or more groups independently chosen from: —$NH_2$, $C_{1-6}$ alkyl and —($C_{1-6}$ alkyl)-OH; or $Cy_1$ is

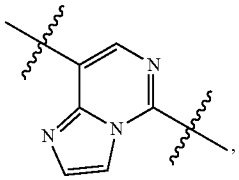 [SMILES: *c1cnc(*)n2ccnc12]

which is optionally substituted with one or more groups independently chosen from: —$NH_2$ and $C_{1-6}$ alkyl.

Embodiment 12. The compound or the pharmaceutically acceptable salt thereof, or the solvate, the racemic mixture, the enantiomer, the diastereomer or the tautomer thereof according to any one of embodiments 1-11, wherein $Cy_2$ is phenyl or 5-14 membered heteroaryl, preferably phenyl or 5-10 membered heteroaryl, and more preferably phenyl, 5-6 membered heteroaryl or 9-10 membered heteroaryl, each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are each independently chosen from hydrogen, $C_{1-6}$ alkyl, $C_{1-6}$ haloalkyl, —($C_{1-6}$ alkyl)-OH, —($C_{1-6}$ alkyl)-O—($C_{1-6}$ alkyl), —($C_{1-6}$ alkyl)-CN and $C_{3-8}$ cycloalkyl.

Embodiment 13. The compound or the pharmaceutically acceptable salt thereof, or the solvate, the racemic mixture, the enantiomer, the diastereomer or the tautomer thereof according to embodiment 1, wherein the compound is a compound of formula (II):

(II)

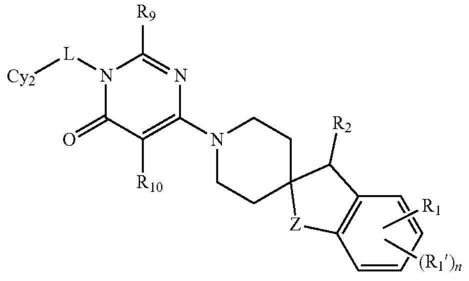

wherein

Z is $CH_2$ or O; and preferably, Z is $CH_2$;

$R_1$ is chosen from $C_{2-6}$ alkynyl, —$NR_3R_4$ and —$SR_5$, wherein the $C_{2-6}$ alkynyl is optionally substituted with one or more groups independently chosen from: halogen, —CN, —OH, —$NH_2$, $C_{3-8}$ cycloalkyl, 4-8 membered heterocyclyl, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —S($C_{3-8}$ cycloalkyl), —S(4-8 membered heterocyclyl), —NH($C_{1-6}$ alkyl), —N($C_{1-6}$ alkyl)$_2$, —NH—CN, —$NHCONH_2$, —NHCO($C_{1-6}$ alkyl), —$CONR_aR_b$, —$COOR_c$ and —$COR_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), —($C_{1-6}$ alkyl)-OH, $C_{3-8}$ cycloalkyl and 4-8 membered heterocyclyl; $R_3$ is independently chosen from hydrogen and $C_{1-6}$ alkyl; $R_4$ and $R_5$ are each independently chosen from $C_{3-8}$ cycloalkyl, 4-8 membered heterocyclyl and 5-6 membered heteroaryl; and the above-mentioned $C_{3-8}$ cycloalkyl, 4-8 membered heterocyclyl and 5-6 membered heteroaryl are each optionally substituted with one or more groups independently chosen from: $C_{1-6}$ alkyl and —O($C_{1-6}$ alkyl); preferably, $R_1$ is $C_{2-6}$ alkynyl, wherein the $C_{2-6}$ alkynyl is optionally substituted with one or more groups independently chosen from: —OH, —$CONH_2$, —O($C_{1-6}$ alkyl), —NH($C_{1-6}$ alkyl), —N($C_{1-6}$ alkyl)$_2$, —CONH($C_{1-6}$ alkyl) and —CON($C_{1-6}$ alkyl)$_2$; further preferably, $R_1$ is ethynyl, propynyl or butynyl, each of which is unsubstituted or substituted with —OH, —$CONH_2$, —$OCH_3$, —NH($CH_3$), —N($CH_3$)$_2$, —CONH($CH_3$) or —CON($CH_3$)$_2$; and more preferably, $R_1$ is ethynyl;

$R_1$' is chosen from halogen, —CN, —O($C_{1-6}$ alkyl) and —S($C_{1-6}$ alkyl), and n is 0 or 1; preferably, $R_1$' is halogen, and n is 0 or 1; and more preferably, n is 0;

$R_2$ is —$NH_2$;

$R_9$ and $R_{10}$ are each independently chosen from hydrogen, —$NH_2$, halogen, $C_{1-6}$ alkyl and $C_{1-6}$ haloalkyl; and preferably, $R_9$ and $R_{10}$ are each independently chosen from hydrogen and $C_{1-6}$ alkyl;

$Cy_2$ is phenyl or 5-14 membered heteroaryl, preferably phenyl or 5-10 membered heteroaryl, and more preferably phenyl, each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl; and L is absent.

Embodiment 14. The compound or the pharmaceutically acceptable salt thereof, or the solvate, the racemic mixture, the enantiomer, the diastereomer or the tautomer thereof according to embodiment 1, wherein the compound is a compound of formula (III):

(III)

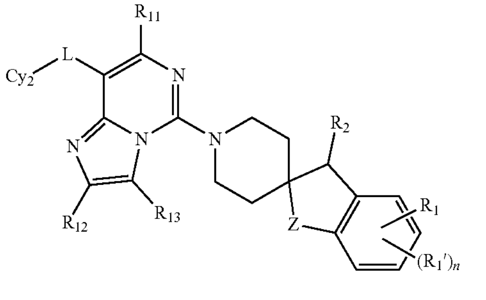

wherein

Z is $CH_2$;

$R_1$ is chosen from $C_{2-6}$ alkynyl, —$NR_3R_4$ and —$SR_5$, wherein the $C_{2-6}$ alkynyl is optionally substituted with one or more groups independently chosen from: halogen, —CN, —OH, —$NH_2$, $C_{3-8}$ cycloalkyl, 4-8 membered heterocyclyl, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —S($C_{3-8}$ cycloalkyl), —S(4-8 membered heterocyclyl), —NH($C_{1-6}$ alkyl), —N($C_{1-6}$ alkyl)$_2$, —NH—CN, —NHCONH$_2$, —NHCO($C_{1-6}$ alkyl), —CONR$_a$R$_b$, —COOR$_c$ and —COR$_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), —($C_{1-6}$ alkyl)-OH, $C_{3-8}$ cycloalkyl and 4-8 membered heterocyclyl; $R_3$ is independently chosen from hydrogen and $C_{1-6}$ alkyl; $R_4$ and $R_5$ are each independently chosen from $C_{3-8}$ cycloalkyl, 4-8 membered heterocyclyl and 5-6 membered heteroaryl; and the above-mentioned $C_{3-8}$ cycloalkyl, 4-8 membered heterocyclyl and 5-6 membered heteroaryl are each optionally substituted with one or more groups independently chosen from: $C_{1-6}$ alkyl and —O($C_{1-6}$ alkyl); preferably, $R_1$ is $C_{2-6}$ alkynyl, wherein the $C_{2-6}$ alkynyl is optionally substituted with one or more groups independently chosen from: —OH, —CONH$_2$, —O($C_{1-6}$ alkyl), —NH($C_{1-6}$ alkyl), —N($C_{1-6}$ alkyl)$_2$, —CONH($C_{1-6}$ alkyl) and —CON($C_{1-6}$ alkyl)$_2$; further preferably, $R_1$ is ethynyl, propynyl or butynyl, each of which is unsubstituted or substituted with —OH, —CONH$_2$, —OCH$_3$, —NH(CH$_3$), —N(CH$_3$)$_2$ or —CONH(CH$_3$); and more preferably, $R_1$ is ethynyl;

$R_1$' is chosen from halogen, —CN, —O($C_{1-6}$ alkyl) and —S($C_{1-6}$ alkyl), and n is 0 or 1; preferably, $R_1$' is halogen, and n is 0 or 1; and more preferably, n is 0;

$R_2$ is chosen from —NH$_2$ and oxo; and preferably, $R_2$ is —NH$_2$;

$R_{11}$, $R_{12}$ and $R_{13}$ are each independently chosen from hydrogen, —NH$_2$, —CN, $C_{1-6}$ alkyl and $C_{1-6}$ haloalkyl; preferably, $R_{11}$, $R_{12}$ and $R_{13}$ are each independently chosen from hydrogen and $C_{1-6}$ alkyl; and more preferably, $R_{11}$, $R_{12}$ and $R_{13}$ are all hydrogen;

$Cy_2$ is phenyl or 5-14 membered heteroaryl, preferably phenyl or 5-10 membered heteroaryl, and more preferably 5-6 membered heteroaryl, each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —NR$_7$R$_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl; and L is absent, or L is S; and preferably, L is S.

Embodiment 15. The compound or the pharmaceutically acceptable salt thereof, or the solvate, the racemic mixture, the enantiomer, the diastereomer or the tautomer thereof according to embodiment 1, wherein the compound is a compound of formula (IV):

(IV)

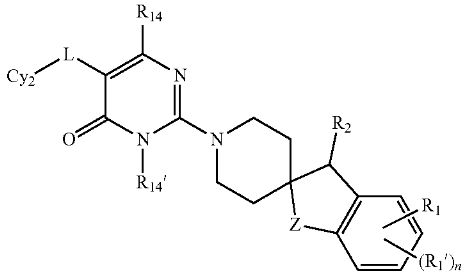

wherein

Z is $CH_2$ or O; and preferably, Z is $CH_2$;

$R_1$ is $C_{2-6}$ alkynyl, wherein the $C_{2-6}$ alkynyl is optionally substituted with one or more groups independently chosen from: halogen, —CN, —OH, —NH$_2$, $C_{3-8}$ cycloalkyl, 4-8 membered heterocyclyl, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —S($C_{3-8}$ cycloalkyl), —S(4-8 membered heterocyclyl), —NH($C_{1-6}$ alkyl), —N($C_{1-6}$ alkyl)$_2$, —NH—CN, —NHCONH$_2$, —NHCO($C_{1-6}$ alkyl), —CONR$_a$R$_b$, —COOR$_c$ and —COR$_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), —($C_{1-6}$ alkyl)-OH, $C_{3-8}$ cycloalkyl and 4-8 membered heterocyclyl; the above-mentioned $C_{3-8}$ cycloalkyl and 4-8 membered heterocyclyl are each optionally substituted with one or more groups independently chosen from: $C_{1-6}$ alkyl and —O($C_{1-6}$ alkyl); preferably, $R_1$ is $C_{2-6}$ alkynyl, wherein the $C_{2-6}$ alkynyl is optionally substituted with one or more groups independently chosen from: —OH, —O($C_{1-6}$ alkyl), —NH($C_{1-6}$ alkyl), —N($C_{1-6}$ alkyl)$_2$, —CONH($C_{1-6}$ alkyl) and —CON($C_{1-6}$ alkyl)$_2$; further preferably, $R_1$ is ethynyl, propynyl or butynyl, each of which is unsubstituted or substituted with —OH, —OCH$_3$, —NH(CH$_3$) or —N(CH$_3$)$_2$; and more preferably, $R_1$ is ethynyl;

$R_1$' is chosen from halogen, —O($C_{1-6}$ alkyl) and —S($C_{1-6}$ alkyl), and n is 0 or 1; preferably, $R_1$' is halogen, and n is 0 or 1; and more preferably, n is 0;

$R_2$ is —NH$_2$;

$R_{14}$ is chosen from hydrogen, —NH$_2$ and $C_{1-6}$ alkyl; preferably, $R_{14}$ is hydrogen or —NH$_2$; and more preferably, $R_{14}$ is hydrogen;

$R_{14}$' is $C_{1-6}$ alkyl;

$Cy_2$ is phenyl or 5-14 membered heteroaryl, preferably phenyl or 5-10 membered heteroaryl, and more preferably 5-6 membered heteroaryl or 9-10 membered heteroaryl, each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —NR$_7$R$_8$, wherein $R_7$ and $R_8$ are each independently chosen from hydrogen, —($C_{1-6}$ alkyl)-OH and —($C_{1-6}$ alkyl)-O—($C_{1-6}$ alkyl); and L is absent, or L is S; and preferably, L is S.

Embodiment 16. The compound or the pharmaceutically acceptable salt thereof, or the solvate, the racemic mixture, the enantiomer, the diastereomer or the tautomer thereof according to embodiment 1, wherein the compound is a compound of formula (V):

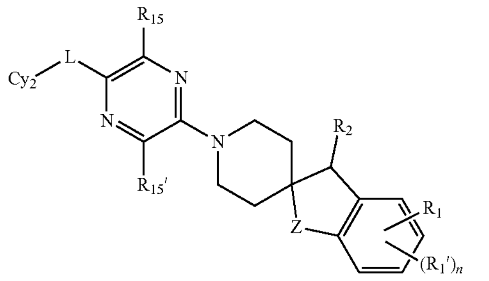

(V)

wherein

Z is $CH_2$ or O; and preferably, Z is $CH_2$;

$R_1$ is $C_{2-6}$ alkynyl, wherein the $C_{2-6}$ alkynyl is optionally substituted with one or more groups independently chosen from: halogen, —CN, —OH, —$NH_2$, $C_{3-8}$ cycloalkyl, 4-8 membered heterocyclyl, —O($C_{1-6}$ alkyl), —O($C_{1-6}$ haloalkyl), —O($C_{3-8}$ cycloalkyl), —O(4-8 membered heterocyclyl), —S($C_{1-6}$ alkyl), —S($C_{3-8}$ cycloalkyl), —S(4-8 membered heterocyclyl), —NH($C_{1-6}$ alkyl), —N($C_{1-6}$ alkyl)$_2$, —NH—CN, —$NHCONH_2$, —NHCO($C_{1-6}$ alkyl), —$CONR_aR_b$, —$COOR_c$ and —$COR_d$, wherein $R_a$, $R_b$, $R_c$ and $R_d$ are each independently chosen from hydrogen, $C_{1-6}$ alkyl, $C_{1-6}$ haloalkyl, —($C_{1-6}$ alkyl)-O—($C_{1-6}$ alkyl), —($C_{1-6}$ alkyl)-OH, —($C_{1-6}$ alkyl)-CN, $C_{3-8}$ cycloalkyl and 4-8 membered heterocyclyl; and the above-mentioned $C_{3-8}$ cycloalkyl and 4-8 membered heterocyclyl are each optionally substituted with one or more groups independently chosen from: $C_{1-6}$ alkyl and —O($C_{1-6}$ alkyl); preferably, $R_1$ is $C_{2-6}$ alkynyl, wherein the $C_{2-6}$ alkynyl is optionally substituted with one or more groups independently chosen from: —OH, —O($C_{1-6}$ alkyl), —NH($C_{1-6}$ alkyl), —N($C_{1-6}$ alkyl)$_2$, —$NHCONH_2$, —$CONR_aR_b$, —$COOR_c$ and —$COR_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), $C_{3-8}$ cycloalkyl and 4-8 membered heterocyclyl, wherein the $C_{3-8}$ cycloalkyl and 4-8 membered heterocyclyl are each optionally substituted with one or more groups independently chosen from: $C_{1-6}$ alkyl and —O($C_{1-6}$ alkyl); more preferably, $R_1$ is $C_{2-6}$ alkynyl, wherein the $C_{2-6}$ alkynyl is optionally substituted with one or more groups independently chosen from: —OH, —$CONH_2$, —O($C_{1-6}$ alkyl), —NH($C_{1-6}$ alkyl), —N($C_{1-6}$ alkyl)$_2$, —$NHCONH_2$, —CONH($C_{1-6}$ alkyl), —CONH($C_{1-6}$ alkyl)-O—($C_{1-6}$ alkyl), —CON($C_{1-6}$ alkyl)$_2$, —CON($C_{1-6}$ alkyl)($C_{1-6}$ alkyl-O—$C_{1-6}$ alkyl), —CONH($C_{3-8}$ cycloalkyl), —COOH, —COO($C_{1-6}$ alkyl), —CO($C_{1-6}$ alkyl), —CO(4-8 membered heterocyclyl) and —CO(4-8 membered heterocyclyl)-O—($C_{1-6}$ alkyl); further preferably, $R_1$ is ethynyl, propynyl or butynyl, each of which is unsubstituted or substituted with —OH, —$CONH_2$, —$OCH_3$, —NH($CH_3$), —N($CH_3$)$_2$, —$NHCONH_2$, —CONH($C_{1-3}$ alkyl), —CONH($CH_2CH_2$)—O—($CH_3$), —CON($CH_3$)$_2$, —CON($CH_3$)($CH_2CH_2$—O—$CH_3$), —CONH(cyclopropyl), —COOH, —COO($CH_3$), —CO($CH_3$), —CO(azetidinyl) or —CO(azetidinyl)-O—($CH_3$); and most preferably, $R_1$ is ethynyl substituted with —CONH($CH_3$), —CONH($CH_2CH_3$) or —CONH($CH_2CH_2$)—O—($CH_3$);

$R_1'$ is chosen from halogen, —O($C_{1-6}$ alkyl) and —S($C_{1-6}$ alkyl), and n is 0 or 1; preferably, $R_1'$ is halogen, and n is 0 or 1; and more preferably, n is 0;

$R_2$ is —$NH_2$;

$R_{15}$ and $R_{15}'$ are each independently chosen from hydrogen, —$NH_2$, —CN, halogen, $C_{1-6}$ alkyl, $C_{1-6}$ haloalkyl and —($C_{1-6}$ alkyl)-OH; preferably, $R_{15}$ and $R_{15}'$ are each independently chosen from hydrogen, —$NH_2$, $C_{1-6}$alkyl and —($C_{1-6}$ alkyl)-OH; and more preferably, both $R_{15}$ and $R_{15}'$ are hydrogen;

$Cy_2$ is phenyl or 5-14 membered heteroaryl, preferably phenyl or 5-10 membered heteroaryl, and more preferably 5-6 membered heteroaryl or 9-10 membered heteroaryl, each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl; and L is absent, or L is S; and preferably, L is S.

Embodiment 17. The compound or the pharmaceutically acceptable salt thereof, or the solvate, the racemic mixture, the enantiomer, the diastereomer or the tautomer thereof according to any one of embodiments 1-16, wherein $Cy_2$ is phenyl, pyridyl, pyrimidyl, indazolyl, pyrrolopyridyl or 1,2,3,4-tetrahydro-1,5-naphthyridinyl, each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl.

Embodiment 18. The compound or the pharmaceutically acceptable salt thereof, or the solvate, the racemic mixture, the enantiomer, the diastereomer or the tautomer thereof according to embodiment 17, wherein $Cy_2$ is chosen from

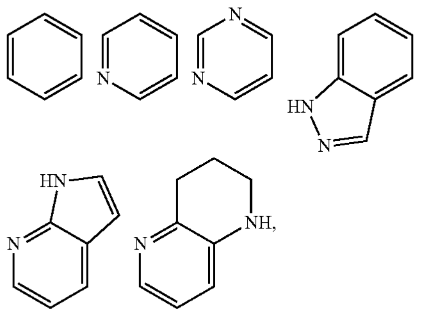

each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl;

preferably, $Cy_2$ is chosen from

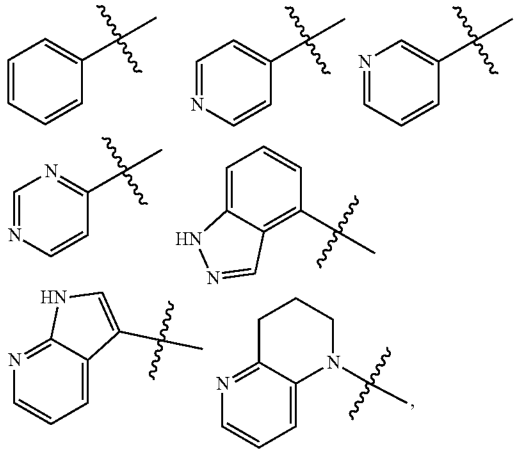

each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl; and more preferably, $Cy_2$ is chosen from

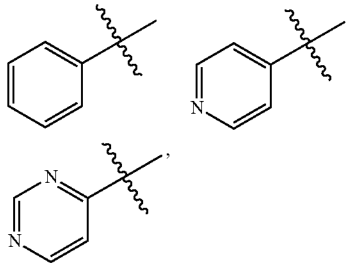

each of which is optionally substituted with one or more groups independently chosen from: halogen, —CN, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl.

Embodiment 19. The compound or the pharmaceutically acceptable salt thereof, or the solvate, the racemic mixture, the enantiomer, the diastereomer or the tautomer thereof according to embodiment 18, wherein $Cy_2$ is

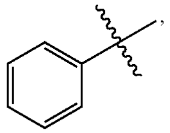 [SMILES: *c1ccccc1]

which is optionally substituted with one or more groups independently chosen from: halogen, —CN, —OH, $C_{1-6}$ alkyl, $C_{1-6}$ haloalkyl, —O($C_{1-6}$ alkyl) and —S($C_{1-6}$ alkyl);

or $Cy_2$ is

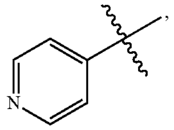 [SMILES: *c1ccncc1]

which is optionally substituted with one or more groups independently chosen from: halogen, $C_{1-6}$ alkyl, —O($C_{1-6}$ alkyl) and —$NR_7R_8$, wherein $R_7$ and $R_8$ are each independently chosen from hydrogen, —($C_{1-6}$ alkyl)-OH, —($C_{1-6}$ alkyl)-O—($C_{1-6}$ alkyl) and $C_{3-8}$ cycloalkyl; and preferably, both $R_7$ and $R_8$ are hydrogen;

$Cy_2$ is

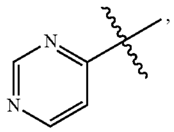 [SMILES: *c1ccncn1]

which is optionally substituted with one or more groups independently chosen from: $C_{1-6}$ alkyl and —$NR_7R_8$, wherein $R_7$ and $R_8$ are each independently chosen from hydrogen, —($C_{1-6}$ alkyl)-OH and —($C_{1-6}$ alkyl)-O—($C_{1-6}$ alkyl); and preferably, both $R_7$ and $R_8$ are hydrogen.

Embodiment 20. The compound or the pharmaceutically acceptable salt thereof, or the solvate, the racemic mixture, the enantiomer, the diastereomer or the tautomer thereof according to embodiment 1, which is chosen from:

| No. | Structural formula | No. | Structural formula |
|---|---|---|---|
| 1 | 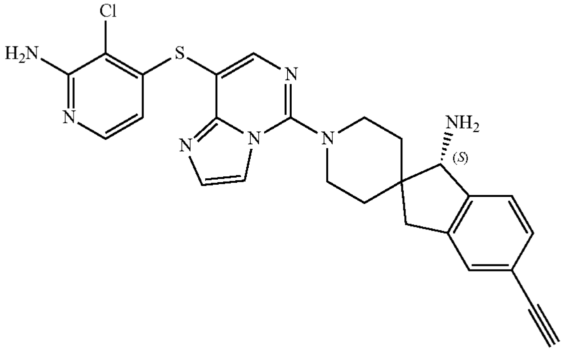 | 2 | 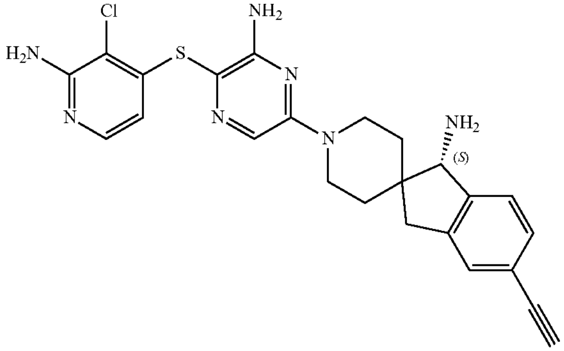 |
| 3 | 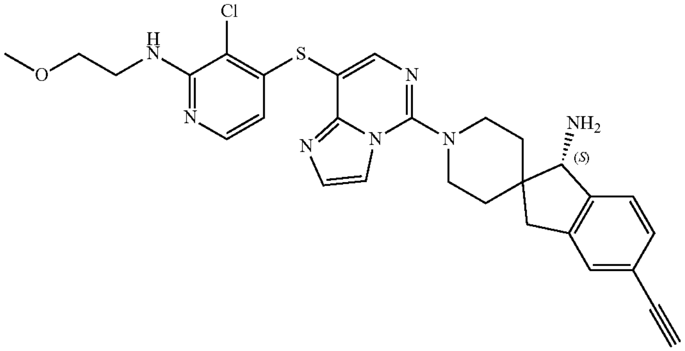 | 4 | 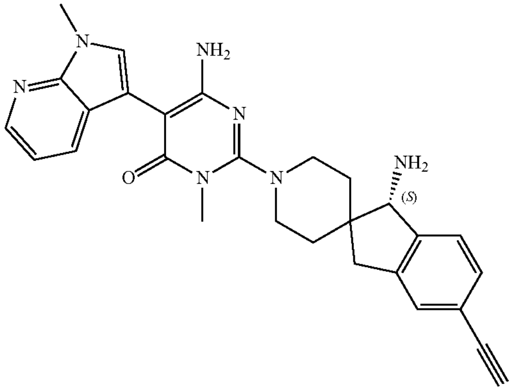 |

-continued
| No. | Structural formula | No. | Structural formula |
|---|---|---|---|
| 5 | 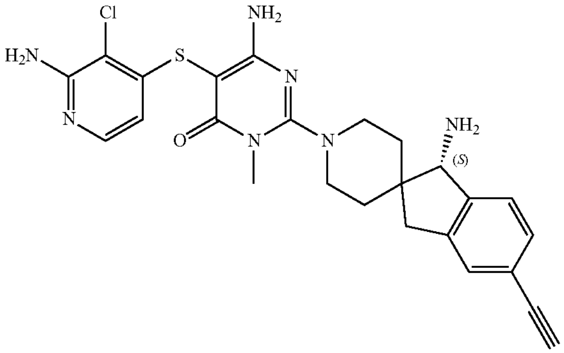 | 6 | 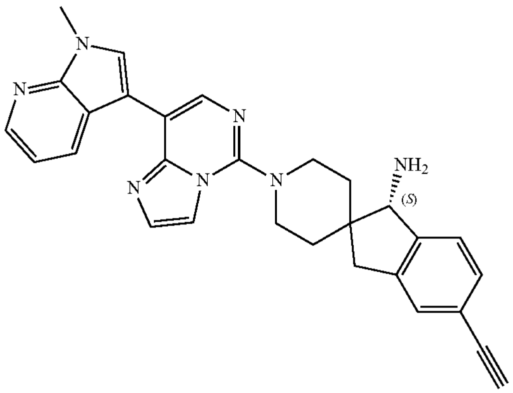 |
| 7 | 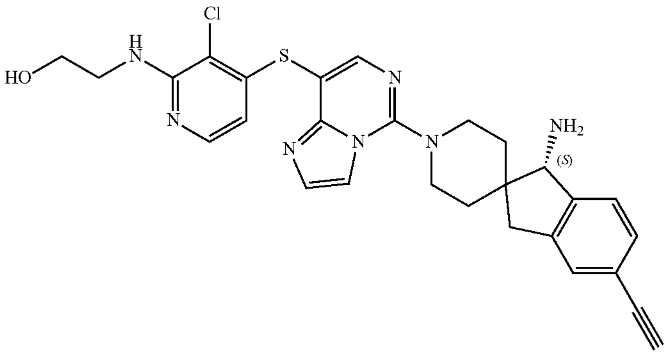 | 8 | 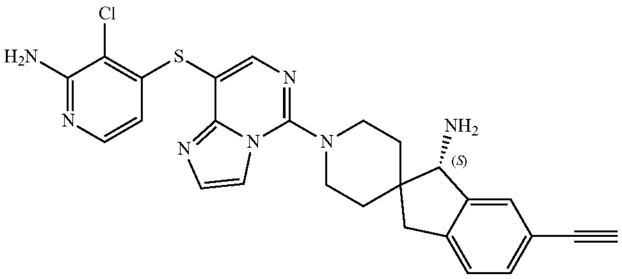 |

-continued
| No. | Structural formula | No. | Structural formula |
|---|---|---|---|
| 9 | 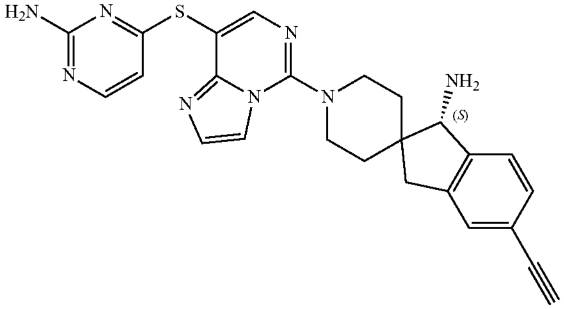 | 10 | 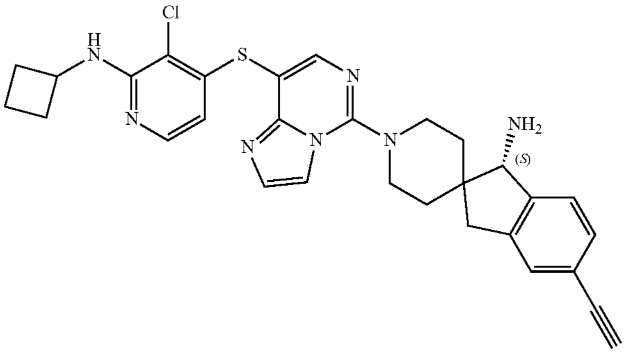 |
| 11 and 28 | 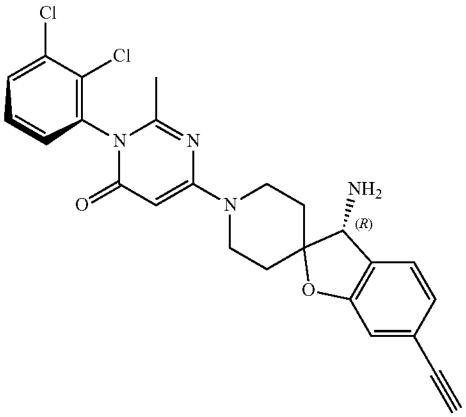 + | 12 and 64 | 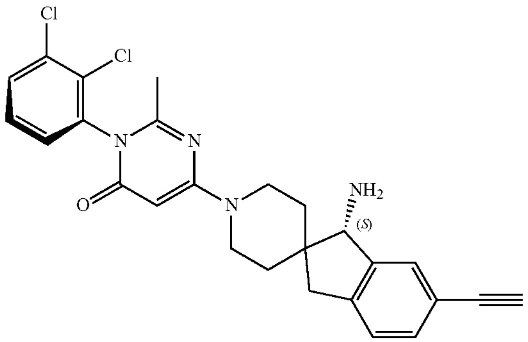 + |

-continued
| No. | Structural formula | No. | Structural formula |
|---|---|---|---|
| | 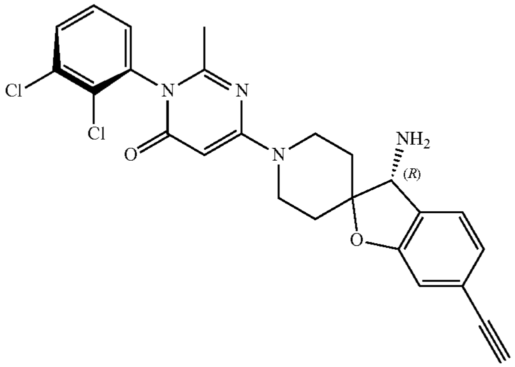 | | 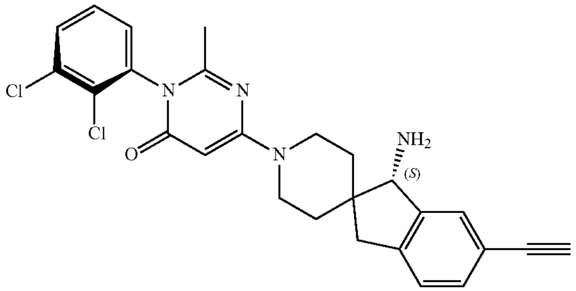 |
| 13 | 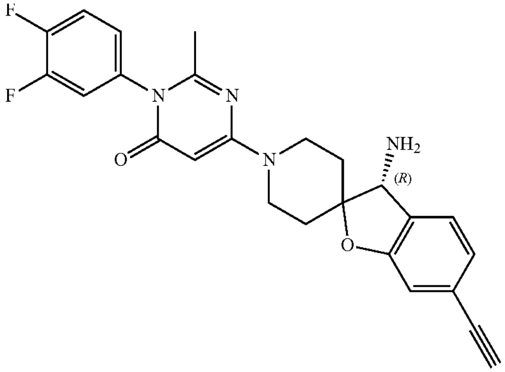 | 14 | 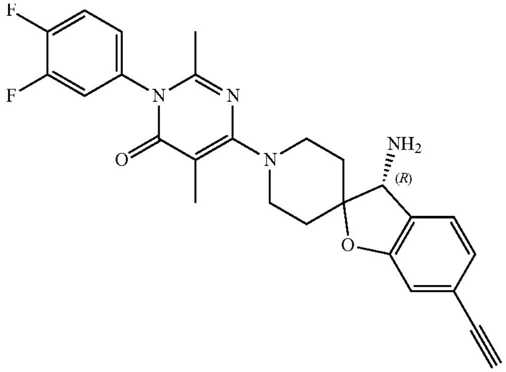 |

-continued
| No. | Structural formula | No. | Structural formula |
|---|---|---|---|
| 15 | 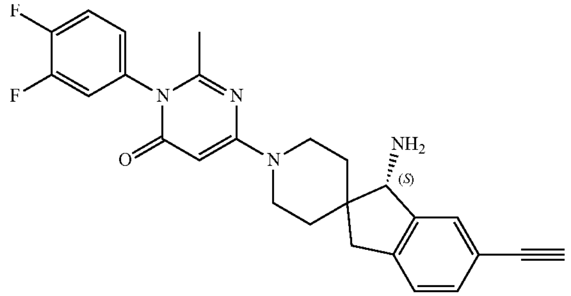 | 16 | 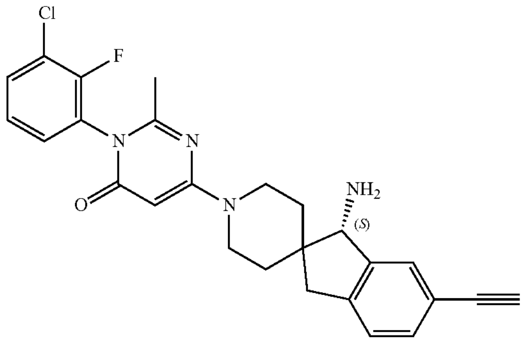 |
| 17 | 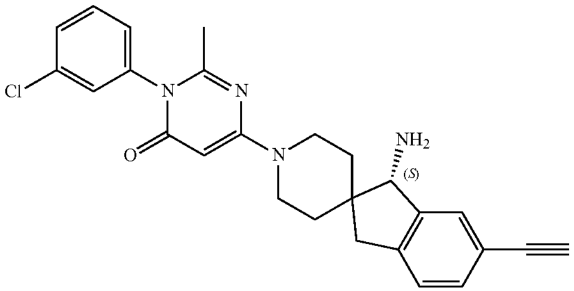 | 18 | 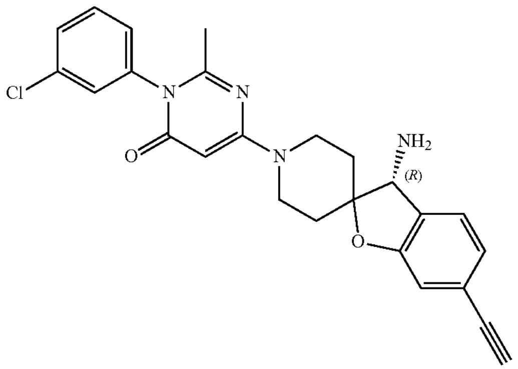 |

-continued
| No. | Structural formula | No. | Structural formula |
| --- | --- | --- | --- |
| 19 | 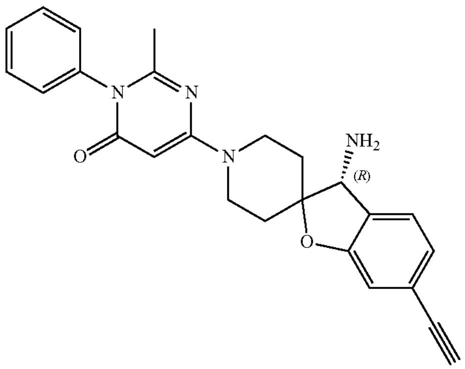 | 21 | 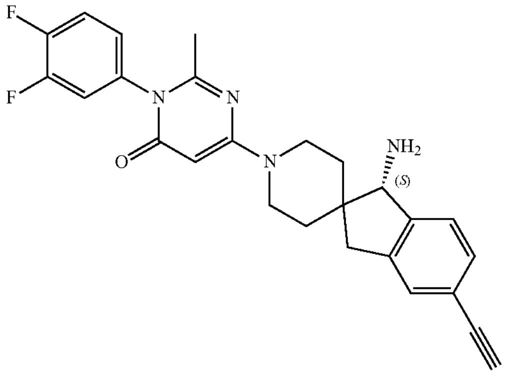 |
| 20 and 24 | 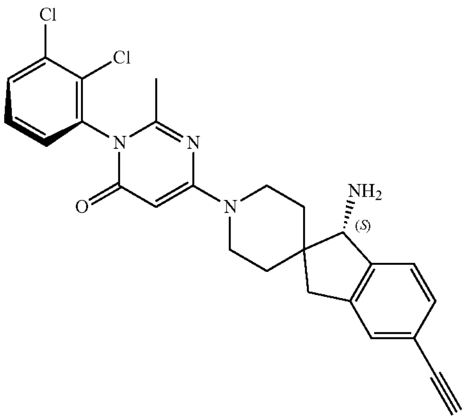<br>+ | 22 | 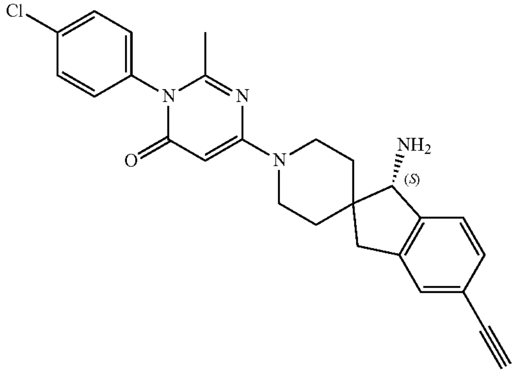 |

-continued
| No. | Structural formula | No. | Structural formula |
|---|---|---|---|
| | 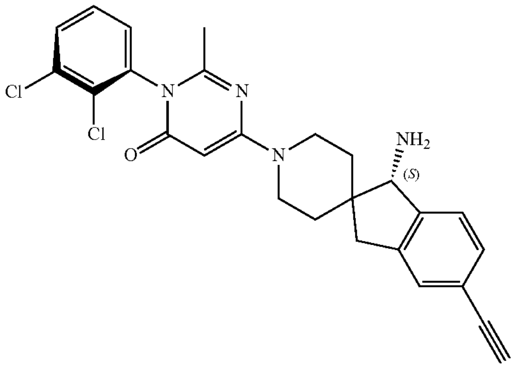 | 23 | 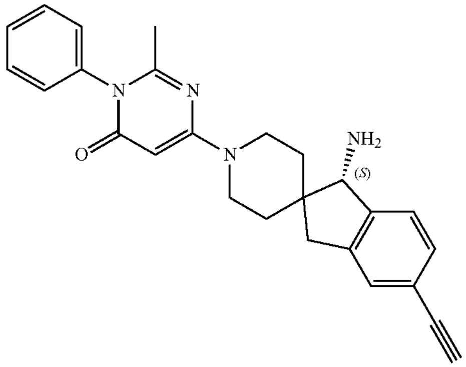 |
| 25 | 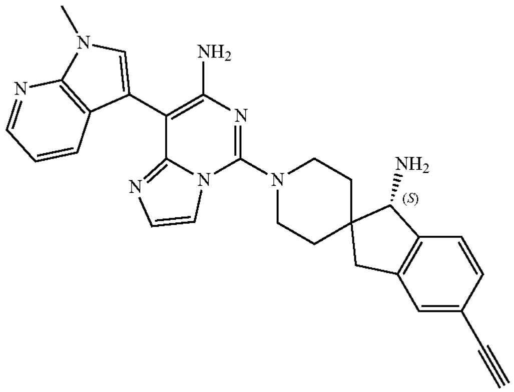 | 26 | 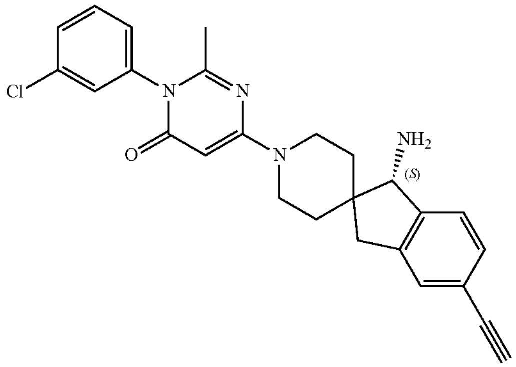 |
| 27 | 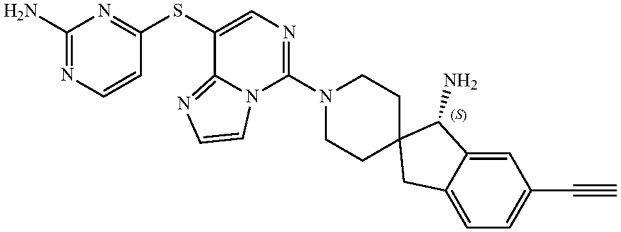 | 29 | 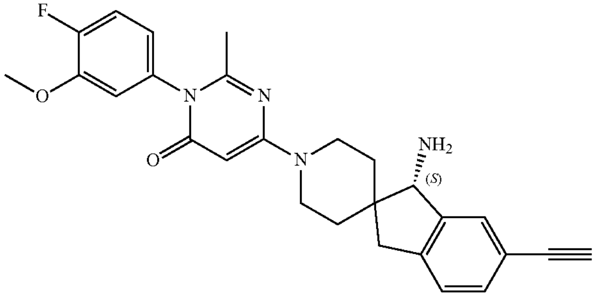 |

-continued
| No. | Structural formula | No. | Structural formula |
|---|---|---|---|
| 30 | 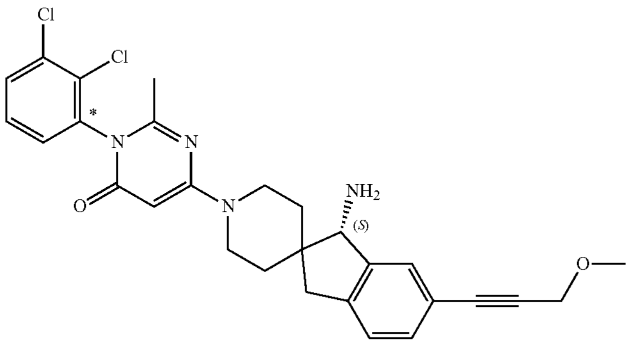 | 31 | 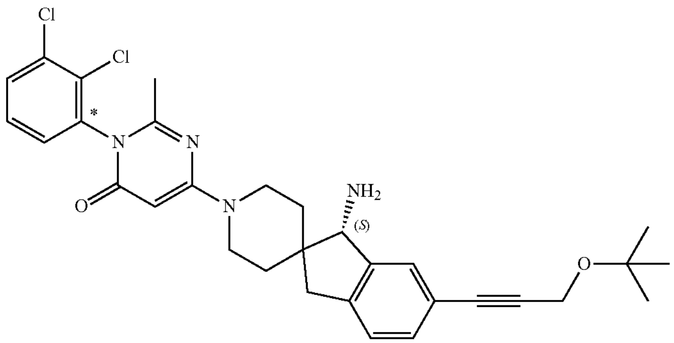 |
| 32 | 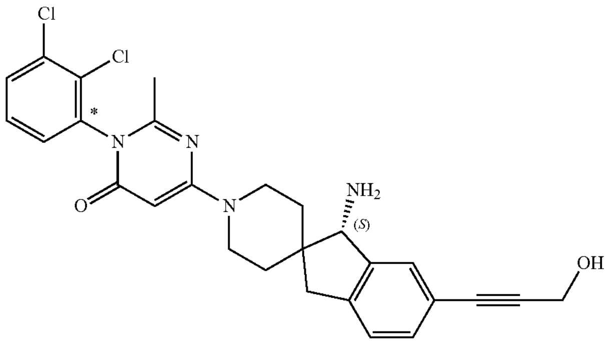 | 33 | 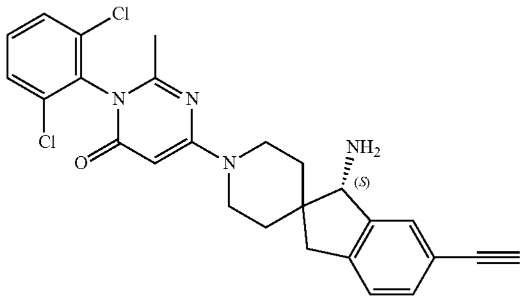 |

-continued
| No. | Structural formula | No. | Structural formula |
|---|---|---|---|
| 34 | 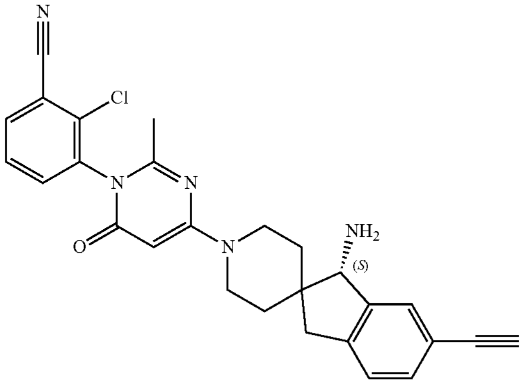 | 35 | 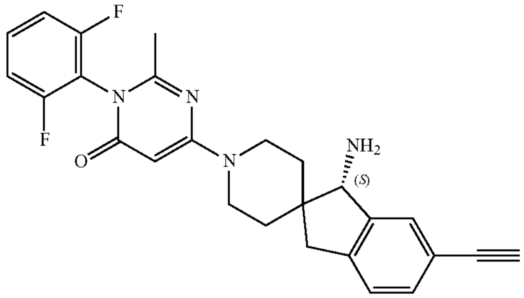 |
| 36 | 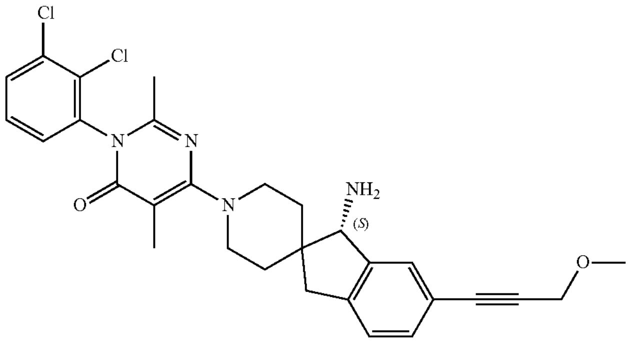 | 37 | 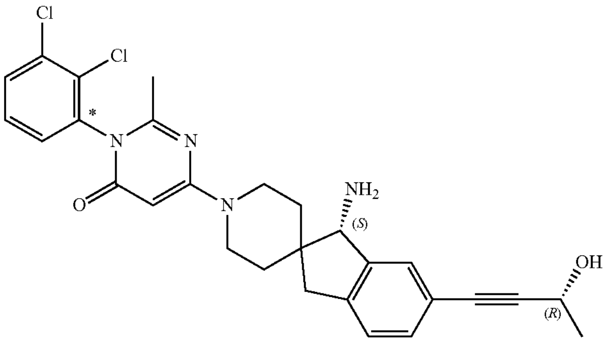 |

-continued
| No. | Structural formula | No. | Structural formula |
|---|---|---|---|
| 38 | 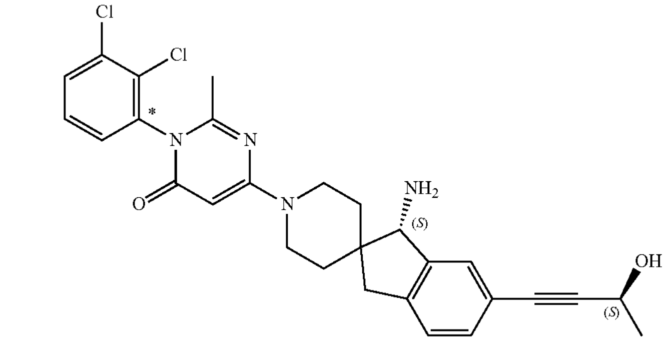 | 39 | 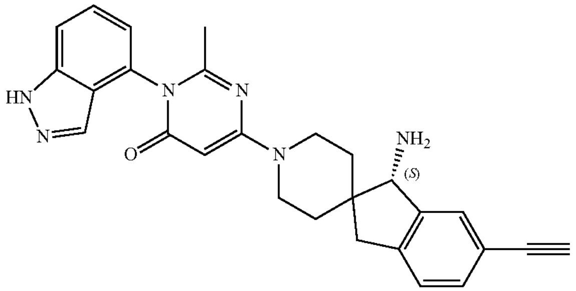 |
| 40 | 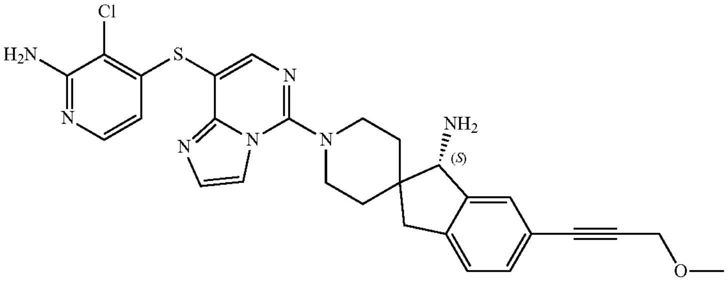 | 41 | 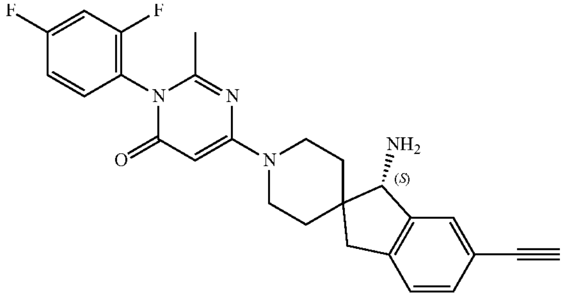 |
| 42 | 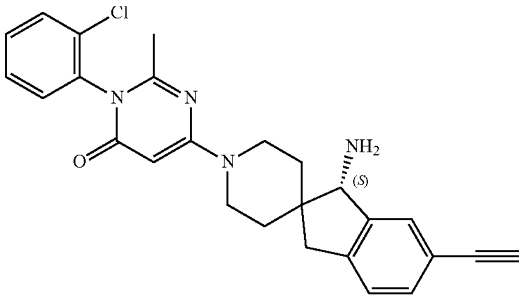 | 43 | 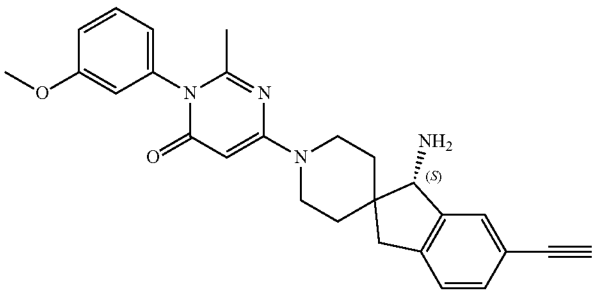 |

-continued
| No. | Structural formula | No. | Structural formula |
|---|---|---|---|
| 44 | 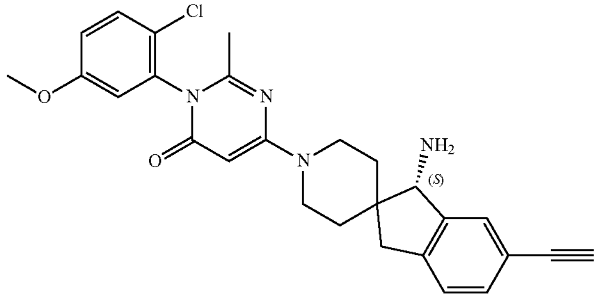 | 45 | 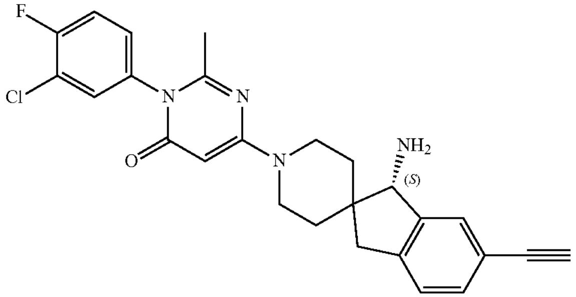 |
| 46 | 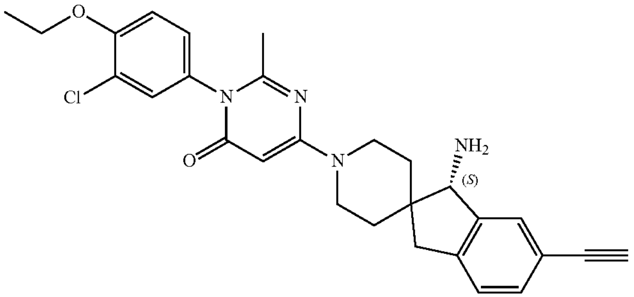 | 47 | 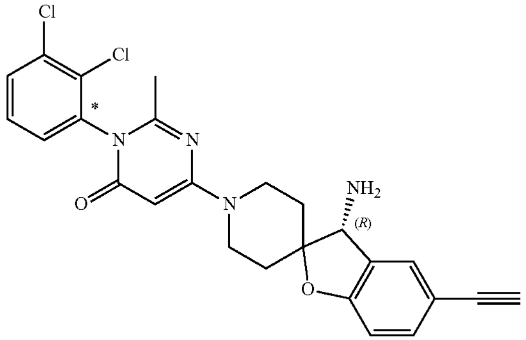 |
| 48 and 49 | 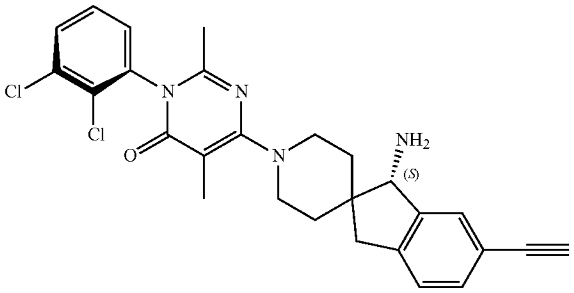 + | 50 and 51 | 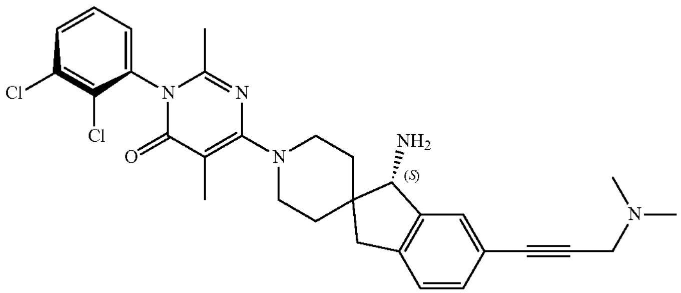 + |

-continued
| No. | Structural formula | No. | Structural formula |
| --- | --- | --- | --- |
| | 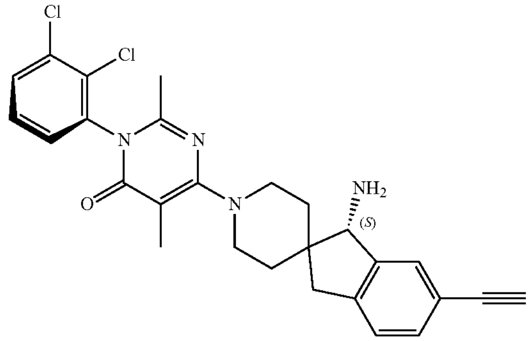 | | 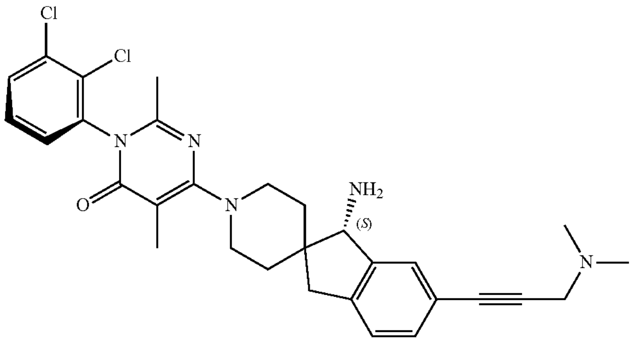 |
| 52 | 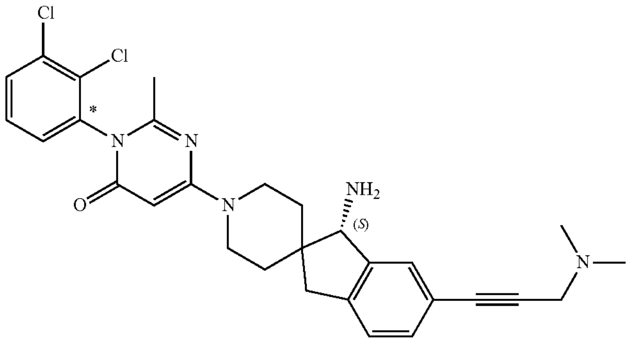 | 53 | 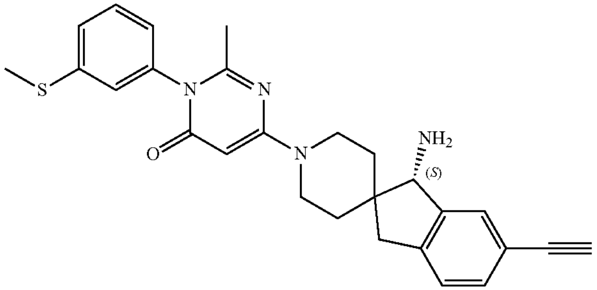 |
| 54 | 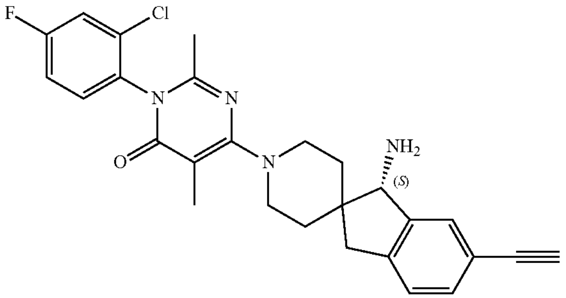 | 55 | 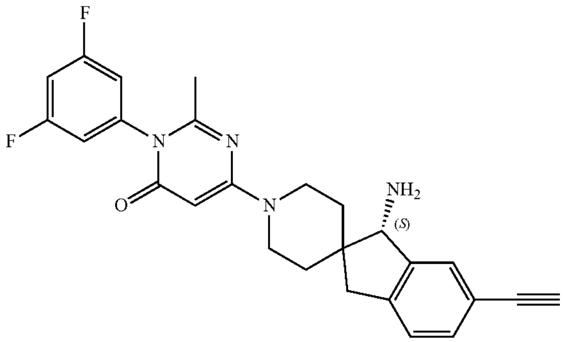 |

-continued
| No. | Structural formula | No. | Structural formula |
|---|---|---|---|
| 56 and 57 | 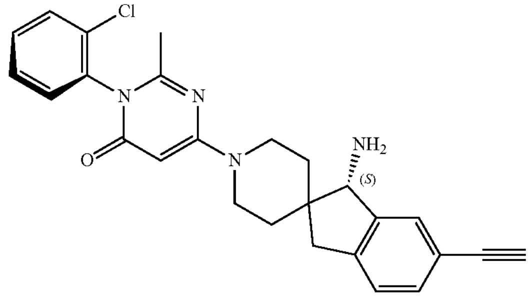 + 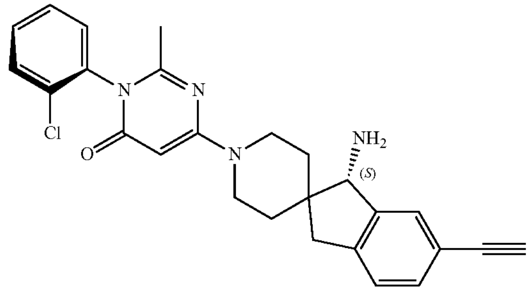 | 58 and 59 | 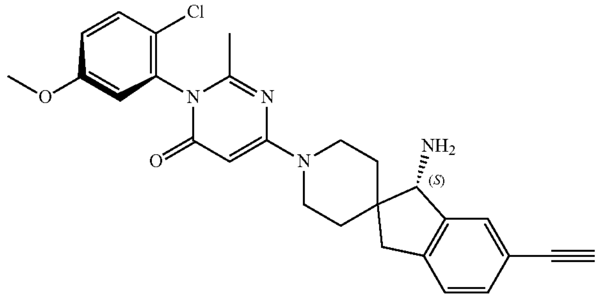 + 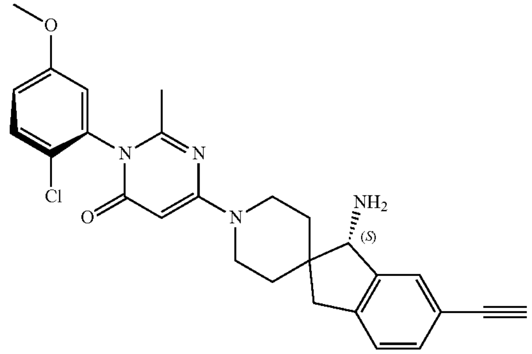 |
| 60 | 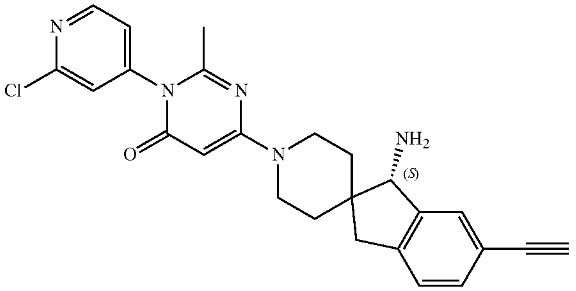 | 61 | 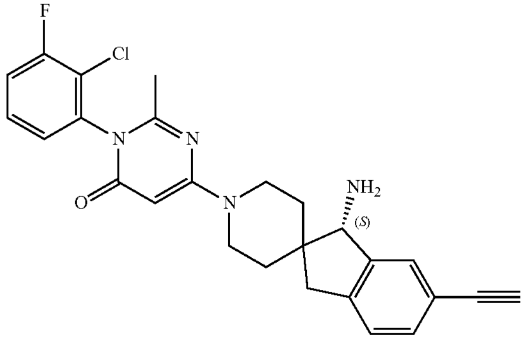 |

-continued
| No. | Structural formula | No. | Structural formula |
|---|---|---|---|
| 62 | 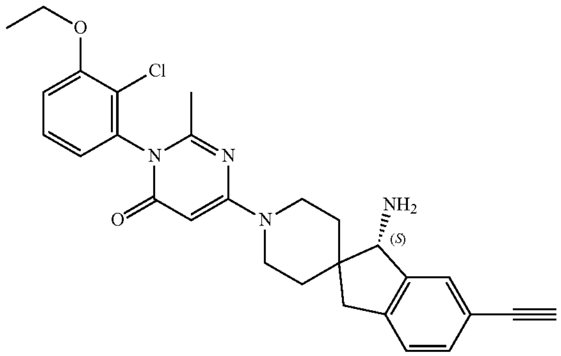 | 63 | 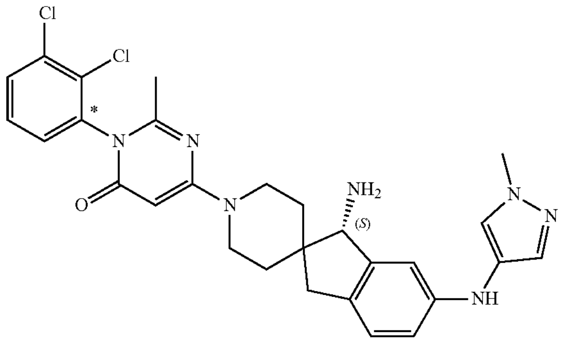 |
| 65 and 66 | 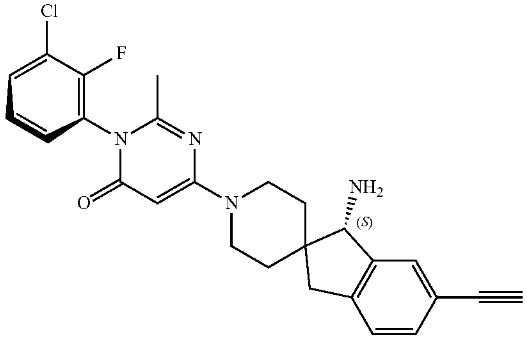 + 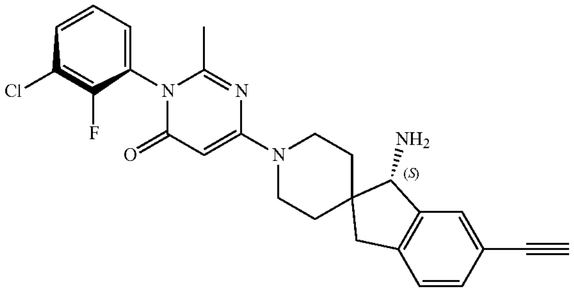 | 67 | 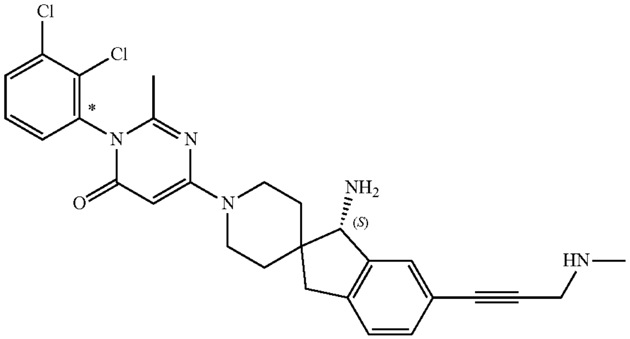 |
| | | 68 | 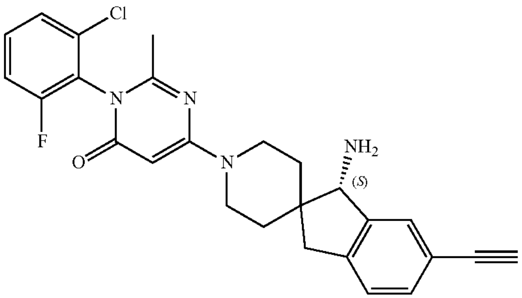 |

-continued
| No. | Structural formula | No. | Structural formula |
| --- | --- | --- | --- |
| 69 | 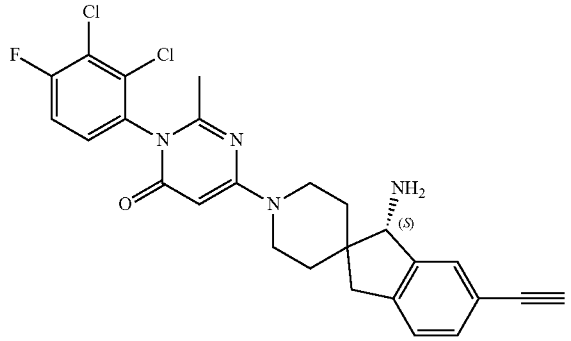 | 70 | 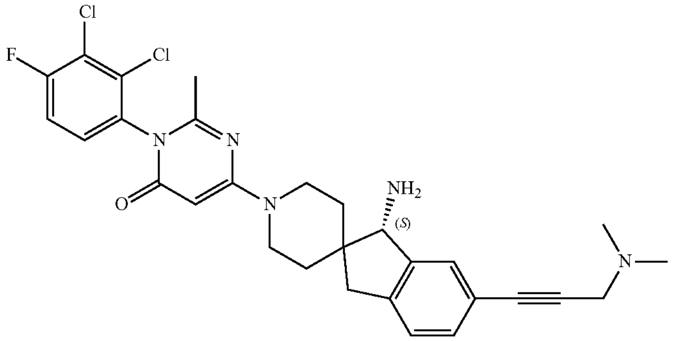 |
| 71 | 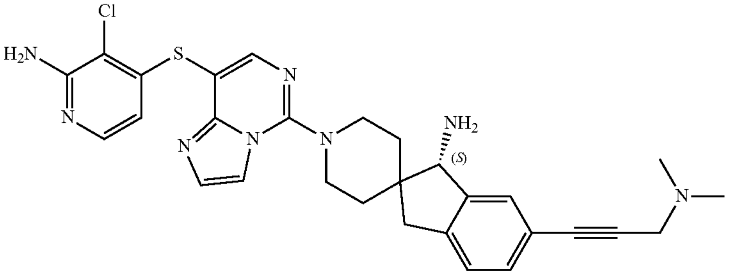 | 72 | 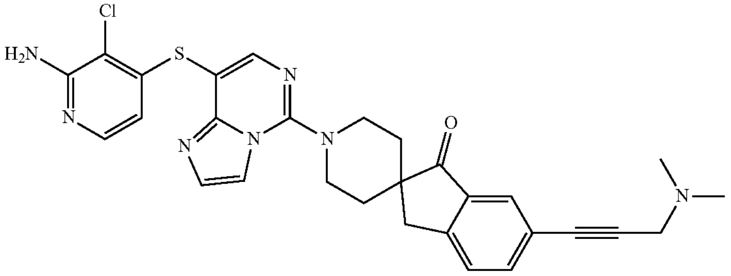 [SMILES: CN(C)CC#Cc1ccc2c(c1)C(=O)C1(CCN(c3ncc(Sc4ccnc(N)c4Cl)c4nccn34)CC1)C2] |
| 73 | 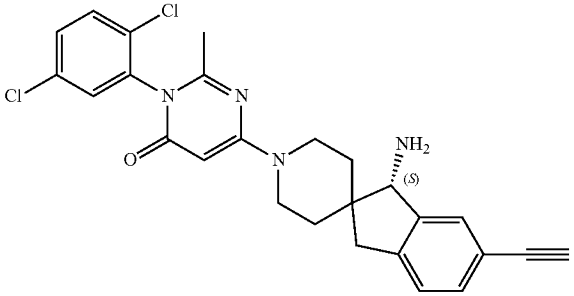 | 74 | 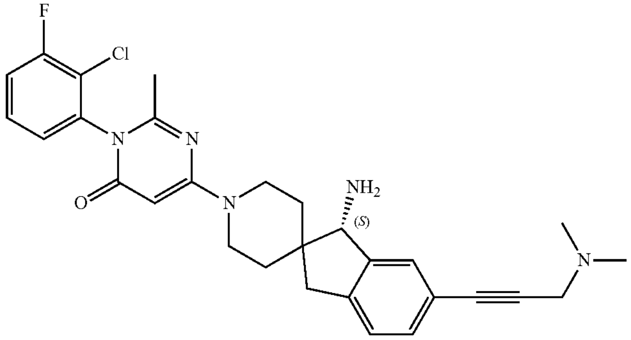 |

-continued
| No. | Structural formula | No. | Structural formula |
|---|---|---|---|
| 75 | 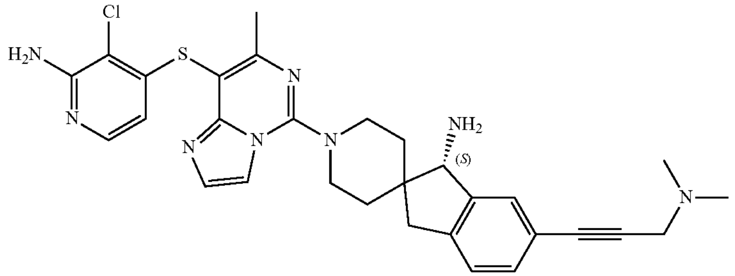 | 76 | 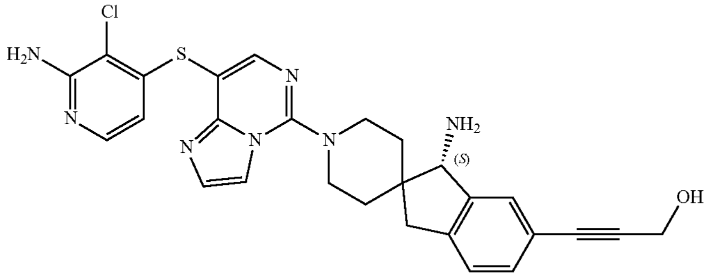 |
| 77 | 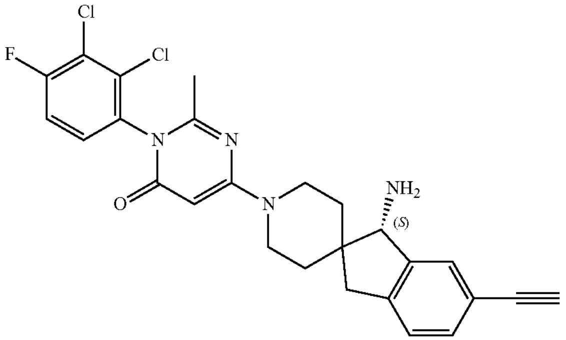 | 78 | 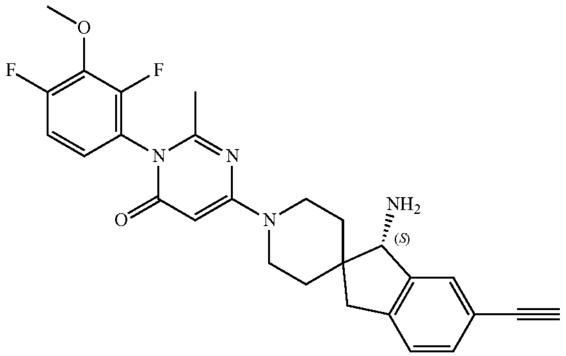 |
| 79 | 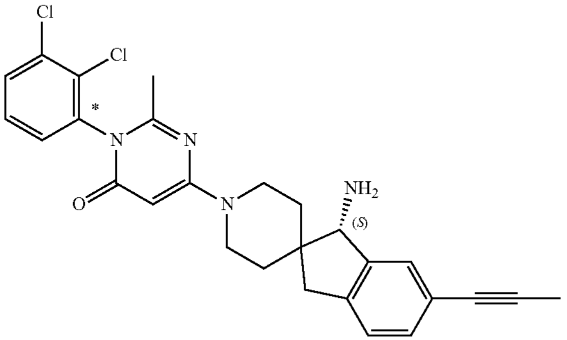 | 80 | 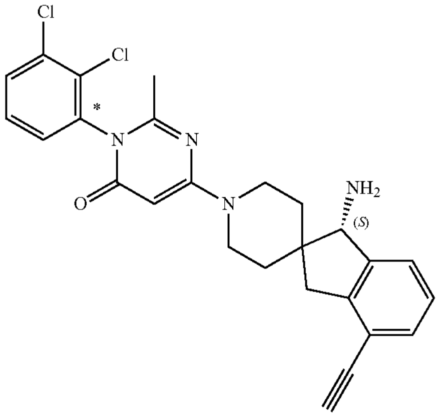 |

-continued
| No. | Structural formula | No. | Structural formula |
|---|---|---|---|
| 81 | 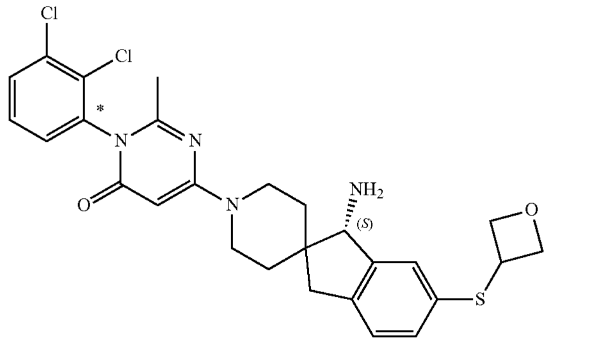 | 82 | 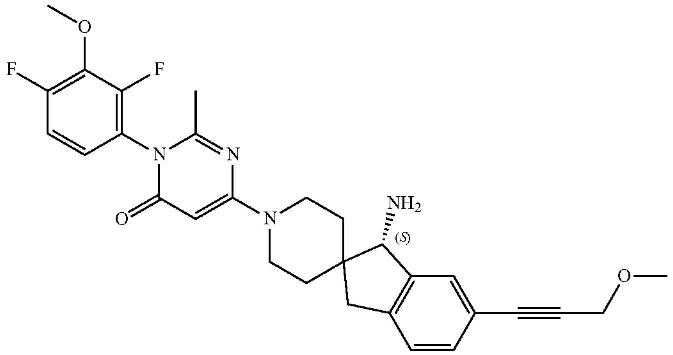 |
| 83 | 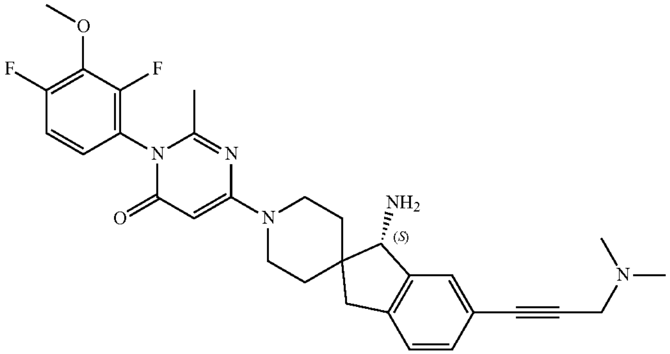 | 84 | 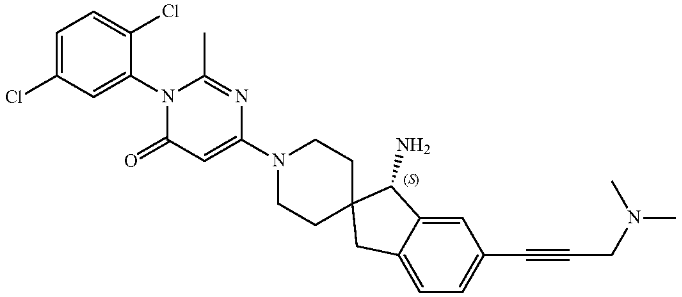 |
| 85 | 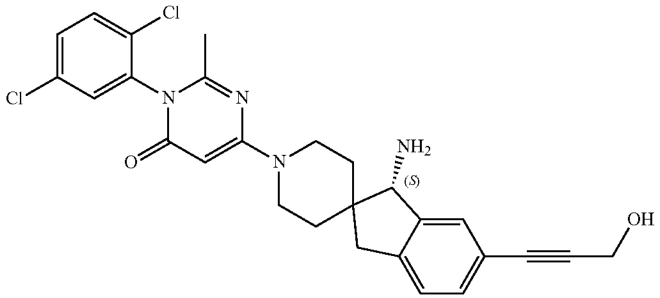 | 86 | 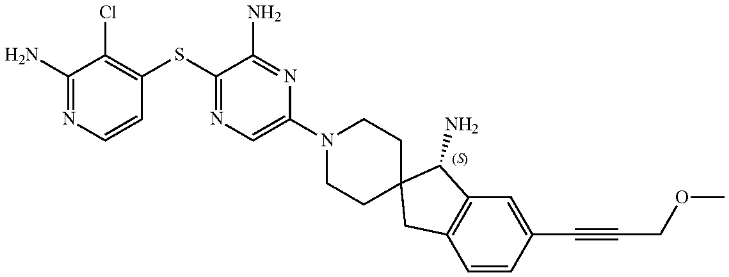 |

-continued
| No. | Structural formula | No. | Structural formula |
|---|---|---|---|
| 87 | 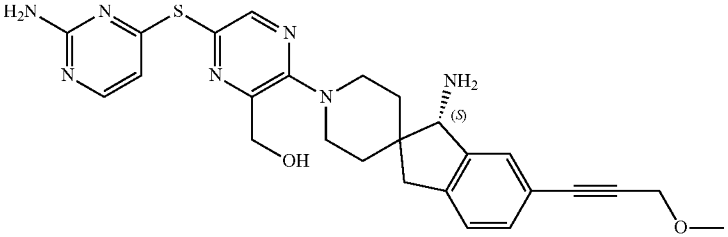 | 90 | 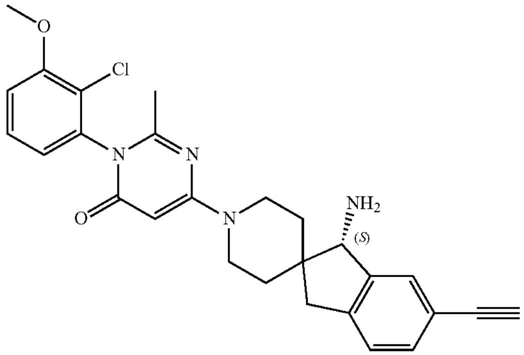 |
| 88 and 89 | 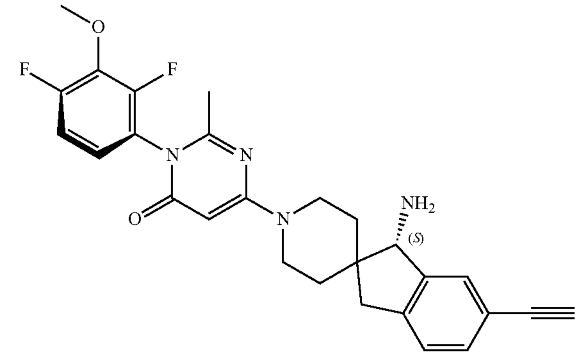 + 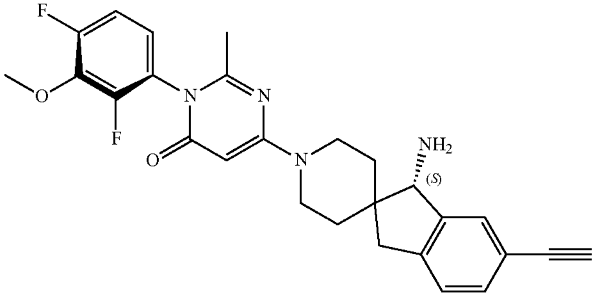 | 91 | 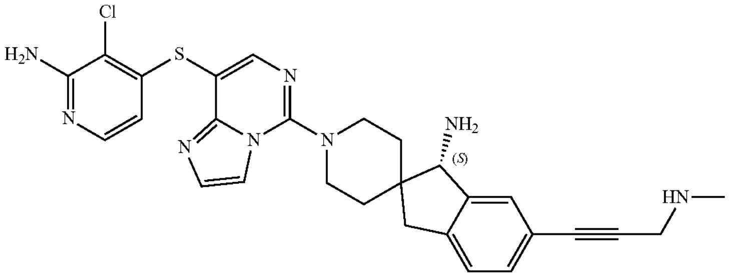 |
| | | 92 | 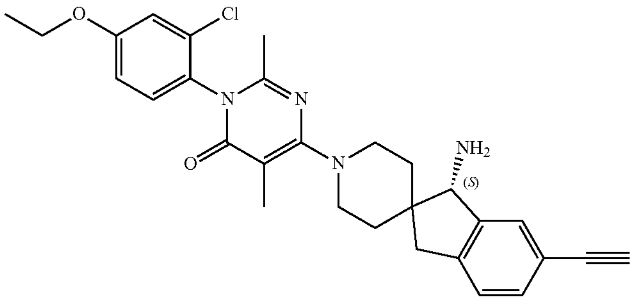 |

-continued
| No. | Structural formula | No. | Structural formula |
|---|---|---|---|
| 93 | 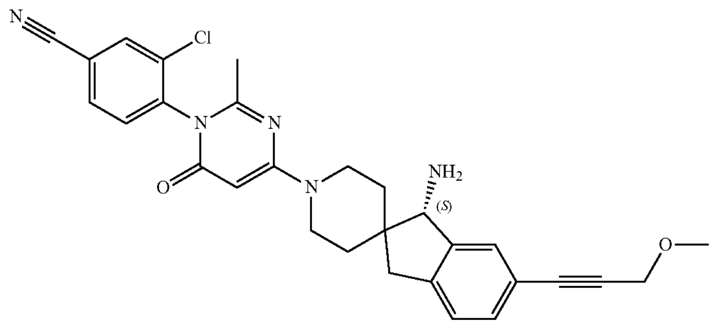 | 94 | 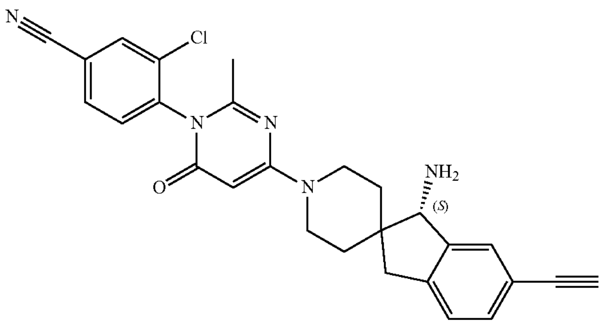 |
| 95 | 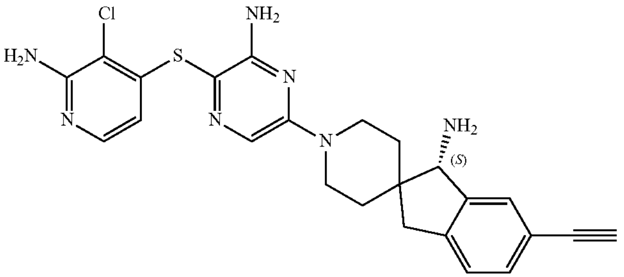 | 96 | 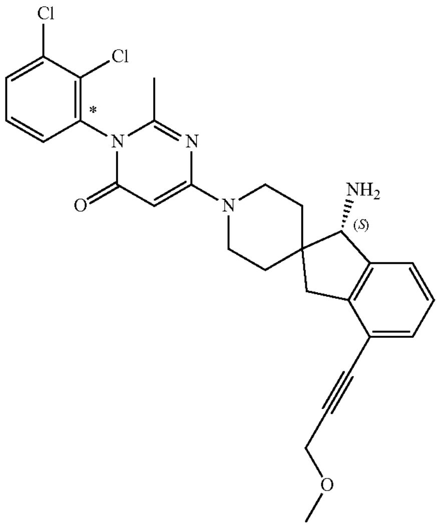 |

-continued
| No. | Structural formula | No. | Structural formula |
|---|---|---|---|
| 97 | 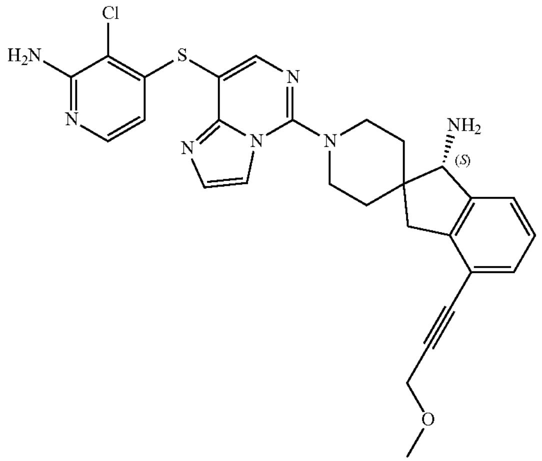 | 98 | 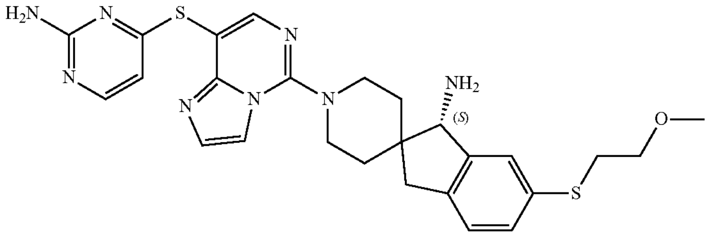 |
| 99 | 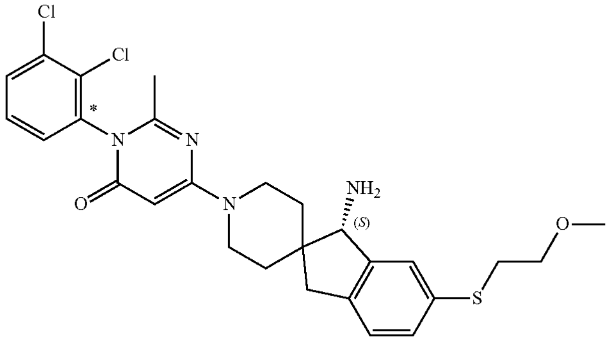 | 100 | 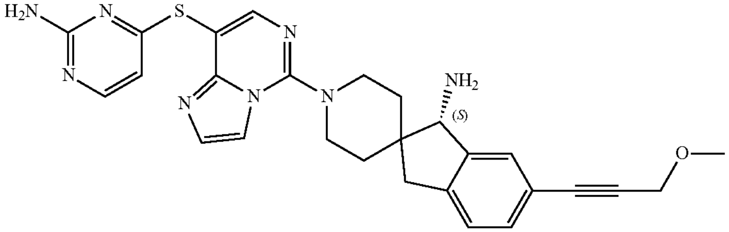 |

-continued
| No. | Structural formula | No. | Structural formula |
| --- | --- | --- | --- |
| 101 | 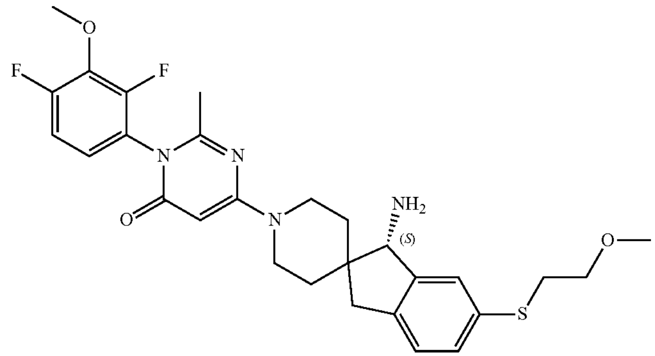 | 104 | 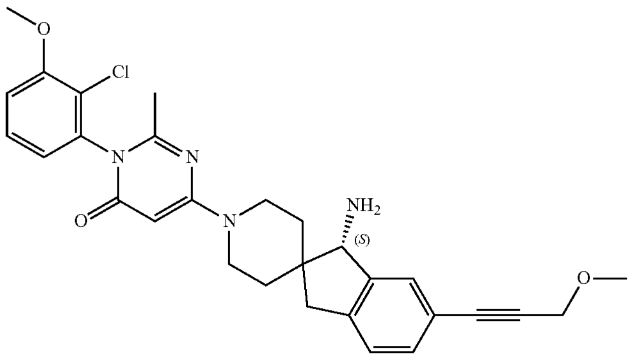 |
| 102 and 103 | 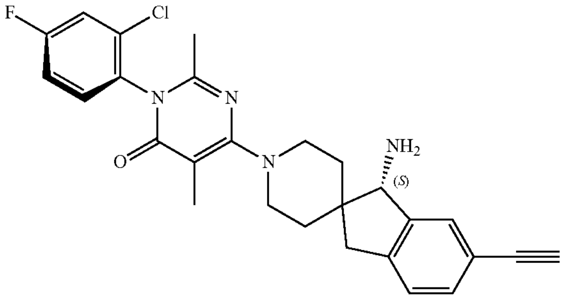<br>+<br>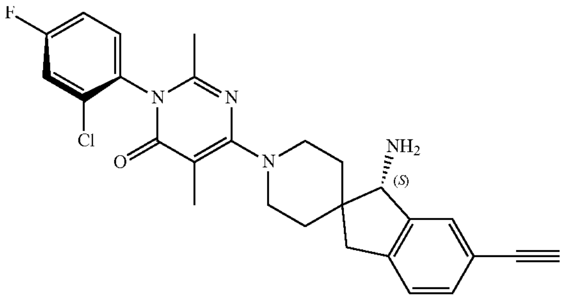 | 106 | 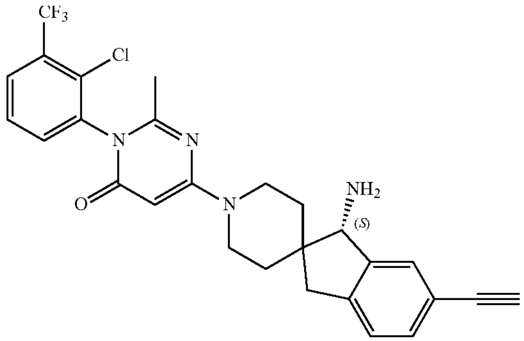 |

-continued
| No. | Structural formula | No. | Structural formula |
|---|---|---|---|
| 107 | 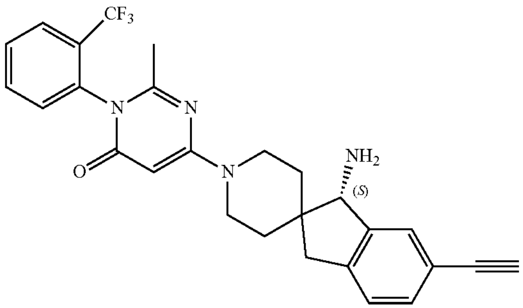 | 112 | 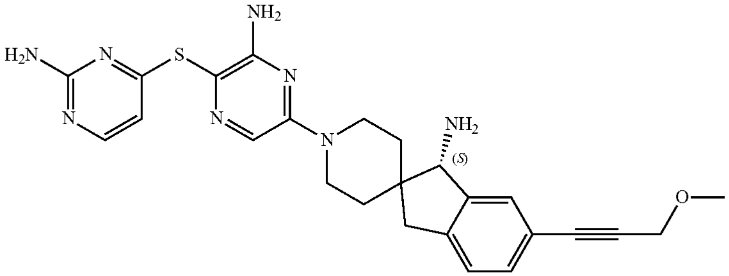 |
| 108 and 109 | 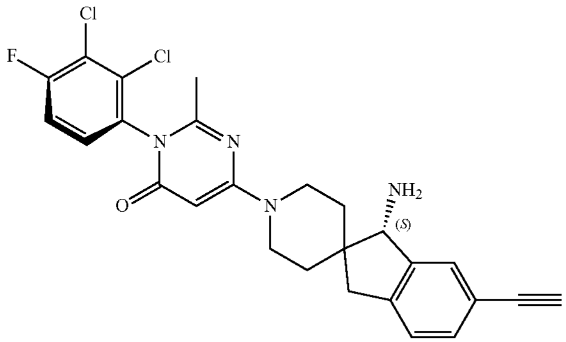 + 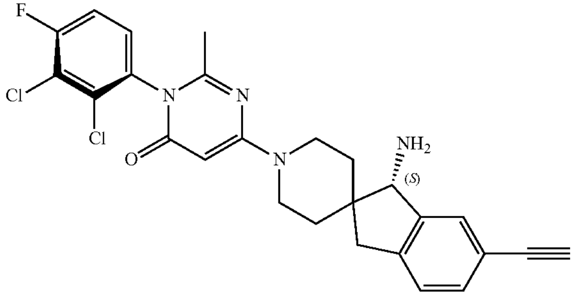 | 110 and 111 | 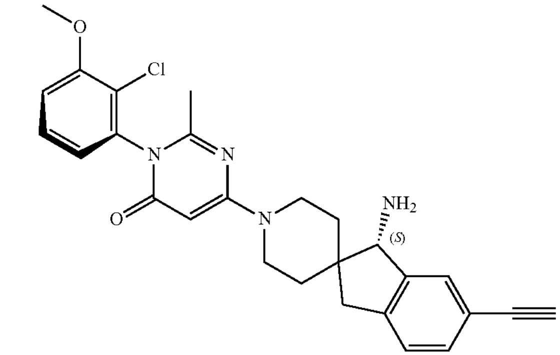 + 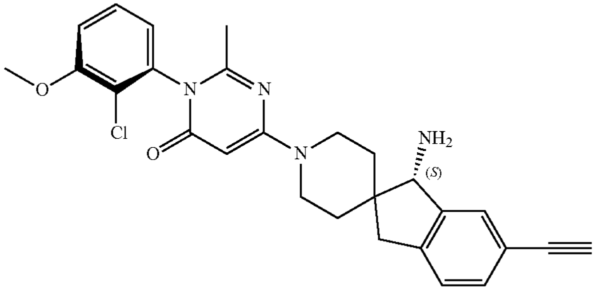 |

-continued
| No. | Structural formula | No. | Structural formula |
|---|---|---|---|
| 113 and 114 | 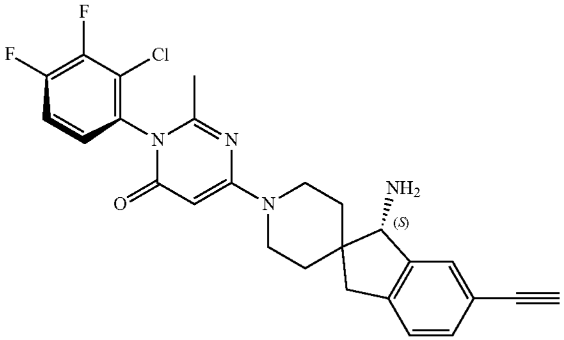 + 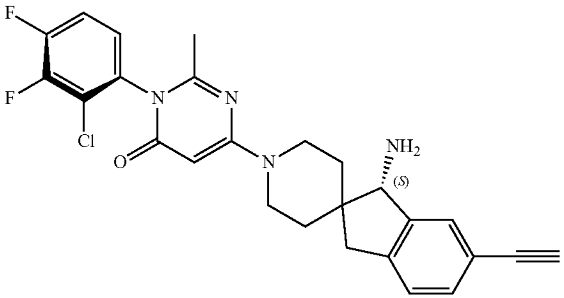 | 115 | 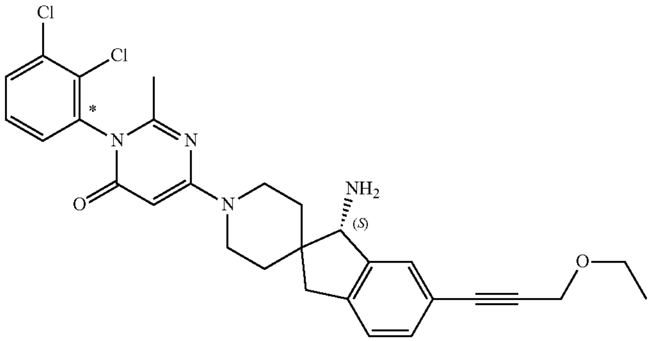 |
| | | 116 | 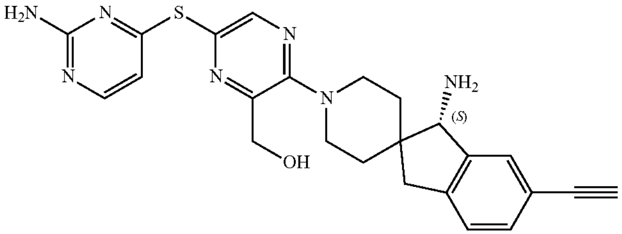 |
| 117 | 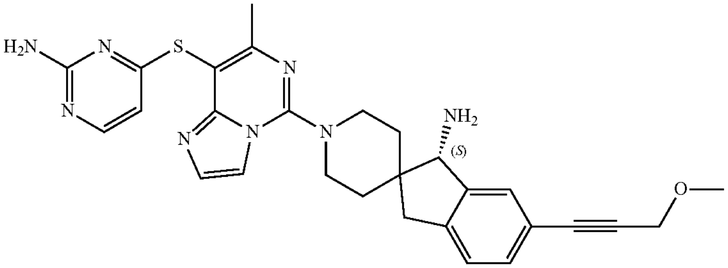 | 120 | 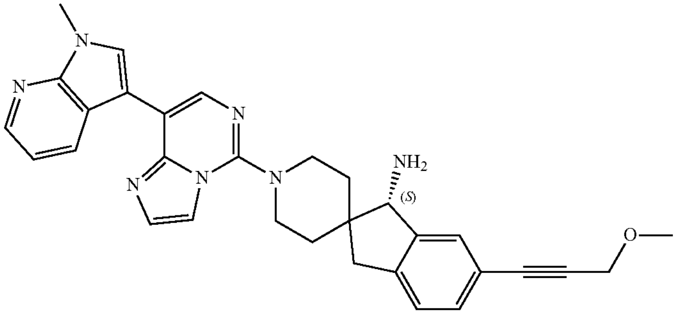 |

-continued
| No. | Structural formula | No. | Structural formula |
|---|---|---|---|
| 118 and 119 | 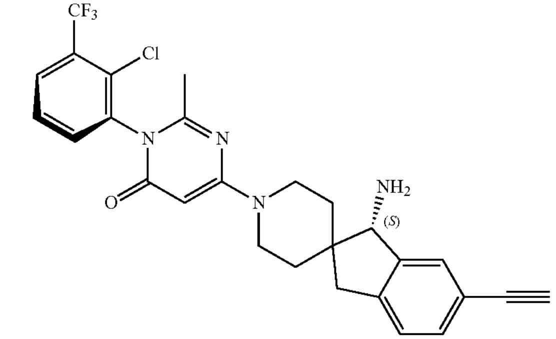 + 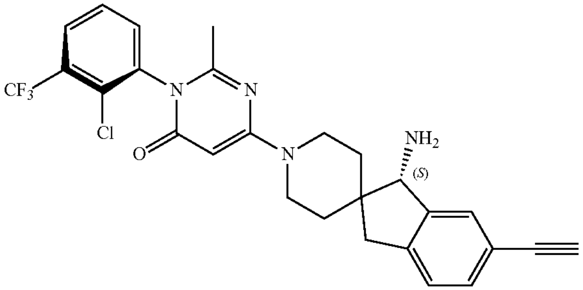 | 121 | 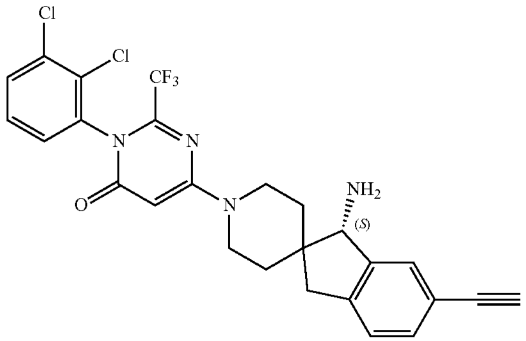 |
| | | 122 | 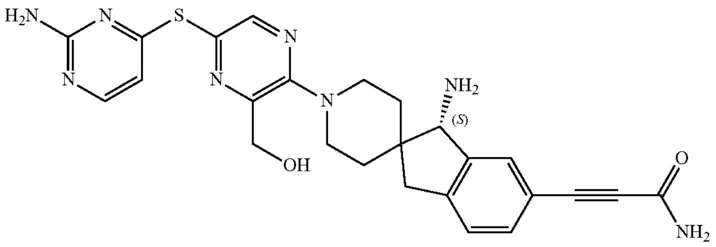 |
| 124 and 125 | 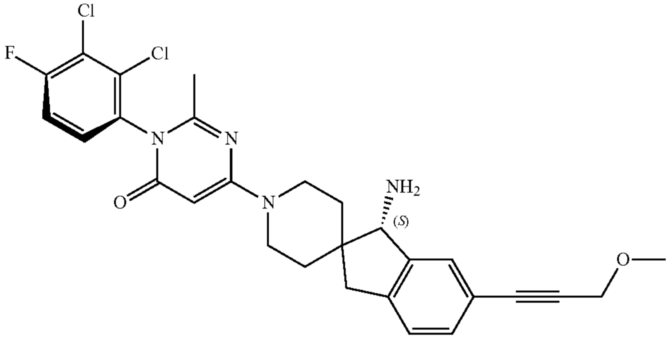 + | 123 | 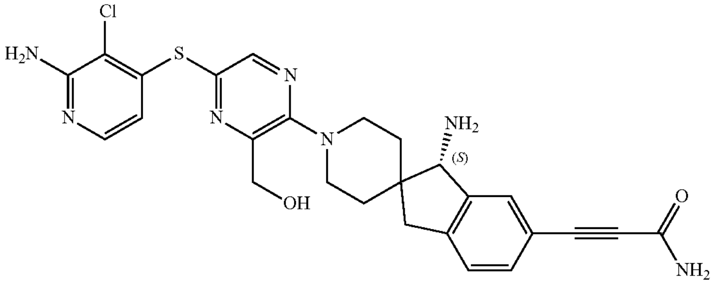 |

-continued
| No. | Structural formula | No. | Structural formula |
|---|---|---|---|
| | 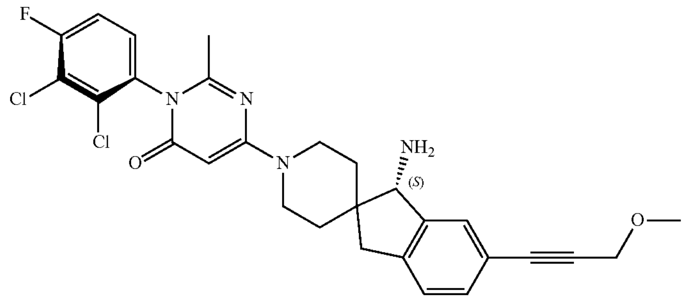 | 126 | 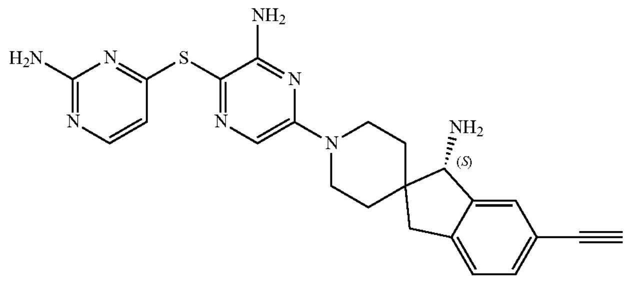 |
| 127 | 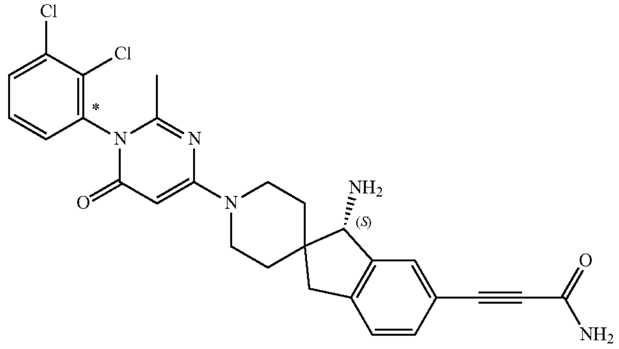 | 128 | 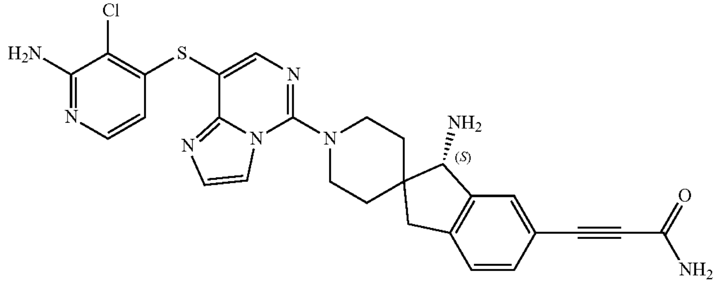 |
| 129 | 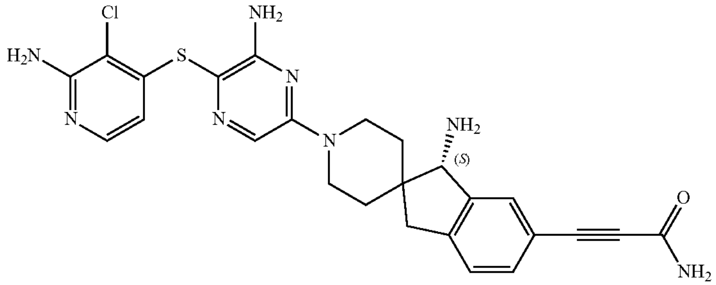 | 130 | 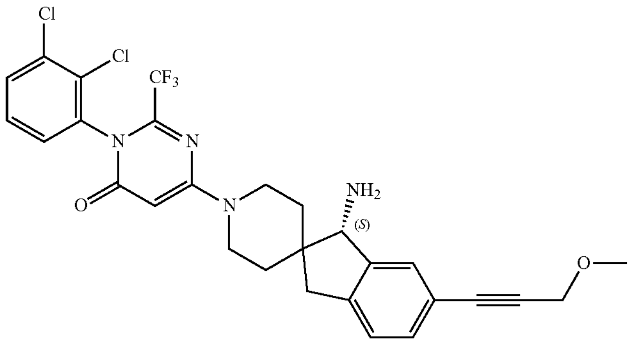 |

-continued
| No. | Structural formula | No. | Structural formula |
|---|---|---|---|
| 131 | 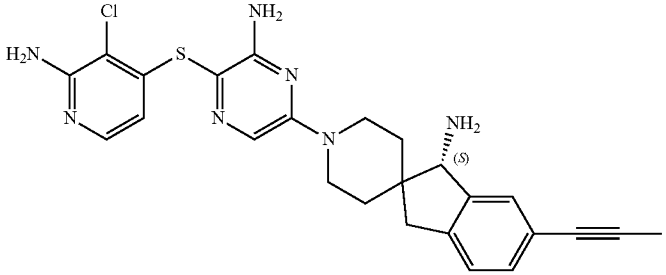 | 132 | 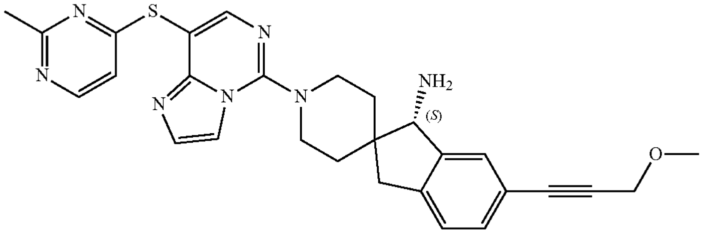 |
| 133 | 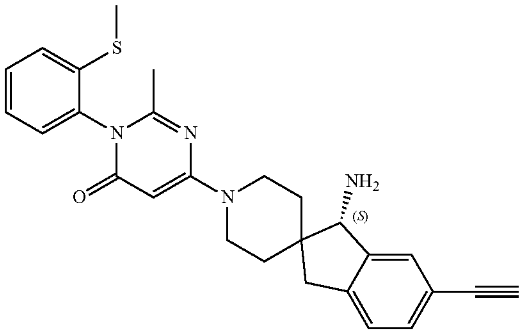 | 134 | 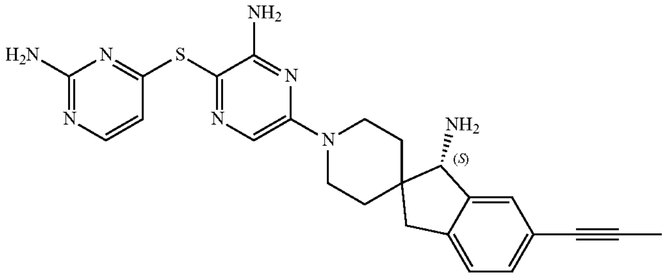 |
| 135 | 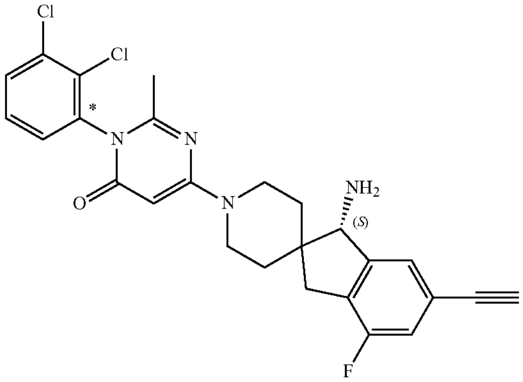 | 136 | 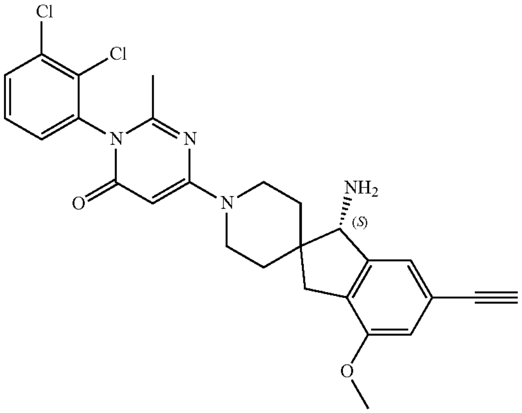 |

-continued
| No. | Structural formula | No. | Structural formula |
|---|---|---|---|
| 137 | 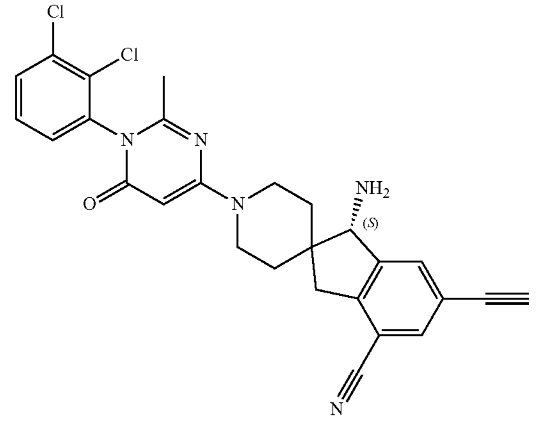 | 138 | 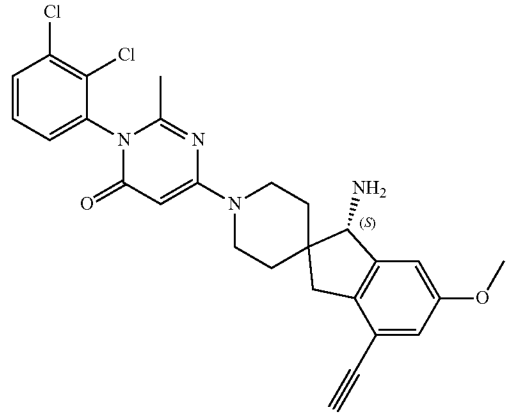 |
| 139 | 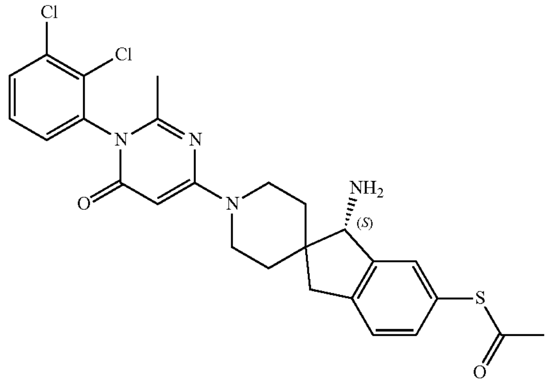 | 140 | 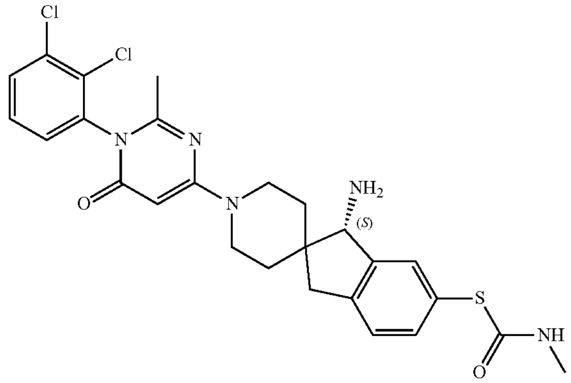 |

-continued
| No. | Structural formula | No. | Structural formula |
|---|---|---|---|
| 141 | 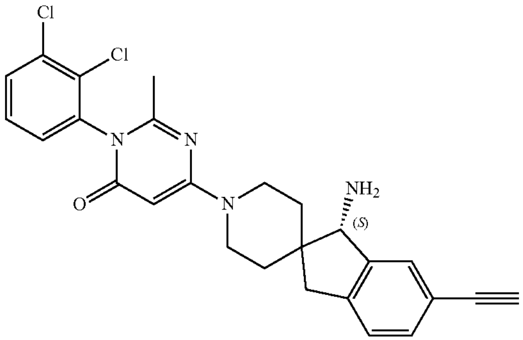 | 142 | 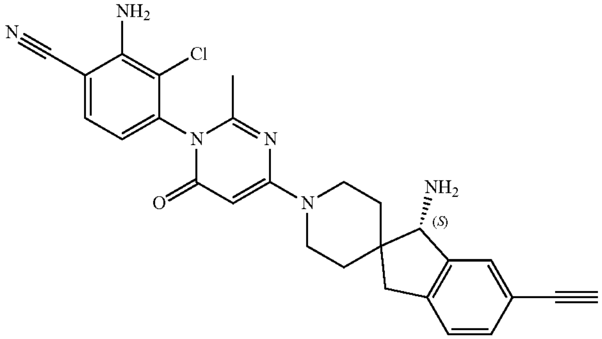 |
| 143 | 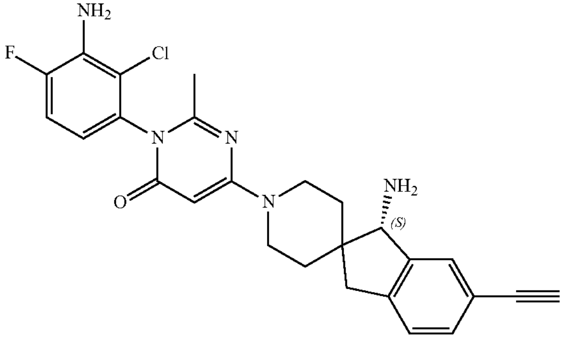 | 144 | 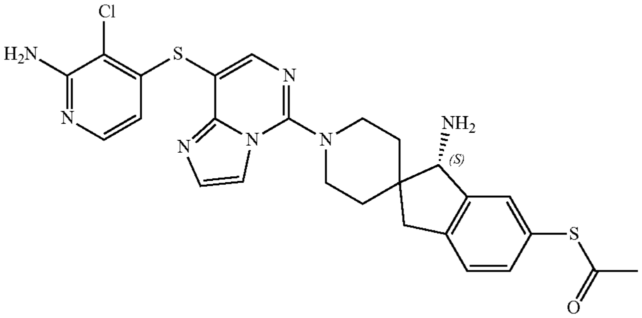 |
| 145 | 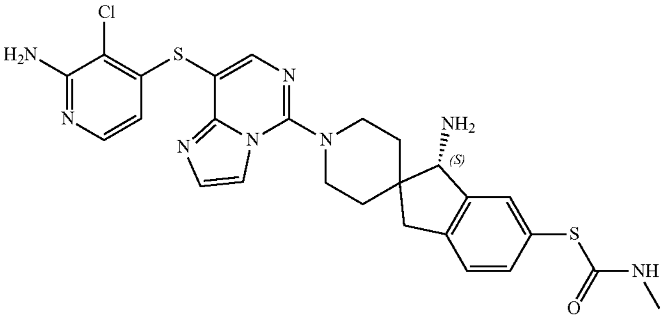 | 146 | 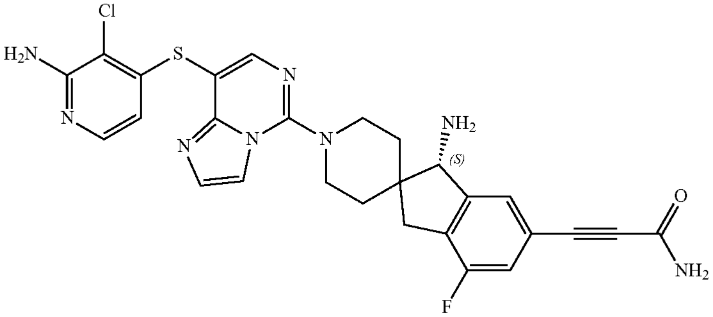 |

-continued
| No. | Structural formula | No. | Structural formula |
|---|---|---|---|
| 147 | 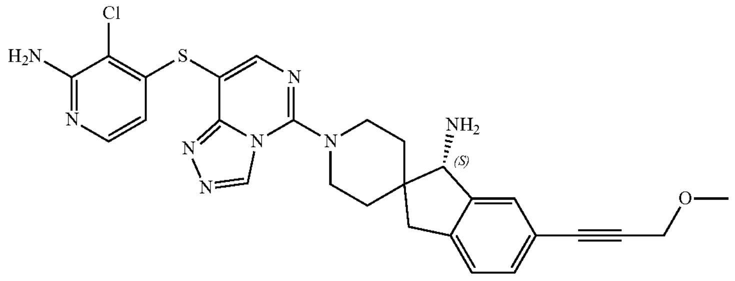 | 148 | 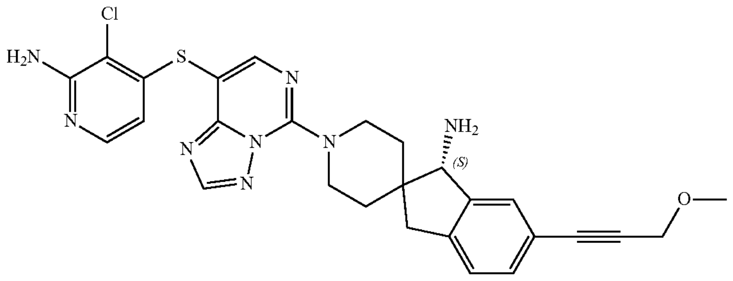 |
| 149 | 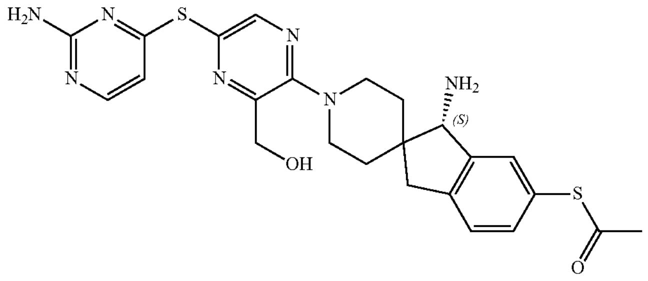 | 150 | 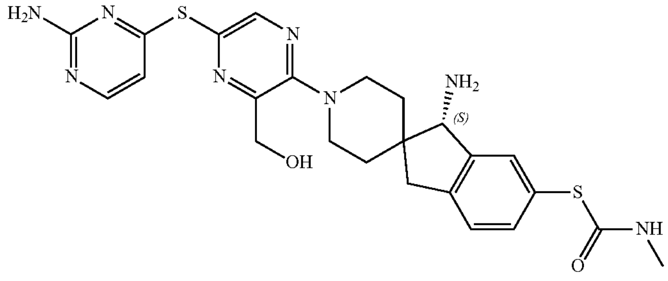 |
| 151 | 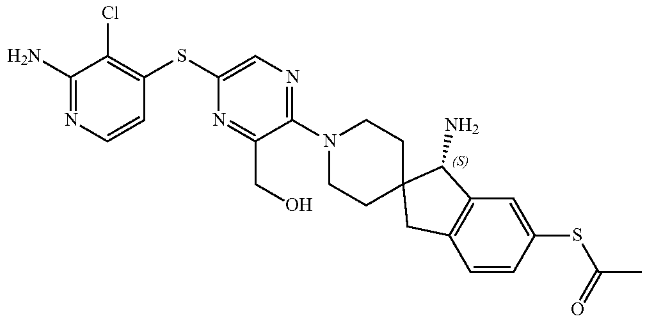 | 152 | 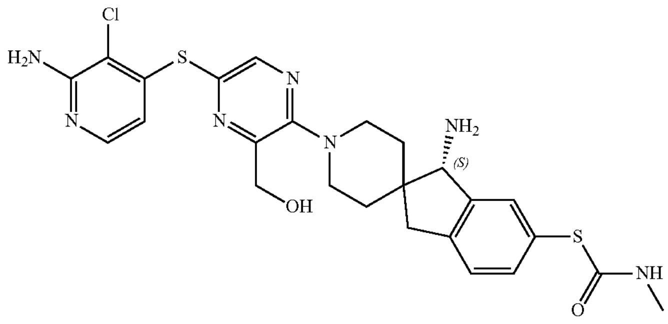 |

-continued
| No. | Structural formula | No. | Structural formula |
| --- | --- | --- | --- |
| 153 | 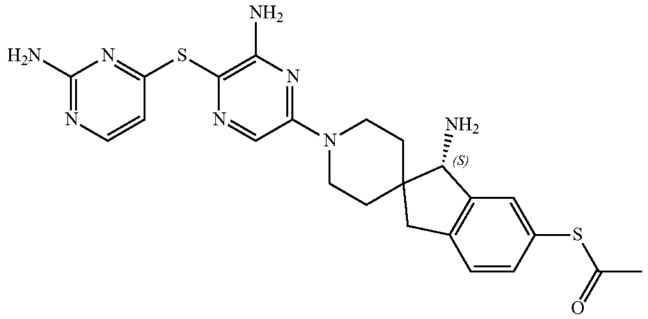 | 154 | 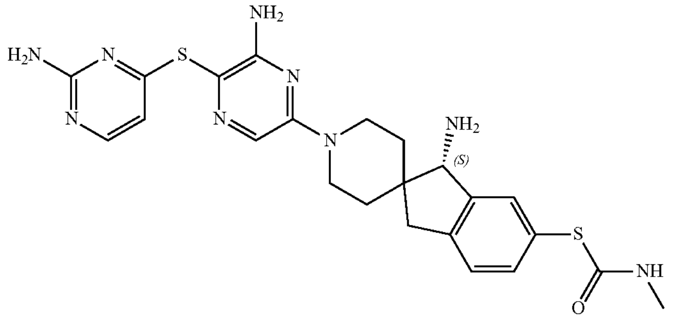 |
| 155 | 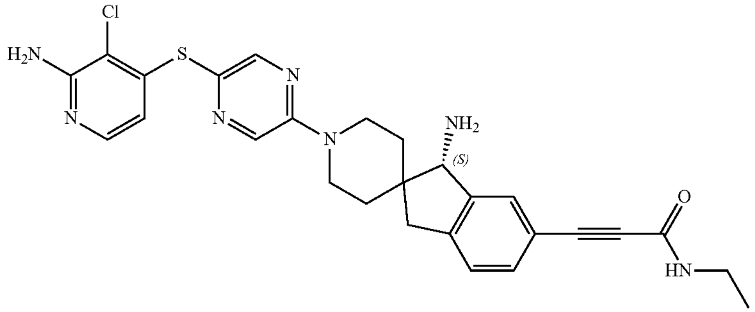 | 156 | 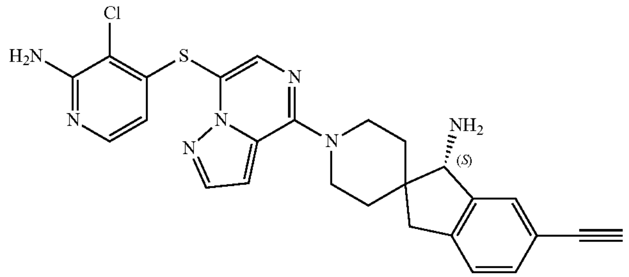 |
| 157 | 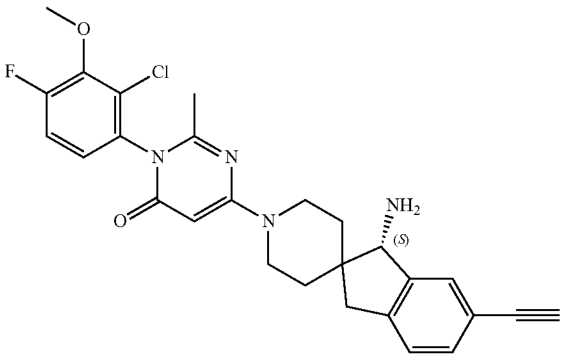 | 158 | 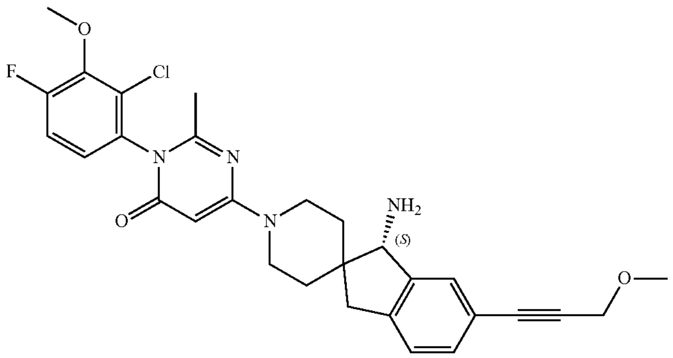 |

-continued
| No. | Structural formula | No. | Structural formula |
|---|---|---|---|
| 159 | 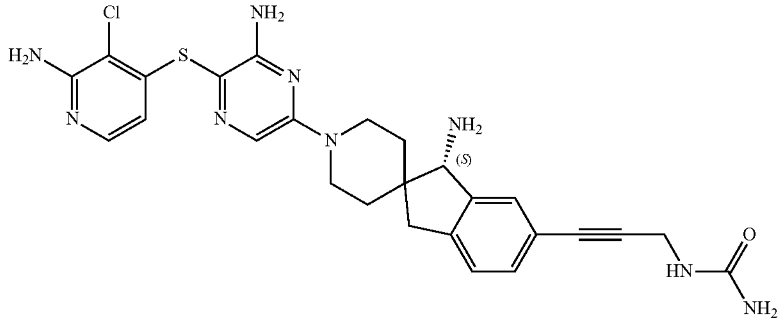 | 160 | 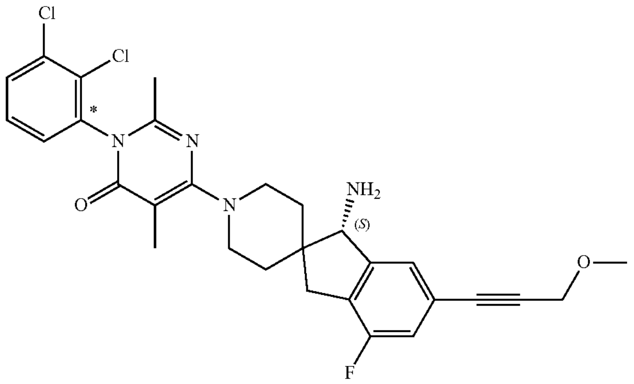 |
| 161 and 162 | 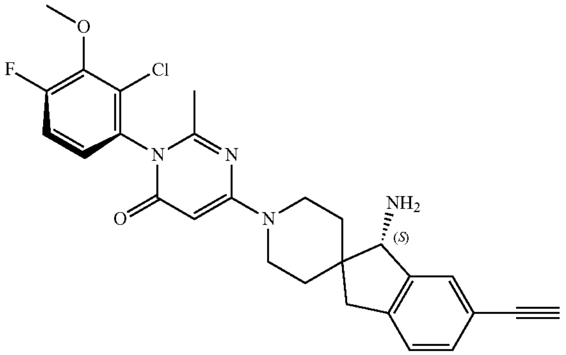 + | 163 and 164 | 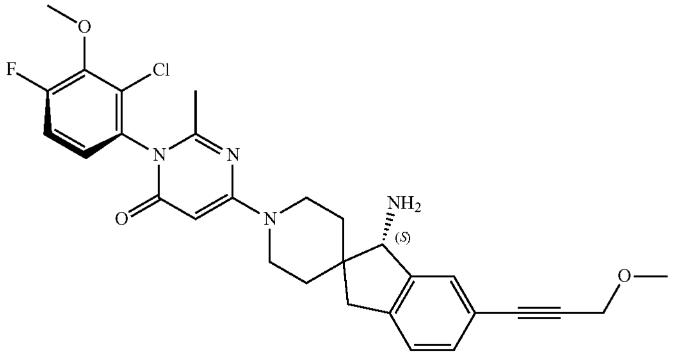 + |

-continued
| No. | Structural formula | No. | Structural formula |
|---|---|---|---|
| | 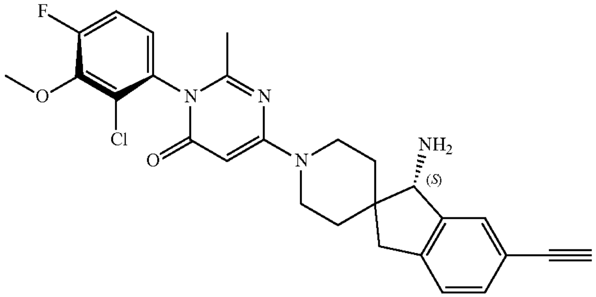 | | 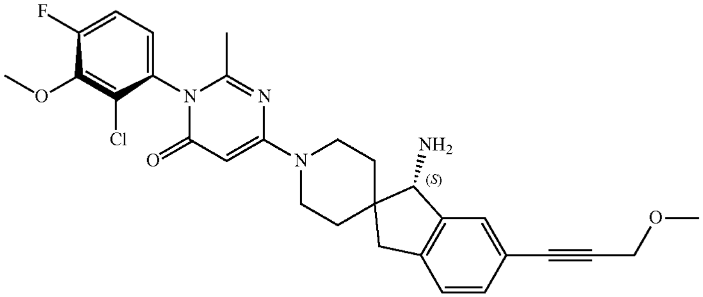 |
| 165 | 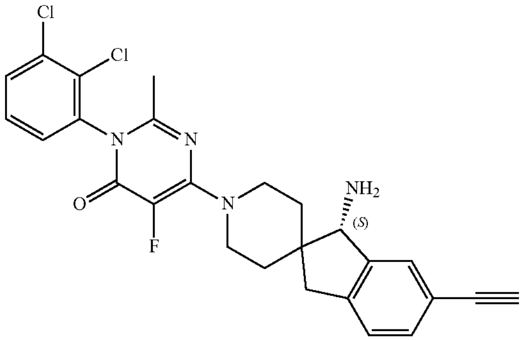 | 166 | 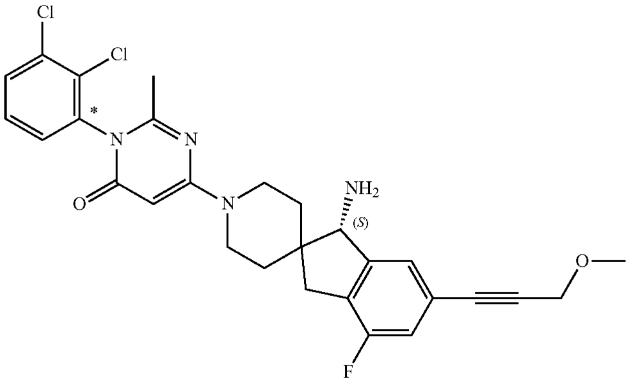 |
| 167 | 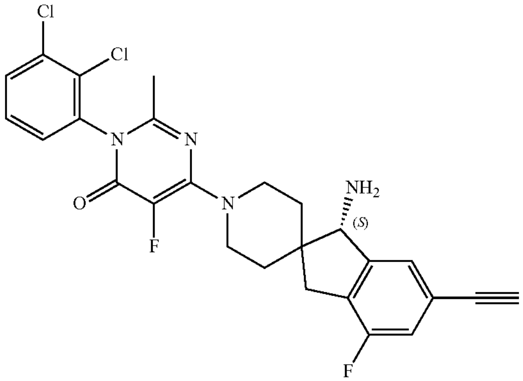 | 168 | 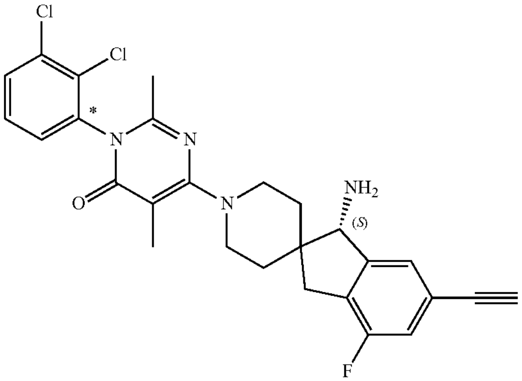 |

-continued
| No. | Structural formula | No. | Structural formula |
| --- | --- | --- | --- |
| 169 | 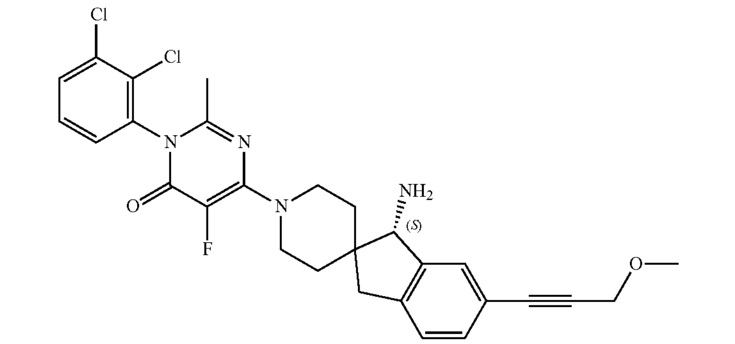 | 170 | 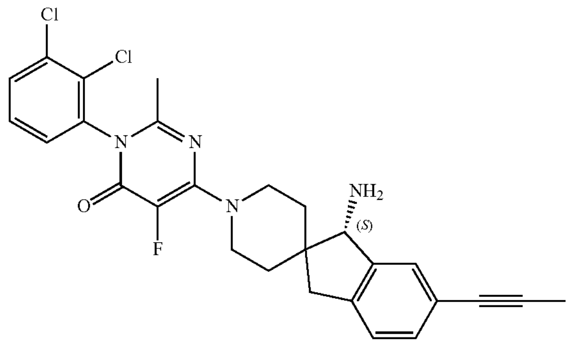 |
| 171 | 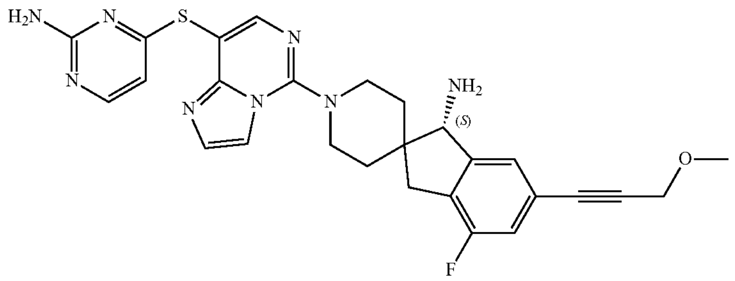 | 172 | 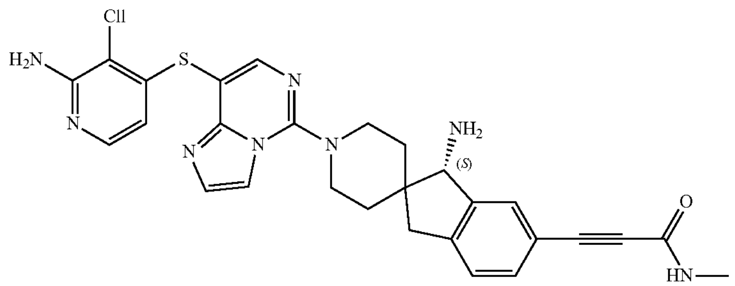 |
| 173 | 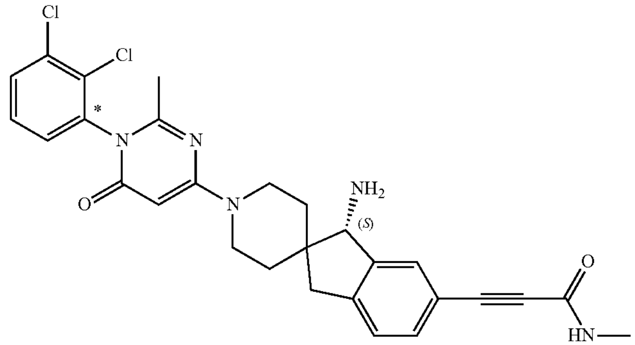 | 174 | 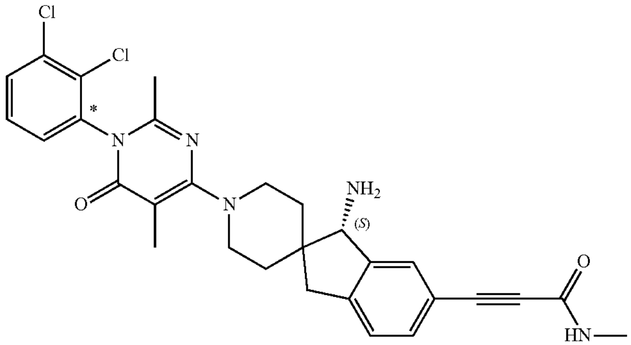 |

-continued
| No. | Structural formula | No. | Structural formula |
| --- | --- | --- | --- |
| 175 | 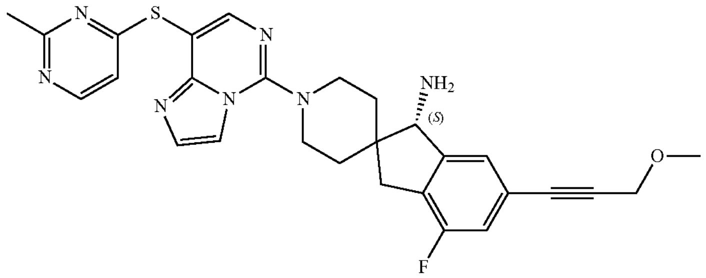 | 176 | 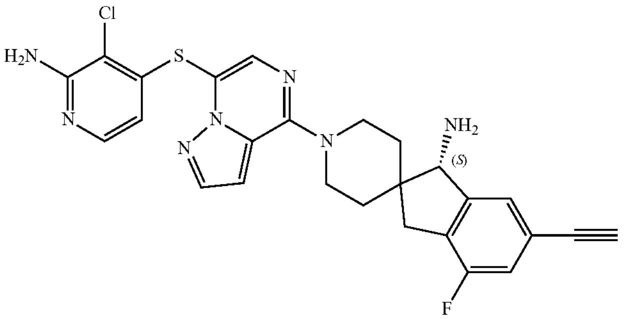 |
| 177 | 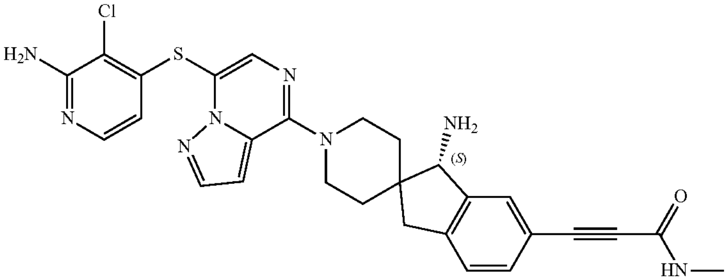 | 178 | 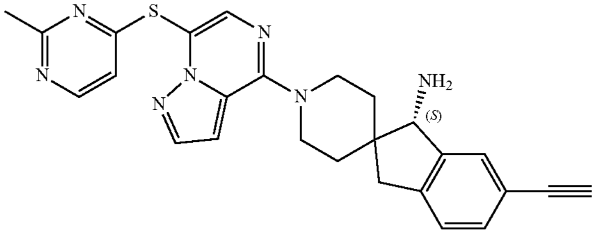 |
| 179 | 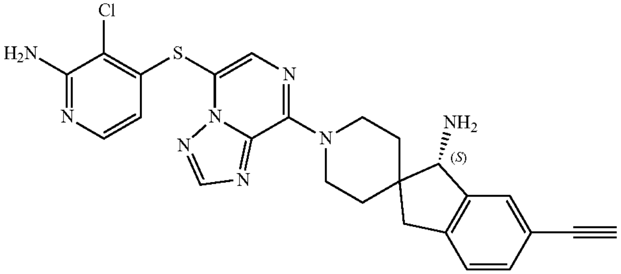 | 180 | 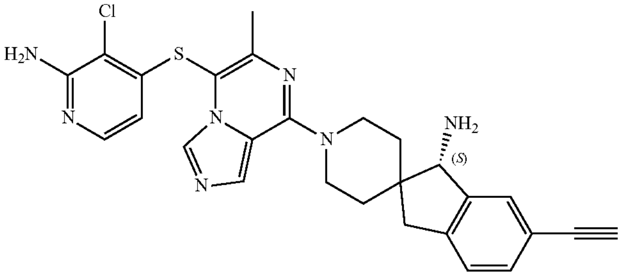 |

-continued
| No. | Structural formula | No. | Structural formula |
|---|---|---|---|
| 181 and 182 | 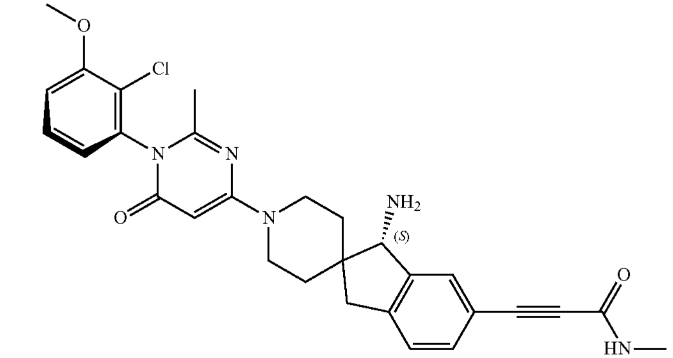 + 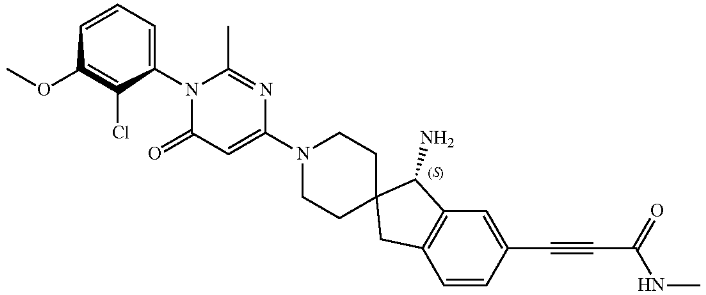 | 183 | 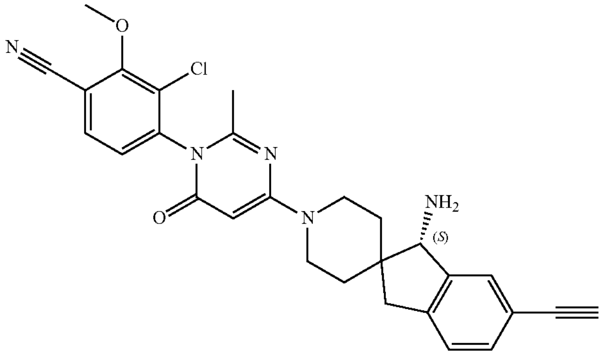 |
| | | 184 | 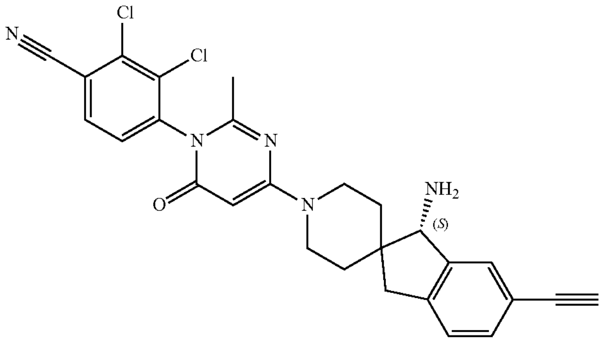 |

-continued
| No. | Structural formula | No. | Structural formula |
|---|---|---|---|
| 185 | 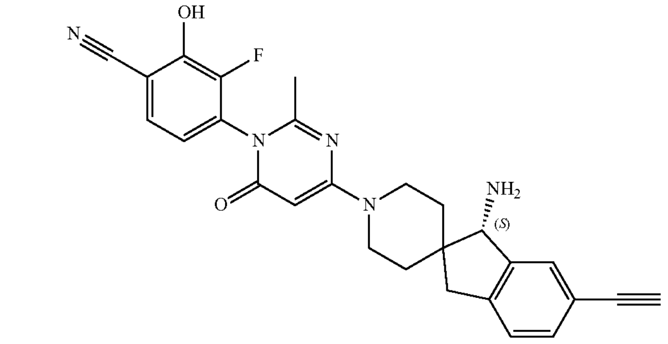 | 186 | 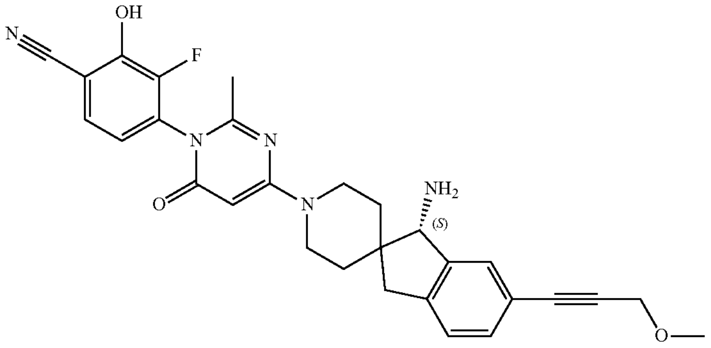 |
| 187 | 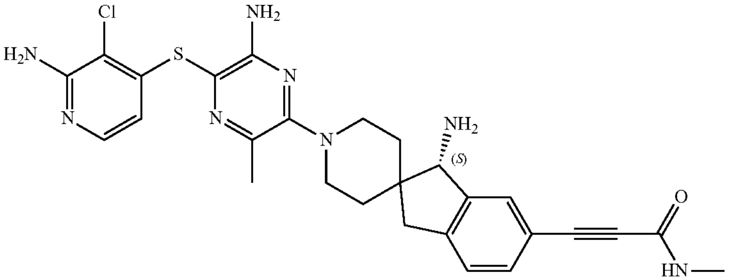 | 188 | 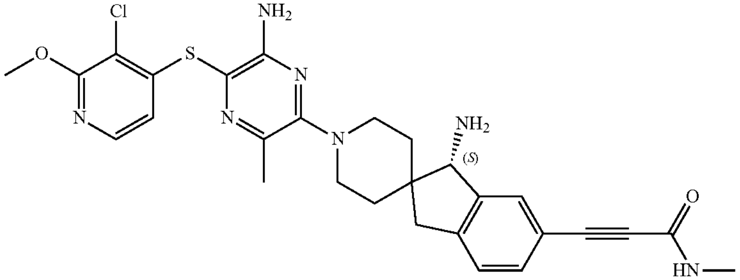 |
| 189 | 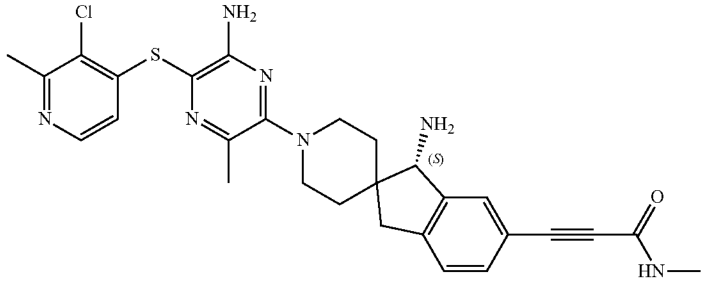 | 194 | 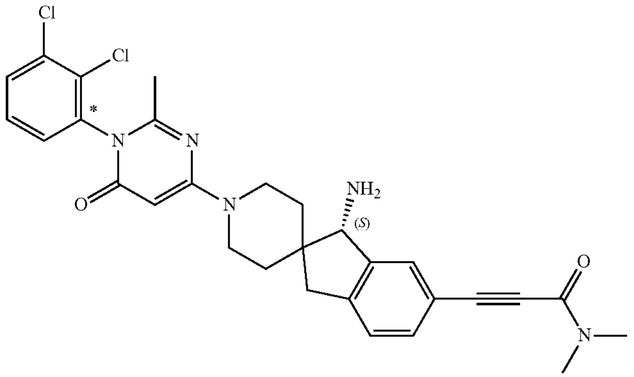 |

-continued
| No. | Structural formula | No. | Structural formula |
|---|---|---|---|
| 190 and 191 | 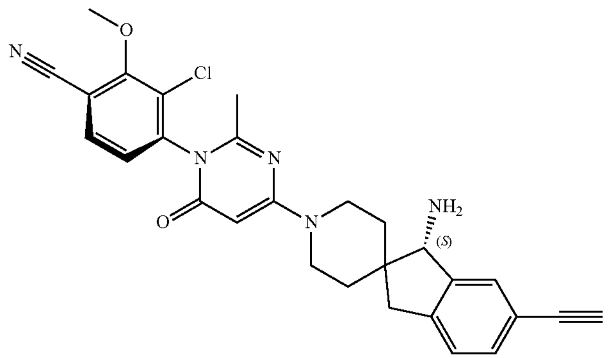 + 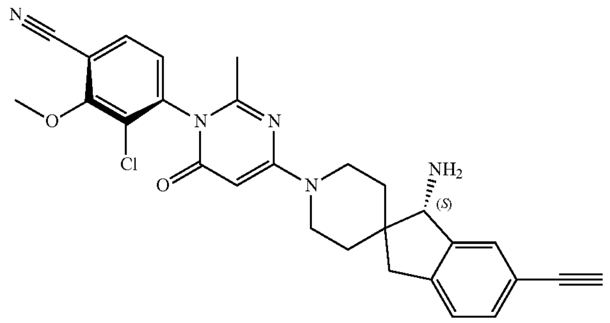 | 192 and 193 | 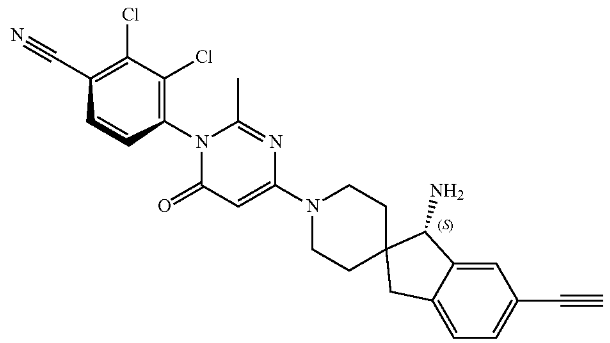 + 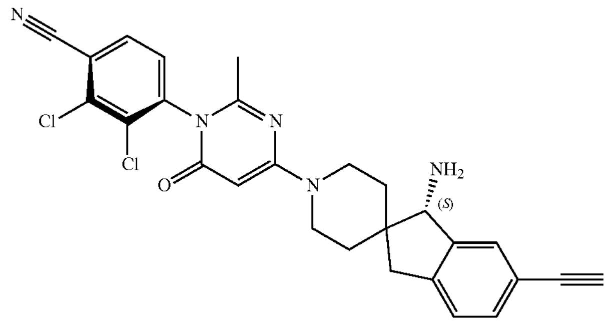 |

-continued
| No. | Structural formula | No. | Structural formula |
|---|---|---|---|
| 195 | 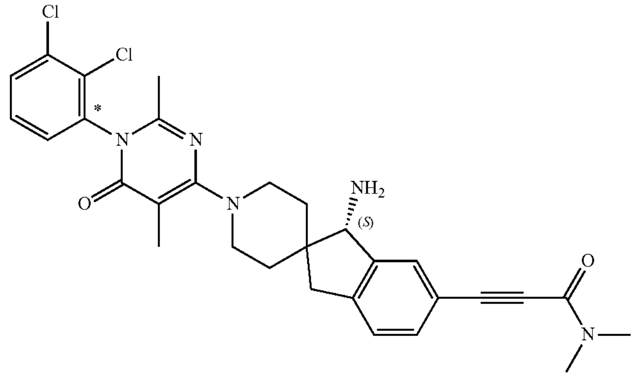 | 196 | 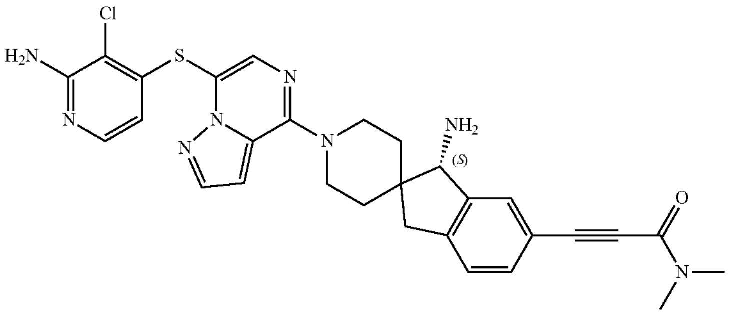 |
| 197 | 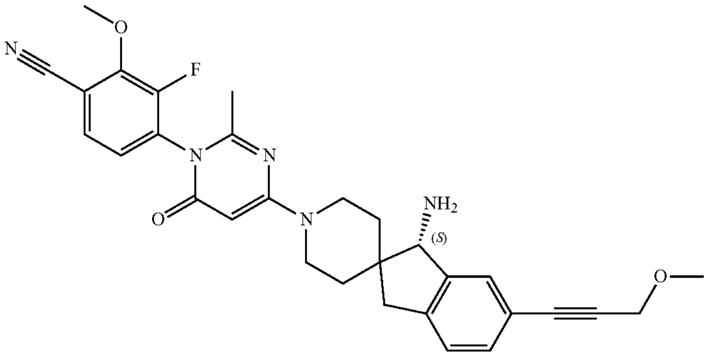 | 198 | 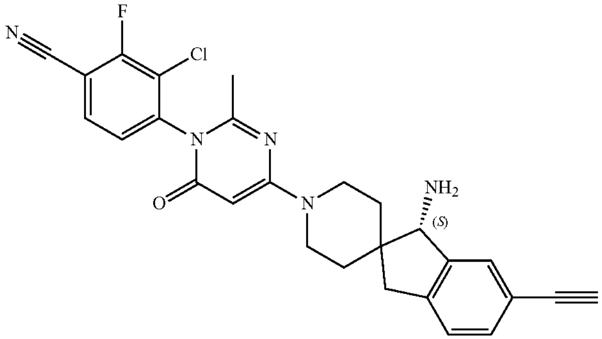 |

-continued
| No. | Structural formula | No. | Structural formula |
|---|---|---|---|
| 199 | 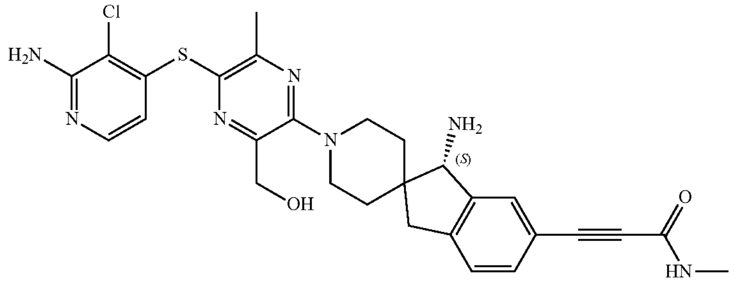 | 200 and 201 | 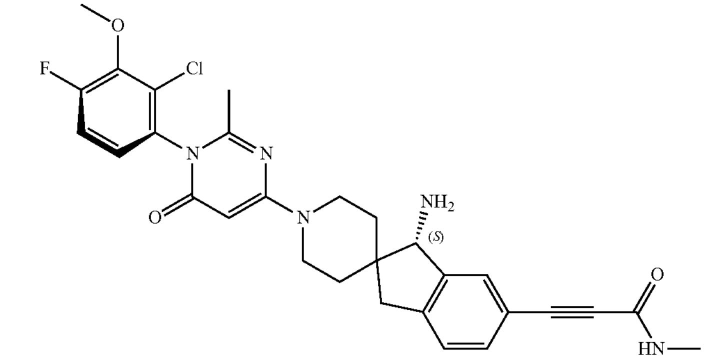 + 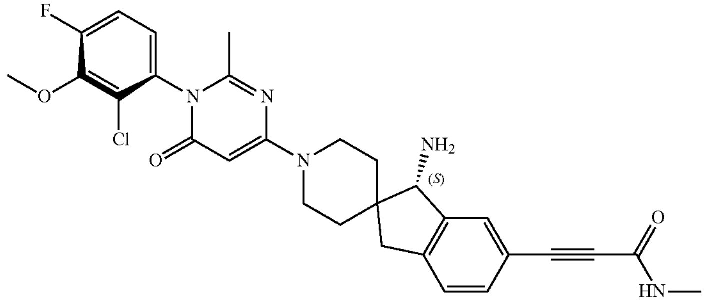 |
| 202 | 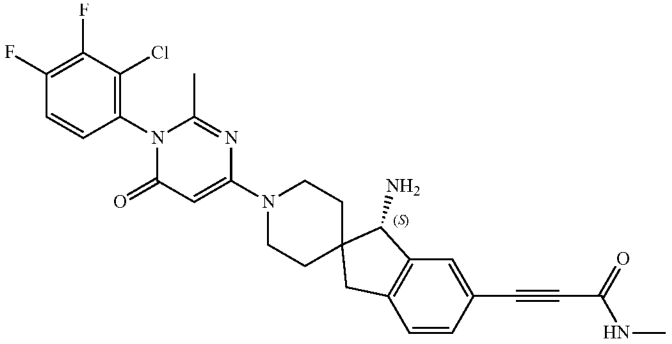 | | |
| 203 | 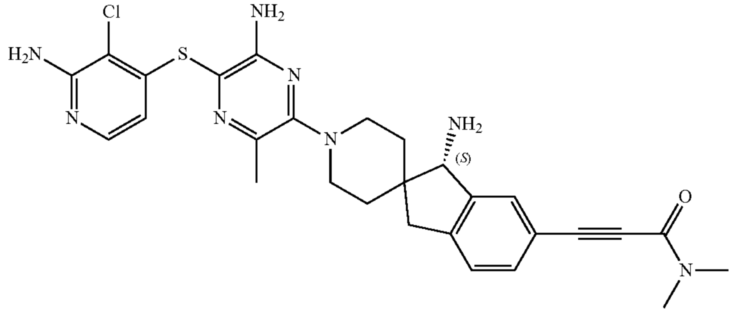 | 204 | 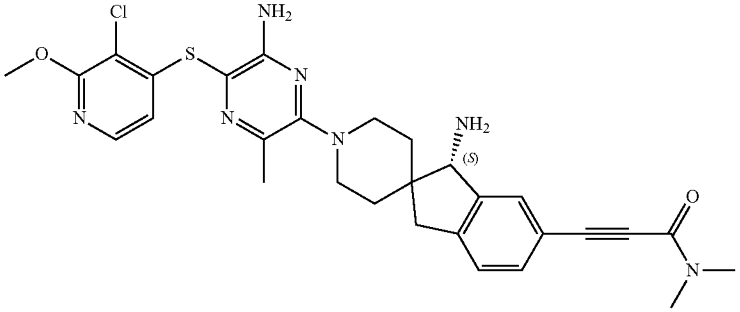 |

-continued
| No. | Structural formula | No. | Structural formula |
|---|---|---|---|
| 205 | 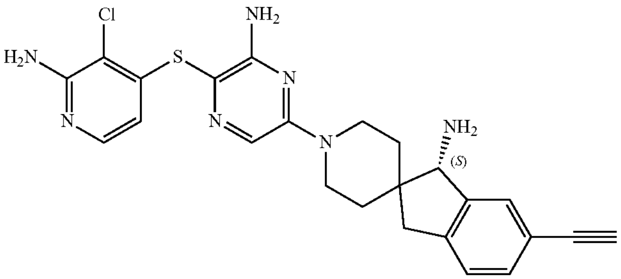 | 206 | 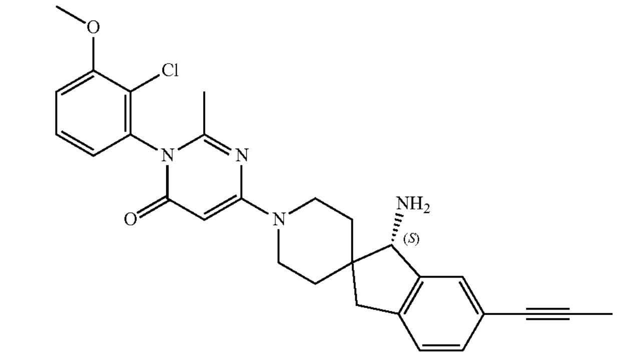 |
| 207 and 208 | 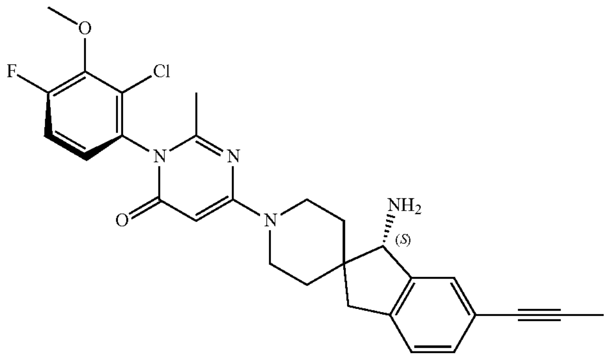 + | 209 and 210 | 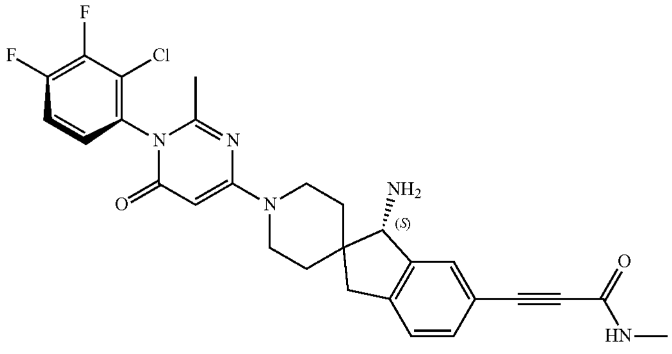 + |

-continued
| No. | Structural formula | No. | Structural formula |
|---|---|---|---|
| | 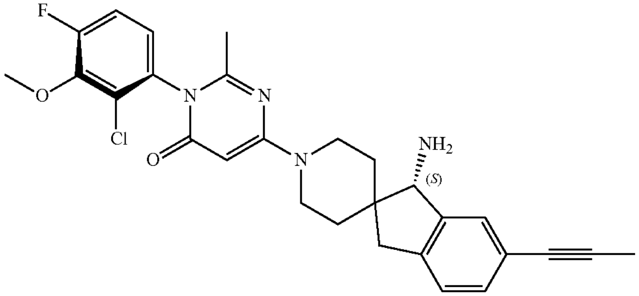 | | 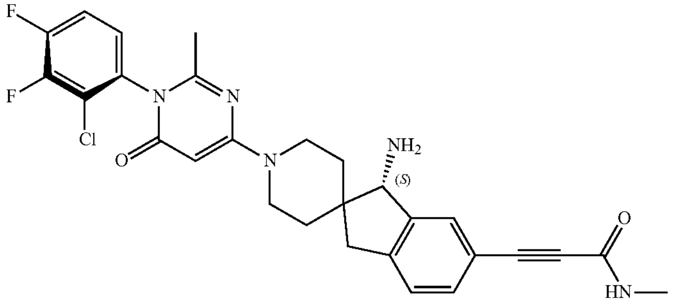 |
| 211 | 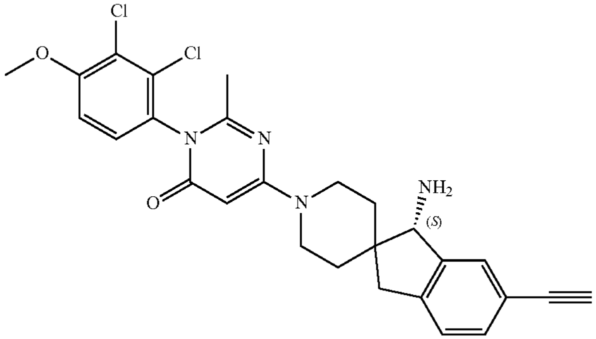 | 212 | 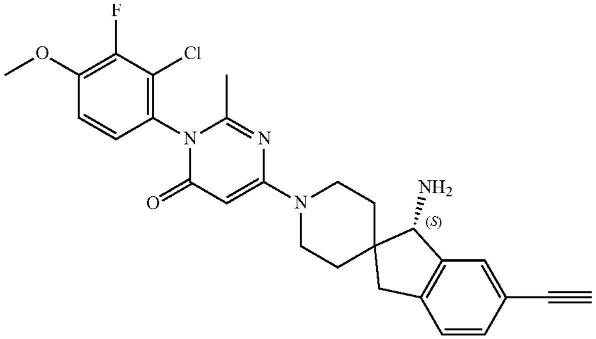 |
| 213 | 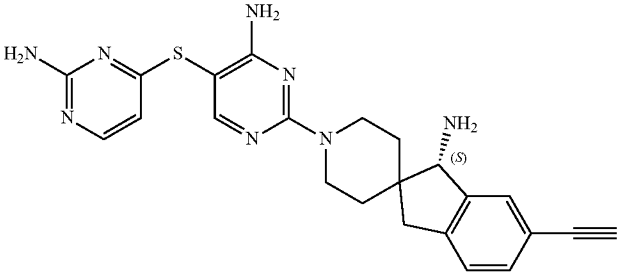 | 214 | 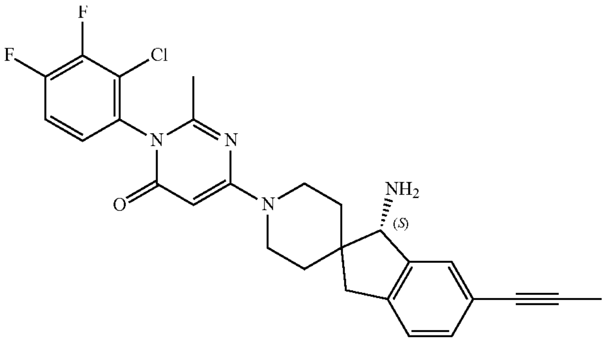 |

-continued
| No. | Structural formula | No. | Structural formula |
|---|---|---|---|
| 215 | 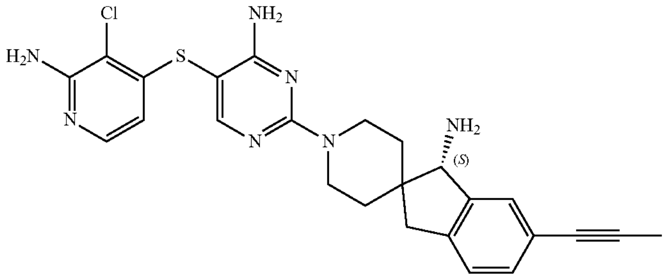 | 216 | 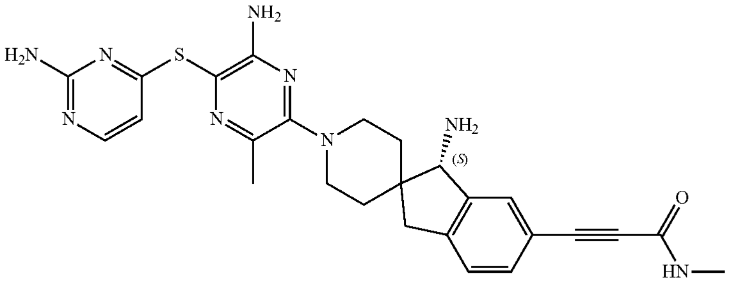 |
| 217 and 218 | 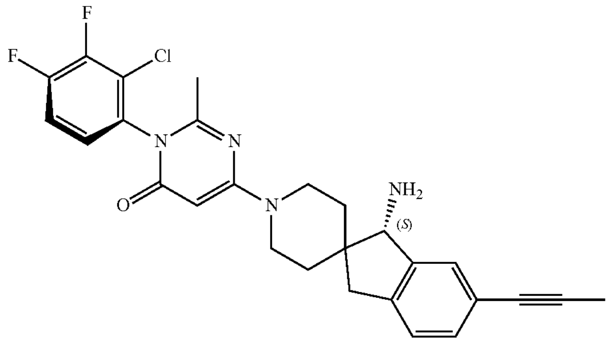 + 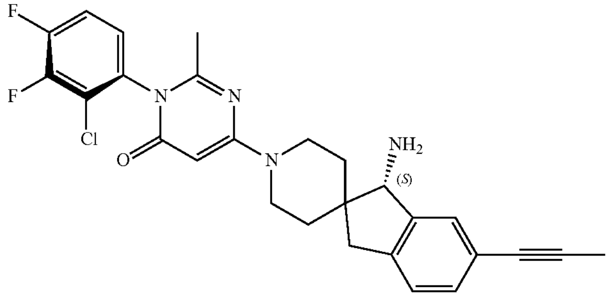 | 220 and 221 | 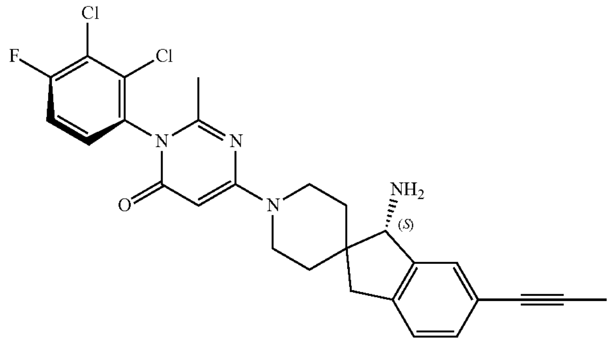 + 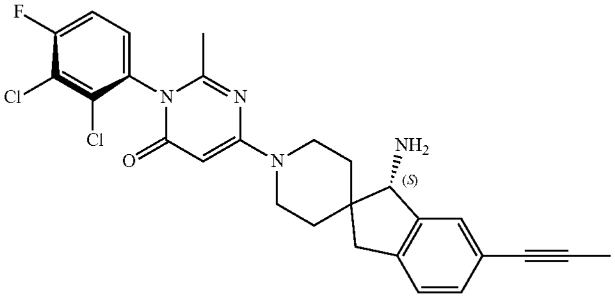 |

-continued
| No. | Structural formula | No. | Structural formula |
|---|---|---|---|
| 219 | 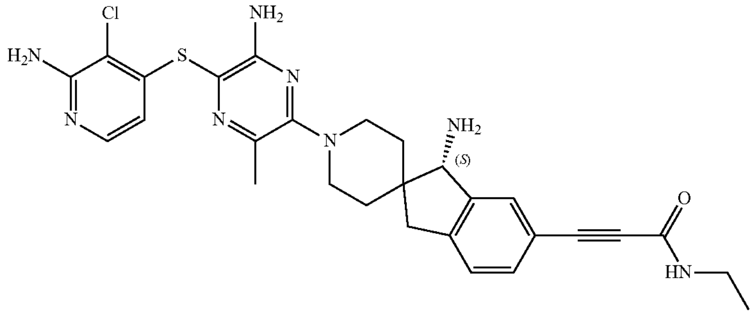 | 222 | 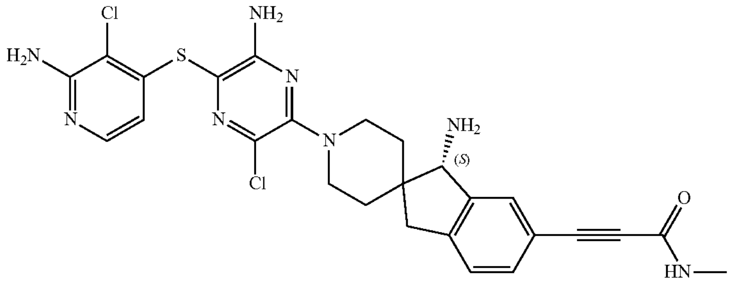 |
| 223 | 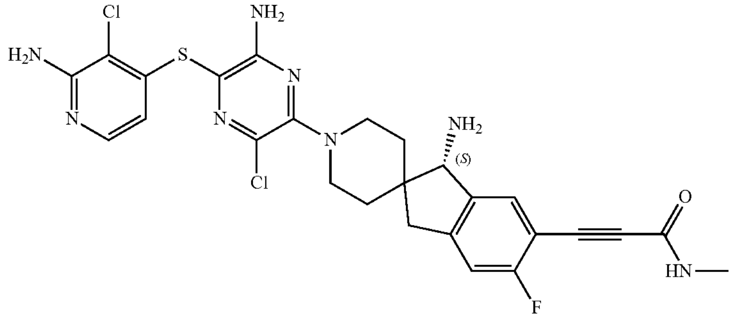 | 224 | 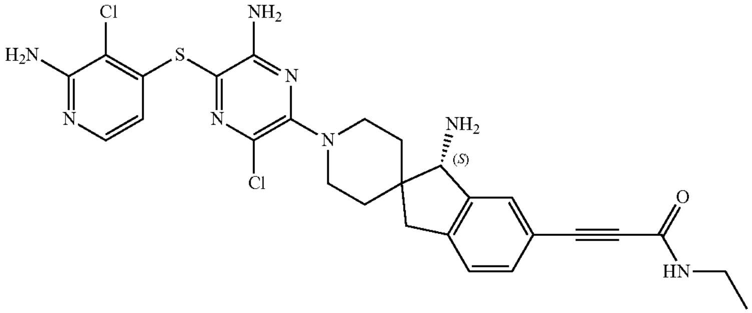 |
| 225 | 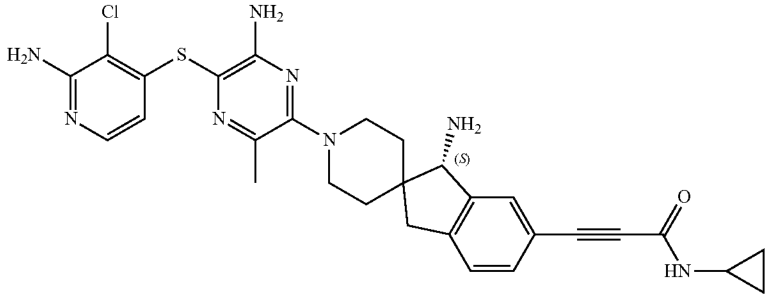 | 226 | 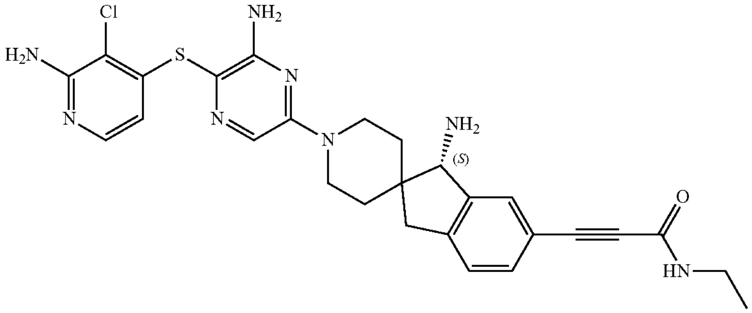 |

-continued
| No. | Structural formula | No. | Structural formula |
|---|---|---|---|
| 227 | 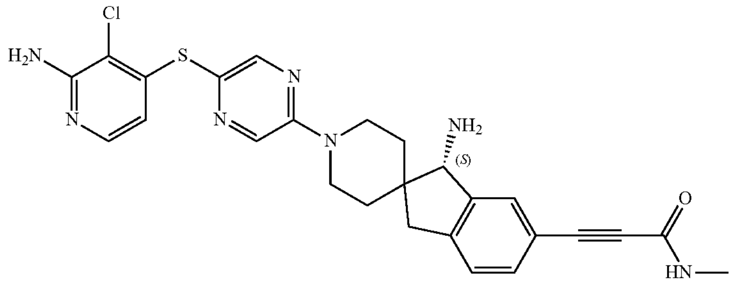 | 228 | 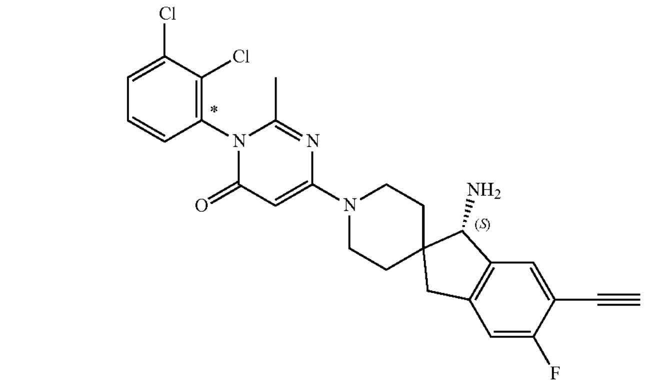 |
| 229 | 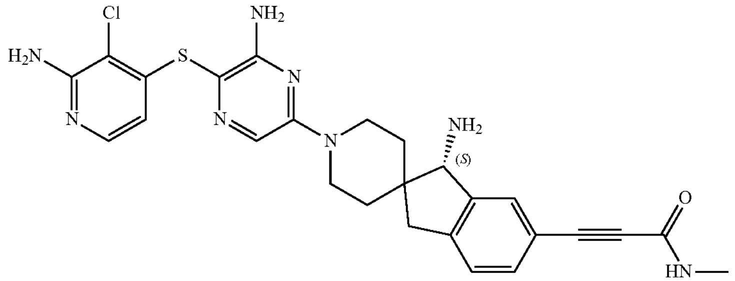 | 230 | 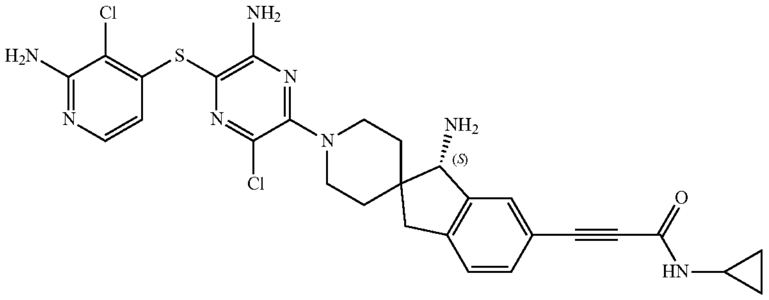 |
| 231 | 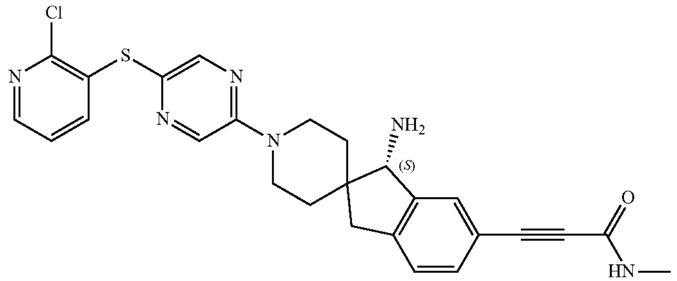 | 232 | 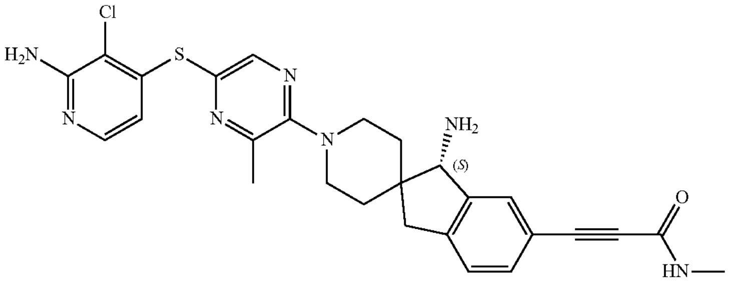 |

-continued
| No. | Structural formula | No. | Structural formula |
|---|---|---|---|
| 233 | 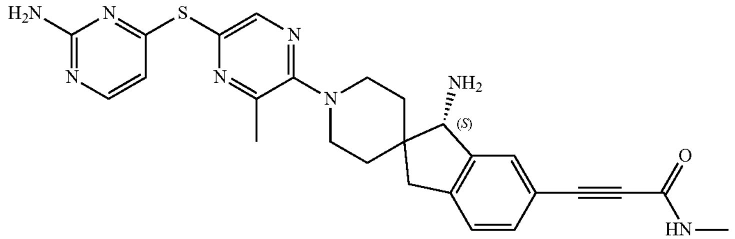 | 234 | 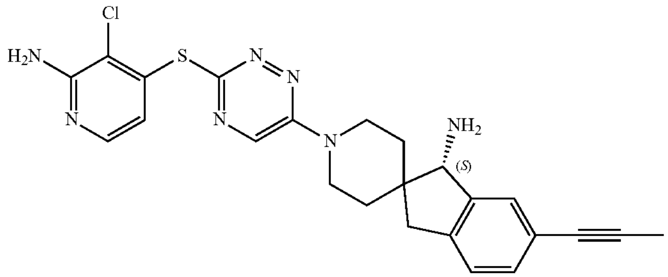 |
| 235 | 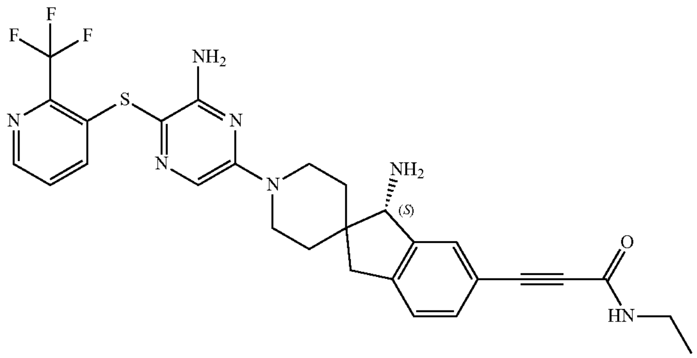 | 236 | 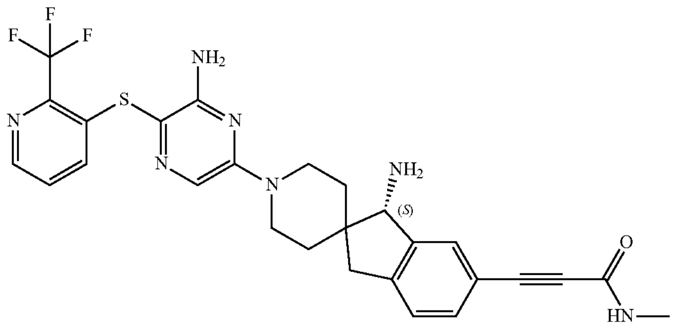 |
| 237 | 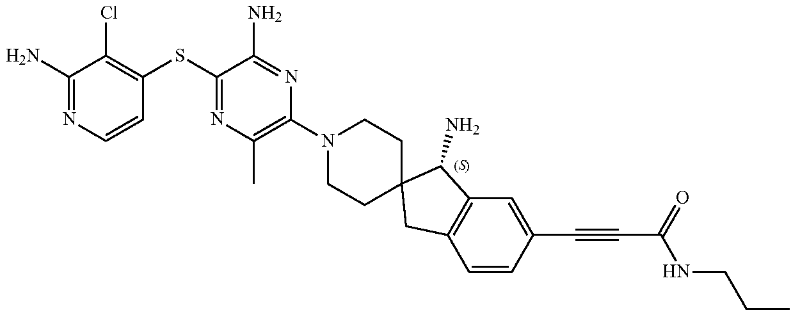 | 238 | 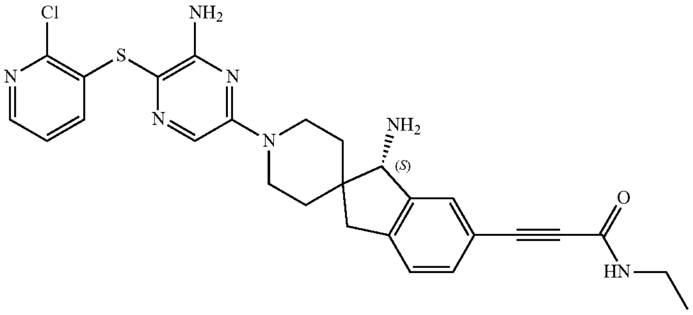 |

-continued
| No. | Structural formula | No. | Structural formula |
|---|---|---|---|
| 239 | 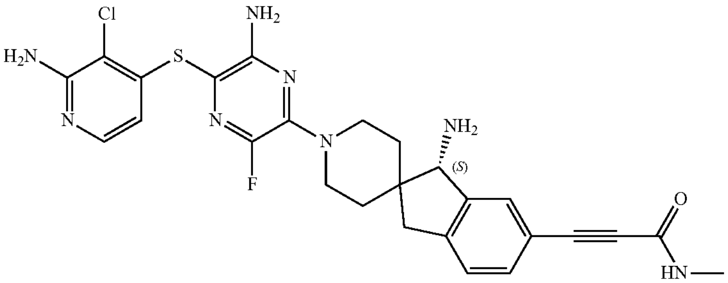 | 240 | 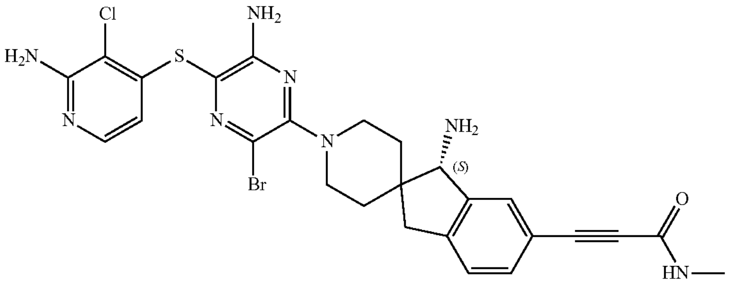 |
| 241 | 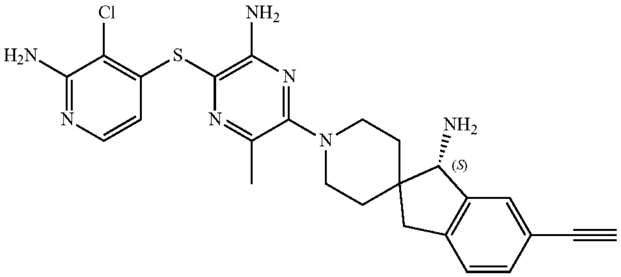 | 242 | 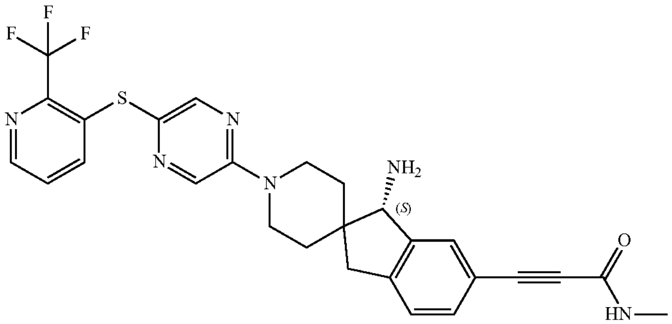 |
| 243 | 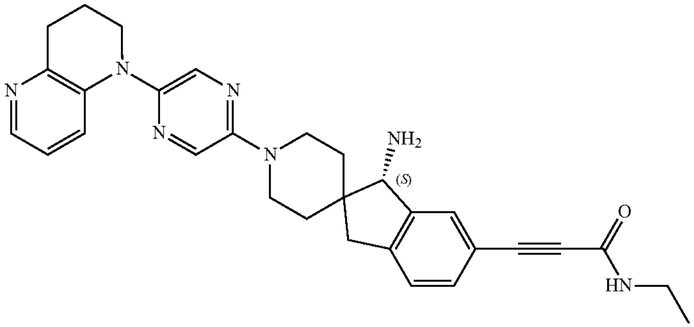 | 244 | 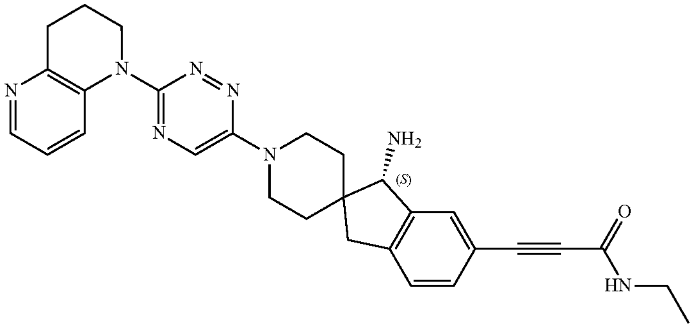 |

-continued
| No. | Structural formula | No. | Structural formula |
| --- | --- | --- | --- |
| 245 | 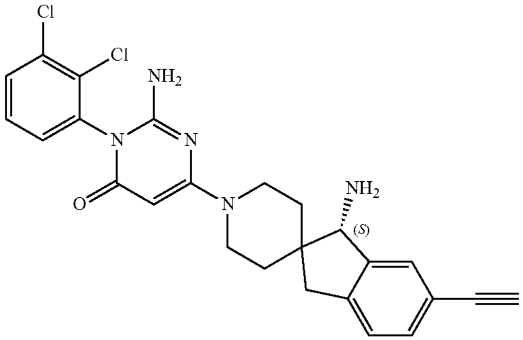 | 246 | 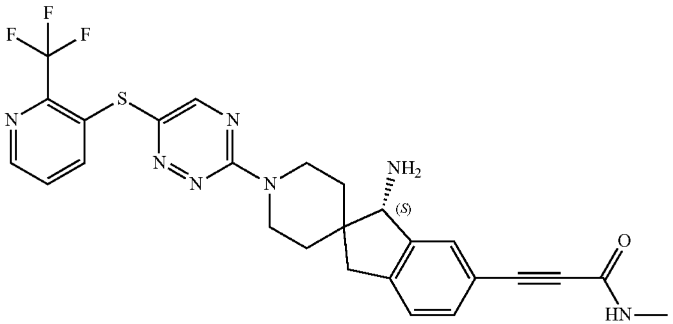 |
| 247 | 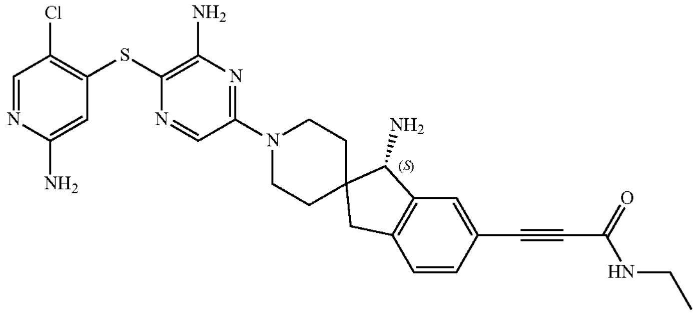 | 248 | 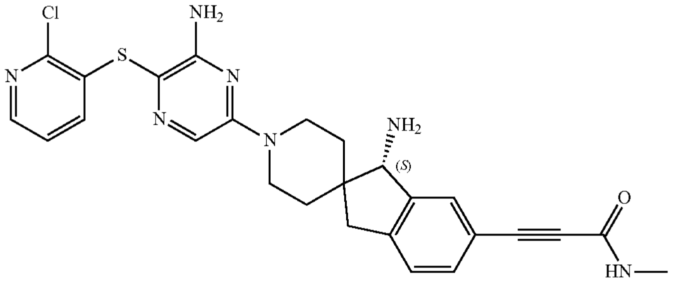 |
| 249 | 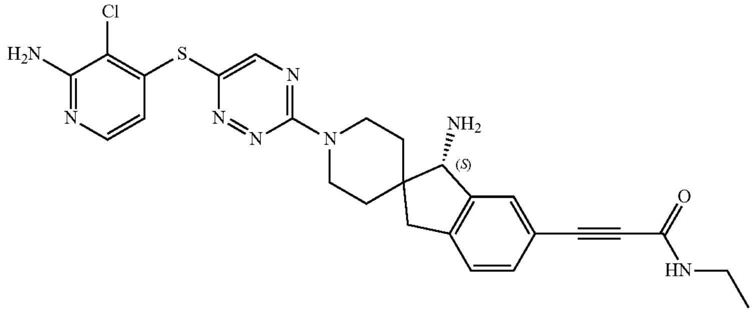 | 250 | 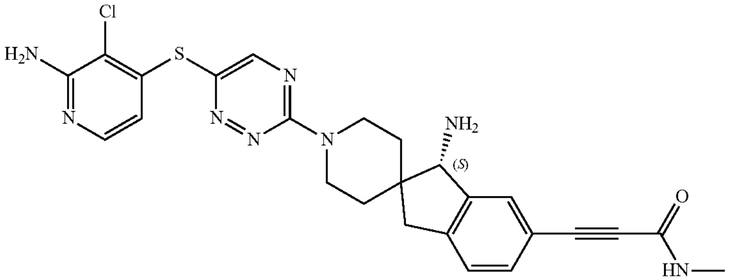 |

-continued
| No. | Structural formula | No. | Structural formula |
| --- | --- | --- | --- |
| 251 | 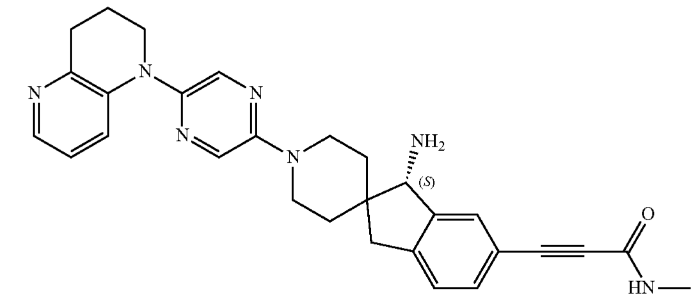 | 252 | 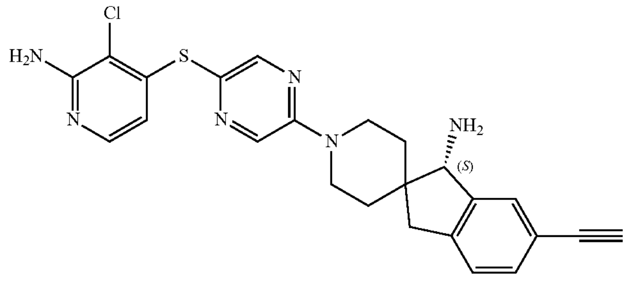 |
| 253 | 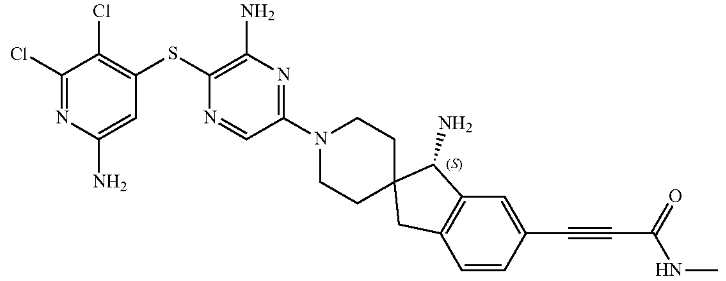 | 254 | 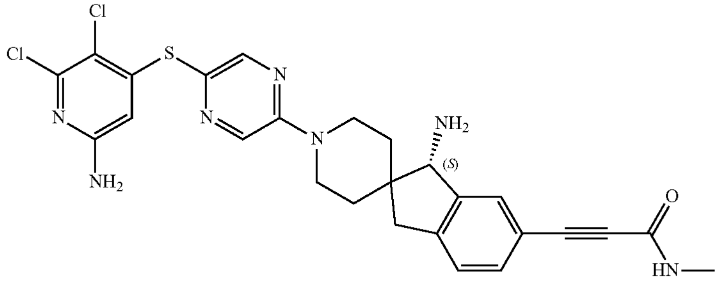 |
| 255 | 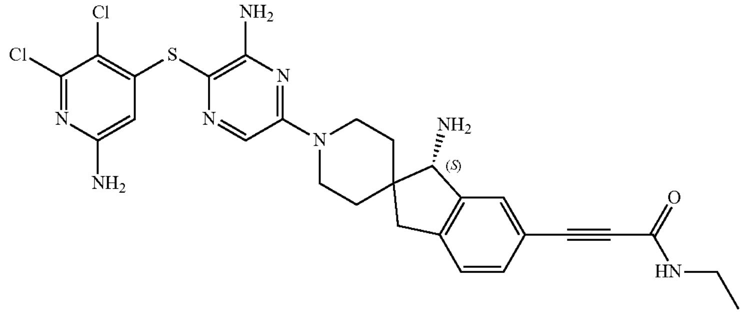 | 256 | 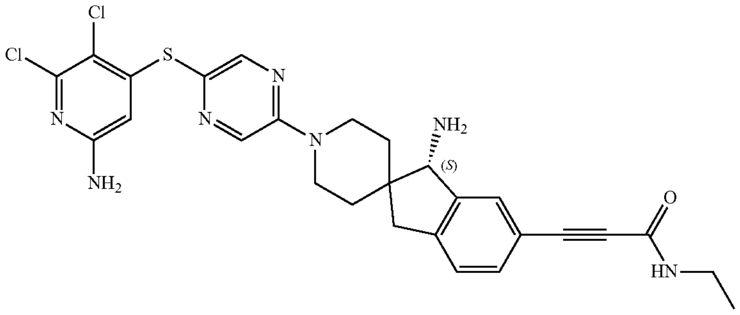 |

-continued
| No. | Structural formula | No. | Structural formula |
|---|---|---|---|
| 257 | 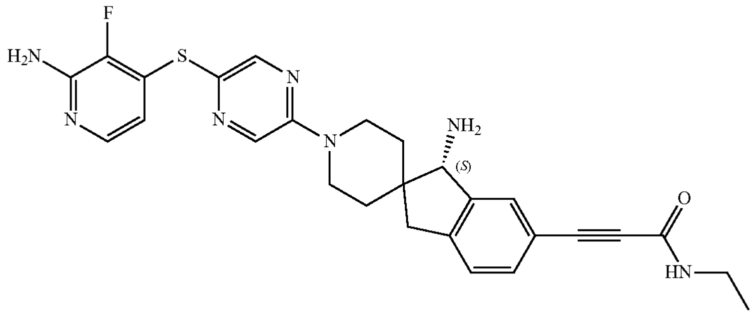 | 258 | 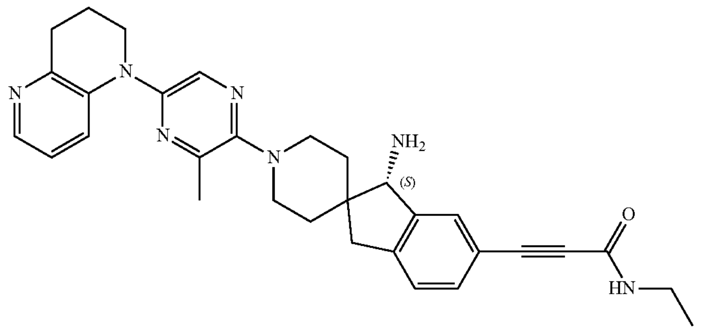 |
| 259 | 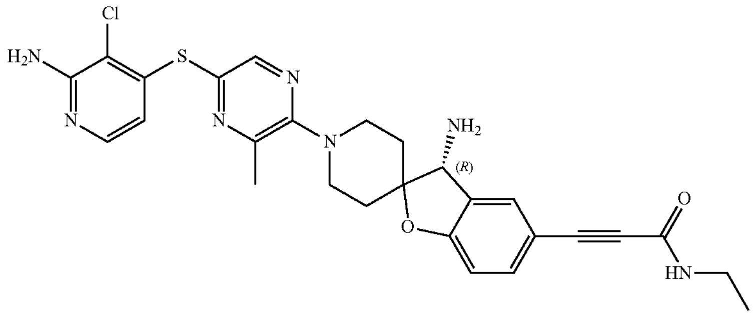 | 260 | 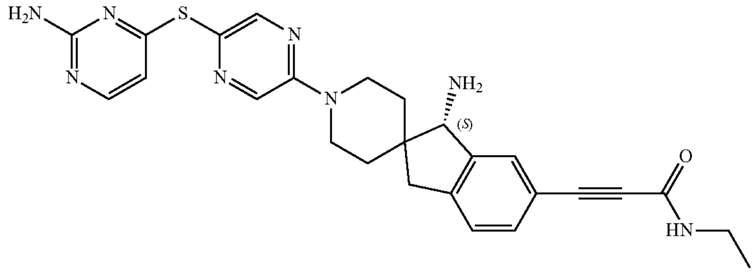 |
| 261 | 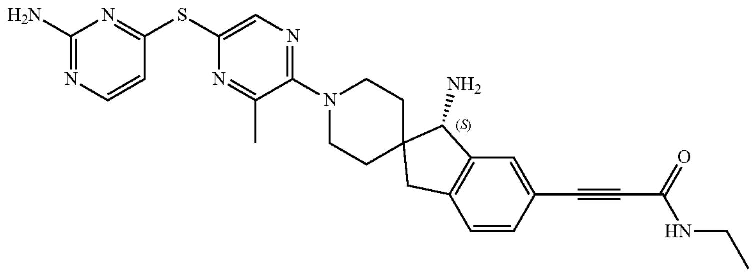 | 262 | 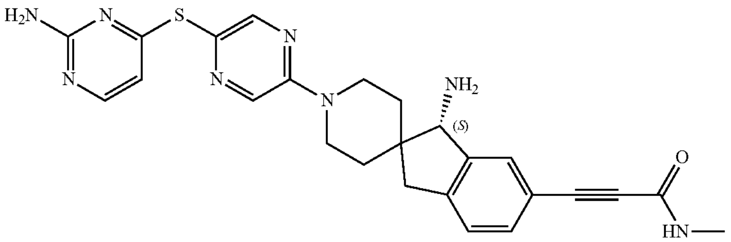 |

-continued
| No. | Structural formula | No. | Structural formula |
|---|---|---|---|
| 263 | 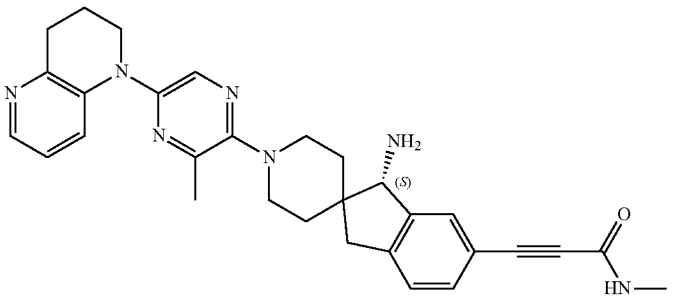 | 264 | 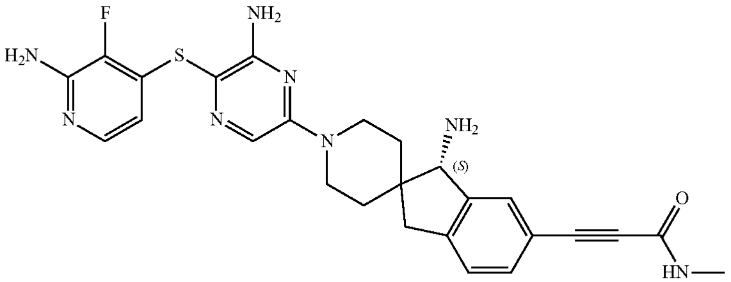 |
| 265 | 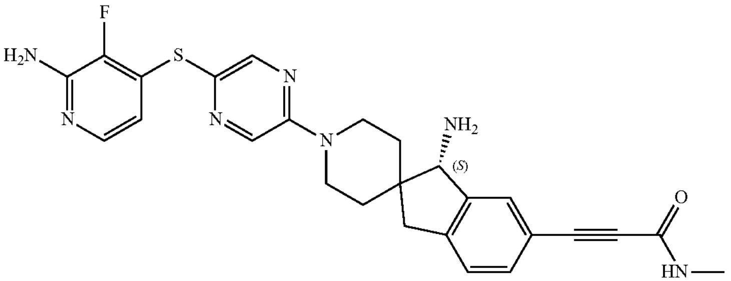 | 266 | 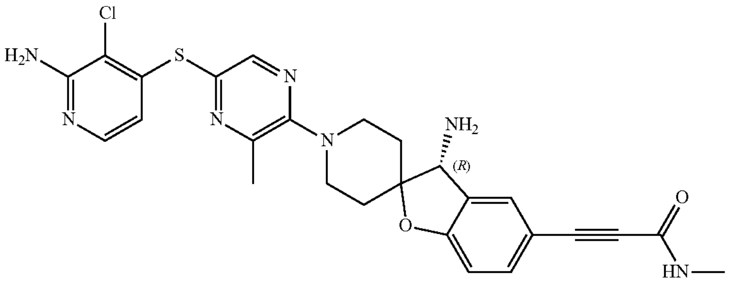 |
| 267 and 268 | 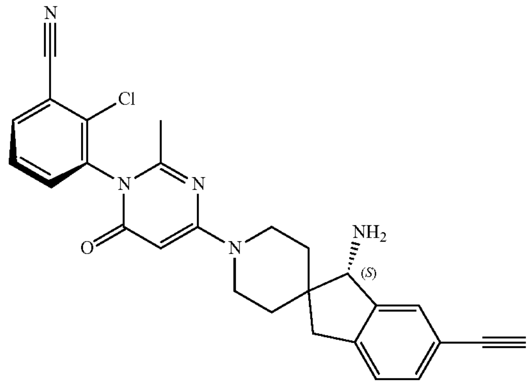 + | 269 | 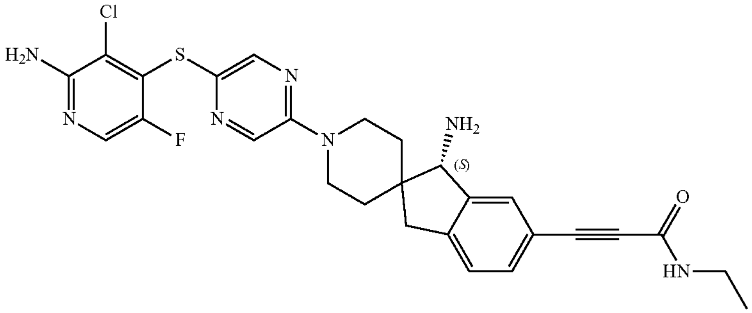 |

-continued
| No. | Structural formula | No. | Structural formula |
| --- | --- | --- | --- |
| | 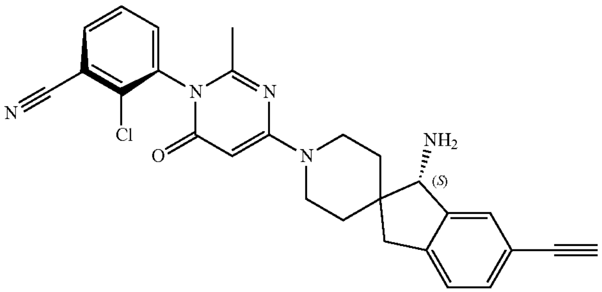 | 270 | 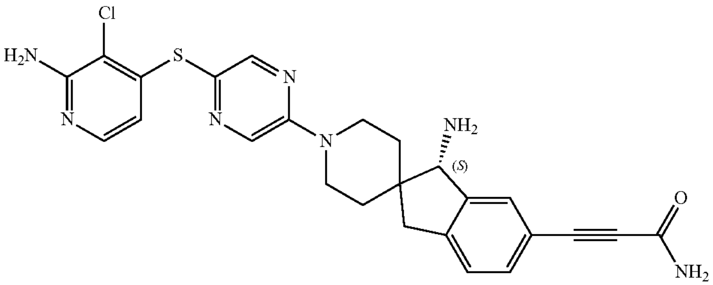 |
| 271 | 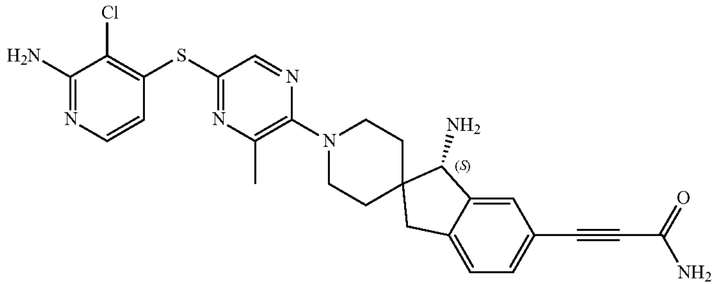 | 272 | 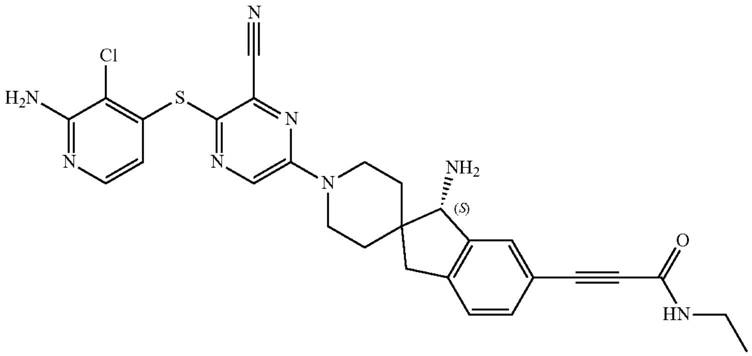 |
| 273 | 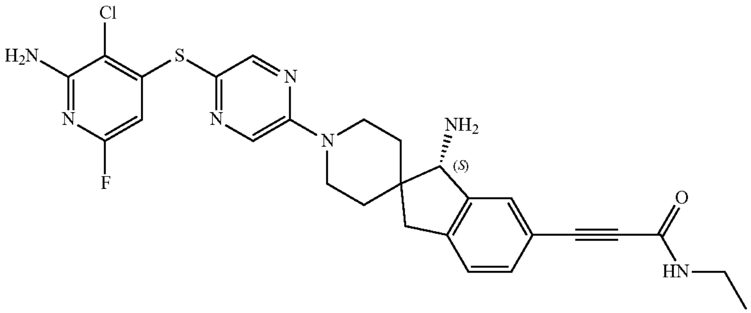 | 274 | 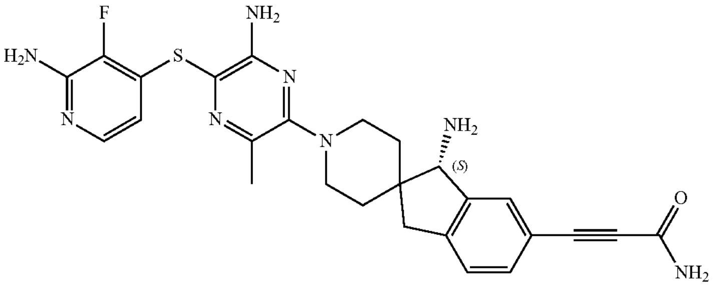 |

-continued
| No. | Structural formula | No. | Structural formula |
|---|---|---|---|
| 275 | 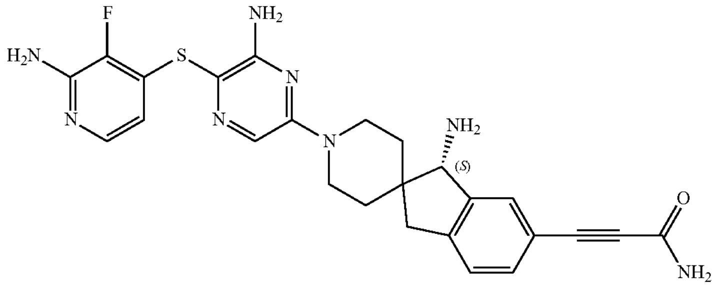 | 276 | 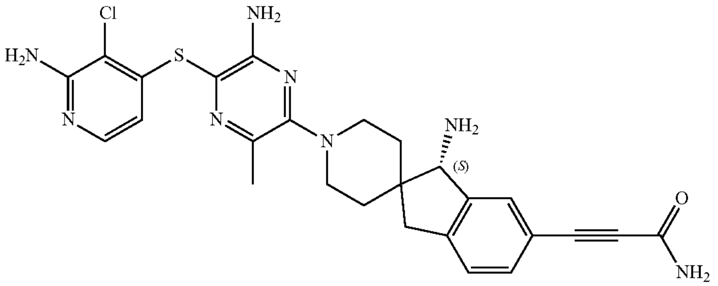 |
| 277 | 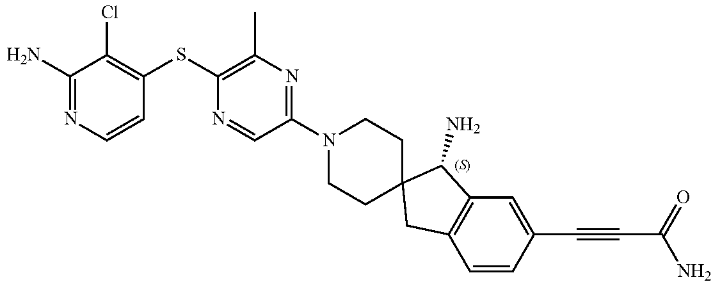 | 278 | 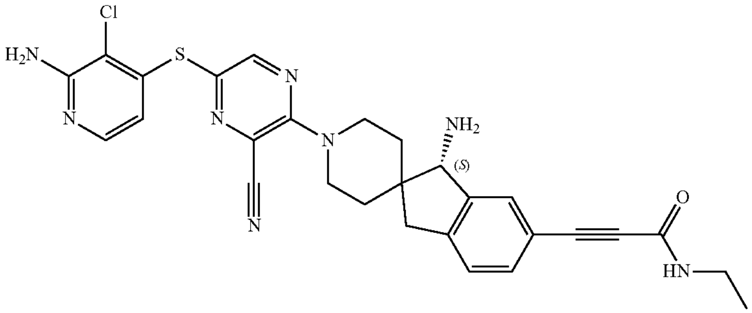 |
| 279 | 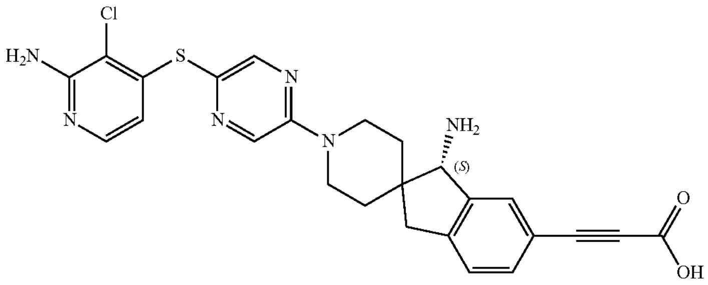 | 280 | 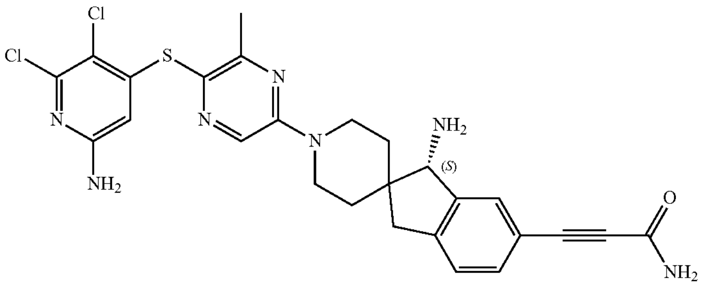 |

-continued
| No. | Structural formula | No. | Structural formula |
|---|---|---|---|
| 281 | 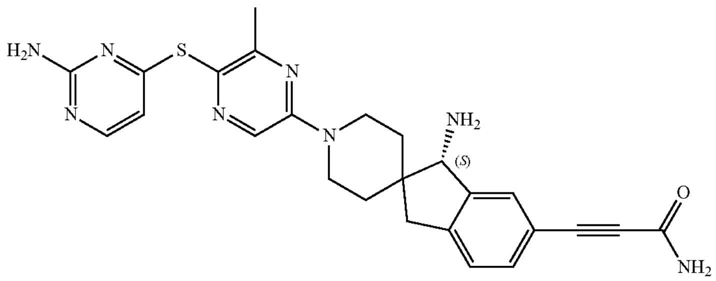 | 282 | 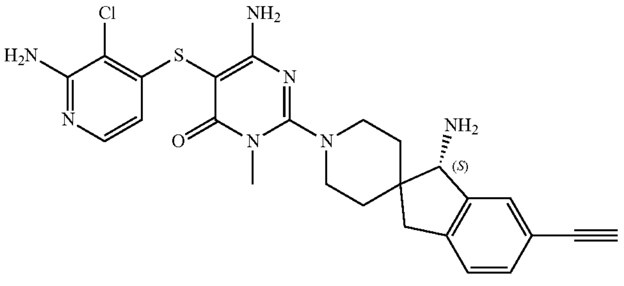 |
| 283 | 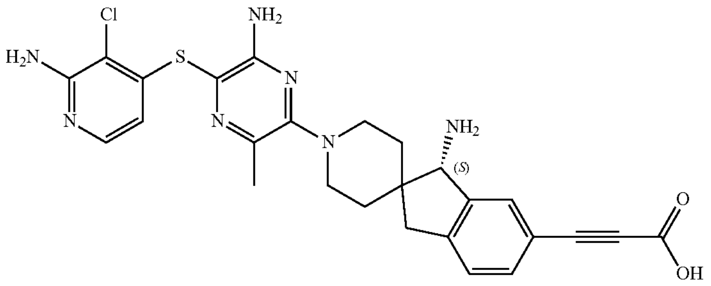 | 284 | 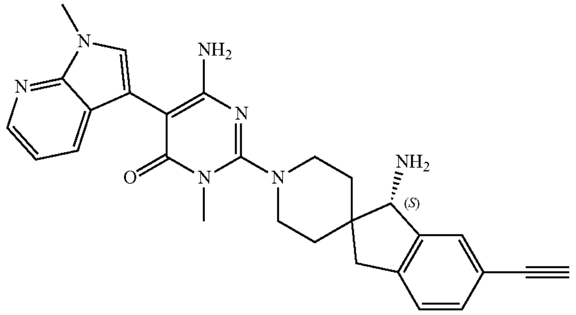 |
| 285 | 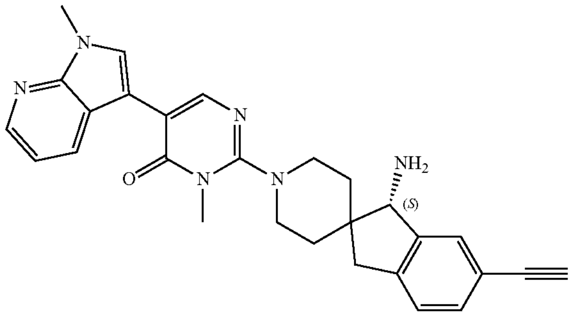 | 286 | 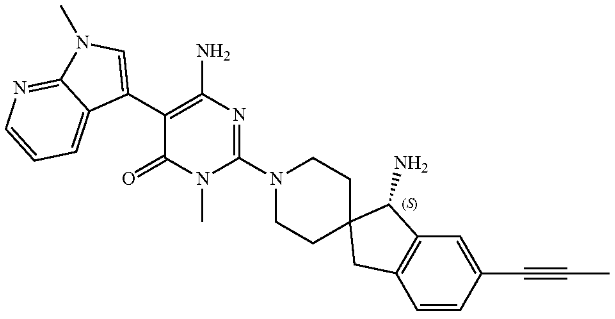 |

-continued
| No. | Structural formula | No. | Structural formula |
|---|---|---|---|
| 287 | 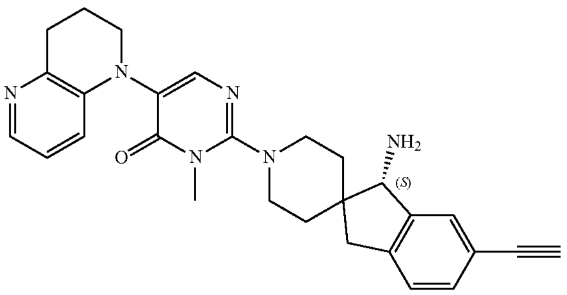 | 288 | 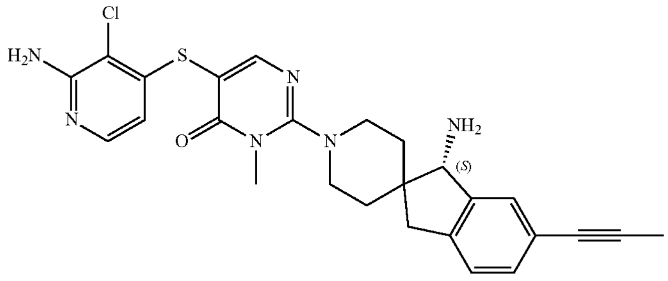 |
| 289 | 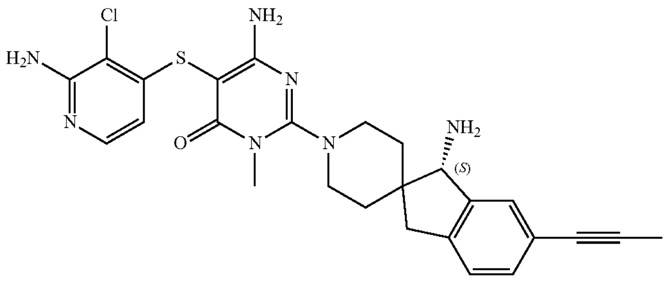 | 290 | 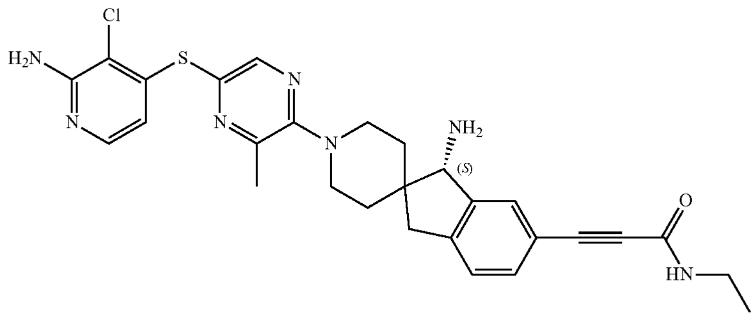 |
| 291 | 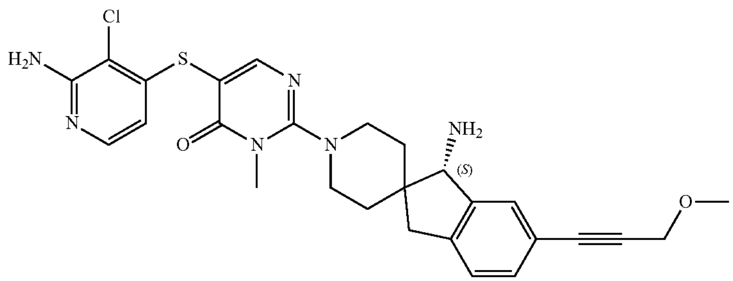 | 292 | 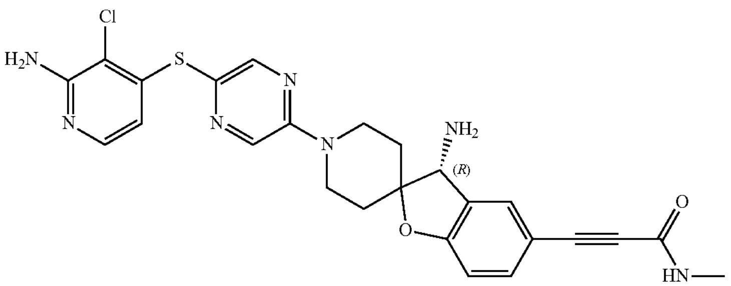 |

-continued
| No. | Structural formula | No. | Structural formula |
|---|---|---|---|
| 293 | 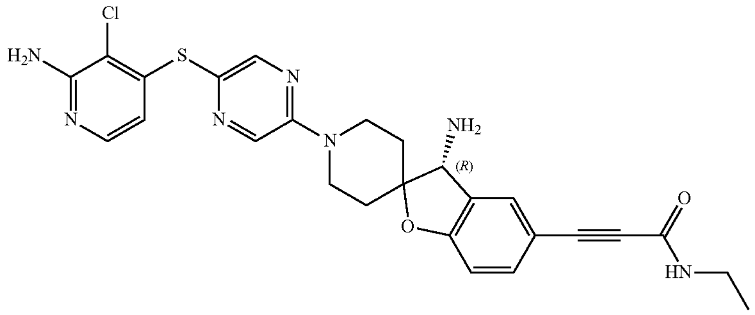 | 294 | 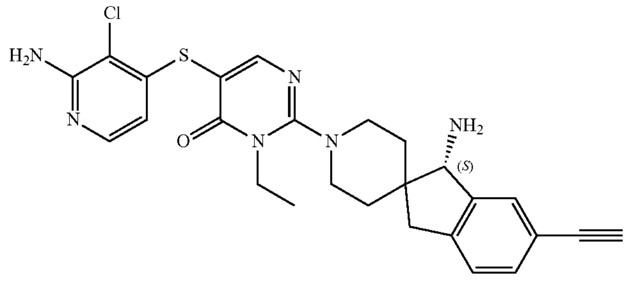 |
| 295 | 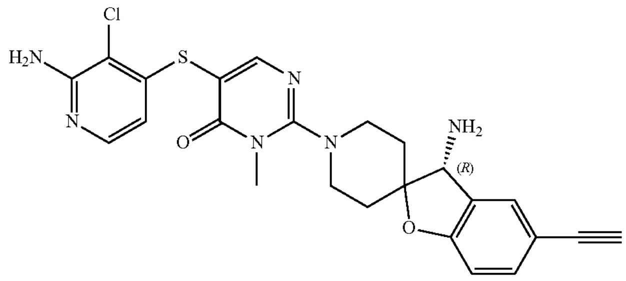 | 296 | 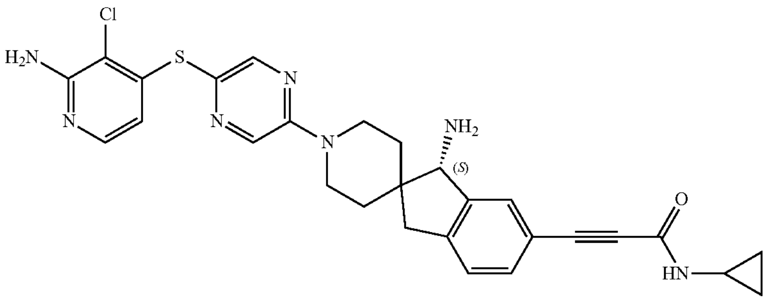 |
| 297 | 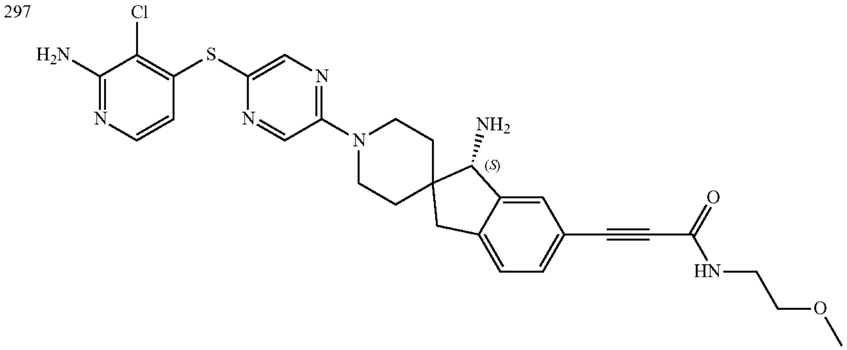 | 298 | 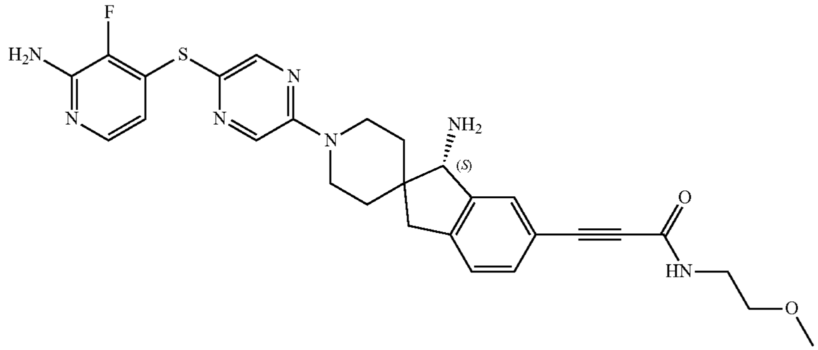 |

-continued
| No. | Structural formula | No. | Structural formula |
|---|---|---|---|
| 299 | 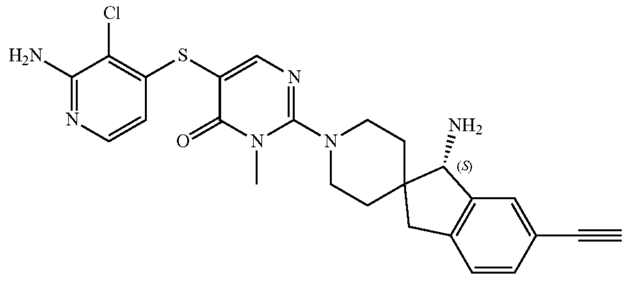 | 300 | 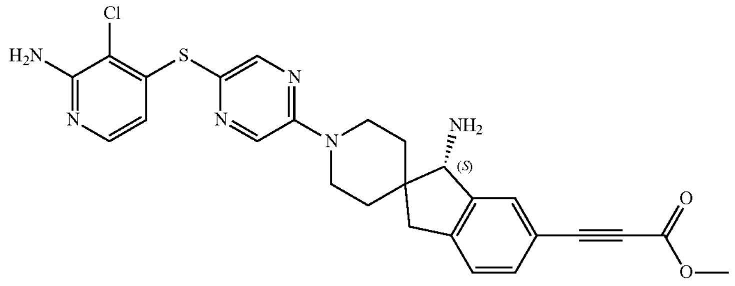 |
| 301 | 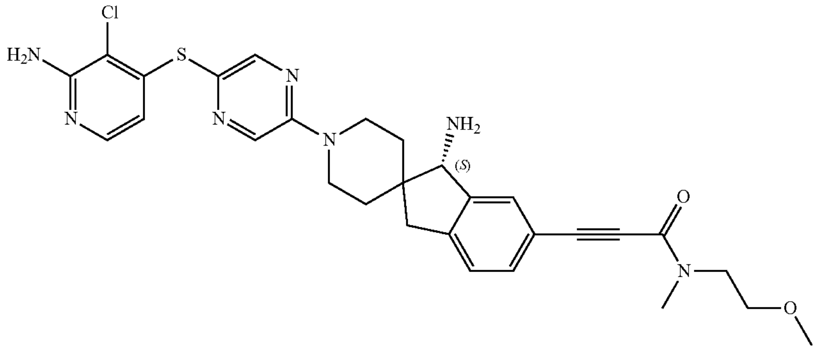 | 302 | 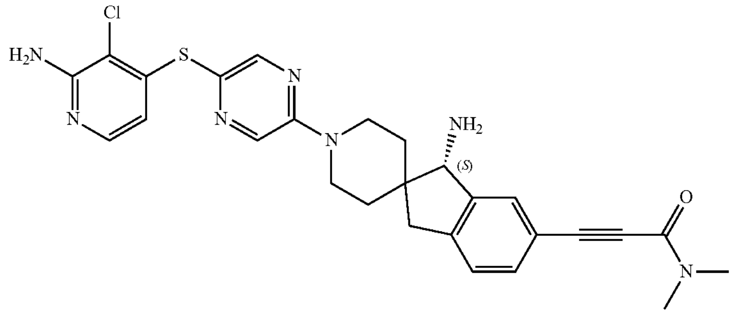 |
| 303 | 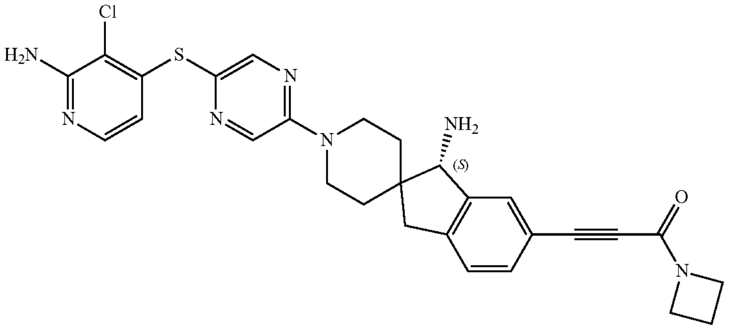 | 304 | 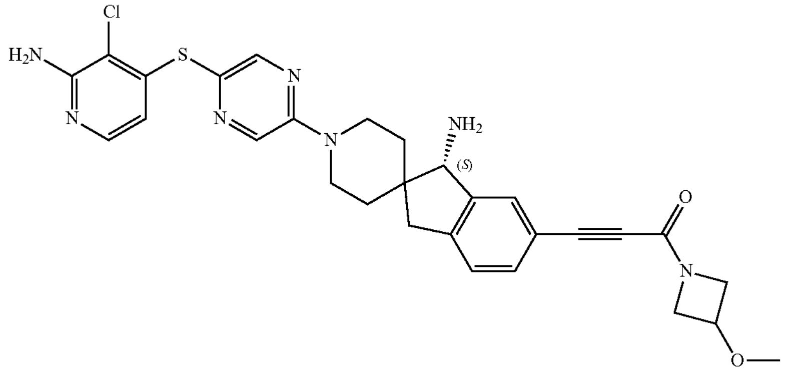 |

-continued
| No. | Structural formula | No. | Structural formula |
|---|---|---|---|
| 305 | 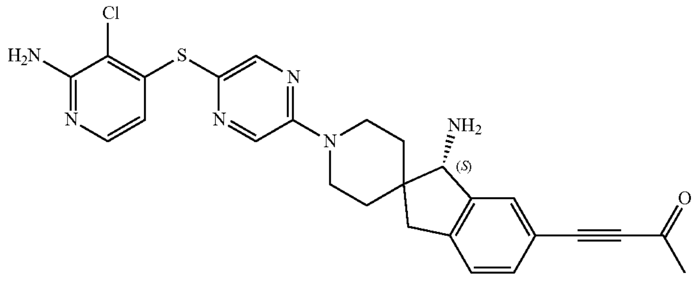 | | |

Embodiment 21. A pharmaceutical composition, comprising the compound and/or the pharmaceutically acceptable salt thereof according to any one of embodiments 1-20, and optionally comprising a pharmaceutically acceptable excipient.

Embodiment 22. A method of in vivo or in vitro inhibiting the activity of SHP2, comprising contacting SHP2 with an effective amount of the compound and/or the pharmaceutically acceptable salt thereof according to any one of embodiments 1-20.

Embodiment 23. Use of the compound and/or the pharmaceutically acceptable salt thereof according to any one of embodiments 1-20 in the manufacture of a medicament for treating or preventing a disease mediated by SHP2 or at least in part by SHP2, and preferably for treating or preventing cancer, Noonan Syndrome and LEOPARD Syndrome, wherein the cancer is preferably a solid tumor or hematologic malignancy, including leukemia, lymphoma and myeloma; and the cancer is more preferably chosen from breast cancer, melanoma, glioblastoma, esophageal cancer, gastric cancer, colon cancer, colorectal cancer, pancreatic cancer, lung cancer, head and neck cancer (such as squamous cell carcinoma of the head and neck), liver cancer, renal cancer, ovarian cancer, cervical cancer, prostate cancer, endometrial cancer, thyroid carcinoma, sarcoma, adrenal carcinoma, acute myelogenous leukemia (AML), juvenile acute myelogenous leukemia, chronic myelogenous leukemia (CML), acute lymphocytic leukemia (ALL), B-cell acute lymphocytic leukemia (B-ALL), acute lymphoblastic leukemia, chronic lymphocytic leukemia (CLL), diffuse large B-cell lymphoma (DLBCL), large B-cell lymphoma (LBCL), B-cell lymphoma, T-cell lymphoma, mantle cell lymphoma, follicular lymphoma, non-Hodgkin's lymphoma, Hodgkin's lymphoma, myelodysplastic syndrome, and myeloma (such as multiple myeloma).

Embodiment 24. A method of treating or preventing a disease in a subject, comprising administering to the subject in need thereof an effective amount of the compound and/or the pharmaceutically acceptable salt thereof according to any one of embodiments 1-20, wherein the disease is a disease mediated by SHP2 or at least in part by SHP2, and the disease is preferably cancer, Noonan Syndrome and LEOPARD Syndrome, wherein the cancer is preferably a solid tumor or hematologic malignancy, including leukemia, lymphoma and myeloma; and the cancer is more preferably chosen from breast cancer, melanoma, glioblastoma, esophageal cancer, gastric cancer, colon cancer, colorectal cancer, pancreatic cancer, lung cancer, head and neck cancer (such as squamous cell carcinoma of the head and neck), liver cancer, renal cancer, ovarian cancer, cervical cancer, prostate cancer, endometrial cancer, thyroid carcinoma, sarcoma, adrenal carcinoma, acute myelogenous leukemia (AML), juvenile acute myelogenous leukemia, chronic myelogenous leukemia (CML), acute lymphocytic leukemia (ALL), B-cell acute lymphocytic leukemia (B-ALL), acute lymphoblastic leukemia, chronic lymphocytic leukemia (CLL), diffuse large B-cell lymphoma (DLBCL), large B-cell lymphoma (LBCL), B-cell lymphoma, T-cell lymphoma, mantle cell lymphoma, follicular lymphoma, non-Hodgkin's lymphoma, Hodgkin's lymphoma, myelodysplastic syndrome, and myeloma (such as multiple myeloma).

Embodiment 25. The compound and/or the pharmaceutically acceptable salt thereof according to any one of embodiments 1-20, for use as a medicament.

Embodiment 26. The compound and/or the pharmaceutically acceptable salt thereof according to any one of embodiments 1-20, for use in treating or preventing a disease mediated by SHP2 or at least in part by SHP2, and preferably for use in treating or preventing cancer, Noonan Syndrome and LEOPARD Syndrome, wherein the cancer is preferably a solid tumor or hematologic malignancy, including leukemia, lymphoma and myeloma; and the cancer is more preferably chosen from breast cancer, melanoma, glioblastoma, esophageal cancer, gastric cancer, colon cancer, colorectal cancer, pancreatic cancer, lung cancer, head and neck cancer (such as squamous cell carcinoma of the head and neck), liver cancer, renal cancer, ovarian cancer, cervical cancer, prostate cancer, endometrial cancer, thyroid carcinoma, sarcoma, adrenal carcinoma, acute myelogenous leukemia (AML), juvenile acute myelogenous leukemia, chronic myelogenous leukemia (CML), acute lymphocytic leukemia (ALL), B-cell acute lymphocytic leukemia (B-ALL), acute lymphoblastic leukemia, chronic lymphocytic leukemia (CLL), diffuse large B-cell lymphoma (DLBCL), large B-cell lymphoma (LBCL), B-cell lymphoma, T-cell lymphoma, mantle cell lymphoma, follicular lymphoma, non-Hodgkin's lymphoma, Hodgkin's lymphoma, myelodysplastic syndrome, and myeloma (such as multiple myeloma).

Embodiment 27. A pharmaceutical combination, comprising the compound and/or the pharmaceutically acceptable salt thereof according to any one of embodiments 1-20, and at least one additional therapeutic agent, wherein the additional therapeutic agent is preferably chosen from: an anti-neoplastic active agent, an anti-inflammatory agent or an immunomodulator, wherein the anti-neoplastic active agent includes a chemotherapeutic agent, an immune checkpoint inhibitor or agonist, and a targeted therapeutic agent.

The various embodiments of the present invention (including the following examples) and the features of the various embodiments should be interpreted as being arbitrarily combined with each other, and the various solutions obtained from these mutual combinations are all included in the scope of the present invention, just like the solutions obtained from the mutual combinations specifically and individually set forth herein, unless clearly stated otherwise in the context.

General Synthetic Methods

The compound of formula (I) and/or a pharmaceutically acceptable salt thereof described herein can be synthesized using commercially available starting materials, by methods known in the art, or methods disclosed in the present patent application. The synthetic routes shown in Scheme 1 to Scheme 4 illustrate the general synthetic methods of the compounds of the present invention.

Scheme 1

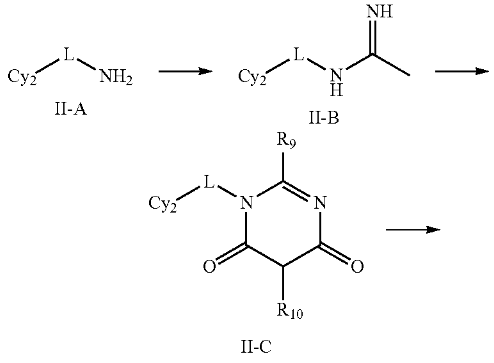

II-A

II-B

II-C

-continued

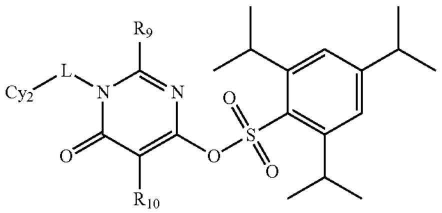

II-D

II-D +

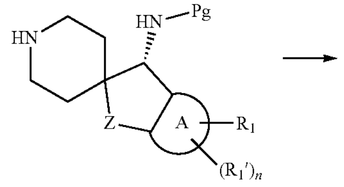

II-E

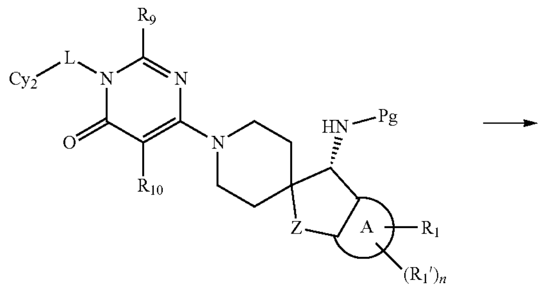

II-F

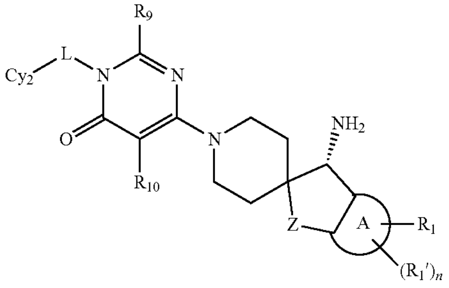

II-G

Ring A, Z, $R_1$, $R_1'$, n, L and $Cy_2$ thereof are defined as for formula (I); Pg is an amino protecting group; and $R_9$ and $R_{10}$ are each independently chosen from hydrogen, —$NH_2$, halogen, $C_{1-6}$ alkyl and $C_{1-6}$ haloalkyl.

As shown in Scheme 1, a compound of formula II-A is reacted with acetonitrile under the catalysis of hydrogen chloride to obtain a compound of formula II-B. The compound of formula II-B is reacted with a corresponding malonate under alkaline conditions (sodium ethoxide/ethanol) to obtain a compound of formula II-C. The compound of formula II-C is reacted with 2,4,6-triisopropyl benzenesulfonyl chloride to obtain a compound of formula II-D. The compound of formula II-D is reacted with a compound of formula II-E under alkaline conditions ($Et_3N$ or DIEA) to obtain a compound of formula II-F. The compound of formula II-F is deprotected with an acid to obtain a compound of formula II-G.

Scheme 2

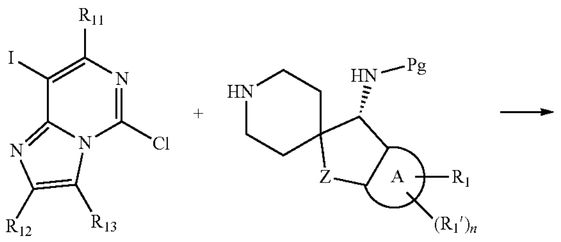

III-A II-B

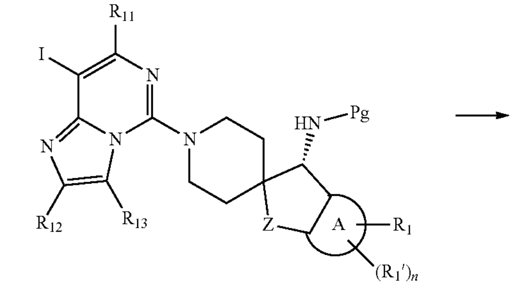

III-C

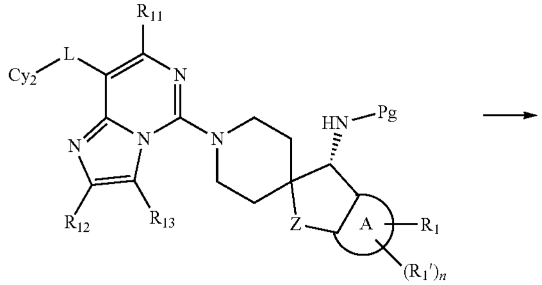

III-D

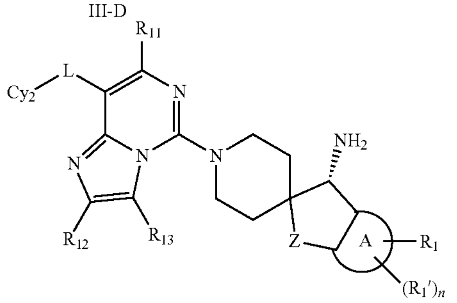

III-E

Ring A, Z, $R_1$, $R_1'$, n, L and $Cy_2$ thereof are defined as for formula (I); Pg is an amino protecting group; and $R_{11}$, $R_{12}$ and $R_{13}$ are each independently chosen from hydrogen, —$NH_2$, —CN, $C_{1-6}$ alkyl and $C_{1-6}$ haloalkyl.

As shown in Scheme 2, a compound of formula III-A and a compound of formula III-B are subjected to a nucleophilic substitution reaction under alkaline conditions ($Et_3N$ or DIEA) to obtain a compound of formula III-C. The compound of formula III-C and a sulfur-containing sodium salt or boronic ester are subjected to a coupling reaction under the catalysis of palladium to obtain a compound of formula III-D. Palladium-catalyzed coupling reaction is carried out under suitable conditions. The base used can be chosen from $Cs_2CO_3$, $K_2CO_3$, DIEA, etc., and the catalyst used can be chosen from $Pd_2(dba)_3$, $Pd(PPh_3)_4$, $Pd(dppf)Cl_2$—$CH_2Cl_2$, etc. The compound of formula III-D is deprotected with an acid to obtain a compound of formula III-E.

Scheme 3

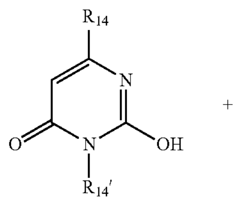

IV-A

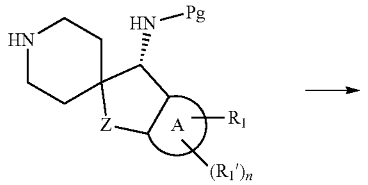

IV-B

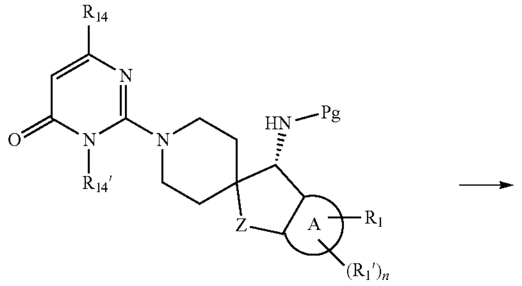

IV-C

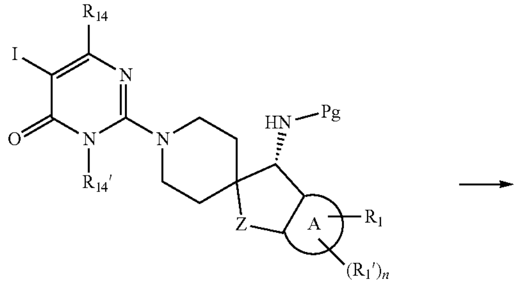

IV-D

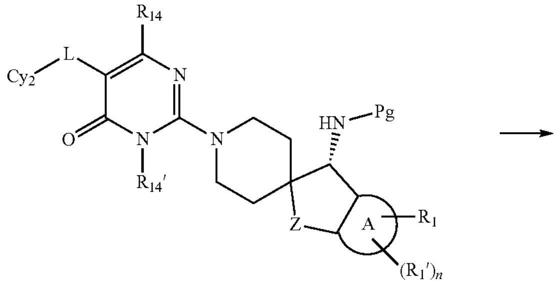

IV-E

-continued

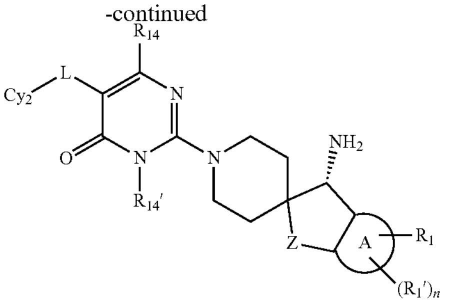

IV-F

Ring A, Z, $R_1$, $R_1$', n, L and $Cy_2$ thereof are defined as for formula (I); Pg is an amino protecting group; $R_{14}$ is chosen from hydrogen, —$NH_2$ and $C_{1-6}$ alkyl; and $R_{14}$' is $C_{1-6}$ alkyl.

As shown in Scheme 3, a compound of formula IV-A is reacted with a compound of formula IV-B under BOP and DBU conditions to obtain a compound of formula IV-C. The compound of formula IV-C is reacted with NIS to obtain a compound of formula IV-D. The compound of formula IV-D and a sulfur-containing sodium salt or boronic ester are subjected to a coupling reaction under the catalysis of palladium to obtain a compound of formula IV-E. Palladium-catalyzed coupling reaction is carried out under suitable conditions. The base used can be chosen from $Cs_2CO_3$, $K_2CO_3$, DIEA, etc., and the catalyst used can be chosen from $Pd_2(dba)_3$, $Pd(PPh_3)_4$, $Pd(dppf)Cl_2·CH_2Cl_2$, etc. The compound of formula IV-E is deprotected with an acid to obtain a compound of formula IV-F.

Scheme 4

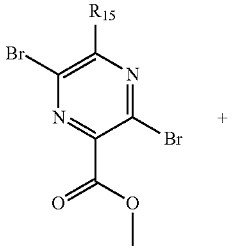

V-A

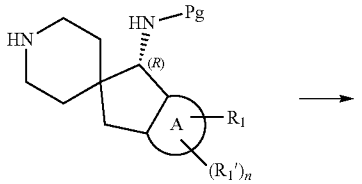

V-B

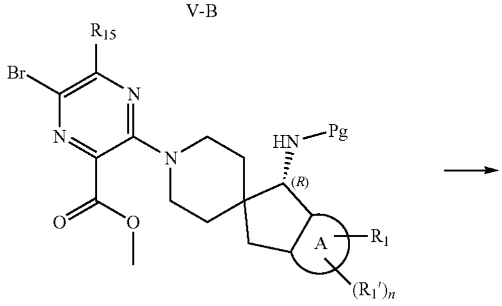

V-C

-continued

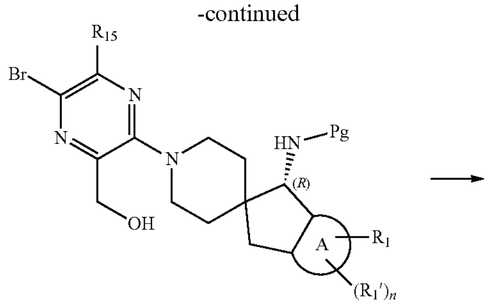

V-D

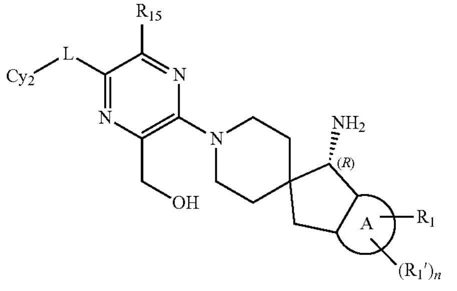

V-E

Ring A, $R_1$, $R_1'$, n, L and $Cy_2$ thereof are defined as for formula (I); Pg is an amino protecting group; and $R_{15}$ is chosen from hydrogen, —$NH_2$, —CN, halogen, $C_{1-6}$ alkyl, $C_{1-6}$ haloalkyl and —($C_{1-6}$ alkyl)-OH.

As shown in Scheme 4, a compound of formula V-A is reacted with a compound of formula V-B under alkaline conditions ($Et_3N$ or DIEA) to obtain a compound of formula V-C. The compound of formula IV-C is reacted with DIBAL-H to obtain a compound of formula V-D. The compound of formula V-D and a sulfur-containing sodium salt or boronic ester are subjected to a coupling reaction under the catalysis of palladium and deprotected with an acid to obtain a compound of formula V-E. Palladium-catalyzed coupling reaction is carried out under suitable conditions. The base used can be chosen from $Cs_2CO_3$, $K_2CO_3$, DIEA, etc., and the catalyst used can be chosen from $Pd_2(dba)_3$, $Pd(PPh_3)_4$, $Pd(dppf)Cl_2{\cdot}CH_2Cl_2$, etc.

The substituents of the compounds thus obtained can be further modified to provide other desired compounds. Synthetic chemistry transformations are described, for example, in R. Larock, *Comprehensive Organic Transformations*, VCH Publishers (1989); L. Fieser and M. Fieser, *Fieser and Fieser's Reagents for Organic Synthesis*, John Wiley and Sons (1994); L. Paquette, ed., *Encyclopedia of Reagents for Organic Synthesis*, John Wiley and Sons (1995) and subsequent editions thereof.

Before use, the compound(s) of the present invention can be purified by column chromatography, high performance liquid chromatography, crystallization or other suitable methods.

Pharmaceutical Compostions and Utility

The compound of the present invention (e.g., a compound of any of the examples as described herein) is used, alone or in combination with one or more additional therapeutic agents, to formulate pharmaceutical compositions. A pharmaceutical composition comprises: (a) an effective amount of the compounds of the present invention; (b) a pharmaceutically acceptable excipient (e.g., one or more pharmaceutically acceptable carriers); and optionally (c) at least one additional therapeutic agent.

A pharmaceutically acceptable excipient refers to an excipient that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compounds of the present invention), can be utilized as pharmaceutical excipients for delivery of the active ingredients. Examples of other excipients include colloidal silicon dioxide, magnesium stearate, cellulose, sodium lauryl sulfate, and pigments such as D&C Yellow #10. Suitable pharmaceutically acceptable excipients are disclosed in Remington's Pharmaceutical Sciences, A. Osol, a standard reference text in the art.

A pharmaceutical composition comprising a compound of the present invention can be administered in various known manners, such as orally, topically, rectally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A pharmaceutical composition described herein can be prepared in the form of tablet, capsule, sachet, dragee, powder, granule, lozenge, powder for reconstitution, liquid preparation, or suppository. In some embodiments, a pharmaceutical composition comprising a compound of the present invention is formulated for intravenous infusion, topical administration, or oral administration.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In some embodiments, the compound of the present invention can be present in an amount of 1, 5, 10, 15, 20, 25, 50, 75, 80, 85, 90, 95, 100, 125, 150, 200, 250, 300, 400 and 500 mg in a tablet. In some embodiments, the compound of the present invention can be present in an amount of 1, 5, 10, 15, 20, 25, 50, 75, 80, 85, 90, 95, 100, 125, 150, 200, 250, 300, 400 and 500 mg in a capsule.

A sterile injectable composition (e.g., aqueous or oleaginous suspension) can be formulated according to techniques known in the art using suitable dispersing or wetting agents (for example, Tween 80) and suspending agents. The sterile injectable composition can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives, and natural pharmaceutically acceptable oils, such as olive oil or castor oil, especially in their polyoxyethylated versions, can be used as sterile injectable medium. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

Suitable in vitro assays can be used to evaluate the effect of the compounds of the present invention in inhibiting the activity of SHP2. The compounds of the present invention can further be examined for additional effects in preventing or treating cancer by in vivo assays. For example, the compound of the present invention can be administered to an animal (e.g., a mouse model) having cancer and its therapeutic effects can be accessed. If the pre-clinical results are successful, the dosage range and administration route for animals, such as humans, can be projected.

The compound of the present invention can be shown to have sufficient pre-clinical practical utility to merit clinical trials hoped to demonstrate a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic malignancies, such as leukemia, lymphoma or myeloma. The term "cancer" encompasses diseases of skin, tissues, organs, bone, cartilage, blood, and vessels. The term "cancer" further encompasses primary cancer, and metastatic cancer, recurrent cancer and refractory cancer.

Non-limiting examples of solid tumors include pancreatic cancer; bladder cancer; colorectal cancer; colon cancer; breast cancer, including metastatic breast cancer; prostate cancer, including androgen-dependent and androgen-independent prostate cancer; testicular cancer; renal cancer, including, e.g., metastatic renal cell carcinoma; urothelial carcinoma; liver cancer; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; endometrial cancer; gastric cancer; esophageal cancer; head and neck cancer, including, e.g., squamous cell carcinoma of the head and neck; skin cancer, including, e.g., melanoma and basal carcinoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; sarcoma, including, e.g., Kaposi's sarcoma; adrenal carcinoma; mesothelioma; mesothelial carcinoma; choriocarcinoma; muscle carcinoma; connective tissue carcinoma; and thyroid carcinoma.

Non-limiting examples of hematologic malignancies include acute myelogenous leukemia (AML); juvenile acute myelogenous leukemia; chronic myelogenous leukemia (CML), including accelerated phase CML and CML blastic phase (CML-BP); acute lymphocytic leukemia (ALL); B-cell acute lymphocytic leukemia (B-ALL); chronic lymphocytic leukemia (CLL), including high risk CLL; human acute monocytic leukemia (M(5)); hairy cell leukemia; lymphocytic leukemia; chronic lymphoid leukemia; myelogenous leukemia; acute lymphoblastic leukemia; small lymphotic lymphoma (SLL); lymphoblastic lymphoma; Hodgkin's lymphoma; non-Hodgkin's lymphoma (NHL); mantle cell lymphoma (MCL); B-cell lymphoma; T-cell lymphoma; diffuse large B-cell lymphoma (DLBCL); large B-cell lymphoma (LBCL); follicular lymphoma; marginal zone lymphoma; Burkitt's lymphoma; non-Burkitt's highly degree B cell malignant lymphoma; extranodal marginal-zone B-cell lymphoma; multiple myeloma (MM); Waldenstrom macroglobulinemia; myelodysplastic syndrome (MDS), including refractory anemia (RA), refractory anemia with ring sideroblasts (RARS), refractory anemia with excess of blasts (RAEB) and refractory anemia with excess blasts in transformation (RAEB-T); and myeloproliferative syndrome.

In some embodiments, solid tumor is breast cancer, melanoma, glioblastoma, esophageal cancer, gastric cancer, colon cancer, colorectal cancer, pancreatic cancer, lung cancer, head and neck cancer (such as squamous cell carcinoma of the head and neck), liver cancer, renal cancer, ovarian cancer, cervical cancer, prostate cancer, endometrial cancer, thyroid carcinoma, sarcoma, adrenal carcinoma.

In some embodiments, hematologic malignancy is acute myelogenous leukemia (AML), juvenile acute myelogenous leukemia, chronic myelogenous leukemia (CML), acute lymphocytic leukemia (ALL), B-cell acute lymphocytic leukemia (B-ALL), acute lymphoblastic leukemia, chronic lymphocytic leukemia (CLL), diffuse large B-cell lymphoma (DLBCL), large B-cell lymphoma (LBCL), B-cell lymphoma, T-cell lymphoma, mantle cell lymphoma, follicular lymphoma, non-Hodgkin's lymphoma, Hodgkin's lymphoma, myelodysplastic syndrome, myeloma (such as multiple myeloma).

The compound of the present invention can be used to achieve a beneficial therapeutic or prophylactic effect, for example, in subjects with cancer.

In addition, the compounds of the present invention (e.g., a compound of any of the examples as described herein) can be administered in combination with additional therapeutic agents for the treatment of diseases or disorders described herein, such as cancer. The additional therapeutic agents may be administered separately with the compound of the present invention or included with such an ingredient in a pharmaceutical composition according to the disclosure, such as a fixed-dose combination drug product. In some embodiments, additional therapeutic agents are those that are known or discovered to be effective in the treatment of diseases mediated by SHP2 or at least in part by SHP2, such as another SHP2 inhibitor or a compound active against another target associated with the particular disease. The combination may serve to increase efficacy (e.g., by including in the combination a compound potentiating the potency or effectiveness of the compound of the present invention), decrease one or more side effects, or decrease the required dose of the compound of the present invention.

In some embodiments, the compounds of the present invention (e.g., a compound of any of the examples as described herein) can be administered in combination with additional therapeutic agents, such as anti-neoplastic active agents, anti-inflammatory agents, or immunomodulators, wherein the anti-neoplastic active agents include chemotherapeutic agents, immune checkpoint inhibitors or agonists, and targeted therapeutic agents. The term "anti-neoplastic active agent" as used herein refers to any agent that is administered to a subject suffering from cancer for the purposes of treating the cancer, such as a chemotherapeutic agent, an immune checkpoint inhibitor or agonist, and a targeted therapeutic agent.

Non-limiting examples of chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); free radical generators such as bleomycin; nucleoside mimetics (e.g., 5-fluorouracil, capecitabine, gemcitabine, fludarabine, cytarabine, azacitidine, mercaptopurine, thioguanine, pentostatin, and hydroxyurea); paclitaxel, docetaxel, and related analogs; vincristine, vinblastin, and related analogs; thalidomide and related analogs (e.g., CC-5013 and CC-4047).

Non-limiting examples of immune checkpoint inhibitors or agonists include PD-1 inhibitors, for example, anti-PD-1 antibodies, such as pembrolizumab, nivolumab, and PDR001 (spartalizumab); PD-L1 inhibitors, for example, anti-PD-L1 antibodies, such as atezolizumab, durvalumab, and avelumab; CTLA-4 inhibitors, such as anti-CTLA-4 antibodies, for example ipilimumab; and BTLA inhibitors, LAG-3 inhibitors, TIM3 inhibitors, TIGIT inhibitors, VISTA inhibitors, OX-40 agonists, and the like.

Targeted therapeutic agents include various small molecule or macromolecular targeted therapeutic agents, and non-limiting examples thereof include: protein tyrosine kinase inhibitors (such as imatinib mesylate and gefitinib); proteasome inhibitors (such as bortezomib); NF-κB inhibitors, including IκB kinase inhibitors; KRAS G12C inhibitors; ERK inhibitors; CDK4/6 inhibitors; PI3Kδ inhibitors; SYK inhibitors; Bcl2 inhibitors; IDO inhibitors; A2AR inhibitors; BRAF inhibitors (such as dabrafenib); MEK inhibitors (such as trametinib); mTOR inhibitors (such as rapamycin); anti-CD40 antibodies (such as APX005M, RO7009789); antibodies that bind to proteins overexpressed in cancer to down-regulate cell replication, such as anti-CD20 antibodies (such as rituximab, ibritumomab tiuxetan, and tositumomab), anti-Her2 monoclonal antibodies (such as trastuzumab), anti-EGFR antibodies (such as cetuximab) and anti-VEGF antibodies (such as bevacizumab); anti-angiogenic drugs, such as lenalidomide; and other protein or enzyme inhibitors, these proteins or enzymes are known to be upregulated, overexpressed or activated in cancers, and the inhibition of which can down-regulate cell replication.

EXAMPLES

The examples below are intended to be purely exemplary and should not be considered to be limiting in any way. Efforts have been made to ensure the accuracy with respect to numbers used (for example, amounts, temperature, etc.), but those skilled in the art should understand that some experimental errors and deviations should be accounted for. Unless indicated otherwise, parts are parts by weight, temperature is in degrees Centigrade, and pressure is at or near atmospheric. All MS data were determined by Agilent 6120 or Agilent 1100. All NMR data were generated using a Varian 400 MR machine. All reagents and materials, except synthesized intermediates, used in the present invention are commercially available. All compound names except the reagents are generated by Chemdraw 16.0.

If there is any atom with empty valence(s) in any one of the structures disclosed herein, the empty balance(s) is (are) the hydrogen atom(s) which is (are) omitted for convenience purpose.

In the present application, in the case of inconsistency of the name and structure of a compound, when the two of which are both given for the compound, it is subject to the structure of the compound, unless the context shows that the structure of the compound is incorrect and the name is correct.

List of abbreviations used in the following examples:

AcOH Acetic acid
$(Boc)_2O$ Di-tert-butyl dicarbonate
BOP Benzotriazol-1-yloxytris(dimethylamino)phosphonium hexafluorophosphate
$CD_3OD$ Deuterated methanol
$CDCl_3$ Deuterated chloroform
m-CPBA m-chloroperoxybenzoic acid
DBU 1,8-diazabicyclo-undec-7-ene
DCM Dichloromethane
DIBAL-H Diisobutylaluminium hydride
DIEA N,N-diisopropylethylamine
DMAP 4-dimethylaminopyridine
DMA N,N-dimethylacetamide
DMF N,N-dimethylformamide
DMSO-$d_6$ Deuterated dimethyl sulfoxide
EA/EtOAc Ethyl acetate
$Et_3N$ Triethylamine
EtOH Ethanol
g Gram
HMDSLi Lithium hexamethyldisilazide
HATU 2-(7-azabenzotriazol-1-yl)-N,N,N'N-tetramethyluronium hexafluorophosphate
KOAc Potassium acetate
L Liter
LDA Lithium diisopropylamide
M Mole/liter
MeCN Acetonitrile
Mel Iodomethane
MeOH Methanol
$MeSO_3H$ Methanesulfonic acid
mg Milligram
mL Milliliter
mmol Millimole
mol Mole
NaOMe Sodium methoxide
NBS N-bromosuccinimide
NCS N-chlorosuccinimide
NFSI N-fluorobisbenzenesulfonamide
NIS N-iodosuccinimide
$Ti(OEt)_4$ Ethyl titanate TMSCN Trimethylsilyl cyanide
$Pd_2(dba)_3$ Tris(dibenzylidene acetone)dipalladium
$Pd(dppf)Cl_2 \cdot CH_2Cl_2$ [1,1'-bis(diphenylphosphino) ferrocene]palladium dichloride dichloromethane complex
$Pd(PPh_3)_2Cl_2$ Bis(triphenylphosphine)palladium chloride
PE Petroleum ether
TFA Trifluoroacetic acid
THF Tetrahydrofuran
Xant-phos 4,5-bis(diphenylphosphino)-9,9-dimethylxanthene

Example 1 Synthesis of Compounds

Intermediate I-A1

Sodium 2-amino-3-chloropyridine-4-thiolate

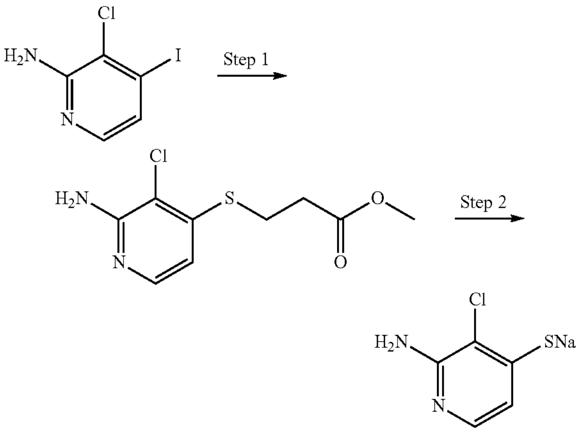

I-A1

Step 1: Methyl 3-((2-amino-3-chloropyridin-4-yl)thio)propanoate

Under nitrogen, 3-chloro-4-iodopyridin-2-amine (10.0 g, 39.3 mmol), methyl 3-mercaptopropanoate (5.20 g, 42.8 mmol), palladium acetate (0.44 g, 1.97 mmol), Xant-phos (2.27 g, 3.93 mmol) and DIEA (10.2 g, 78.6 mmol) were placed in 1,4-dioxane (160 mL). The reaction solution was refluxed and stirred for 2 hours, cooled to room temperature and concentrated in vacuum under reduced pressure, and the resulting residue was purified with silica gel column chromatography (petroleum ether/ethyl acetate) to give the target product (9.70 g, yield 100%). $[M+H]^+$ 201.1

Step 2: Sodium 2-amino-3-chloropyridine-4-thiolate

Under nitrogen, to a solution of methyl 3-((2-amino-3-chloropyridin-4-yl)thio)propanoate (9.70 g, 39.3 mmol) in tetrahydrofuran was added 2 M sodium ethoxide/ethanol solution (20 mL, 40 mmol). The reaction was stirred at room temperature for 2 hours and concentrated in vacuum under reduced pressure. To the resulting residue was added dichloromethane and the mixture was stirred. A solid was precipitated and the mixture was filtered. The filter cake was collected to give the target product (7.18 g, yield 100%). $[M+2H-Na]^+$ 161.0

The intermediates in the table below were prepared by following the steps for preparing intermediate I-A1 from corresponding starting materials and reagents:

| Intermediates | Structural formula | LC-MS $[M + 2H - Na]^+$ |
|---|---|---|
| I-A3 | 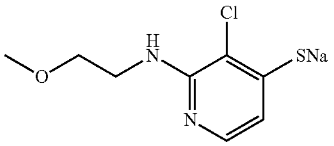 | 219.0 |
| I-A5 | 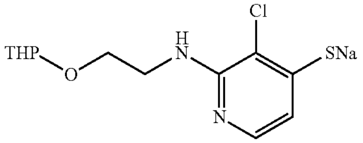 | 289.0 |
| I-A6 | 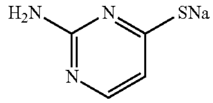 | 128.1 |
| I-A7 | 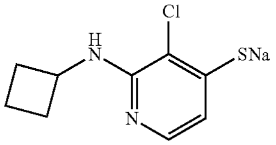 | 215.0 |
| I-A10 | 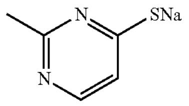 | 127.2 |
| I-A20 | 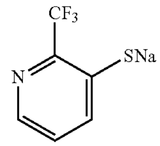 | 180.1 |

Intermediate I-A2

3-((2-amino-3-chloropyridin-4-yl)thio)-6-chloropyrazin-2-amine

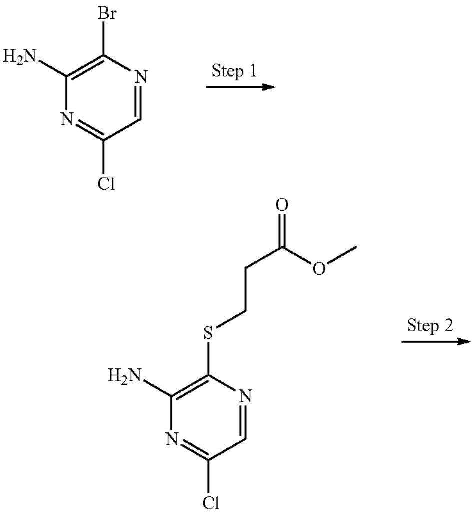

-continued

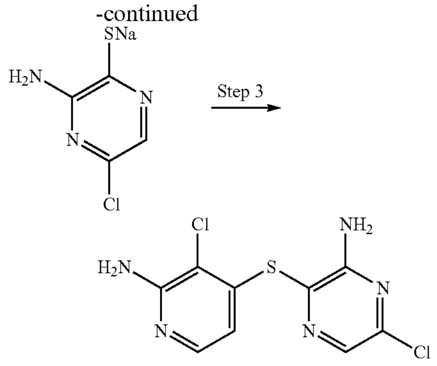

I-A2

Step 1: Methyl 3-((3-amino-5-chloropyrazin-2-yl)thio)propanoate

Under nitrogen, 3-bromo-6-chloropyrazin-2-amine (500 mg, 2.4 mmol), methyl 3-mercaptopropanoate (317 mg, 2.6 mmol), $Pd_2(dba)_3$ (110 mg, 0.12 mmol), Xant-phos (138 mg, 0.24 mmol) and DIEA (620 mg, 4.8 mmol) were placed in 1,4-dioxane (20 mL). The reaction solution was refluxed and stirred for 16 hours, cooled to room temperature and concentrated in vacuum under reduced pressure, and the resulting residue was purified with silica gel column chromatography (petroleum ether/ethyl acetate) to give the target product (460 mg, yield 78%). $[M+H]^+$ 248.0

Step 2: Sodium 3-amino-5-chloropyrazine-2-thiolate

Under nitrogen, to a solution of methyl 3-((3-amino-5-chloropyrazin-2-yl)thio)propanoate (460 mg, 1.87 mmol) in tetrahydrofuran was added 2 M sodium ethoxide/ethanol solution. The reaction was stirred at room temperature for 2 hours and concentrated in vacuum under reduced pressure. To the resulting residue was added dichloromethane and the mixture was stirred. A solid was precipitated and the mixture was filtered. The filter cake was collected to give the target product (400 mg, yield 118%). [M+2H−Na]+162.0

Step 3: 3-((2-amino-3-chloropyridin-4-yl)thio)-6-chloropyrazin-2-amine

Under nitrogen, sodium 3-amino-5-chloropyrazine-2-thiolate (300 mg, 1.63 mmol), 3-chloro-4-iodopyridin-2-amine (414 mg, 1.63 mmol), $Pd_2(dba)_3$ (75 mg, 0.08 mmol), Xant-phos (93 mg, 0.16 mmol) and DIEA (0.55 mL, 3.26 mmol) were placed in 1,4-dioxane (20 mL). The reaction solution was refluxed and stirred for 4 hours and cooled to room temperature. The reaction solution was concentrated in vacuum under reduced pressure, and the resulting residue was purified with silica gel column chromatography (water/methanol) to give the target product (300 mg, yield 65%/). $[M+H]^+$ 288.0

The intermediates in the table below were prepared by following the steps for preparing intermediate I-A2 from corresponding starting materials and reagents:

| Inter-mediate | Structural formula | LC-MS $[M + H]^+$ |
|---|---|---|
| I-A9 | 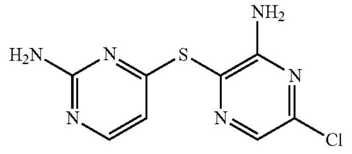 [SMILES: Nc1nccc(Sc2ncc(Cl)nc2N)n1] | 254.0 |
| I-A11 | 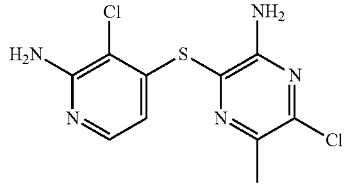 [SMILES: Cc1nc(Sc2ccnc(N)c2Cl)c(N)nc1Cl] | 302.0 |
| I-A12 | 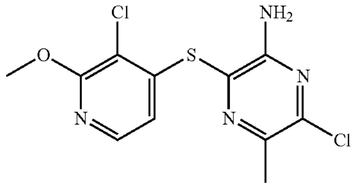 [SMILES: COc1nccc(Sc2nc(C)c(Cl)nc2N)c1Cl] | 317.0 |
| I-A13 | 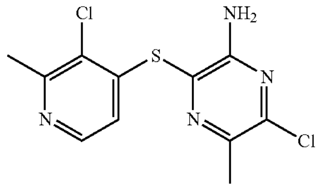 [SMILES: Cc1nc(Sc2ccnc(C)c2Cl)c(N)nc1Cl] | 301.0 |
| I-A14 | 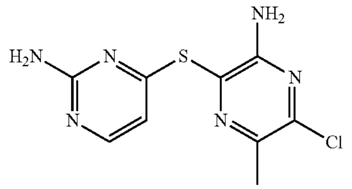 [SMILES: Cc1nc(Sc2ccnc(N)n2)c(N)nc1Cl] | 269.0 |
| I-A15 | 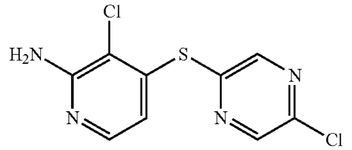 [SMILES: Nc1nccc(Sc2cnc(Cl)cn2)c1Cl] | 273.0 |
| I-A16 | 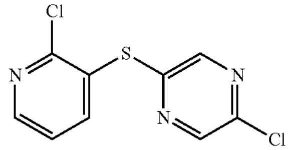 [SMILES: Clc1cnc(Sc2cccnc2Cl)cn1] | 258.0 |
| I-A17 | 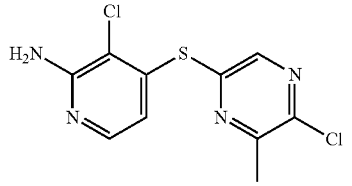 [SMILES: Cc1nc(Sc2ccnc(N)c2Cl)cnc1Cl] | 287.0 |

-continued
| Intermediate | Structural formula | LC-MS [M + H]+ |
|---|---|---|
| I-A18 | 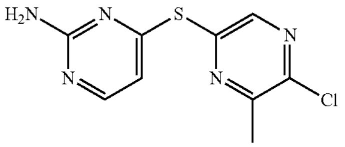 [SMILES: Cc1nc(Sc2ccnc(N)n2)cnc1Cl] | 254.0 |
| I-A19 | 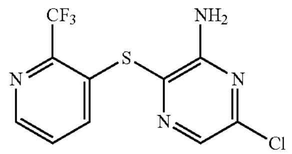 [SMILES: Nc1nc(Cl)cnc1Sc1cccnc1C(F)(F)F] | 307.0 |
| I-A21 | 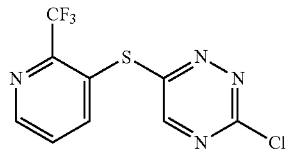 [SMILES: FC(F)(F)c1ncccc1Sc1cnc(Cl)nn1] | 293.0 |
| I-A22 | 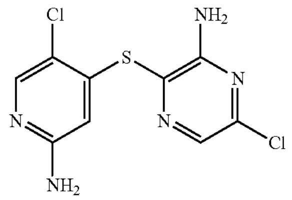 [SMILES: Nc1cc(Sc2ncc(Cl)nc2N)c(Cl)cn1] | 288.0 |
| I-A23 | 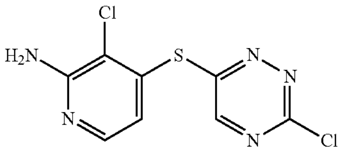 [SMILES: Nc1nccc(Sc2cnc(Cl)nn2)c1Cl] | 274.0 |
| I-A24 | 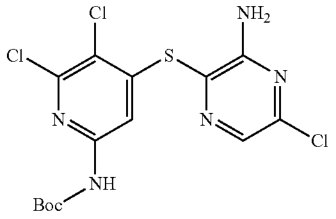 [SMILES: CC(C)(C)OC(=O)Nc1cc(Sc2ncc(Cl)nc2N)c(Cl)c(Cl)n1] | 444.0 |
| I-A25 | 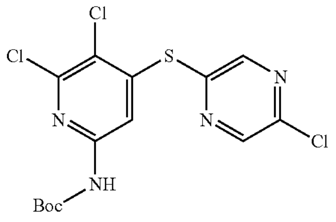 [SMILES: CC(C)(C)OC(=O)Nc1cc(Sc2cnc(Cl)cn2)c(Cl)c(Cl)n1] | $[M + Na]^+$ 428.9 |
| I-A26 | 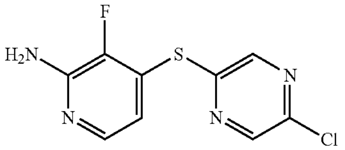 [SMILES: Nc1nccc(Sc2cnc(Cl)cn2)c1F] | 257.0 |
| I-A27 | 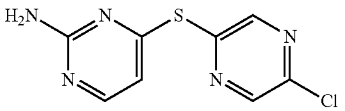 [SMILES: Nc1nccc(Sc2cnc(Cl)cn2)n1] | 240.1 |
-continued
| Intermediate | Structural formula | LC-MS [M + H]+ |
|---|---|---|
| I-A28 | 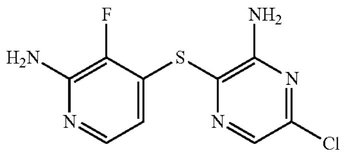 [SMILES: Nc1nc(Cl)cnc1Sc1ccnc(N)c1F] | 272.0 |
| I-A29 | 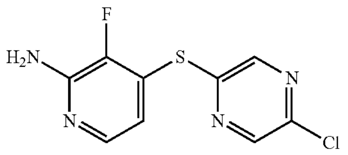 [SMILES: Nc1nccc(Sc2cnc(Cl)cn2)c1F] | 257.0 |
| I-A30 | 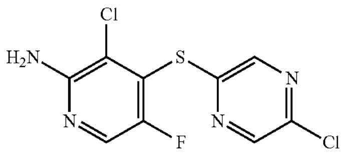 [SMILES: Nc1ncc(F)c(Sc2cnc(Cl)cn2)c1Cl] | 292.0 |
| I-A31 | 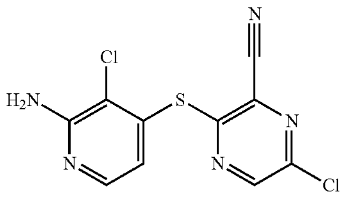 [SMILES: N#Cc1nc(Cl)cnc1Sc1ccnc(N)c1Cl] | 298.1 |
| I-A32 | 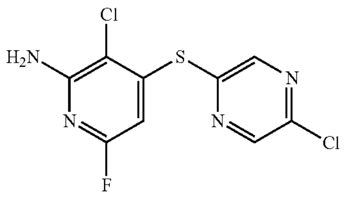 [SMILES: Nc1nc(F)cc(Sc2cnc(Cl)cn2)c1Cl] | 291.1 |
| I-A33 | 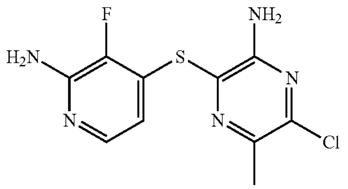 [SMILES: Cc1nc(Sc2ccnc(N)c2F)c(N)nc1Cl] | 286.0 |
| I-A34 | 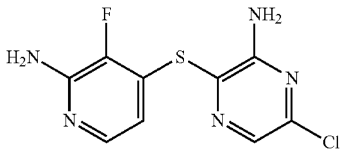 [SMILES: Nc1nc(Cl)cnc1Sc1ccnc(N)c1F] | 272.1 |
| I-A35 | 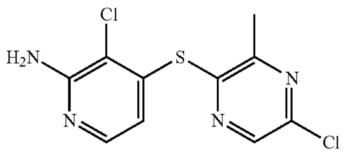 [SMILES: Cc1nc(Cl)cnc1Sc1ccnc(N)c1Cl] | 287.0 |

-continued

| Inter-mediate | Structural formula | LC-MS [M + H]$^+$ |
|---|---|---|
| I-A36 | 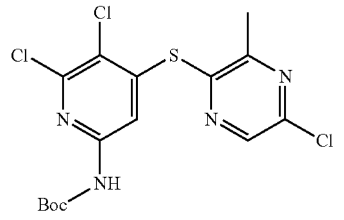 [SMILES: Cc1nc(Cl)cnc1Sc1cc(NC(=O)OC(C)(C)C)nc(Cl)c1Cl] | 443.0 |
| I-A37 | 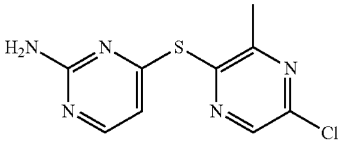 [SMILES: Cc1nc(Cl)cnc1Sc1ccnc(N)n1] | 254.0 |
| I-A38 | 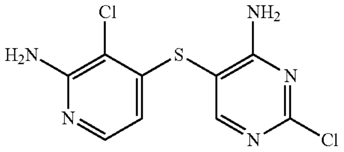 [SMILES: Nc1nc(Cl)ncc1Sc1ccnc(N)c1Cl] | 288.0 |
| I-A39 | 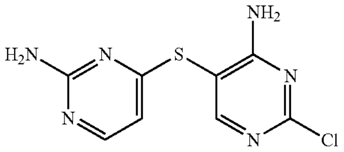 [SMILES: Nc1nccc(Sc2cnc(Cl)nc2N)n1] | 255.0 |
| I-A40 | 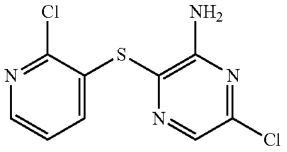 [SMILES: Nc1nc(Cl)cnc1Sc1cccnc1Cl] | 273.0 |

Intermediate I-A4

6-amino-2-hydroxy-5-iodo-3-methylpyrimidin-4(3H1)-one

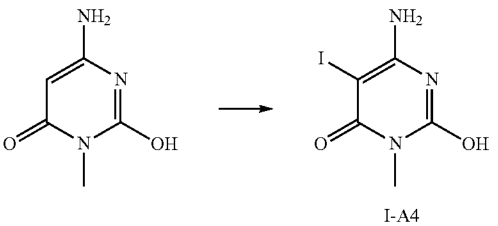

I-A4

Under nitrogen, 6-amino-2-hydroxy-3-methylpyrimidin-4(3H)-one (1.41 g, 10 mmol) and NIS (2.47 g, 11 mmol) were placed in tetrahydrofuran (20 mL) and stirred at room temperature for 16 hours. The mixture was filtered, and the filter cake was collected to give the target product (2.40 g, yield 90%). [M+H]$^+$ 267.9

Intermediate I-A8

Tert-butyl (8-bromo-5-(methylsulfinyl)imidazo[1,2-c]pyrimidin-7-yl)(tert-butoxycarbonyl)carbamate

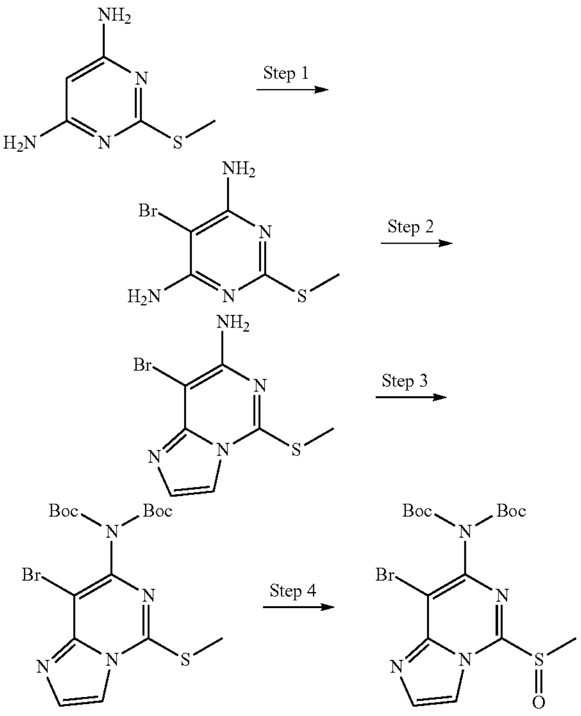

I-A8

Step 1: 5-bromo-2-(methylthio)pyrimidine-4,6-diamine

At 0° C., to a solution of 2-(methylthio)pyrimidine-4,6-diamine (5 g, 32 mmol) in N,N-dimethylformamide (50 mL) was added NBS (6.2 g, 35 mmol). The reaction was stirred at room temperature for 12 hours, and the reaction solution was poured into water (200 mL), filtered and dried to give the target product as a yellow solid (5.7 g, yield 76%). [M+H]$^+$ 234.9, 236.9

Step 2: 8-bromo-5-(methylthio)imidazo[1,2-c]pyrimidin-7-amine

To a solution of 5-bromo-2-(methylthio)pyrimidine-4,6-diamine (5.7 g, 24.2 mmol) in N,N-dimethylformamide (70 mL) was added 40% 2-chloroacetaldehyde aqueous solution (7.1 g, 36 mmol). The reaction was stirred at 80° C. for 2 hours, and the reaction solution was poured into water (500 mL), adjusted with solid sodium hydroxide to a pH value of 10 and extracted with ethyl acetate. The organic phases were collected and combined, and concentrated in vacuum under reduced pressure, and the resulting residue was purified with silica gel column chromatography (petroleum ether/ethyl acetate) to give the target product (3.0 g, yield 48%). [M+H]$^+$ 258.9, 260.9

Step 3: Tert-butyl (8-bromo-5-(methylthio)imidazo[1,2-c]pyrimidin-7-yl)(tert-butoxycarbonyl)carbamate To a solution of 8-bromo-5-(methylthio)imidazo[1,2-c]pyrimidin-7-amine (3.0 g, 11.6 mmol) in tetrahydrofuran (40 mL) were added $(Boc)_2O$ (7.6 g, 24.8 mmol) and DMAP (283 mg, 2.3 mmol). The reaction was stirred at room temperature for 12 hours, and the reaction solution was poured into water (200 mL) and extracted with ethyl acetate. The organic phases were collected and combined, and concentrated in vacuum under reduced pressure, and the resulting residue was purified with silica gel column chromatography (petroleum ether/ethyl acetate) to give the target product (3.6 g, yield 68%). $[M+H]^+$ 459.2, 461.2. $^1H$ NMR (400 MHz, $CDCl_3$): δ 7.71 (d, J=1.4 Hz, 1H), 7.57 (d, J=1.4 Hz, 1H), 2.72 (s, 3H), 1.42 (s, 18H).

Step 4: Tert-butyl (8-bromo-5-(methylsulfinyl)imidazo[1,2-c]pyrimidin-7-yl)(tert-butoxycarbonyl) carbamate At 0° C., to a solution of tert-butyl (8-bromo-5-(methylthio)imidazo[1,2-c]pyrimidin-7-yl)(tert-butoxycarbonyl) carbamate (400 mg, 0.87 mmol) in dichloromethane (10 mL) was added m-chloroperoxybenzoic acid (530 mg, 2.6 mmol). The reaction was stirred at 0° C. for 2 hours, and a saturated sodium hydrogen sulfite aqueous solution (2 mL) was added thereto. The reaction solution was adjusted with a saturated sodium bicarbonate aqueous solution to a pH value of 8 and extracted with dichloromethane. The organic phases were combined, dried over anhydrous sodium sulfate, and concentrated to give a crude target product (500 mg, yield 120%), which was used in the reaction of the next step directly. $[M+H]^+$ 475.0

Intermediates I-B1 and I-B2

Enantiomers of 1-(2,3-dichlorophenyl)-2-methyl-6-oxo-1,6-dihydropyrimidin-4-yl 2,4,6-triisopropylbenzenesulfonate

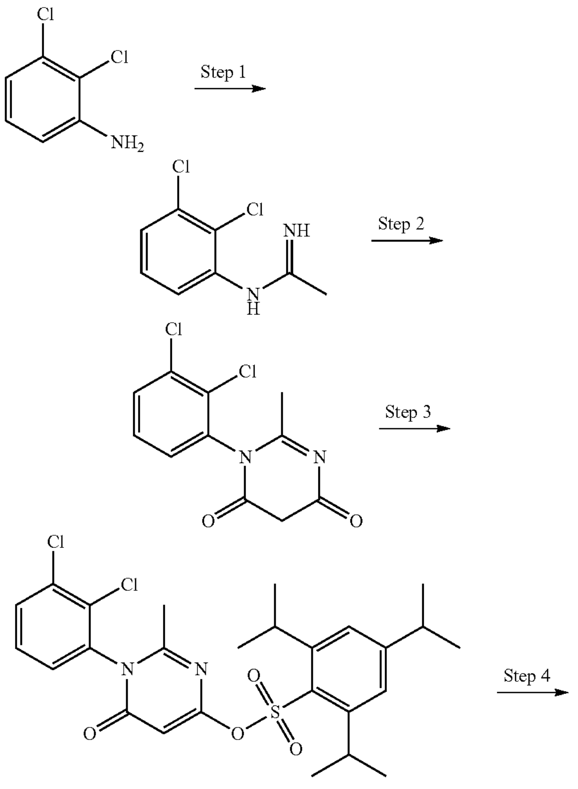

-continued

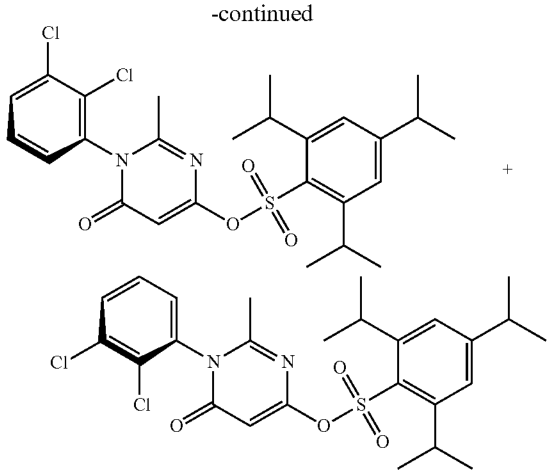

I-B1 + I-B2

Step 1: N-(2,3-dichlorophenyl)acetimidamide 2,3-dichloroaniline (13.0 g, 80.0 mmol) was placed in 1 M hydrogen chloride/acetonitrile (160 mL, 160 mmol). The reaction was stirred at 120° C. for 16 hours and concentrated in vacuum under reduced pressure to give the target product (19.5 g, yield 120/6), which was used in the reaction of the next step directly.

Step 2: 1-(2,3-dichlorophenyl)-2-methylpyrimidine-4,6(1H,5H)-dione

N-(2,3-dichlorophenyl)acetimidamide (19.5 g, 80 mmol) and diethyl malonate (25.6 g, 160 mmol) were placed in ethanol (80 mL), and to the solution was added 2 M sodium ethoxide/ethanol solution (120 mL, 240 mmol). The reaction was stirred at 120° C. for 16 hours and concentrated in vacuum under reduced pressure. The resulting residue was dissolved in water (100 mL), and the solution was adjusted with 6 M hydrochloric acid to a pH value of 2, and a solid was precipitated. The mixture was filtered, and the filter cake was collected and dried under reduced pressure to give the target product (10.5 g, yield 49%). $[M+H]^+$ 271.0

Step 3: 1-(2,3-dichlorophenyl)-2-methyl-6-oxo-1,6-dihydropyrimidin-4-yl 2,4,6-triisopropylbenzenesulfonate To a solution of 3-(2,3-dichlorophenyl)-6-hydroxy-2-methylpyrimidin-4(3H)-one (10.5 g, 38.7 mmol) and 2,4,6-triisopropylbenzenesulfonic acid (17.7 g, 58.5 mmol) in dichloromethane (50 mL) were added DMAP (240 mg, 1.9 mmol) and triethylamine (9.9 g, 97.4 mmol). The reaction was stirred at room temperature for 2 hours and concentrated in vacuum under reduced pressure. The resulting residue was purified with silica gel column chromatography (ethyl acetate/petroleum ether=1/3) to give the target product (18.0 g, yield 87%). $[M+H]^+$ 537.2

Step 4: Enantiomers of 1-(2,3-dichlorophenyl)-2-methyl-6-oxo-1,6-dihydropyrimidin-4-yl 2,4,6-triisopropylbenzenesulfonate 1-(2,3-dichlorophenyl)-2-methyl-6-oxo-1,6-dihydropyrimidin-4-yl 2,4,6-triisopropylbenzenesulfonate (19.0 g)

was resolved by chiral HPLC to obtain a pair of enantiomers. Chiral HPLC resolution conditions: column: IG-H (0.46 cm I.D.×15 cm L); mobile phase: carbon dioxide/ethanol=60:40; flow rate: 2.5 mL/minute; detector: UV 254 nm. First eluent (intermediate I-B2, 8.66 g, RT=0.808 minutes), ee %=100%. Second eluent (intermediate 1-B1, 9.66 g, RT=1.236 minutes), ee %=99.94%.

The intermediates in the table below were prepared by following the steps 1-3 for preparing intermediates I-B1 and I-B2 from corresponding starting materials and reagents:

| Intermediates | Structural formula | LC-MS [M + H]$^+$ |
|---|---|---|
| I-B3 | 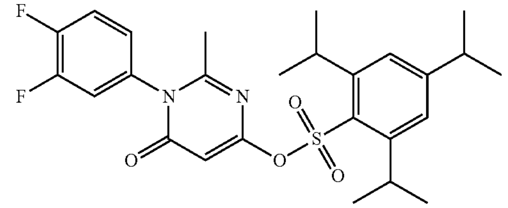 [SMILES: Cc1nc(OS(=O)(=O)c2c(C(C)C)cc(C(C)C)cc2C(C)C)cc(=O)n1-c1ccc(F)c(F)c1] | 505.2 |
| I-B5 | 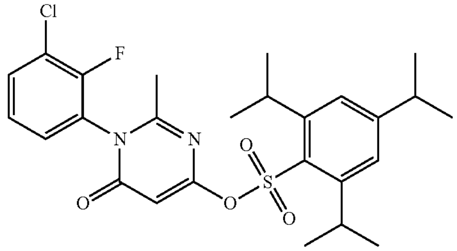 [SMILES: Cc1nc(OS(=O)(=O)c2c(C(C)C)cc(C(C)C)cc2C(C)C)cc(=O)n1-c1cccc(Cl)c1F] | 521.2 |
| I-B6 | 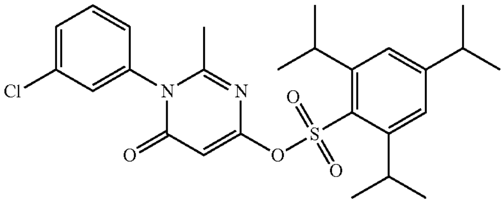 [SMILES: Cc1nc(OS(=O)(=O)c2c(C(C)C)cc(C(C)C)cc2C(C)C)cc(=O)n1-c1cccc(Cl)c1] | 503.1 |
| I-B7 | 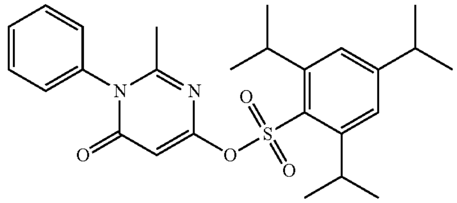 [SMILES: Cc1nc(OS(=O)(=O)c2c(C(C)C)cc(C(C)C)cc2C(C)C)cc(=O)n1-c1ccccc1] | 469.2 |
| I-B8 | 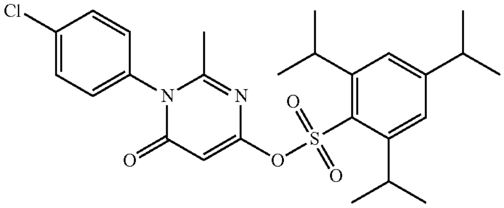 [SMILES: Cc1nc(OS(=O)(=O)c2c(C(C)C)cc(C(C)C)cc2C(C)C)cc(=O)n1-c1ccc(Cl)cc1] | 503.2 |
| I-B9 | 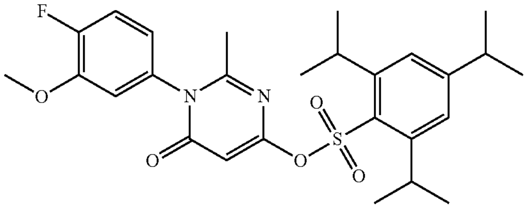 [SMILES: COc1cc(-n2c(C)nc(OS(=O)(=O)c3c(C(C)C)cc(C(C)C)cc3C(C)C)cc2=O)ccc1F] | 517.2 |

-continued
| Intermediates | Structural formula | LC-MS [M + H]+ |
|---|---|---|
| I-B10 | 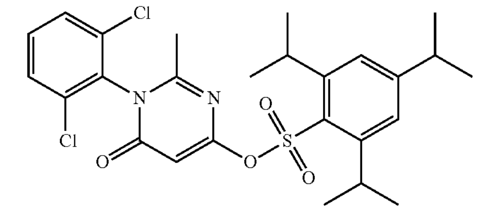 | 537.1 |
| I-B11 | 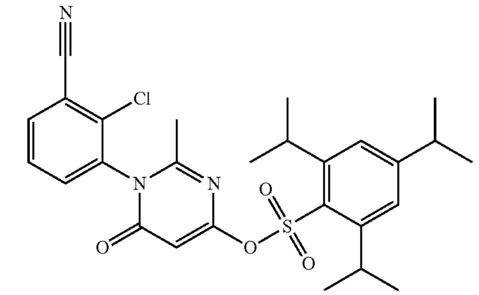 [SMILES: Cc1nc(OS(=O)(=O)c2c(C(C)C)cc(C(C)C)cc2C(C)C)cc(=O)n1-c1cccc(C#N)c1Cl] | 528.2 |
| I-B12 | 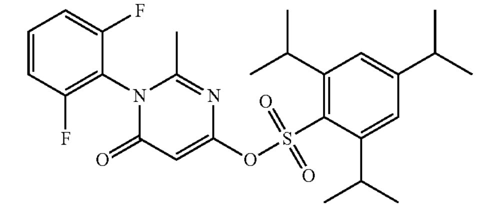 [SMILES: Cc1nc(OS(=O)(=O)c2c(C(C)C)cc(C(C)C)cc2C(C)C)cc(=O)n1-c1c(F)cccc1F] | 505.2 |
| I-B14 | 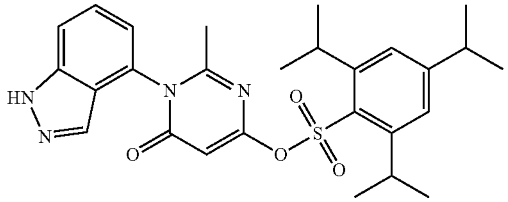 [SMILES: Cc1nc(OS(=O)(=O)c2c(C(C)C)cc(C(C)C)cc2C(C)C)cc(=O)n1-c1cccc2[nH]ncc12] | 509.2 |
| I-B15 | 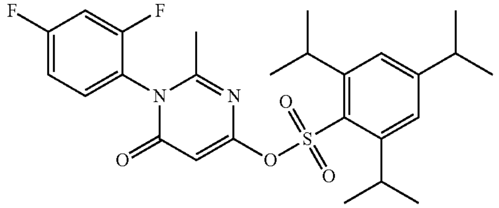 | 505.2 |
| I-B16 | 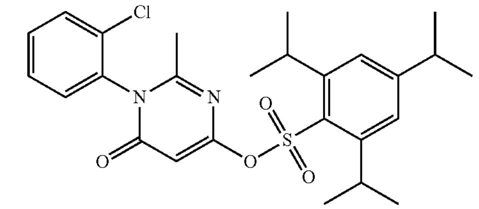 [SMILES: Cc1nc(OS(=O)(=O)c2c(C(C)C)cc(C(C)C)cc2C(C)C)cc(=O)n1-c1ccccc1Cl] | 503.2 |

-continued
| Intermediates | Structural formula | LC-MS [M + H]+ |
|---|---|---|
| I-B17 | 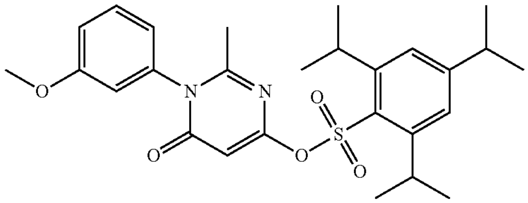 | 499.2 |
| I-B18 | 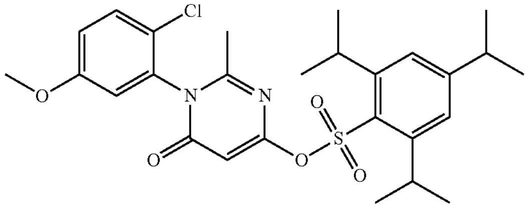 [SMILES: COc1ccc(Cl)c(-n2c(C)nc(OS(=O)(=O)c3c(C(C)C)cc(C(C)C)cc3C(C)C)cc2=O)c1] | 533.2 |
| I-B19 | 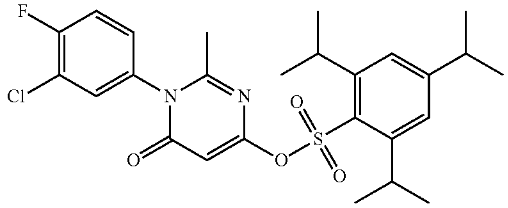 [SMILES: Cc1nc(OS(=O)(=O)c2c(C(C)C)cc(C(C)C)cc2C(C)C)cc(=O)n1-c1ccc(F)c(Cl)c1] | 521.1 |
| I-B20 | 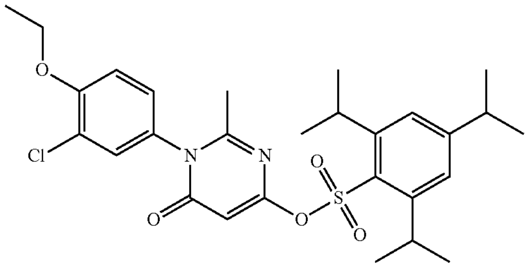 [SMILES: CCOc1ccc(-n2c(C)nc(OS(=O)(=O)c3c(C(C)C)cc(C(C)C)cc3C(C)C)cc2=O)cc1Cl] | 547.2 |
| I-B23 | 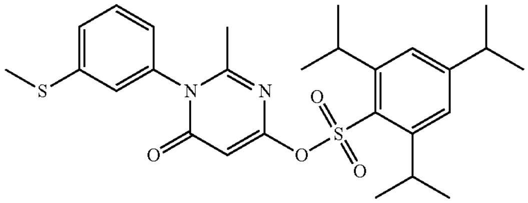 [SMILES: CSc1cccc(-n2c(C)nc(OS(=O)(=O)c3c(C(C)C)cc(C(C)C)cc3C(C)C)cc2=O)c1] | 515.2 |
| I-B25 | 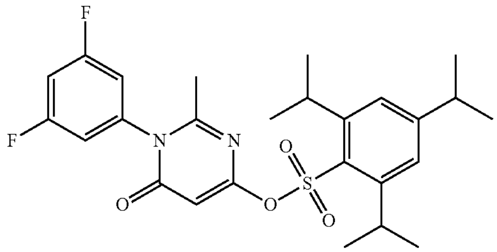 [SMILES: Cc1nc(OS(=O)(=O)c2c(C(C)C)cc(C(C)C)cc2C(C)C)cc(=O)n1-c1cc(F)cc(F)c1] | 505.2 |

-continued
| Intermediates | Structural formula | LC-MS [M + H]$^+$ |
| --- | --- | --- |
| I-B27 | 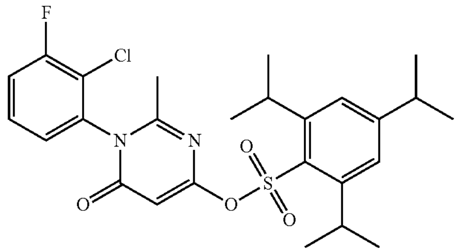 [SMILES: Cc1nc(OS(=O)(=O)c2c(C(C)C)cc(C(C)C)cc2C(C)C)cc(=O)n1-c1cccc(F)c1Cl] | 521.2 |
| I-B28 | 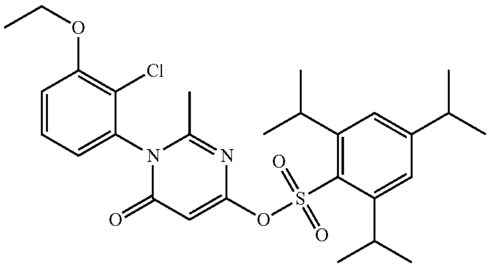 [SMILES: CCOc1cccc(-n2c(C)nc(OS(=O)(=O)c3c(C(C)C)cc(C(C)C)cc3C(C)C)cc2=O)c1Cl] | 547.2 |
| I-B29 | 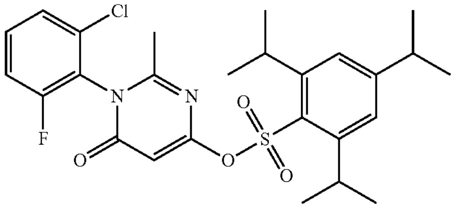 [SMILES: Cc1nc(OS(=O)(=O)c2c(C(C)C)cc(C(C)C)cc2C(C)C)cc(=O)n1-c1c(F)cccc1Cl] | 521.1 |
| I-B30 | 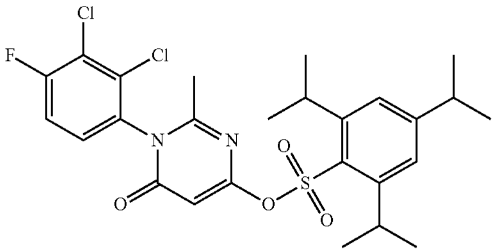 [SMILES: Cc1nc(OS(=O)(=O)c2c(C(C)C)cc(C(C)C)cc2C(C)C)cc(=O)n1-c1ccc(F)c(Cl)c1Cl] | 555.2 |
| I-B31 | 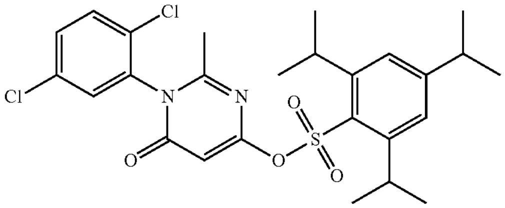 [SMILES: Cc1nc(OS(=O)(=O)c2c(C(C)C)cc(C(C)C)cc2C(C)C)cc(=O)n1-c1cc(Cl)ccc1Cl] | 537.2 |
| I-B34 | 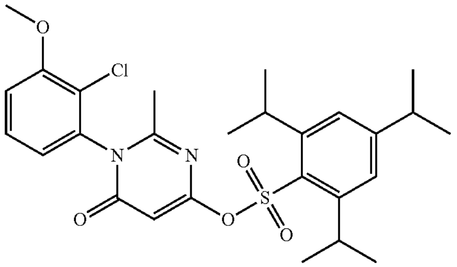 [SMILES: COc1cccc(-n2c(C)nc(OS(=O)(=O)c3c(C(C)C)cc(C(C)C)cc3C(C)C)cc2=O)c1Cl] | 533.1 |

-continued
| Intermediates | Structural formula | LC-MS [M + H]+ |
| --- | --- | --- |
| I-B37 | 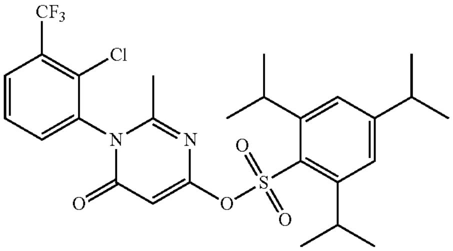 [SMILES: Cc1nc(OS(=O)(=O)c2c(C(C)C)cc(C(C)C)cc2C(C)C)cc(=O)n1-c1cccc(C(F)(F)F)c1Cl] | 571.2 |
| I-B38 | 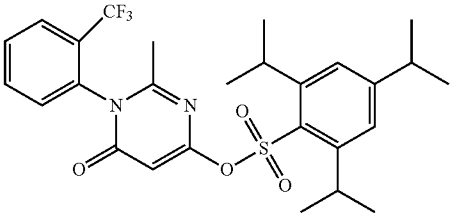 [SMILES: Cc1nc(OS(=O)(=O)c2c(C(C)C)cc(C(C)C)cc2C(C)C)cc(=O)n1-c1ccccc1C(F)(F)F] | 537.2 |
The intermediates in the table below were prepared by following the steps 1-3 for preparing intermediates I-B1 and I-B2 from corresponding substituted aniline, diethyl 2-methylmalonate or diethyl 2-fluoromalonate, and reagents:
| Intermediates | Structural formula | LC-MS [M + H]+ |
| --- | --- | --- |
| I-B4 | 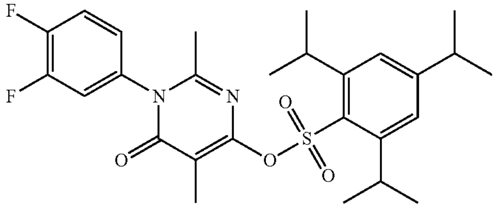 [SMILES: Cc1c(OS(=O)(=O)c2c(C(C)C)cc(C(C)C)cc2C(C)C)nc(C)n(-c2ccc(F)c(F)c2)c1=O] | 519.2 |
| I-B13 | 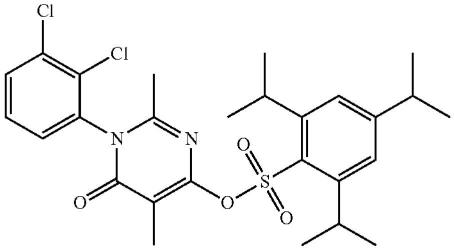 | 551.1 |
| I-B24 | 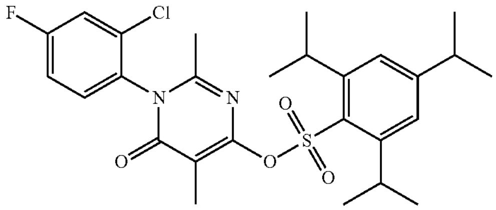 [SMILES: Cc1c(OS(=O)(=O)c2c(C(C)C)cc(C(C)C)cc2C(C)C)nc(C)n(-c2ccc(F)cc2Cl)c1=O] | 535.2 |

-continued

| Intermediates | Structural formula | LC-MS [M + H]+ |
|---|---|---|
| I-B35 | 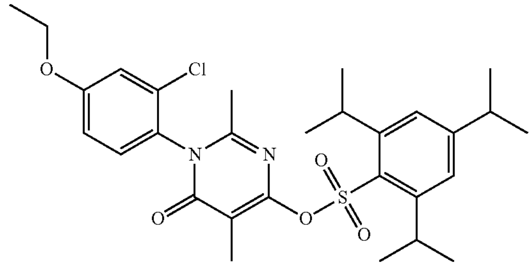 [SMILES: CCOc1ccc(-n2c(C)nc(OS(=O)(=O)c3c(C(C)C)cc(C(C)C)cc3C(C)C)c(C)c2=O)c(Cl)c1] | 561.2 |
| I-B42 | 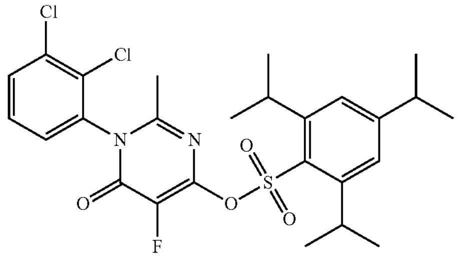 [SMILES: Cc1nc(OS(=O)(=O)c2c(C(C)C)cc(C(C)C)cc2C(C)C)c(F)c(=O)n1-c1cccc(Cl)c1Cl] | 555.1 |

The intermediates in the table below were prepared from intermediate I-B13 by chiral resolution by following the step 4 for preparing intermediates I-B1 and I-B2:

Chiral HPLC resolution conditions: column: IG-H (0.46 cm I.D.×15 cm L); mobile phase: carbon dioxide/ethanol=80:20; flow rate: 2.5 mL/minute; detector: UV 254 nm. First eluent (intermediate I-B21, RT=2.784 minutes), ee %=100%. Second eluent (intermediate I-B22, RT=3.119 minutes), ee %=99.92%.

| Intermediates | Structural formula | LC-MS [M + H]+ |
|---|---|---|
| I-B21<br>I-B22 | 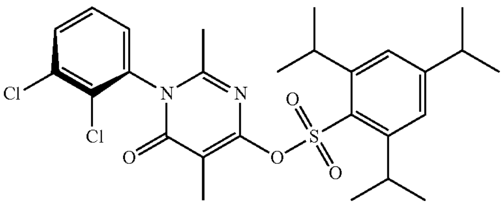<br>+<br>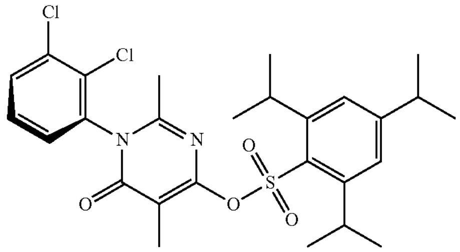 | 551.1<br>551.1 |

Intermediate I-B26

1-(2-chloropyridin-4-yl)-2-methyl-6-oxo-1,6-dihydropyrimidin-4-yl 2,4,6-triisopropylbenzenesulfonate

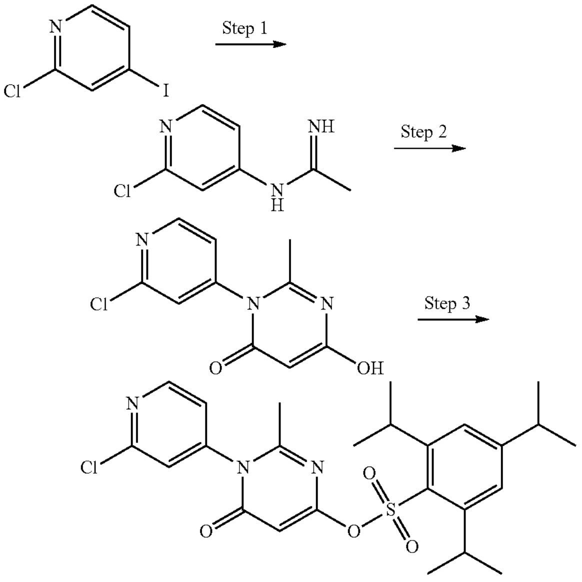

I-B26

Step 1: N-(2-chloropyridin-4-yl)acetimidamide 2-chloro-4-iodopyridine (3.78 g, 15.8 mmol), acetimidamide hydrochloride (1.92 g, 20.3 mmol), cuprous iodide (301 mg, 1.58 mmol), cesium carbonate (13.2 g, 40.6 mmol) and N,N-dimethylformamide (22 mL) were placed in a sealed tube. The reaction was stirred at 90° C. for 12 hours and cooled to room temperature, and acetonitrile (200 mL) was added thereto. The mixture was filtered, and the filtrate was concentrated in vacuum under reduced pressure to give the target product (1.75 g, yield 70%), which was used in the reaction of the next step directly. $[M+H]^+$ 170.0

Step 2: 3-(2-chloropyridin-4-yl)-6-hydroxy-2-methylpyrimidin-4(3H)-one

N-(2-chloropyridin-4-yl)acetimidamide (1.70 g, 10.0 mmol), bis(2,4,6-trichlorophenyl)malonate (5.55 g, 12 mmol) and tetrahydrofuran (20 mL) were placed in a sealed tube. The reaction was stirred at 90° C. for 16 hours and concentrated in vacuum under reduced pressure. The resulting residue was purified with silica gel column chromatography (water/methanol) to give the target product (1.19 g, yield 50%). $[M+H]^+$ 238.0

Step 3: 1-(2-chloropyridin-4-yl)-2-methyl-6-oxo-1,6-dihydropyrimidin-4-yl 2,4,6-triisopropylbenzenesulfonate The target product was prepared by following the step 3 for preparing intermediates I-B1 and I-B2 from corresponding starting materials and reagents. $[M+H]^+$ 504.2

The intermediates in the table below were prepared by following the steps for preparing intermediate I-B26 from corresponding starting materials and reagents:

| Intermediates | Structural formula | LC-MS $[M + H]^+$ |
|---|---|---|
| I-B32 | 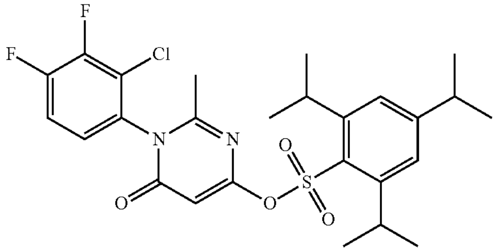 [SMILES: Cc1nc(OS(=O)(=O)c2c(C(C)C)cc(C(C)C)cc2C(C)C)cc(=O)n1-c1ccc(F)c(F)c1Cl] | 539.2 |
| I-B33 | 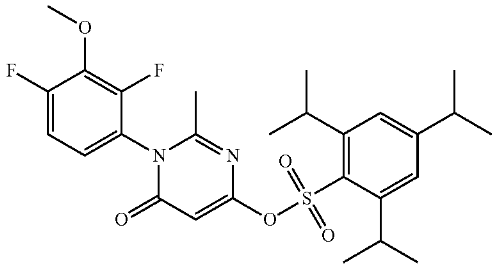 [SMILES: COc1c(F)ccc(-n2c(C)nc(OS(=O)(=O)c3c(C(C)C)cc(C(C)C)cc3C(C)C)cc2=O)c1F] | 535.2 |

-continued
| Intermediates | Structural formula | LC-MS [M + H]$^+$ |
|---|---|---|
| I-B36 | 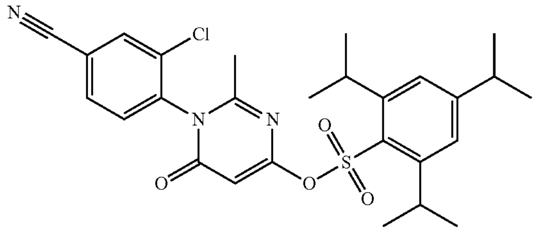 [SMILES: Cc1nc(OS(=O)(=O)c2c(C(C)C)cc(C(C)C)cc2C(C)C)cc(=O)n1-c1ccc(C#N)cc1Cl] | 528.2 |
| I-B39 | 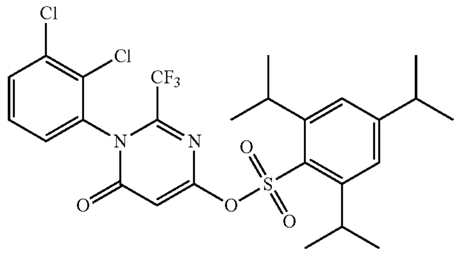 [SMILES: CC(C)c1cc(C(C)C)c(S(=O)(=O)Oc2cc(=O)n(-c3cccc(Cl)c3Cl)c(C(F)(F)F)n2)c(C(C)C)c1] | 591.1 |
| I-B40 | 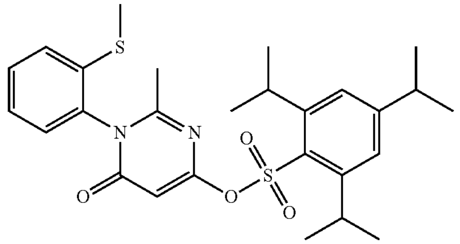 [SMILES: CSc1ccccc1-n1c(C)nc(OS(=O)(=O)c2c(C(C)C)cc(C(C)C)cc2C(C)C)cc1=O] | 515.2 |
| I-B41 | 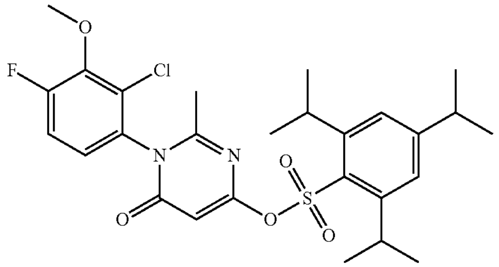 [SMILES: COc1c(F)ccc(-n2c(C)nc(OS(=O)(=O)c3c(C(C)C)cc(C(C)C)cc3C(C)C)cc2=O)c1Cl] | 551.2 |
| I-B43 | 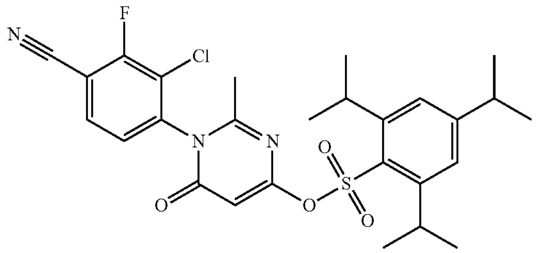 [SMILES: Cc1nc(OS(=O)(=O)c2c(C(C)C)cc(C(C)C)cc2C(C)C)cc(=O)n1-c1ccc(C#N)c(F)c1Cl] | 546.2 |
| I-B44 | 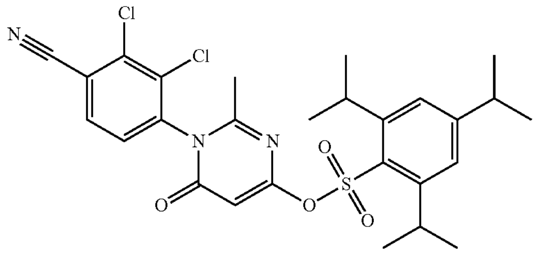 [SMILES: Cc1nc(OS(=O)(=O)c2c(C(C)C)cc(C(C)C)cc2C(C)C)cc(=O)n1-c1ccc(C#N)c(Cl)c1Cl] | 562.1 |

-continued
| Intermediates | Structural formula | LC-MS [M + H]+ |
|---|---|---|
| I-B45 | 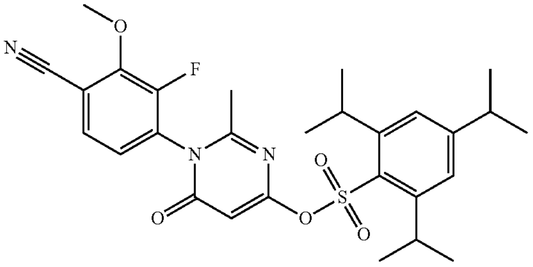 [SMILES: COc1c(C#N)ccc(-n2c(C)nc(OS(=O)(=O)c3c(C(C)C)cc(C(C)C)cc3C(C)C)cc2=O)c1F] | 542.1 |
| I-B46 | 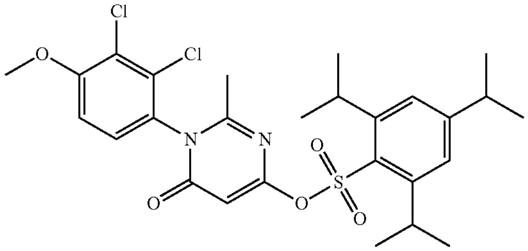 [SMILES: COc1ccc(-n2c(C)nc(OS(=O)(=O)c3c(C(C)C)cc(C(C)C)cc3C(C)C)cc2=O)c(Cl)c1Cl] | 567.1 |
| I-B47 | 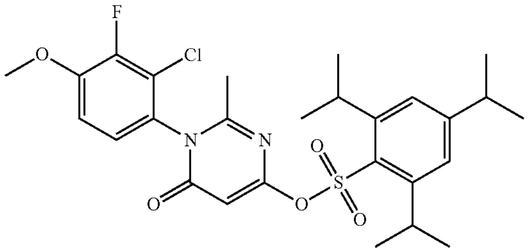 [SMILES: COc1ccc(-n2c(C)nc(OS(=O)(=O)c3c(C(C)C)cc(C(C)C)cc3C(C)C)cc2=O)c(Cl)c1F] | 551.2 |
Intermediate I-B48
2-amino-1-(2,3-dichlorophenyl)-6-oxo-1,6-dihydropyrimidin-4-yl 2,4,6-triisopropylbenzenesulfonate
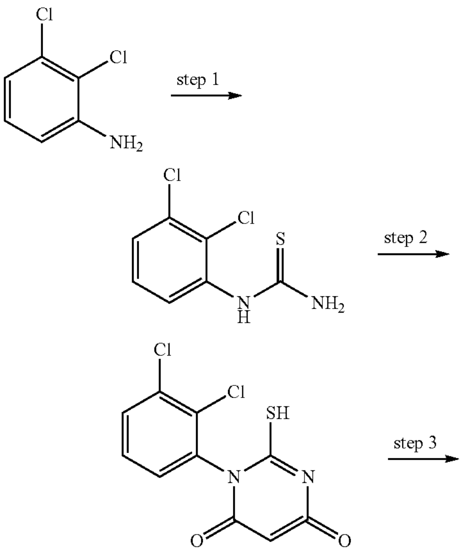
-continued
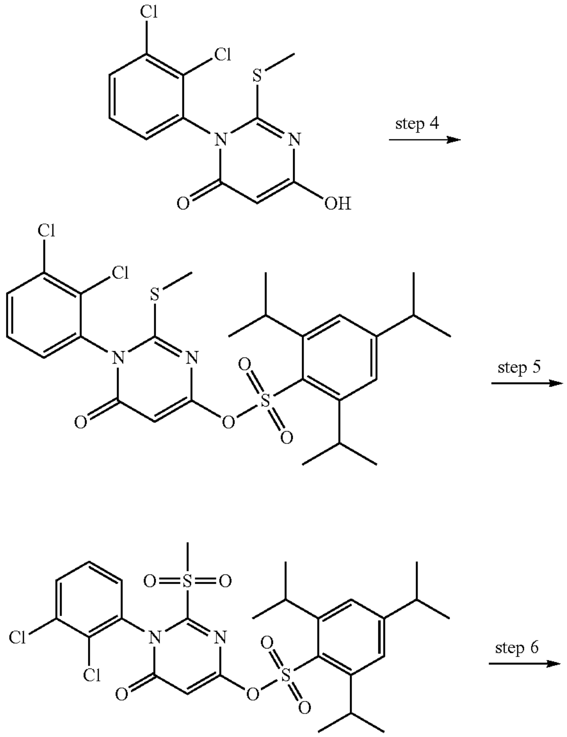

-continued

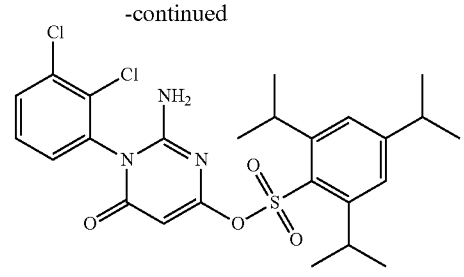

I-B48

Step 1: 1-(2,3-dichlorophenyl)thiourea

The solution of 2,3-dichloroaniline (6.48 g, 40 mmol) and benzoyl isothiocyanate (9.79 g, 60 mmol) in acetone (20 mL) was stirred at reflux for 30 minutes. The reaction solution was poured into ice-water, filtered. The filter cake was washed with cold acetone, collected, added with 1 M NaOH aqueous solution (50 mL) and stirred at 80° C. for 3 hours. After cooling to room temperature, the mixture was extracted with DCM. The organic layer was collected and concentrated in vacuum under reduced pressure. The residue was purified by silica gel column chromatography (eluting with PE/EA) to give target product as white solid (8.2 g, 93% yield).

Step 2: 3-(2,3-dichlorophenyl)-6-hydroxy-2-mercaptopyrimidin-4(3H)-one

The solution of 1-(2,3-dichlorophenyl)thiourea (1.1 g, 5.0 mmol), diethyl malonate (1.6 g, 10.0 mmol), 18-crown-6 (661 mg, 2.5 mmol) and 2 M NaOMe/MeOH (5.0 mL, 10.0 mmol) in 1,4-dioxane (15 mL) was stirred at 70° C. for 3 hours. The reaction solution was purified by silica gel column chromatography (eluting with DCM/MeOH) to give target product as yellow solid (1.8 g, 99% yield). $[M+H]^+$ 289.0

Step 3: 3-(2,3-dichlorophenyl)-6-hydroxy-2-(methylthio)pyrimidin-4(3H)-one

At 0° C., to the solution of 3-(2,3-dichlorophenyl)-6-hydroxy-2-mercaptopyrimidin-4(3H)-one (1.45 g, 5.0 mmol) in THF (10 mL) was added MeI (1.42 g, 10.0 mmol) and stirred at room temperature for 3 hours. The reaction solution was concentrated in vacuum under reduced pressure. The residue was purified by silica gel column chromatography (eluting with DCM/MeOH) to give target product as yellow oil (1.18 g, 78% yield).

Step 4: 1-(2,3-dichlorophenyl)-2-(methylthio)-6-oxo-1,6-dihydropyrimidin-4-yl 2,4,6-triisopropylbenzenesulfonate The solution of 3-(2,3-dichlorophenyl)-6-hydroxy-2-(methylthio)pyrimidin-4(3H)-one (1.18 g, 3.9 mmol), bis(2,4,6-trichlorophenyl) malonate (1.77 g, 5.9 mmol), DMAP (24 mg, 0.20 mmol) and $Et_3N$ (790 mg, 7.8 mmol) in DCM (25 mL) was stirred at room temperature for 2 hours. The reaction solution was concentrated in vacuum under reduced pressure. The residue was purified by silica gel column chromatography (eluting with PE/EA) to give target product as white solid (500 mg, 22% yield). $[M+H]^+$ 568.4

Step 5: 1-(2,3-dichlorophenyl)-2-(methylsulfonyl)-6-oxo-1,6-dihydropyrimidin-4-yl 2,4,6-triisopropylbenzenesulfonate At 0° C., to the solution of 1-(2,3-dichlorophenyl)-2-(methylthio)-6-oxo-1,6-dihydropyrimidin-4-yl 2,4,6-triisopropylbenzenesulfonate (500 mg, 0.88 mmol) in DCM (30 mL) was added the solution of m-CPBA (757 mg, 4.4 mmol) in DCM dropwise, and stirred at room temperature for 4 hours. The reaction solution was concentrated in vacuum under reduced pressure. The residue was purified by silica gel column chromatography (eluting with PE/EA) to give target product (420 mg, 80% yield).

Step 6: 2-amino-1-(2,3-dichlorophenyl)-6-oxo-1,6-dihydropyrimidin-4-yl 2,4,6-triisopropylbenzenesulfonate 1-(2,3-dichlorophenyl)-2-(methylsulfonyl)-6-oxo-1,6-dihydropyrimidin-4-yl 2,4,6-triisopropylbenzenesulfonate (420 mg, 0.70 mmol) was dissolved in 0.5 M $NH_3$/THF solution (7.0 mL, 3.5 mmol) and stirred at room temperature for 6 hours. The reaction solution was concentrated in vacuum under reduced pressure. The residue was purified by silica gel column chromatography (eluting with PE/EA) to give target product as yellow oil (120 mg, 48% yield). $[M+H]^+$ 538.2.

Intermediate I-C3

(R)-2-methyl-N—((S)-5-((trimethylsilyl)ethynyl)-1,3-dihydrospiro[indene-2,4'-piperidin]-3-yl)propane-2-sulfinamide

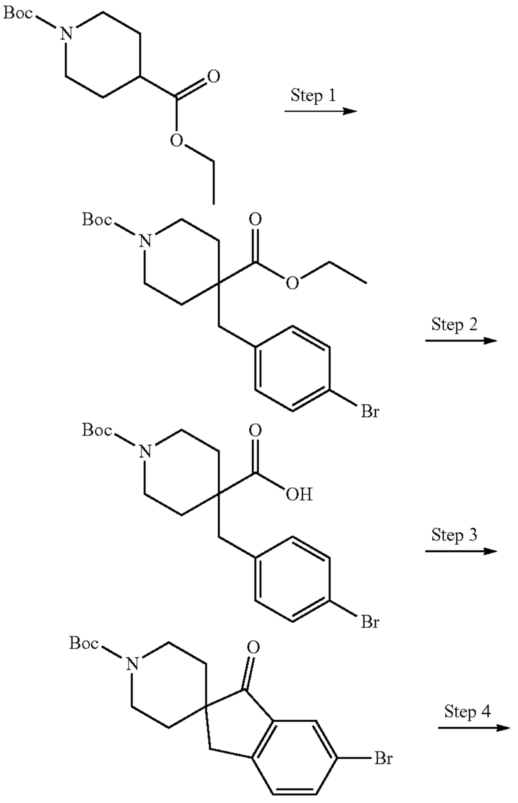

-continued

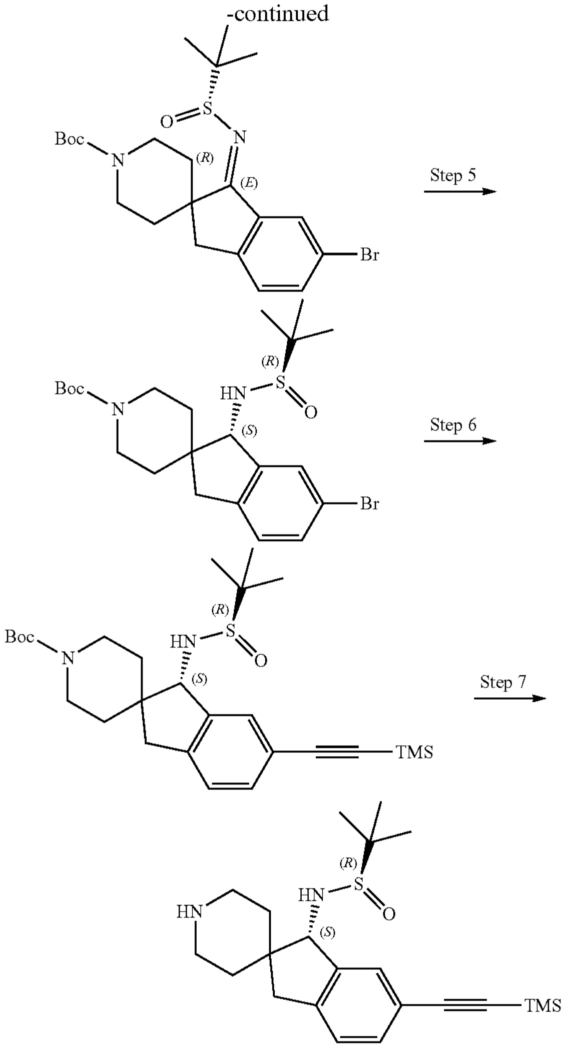

I-C3

Step 1: 1-(tert-butyl) 4-ethyl 4-(4-bromobenzyl) piperidine-1,4-dicarboxylate

At −78° C., under nitrogen, to a solution of 1-tert-butyl-4-ethylpiperidine-1,4-dicarboxylate (20.6 g, 80 mmol) in anhydrous tetrahydrofuran (100 mL) was added dropwise 2 M LDA/tetrahydrofuran solution (52 mL, 104 mmol). The reaction was stirred at −78° C. for 2 hours, and a solution of 1-bromo-4-(bromomethyl)benzene (19.4 g, 80 mmol) in anhydrous tetrahydrofuran was added dropwise thereto. The reaction was stirred at −78° C. for 3 hours and warmed to room temperature, and the reaction solution was poured into water and extracted with ethyl acetate. The organic phase was washed with saturated brine, dried over anhydrous sodium sulfate, and concentrated in vacuum under reduced pressure to give the target product as a white solid, which was used in the reaction of the next step directly.

Step 2: 4-(4-bromobenzyl)-1-(tert-butoxycarbonyl) piperidine-4-carboxylic acid 1-(tert-butyl) 4-ethyl 4-(4-bromobenzyl)piperidine-1,4-dicarboxylate (80 mmol) and lithium hydroxide (18.7 g, 780 mmol) were placed in ethanol (200 mL) and water (100 mL). The reaction was stirred at 90° C. for 16 hours and concentrated in vacuum under reduced pressure. The residue was dissolved in water and washed with ethyl acetate/petroleum ether (volume ratio 1:1). The aqueous phase was collected, adjusted with 6 M hydrochloric acid to a pH value of 3, and extracted with ethyl acetate. The organic phase was washed with saturated brine, dried over anhydrous sodium sulfate, and concentrated in vacuum under reduced pressure to give the target product as a white solid (34.0 g, two-step yield 107%), which was used in the reaction of the next step directly. $[M+H-56]^+$ 342.2

Step 3: Tert-butyl 6-bromo-1-oxo-1,3-dihydrospiro [indene-2,4'-piperidine]-1'-carboxylate 4-(4-bromobenzyl)-1-(tert-butoxycarbonyl)piperidine-4-carboxylic acid (34.0 g, 85 mmol) was placed in polyphosphoric acid (200 mL). The reaction was stirred at 120° C. for 16 hours, cooled to room temperature, and dissolved by adding water, and the mixture was adjusted with sodium hydroxide to a pH value of 9. To the solution was added $(Boc)_2O$, and the mixture was stirred at room temperature for 16 hours. The reaction solution was extracted with ethyl acetate, and the organic phase was collected and concentrated in vacuum under reduced pressure. The resulting residue was purified with silica gel column chromatography (petroleum ether/ethyl acetate) to give the target product as a yellow solid (23.4 g, yield 72%). $[M+H-56]^+$ 324.0

Step 4: Tert-butyl (R,E)-6-bromo-1-((tert-butylsulfinyl)imino)-1,3-dihydrospiro[indene-2,4'-piperidine]-1'-carboxylate Under nitrogen, tert-butyl 6-bromo-1-oxo-1,3-dihydrospiro[indene-2,4'-piperidine]-1'-carboxylate (23.4 g, 62 mmol) and (R)-2-methylpropane-2-sulfinamide (28.7 g, 237 mmol) were placed in $Ti(OEt)_4$ (200 mL). The reaction was stirred at 80° C. for 16 hours, and the reaction solution was poured into water/ethyl acetate and filtered. The organic phase was washed with saturated brine, dried over anhydrous sodium sulfate, and concentrated in vacuum under reduced pressure to give the target product, which was used in the reaction of the next step directly.

Step 5: Tert-butyl (S)-6-bromo-1-(((R)-tert-butylsulfinyl)amino)-1,3-dihydrospiro[indene-2,4'-piperidine]-1'-carboxylate Under nitrogen, tert-butyl (R,E)-6-bromo-1-((tert-butylsulfinyl)imino)-1,3-dihydrospiro[indene-2,4'-piperidine]-1'-carboxylate (62 mmol) was placed in anhydrous tetrahydrofuran (200 mL). Sodium borohydride (9.07 g, 240 mmol) was added in batches to the mixture at −78° C., and the resulting solution was stirred at this temperature for 30 minutes, warmed to room temperature, poured into water, and extracted with ethyl acetate. The organic phase was collected and concentrated in vacuum under reduced pressure, and the resulting residue was purified with silica gel column chromatography (petroleum ether/ethyl acetate) to give the target product as a yellow solid (14.5 g, yield 48%). $[M+H]^+$ 485.2

Step 6: Tert-butyl (S)-1-(((R)-tert-butylsulfinyl) amino)-6-((trimethylsilyl)ethynyl)-1,3-dihydrospiro [indene-2,4'-piperidine]-1'-carboxylate Under nitrogen, tert-butyl (S)-6-bromo-1-(((R)-tert-butylsulfinyl)amino)-1,3-dihydrospiro[indene-2,4'-piperidine]-1'-carboxylate (6.0 g, 12.4 mmol), ethynyltrimethylsilane (20 ml), $Pd(PPh_3)_2Cl_2$ (0.87 g, 1.2 mmol), cuprous iodide (0.24 g, 1.2 mmol), triethylamine (40 mL) and N,N-dimethylformamide (40 mL) were placed in a sealed tube. The reaction was stirred at 90° C. for 16 hours and concentrated in vacuum under reduced pressure, and the resulting residue was purified with silica gel column chromatography (petroleum ether/ethyl acetate) to give the target product.

Step 7: (R)-2-methyl-N—((S)-5-((trimethylsilyl)ethynyl)-1,3-dihydrospiro[indene-2,4'-piperidin]-3-yl)propane-2-sulfinamide To a solution of tert-butyl (S)-1-(((R)-tert-butylsulfinyl)amino)-6-((trimethylsilyl)ethynyl)-1,3-dihydrospiro[indene-2,4'-piperidine]-1'-carboxylate (12.4 mmol) in dichloromethane (60 mL) was added dropwise methanesulfonic acid (3.6 g, 37.1 mmol). The reaction was stirred at room temperature for 30 minutes, and the reaction solution was adjusted with aqueous ammonia to a pH value of 8 under ice bath cooling. The organic phase was collected and concentrated in vacuum under reduced pressure to give the target product as a brown solid (3.9 g, two-step yield 78%). $[M+H]^+$ 403.2

The intermediates in the table below were prepared by following the steps for preparing intermediate I-C3 from corresponding starting materials and reagents:

| Inter-medi-ates | Structural formula | LC-MS $[M+H]^+$ |
|---|---|---|
| I-C4 | 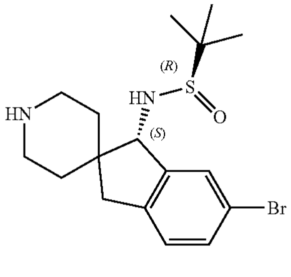 | 385.2 |
| I-C6 | 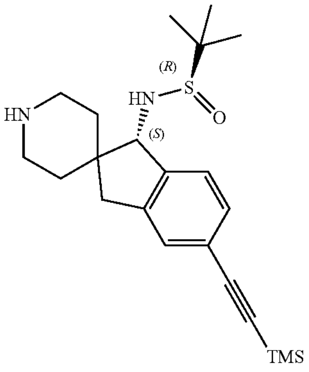 | 403.2 |

-continued

| Inter-medi-ates | Structural formula | LC-MS $[M+H]^+$ |
|---|---|---|
| I-C7 | 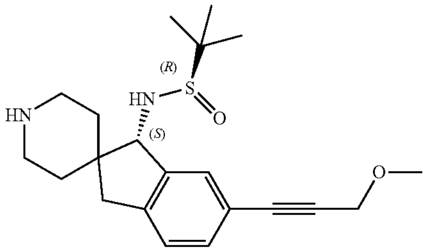 | 375.2 |
| I-C10 | 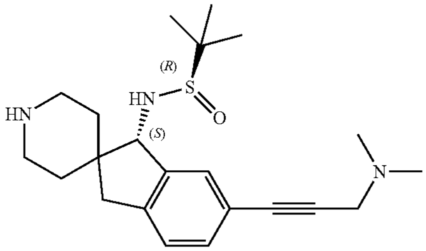 | 388.4 |
| I-C12 | 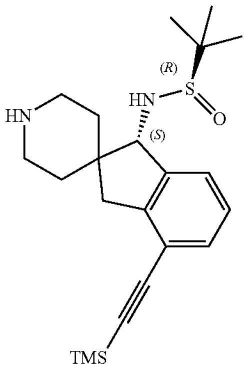 | 403.2 |
| I-C13 | 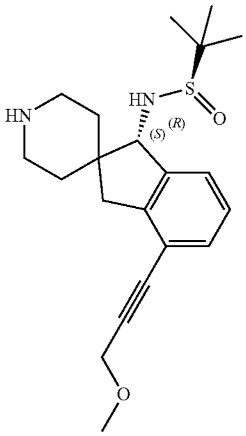 | 375.2 |

-continued
| Inter-medi-ates | Structural formula | LC-MS [M + H]+ |
| --- | --- | --- |
| I-C14 | 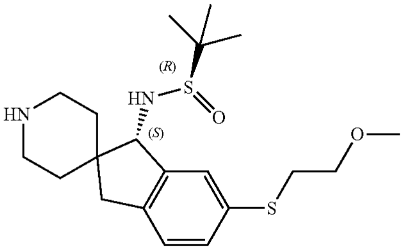 | 397.2 |
| I-C15 | 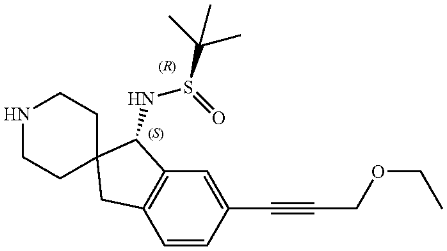 | 389.2 |
| I-C16 | 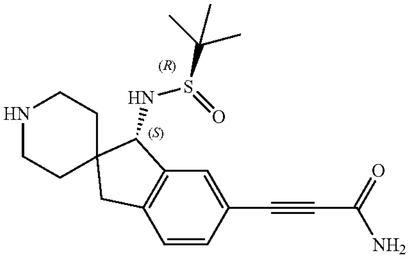 | 374.2 |
| I-C17 | 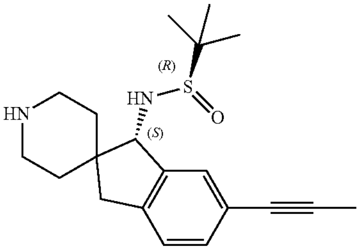 | 345.2 |
| I-C18 | 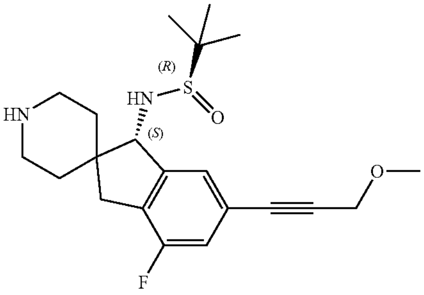 | 393.2 |
-continued
| Inter-medi-ates | Structural formula | LC-MS [M + H]+ |
| --- | --- | --- |
| I-C19 | 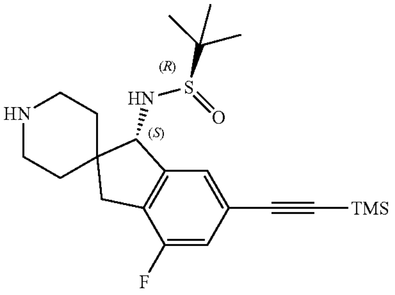 | 421.2 |
| I-C26 | 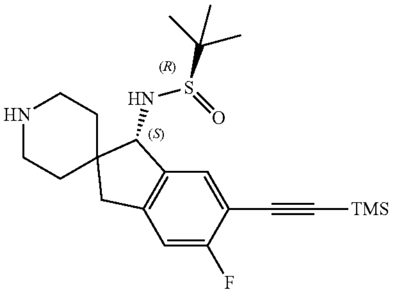 | 421.2 |
| I-C30 | 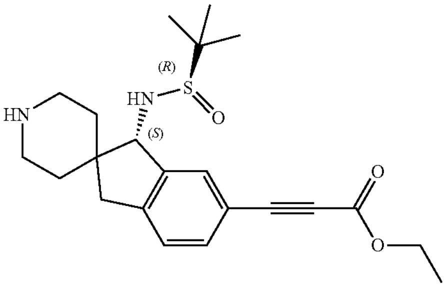 | 403.2 |
| I-C31 | 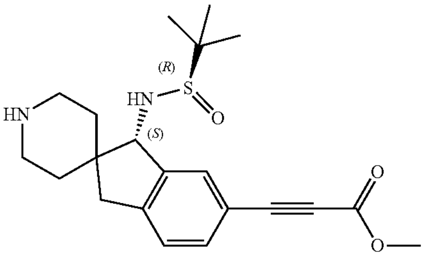 | 389.0 |
| I-C34 | 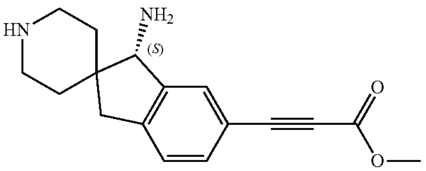 | 285.2 |

Intermediate I-C220

3-((S)-1-(((R)-tert-butylsulfinyl)amino)-1,3-dihydrospiro[indene-2,4'-piperidin]-6-yl)-N-methylpropiolamide

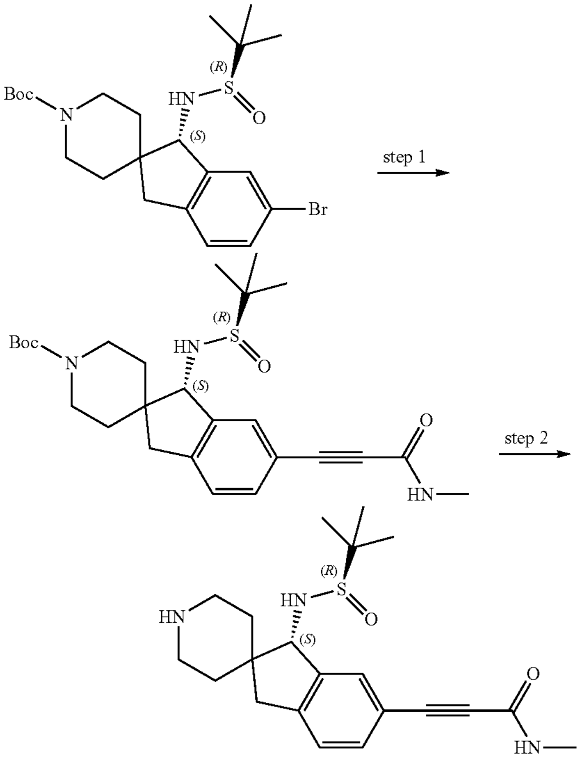

I-C20

Step 1: tert-butyl (S)-1-(((R)-tert-butylsulfinyl)amino)-6-(3-(methylamino)-3-oxoprop-1-yn-1-yl)-1,3-dihydrospiro[indene-2,4'-piperidine]-1'-carboxylate Under $N_2$, tert-butyl (S)-6-bromo-1-(((R)-tert-butylsulfinyl)amino)-1,3-dihydrospiro[indene-2,4'-piperidine]-1'-carboxylate (4.85 g, 10.0 mmol), $Pd(PPh_3)_2Cl_2$ (701 mg, 0.1 mmol), CuI (380 mg, 0.2 mmol), KOAc (2.94 g, 30.0 mmol) and DMSO (100 mL) were placed in three-necked flask. At 90° C., to the stirred mixture was added dropwise the solution of N-methylpropiolamide (2.49 g, 30.0 mmol) in DMSO (50 mL) during 2 hours, and then stirred for additional 3 hours. The reaction solution was poured into water and filtered. The solid was collected and purified by silica gel column chromatography (eluting with DCM/EA) to give target product.

Step 2: 3-((S)-1-(((R)-tert-butylsulfinyl)amino)-1,3-dihydrospiro[indene-2,4'-piperidin]-6-yl)-N-methylpropiolamide In an ice-bath, to the solution of tert-butyl (S)-1-(((R)-tert-butylsulfinyl)amino)-6-(3-(methylamino)-3-oxoprop-1-yn-1-yl)-1,3-dihydrospiro[indene-2,4'-piperidine]-1'-carboxylate in DCM (15 mL) was added $MeSO_3H$ (3.84 g, 40.0 mmol) dropwise. The reaction solution was stirred at room temperature for 30 minutes, adjusted pH to 8 with aqueous ammonia in an ice-bath. The organic layer was collected, concentrated in vacuum under reduced pressure to give target product as yellow solid (2.2 g, 57% yield of two steps). $[M+H]^+$ 388.2

The intermediates in the table below were prepared by following the steps for preparing intermediate I-C20 from corresponding starting materials and reagents:

| Intermediates | Structural formula | LC-MS $[M + H]^+$ |
|---|---|---|
| I-C21 | 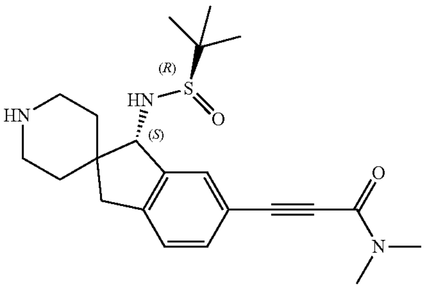 | 402.2 |
| I-C23 | 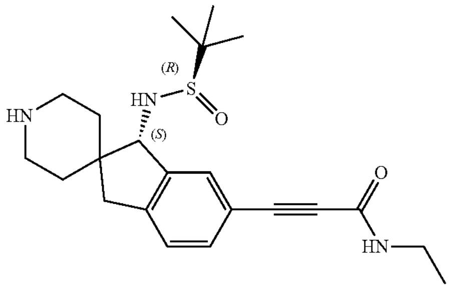 | 402.2 |

-continued
| Intermediates | Structural formula | LC-MS [M + H]+ |
|---|---|---|
| I-C24 | 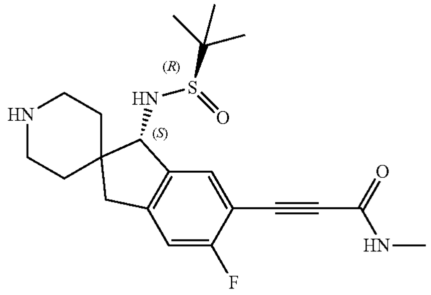 | 406.2 |
| I-C25 | 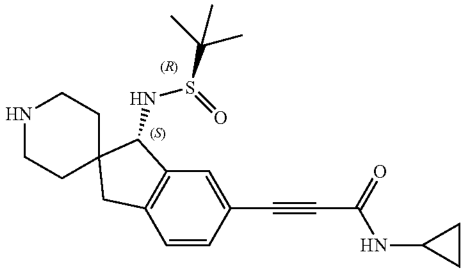 | 414.2 |
| I-C27 | 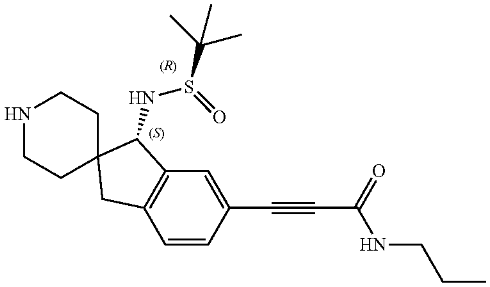 | 416.2 |
| I-C33 | 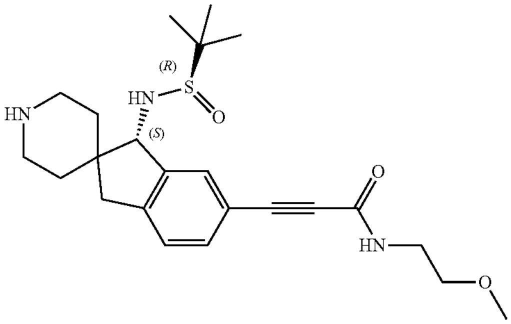 | 432.2 |
| I-C36 | 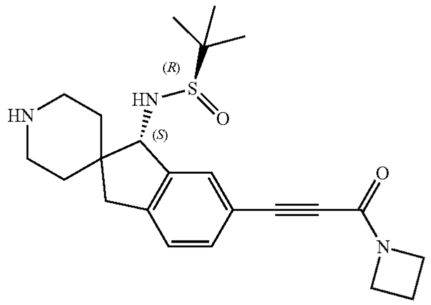 | 414.2 |

Intermediate I-C35

3-((S)-1-(((R)-tert-butylsulfinyl)amino)-1,3-dihydrospiro[indene-2,4'-piperidin]-6-yl)-N-(2-methoxyethyl)-N-methylpropiolamide

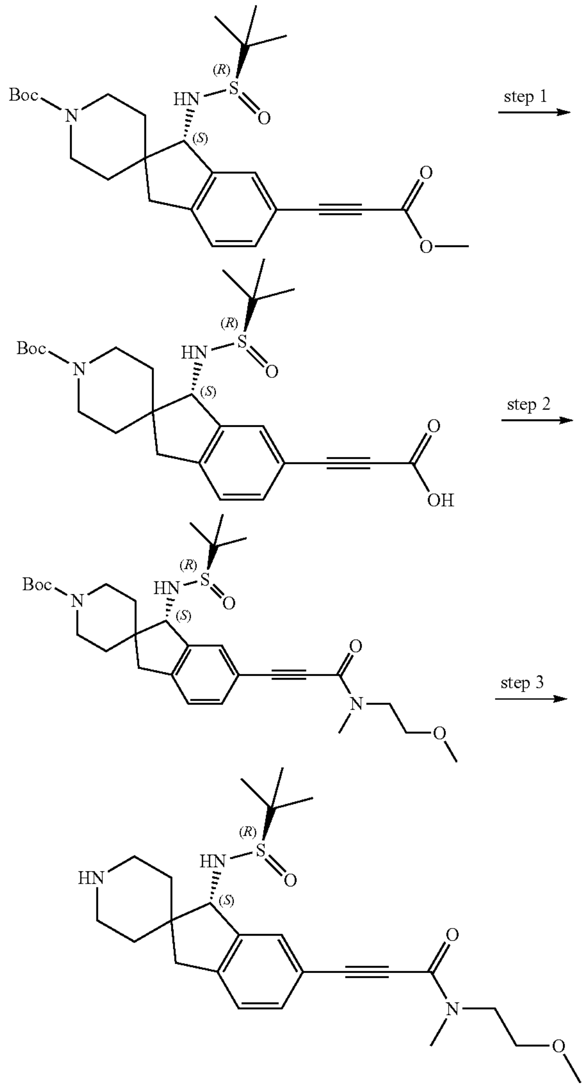

I-C35

Step 1: 3-((S)-1'-(tert-butoxycarbonyl)-1-(((R)-tert-butylsulfinyl)amino)-1,3-dihydrospiro[indene-2,4'-piperidin]-6-yl)propiolic acid To the solution of tert-butyl (S)-1-(((R)-tert-butylsulfinyl)amino)-6-(3-methoxy-3-oxoprop-1-yn-1-yl)-1,3-dihydrospiro[indene-2,4'-piperidine]-1'-carboxylate (1.0 g, 2.05 mmol; prepared by following the steps 1-6 for preparing intermediate 1-C3) in EtOH/water (10 mL/2 mL) was added LiOH (245 mg, 10.23 mmol), stirred at 85° C. for 1 hour and concentrated in vacuum under reduced pressure. The residue was dissolved in water, extracted with EA. The aqueous layer was collected, adjusted pH to 6 with AcOH, extracted with DCM. The organic layer was collected, dried over anhydrous $Na_2SO_4$, and concentrated in vacuum under reduced pressure to give target product as white solid (920 mg, 95% yield). $[M+H]^+$ 475.2.

Step 2: tert-butyl (S)-1-(((R)-tert-butylsulfinyl)amino)-6-(3-((2-methoxyethyl)(methyl)amino)-3-oxoprop-1-yn-1-yl)-1,3-dihydrospiro[indene-2,4'-piperidine]-1'-carboxylate To the solution of 3-((S)-1'-(tert-butoxycarbonyl)-1-(((R)-tert-butylsulfinyl)amino)-1,3-dihydrospiro[indene-2,4'-piperidin]-6-yl)propiolic acid (477 mg, 1.0 mmol), 2-methoxy-N-methylethan-1-amine (178 mg, 2.0 mmol) and HATU (760 mg, 2.0 mmol) in DMF (5 mL) was added $Et_3N$ (202 mg, 2.0 mmol) dropwise. The reaction mixture was stirred at room temperature for 1 hour, poured into water and filtered. The solid was collected to give target product.

Step 3: 3-((S)-1-(((R)-tert-butylsulfinyl)amino)-1,3-dihydrospiro[indene-2,4'-piperidin]-6-yl)-N-(2-methoxyethyl)-N-methylpropiolamide The target product was prepared by following the step 7 for preparing intermediate I-C3 from corresponding starting materials and reagents (380 mg, 85% yield of two steps). $[M+H]^+$ 446.2

Intermediate I-C1

(R)—N—((S)-5-ethynyl-1,3-dihydrospiro[indene-2,4'-piperidin]-1-yl)-2-methylpropane-2-sulfinamide

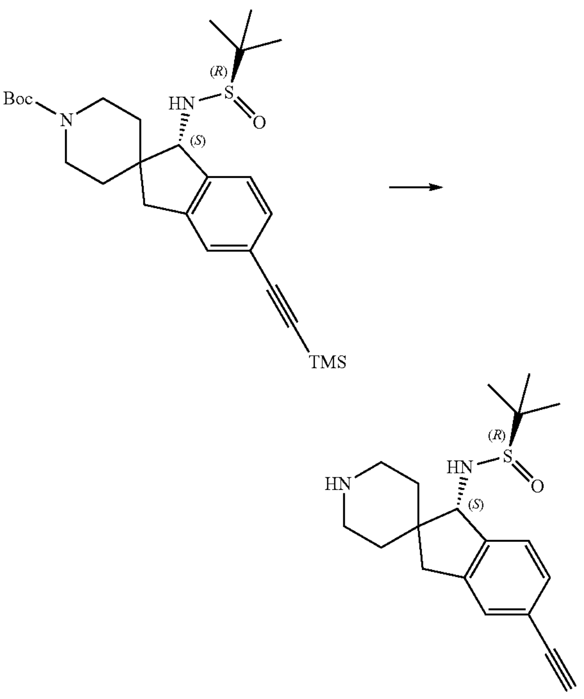

I-C1

To a solution of tert-butyl (S)-1-(((R)-tert-butylsulfinyl)amino)-5-((trimethylsilyl)ethynyl)-1,3-dihydrospiro[indene-2,4'-piperidine]-1'-carboxylate (1.08 g, 2.2 mmol) in dichloromethane (10 mL) was added dropwise trifluoroacetic acid (5 mL). The reaction was stirred at room temperature for 5 minutes and concentrated in vacuum under reduced pressure, and the resulting residue was purified with silica gel column chromatography (water/methanol) to give the target product (0.25 g, yield 35%). $[M+H]^+$ 331.2

The intermediates in the table below were prepared by following the steps for preparing intermediate I-C1 from corresponding starting materials and reagents:

| Intermediate | Structural formula | LC-MS $[M + H]^+$ |
|---|---|---|
| I-C2 | 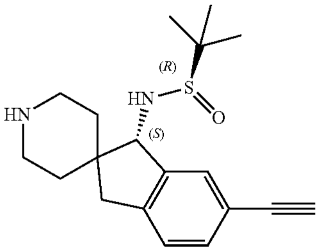 | 331.2 |
| I-C22 | 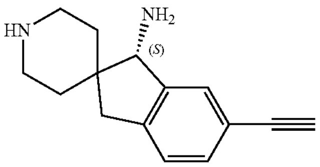 | 227.2 |

-continued

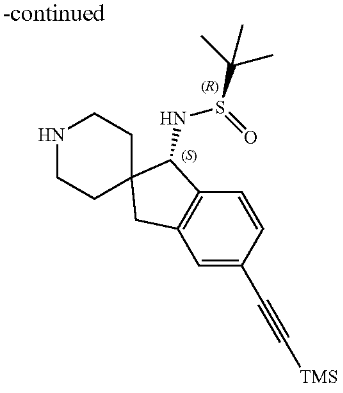

I-C5

Intermediate I-C5

(R)-2-methyl-N—((R)-6-((trimethylsilyl)ethynyl)-3H-spiro[benzofuran-2,4'-piperidin]-3-yl)propane-2-sulfinamide

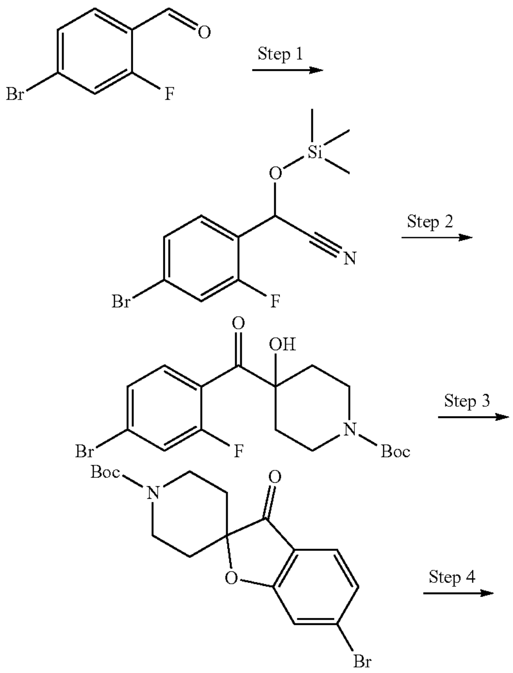

Step 1: 2-(4-bromo-2-fluorophenyl)-2-((trimethylsilyl)oxy)acetonitrile

Under nitrogen, to a solution of 4-bromo-2-fluorobenzaldehyde (6.84 g, 33.7 mmol) and DMAP (50 mg) in acetonitrile (50 mL) was added dropwise TMSCN (3.78 g, 38.0 mmol). The reaction was stirred at room temperature for 4 hours and concentrated in vacuum under reduced pressure, and the residue was used in the reaction of the next step directly.

Step 2: Tert-butyl 4-(4-bromo-2-fluorobenzoyl)-4-hydroxypiperidine-1-carboxylate At −78° C., under nitrogen, 2-(4-bromo-2-fluorophenyl)-2-((trimethylsilyl)oxy)acetonitrile was dissolved in anhydrous tetrahydrofuran (150 mL), and 1 M LiHMDS/tetrahydrofuran solution (37.1 mL, 37.1 mmol) was added dropwise thereto. The reaction was stirred at −78° C. for 1.5 hours, and a solution of tert-butyl 4-oxopiperidine-1-carboxylate (7.39 g, 37.1 mmol) in anhydrous tetrahydrofuran (30 mL) was added dropwise thereto. The reaction was stirred at −78° C. for 3 hours, and 1 M hydrochloric acid (200 mL) was added dropwise thereto. The reaction solution was warmed to room temperature, the organic phase was collected, and the aqueous phase was extracted with ethyl acetate. The organic phases were combined, washed with saline, dried over anhydrous sodium sulfate and concentrated in vacuum under reduced pressure, and the residue was used in the reaction of the next step directly.

Step 3: Tert-butyl 6-bromo-3-oxo-3H-spiro[benzofuran-2,4'-piperidine]-1'-carboxylate Tert-butyl 4-(4-bromo-2-fluorobenzoyl)-4-hydroxypiperidine-1-carboxylate (13.56 g, 33.7 mmoL) was dissolved in 1,4-dioxane, and potassium t-butoxide (4.16 g, 37.1 mmol) was added thereto. The reaction was stirred at 85° C. for 3 hours and concentrated in vacuum under reduced pressure, and the resulting residue was purified with silica gel column chromatography (petroleum ether/ethyl acetate) to give the target product (6.6 g, yield 51.2%). $[M+H-56]^+$ 326.0

Step 4: (R)-2-methyl-N—((R)-6-((trimethylsilyl)ethynyl)-3H-spiro[benzofuran-2,4'-piperidin]-3-yl)propane-2-sulfinamide The target product was prepared by following the steps 4-7 for preparing intermediate I-C3 from corresponding starting materials and reagents. $[M+H]^+$ 405.2

The intermediates in the table below were prepared by following the steps for preparing intermediate I-C5 from corresponding starting materials and reagents:
| Intermediate | Structural formula | LC-MS [M + H]$^+$ |
| --- | --- | --- |
| I-C9 | 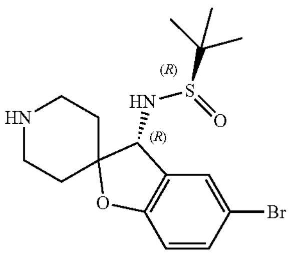 | 387.2 |
| I-C28 | 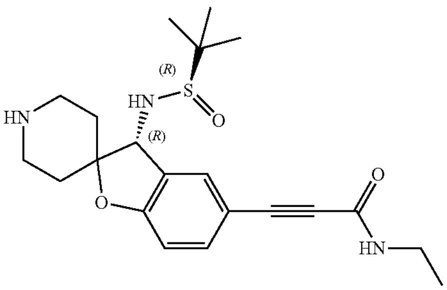 | 404.2 |
| I-C29 | 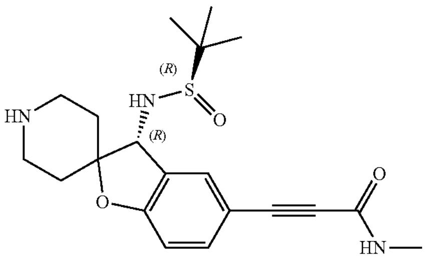 | 390.2 |
| I-C32 | 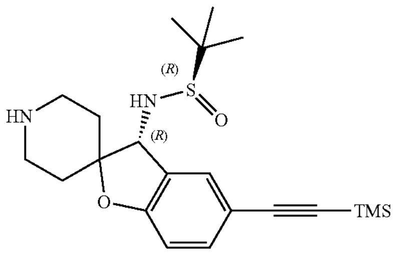 | 405.2 |

Intermediates I-C8 and I-C8'

(R)—N—((S)-5-(3-hydroxyprop-1-yn-1-yl)-1,3-dihydrospiro[indene-2,4'-piperidin]-3-yl)-2-methylpropane-2-sulfinamide and (R)—N—((S)-5-(3-(tert-butoxy)prop-1-yn-1-yl)-1,3-dihydrospiro[indene-2,4'-piperidin]-3-yl)-2-methylpropane-2-sulfinamide

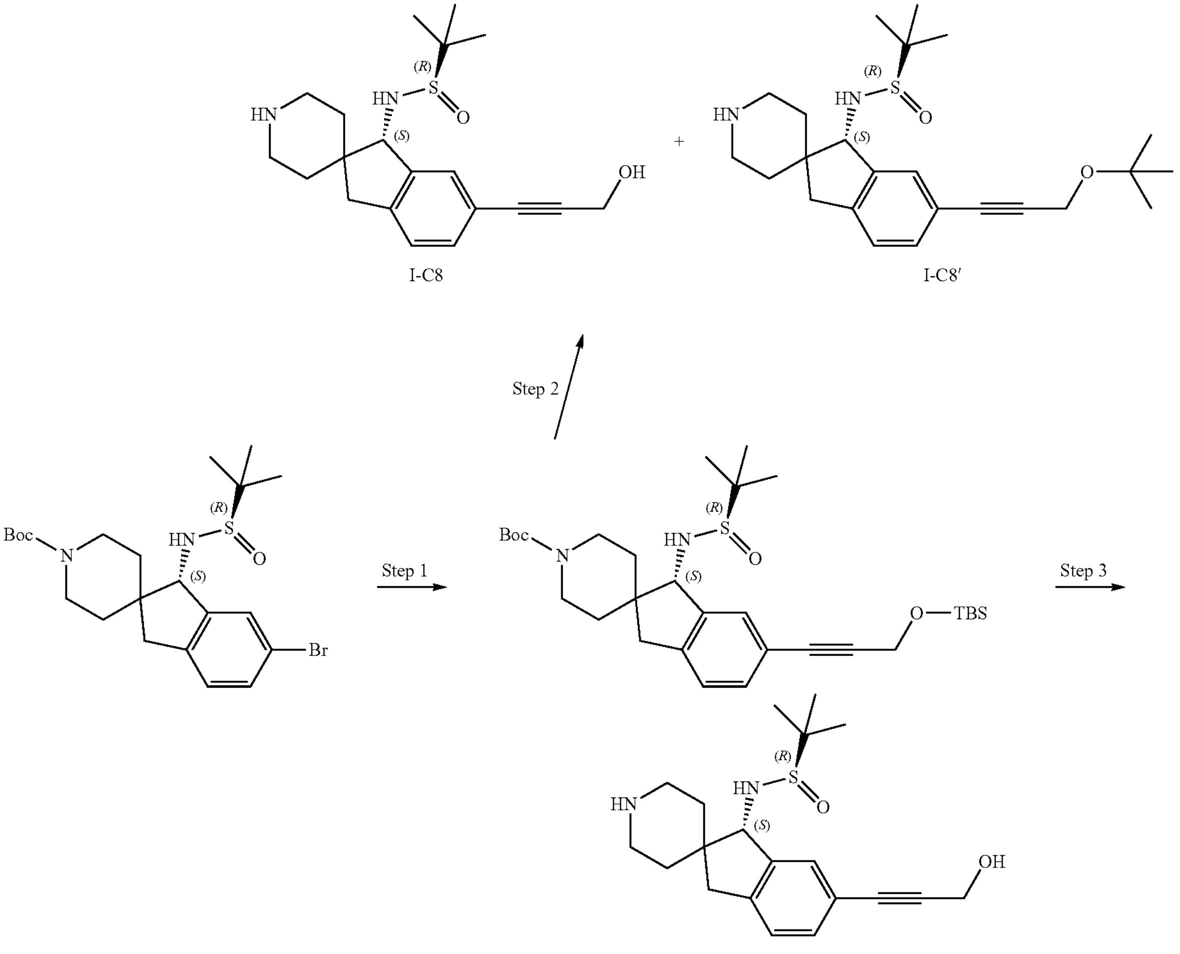

I-C8 + I-C8'

I-C8

Step 1: Tert-butyl (S)-6-(3-((tert-butyldimethylsilyl)oxy)prop-1-yn-1-yl)-1-(((R)-tert-butylsulfinyl)amino)-1,3-dihydrospiro[indene-2,4'-piperidine]-1'-carboxylate The target product was prepared by following the step 6 for preparing intermediate I-C3 from corresponding starting materials and reagents. $[M+H]^+$ 575.2

Step 2: (R)—N—((S)-5-(3-hydroxyprop-1-yn-1-yl)-1,3-dihydrospiro[indene-2,4'-piperidin]-3-yl)-2-methylpropane-2-sulfinamide and (R)—N—((S)-5-(3-(tert-butoxy)prop-1-yn-1-yl)-1,3-dihydrospiro[indene-2,4'-piperidin]-3-yl)-2-methylpropane-2-sulfinamide The mixture of target products I-C8 and I-C8' was prepared by following the step 7 for preparing intermediate I-C3 from corresponding starting materials and reagents. $[M+H]^+$ 361.2, 417.2

Step 3: (R)—N—((S)-5-(3-hydroxyprop-1-yn-1-yl)-1,3-dihydrospiro[indene-2,4'-piperidin]-3-yl)-2-methylpropane-2-sulfinamide The target product was prepared by following the steps for preparing intermediate I-C1 from corresponding starting materials and reagents. $[M+H]^+$ 361.2

Intermediate I-C11

(R)-2-methyl-N—((S)-5-((1-methyl-1H-pyrazol-4-yl)amino)-1,3-dihydrospiro[indene-2,4'-piperidin]-3-yl)propane-2-sulfinamide

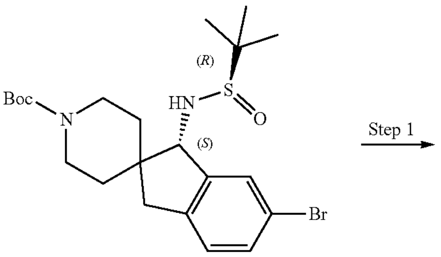

-continued

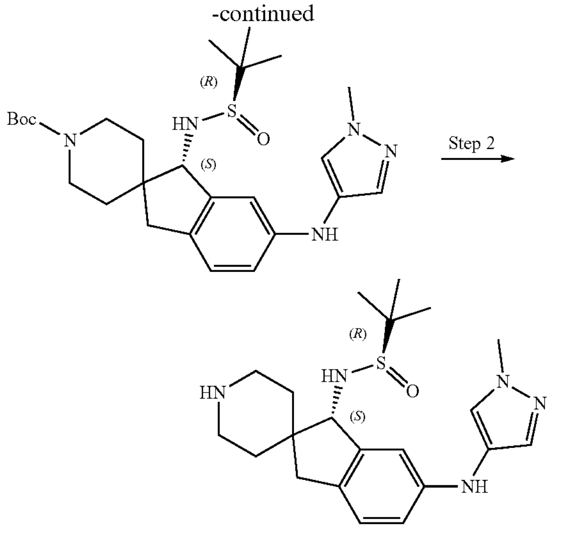

I-C11

Step 1: Tert-butyl (S)-1-(((R)-tert-butylsulfinyl)amino)-6-((1-methyl-1H-pyrazol-4-yl)amino)-1,3-dihydrospiro[indene-2,4'-piperidine]-1'-carboxylate Under nitrogen, tert-butyl (S)-6-bromo-1-(((R)-tert-butylsulfinyl)amino)-1,3-dihydrospiro[indene-2,4'-piperidine]-1'-carboxylate (485 mg, 1.0 mmol), 1-methyl-1H-pyrazol-4-amine (135 mg, 1.4 mmol), Xant-phos (35 mg, 0.06 mmol), $Pd_2(dba)_3$ (27 mg, 0.03 mmol) and $CsCO_3$ (650 mg, 2.0 mmol) were placed in 1,4-dioxane (15 mL). The reaction was stirred at 110° C. for 16 hours and concentrated in vacuum under reduced pressure, and the resulting residue was purified with silica gel column chromatography (water/methanol) to give the target product. $[M+H]^+$ 502.3

Step 2: (R)-2-methyl-N—((S)-5-((1-methyl-1H-pyrazol-4-yl)amino)-1,3-dihydrospiro[indene-2,4'-piperidin]-3-yl)propane-2-sulfinamide The target product was prepared by following the steps for preparing intermediate I-C1 from corresponding starting materials and reagents. $[M+H]^+$ 402.2

Compound 1

(S)-1'-(8-((2-amino-3-chloropyridin-4-yl)thio)imidazo[1,2-c]pyrimidin-5-yl)-5-ethynyl-1,3-dihydrospiro[indene-2,4'-piperidin]-1-amine

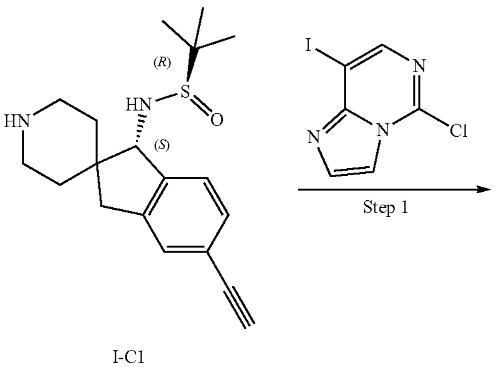

I-C1

-continued

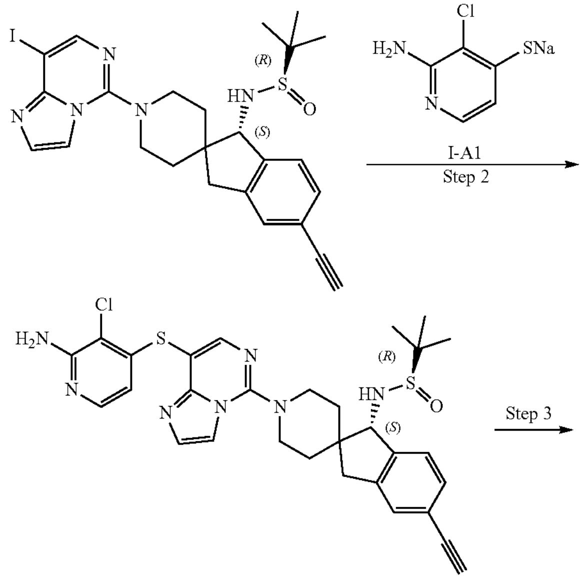

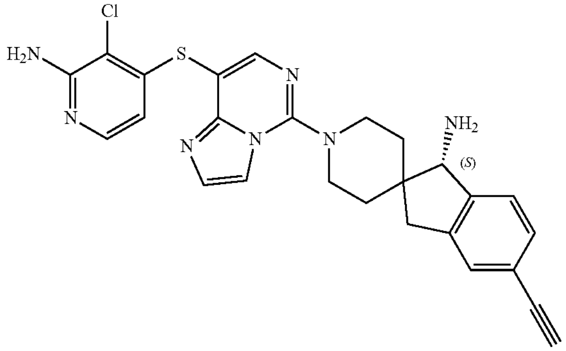

1

Step 1: (R)—N—((S)-5-ethynyl-1'-(8-iodoimidazo[1,2-c]pyrimidin-5-yl)-1,3-dihydrospiro[indene-2,4'-piperidin]-1-yl-2-methylpropane-2-sulfinamide Intermediate I-C1 (149 mg, 0.45 mmol), 5-chloro-8-iodoimidazo[1,2-c]pyrimidine (126 mg, 0.45 mmol) and diisopropylethylamine (116 mg, 0.90 mmol) were placed in N,N-dimethylformamide (2 mL). The reaction was stirred at room temperature for 30 minutes. The reaction solution was purified with silica gel column chromatography (water/methanol) to give the target product (132 mg, yield 51%). $[M+H]^+$ 574.1

Step 2: (R)—N—((S)-1'-(8-((2-amino-3-chloropyridin-4-yl)thio)imidazo[1,2-c]pyrimidin-5-yl)-5-ethynyl-1,3-dihydrospiro[indene-2,4'-piperidin]-1-yl)-2-methylpropane-2-sulfinamide Under nitrogen, (R)—N—((S)-5-ethynyl-1'-(8-iodoimidazo[1,2-c]pyrimidin-5-yl)-1,3-dihydrospiro[indene-2,4'-piperidin]-1-yl)-2-methylpropane-2-sulfinamide (132 mg, 0.23 mmol), intermediate I-A1 (42 mg, 0.23 mmol), Xant-phos (13.3 mg, 0.023 mmol), $Pd_2(dba)_3$ (10.5 mg, 0.012 mmol) and diisopropylethylamine (59 mg, 0.46 mmol) were placed in 1,4-dioxane (4 mL). The reaction was stirred at 100° C. for 3 hours and concentrated in vacuum under reduced pressure, and the resulting residue was purified with silica gel column chromatography (water/methanol) to give the target product (101 mg, yield 72%). $[M+H]^+$ 606.2

Step 3: (S)-1'-(8-((2-amino-3-chloropyridin-4-yl)thio)imidazo[1,2-c]pyrimidin-5-yl)-5-ethynyl-1,3-dihydrospiro[indene-2,4'-piperidin]-1-amine (R)—N—((S)-1'-(8-((2-amino-3-chloropyridin-4-yl)thio)imidazo[1,2-c]pyrimidin-5-yl)-5-ethynyl-1,3-dihydrospiro[indene-2,4'-piperidin]-1-yl)-2-methylpropane-2-sulfinamide (101 mg, 0.17 mmol) was dissolved in 2 M hydrogen chloride/methanol solution. The reaction was stirred at room temperature for 3 minutes. Under ice bath cooling, the reaction solution was diluted with dichloromethane (15 mL) and adjusted with aqueous ammonia to a pH value of 8. The organic phase was collected and concentrated in vacuum under reduced pressure, and the resulting residue was purified with thin layer chromatography (dichloromethane/methanol=12/1) to give the target product (76 mg, two-step yield 91%). $[M+H]^+$ 502.1. $^1H$ NMR (400 MHz, $CD_3OD$): δ 8.08-7.97 (m, 1H), 7.85-7.79 (m, 1H), 7.57-7.51 (m, 1H), 7.51-7.45 (m, 1H), 7.39-7.28 (m, 3H), 5.93-5.82 (m, 1H), 4.06-3.96 (m, 3H), 3.43-3.33 (m, 3H), 3.20-3.13 (m, 1H), 2.86-2.74 (m, 1H), 2.14-2.05 (m, 1H), 2.04-1.95 (m, 1H), 1.76-1.65 (m, 1H), 1.53-1.42 (m, 1H).

The compounds in the table below were prepared by following the steps for preparing compound 1 from corresponding intermediates and reagents:

| Compounds | Structural formula | LC-MS $[M + H]^+$ |
|---|---|---|
| 3 | 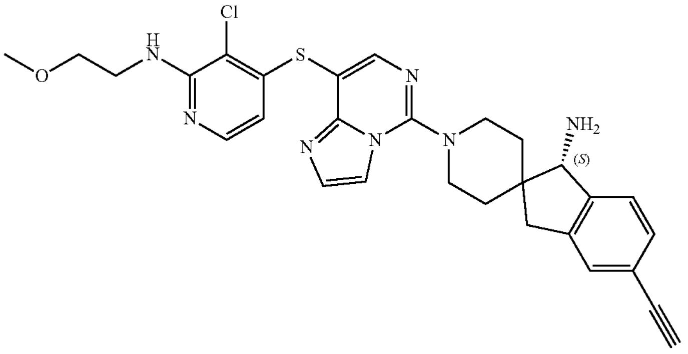 | 560.2 |
| 7 | 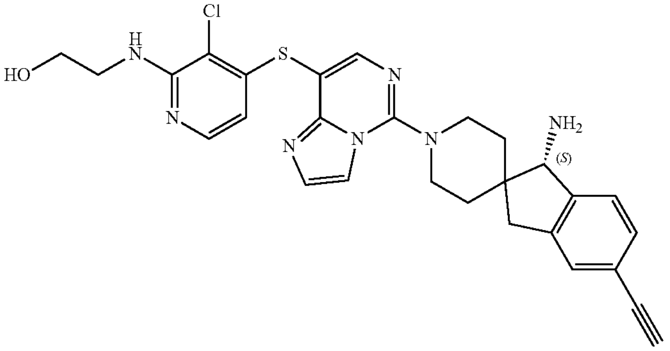 | 546.2 |
| 8 | 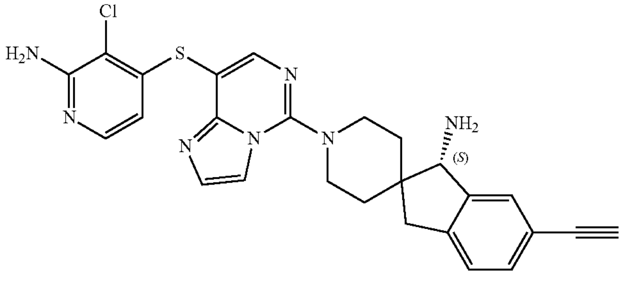 | 502.2 |

-continued
| | | |
|---|---|---|
| 9 | 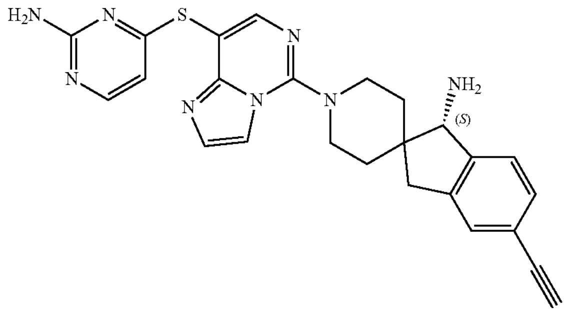 | 469.2 |
| 10 | 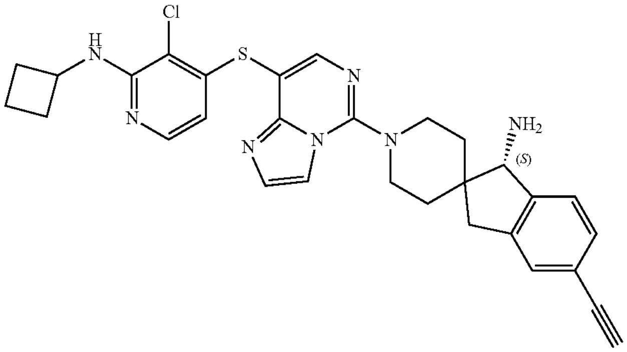 | 556.2 |
| 27 | 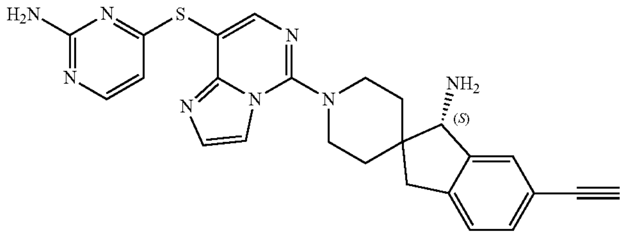 | 469.2 |
| 40 | 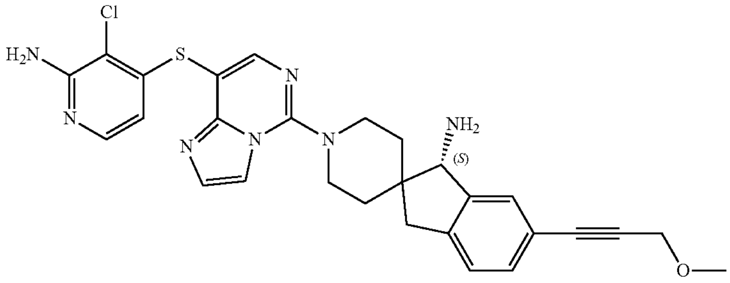 | 546.2 |
| 71 | 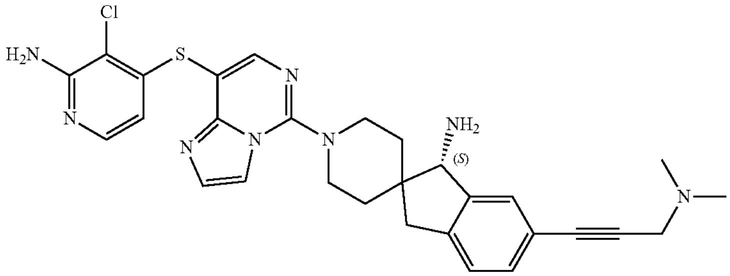 | 559.2 |

-continued
| | | |
|---|---|---|
| 72 | 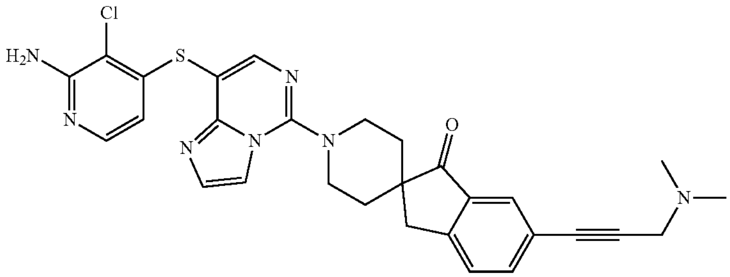 [SMILES: CN(C)CC#Cc1ccc2c(c1)C(=O)C1(CCN(c3ncc(Sc4ccnc(N)c4Cl)c4nccn34)CC1)C2] | 558.2 |
| 75 | 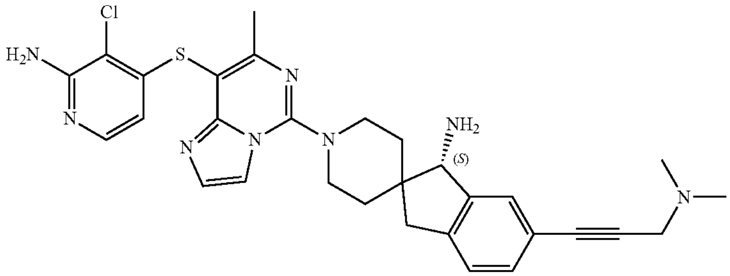 | 573.2 |
| 76 | 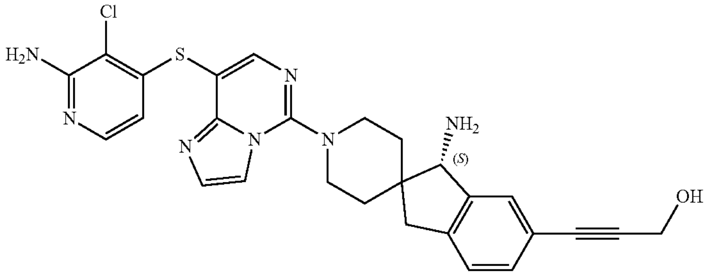 | 532.2 |
| 97 | 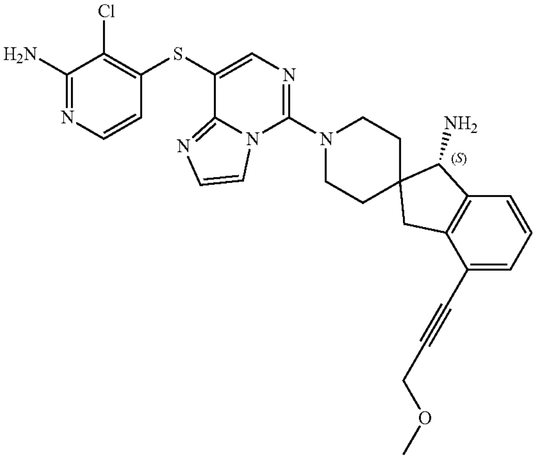 | 546.2 |
| 98 | 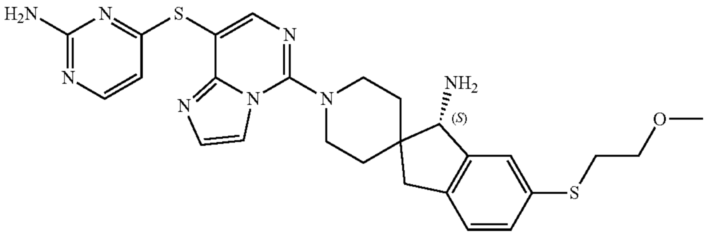 | 535.3 |

-continued
| | | |
|---|---|---|
| 100 | 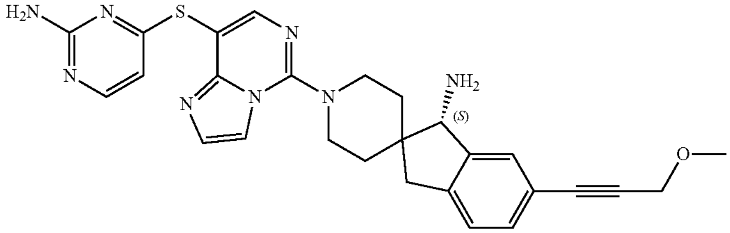 | 513.2 |
| 117 | 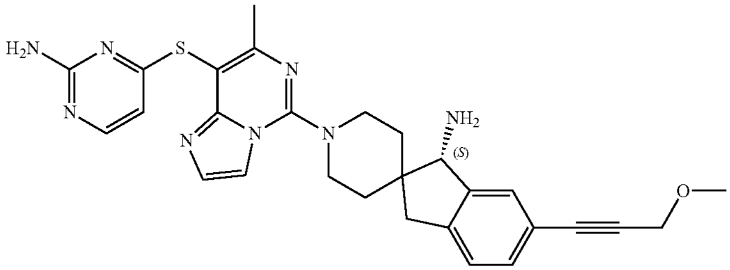 | 527.2 |
| 128 | 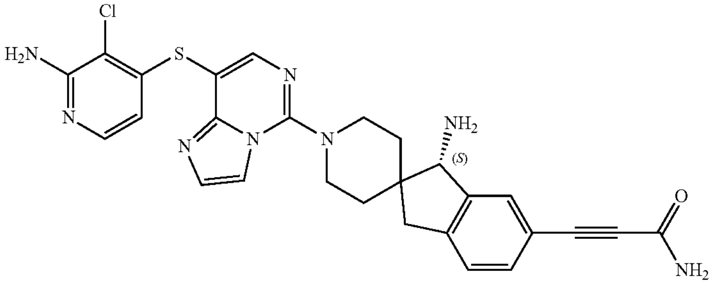 | 545.2 |
| 132 | 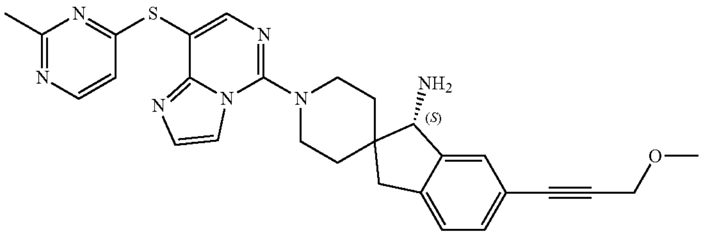 | 512.2 |
| 147 | 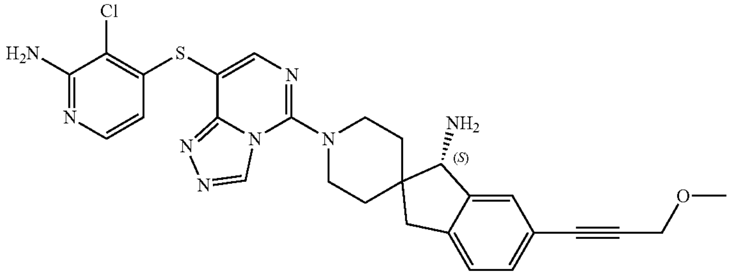 | 547.2 |
| 148 | 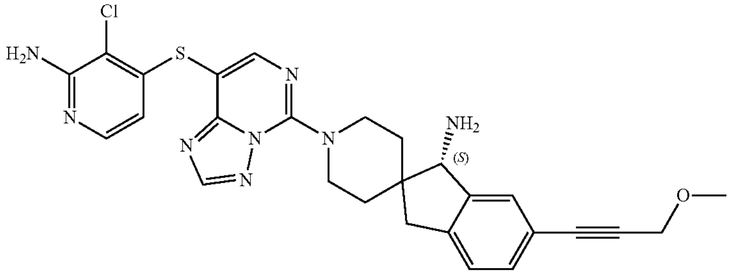 | 547.2 |

-continued
| | | |
|---|---|---|
| 156 | 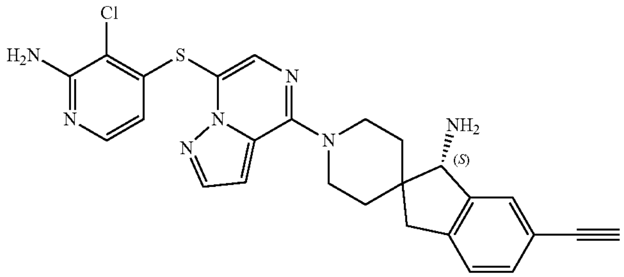 | 502.2 |
| 171 | 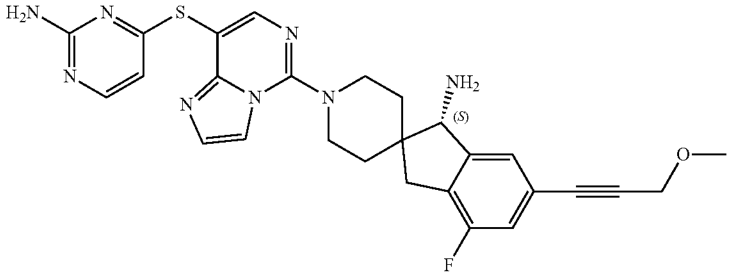 | 531.2 |
| 172 | 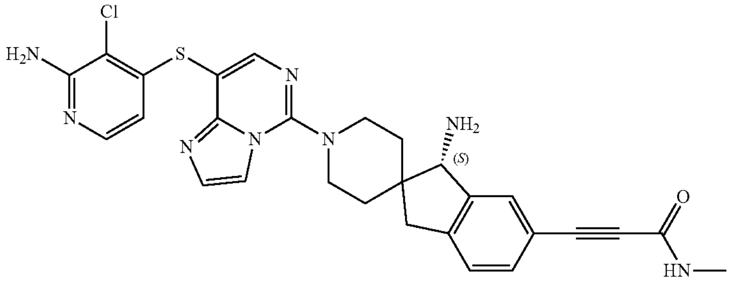 | 559.2 |
| 175 | 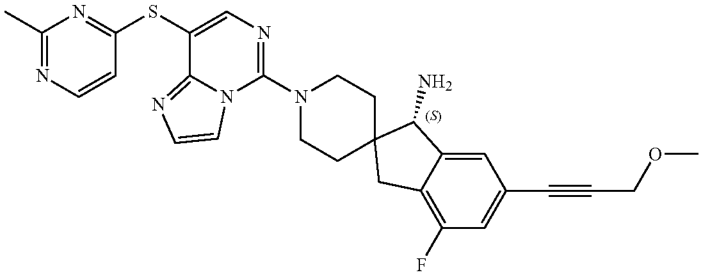 | 530.2 |
| 176 | 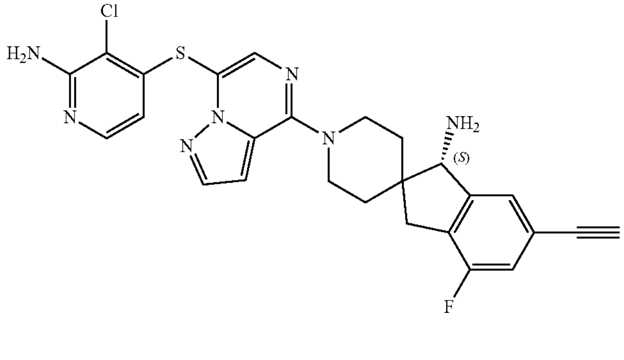 | 520.2 |

-continued
| | | |
|---|---|---|
| 177 | 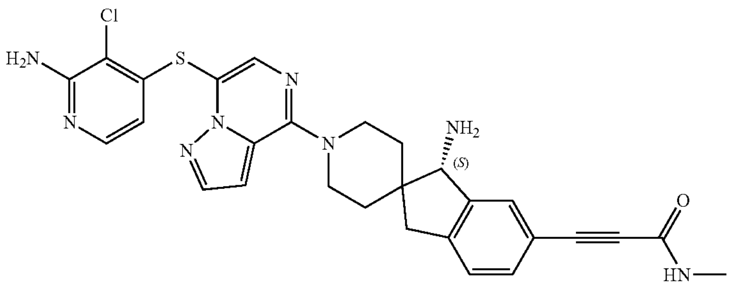 | 559.2 |
| 178 | 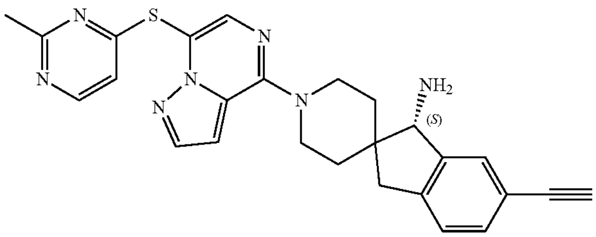 | 468.2 |
| 179 | 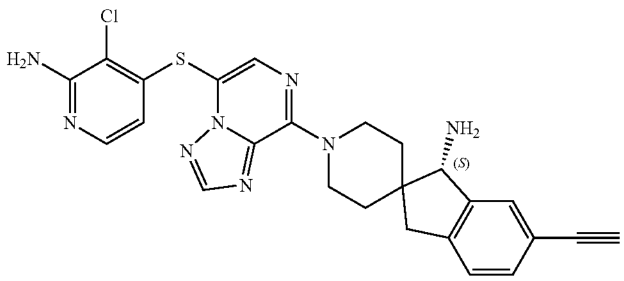 | 503.2 |
| 180 | 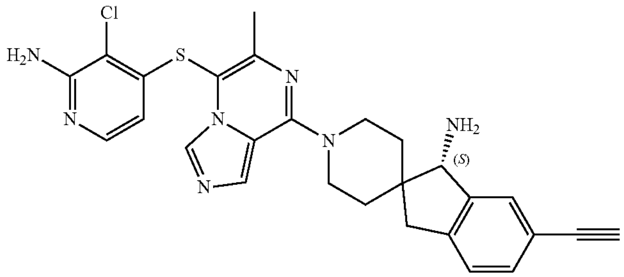 | 516.2 |
| 196 | 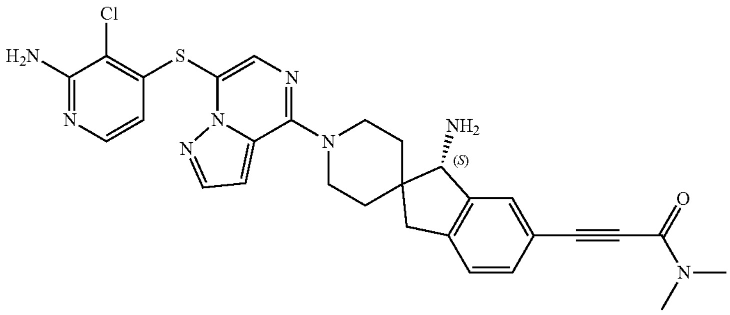 | 573.2 |

-continued

| | | |
|---|---|---|
| 234 | 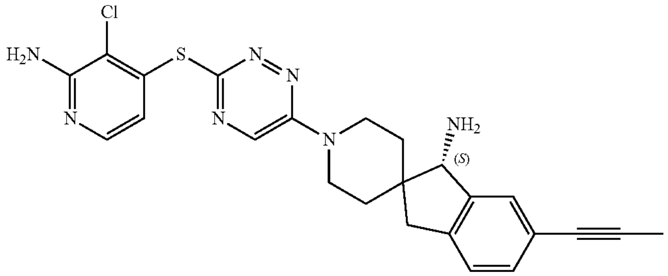 | 478.2 |
| 242 | 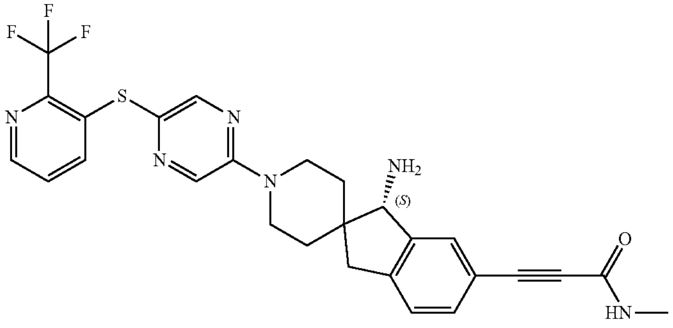 | 539.2 |
| 278 | 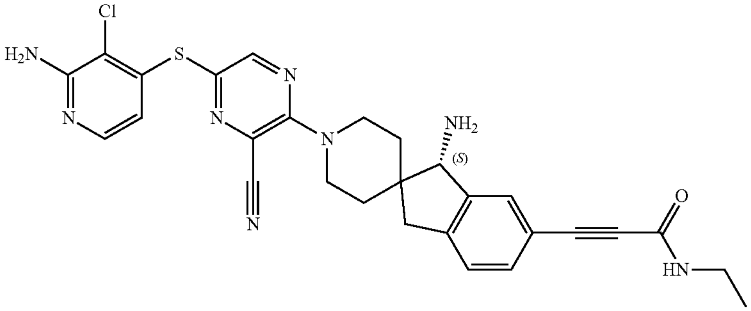 | 559.2 |

| Compounds | $^1$HNMR | Intermediates |
|---|---|---|
| 3 | $^1$H NMR (400 MHz, $CD_3OD$): δ 8.06-7.99 (m, 1H), 7.85-7.80 (m, 1H), 7.59-7.51 (m, 2H), 7.38-7.30 (m, 3H), 5.88-5.79 (m, 1H), 4.06-3.96 (m, 3H), 3.60-3.52 (m, 4H), 3.43-3.33 (m, 6H), 3.21-3.14 (m, 1H), 2.87-2.75 (m, 1H), 2.15-2.05 (m, 1H), 2.04-1.94 (m, 1H), 1.75-1.64 (m, 1H), 1.54-1.43 (m, 1H). | I-A3<br>I-C1 |
| 7 | $^1$H NMR (400 MHz, $CD_3OD$): δ 8.04-8.01 (m, 1H), 7.84-7.81 (m, 1H), 7.57-7.53 (m, 2H), 7.38-7.31 (m, 3H), 5.86-5.82 (m, 1H), 4.07-3.96 (m, 3H), 3.72-3.67 (m, 2H), 3.55-3.50 (m, 2H), 3.45-3.34 (m, 3H), 3.21-3.14 (m, 1H), 2.86-2.77 (m, 1H), 2.15-2.04 (m, 1H), 2.04-1.95 (m, 1H), 1.73-1.67 (m, 1H), 1.52-1.45 (m, 1H). | I-A5<br>I-C1 |
| 8 | $^1$H NMR (400 MHz, $CD_3OD$): δ 8.00 (s, 1H), 7.81-7.77 (m, 1H), 7.54-7.50 (m, 1H), 7.48 (s, 1H), 7.46-7.43 (m, 1H), 7.31-7.27 (m, 1H), 7.21-7.16 (m, 1H), 5.87-5.83 (m, 1H), 4.01-3.94 (m, 3H), 3.41-3.39 (m, 1H), 3.37-3.34 (m, 1H), 3.31-3.27 (m, 1H), 3.20-3.12 (m, 1H), 2.82-2.75 (m, 1H), 2.12-2.02 (m, 1H), 2.02-1.92 (m, 1H), 1.72-1.62 (m, 1H), 1.50-1.40 (m, 1H). | I-A1<br>I-C2 |
| 9 | $^1$H NMR (400 MHz, $CD_3OD$): δ 8.03-7.97 (m, 1H), 7.86-7.82 (m, 1H), 7.81-7.78 (m, 1H), 7.57-7.51 (m, 1H), 7.37-7.29 (m, 3H), 6.25-6.18 (m, 1H), 4.02-3.94 (m, 3H), 3.42-3.34 (m, 3H), 3.20-3.13 (m, 1H), 2.85-2.76 (m, 1H), 2.13-2.05 (m, 1H), 2.03-1.95 (m, 1H), 1.74-1.64 (m, 1H), 1.54-1.43 (m, 1H). | I-A6<br>I-C1 |
| 10 | $^1$H NMR (400 MHz, $CD_3OD$): δ 8.03-7.99 (m, 1H), 7.83-7.79 (m, 1H), 7.56-7.50 (m, 2H), 7.37-7.29 (m, 3H), 5.86-5.77 (m, 1H), 4.46-4.37 (m, 1H), 4.04-3.96 (m, 3H), 3.44-3.34 (m, 3H), 3.19-3.14 (m, 1H), 2.85-2.75 (m, 1H), 2.41-2.31 (m, 2H), 2.13-2.05 (m, 1H), 2.03-1.94 (m, 3H), 1.79-1.66 (m, 3H), 1.52-1.43 (m, 1H). | I-A7<br>I-C1 |
| 27 | $^1$H NMR (400 MHz, $CD_3OD$): δ 8.00 (s, 1H), 7.83 (d, J = 5.5 Hz, 1H), 7.79 (d, J = 1.6 Hz, ,1H), 7.54 (d, J = 1.6 Hz, 1H), 7.49 (s, 1H), 7.32-7.27 (m, 1H), 7.24-7.17 (m, 1H), 6.21 (d, J = 5.5 Hz, 1H), 4.03-3.93 (m, 3H), 3.40 (s, 1H), 3.37-3.33 (m, 2H), 3.23-3.12 (m, 1H), 2.86-2.75 (m, 1H), 2.14-2.04 (m, 1H), 2.04-1.92 (m, 1H), 1.75-1.63 (m, 1H), 1.52-1.40 (m, 1H). | I-A6<br>I-C3 |

-continued

| | | |
|---|---|---|
| 40 | $^1$H NMR (400 MHz, $CD_3OD$): δ 8.02 (s, 1H), 7.84-7.78 (m, 1H), 7.56-7.50 (m, 1H), 7.50-7.44 (m, 2H), 7.31-7.25 (m, 1H), 7.23-7.17 (m, 1H), 5.91-5.82 (m, 1H), 4.29 (s, 2H), 4.07-3.93 (m, 3H), 3.42-3.32 (m, 5H), 3.21-3.14 (m, 1H), 2.86-2.75 (m, 1H), 2.13-1.95 (m, 2H), 1.73-1.64 (m, 1H), 1.50-1.42 (m, 1H). | I-A1<br>I-C7 |
| 71 | $^1$H NMR (400 MHz, $CD_3OD$): δ 8.03 (s, 1H), 7.84-7.80 (m, 1H), 7.56-7.51 (m, 1H), 7.50-7.44 (m, 2H), 7.31-7.25 (m, 1H), 7.23-7.17 (m, 1H), 5.89-5.85 (m, 1H), 4.05-3.96 (m, 3H), 3.49-3.45 (m, 2H), 3.42-3.33 (m, 2H), 3.23-3.14 (m, 1H), 2.85-2.77 (m, 1H), 2.36 (s, 6H), 2.14-2.06 (m, 1H), 2.03-1.95 (m, 1H), 1.74-1.64 (m, 1H), 1.52-1.42 (m, 1H). | I-A1<br>I-C10 |
| 72 | $^1$H NMR (400 MHz, $CD_3OD$): δ 8.06 (s, 1H), 7.86 (s, 1H), 7.79-7.69 (m, 2H), 7.60-7.53 (m, 2H), 7.51-7.47 (m, 1H), 5.94-5.85 (m, 1H), 4.19-4.11 (m, 2H), 3.53-3.48 (m, 2H), 3.46-3.38 (m, 2H), 3.34-3.30 (m, 2H), 2.38 (s, 6H), 2.23-2.15 (m, 2H), 1.70-1.62 (m, 2H). | I-A1<br>I-C10 |
| 75 | $^1$H NMR (400 MHz, $CD_3OD$): δ 7.74 (d, J = 1.6 Hz, 1H), 7.51-7.41 (m, 3H), 7.28 (dd, J = 7.7, 1.2 Hz, 1H), 7.20 (d, J = 7.8 Hz, 1H), 5.79 (d, J = 5.6 Hz, 1H), 4.05-3.97 (m, 3H), 3.47 (s, 2H), 3.42-3.33 (m, 2H), 3.18 (d, J = 16.2 Hz, 1H), 2.81 (d, J = 16.1 Hz, 1H), 2.53 (s, 3H), 2.36 (s, 6H), 2.15-2.04 (m, 1H), 2.03-1.93 (m, 1H), 1.69 (d, J = 13.0 Hz, 1H), 1.47 (d, J = 13.3 Hz, 1H). | I-A1<br>I-C10 |
| 76 | $^1$H NMR (400 MHz, $CD_3OD$): δ 8.03 (s, 1H), 7.83 (d, J = 1.6 Hz, 1H), 7.55-7.42 (m, 3H), 7.27 (dd, J = 7.7, 1.3 Hz, 1H), 7.20 (d, J = 7.7 Hz, 1H), 5.87 (d, J = 5.6 Hz, 1H), 4.37 (s, 2H), 4.04-3.97 (m, 3H), 3.43-3.35 (m, 2H), 3.18 (d, J = 16.1 Hz, 1H), 2.81 (d, J = 16.0 Hz, 1H), 2.16-1.95 (m, 2H), 1.69 (d, J = 12.2 Hz, 1H), 1.47 (d, J = 12.9 Hz, 1H). | I-A1<br>I-C8 |
| 97 | $^1$H NMR (400 MHz, $CD_3OD$): δ 8.06-8.00 (m, 1H), 7.85-7.81 (m, 1H), 7.56-7.51 (m, 1H), 7.50-7.46 (m, 1H), 7.42-7.37 (m, 1H), 7.32-7.26 (m, 1H), 7.24-7.19 (m, 1H), 5.90-5.85 (m, 1H), 4.35 (s, 2H), 4.06-3.97 (m, 3H), 3.43 (s, 3H), 3.42-3.35 (m, 2H), 3.27-3.22 (m, 1H), 2.93-2.85 (m, 1H), 2.12-1.98 (m, 2H), 1.74-1.67 (m, 1H), 1.56-1.49 (m, 1H). | I-A1<br>I-C13 |
| 98 | $^1$H NMR (400 MHz, $CD_3OD$): δ 8.01 (s, 1H), 7.85-7.80 (m, 2H), 7.55 (d, J = 1.3 Hz, 1H), 7.44 (s, 1H), 7.27-7.14 (m, 2H), 6.24-6.17 (m, 1H), 4.03-3.94 (m, 3H), 3.54 (t, J = 6.7 Hz, 2H), 3.42-3.32 (m, 2H), 3.31 (s, 3H), 3.15 (d, J = 15.8 Hz, 1H), 3.07 (d, J = 6.7 Hz, 2H), 2.78 (d, J = 15.8 Hz, 1H), 2.12-1.93 (m, 2H), 1.74-1.65 (m, 1H), 1.52-1.44 (m, 1H). | I-A6<br>I-C14 |
| 100 | $^1$H NMR (400 MHz, $CD_3OD$): δ 8.01 (s, 1H), 7.85-7.80 (m, 2H), 7.56-7.54 (m, 1H), 7.51-7.44 (m, 1H), 7.33-7.28 (m, 1H), 7.26-7.20 (m, 1H), 6.23-6.19 (m, 1H), 4.30 (s, 2H), 4.04-3.95 (m, 3H), 3.43-3.32 (m, 5H), 3.22-3.14 (m, 1H), 2.90-2.80 (m, 1H), 2.12-1.97 (m, 2H), 1.73-1.66 (m, 1H), 1.54-1.46 (m, 1H). | I-A6<br>I-C7 |
| 117 | $^1$H NMR (400 MHz, $CD_3OD$): δ 7.87-7.80 (m, 1H), 7.72 (s, 1H), 7.50-7.41 (m, 2H), 7.31-7.25 (m, 1H), 7.23-7.18 (m, 1H), 6.20-6.15 (m, 1H), 4.34-4.25 (m, 2H), 4.02-3.92 (m, 3H), 3.43-3.31 (m, 5H), 3.21-3.15 (m, 1H), 2.84-2.76 (m, 1H), 2.55 (s, 3H), 2.13-2.05 (m, 1H), 2.02-1.94 (m, 1H), 1.74-1.62 (m, 1H), 1.50-1.42 (m, 1H). | I-A6<br>I-C7 |
| 128 | $^1$H NMR (400 MHz, $CD_3OD$): δ 8.04-8.02 (m, 1H), 7.83-7.82 (m, 1H), 7.60-7.58 (m, 1H), 7.55-7.53 (m, 1H), 7.49-7.47 (m, 1H), 7.45-7.42 (m, 1H), 7.32-7.28 (m, 1H), 5.88-5.86 (m, 1H), 4.05-3.98 (m, 3H), 3.44-3.35 (m, 2H), 3.26-3.20 (m, 1H), 2.91-2.82 (m, 1H), 2.15-2.07 (m, 1H), 2.04-1.97 (m, 1H), 1.74-1.67 (m, 1H), 1.51-1.43 (m, 1H). | I-A1<br>I-C16 |
| 132 | $^1$H NMR (400 MHz, $CD_3OD$): δ 8.25-8.17 (m, 1H), 8.06 (s, 1H), 7.87-7.80 (m, 1H), 7.58-7.52 (m, 1H), 7.47 (s, 1H), 7.31-7.25 (m, 1H), 7.23-7.17 (m, 1H), 6.83-6.76 (m, 1H), 4.30 (s, 2H), 4.09-3.91 (m, 3H), 3.44-3.33 (m, 5H), 3.22-3.15 (m, 1H), 2.85-2.79 (m, 1H), 2.52 (s, 3H), 2.13-2.05 (m, 1H), 2.03-1.96 (m, 1H), 1.75-1.65 (m, 1H), 1.53-1.42 (m, 1H). | I-A10<br>I-C7 |
| 147 | $^1$H NMR (400 MHz, $CD_3OD$): δ 8.37-8.26 (m, 1H), 8.21-8.11 (m, 1H), 7.53-7.49 (m, 1H), 7.45 (s, 1H), 7.31-7.27 (m, 1H), 7.23-7.20 (m, 1H), 5.94-5.90 (m, 1H), 5.20-5.09 (m, 2H), 4.30 (s, 2H), 3.95 (s, 1H), 3.67-3.57 (m, 2H), 3.45-3.36 (m, 3H), 3.25-3.20 (m, 1H), 2.86-2.80 (m, 1H), 2.07-1.99 (m, 1H), 1.97-1.88 (m, 1H), 1.72-1.65 (m, 1H), 1.48-1.42 (m, 1H). | I-A1<br>I-C7 |
| 148 | $^1$H NMR (400 MHz, $CD_3OD$): δ 8.35-8.27 (m, 1H), 8.19-8.13 (m, 1H), 7.53-7.48 (m, 1H), 7.45 (s, 1H), 7.31-7.25 (m, 1H), 7.24-7.18 (m, 1H), 5.97-5.88 (m, 1H), 5.22-5.06 (m, 2H), 4.30 (s, 2H), 3.95 (s, 1H), 3.67-3.55 (m, 2H), 3.45-3.37 (m, 3H), 3.24-3.18 (m, 1H), 2.86-2.78 (m, 1H), 2.06-1.98 (m, 1H), 1.96-1.88 (m, 1H), 1.73-1.64 (m, 1H), 1.47-1.40 (m, 1H). | I-A1<br>I-C7 |

-continued

| | | |
|---|---|---|
| 156 | $^1$H NMR (400 MHz, $CD_3OD$): δ 7.92-7.88 (m, 1H), 7.76-7.73 (m, 1H), 7.5-7.47 (m, 1H), 7.47-7.44 (m, 1H), 7.34-7.30 (m, 1H), 7.24-7.20 (m, 1H), 7.13-7.10 (m, 1H), 5.71-5.66 (m, 1H), 4.58-4.50 (m, 2H), 3.96 (s, 1H), 3.56-3.45 (m, 2H), 3.41 (s, 1H), 3.24-3.19 (m, 1H), 2.87-2.80 (m, 1H), 2.03-1.94 (m, 1H), 1.92-1.83 (m, 1H), 1.71-1.64 (m, 1H), 1.48-1.41 (m, 1H). | I-A1<br>I-C3 |
| 171 | $^1$H NMR (400 MHz, $CD_3OD$): δ 8.02 (s, 1H), 7.88-7.78 (m, 2H), 7.59-7.52 (m, 1H), 7.32 (s, 1H), 7.07-6.99 (m, 1H), 6.25-6.19 (m, 1H), 4.31 (s, 2H), 4.06-3.95 (m, 3H), 3.47-3.32 (m, 5H), 3.26-3.17 (m, 1H), 2.87-2.76 (m, 1H), 2.17-1.96 (m, 2H), 1.78-1.67 (m, 1H), 1.55-1.43 (m, 1H). | I-A6<br>I-C18 |
| 172 | $^1$H NMR (400 MHz, $CD_3OD$): δ 8.05-8.03 (m, 1H), 7.85-7.83 (m, 1H), 7.61-7.57 (m, 1H), 7.56-7.54 (m, 1H), 7.51-7.48 (m, 1H), 7.45-7.42 (m, 1H), 7.32-7.29 (m, 1H), 5.90-5.87 (m, 1H), 4.06-3.99 (m, 3H), 3.42-3.36 (m, 2H), 3.26-3.21 (m, 1H), 2.89-2.84 (m, 1H), 2.81 (s, 3H), 2.16-2.08 (m, 1H), 2.05-1.98 (m, 1H), 1.75-1.68 (m, 1H), 1.51-1.45 (m, 1H). | I-A1<br>I-C20 |
| 175 | $^1$H NMR (400 MHz, $CD_3OD$): δ 8.24-8.20 (m, 1H), 8.08 (s, 1H), 7.88-7.82 (m, 1H), 7.58-7.54 (m, 1H), 7.33 (s, 1H), 7.08-7.01 (m, 1H), 6.84-6.78 (m, 1H), 4.31 (s, 2H), 4.10-3.98 (m, 3H), 3.47-3.37 (m, 5H), 3.26-3.22 (m, 1H), 2.89-2.79 (m, 1H), 2.54 (s, 3H), 2.16-2.07 (m, 1H), 2.03-2.00 (m, 1H), 1.79-1.69 (m, 1H), 1.55-1.47 (m, 1H). | I-A10<br>I-C18 |
| 176 | $^1$H NMR (400 MHz, $CD_3OD$): δ 7.91 (d, J = 2.5 Hz, 1H), 7.75 (s, 1H), 7.46 (d, J = 5.5 Hz, 1H), 7.33 (s, 1H), 7.11 (d, J = 2.5 Hz, 1H), 7.06 (d, J = 9.2 Hz, 1H), 5.69 (d, J = 5.6 Hz, 1H), 4.60-4.47 (m, 2H), 3.99 (s, 1H), 3.61-3.43 (m, 3H), 3.27-3.21 (m, 1H), 2.85-2.81 (m, 1H), 2.04-1.83 (m, 2H), 1.72-1.68 (m, 1H), 1.48-1.44 (m, 1H). | I-A1<br>I-C19 |
| 177 | $^1$H NMR (400 MHz, $CD_3OD$): δ 7.93-7.89 (m, 1H), 7.78-7.74 (m, 1H), 7.59-7.55 (m, 1H), 7.49-7.46 (m, 1H), 7.45-7.40 (m, 1H), 7.33-7.28 (m, 1H), 7.14-7.11 (m, 1H), 5.72-5.67 (m, 1H), 4.59-4.51 (m, 2H), 4.01-3.96 (m, 1H), 3.58-3.45 (m, 2H), 3.27-3.23 (m, 1H), 2.90-2.83 (m, 1H), 2.80 (s, 3H), 2.05-1.96 (m, 1H), 1.93-1.85 (m, 1H), 1.74-1.65 (m, 1H), 1.49-1.40 (m, 1H). | I-A1<br>I-C20 |
| 178 | $^1$H NMR (400 MHz, $CD_3OD$): δ 8.26-8.22 (m, 1H), 7.92-7.88 (m, 1H), 7.78-7.76 (m, 1H), 7.51-7.47 (m, 1H), 7.34-7.31 (m, 1H), 7.24-7.21 (m, 1H), 7.13-7.12 (m, 1H), 6.70-6.67 (m, 1H), 4.60-4.50 (m, 2H), 3.97 (s, 1H), 3.58-3.48 (m, 2H), 3.41 (s, 1H), 3.25-3.20 (m, 1H), 2.88-2.81 (m, 1H), 2.53 (s, 3H), 2.04-1.96 (m, 1H), 1.94-1.84 (m, 1H), 1.73-1.64 (m, 1H), 1.50-1.43 (m, 1H). | I-A10<br>I-C3 |
| 179 | $^1$H NMR (400 MHz, $CD_3OD$): δ 8.32 (s, 1H), 7.93 (s, 1H), 7.54-7.44 (m, 2H), 7.32 (dd, J = 7.7, 1.1 Hz, 1H), 7.23 (d, J = 7.8 Hz, 1H), 5.79 (d, J = 5.5 Hz, 1H), 5.51-5.22 (m, 1H), 3.94 (s, 1H), 3.67-3.51 (m, 2H), 3.41 (s, 1H), 3.24 (d, J = 16.1 Hz, 1H), 2.85 (d, J = 16.1 Hz, 1H), 2.04-1.79 (m, 2H), 1.67 (d, J = 13.6 Hz, 1H), 1.44 (d, J = 13.7 Hz, 1H). | I-A1<br>I-C3 |
| 180 | $^1$H NMR (400 MHz, $CD_3OD$): δ 8.18 (d, J = 0.7 Hz, 1H), 7.91 (d, J = 0.7 Hz, 1H), 7.56 (d, J = 5.5 Hz, 1H), 7.49 (s, 1H), 7.32 (dd, J = 7.7, 1.1 Hz, 1H), 7.22 (d, J = 7.7 Hz, 1H), 5.82 (d, J = 5.5 Hz, 1H), 4.70-4.56 (m, 2H), 3.96 (s, 1H), 3.60-3.47 (m, 2H), 3.41 (s, 1H), 3.26-3.17 (m, 1H), 2.84 (d, J = 16.0 Hz, 1H), 2.42 (s, 3H), 2.01-1.81 (m, 2H), 1.68 (d, J = 12.0 Hz, 1H), 1.45 (d, J = 13.3 Hz, 1H). | I-A1<br>I-C3 |
| 196 | $^1$H NMR (400 MHz, $CD_3OD$): δ 7.91 (d, J = 2.4 Hz, 1H), 7.75 (s, 1H), 7.61 (s, 1H), 7.52-7.43 (m, 2H), 7.33-7.31 (m, 1H), 7.13-7.11 (m, 1H), 5.69 (d, J = 5.5 Hz, 1H), 4.61-4.46 (m, 2H), 4.00 (s, 1H), 3.53-3.49 (m, 2H), 3.32 (s, 3H), 3.26-3.22 (m, 1H), 3.00 (s, 3H), 2.89-2.85 (m, 1H), 2.03-1.83 (m, 2H), 1.71-1.67 (m, 1H), 1.46-1.42 (m, 1H). | I-A1<br>I-C21 |
| 234 | $^1$H NMR (400 MHz, $CD_3OD$): δ 8.36 (s, 1H), 7.66 (d, J = 5.5 Hz, 1H), 7.36 (s, 1H), 7.22-7.12 (m, 2H), 6.04 (d, J = 5.5 Hz, 1H), 4.73-4.60 (m, 2H), 3.92 (s, 1H), 3.46-3.35 (m, 2H), 3.18 (d, J = 16.0 Hz, 1H), 2.79 (d, J = 15.9 Hz, 1H), 2.00 (s, 3H), 1.92-1.72 (m, 2H), 1.63 (d, J = 12.9 Hz, 1H), 1.41 (d, J = 13.4 Hz, 1H). | I-A1<br>I-C17 |
| 242 | $^1$H NMR (400 MHz, $CD_3OD$): δ 8.46-8.42 (m, 1H), 8.29-8.22 (m, 2H), 7.65-7.61 (m, 1H), 7.57-7.53 (m, 1H), 7.48-7.40 (m, 2H), 7.30-7.26 (m, 1H), 4.37-4.27 (m, 2H), 3.95 (s, 1H), 3.35-3.31 (m, 1H), 3.28-3.17 (m, 2H), 2.85-2.76 (m, 4H), 1.93-1.84 (m, 1H), 1.81-1.72 (m, 1H), 1.64-1.59 (m, 1H), 1.41-1.36 (m, 1H). | I-A20<br>I-C20 |
| 278 | $^1$H NMR (400 MHz, $CD_3OD$): δ 8.44 (s, 1H), 7.69-7.62 (m, 2H), 7.59-7.53 (m, 1H), 7.40 (d, J = 7.9 Hz, 1H), 6.12 (d, J = 5.5 Hz, 1H), 4.59-4.43 (m, 2H), 4.36 (s, 1H), 3.57-3.46 (m, 2H), 3.31-3.30 (m, 1H), 3.27-3.19 (m, 2H), 3.12 (d, J = 16.8 Hz, 1H), 1.99-1.86 (m, 2H), 1.74-1.63 (m, 2H), 1.15 (t, J = 7.3 Hz, 3H). | I-A1<br>I-C23 |

The compounds in the table below were prepared by following the steps 1 and 3 for preparing compound 1 from corresponding intermediates and reagents:
| Compounds | Structural formula | LC-MS $[M + H]^+$ |
|---|---|---|
| 2 | 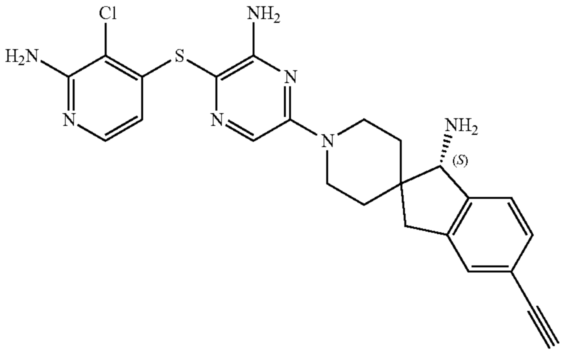 | 478.1 |
| 86 | 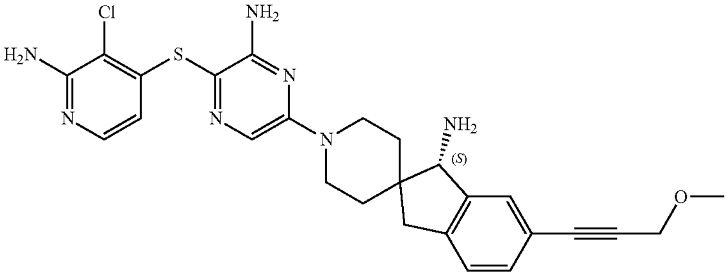 | 522.2 |
| 95 | 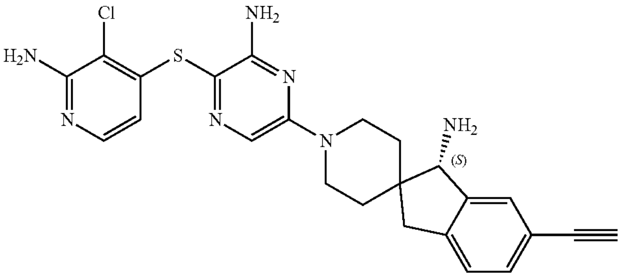 | 480.2 |
| 112 | 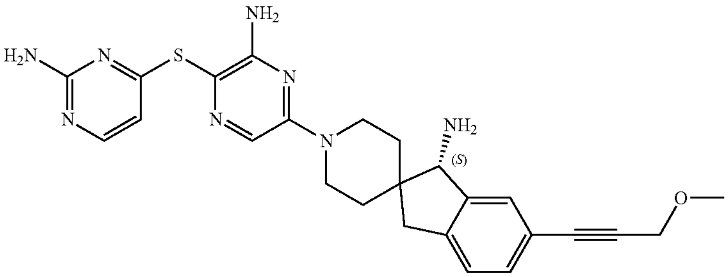 | 489.2 |
| 126 | 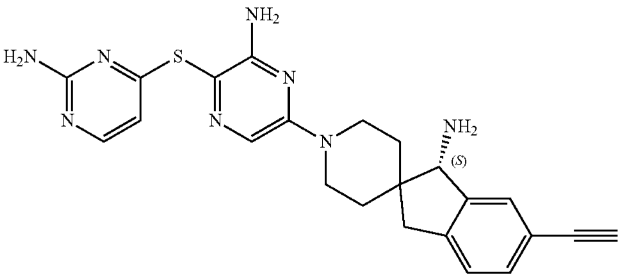 | 445.2 |

-continued
| | | |
|---|---|---|
| 129 | 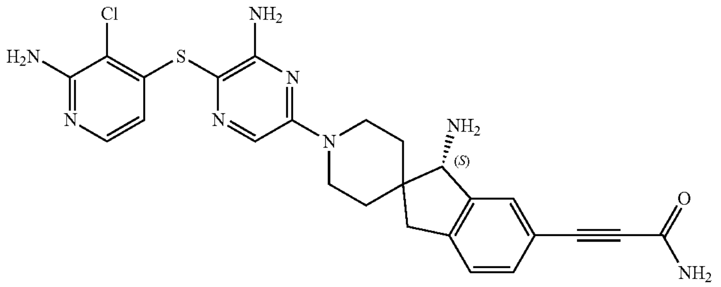 | 521.1 |
| 131 | 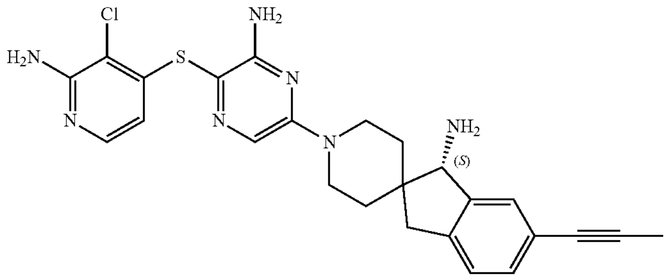 | 492.2 |
| 134 | 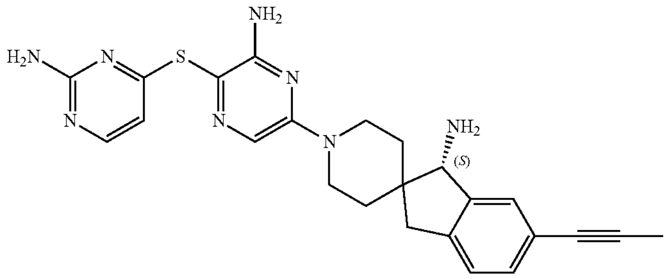 | 459.2 |
| 155 | 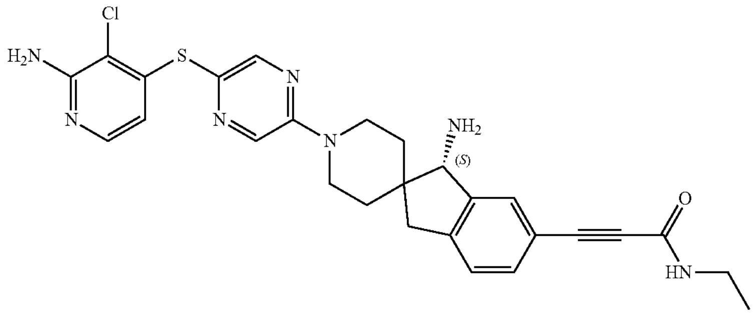 | 534.2 |
| 187 | 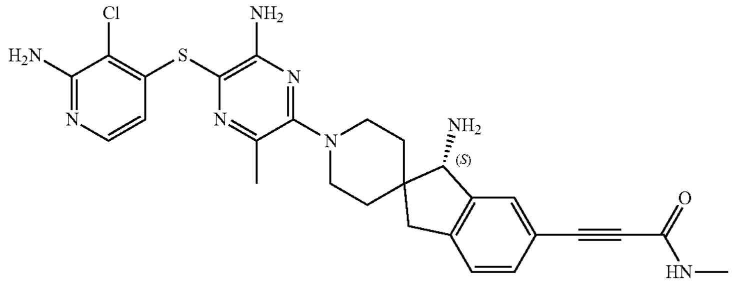 | 549.2 |

-continued
| | | |
|---|---|---|
| 188 | 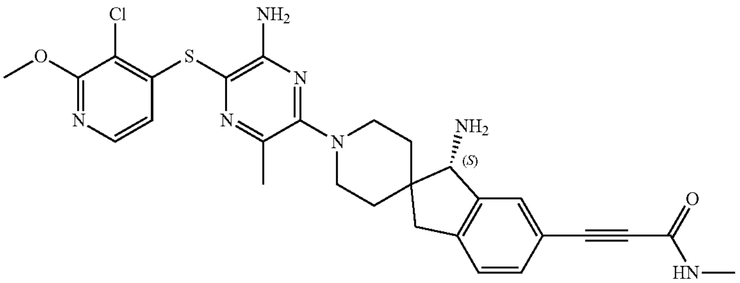 | 564.2 |
| 189 | 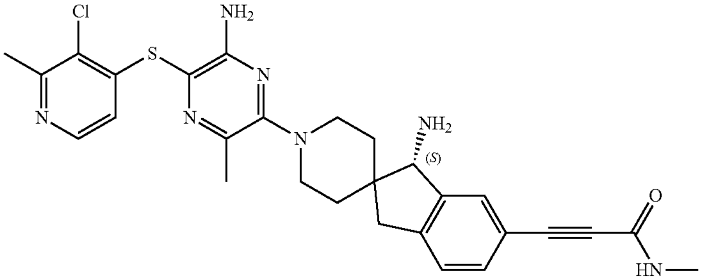 | 548.2 |
| 203 | 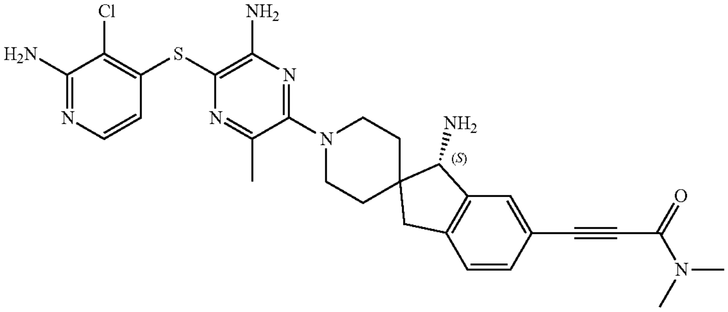 | 563.3 |
| 204 | 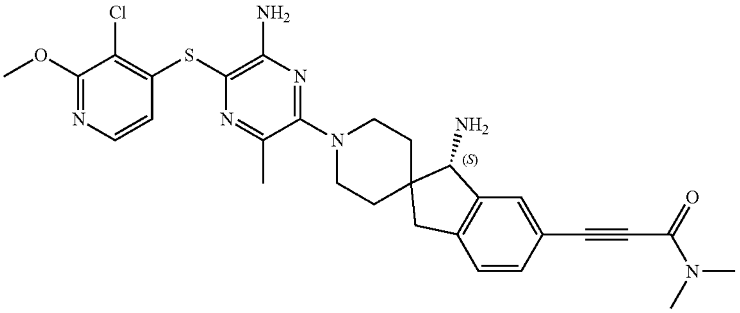 | 578.2 |
| 205 | 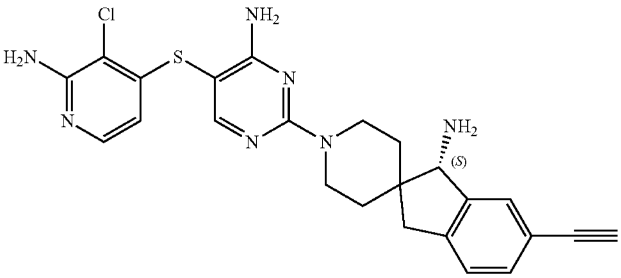 | 478.2 |

-continued
213 445.2
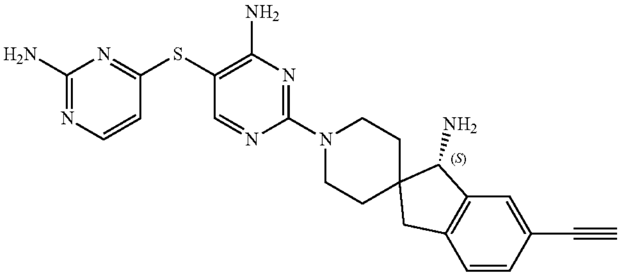
215 492.2
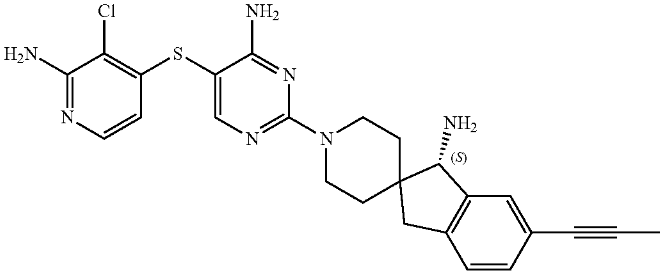
216 516.3
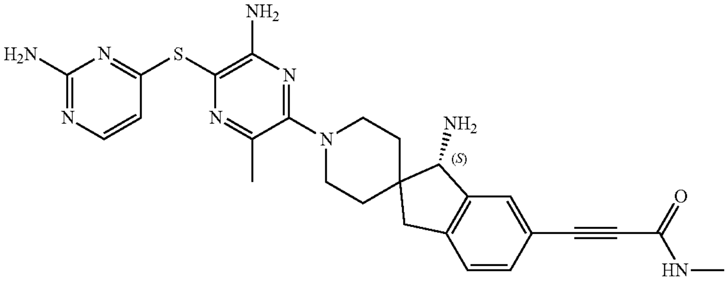
219 563.2
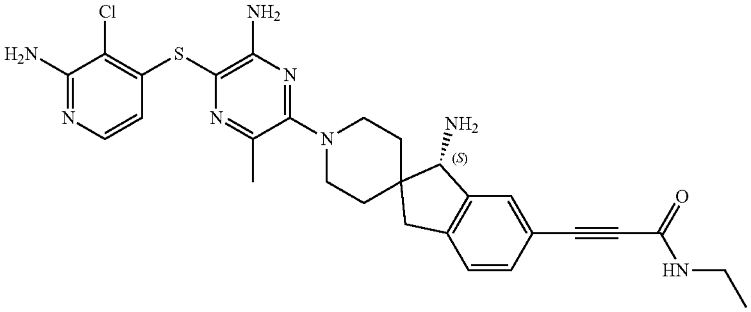
225 575.2
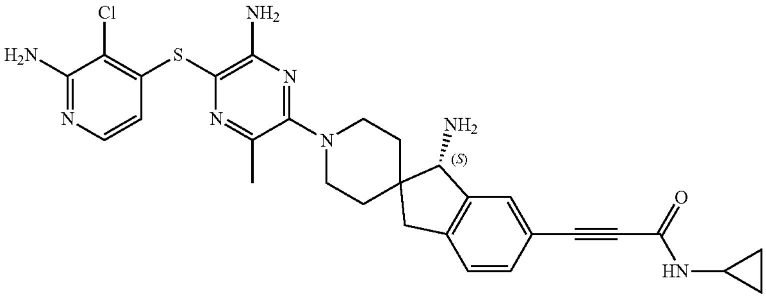

-continued
226 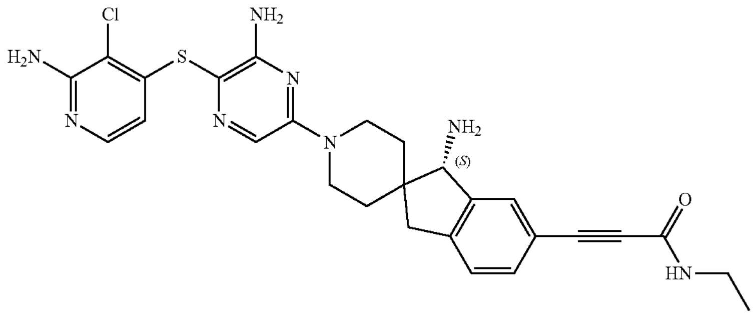 549.2
227 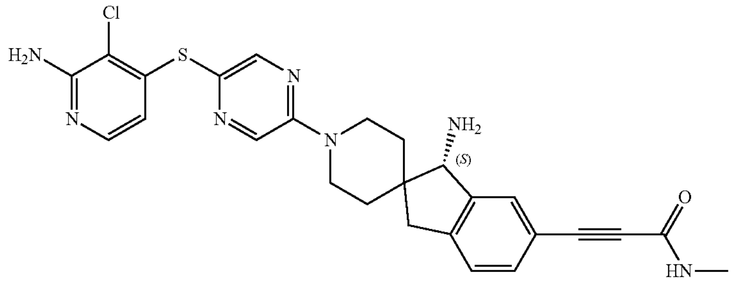 520.1
229 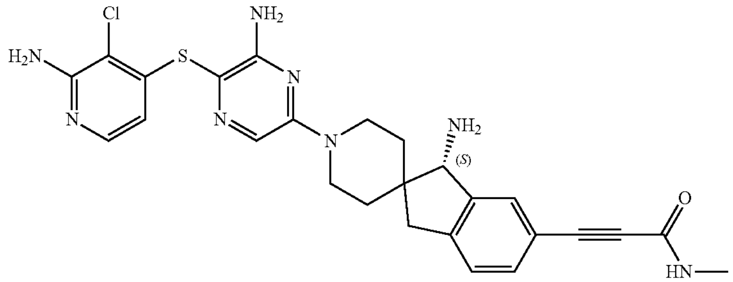 535.2
231 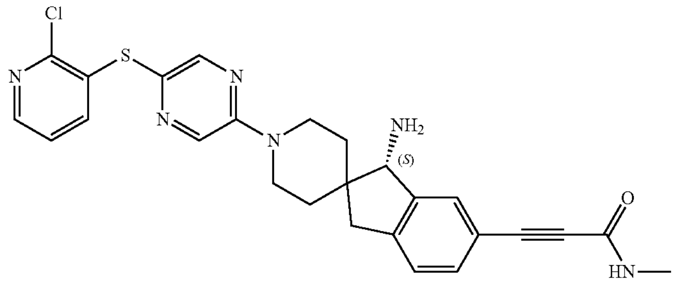 505.2
232 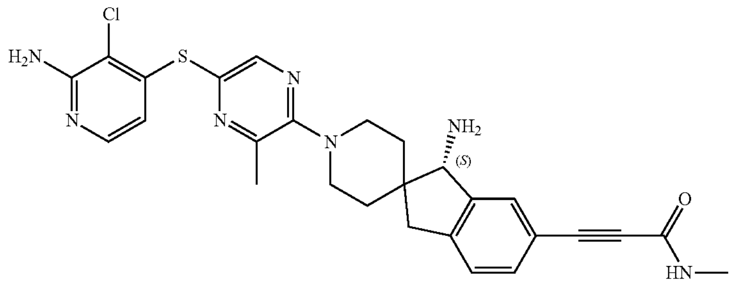 534.2

-continued
233 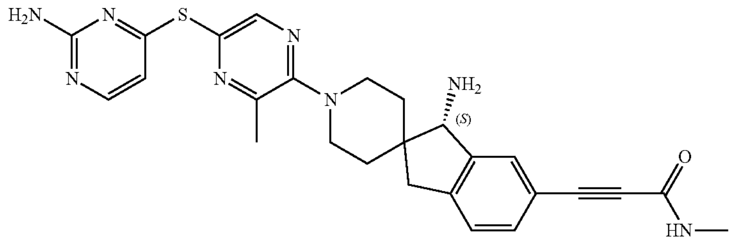 501.2
235 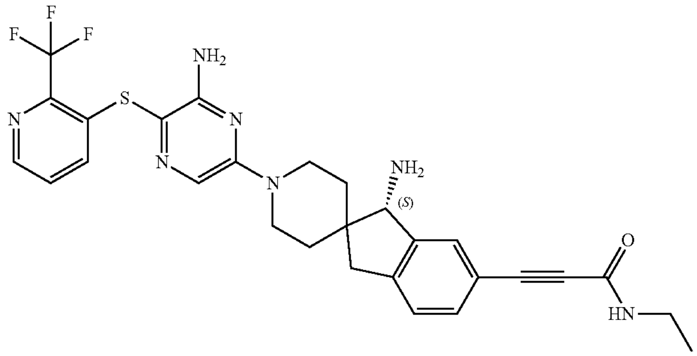 568.2
236 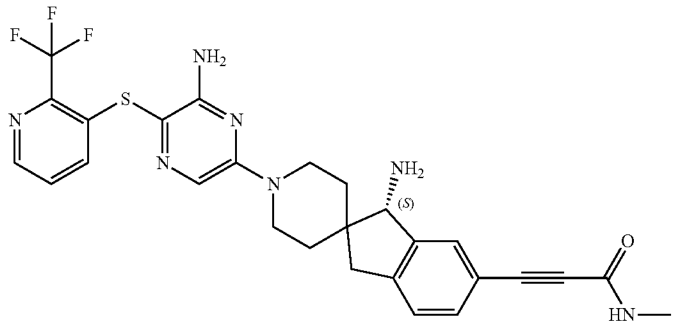 554.2
237 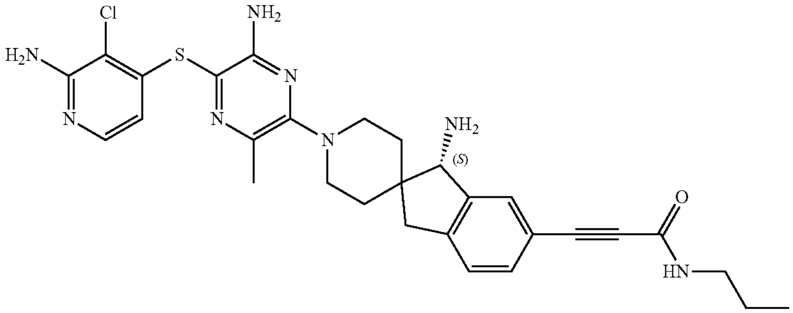 577.2
238 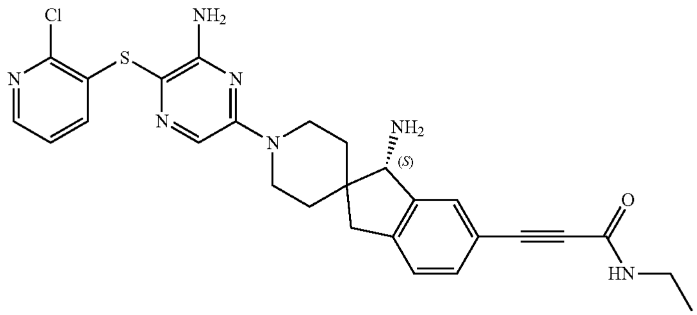 534.2

-continued
| | | |
|---|---|---|
| 241 | 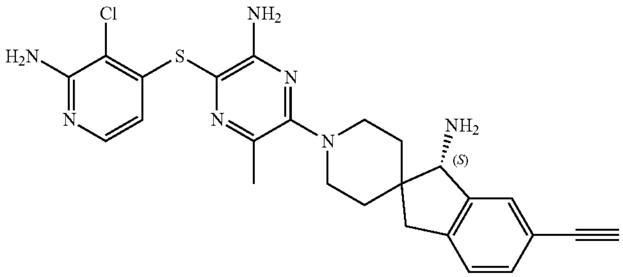 | 492.2 |
| 246 | 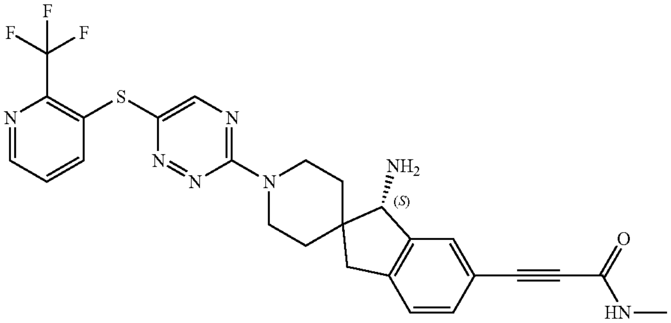 | 540.2 |
| 247 | 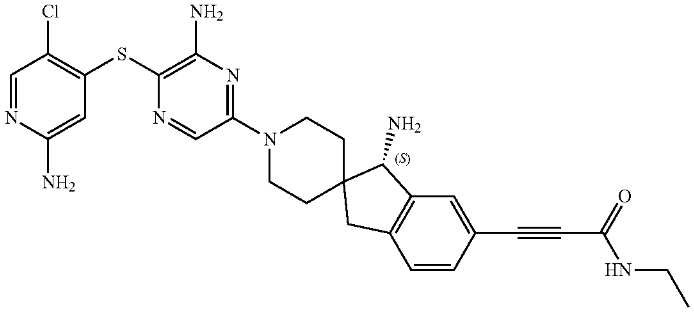 | 549.2 |
| 248 | 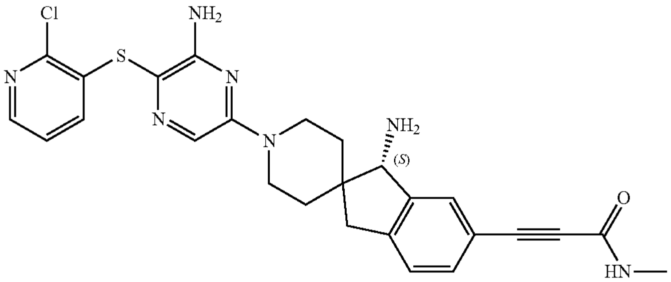 | 520.2 |
| 249 | 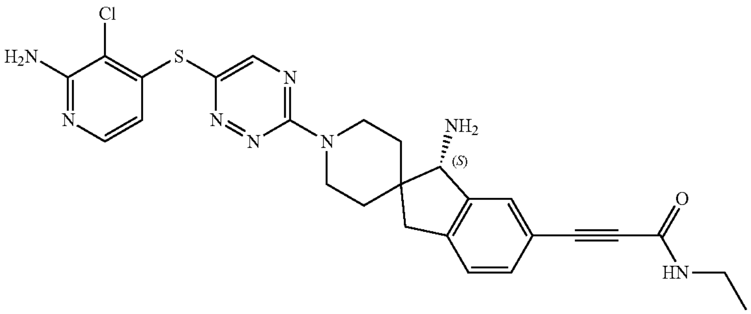 | 535.2 |

-continued
| | | |
|---|---|---|
| 250 | 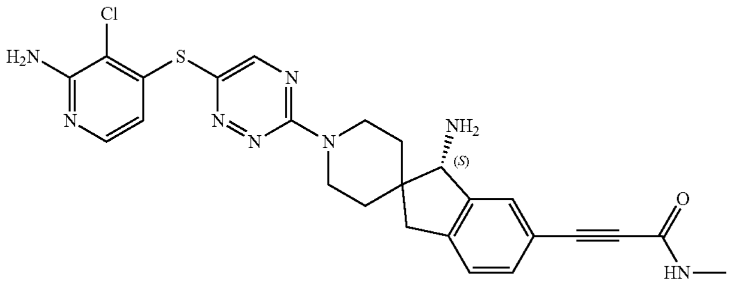 | 521.2 |
| 252 | 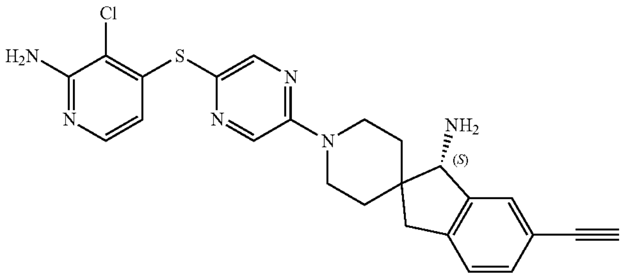 | 463.2 |
| 253 | 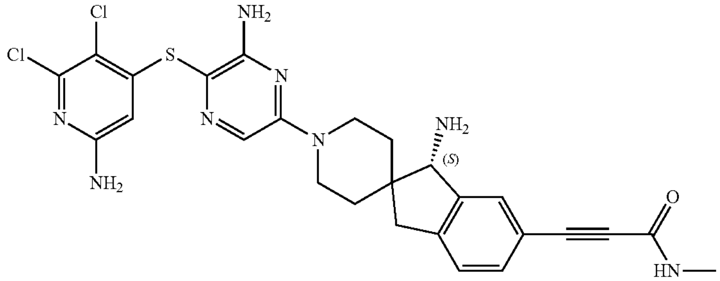 | 569.2 |
| 254 | 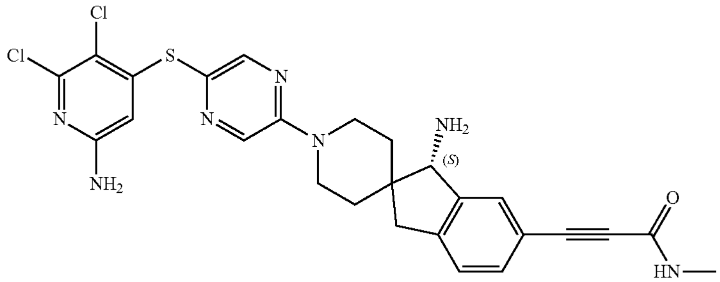 | 554.1 |
| 255 | 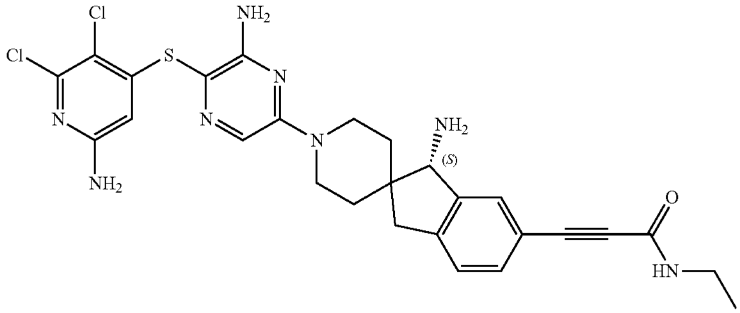 | 583.2 |

-continued
| | | |
|---|---|---|
| 256 | 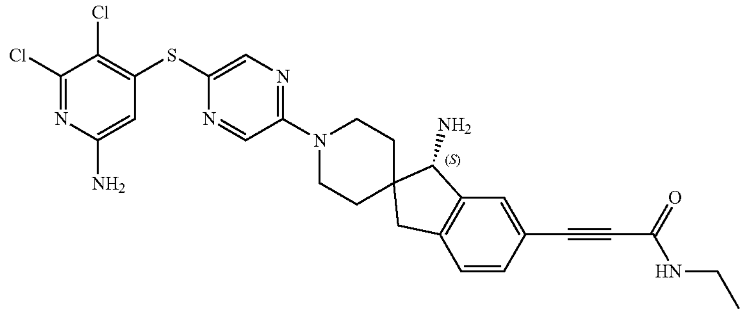 | 568.2 |
| 257 | 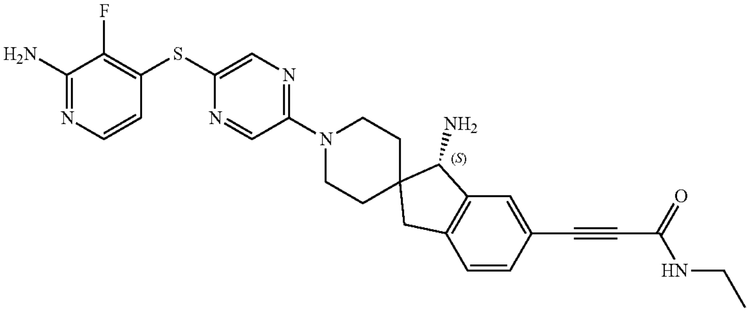 | 518.2 |
| 259 | 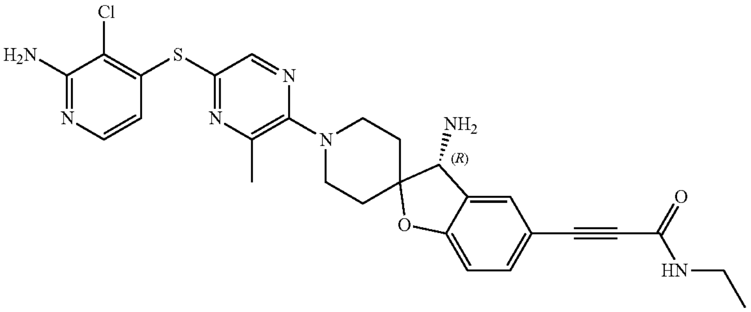 | 550.2 |
| 260 | 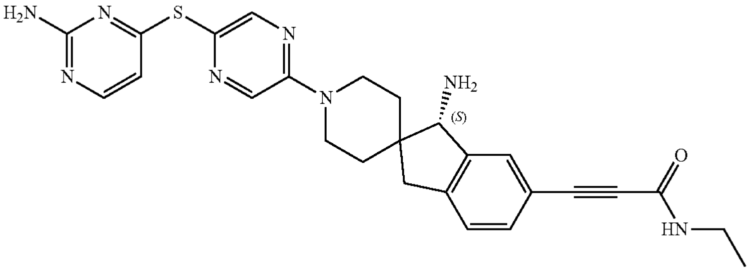 | 501.2 |
| 261 | 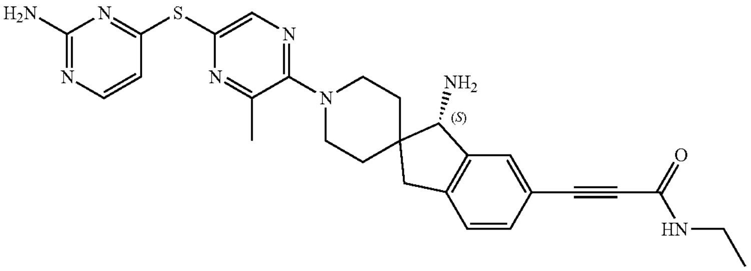 | 515.2 |

-continued
| | | |
|---|---|---|
| 262 | 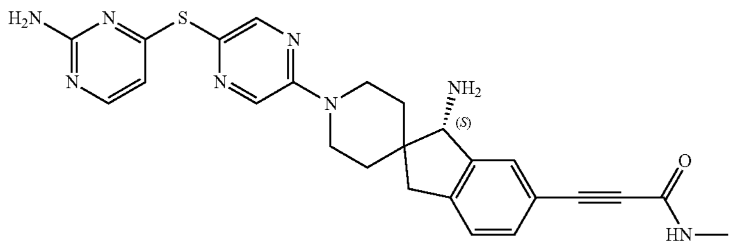 | 487.2 |
| 264 | 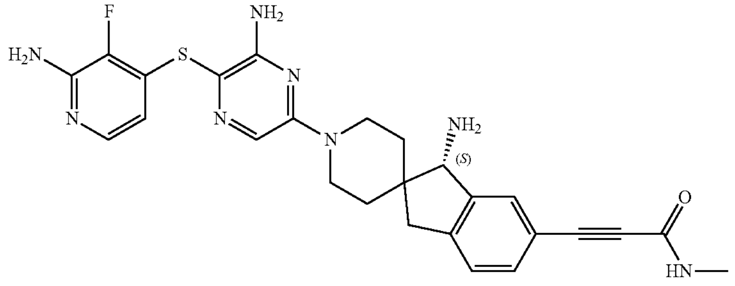 | 519.2 |
| 265 | 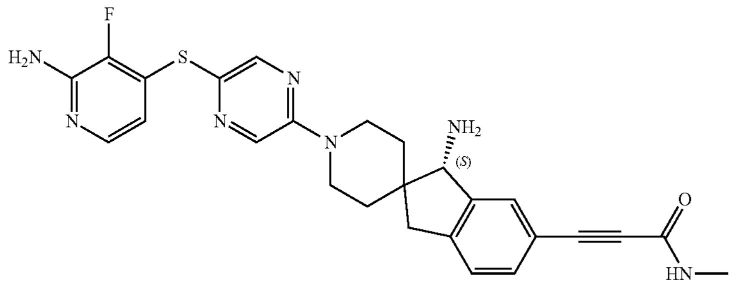 | 504.2 |
| 266 | 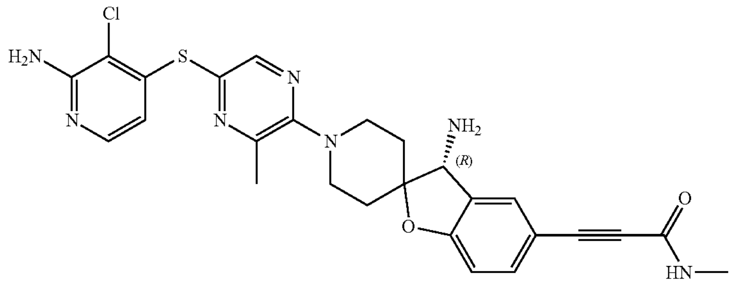 | 536.1 |
| 269 | 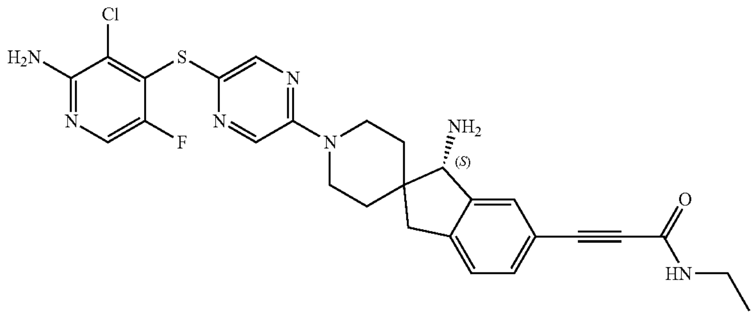 | 552.2 |

-continued
| | | |
|---|---|---|
| 270 | 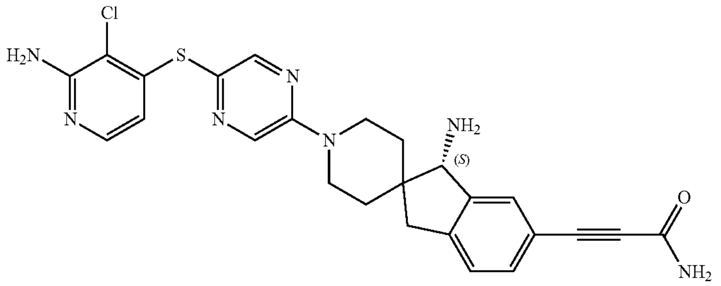 | 506.2 |
| 271 | 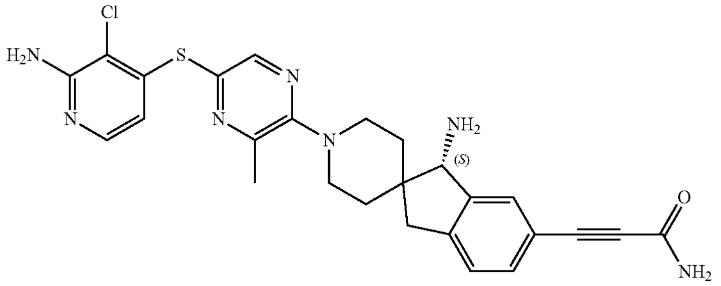 | 520.2 |
| 272 | 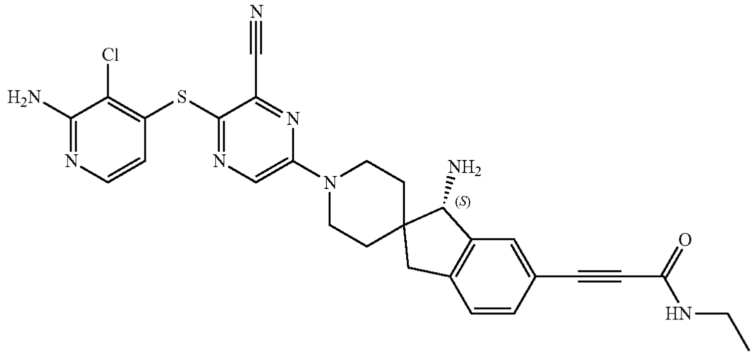 | 559.1 |
| 273 | 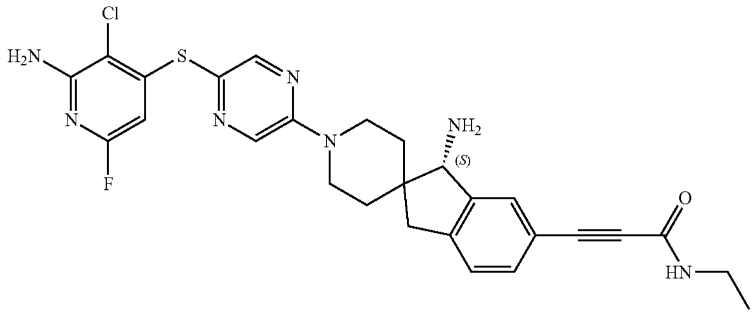 | 552.2 |
| 274 | 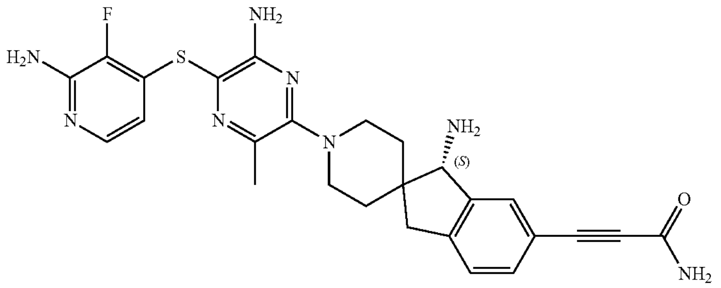 | 519.2 |

-continued
| | | |
|---|---|---|
| 275 | 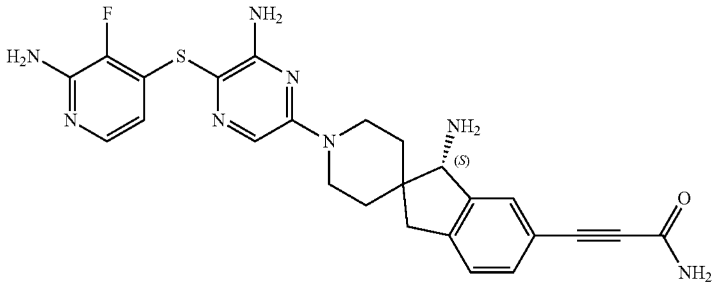 | 505.2 |
| 276 | 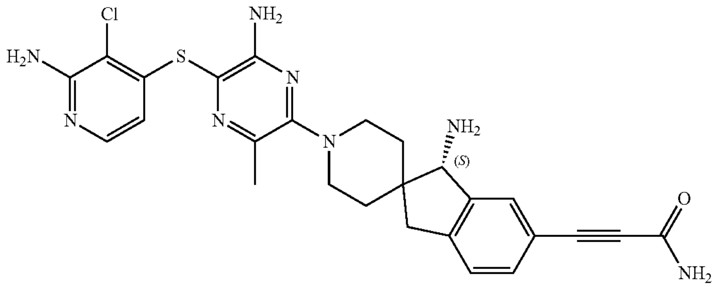 | 535.2 |
| 277 | 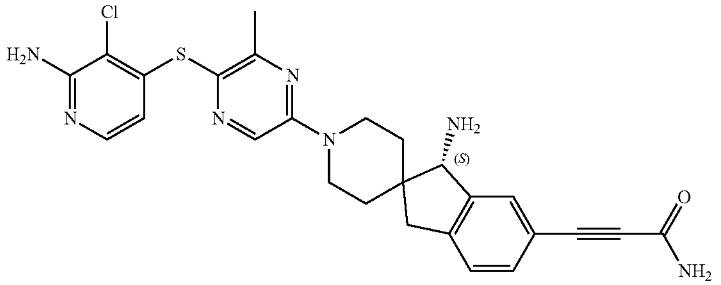 | 520.2 |
| 280 | 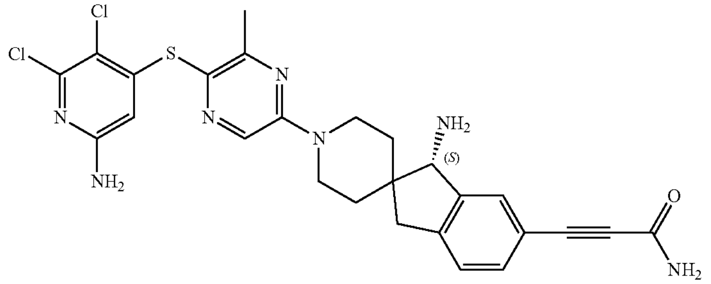 | 554.1 |
| 281 | 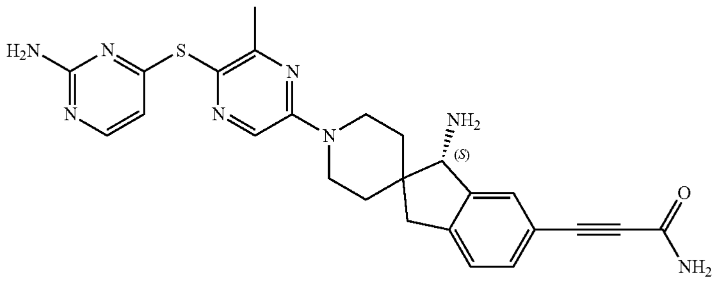 | 487.2 |

-continued
| | | |
|---|---|---|
| 290 | 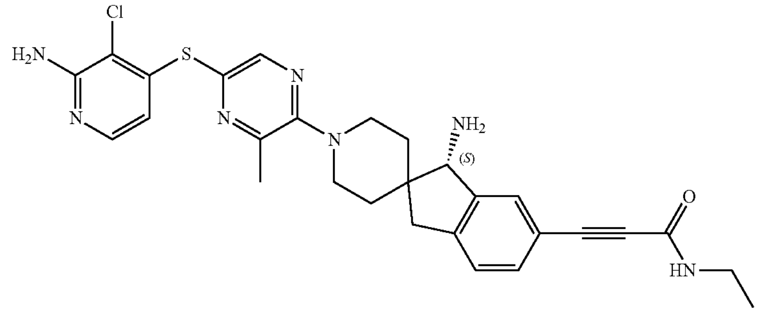 | 548.2 |
| 292 | 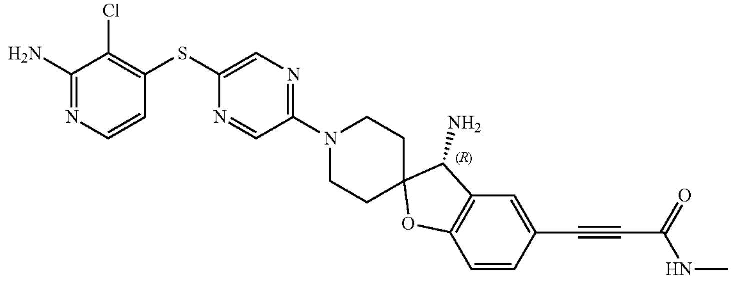 | 522.2 |
| 293 | 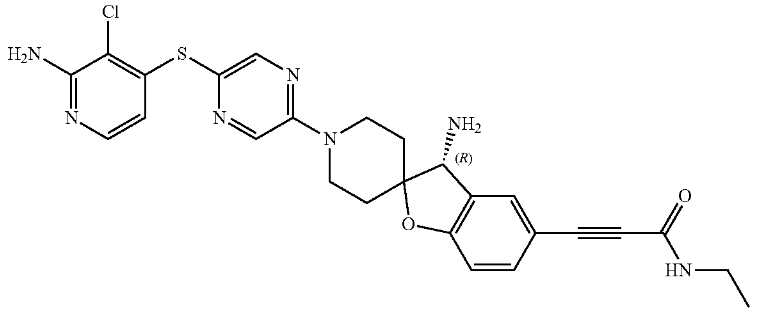 | 536.2 |
| 296 | 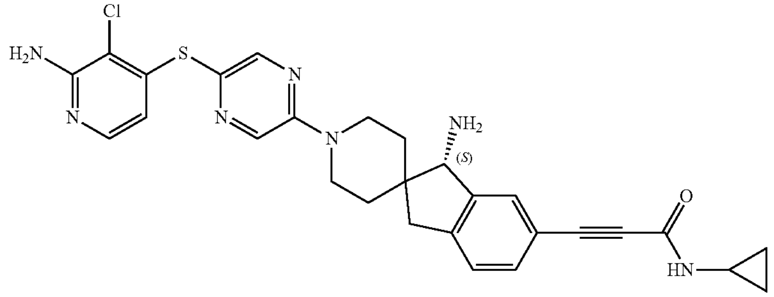 | 546.6 |
| 297 | 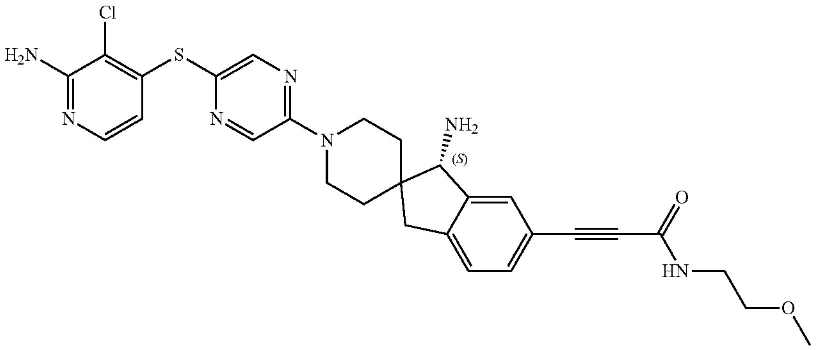 | 564.2 |

-continued
298 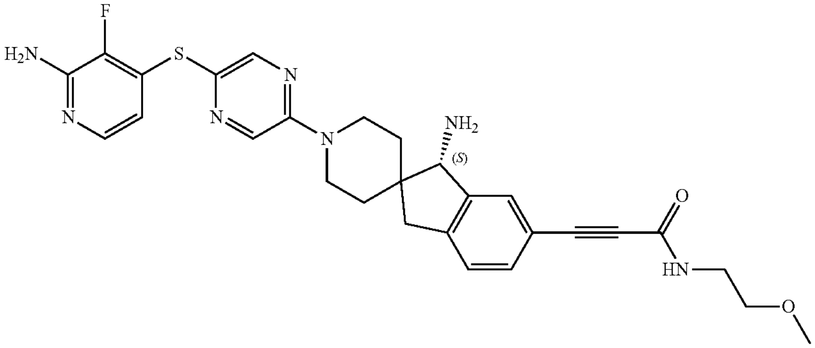 548.2
300 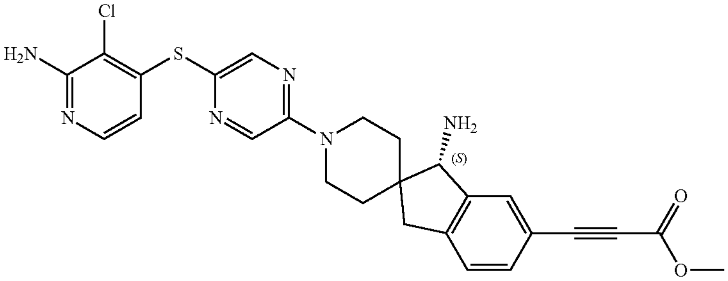 521.2
301 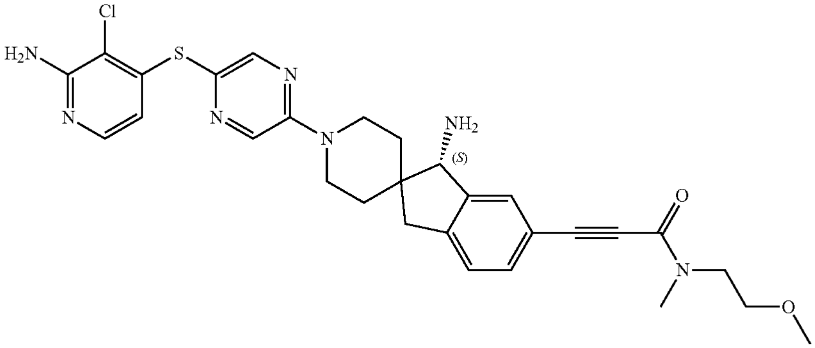 578.2
302 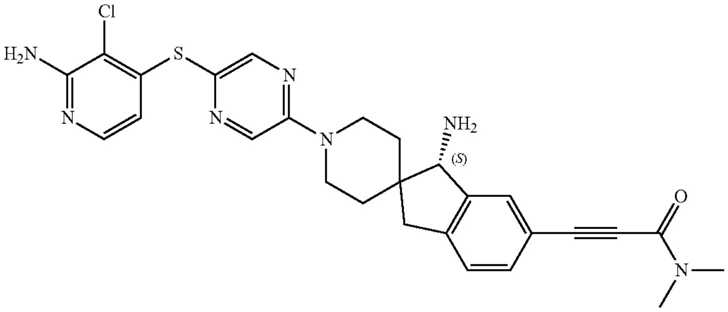 534.2

-continued

| | | |
|---|---|---|
| 303 | 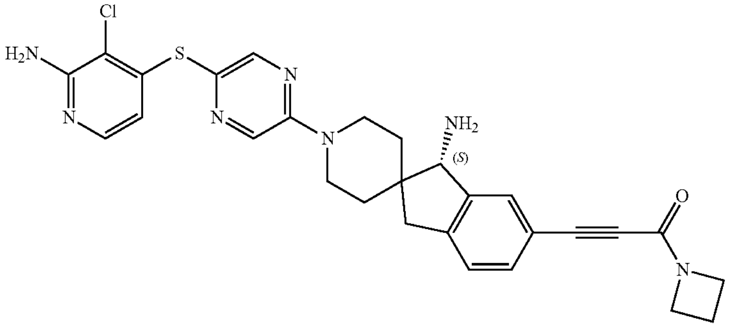 | 546.2 |

| Compounds | $^{1}$HNMR | Intermediates |
|---|---|---|
| 2 | $^{1}$H NMR (400 MHz, $CD_3OD$): δ 7.65-7.55 (m, 2H), 7.42-7.28 (m, 3H), 5.92 (d, J = 5.5 Hz, 1H), 4.33-4.22 (m, 2H), 3.95 (s, 1H), 3.42 (s, 1H), 3.24-3.09 (m, 3H), 2.82-2.76 (m, 1H), 1.85-1.67 (m, 2H), 1.59-1.55 (m, 1H), 1.40-1.33 (m, 1H). | I-A2<br>I-C1 |
| 86 | $^{1}$H NMR (400 MHz, $CD_3OD$): δ 7.71-7.58 (m, 2H), 7.48 (s, 1H), 7.32 (d, J = 7.6 Hz, 1H), 7.24 (d, J = 7.6 Hz, 1H), 5.99-5.92 (m, 1H), 4.45-4.20 (m, 4H), 3.95 (s, 1H), 3.45 (s, 3H), 3.31-3.15 (m, 3H), 2.87-2.76 (m, 1H), 1.95-1.70 (m, 2H), 1.61 (d, J = 13.2 Hz, 1H), 1.39 (d, J = 13.2 Hz, 1H). | I-A2<br>I-C7 |
| 95 | $^{1}$H NMR (400 MHz, $CD_3OD$): δ 7.66-7.59 (m, 2H), 7.52 (s, 1H), 7.37-7.33 (m, 1H), 7.27-7.22 (m, 1H), 5.98-5.93 (m, 1H), 4.39-4.29 (m, 2H), 3.95 (s, 2H), 3.33-3.13 (m, 4H), 2.87-2.78 (m, 1H), 1.95-1.86 (m, 1H), 1.82-1.72 (m, 1H), 1.66-1.59 (m, 1H), 1.43-1.38 (m, 1H). | I-A2<br>I-C3 |
| 112 | $^{1}$H NMR (400 MHz, $CD_3OD$): δ 7.88 (d, J = 5.2 Hz, 1H), 7.53-7.51 (m, 1H), 7.44 (s, 1H), 7.35-7.10 (m, 2H), 6.11 (d, J = 5.0 Hz, 1H), 4.35-4.20 (m, 4H), 3.91 (s, 1H), 3.39 (s, 3H), 3.22-3.04 (m, 3H), 2.83-2.70 (m, 1H), 1.90-1.63 (m, 2H), 1.58-1.54 (m, 1H), 1.36-1.32 (m, 1H). | I-A9<br>I-C7 |
| 126 | $^{1}$H NMR (400 MHz, $CD_3OD$): δ 7.97-7.89 (m, 1H), 7.63-7.47 (m, 2H), 7.35 (d, J = 7.8 Hz, 1H), 7.24 (d, J = 7.8 Hz, 1H), 6.22-6.12 (m, 1H), 4.38-4.24 (m, 2H), 3.95 (s, 1H), 3.44 (s, 1H), 3.29-3.16 (m, 3H), 2.87-2.76 (m, 1H), 1.93-1.84 (m, 1H), 1.81-1.73 (m, 1H), 1.65-1.59 (m, 1H), 1.44-1.39 (m, 1H). | I-A9<br>I-C3 |
| 129 | $^{1}$H NMR (400 MHz, $CD_3OD$): δ 7.61-7.55 (m, 3H), 7.45-7.41 (m, 1H), 7.30-7.26 (m, 1H), 5.93-5.89 (m, 1H), 4.34-4.23 (m, 2H), 3.94 (s, 1H), 3.26-3.15 (m, 3H), 2.85-2.77 (m, 1H), 1.91-1.82 (m, 1H), 1.78-1.69 (m, 1H), 1.61-1.55 (m, 1H), 1.37-1.32 (m, 1H). | I-A2<br>I-C16 |
| 131 | $^{1}$H NMR (400 MHz, $CD_3OD$): δ 7.60-7.51 (m, 2H), 7.33 (s, 1H), 7.22-7.07 (m, 2H), 5.89 (d, J = 5.6 Hz, 1H), 4.31-4.19 (m, 2H), 3.86 (s, 1H), 3.23-3.06 (m, 3H), 2.72 (d, J = 16.0 Hz, 1H), 1.97 (s, 3H), 1.87-1.77 (m, 1H), 1.75-1.63 (m, 1H), 1.53 (d, J = 13.4 Hz, 1H), 1.33 (d, J = 13.4 Hz, 1H). | I-A2<br>I-C17 |
| 134 | $^{1}$H NMR (400 MHz, $CD_3OD$): δ 7.93-7.83 (m, 1H), 7.54 (s, 1H), 7.35 (s, 1H), 7.22-7.09 (m, 2H), 6.16-6.07 (m, 1H), 4.37-4.12 (m, 2H), 3.88 (s, 1H), 3.25-3.09 (m, 3H), 2.83-2.67 (m, 1H), 1.99 (s, 3H), 1.87-1.78 (m, 1H), 1.76-1.67 (m, 1H), 1.59-1.52 (m, 1H), 1.38-1.32 (m, 1H). | I-A9<br>I-C17 |
| 155 | $^{1}$H NMR (400 MHz, $CD_3OD/CDCl_3$ = 2/1): δ 8.28-8.22 (m, 2H), 7.58-7.56 (m, 1H), 7.52 (s, 1H), 7.42-7.36 (m, 1H), 7.27-7.21 (m, 1H), 5.95-5.89 (m, 1H), 4.34-4.26 (m, 2H), 3.95 (s, 1H), 3.28-3.23 (m, 4H), 3.20-3.14 (m, 1H), 2.84-2.77 (m, 1H), 1.91-1.82 (m, 1H), 1.79-1.71 (m, 1H), 1.65-1.59 (m, 1H), 1.43-1.36 (m, 1H), 1.19-1.11 (m, 3H). | I-A15<br>I-C23 |
| 187 | $^{1}$H NMR (400 MHz, $CD_3OD$): δ 7.60-7.56 (m, 2H), 7.44-7.40 (m, 1H), 7.30-7.26 (m, 1H), 5.89-5.87 (m, 1H), 3.97 (s, 1H), 3.72-3.64 (m, 2H), 3.19-3.14 (m, 1H), 3.13-3.06 (m, 2H), 2.82-2.76 (m, 4H), 2.37 (s, 3H), 2.03-1.95 (m, 1H), 1.92-1.83 (m, 1H), 1.63-1.58 (m, 1H), 1.41-1.35 (m, 1H). | I-A11<br>I-C20 |
| 188 | $^{1}$H NMR (400 MHz, $CD_3OD$): δ 7.78-7.75 (m, 1H), 7.58-7.55 (m, 1H), 7.44-7.40 (m, 1H), 7.30-7.26 (m, 1H), 6.20-6.17 (m, 1H), 3.98-3.96 (m, 4H), 3.73-3.66 (m, 2H), 3.20-3.04 (m, 3H), 2.83-2.76 (m, 4H), 2.38 (s, 3H), 2.04-1.97 (m, 1H), 1.94-1.83 (m, 1H), 1.63-1.58 (m, 1H), 1.40-1.35 (m, 1H). | I-A12<br>I-C20 |
| 189 | $^{1}$H NMR (400 MHz, $CD_3OD$): δ 8.04-8.01 (m, 1H), 7.59-7.55 (m, 1H), 7.44-7.40 (m, 1H), 7.30-7.26 (m, 1H), 6.51-6.48 (m, 1H), 3.97 (s, 1H), 3.75-3.67 (m, 2H), 3.20-3.15 (m, 1H), 3.15-3.06 (m, 2H), 2.84-2.76 (m, 4H), 2.59 (s, 3H), 2.38 (s, 3H), 2.04-1.97 (m, 1H), 1.94-1.84 (m, 1H), 1.64-1.58 (m, 1H), 1.41-1.35 (m, 1H). | I-A13<br>I-C20 |

-continued

| | | |
|---|---|---|
| 203 | $^1$H NMR (400 MHz, $CD_3OD$): δ 7.61-7.58 (m, 1H), 7.58-7.55 (m, 1H), 7.45-7.40 (m, 1H), 7.30-7.25 (m, 1H), 5.88-5.84 (m, 1H), 3.96 (s, 1H), 3.71-3.62 (m, 2H), 3.19-3.13 (m, 1H), 3.12-3.04 (m, 2H), 3.00 (s, 3H), 2.81-2.75 (m, 1H), 2.36 (s, 3H), 2.02-1.94 (m, 1H), 1.91-1.82 (m, 1H), 1.63-1.56 (m, 1H), 1.39-1.32 (m, 1H). | I-A11<br>I-C21 |
| 204 | $^1$H NMR (400 MHz, $CD_3OD$): δ 7.77-7.73 (m, 1H), 7.61-7.58 (m, 1H), 7.46-7.41 (m, 1H), 7.31-7.26 (m, 1H), 6.19-6.15 (m, 1H), 3.98 (s, 1H), 3.94 (s, 3H), 3.73-3.62 (m, 2H), 3.19-3.14 (m, 1H), 3.14-3.05 (m, 2H), 3.00 (s, 3H), 2.84-2.77 (m, 1H), 2.36 (s, 3H), 2.03-1.93 (m, 1H), 1.93-1.82 (m, 1H), 1.63-1.56 (m, 1H), 1.41-1.34 (m, 1H). | I-A12<br>I-C21 |
| 205 | $^1$H NMR (400 MHz, $CD_3OD$): δ 7.94-7.91 (m, 1H), 7.62-7.60 (m, 1H), 7.47-7.45 (m, 1H), 7.31-7.27 (m, 1H), 7.21-7.16 (m, 1H), 6.03-6.00 (m, 1H), 4.58-4.51 (m, 2H), 3.89 (s, 1H), 3.38 (s, 1H), 3.23-3.11 (m, 3H), 2.80-2.73 (m, 1H), 1.84-1.75 (m, 1H), 1.71-1.63 (m, 1H), 1.55-1.49 (m, 1H), 1.34-1.29 (m, 1H). | I-A38<br>I-C3 |
| 213 | $^1$H NMR (400 MHz, $CD_3OD$): δ 7.93-7.91 (m, 1H), 7.91-7.88 (m, 1H), 7.48-7.44 (m, 1H), 7.31-7.27 (m, 1H), 7.20-7.17 (m, 1H), 6.23-6.20 (m, 1H), 4.56-4.49 (m, 2H), 3.89 (s, 1H), 3.37 (s, 1H), 3.21-3.11 (m, 3H), 2.79-2.73 (m, 1H), 1.82-1.74 (m, 1H), 1.71-1.63 (m, 1H), 1.54-1.49 (m, 1H), 1.33-1.31 (m, 1H). | I-A39<br>I-C3 |
| 215 | $^1$H NMR (400 MHz, $CD_3OD$): δ 7.94-7.91 (s, 1H), 7.62-7.59 (m, 1H), 7.37-7.33 (m, 1H), 7.20-7.12 (m, 2H), 6.03-6.00 (m, 1H), 4.57-4.50 (m, 2H), 3.90 (s, 1H), 3.24-3.15 (m, 2H), 3.14-3.09 (m, 1H), 2.80-2.72 (m, 1H), 1.98 (s, 3H), 1.81-1.73 (m, 1H), 1.71-1.63 (m, 1H), 1.54-1.48 (m, 1H), 1.35-1.30 (m, 1H). | I-A38<br>I-C17 |
| 216 | $^1$H NMR (400 MHz, $CD_3OD$): δ 7.90-7.85 (m, 1H), 7.57-7.54 (m, 1H), 7.42-7.38 (m, 1H), 7.28-7.24 (m, 1H), 6.13-6.09 (m, 1H), 3.98-3.94 (m, 1H), 3.69-3.59 (m, 2H), 3.17-3.04 (m, 3H), 2.80-2.75 (m, 4H), 2.35 (s, 3H), 2.01-1.93 (m, 1H), 1.90-1.82 (m, 1H), 1.61-1.56 (m, 1H), 1.39-1.34 (m, 1H). | I-A14<br>I-C20 |
| 219 | $^1$H NMR (400 MHz, $CD_3OD$): δ 7.59-7.54 (m, 2H), 7.43-7.39 (m, 1H), 7.28-7.24 (m, 1H), 5.88-5.84 (m, 1H), 3.96 (s, 1H), 3.71-3.62 (m, 2H), 3.28-3.24 (m, 2H), 3.17-3.05 (m, 3H), 2.83-2.75 (m, 1H), 2.36 (s, 3H), 2.02-1.93 (m, 1H), 1.91-1.83 (m, 1H), 1.62-1.56 (m, 1H), 1.40-1.34 (m, 1H), 1.17-1.12 (m, 3H). | I-A11<br>I-C23 |
| 225 | $^1$H NMR (400 MHz, $CD_3OD$): δ 7.59-7.51 (m, 2H), 7.41-7.37 (m, 1H), 7.27-7.22 (m, 1H), 5.88-5.83 (m, 1H), 3.94 (s, 1H), 3.72-3.61 (m, 2H), 3.18-3.03 (m, 3H), 2.81-2.71 (m, 2H), 2.35 (s, 3H), 2.01-1.92 (m, 1H), 1.90-1.82 (m, 1H), 1.61-1.55 (m, 1H), 1.38-1.32 (m, 1H), 0.82-0.70 (m, 2H), 0.60-0.49 (m, 2H). | I-A11<br>I-C25 |
| 226 | $^1$H NMR (400 MHz, $CD_3OD/CDCl_3$ = 2/1): δ 7.57-7.55 (m, 1H), 7.53 (s, 1H), 7.51 (s, 1H), 7.41-7.36 (m, 1H), 7.25-7.20 (m, 1H), 5.97-5.90 (m, 1H), 4.26-4.19 (m, 2H), 3.93 (s, 1H), 3.28-3.23 (m, 2H), 3.22-3.11 (m, 3H), 2.82-2.75 (m, 1H), 1.87-1.78 (m, 1H), 1.76-1.67 (m, 1H), 1.61-1.55 (m, 1H), 1.40-1.33 (m, 1H), 1.17-1.11 (m, 3H). | I-A2<br>I-C23 |
| 227 | $^1$H NMR (400 MHz, $CD_3OD$): δ 8.32-8.30 (m, 1H), 8.27-8.23 (m, 1H), 7.59-7.57 (m, 1H), 7.54 (s, 1H), 7.43-7.38 (m, 1H), 7.29-7.25 (m, 1H), 5.93-5.91 (m, 1H), 4.37-4.30 (m, 2H), 3.95 (s, 1H), 3.28-3.17 (m, 3H), 2.85-2.78 (m, 4H), 1.92-1.84 (m, 1H), 1.80-1.72 (m, 1H), 1.64-1.58 (m, 1H), 1.40-1.34 (m, 1H). | I-A15<br>I-C20 |
| 229 | $^1$H NMR (400 MHz, $CD_3OD$): δ 7.60-7.52 (m, 3H), 7.41-7.39 (m, 1H), 7.27-7.25 (m, 1H), 5.91 (d, J = 5.5 Hz, 1H), 4.26 (br, 2H), 3.93 (s, 1H), 3.35-3.33 (m, 1H), 3.24-3.13 (m, 3H), 2.78 (s, 3H), 1.90-1.70 (m, 2H), 1.59-1.55 (m, 1H), 1.36-1.32 (m, 1H). | I-A2<br>I-C20 |
| 231 | $^1$H NMR (400 MHz, $CD_3OD$): δ 8.31-8.29 (m, 1H), 8.27-8.25 (m, 1H), 8.17-8.13 (m, 1H), 7.57-7.55 (m, 1H), 7.44-7.40 (m, 1H), 7.37-7.34 (m, 1H), 7.30-7.26 (m, 1H), 7.25-7.22 (m, 1H), 4.36-4.29 (m, 2H), 3.96 (s, 1H), 3.29-3.24 (m, 2H), 3.24-3.18 (m, 1H), 2.85-2.79 (m, 4H), 1.93-1.85 (m, 1H), 1.81-1.73 (m, 1H), 1.65-1.59 (m, 1H), 1.41-1.35 (m, 1H). | I-A16<br>I-C20 |
| 232 | $^1$H NMR (400 MHz, $CD_3OD$): δ 8.26-8.23 (m, 1H), 7.62-7.60 (m, 1H), 7.58-7.55 (m, 1H), 7.44-7.39 (m, 1H), 7.30-7.26 (m, 1H), 6.00-5.98 (m, 1H), 3.98 (s, 1H), 3.75-3.67 (m, 2H), 3.21-3.11 (m, 3H), 2.83-2.77 (m, 4H), 2.55 (s, 3H), 2.05-1.97 (m, 1H), 1.95-1.86 (m, 1H), 1.67-1.60 (m, 1H), 1.44-1.37 (m, 1H). | I-A17<br>I-C20 |
| 233 | $^1$H NMR (400 MHz, $CD_3OD$): δ 8.30-8.26 (m, 1H), 7.93-7.90 (m, 1H), 7.59-7.55 (m, 1H), 7.44-7.40 (m, 1H), 7.29-7.26 (m, 1H), 6.27-6.24 (m, 1H), 3.98 (s, 1H), 3.73-3.66 (m, 2H), 3.20-3.11 (m, 3H), 2.83-2.78 (m, 4H), 2.55 (s, 3H), 2.06-1.98 (m, 1H), 1.95-1.87 (m, 1H), 1.67-1.61 (m, 1H), 1.44-1.38 (m, 1H). | I-A18<br>I-C20 |
| 235 | $^1$H NMR (400 MHz, $CD_3OD$): δ 8.37 (dd, J = 4.3, 1.6 Hz, 1H), 7.59 (s, 1H), 7.54 (s, 1H), 7.45-7.36 (m, 3H), 7.26 (d, J = 7.7 Hz, 1H), 4.34-4.21 (m, 2H), 3.93 (s, 1H), 3.28-3.13 (m, 5H), 2.79 (d, J = 16.4 Hz, 1H), 1.89-1.68 (m, 2H), 1.57 (d, J = 13.2 Hz, 1H), 1.34 (d, J = 13.6 Hz, 1H), 1.14 (t, J = 7.3 Hz, 3H). | I-A19<br>I-C23 |

-continued

| | | |
|---|---|---|
| 236 | $^1$H NMR (400 MHz, $CD_3OD$): δ 8.37 (dd, J = 4.3, 1.5 Hz, 1H), 7.59 (s, 1H), 7.54 (s, 1H), 7.44-7.34 (m, 3H), 7.26 (d, J = 7.8 Hz, 1H), 4.34-4.21 (m, 2H), 3.93 (s, 1H), 3.27-3.15 (m, 3H), 2.83-2.76 (m, 4H), 1.91-1.69 (m, 2H), 1.57 (d, J = 11.8 Hz, 1H), 1.34 (d, J = 13.3 Hz, 1H). | I-A19 I-C20 |
| 237 | $^1$H NMR (400 MHz, $CD_3OD$): δ 7.62-7.55 (m, 2H), 7.45-7.38 (m, 1H), 7.30-7.24 (m, 1H), 5.91-5.85 (m, 1H), 3.96 (s, 1H), 3.74-3.62 (m, 2H), 3.25-3.05 (m, 5H), 2.86-2.72 (m, 1H), 2.37 (s, 3H), 2.05-1.94 (m, 1H), 1.94-1.82 (m, 1H), 1.66-1.50 (m, 3H), 1.42-1.33 (m, 1H), 1.00-0.83 (m, 3H). | I-A11 I-C27 |
| 238 | $^1$H NMR (400 MHz, $CD_3OD$): δ 8.13-8.08 (m, 1H), 7.59 (s, 1H), 7.56 (s, 1H), 7.44-7.39 (m, 1H), 7.31-7.25 (m, 1H), 7.24-7.19 (m, 1H), 7.15-7.09 (m, 1H), 4.33-4.24 (m, 2H), 3.95 (s, 1H), 3.34 (s, 1H), 3.27-3.16 (m, 4H), 2.87-2.76 (m, 1H), 1.93-1.81 (m, 1H), 1.80-1.69 (m, 1H), 1.62-1.56 (m, 1H), 1.38-1.34 (m, 1H), 1.21-1.12 (m, 3H). | I-A40 I-C23 |
| 241 | $^1$H NMR (400 MHz, $CD_3OD$): δ 7.58 (d, J = 5.5 Hz, 1H), 7.48 (s, 1H), 7.30 (d, J = 7.7 Hz, 1H), 7.19 (d, J = 7.7 Hz, 1H), 5.88 (d, J = 5.5 Hz, 1H), 3.94 (s, 1H), 3.68-3.64 (m, 2H), 3.39 (s, 1H), 3.15-3.02 (m, 3H), 2.77-2.73 (m, 1H), 2.37 (s, 3H), 2.01-1.82 (m, 2H), 1.60-1.56 (m, 1H), 1.40-1.36 (m, 1H). | I-A11 I-C3 |
| 246 | $^1$H NMR (400 MHz, $CD_3OD$): δ 8.68 (dd, J = 4.7, 1.4 Hz, 1H), 8.42 (s, 1H), 8.19 (d, J = 7.4 Hz, 1H), 7.67 (dd, J = 8.0, 4.7 Hz, 1H), 7.55 (s, 1H), 7.41 (dd, J = 7.7, 1.3 Hz, 1H), 7.27 (d, J = 7.8 Hz, 1H), 4.29-4.16 (m, 2H), 3.94 (s, 1H), 3.30-3.16 (m, 3H), 2.84-2.77 (m, 4H), 1.98-1.72 (m, 2H), 1.61 (d, J = 13.5 Hz, 1H), 1.36 (d, J = 13.6 Hz, 1H). | I-A21 I-C20 |
| 247 | $^1$H NMR (400 MHz, $CD_3OD$): δ 7.74 (s, 1H), 7.64-7.55 (m, 2H), 7.47-7.41 (m, 1H), 7.34-7.27 (m, 1H), 5.89 (s, 1H), 4.37-4.24 (m, 2H), 3.97 (s, 1H), 3.30-3.12 (m, 5H), 2.91-2.77 (m, 1H), 1.96-1.81 (m, 1H), 1.81-1.69 (m, 1H), 1.64-1.57 (m, 1H), 1.40-1.34 (m, 1H), 1.20-1.14 (m, 3H). | I-A22 I-C23 |
| 248 | $^1$H NMR (400 MHz, $CD_3OD/CDCl_3$): δ 8.11-8.05 (m, 1H), 7.55 (s, 1H), 7.50 (s, 1H), 7.42-7.37 (m, 1H), 7.25-7.21 (m, 1H), 7.17-7.10 (m, 2H), 4.26-4.19 (m, 2H), 3.95 (s, 1H), 3.24-3.10 (m, 3H), 2.89-2.74 (m, 4H), 1.87-1.78 (m, 1H), 1.75-1.67 (m, 1H), 1.63-1.57 (m, 1H), 1.41-1.34 (m, 1H). | I-A40 I-C20 |
| 249 | $^1$H NMR (400 MHz, $CD_3OD$): δ 8.54 (s, 1H), 7.73 (d, J = 5.5 Hz, 1H), 7.57 (s, 1H), 7.43 (d, J = 7.7 Hz, 1H), 7.29 (d, J = 7.8 Hz, 1H), 6.50 (d, J = 5.5 Hz, 1H), 4.39-4.28 (m, 2H), 3.97 (s, 1H), 3.41-3.32 (m, 3H), 3.28-3.19 (m, 2H), 2.84 (d, J = 16.2 Hz, 1H), 1.98-1.75 (m, 2H), 1.66 (d, J = 13.7 Hz, 1H), 1.40 (d, J = 13.9 Hz, 1H), 1.17 (t, J = 7.3 Hz, 3H). | I-A23 I-C23 |
| 250 | $^1$H NMR (400 MHz, $CD_3OD$): δ 8.53 (s, 1H), 7.73 (d, J = 5.5 Hz, 1H), 7.56 (s, 1H), 7.45-7.39 (m, 1H), 7.29 (d, J = 7.8 Hz, 1H), 6.49 (d, J = 5.5 Hz, 1H), 4.38-4.28 (m, 2H), 3.96 (s, 1H), 3.41-3.32 (m, 2H), 3.23 (d, J = 16.3 Hz, 1H), 2.87-2.79 (m, 4H), 1.97-1.73 (m, 2H), 1.65 (d, J = 13.2 Hz, 1H), 1.40 (d, J = 13.5 Hz, 1H). | I-A23 I-C20 |
| 252 | $^1$H NMR (400 MHz, $CD_3OD$): δ 8.32 (d, J = 1.3 Hz, 1H), 8.27 (d, J = 1.3 Hz, 1H), 7.59 (d, J = 5.5 Hz, 1H), 7.48 (s, 1H), 7.32 (dd, J = 7.7, 1.3 Hz, 1H), 7.21 (d, J = 7.7 Hz, 1H), 5.97-5.90 (m, 1H), 4.4-4.29 (m, 2H), 3.94 (s, 1H), 3.41 (s, 1H), 3.36-3.30 (m, 2H), 3.20-3.16 (m, 1H), 2.82-2.78 (m, 1H), 1.92-1.70 (m, 2H), 1.64-1.58 (m, 1H), 1.44-1.37 (m, 1H). | I-A15 I-C3 |
| 253 | $^1$H NMR (400 MHz, $CD_3OD$): δ 7.62-7.59 (m, 1H), 7.58-7.55 (m, 1H), 7.45-7.41 (m, 1H), 7.32-7.27 (m, 1H), 5.79 (s, 1H), 4.36-4.24 (m, 2H), 3.96 (s, 1H), 3.28-3.18 (m, 3H), 2.88-2.77 (m, 4H), 1.93-1.83 (m, 1H), 1.79-1.69 (m, 1H), 1.63-1.57 (m, 1H), 1.38-1.33 (m, 1H). | I-A24 I-C20 |
| 254 | $^1$H NMR (400 MHz, $CD_3OD$): δ 8.40-8.34 (m, 1H), 8.33-8.26 (m, 1H), 7.61-7.54 (m, 1H), 7.47-7.41 (m, 1H), 7.34-7.27 (m, 1H), 5.79 (s, 1H), 4.43-4.33 (m, 2H), 3.97 (s, 1H), 3.38-3.20 (m, 3H), 2.90-2.76 (m, 4H), 1.97-1.86 (m, 1H), 1.82-1.73 (m, 1H), 1.69-1.61 (m, 1H), 1.44-1.36 (m, 1H). | I-A25 I-C20 |
| 255 | $^1$H NMR (400 MHz, $CD_3OD$): δ 7.61-7.59 (m, 1H), 7.59-7.55 (m, 1H), 7.46-7.41 (m, 1H), 7.32-7.27 (m, 1H), 5.80 (s, 1H), 4.34-4.26 (m, 2H), 3.95 (s, 1H), 3.30-3.16 (m, 5H), 2.86-2.79 (m, 1H), 1.92-1.84 (m, 1H), 1.79-1.70 (m, 1H), 1.63-1.57 (m, 1H), 1.38-1.32 (m, 1H), 1.20-1.14 (m, 3H). | I-A24 I-C23 |
| 256 | $^1$H NMR (400 MHz, $CD_3OD$): δ 8.37-8.35 (m, 1H), 8.31-8.26 (m, 1H), 7.59-7.55 (m, 1H), 7.46-7.41 (m, 1H), 7.32-7.27 (m, 1H), 5.78 (s, 1H), 4.41-4.33 (m, 2H), 3.96 (s, 1H), 3.37-3.30 (m, 5H), 2.88-2.80 (m, 1H), 1.96-1.86 (m, 1H), 1.81-1.72 (m, 1H), 1.68-1.61 (m, 1H), 1.42-1.36 (m, 1H), 1.20-1.13 (m, 3H). | I-A25 I-C23 |

-continued

| | | |
|---|---|---|
| 257 | $^1$H NMR (400 MHz, $CD_3OD$): δ 8.28 (dd, J = 9.4, 1.2 Hz, 2H), 7.57 (s, 1H), 7.50 (d, J = 5.6 Hz, 1H), 7.43 (d, J = 7.7 Hz, 1H), 7.29 (d, J = 7.7 Hz, 1H), 6.06 (t, J = 5.3 Hz, 1H), 4.38-4.30 (m, 2H), 3.96 (s, 1H), 3.35-3.31 (m, 2H), 3.28-3.19 (m, 3H), 2.83 (d, J = 16.3 Hz, 1H), 1.95-1.73 (m, 2H), 1.63 (d, J = 12.7 Hz, 1H), 1.38 (d, J = 13.2 Hz, 1H), 1.17 (t, J = 7.3 Hz, 3H). | I-A26<br>I-C23 |
| 259 | $^1$H NMR (400 MHz, $CD_3OD$): δ 8.31 (s, 1H), 7.65 (d, J = 5.3 Hz, 2H), 7.51-7.41 (m, 1H), 6.91-6.83 (m, 1H), 6.03 (d, J = 5.3 Hz, 1H), 4.20 (s, 1H), 3.91-3.72 (m, 2H), 3.47-3.39 (m, 2H), 3.33-3.26 (m, 2H), 2.60 (s, 3H), 2.22-2.11 (m, 1H), 2.09-1.88 (m, 2H), 1.94-1.83 (m, 1H), 1.24-1.15 (m, 3H). | I-A17<br>I-C28 |
| 260 | $^1$H NMR (400 MHz, $CD_3OD$): δ 8.31-8.26 (m, 2H), 7.92-7.89 (m, 1H), 7.58-7.55 (m, 1H), 7.45-7.41 (m, 1H), 7.31-7.27 (m, 1H), 6.21-6.18 (m, 1H), 4.38-4.31 (m, 2H), 3.98-3.95 (m, 1H), 3.30-3.18 (m, 5H), 2.86-2.81 (m, 1H), 1.94-1.86 (m, 1H), 1.81-1.73 (m, 1H), 1.66-1.60 (m, 1H), 1.42-1.36 (m, 1H), 1.18-1.14 (m, 3H). | I-A27<br>I-C23 |
| 261 | $^1$H NMR (400 MHz, $CD_3OD$): δ 8.30-8.26 (m, 1H), 7.93-7.90 (m, 1H), 7.59-7.56 (m, 1H), 7.44-7.41 (m, 1H), 7.30-7.27 (m, 1H), 6.26-6.24 (m, 1H), 3.99-3.97 (m, 1H), 3.73-3.66 (m, 2H), 3.29-3.11 (m, 5H), 2.83-2.78 (m, 1H), 2.55 (s, 3H), 2.06-1.99 (m, 1H), 1.95-1.87 (m, 1H), 1.67-1.61 (m, 1H), 1.44-1.38 (m, 1H), 1.18-1.14 (m, 3H). | I-A18<br>I-C23 |
| 262 | $^1$H NMR (400 MHz, $CD_3OD$): δ 8.31-8.26 (m, 2H), 7.92-7.88 (m, 1H), 7.58-7.54 (m, 1H), 7.45-7.40 (m, 1H), 7.31-7.27 (m, 1H), 6.22-6.18 (m, 1H), 4.38-4.31 (m, 2H), 3.98-3.94 (m, 1H), 3.30-3.18 (m, 3H), 2.86-2.79 (m, 4H), 1.94-1.86 (m, 1H), 1.81-1.73 (m, 1H), 1.66-1.60 (m, 1H), 1.42-1.36 (m, 1H). | I-A27<br>I-C20 |
| 264 | $^1$H NMR (400 MHz, $CD_3OD$): δ 7.56 (s, 2H), 7.47 (d, J = 5.6 Hz, 1H), 7.42 (d, J = 7.8 Hz, 1H), 7.28 (d, J = 7.8 Hz, 1H), 5.96 (t, J = 5.3 Hz, 1H), 4.35-4.23 (m, 2H), 3.94 (s, 1H), 3.26-3.16 (m, 3H), 2.84-2.78 (m, 4H), 1.91-1.69 (m, 2H), 1.59 (d, J = 13.3 Hz, 1H), 1.34 (d, J = 13.5 Hz, 1H). | I-A28<br>I-C20 |
| 265 | $^1$H NMR (400 MHz, $CD_3OD$): δ 8.27 (dd, J = 9.5, 1.3 Hz, 2H), 7.56 (s, 1H), 7.49 (d, J = 5.5 Hz, 1H), 7.42 (d, J = 7.6 Hz, 1H), 7.28 (d, J = 7.7 Hz, 1H), 6.05 (t, J = 5.3 Hz, 1H), 4.38-4.28 (m, 2H), 3.95 (s, 1H), 3.30-3.18 (m, 3H), 2.86-2.76 (m, 4H), 1.95-1.71 (m, 2H), 1.62 (d, J = 12.9 Hz, 1H), 1.38 (d, J = 13.2 Hz, 1H). | I-A29<br>I-C20 |
| 266 | $^1$H NMR (400 MHz, $CD_3OD$): δ 8.20 (s, 1H), 7.60-7.49 (m, 2H), 7.39-7.33 (m, 1H), 6.80-6.75 (m, 1H), 5.95-5.90 (m, 1H), 4.11 (s, 1H), 3.79-3.61 (m, 2H), 3.35-3.31 (m, 1H), 3.26-3.24 (m, 1H), 2.74 (s, 3H), 2.50 (s, 3H), 2.12-2.02 (m, 1H), 1.98-1.88 (m, 2H), 1.83-1.75 (m, 1H). | I-A17<br>I-C29 |
| 269 | $^1$H NMR (400 MHz, $CD_3OD$): δ 8.19-8.13 (m, 1H), 8.13-8.06 (m, 1H), 7.78-7.71 (m, 1H), 7.54 (s, 1H), 7.43-7.38 (m, 1H), 7.29-7.23 (m, 1H), 4.29-4.19 (m, 2H), 3.93 (s, 1H), 3.28-3.15 (m, 5H), 2.84-2.75 (m, 1H), 1.90-1.81 (m, 1H), 1.77-1.69 (m, 1H), 1.62-1.55 (m, 1H), 1.37-1.32 (m, 1H), 1.20-1.09 (m, 3H). | I-A30<br>I-C23 |
| 270 | $^1$H NMR (400 MHz, $CD_3OD$): δ 8.43-8.25 (m, 2H), 7.66-7.57 (m, 2H), 7.51-7.44 (m, 1H), 7.37-7.29 (m, 1H), 6.01-5.93 (m, 1H), 4.46-4.32 (m, 2H), 4.01 (s, 1H), 3.40-3.38 (m, 1H), 3.33-3.22 (m, 2H), 2.93-2.82 (m, 1H), 1.99-1.89 (m, 1H), 1.87-1.74 (m, 1H), 1.67 (d, J = 13.3 Hz, 1H), 1.43 (d, J = 13.3 Hz, 1H). | I-A15<br>I-C16 |
| 271 | $^1$H NMR (400 MHz, $CD_3OD$): δ 8.24 (s, 1H), 7.63-7.55 (m, 2H), 7.46-7.36 (m, 1H), 7.30-7.25 (m, 1H), 5.99-5.94 (m, 1H), 3.97 (s, 1H), 3.77-3.64 (m, 2H), 3.21-3.10 (m, 3H), 2.84-2.76 (m, 1H), 2.54 (s, 3H), 2.07-1.82 (m, 2H), 1.63 (d, J = 13.2 Hz, 1H), 1.40 (d, J = 13.2 Hz, 1H). | I-A17<br>I-C16 |
| 272 | $^1$H NMR (400 MHz, $CD_3OD$): δ 8.53 (s, 1H), 7.65 (d, J = 5.5 Hz, 1H), 7.55 (s, 1H), 7.42 (d, J = 7.6 Hz, 1H), 7.28 (d, J = 7.7 Hz, 1H), 6.02 (d, J = 5.5 Hz, 1H), 4.42-4.31 (m, 2H), 3.96 (s, 1H), 3.40-3.32 (m, 2H), 3.28-3.18 (m, 3H), 2.83 (d, J = 16.7 Hz, 1H), 1.96-1.86 (m, 1H), 1.81-1.72 (m, 1H), 1.65 (d, J = 13.9 Hz, 1H), 1.39 (d, J = 14.5 Hz, 1H), 1.15 (t, J = 7.3 Hz, 3H) | I-A31<br>I-C23 |
| 273 | $^1$H NMR (400 MHz, $CD_3OD$): δ 8.33 (d, J = 1.3 Hz, 1H), 8.26 (d, J = 1.2 Hz, 1H), 7.55 (s, 1H), 7.44-7.38 (m, 1H), 7.27 (d, J = 7.8 Hz, 1H), 5.43 (d, J = 1.4 Hz, 1H), 4.42-4.29 (m, 2H), 3.94 (s, 1H), 3.37-3.30 (m, 2H), 3.28-3.18 (m, 3H), 2.82 (d, J = 16.4 Hz, 1H), 1.95-1.85 (m, 1H), 1.81-1.71 (m, 1H), 1.62 (d, J = 11.7 Hz, 1H), 1.37 (d, J = 11.7 Hz, 1H), 1.15 (t, J = 7.3 Hz, 3H). | I-A32<br>I-C23 |
| 274 | $^1$H NMR (400 MHz, $CD_3OD$): δ 7.57 (s, 1H), 7.48-7.38 (m, 2H), 7.26 (d, J = 7.6 Hz, 1H), 5.93 (t, J = 5.3 Hz, 1H), 3.95 (s, 1H), 3.72-3.61 (m, 2H), 3.18-3.03 (m, 3H), 2.77 (d, J = 16.5 Hz, 1H), 2.36 (s, 3H), 2.02-1.82 (m, 2H), 1.59 (d, J = 12.2 Hz, 1H), 1.36 (d, J = 11.8 Hz, 1H). | I-A33<br>I-C16 |
| 275 | $^1$H NMR (400 MHz, $CD_3OD$): δ 7.59-7.53 (m, 2H), 7.48-7.39 (m, 2H), 7.27 (d, J = 7.8 Hz, 1H), 5.95 (t, J = 5.3 Hz, 1H), 4.32-4.21 (m, 2H), 3.94 (s, 1H), 3.26-3.13 (m, 3H), 2.80 (d, J = 16.3 Hz, 1H), 1.93-1.67 (m, 2H), 1.57 (d, J = 12.9 Hz, 1H), 1.34 (d, J = 13.5 Hz, 1H). | I-A34<br>I-C16 |

-continued

| | | |
|---|---|---|
| 276 | $^1$H NMR (400 MHz, $CD_3OD$): δ 7.59-7.55 (m, 2H), 7.43-7.40 (m, 1H), 7.28-7.25 (m, 1H), 5.88-5.85 (m, 1H), 3.95 (s, 1H), 3.71-3.63 (m, 2H), 3.18-3.04 (m, 3H), 2.81-2.74 (m, 1H), 2.36 (s, 3H), 2.02-1.94 (m, 1H), 1.91-1.83 (m, 1H), 1.62-1.56 (m, 1H), 1.39-1.33 (m, 1H). | I-A11 I-C16 |
| 277 | $^1$H NMR (400 MHz, $CD_3OD/CDCl_3$ = 3/1): δ 8.11-8.08 (m, 1H), 7.62-7.55 (m, 2H), 7.47-7.43 (m, 1H), 7.30-7.27 (m, 1H), 5.84-5.81 (m, 1H), 4.40-4.33 (m, 2H), 3.99 (s, 1H), 3.32-3.18 (m, 3H), 2.87-2.82 (m, 1H), 2.46 (s, 3H), 1.94-1.86 (m, 1H), 1.82-1.74 (m, 1H), 1.69-1.62 (m, 1H), 1.46-1.40 (m, 1H). | I-A35 I-C16 |
| 280 | $^1$H NMR (400 MHz, $CD_3OD$): δ 8.14-8.12 (m, 1H), 7.58-7.53 (m, 1H), 7.44-7.40 (m, 1H), 7.30-7.26 (m, 1H), 5.65 (s, 1H), 4.40-4.32 (m, 2H), 3.94 (s, 1H), 3.28-3.18 (m, 3H), 2.85-2.78 (m, 1H), 2.44 (s, 3H), 1.92-1.84 (m, 1H), 1.78-1.70 (m, 1H), 1.65-1.59 (m, 1H), 1.39-1.33 (m, 1H). | I-A36 I-C16 |
| 281 | $^1$H NMR (400 MHz, $CD_3OD$): δ 8.08 (s, 1H), 7.92-7.84 (m, 1H), 7.56 (s, 1H), 7.46-7.39 (m, 1H), 7.32-7.24 (m, 1H), 6.17-6.09 (m, 1H), 4.41-4.28 (m, 2H), 3.95 (s, 1H), 3.28-3.15 (m, 3H), 2.88-2.76 (m, 1H), 2.44 (s, 3H), 1.94-1.82 (m, 1H), 1.81-1.69 (m, 1H), 1.66-1.56 (m, 1H), 1.41-1.34 (m, 1H). | I-A37 I-C16 |
| 290 | $^1$H NMR (400 MHz, $CD_3OD$): δ 8.27-8.23 (m, 1H), 7.63-7.56 (m, 2H), 7.47-7.39 (m, 1H), 7.32-7.26 (m, 1H), 6.00-5.96 (m, 1H), 3.98 (s, 1H), 3.76-3.67 (m, 2H), 3.29-3.25 (m, 2H), 3.21-3.11 (m, 3H), 2.85-2.76 (m, 1H), 2.55 (s, 3H), 2.06-1.97 (m, 1H), 1.96-1.85 (m, 1H), 1.68-1.59 (m, 1H), 1.45-1.36 (m, 1H), 1.26-1.14 (m, 3H). | I-A17 I-C23 |
| 292 | $^1$H NMR (400 MHz, $CD_3OD/CDCl_3$ = 2/1): δ 8.35-8.33 (m, 1H), 8.33-8.29 (m, 1H), 7.65-7.57 (m, 2H), 7.48-7.42 (m, 1H), 6.88-6.82 (m, 1H), 5.99-5.95 (m, 1H), 4.52-4.46 (m, 1H), 4.42-4.35 (m, 1H), 4.15 (s, 1H), 3.56-3.48 (m, 2H), 2.83 (s, 3H), 2.04-1.97 (m, 2H), 1.94-1.83 (m, 2H). | I-A15 I-C29 |
| 293 | $^1$H NMR (400 MHz, $CD_3OD/CDCl_3$): δ 8.35-8.24 (m, 2H), 7.62-7.54 (m, 2H), 7.43 (dd, J = 8.3, 1.6 Hz, 1H), 6.82 (d, J = 8.3 Hz, 1H), 5.94 (d, J = 5.6 Hz, 1H), 4.50-4.42 (m, 1H), 4.40-4.32 (m, 1H), 4.13 (s, 1H), 3.53-3.44 (m, 2H), 3.29-3.24 (m, 2H), 2.02-1.94 (m, 2H), 1.90-1.81 (m, 2H), 1.15 (t, J = 7.3 Hz, 3H). | I-A15 I-C28 |
| 296 | $^1$H NMR (400 MHz, $CD_3OD$): δ 8.33-8.31 (m, 1H), 8.28-8.26 (m, 1H), 7.61-7.53 (m, 2H), 7.43-7.41 (m, 1H), 7.29-7.27 (m, 1H), 5.93 (d, J = 5.6 Hz, 1H), 4.42-4.27 (m, 2H), 3.96 (s, 1H), 3.30-3.15 (m, 3H), 2.89-2.68 (m, 2H), 1.93-1.85 (m, 1H), 1.81-1.75 (m, 1H), 1.66-1.60 (m, 1H), 1.42-1.36 (m, 1H), 0.80-0.74 (m, 2H), 0.59-0.53 (m, 2H). | I-A15 I-C25 |
| 297 | $^1$H NMR (400 MHz, $CD_3OD$): δ 8.38-8.26 (m, 2H), 7.69-7.57 (m, 2H), 7.49-7.43 (m, 1H), 7.35-7.27 (m, 1H), 5.99-5.09 (m, 1H), 4.43-4.32 (m, 2H), 3.99 (s, 1H), 3.55-3.51 (m, 2H), 3.49-3.45 (m, 2H), 3.42-3.36 (m, 4H), 3.32-3.21 (m, 2H), 2.91-2.81 (m, 1H), 1.97-1.87 (m, 1H), 1.85-1.75 (m, 1H), 1.66 (d, J = 13.3 Hz, 1H), 1.41 (d, J = 13.3 Hz, 1H). | I-A15 I-C33 |
| 298 | $^1$H NMR (400 MHz, $CD_3OD$): δ 8.32-8.24 (m, 2H), 7.57 (s, 1H), 7.49 (d, J = 5.5 Hz, 1H), 7.44 (d, J = 9.2 Hz, 1H), 7.29 (d, J = 7.7 Hz, 1H), 6.05 (t, J = 5.3 Hz, 1H), 4.39-4.29 (m, 2H), 3.96 (s, 1H), 3.51-3.47 (m, 2H), 3.46-3.41 (m, 2H), 3.36 (s, 3H), 3.29-3.26 (m, 2H), 3.22 (d, J = 16.4 Hz, 1H), 2.83 (d, J = 16.3 Hz, 1H), 1.93-1.71 (m, 2H), 1.63 (d, J = 13.6 Hz, 1H), 1.38 (d, J = 13.5 Hz, 1H). | I-A26 I-C33 |
| 300 | $^1$H NMR (400 MHz, $CDCl_3$): δ 8.35-8.09 (m, 2H), 7.81-7.63 (m, 1H), 7.55 (s, 1H), 7.50-7.38 (m, 1H), 7.24-7.12 (m, 1H), 6.17-6.01 (m, 1H), 4.93-4.76 (m, 2H), 4.30-4.17 (m, 2H), 4.04-3.95 (m, 1H), 3.83 (s, 3H), 3.34-3.21 (m, 2H), 3.16-3.05 (m, 1H), 2.83-2.65 (m, 1H), 1.94-1.78 (m, 2H), 1.68-1.61 (m, 1H), 1.42-1.30 (m, 3H). | I-A15 I-C34 |
| 301 | $^1$H NMR (400 MHz, $CD_3OD$): δ 8.26 (dd, J = 16.9, 1.0 Hz, 2H), 7.64-7.52 (m, 2H), 7.42 (t, J = 6.2 Hz, 1H), 7.27 (d, J = 7.6 Hz, 1H), 5.98 (dd, J = 5.5, 1.0 Hz, 1H), 4.36-4.22 (m, 2H), 3.96 (s, 1H), 3.86 (t, J = 5.4 Hz, 1H), 3.66-3.60 (m, 2H), 3.59-3.56 (m, 1H), 3.38-3.31 (m, 5H), 3.29-3.26 (m, 2H), 3.19 (d, J = 16.2 Hz, 1H), 3.02-3.01 (m, 1H), 2.81 (d, J = 16.3 Hz, 1H), 1.93-1.75 (m, 2H), 1.62 (d, J = 12.9 Hz, 1H), 1.39 (d, J = 12.9 Hz, 1H). | I-A15 I-C35 |
| 302 | $^1$H NMR (400 MHz, $CD_3OD/CDCl_3$ = 1/1): δ 8.23-8.19 (m, 2H), 7.58 (d, J = 5.6 Hz, 1H), 7.52 (s, 1H), 7.40 (d, J = 7.7 Hz, 1H), 7.23 (d, J = 7.7 Hz, 1H), 5.98 (d, J = 5.6 Hz, 1H), 4.25-4.21 (m, 2H), 3.97 (s, 1H), 3.35-3.30 (m, 1H), 3.28-3.23 (m, 4H), 3.16-3.10 (m, 1H), 2.99 (s, 3H), 2.83-2.77 (m, 1H), 1.89-1.71 (m, 2H), 1.65-1.59 (m, 1H), 1.46-1.40 (m, 1H). | I-A15 I-C21 |
| 303 | $^1$H NMR (400 MHz, $CD_3OD/CDCl_3$ = 1/1): δ 8.29-8.22 (m, 2H), 7.64-7.61 (m, 1H), 7.55-7.52 (m, 1H), 7.44-7.41 (m, 1H), 7.29-7.25 (m, 1H), 6.04-6.00 (m, 1H), 4.38-4.30 (m, 4H), 4.14-4.09 (m, 2H), 4.01-3.98 (m, 1H), 3.37-3.28 (m, 2H), 3.21-3.13 (m, 1H), 2.88-2.79 (m, 1H), 2.45-2.34 (m, 2H), 1.94-1.78 (m, 2H), 1.70-1.64 (m, 1H), 1.49-1.43 (m, 1H). | I-A15 I-C36 |

Compound 4

(S)-6-amino-2-(1-amino-5-ethynyl-1,3-dihydrospiro[indene-2,4'-piperidin]-1'-yl)-3-methyl-5-(1-methyl-1H-pyrrolo[2,3-b]pyridin-3-yl)pyrimidin-4(3H)-one

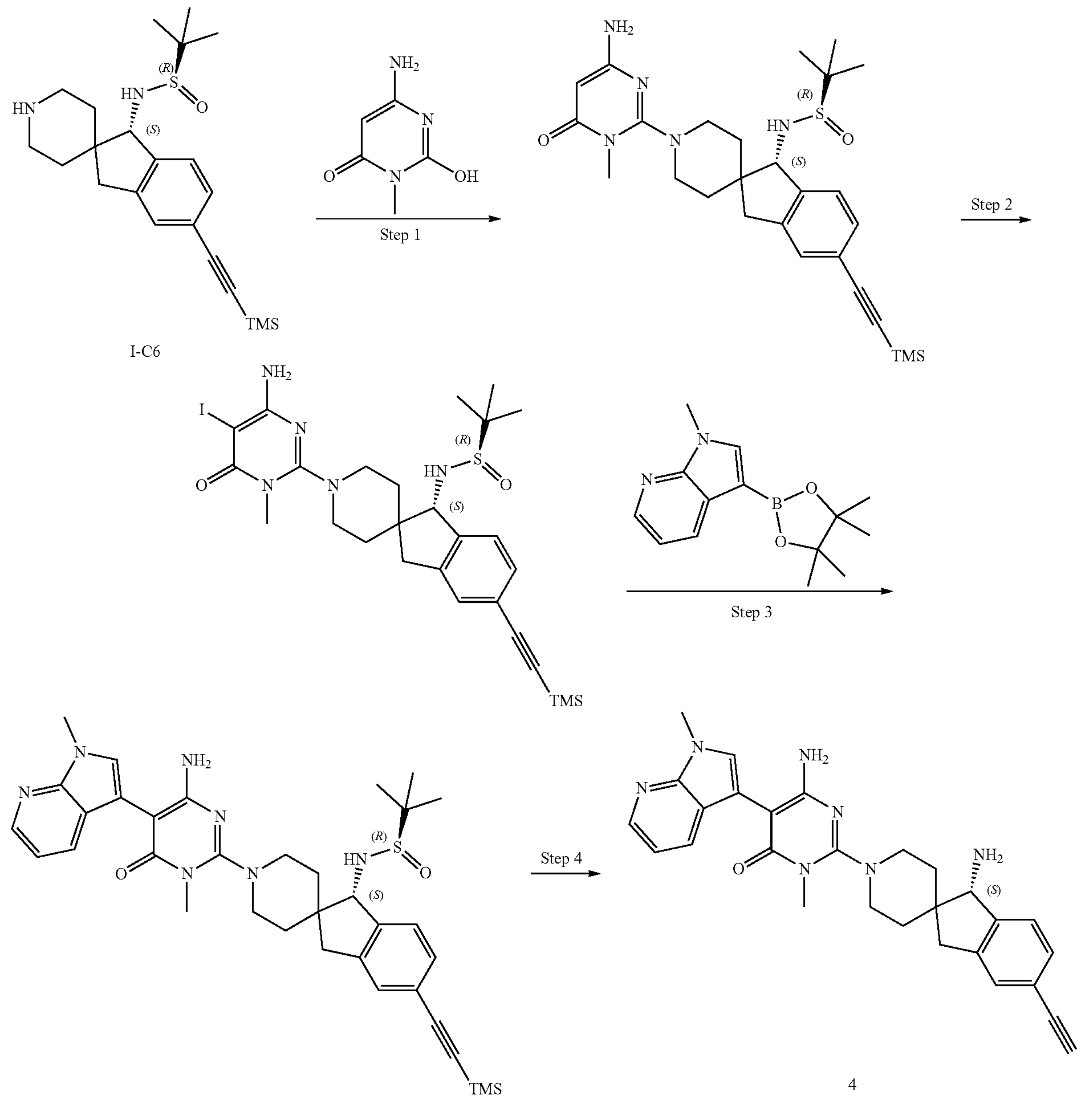

I-C6

4

Step 1: (R)—N—((S)-1'-(4-amino-1-methyl-6-oxo-1,6-dihydropyrimidin-2-yl)-5-((trimethylsilyl)ethynyl)-1,3-dihydrospiro[indene-2,4'-piperidin]-1-yl)-2-methylpropane-2-sulfinamide 6-amino-2-hydroxy-3-methylpyrimidin-4(3H)-one (170 mg, 1.20 mmol), BOP (1.06 g, 2.40 mmol) and DBU (366 mg, 2.40 mmol) were placed in anhydrous acetonitrile (10 mL), and the reaction was stirred at room temperature for 30 minutes. Intermediate I-C6 (242 mg, 0.60 mmol) was added thereto, and the reaction was stirred at room temperature for 16 hours. The reaction solution was purified with silica gel column chromatography (water/methanol) to give the target product (95 mg, yield 15%). $[M+H]^+$ 526.3

Step 2: (R)—N—((S)-1'-(4-amino-5-iodo-1-methyl-6-oxo-1,6-dihydropyrimidin-2-yl)-5-((trimethylsilyl)ethynyl)-1,3-dihydrospiro[indene-2,4'-piperidin]-1-yl)-2-methylpropane-2-sulfinamide Under nitrogen, (R)—N—((S)-1'-(4-amino-1-methyl-6-oxo-1,6-dihydropyrimidin-2-yl)-5-((trimethylsilyl)ethynyl)-1,3-dihydrospiro[indene-2,4'-piperidin]-1-yl)-2-methylpropane-2-sulfinamide (95 mg, 0.18 mmol) and NIS (45 mg, 0.20 mmol) were placed in N,N-dimethylformamide (2 mL). The reaction was stirred at room temperature for 1 hour, and the reaction solution was purified with silica gel column chromatography (water/methanol) to give the target product (70 mg, yield 60%). $[M+H]^+$ 652.3

Step 3: (R)—N—((S)-1'-(4-amino-1-methyl-5-(1-methyl-1H-pyrrolo[2,3-b]pyridin-3-yl)-6-oxo-1,6-dihydropyrimidin-2-yl)-5-((trimethylsilyl)ethynyl)-1,3-dihydrospiro[indene-2,4'-piperidin]-1-yl)-2-methylpropane-2-sulfinamide Under nitrogen, (R)—N—((S)-1'-(4-amino-5-iodo-1-methyl-6-oxo-1,6-dihydropyrimidin-2-yl)-5-((trimethylsilyl)ethynyl)-1,3-dihydrospiro[indene-2,4'-piperidin]-1-yl)-2-methylpropane-2-sulfinamide (70 mg, 0.11 mmol), 1-methyl-3-(4,4,5,5-tetramethyl-1,3,2-dioxaborolan-2-yl)-1H-pyrrolo[2,3-b]pyridine (36 mg, 0.14 mmol), $Pd(PPh_3)_4$ (12 mg, 0.01 mmol) and potassium carbonate (45 mg, 0.32 mmol) were placed in 1,4-dioxane (3 mL) and water (0.3 mL). The reaction was reacted at 100° C. for 1 hour, and the reaction solution was purified with silica gel column chromatography (water/methanol) to give the target product (10 mg, yield 14%). $[M+H]^+$ 656.3

Step 4: (S)-6-amino-2-(1-amino-5-ethynyl-1,3-dihydrospiro[indene-2,4'-piperidin]-1'-yl)-3-methyl-5-(1-methyl-1H-pyrrolo[2,3-b]pyridin-3-yl)pyrimidin-4(3H)-one (R)—N—((S)-1'-(4-amino-1-methyl-5-(1-methyl-1H-pyrrolo[2,3-b]pyridin-3-yl)-6-oxo-1,6-dihydropyrimidin-2-yl)-5-((trimethylsilyl)ethynyl)-1,3-dihydrospiro[indene-2,4'-piperidin]-1-yl)-2-methylpropane-2-sulfinamide (10 mg, 0.015 mmol) was dissolved in 2 M hydrogen chloride/methanol solution. The reaction was stirred at room temperature for 3 minutes. Under ice bath cooling, the reaction solution was diluted with dichloromethane (15 mL) and adjusted with aqueous ammonia to a pH value of 8. The organic phase was collected and concentrated in vacuum under reduced pressure. The resulting residue and potassium carbonate (10 mg, 0.072 mmol) were placed in methanol (0.5 mL). The mixture was stirred at room temperature for 10 minutes and purified with thin layer chromatography (dichloromethane/methanol=15/1) to give the target product (5.5 mg, yield 75%). $[M+H]^+$ 480.2. $^1H$ NMR (400 MHz, $CD_3OD$): δ 8.26-8.20 (m, 1H), 7.82-7.75 (m, 1H), 7.37-7.30 (m, 4H), 7.11-7.07 (m, 1H), 3.99-3.96 (m, 1H), 3.90 (s, 3H), 3.54-3.49 (m, 2H), 3.47 (s, 3H), 3.41-3.39 (m, 1H), 3.16-3.07 (m, 3H), 2.78-2.72 (m, 1H), 2.05-1.98 (m, 1H), 1.96-1.86 (m, 1H), 1.65-1.59 (m, 1H), 1.44-1.37 (m, 1H).

The compounds in the table below were prepared by following the steps for preparing compound 4 from corresponding intermediates and reagents:

| Compounds | Structural formula | LC-MS $[M + H]^+$ | $^1$HNMR | Interme-diates |
|---|---|---|---|---|
| 5 | 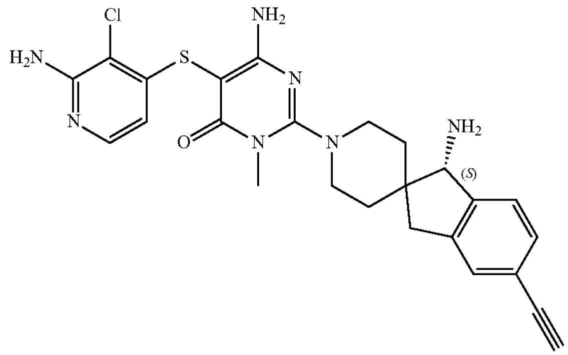 | 508.2 | $^1$H NMR (400 MHz, $CD_3OD$): δ 7.60-7.56 (m, 1H), 7.36-7.29 (m, 3H), 6.17-6.11 (m, 1H), 3.97-3.94 (m, 1H), 3.67-3.59 (m, 2H), 3.42 (s, 3H), 3.40-3.39 (m, 1H), 3.22-3.07 (m, 3H), 2.78-2.71 (m, 1H), 2.02-1.95 (m, 1H), 1.92-1.84 (m, 1H), 1.62-1.58 (m, 1H), 1.41-1.36 (m, 1H). | I-A1 I-A4 I-C1 |
| 6 | 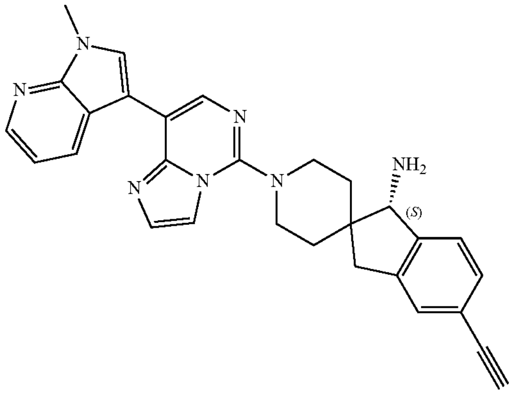 | 474.2 | $^1$H NMR (400 MHz, $CD_3OD$): δ 8.33-8.30 (m, 1H), 8.29-8.25 (m, 1H), 8.16-8.12 (m, 1H), 8.11-8.07 (m, 1H), 7.80-7.76 (m, 1H), 7.66-7.60 (m, 1H), 7.38-7.30 (m, 3H), 7.23-7.18 (m, 1H), 4.02-3.99 (m, 1H), 3.96 (s, 3H), 3.82-3.75 (m, 2H), 3.42-3.39 (m, 1H), 3.27-3.20 (m, 2H), 3.17-3.12 (m, 1H), 2.82-2.75 (m, 1H), 2.16-2.08 (m, 1H), 2.05-1.98 (m, 1H), 1.73-1.66 (m, 1H), 1.52-1.45 (m, 1H). | I-C1 |

-continued
| Compounds | Structural formula | LC-MS $[M + H]^+$ | $^1$HNMR | Interme-diates |
|---|---|---|---|---|
| 25 | 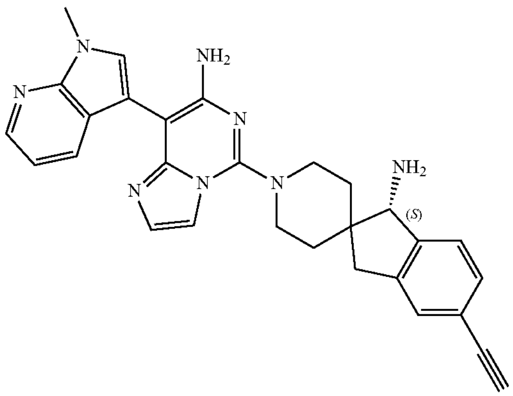 | 489.2 | $^1$H NMR (400 MHz, $CD_3OD$): δ 8.29-8.25 (m, 1H), 7.81-7.77 (m, 1H), 7.54 (s, 1H), 7.43 (d, J = 1.5 Hz, 1H), 7.38-7.30 (m, 3H), 7.20 (d, J = 1.3 Hz, 1H), 7.13-7.09 (m, IH), 4.01 (s, 1H), 3.94 (s, 3H), 3.85-3.77 (m, 2H), 3.41 (s, 1H), 3.26-3.11 (m, 3H), 2.81-2.77 (m, 1H), 2.09-1.96 (m, 2H), 1.68-1.64 (m, 1H), 1.48-1.44 (m, 1H). | I-A8 I-C6 |
| 120 | 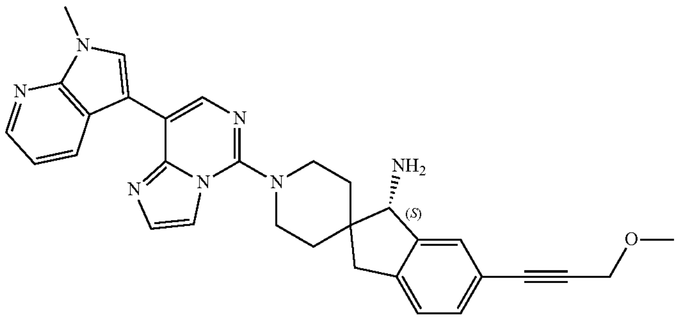 | 518.2 | $^1$H NMR (400 MHz, $CD_3OD$): δ 8.39-8.30 (m, 2H), 8.19 (s, 1H), 8.15 (s, 1H), 7.85 (d, J = 1.5 Hz, 1H), 7.69 (d, J = 1.5 Hz, 1H), 7.52 (s, 1H), 7.36-7.31 (m, 1H), 7.29-7.22 (m, 2H), 4.35 (s, 2H), 4.04 (s, 1H), 4.01 (s, 3H), 3.90-3.79 (m, 2H), 3.46 (s, 3H), 3.32-3.19 (m, 3H), 2.89-2.82 (m, 1H), 2.23-2.03 (m, 2H), 1.75 (d, J = 12.8 Hz, 1H), 1.53 (d, J = 12.8 Hz, 1H). | I-C7 |
| 282 | 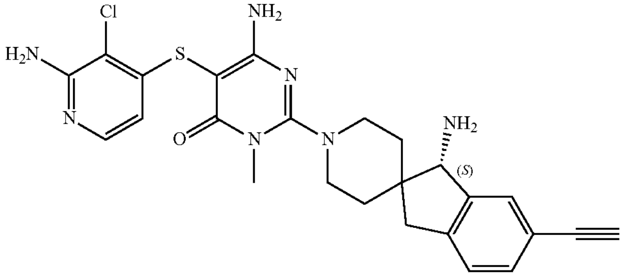 | 508.1 | $^1$H NMR (400 MHz, $CD_3OD$): δ 7.62-7.53 (m, 1H), 7.52-7.43 (m, 1H), 7.33-7.25 (m, 1H), 7.23-7.15 (m, 1H), 6.20-6.08 (m, 1H), 3.93 (s, 1H), 3.67-3.56 (m, 2H), 3.46-3.37 (m, 4H), 3.20-3.08 (m, 3H), 2.80-2.70 (m, 1H), 2.03-1.94 (m, 1H), 1.92-1.82 (m, 1H), 1.63-1.55 (m, 1H), 1.40-1.33 (m, 1H). | I-A1 I-C3 |

-continued
| Compounds | Structural formula | LC-MS $[M + H]^+$ | $^1$HNMR | Interme-diates |
|---|---|---|---|---|
| 284 | 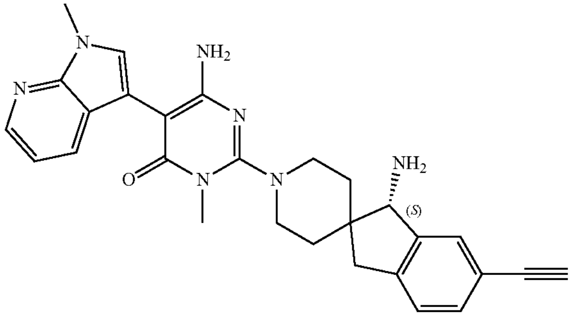 | 480.2 | $^1$H NMR (400 MHz, $CD_3OD$): δ 8.26-8.20 (m, 1H), 7.81-7.74 (m, 1H), 7.51-7.46 (m, 1H), 7.38-7.34 (m, 1H), 7.32-7.28 (m, 1H), 7.21-7.18 (m, 1H), 7.11-7.07 (m, 1H), 3.97-3.94 (m, 1H), 3.89 (s, 3H), 3.55-3.49 (m, 2H), 3.47 (s, 3H), 3.39 (s, 1H), 3.15-3.08 (m, 3H), 2.79-2.73 (m, 1H), 2.06-1.98 (m, 1H), 1.94-1.86 (m, 1H), 1.64-1.58 (m, 1H), 1.42-1.36 (m, 1H). | I-C3 |
| 285 | 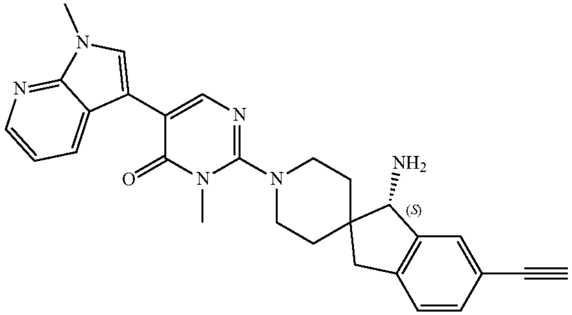 | 465.2 | $^1$H NMR (400 MHz, $CD_3OD/CDCl_3$ = 4/1): δ 8.31-8.27 (m, 1H), 8.22-8.18 (m, 2H), 7.96-7.93 (m, 1H), 7.53-7.47 (m, 1H), 7.35-7.32 (m, IH), 7.22-7.17 (m, 2H), 4.01-3.98 (m, 1H), 3.93 (s, 3H), 3.64 (s, 3H), 3.55-3.49 (m, 2H), 3.20-3.11 (m, 3H), 2.82-2.75 (m, 1H), 2.09-2.01 (m, 1H), 1.98-1.88 (m, 1H), 1.71-1.64 (m, 1H), 1.49-1.43 (m, 1H). | I-C3 |
| 286 | 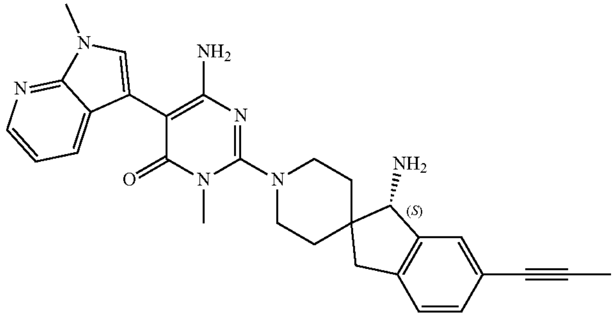 | 494.2 | $^1$H NMR (400 MHz, $CD_3OD$): δ 8.25-8.20 (m, 1H), 7.81-7.75 (m, 1H), 7.39-7.33 (m, 2H), 7.20-7.12 (m, 2H), 7.11-7.07 (m, 1H), 3.94-3.92 (m, 1H), 3.89 (s, 3H), 3.54-3.48 (m, 2H), 3.46 (s, 3H), 3.14-3.05 (m, 3H), 2.77-2.69 (m, 1H), 2.04-1.97 (m, 4H), 1.93-1.85 (m, 1H), 1.63-1.57 (m, 1H), 1.43-1.36 (m, 1H). | I-C17 |

-continued
| Compounds | Structural formula | LC-MS $[M + H]^+$ | $^1$HNMR | Interme-diates |
|---|---|---|---|---|
| 289 | 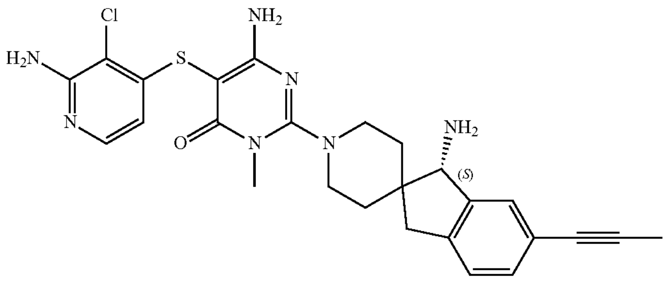 | 522.2 | $^1$H NMR (400 MHz, $CD_3OD$): δ 7.59-7.55 (m, 1H), 7.38-7.34 (m, 1H), 7.21-7.11 (m, 2H), 6.17-6.11 (m, 1H), 3.93 (s, 1H), 3.65-3.57 (m, 2H), 3.41 (s, 3H), 3.20-3.05 (m, 3H), 2.78-2.69 (m, 1H), 2.01-1.93 (m, 4H), 1.91-1.82 (m, 1H), 1.62-1.55 (m, 1H), 1.41-1.35 (m, 1H). | I-A1 I-C17 |

Compound 299

(S)-5-((2-amino-3-chloropyridin-4-yl)thio)-2-(1-amino-6-ethynyl-1,3-dihydrospiro[indene-2,4'-piperidin]-1'-yl)-3-methylpyrimidin-4(3H)-one

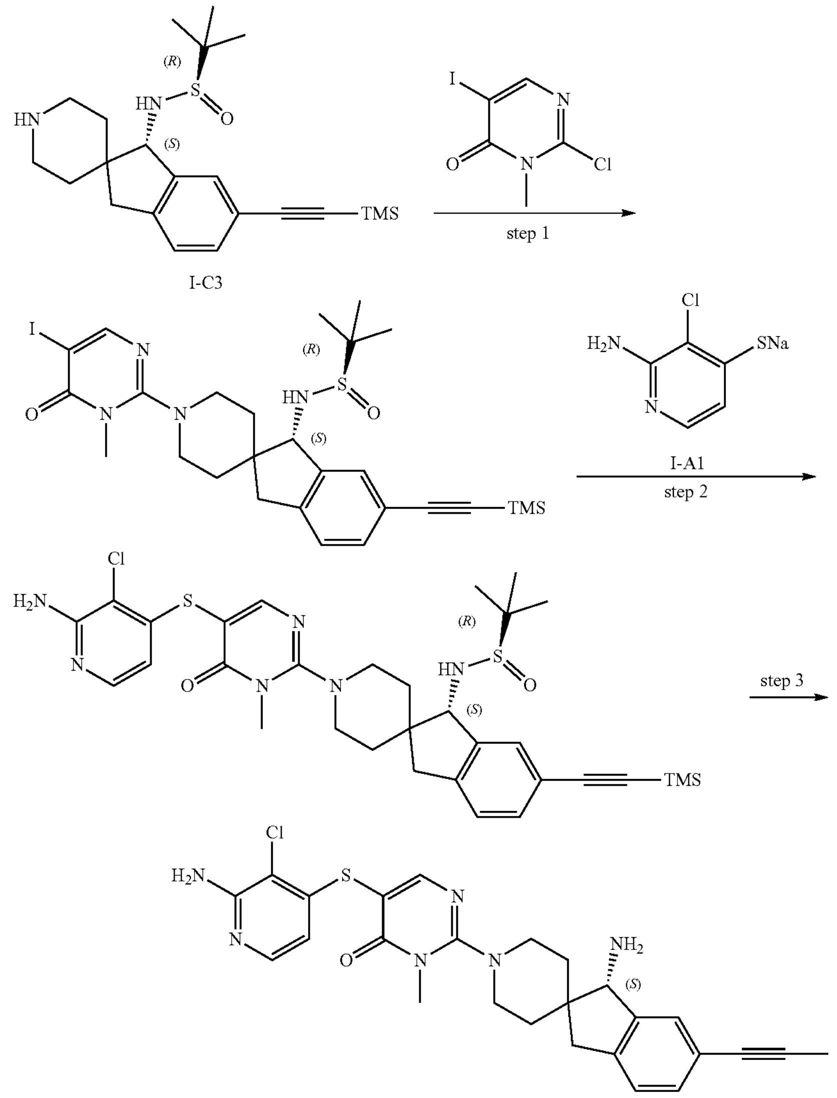

I-C3

299

Step 1: (R)—N—((S)-1'-(5-iodo-1-methyl-6-oxo-1,6-dihydropyrimidin-2-yl)-5-((trimethylsilyl)ethynyl)-1,3-dihydrospiro[indene-2,4'-piperidin]-3-yl)-2-methylpropane-2-sulfinamide Intermediate 1-C3 (0.88 g, 2.19 mmol), 2-chloro-5-iodo-3-methylpyrimidin-4(3H)-one (0.59 g, 2.19 mmol) and DIEA (0.57 g, 4.38 mmol) were placed in DMA (5 mL) and stirred at 90° C. for 3 hours. The reaction solution was purified by silica gel column chromatography (eluting with water/MeOH) to give target product (0.82 g, 59% yield). $[M+H]^+$ 637.2

Step 2: (R)—N—((S)-1'-(5-((2-amino-3-chloropyridin-4-yl)thio)-1-methyl-6-oxo-1,6-dihydropyrimidin-2-yl)-5-((trimethylsilyl)ethynyl)-1,3-dihydrospiro[indene-2,4'-piperidin]-3-yl)-2-methylpropane-2-sulfinamide Under $N_2$, (R)—N—((S)-1'-(5-iodo-1-methyl-6-oxo-1,6-dihydropyrimidin-2-yl)-5-((trimethylsilyl)ethynyl)-1,3-dihydrospiro[indene-2,4'-piperidin]-3-yl)-2-methylpropane-2-sulfinamide (637 mg, 1.0 mmol), intermediate I-A1 (337 mg, 1.85 mmol), 4,7-dimethoxy-1,10-phenanthroline (156 mg, 0.65 mmol), CuI (43 mg, 0.23 mmol) and anhydrous $K_3PO_4$ (420 mg, 1.98 mmol) were placed in 1,4-dioxane (10 mL). The reaction solution was stirred at 100° C. for 3 hours, and concentrated in vacuum under reduced pressure. The residue was purified by silica gel column chromatography (eluting with water/MeOH) to give target product (506 mg, 76% yield). $[M+H]^+$ 669.2

Step 3: (S)-5-((2-amino-3-chloropyridin-4-yl)thio)-2-(1-amino-6-ethynyl-1,3-dihydrospiro[indene-2,4'-piperidin]-1'-yl)-3-methylpyrimidin-4(3H)-one (R)—N—((S)-1'-(5-((2-amino-3-chloropyridin-4-yl)thio)-1-methyl-6-oxo-1,6-dihydropyrimidin-2-yl)-5-((trimethylsilyl)ethynyl)-1,3-dihydrospiro[indene-2,4'-piperidin]-3-yl)-2-methylpropane-2-sulfinamide (506 mg, 0.76 mmol) was dissolved in 2 M HCl/MeOH solution (6 mL). The reaction solution was stirred at room temperature for 5 minutes, diluted with DCM (15 mL) and adjusted pH to 8 with aqueous ammonia in an ice-bath. The organic layer was collected and concentrated in vacuum under reduced pressure. The residue was dissolved in MeOH (5 mL), added $K_2CO_3$ powder (522 mg, 3.78 mmol) and stirred at room temperature for 15 minutes. The reaction solution was purified by thin layer chromatography (eluting with DCM/MeOH=12/1) to give target product (96 mg, 26% yield). $[M+H]^+$ 493.2. $^1H$ NMR (400 MHz, $CD_3OD$): δ 8.16-8.11 (m, 1H), 7.62-7.56 (m, 1H), 7.51-7.48 (m, 1H), 7.35-7.30 (m, 1H), 7.24-7.19 (m, 1H), 6.17-6.10 (m, 1H), 3.99 (s, 1H), 3.77-3.69 (m, 2H), 3.53 (s, 3H), 3.42 (s, 1H), 3.29-3.19 (m, 2H), 3.18-3.12 (m, 1H), 2.85-2.76 (m, 1H), 2.05-1.96 (m, 1H), 1.94-1.86 (m, 1H), 1.68-1.60 (m, 1H), 1.46-1.38 (m, 1H).

The compounds in the table below were prepared by following the steps for preparing compound 299 from corresponding intermediates and reagents:

| Compounds | Structural formula | LC-MS $[M + H]^+$ | $^1$HNMR | Interme-diates |
|---|---|---|---|---|
| 288 | 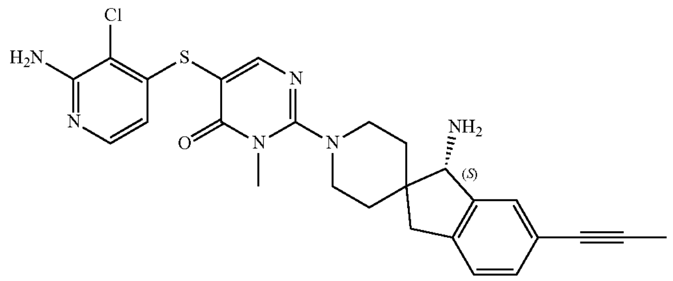 | 507.2 | $^1$H NMR (400 MHz, $CD_3OD$): δ 8.14-8.09 (m, 1H), 7.62-7.54 (m, 1H), 7.40-7.32 (m, 1H), 7.21-7.11 (m, 2H), 6.17-6.08 (m, 1H), 3.93 (s, 1H), 3.75-3.67 (m, 2H), 3.51 (s, 3H), 3.27-3.18 (m, 2H), 3.14-3.06 (m, 1H), 2.80-2.69 (m, 1H), 2.02-1.95 (m, 4H), 1.92-1.83 (m, 1H), 1.65-1.57 (m, 1H), 1.43-1.36 (m, 1H). | I-A1<br>I-C17 |
| 291 | 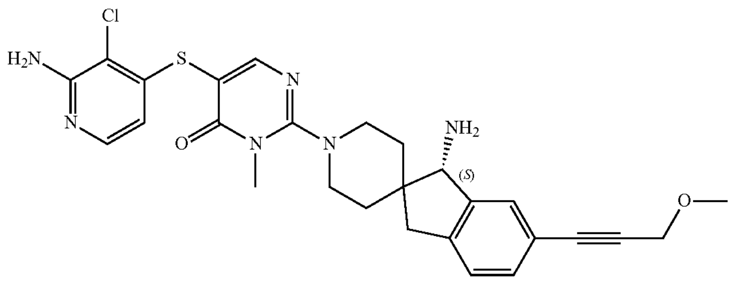 | 537.2 | $^1$H NMR (400 MHz, $CD_3OD$): δ 8.16-8.11 (m, 1H), 7.61-7.57 (m, 1H), 7.49-7.45 (m, 1H), 7.33-7.28 (m, 1H), 7.24-7.20 (m, 1H), 6.16-6.11 (m, 1H), 4.31 (s, 2H), 3.99 (s, 1H), 3.77-3.69 (m, 2H), 3.53 (s, 3H), 3.42 (s, 3H), 3.28-3.20 (m, 2H), 3.17-3.12 (m, 1H), 2.85-2.76 (m, 1H), 2.05-1.97 (m, 1H), 1.95-1.85 (m, 1H), 1.66-1.60 (m, 1H), 1.46-1.39 (m, 1H). | I-A1<br>I-C7 |
| 294 | 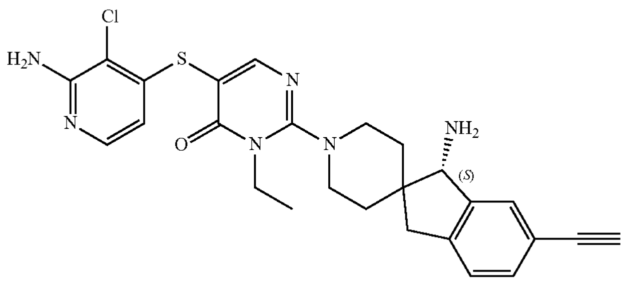 | 507.1 | $^1$H NMR (400 MHz, $CD_3OD$): δ 8.12 (s, 1H), 7.60 (d, J = 5.6 Hz, 1H), 7.49 (s, 1H), 7.31 (d, J = 7.7 Hz, 1H), 7.20 (d, J = 7.7 Hz, 1H), 6.10 (d, J = 5.6 Hz, 1H), 4.11 (q, J = 6.9 Hz, 2H), 3.95 (s, 1H), 3.66-3.58 (m, 2H), 3.41 (s, 1H), 3.29-3.19 (m, 2H), 3.13 (d, J = 16.1 Hz, 1H), 2.76 (d, J = 16.1 Hz, 1H), 2.06-1.86 (m, 2H), 1.63 (d, J = 13.5 Hz, 1H), 1.40 (d, J = 13.2 Hz, 1H), 1.34 (t, J = 6.9 Hz, 3H). | I-A1<br>I-C3 |

-continued
| Compounds | Structural formula | LC-MS $[M + H]^+$ | $^1$HNMR | Interme-diates |
|---|---|---|---|---|
| 295 | 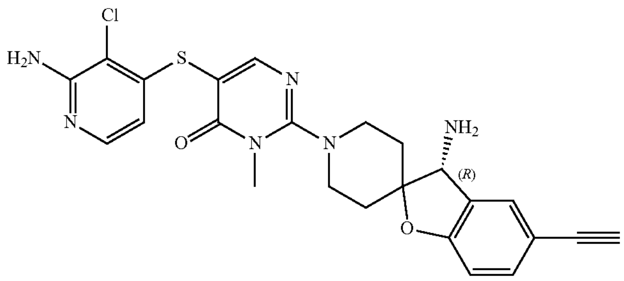 | 495.1 | $^1$H NMR (400 MHz, $CD_3OD$): δ 8.14 (s, 1H), 7.61-7.57 (m, 1H), 7.53-7.49 (m, 1H), 7.35-7.28 (m, 1H), 6.80-6.74 (m, 1H), 6.17-6.12 (m, 1H), 4.14 (s, 1H), 3.87-3.80 (m, 1H), 3.77-3.71 (m, 1H), 3.54 (s, 3H), 3.50-3.41 (m, 2H), 3.34 (s, 1H), 2.17-2.09 (m, 1H), 2.04-1.94 (m, 2H), 1.88-1.80 (m, 1H). | I-A1<br>I-C32 |

Compound 12

(S)-6-(1-amino-6-ethynyl-1,3-dihydrospiro[indene-2,4'-piperidin]-1'-yl)-3-(2,3-dichlorophenyl)-2-methylpyrimidin-4(3H)-one

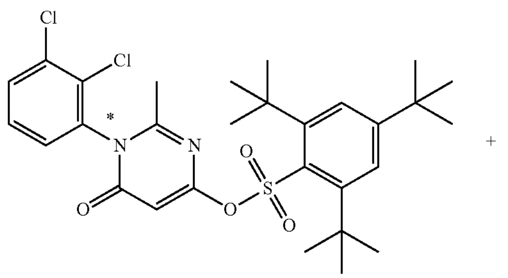

I-B1

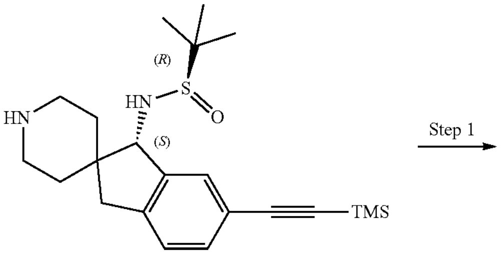

I-C3

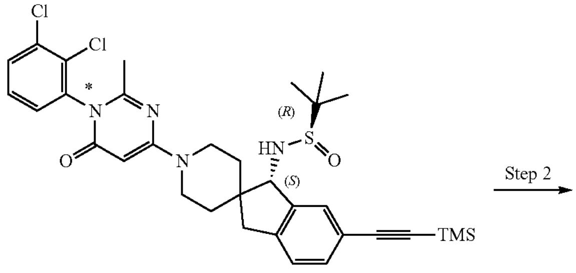

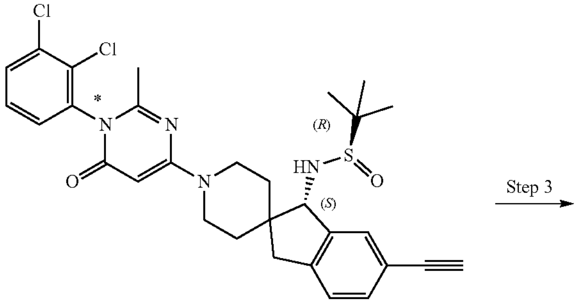

-continued

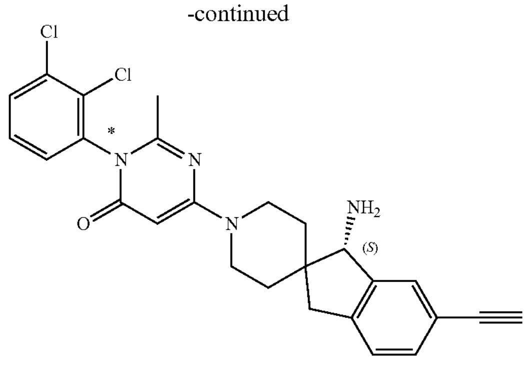

12

Step 1: (R)—N—((S)-1'-(1-(2,3-dichlorophenyl)-2-methyl-6-oxo-1,6-dihydropyrimidin-4-yl)-5-((trimethylsilyl)ethynyl)-1,3-dihydrospiro[indene-2,4'-piperidin]-3-yl)-2-methylpropane-2-sulfinamide Intermediate I-B1 (2.0 g, 3.73 mmoL), intermediate I-C3 (1.5 g, 3.73 mmoL) and DIEA (1.9 g, 14.9 mmoL) were placed in N,N-dimethylformamide (5 mL). The reaction was stirred at 100° C. for 3 hours, and the reaction solution was purified with silica gel column chromatography (water/methanol) to give the target product.

Step 2: (R)—N—((S)-1'-(1-(2,3-dichlorophenyl)-2-methyl-6-oxo-1,6-dihydropyrimidin-4-yl)-5-ethynyl-1,3-dihydrospiro[indene-2,4'-piperidin]-3-yl)-2-methylpropane-2-sulfinamide (R)—N—((S)-1'-(1-(2,3-dichlorophenyl)-2-methyl-6-oxo-1,6-dihydropyrimidin-4-yl)-5-((trimethylsilyl)ethynyl)-1,3-dihydrospiro[indene-2,4'-piperidin]-3-yl)-2-methylpropane-2-sulfinamide was dissolved in 2 M hydrogen chloride/methanol solution (5 mL, 10 mmol). The reaction was stirred at room temperature for 10 minutes, and under ice bath cooling, aqueous ammonia (3 mL) and water (30 mL) were added thereto. The mixture was extracted with dichloromethane. The organic phases were collected and combined, and concentrated in vacuum under reduced pressure to give a crude target product. $[M+H]^+$ 551.2

Step 3: (S)-6-(1-amino-6-ethynyl-1,3-dihydrospiro[indene-2,4'-piperidin]-1'-yl)-3-(2,3-dichlorophenyl)-2-methylpyrimidin-4(3H)-one The crude (R)—N—((S)-1'-(1-(2,3-dichlorophenyl)-2-methyl-6-oxo-1,6-dihydropyrimidin-4-yl)-5-ethynyl-1,3-dihydrospiro[indene-2,4'-piperidin]-3-yl)-2-methylpropane-2-sulfinamide and potassium carbonate (2.1 g, 14.9 mmol) were placed in methanol (15 mL), and the mixture was stirred at room temperature for 30 minutes. Water was added thereto, and the mixture was extracted with dichloromethane. The organic phases were collected and combined, and concentrated in vacuum under reduced pressure, and the residue was purified with silica gel column chromatography (dichloromethane/methanol) to give the target product (490 mg, three-step yield 27%). $[M+H]^+$ 479.2. $^1H$ NMR (400 MHz, $CD_3OD$): δ 7.70 (dd, J=8.2, 1.5 Hz, 1H), 7.52-7.45 (m, 2H), 7.38 (dd, J=7.9, 1.5 Hz, 1H), 7.33-7.27 (m, 1H), 7.19 (d, J=7.7 Hz, 1H), 5.48 (s, 1H), 4.51-4.05 (m, 2H), 3.92

(s, 1H), 3.39 (s, 1H), 3.26-3.12 (m, 3H), 2.77 (d, J=16.1 Hz, 1H), 2.06 (s, 3H), 1.89-1.67 (m, 2H), 1.63-1.54 (m, 1H), 1.39-1.31 (m, 1H).

The compounds in the table below were prepared by following the steps for preparing compound 12 from corresponding intermediates and reagents:

| Compounds | Structural formula | LC-MS $[M + H]^+$ | $^1$HNMR | Interme-diates |
|---|---|---|---|---|
| 11 | 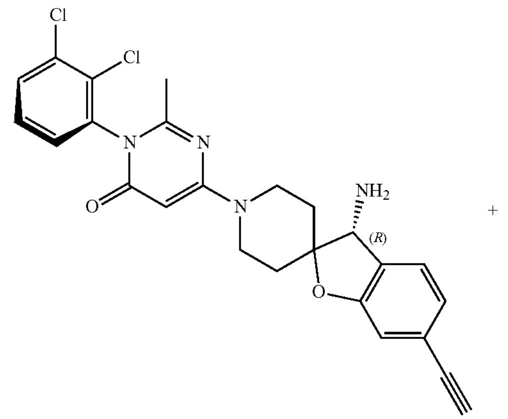 | 481.1 | $^1$H NMR (400 MHz, $CD_3OD$): δ 7.71 (dd, J = 8.1, 1.5 Hz, 1H), 7.48 (t, J = 8.0 Hz, 1H), 7.41-7.31 (m, 2H), 7.02 (dd, J = 7.6, 1.3 Hz, 1H), 6.87 (s, 1H), 5.54 (s, 1H), 4.57-4.18 (m, 2H), 4.11 (s, 1H), 3.47-3.34 (m, 3H), 2.07 (s, 3H), 1.96-1.89 (m, 2H), 1.84-1.76 (m, 2H). | I-B1 I-C5 |
| 28 | 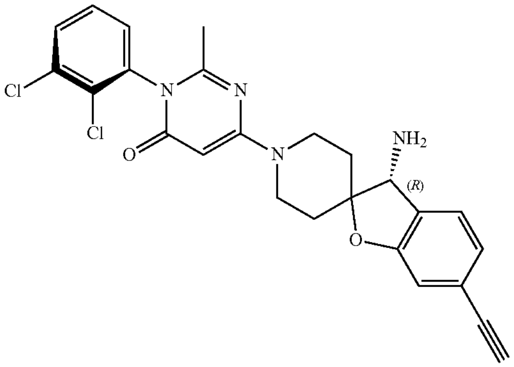 | 481.1 | $^1$H NMR (400 MHz, $CD_3OD/CDCl_3$): δ 7.62-7.55 (m, 1H), 7.40-7.34 (m, 1H), 7.29-7.24 (m, 1H), 7.23-7.18 (m, 1H), 7.05-6.99 (m, 1H), 6.90-6.86 (m, 1H), 5.46 (s, 1H), 4.37-4.11 (m, 2H), 4.06 (s, 1H), 3.43-3.33 (m, 2H), 3.13 (s, 1H), 2.05 (s, 3H), 1.90-1.78 (m, 3H), 1.76-1.67 (m, 1H). | I-B2 I-C5 |

-continued
| Compounds | Structural formula | LC-MS $[M + H]^+$ | $^1$HNMR | Interme-diates |
|---|---|---|---|---|
| 13 | 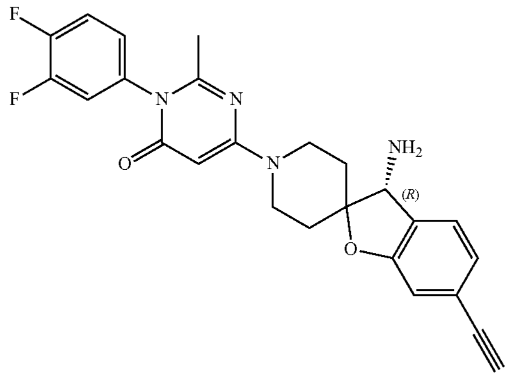 | 449.1 | $^1$H NMR (400 MHz, $CD_3OD$): δ 7.47-7.39 (m, 1H), 7.36-7.30 (m, 2H), 7.14-7.09 (m, 1H), 7.04-6.99 (m, 1H), 6.88-6.84 (m, 1H), 5.54-5.50 (m, 1H), 4.44-4.21 (m, 2H), 4.12-4.07 (m, 1H), 3.43-3.34 (m, 3H), 2.13 (s, 3H), 1.94-1.88 (m, 2H), 1.82-1.75 (m, 2H). | I-B3 I-C5 |
| 14 | 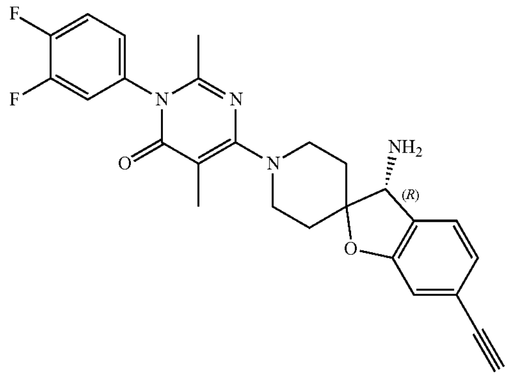 | 463.2 | $^1$H NMR (400 MHz, $CD_3OD$ ): δ 7.48-7.40 (m, 1H), 7.38-7.29 (m, 2H), 7.14-7.08 (m, 1H), 7.04-6.97 (m, 1H), 6.88-6.82 (m, 1H), 4.12-4.08 (m, 1H), 3.99-3.91 (m, 1H), 3.91-3.83 (m, 1H), 3.45-3.36 (m, 3H), 2.12 (s, 3H), 2.07-2.01 (m, 1H), 2.00 (s, 3H), 1.93-1.84 (m, 2H), 1.83-1.74 (m, 1H). | I-B4 I-C5 |

-continued
| Compounds | Structural formula | LC-MS $[M + H]^+$ | $^1$HNMR | Interme-diates |
|---|---|---|---|---|
| 15 | 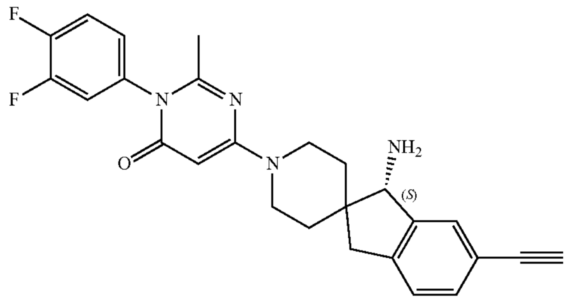 | 447.2 | $^1$H NMR (400 MHz, $CD_3OD$): δ 7.50-7.37 (m, 2H), 7.36-7.27 (m, 2H), 7.22-7.16 (m, 1H), 7.13-7.08 (m, 1H), 5.50-5.42 (m, 1H), 4.35-4.08 (m, 2H), 3.94-3.88 (m, 1H), 3.38 (s, 1H), 3.25-3.11 (m, 3H), 2.81-2.72 (m, 1H), 2.11 (s, 3H), 1.85-1.76 (m, 1H), 1.75-1.66 (m, 1H), 1.59-1.52 (m, 1H), 1.38-1.31 (m, 1H). | I-B3<br>I-C3 |
| 16 | 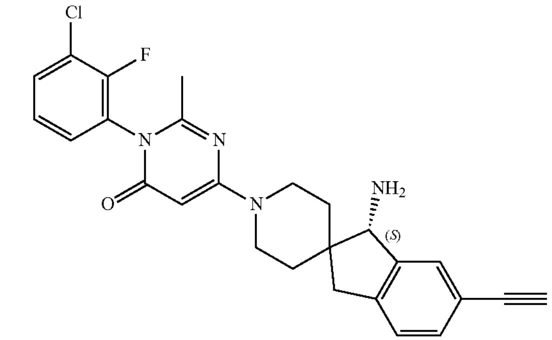 | 463.1 | $^1$H NMR (400 MHz, $CD_3OD$): δ 7.67-7.65 (m, 1H), 7.49 (s, 1H), 7.40-7.28 (m, 3H), 7.25-7.18 (m, 1H), 5.50 (s, 1H), 4.50-4.10 (m, 2H), 3.94 (s, 1H), 3.42-3.34 (m, 1H), 3.30-3.12 (m, 3H), 2.83-2.75 (m, 1H), 2.13 (s, 3H), 1.85-1.63 (m, 2H), 1.63-1.57 (m, 1H), 1.41-1.33 (m, 1H). | I-B5<br>I-C3 |
| 17 | 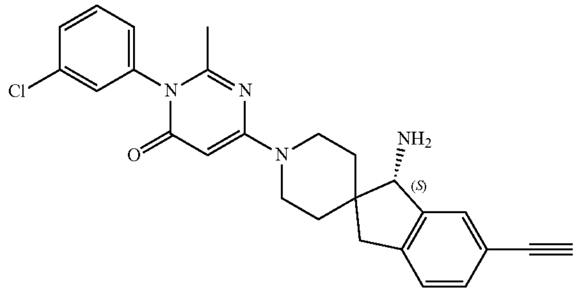 | 445.2 | $^1$H NMR (400 MHz, $CD_3OD$): δ 7.54-7.48 (m, 2H), 7.47-7.45 (m, 1H), 7.37-7.34 (m, 1H), 7.32-7.27 (m, 1H), 7.23-7.16 (m, 2H), 5.47 (s, 1H), 4.33-4.15 (m, 2H), 3.90 (s, 1H), 3.40 (s, 1H), 3.26-3.10 (m, 3H), 2.82-2.69 (m, 1H), 2.09 (s, 3H), 1.86-1.75 (m, 1H), 1.74-1.63 (m, 1H), 1.60-1.49 (m, 1H), 1.36-1.30 (m, 1H). | I-B6<br>I-C3 |

-continued
| Compounds | Structural formula | LC-MS $[M+H]^+$ | $^1$HNMR | Interme-diates |
|---|---|---|---|---|
| 18 | 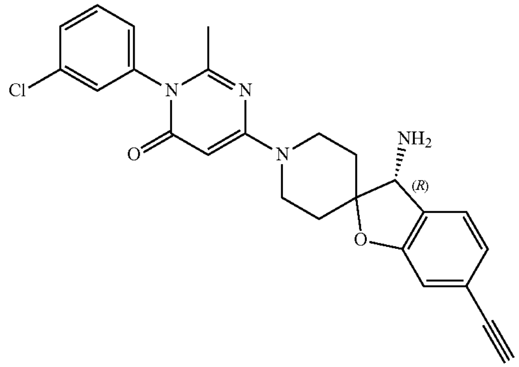 | 447.1 | $^1$H NMR (400 MHz, $CD_3OD$): δ 7.55-7.49 (m, 2H), 7.39-7.36 (m, 1H), 7.36-7.31 (m, 1H), 7.25-7.18 (m, 1H), 7.05-6.99 (m, 1H), 6.86 (s, 1H), 5.52 (s, 1H), 4.47-4.17 (m, 2H), 4.09 (s, 1H), 3.46-3.34 (m, 3H), 2.11 (s, 3H), 1.95-1.87 (m, 2H), 1.82-1.75 (m, 2H). | I-B6<br>I-C5 |
| 19 | 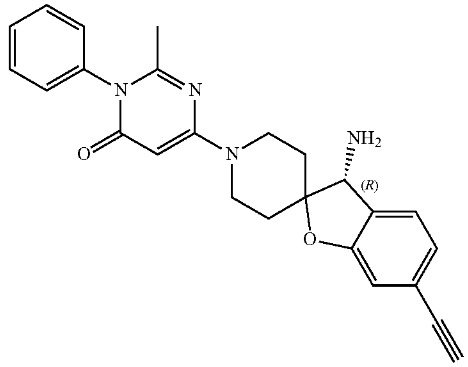 | 413.2 | $^1$H NMR (400 MHz, $CD_3OD$): δ 7.62-7.51 (m, 3H), 7.49 (d, J = 7.5 Hz, 1H), 7.33-7.26 (m, 2H), 7.15 (d, J = 7.5 Hz, 1H), 7.03 (s, 1H), 5.61 (s, 1H), 4.55-4.34 (m, 3H), 3.58 (s, 1H), 3.52-3.39 (m, 2H), 2.14 (s, 3H), 2.09-1.99 (m, 2H), 1.93-1.79 (m, 2H). | I-B7<br>I-C5 |

-continued
| Compounds | Structural formula | LC-MS $[M + H]^+$ | $^1$HNMR | Interme-diates |
|---|---|---|---|---|
| 20 | 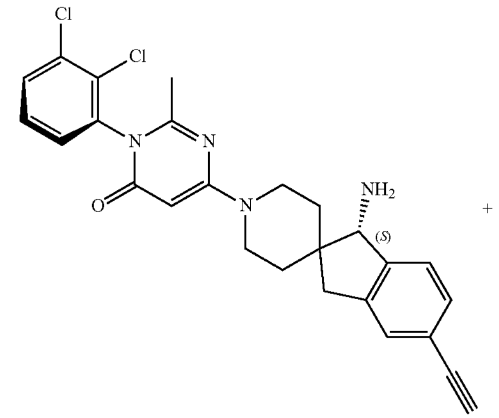 | 479.1 | $^1$H NMR (400 MHz, $CD_3OD$): δ 7.70 (dd, J = 8.1, 1.5 Hz, 1H), 7.48 (t, J = 8.0 Hz, 1H), 7.40-7.26 (m, 4H), 5.48 (s, 1H), 4.48-4.10 (m, 2H), 3.93 (s, 1H), 3.39 (s, 1H), 3.26-3.11 (m, 3H), 2.76 (d, J = 15.7 Hz, 1H), 2.06 (s, 3H), 1.90-1.67 (m, 2H), 1.63-1.51 (m, 1H), 1.40-1.32 (m, 1H). | I-B1 I-C6 |
| 24 | 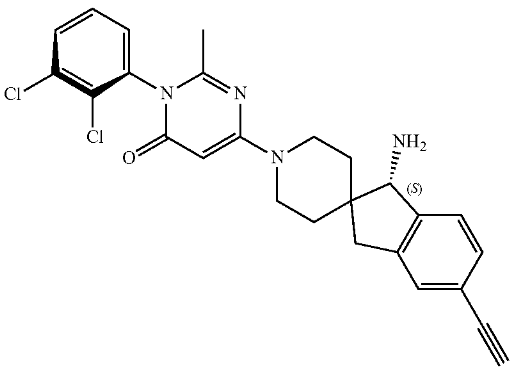 | 479.2 | $^1$H NMR (400 MHz, $CD_3OD$): δ 7.78-7.71 (m, 1H), 7.55-7.49 (m, 1H), 7.44-7.40 (m, 1H), 7.39-7.32 (m, 3H), 5.52 (s, 1H), 4.31 (s, 2H), 3.97 (s, 1H), 3.37 (s, 1H), 3.31-3.22 (m, 2H), 3.18 (d, J = 15.8 Hz, 1H), 2.80 (d, J = 15.8 Hz, 1H), 2.10 (s, 3H), 1.92-1.82 (m, 1H), 1.76 (m, 1H), 1.66-1.58 (m, 1H), 1.44-1.36 (m, 1H). | I-B2 I-C6 |

-continued
| Compounds | Structural formula | LC-MS $[M + H]^+$ | $^1$HNMR | Interme-diates |
|---|---|---|---|---|
| 21 | 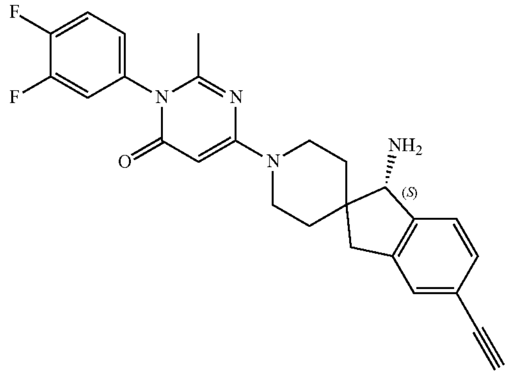 | 447.2 | $^1$H NMR (400 MHz, $CD_3OD$): δ 7.47-7.39 (m, 1H), 7.37-7.26 (m, 4H), 7.14-7.08 (m, 1H), 5.49-5.45 (m, 1H), 4.39-4.08 (m, 2H), 3.94-3.90 (m, 1H), 3.40 (s, 1H), 3.27-3.17 (m, 2H), 3.16-3.10 (m, 1H), 2.80-2.71 (m, 1H), 1.85-1.76 (m, 1H), 1.74-1.66 (m, 1H), 1.59-1.53 (m, 1H), 1.37-1.32 (m, 1H). | I-B3 I-C6 |
| 22 | 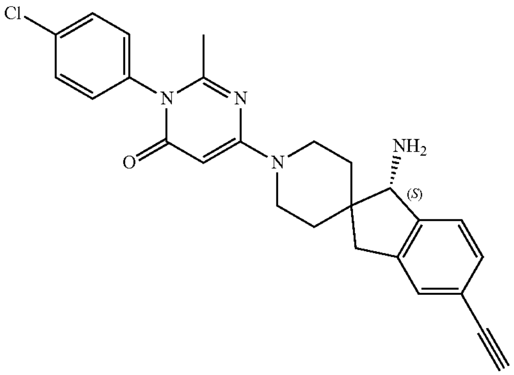 | 445.2 | $^1$H NMR (400 MHz, $CD_3OD$): δ 7.56-7.51 (m, 2H), 7.35-7.28 (m, 3H), 7.27-7.23 (m, 2H), 5.49-5.46 (m, 1H), 4.40-4.10 (m, 2H), 3.94-3.90 (m, 1H), 3.39 (s, 1H), 3.27-3.17 (m, 2H), 3.16-3.10 (m, 1H), 2.79-2.72 (m, 1H), 2.09 (s, 3H), 1.86-1.76 (m, 1H), 1.75-1.65 (m, 1H), 1.59-1.53 (m, 1H), 1.37-1.32 (m, 1H). | I-B8 I-C6 |

-continued
| Compounds | Structural formula | LC-MS $[M + H]^+$ | $^1$HNMR | Interme-diates |
| --- | --- | --- | --- | --- |
| 23 | 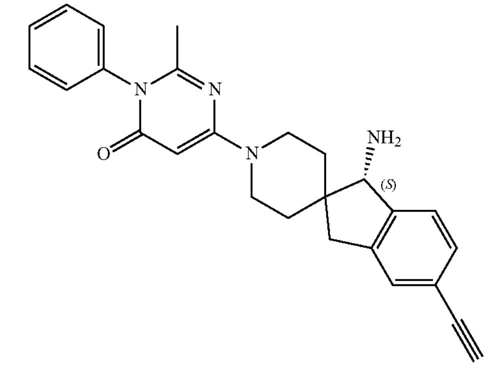 | 411.2 | $^1$H NMR (400 MHz, DMSO-$d_6$): δ 7.57-7.40 (m, 3H), 7.36-7.19 (m, 5H), 5.37 (s, 1H), 4.24-4.00 (m, 2H), 3.89-3.75 (m, 1H), 3.20-3.18 (m, 2H), 3.13-3.01 (m, 3H), 2.68-2.56 (m, 2H), 1.99 (s, 3H), 1.79-1.69 (m, 2H), 1.63-1.42 (m, 2H). | I-B7 I-C6 |
| 26 | 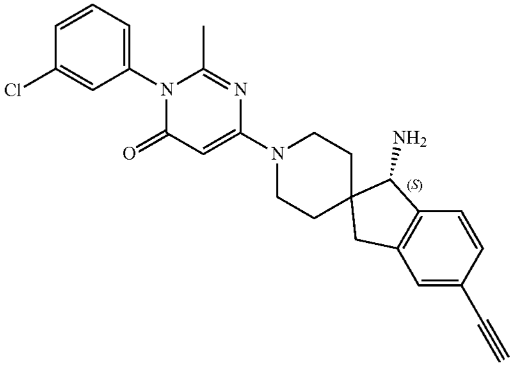 | 445.2 | $^1$H NMR (400 MHz, $CD_3OD$): δ 7.55-7.48 (m, 2H), 7.38-7.27 (m, 4H), 7.24-7.16 (m, 1H), 5.47 (s, 1H), 4.46-4.00 (m, 2H), 3.91 (s, 1H), 3.40 (s, 1H), 3.26-3.15 (m, 2H), 3.15-3.08 (m, 1H), 2.79-2.69 (m, 1H), 2.09 (s, 3H), 1.85-1.75 (m, 1H), 1.75-1.63 (m, 1H), 1.61-1.49 (m, 1H), 1.37-1.29 (m, 1H). | I-B6 I-C6 |
| 29 | 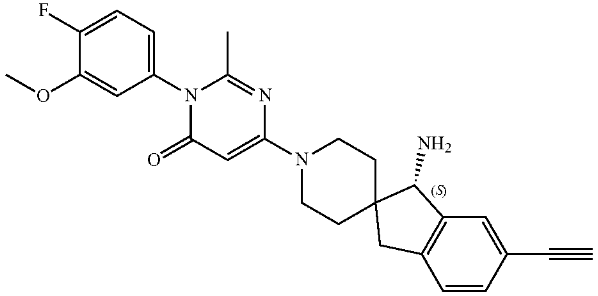 | 459.2 | $^1$H NMR (400 MHz, $CD_3OD$): δ 7.49-7.45 (m, 1H), 7.33-7.28 (m, 1H), 7.25-7.18 (m, 2H), 7.07-7.01 (m, 1H), 6.83-6.77 (m, 1H), 5.55-5.47 (s, 1H), 4.25 (br, 2H), 3.93-3.91 (m, 1H), 3.87 (s, 3H), 3.41-3.36 (m, 1H), 3.26-3.10 (m, 3H), 2.83-2.73 (m, 1H), 2.12 (s, 3H), 1.85-1.76 (m, 1H), 1.76-1.65 (m, 1H), 1.60-1.53 (m, 1H), 1.38-1.32 (m, 1H). | I-B9 I-C3 |

-continued
| Compounds | Structural formula | LC-MS $[M + H]^+$ | $^1$HNMR | Interme-diates |
|---|---|---|---|---|
| 30 | 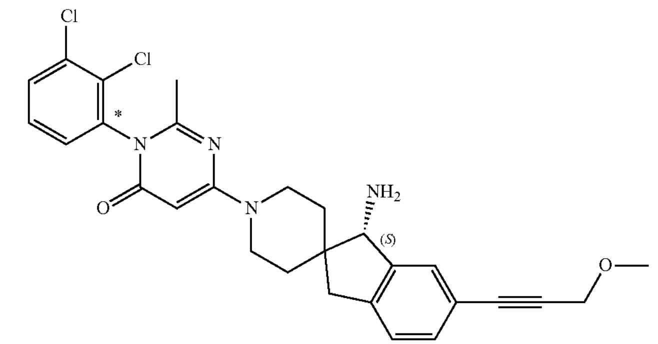 | 523.2 | $^1$H NMR (400 MHz, $CD_3OD$): δ 7.73-7.68 (m, 1H), 7.50-7.43 (m, 2H), 7.40-7.35 (m, 1H), 7.30-7.26 (m, 1H), 7.22-7.18 (m, 1H), 5.50-5.46 (m, 1H), 4.43-4.12 (m, 4H), 3.95-3.91 (m, 1H), 3.40 (s, 3H), 3.27-3.10 (m, 3H), 2.84-2.74 (m, 1H), 2.06 (s, 3H), 1.88-1.79 (m, 1H), 1.76-1.68 (m, 1H), 1.61-1.55 (m, 1H), 1.40-1.34 (m, 1H). | I-B1 I-C7 |
| 31 | 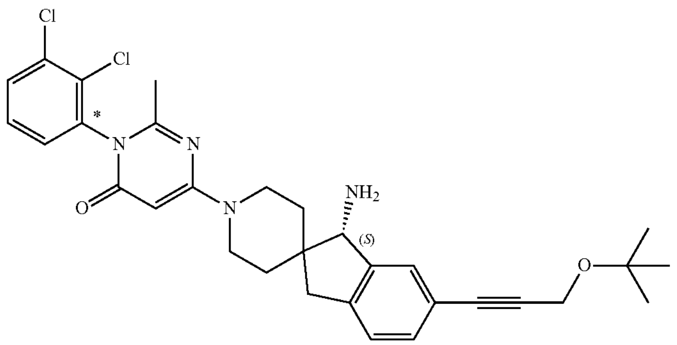 | 565.2 | $^1$H NMR (400 MHz, $CD_3OD$): δ 7.70 (dd, J = 8.2, 1.5 Hz, 1H), 7.48 (t, J = 8.0 Hz, 1H), 7.42 (s, 1H), 7.38 (dd, J = 7.9, 1.5 Hz, 1H), 7.26 (d, J = 7.7 Hz, 1H), 7.18 (d, J = 7.8 Hz, 1H), 5.48 (s, 1H), 4.43-4.09 (m, 4H), 3.91 (s, 1H), 3.26-3.11 (m, 3H), 2.77 (d, J = 16.0 Hz, 1H), 2.06 (s, 3H), 1.89-1.79 (m, 1H), 1.76-1.66 (m, 1H), 1.66-1.53(m, 1H), 1.39-1.32(m, 1H), 1.26 (s, 9H). | I-B1 I-C8' |

-continued
| Compounds | Structural formula | LC-MS $[M + H]^+$ | $^1$HNMR | Interme-diates |
| --- | --- | --- | --- | --- |
| 32 | 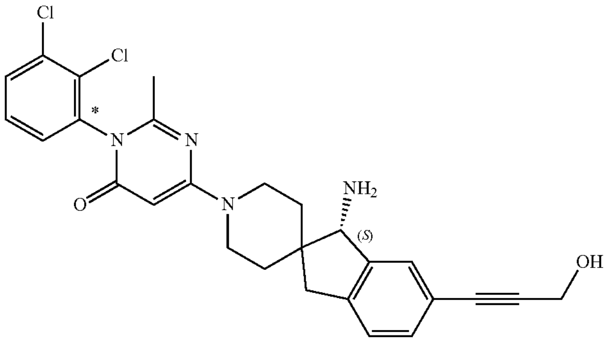 | 509.1 | $^1$H NMR (400 MHz, $CD_3OD$): δ 7.70 (dd, J = 8.1, 1.4 Hz, 1H), 7.53-7.34 (m, 3H), 7.26 (d, J = 6.8 Hz, 1H), 7.18 (d, J = 7.8 Hz, 1H), 5.48 (s, 1H), 4.34-4.09 (m, 4H), 3.91 (s, 1H), 3.25-3.11 (m, 3H), 2.81-2.71 (m, 1H), 2.06 (s, 3H), 1.88-1.78 (m, 1H), 1.76-1.67 (m, 1H), 1.62-1.53 (m, 1H), 1.40-1.31 (m, 1H). | I-B1<br>I-C8 |
| 33 | 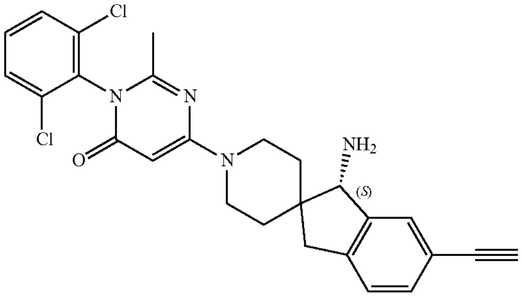 | 479.1 | $^1$H NMR (400 MHz, $CD_3OD$): δ 7.66-7.57 (m, 2H), 7.55-7.43 (m, 2H), 7.33-7.27 (m, 1H), 7.23-7.17 (m, 1H), 5.48 (s, 1H), 4.35-4.25 (m, 2H), 3.93 (s, 1H), 3.39 (s, 1H), 3.28-3.12 (m, 3H), 2.82-2.74 (m, 1H), 2.05 (s, 3H), 1.91-1.67 (m, 2H), 1.61-1.57 (m, 1H), 1.38-1.34 (m, 1H). | I-B10<br>I-C3 |
| 34 | 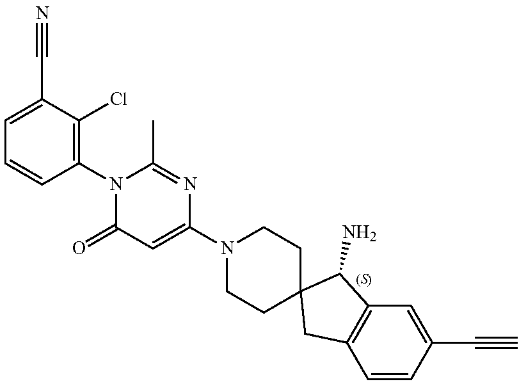 | 470.2 | $^1$H NMR (400 MHz, $CD_3OD$): δ 8.00-7.94 (m, 1H), 7.77-7.72 (m, 1H), 7.69-7.62 (m, 1H), 7.47 (s, 1H), 7.33-7.27 (m, 1H), 7.22-7.16 (m, 1H), 5.48 (s, 1H), 4.45-4.08 (m, 2H), 3.91 (s, 1H), 3.39 (s, 1H), 3.26-3.10 (m, 3H), 2.85-2.70 (m, 1H), 2.06 (s, 3H), 1.87-1.68 (m, 2H), 1.60-1.53 (m,1H), 1.39-1.33 (m, 1H). | I-B11<br>I-C3 |

-continued
| Compounds | Structural formula | LC-MS $[M + H]^+$ | $^1$HNMR | Interme-diates |
|---|---|---|---|---|
| 35 | 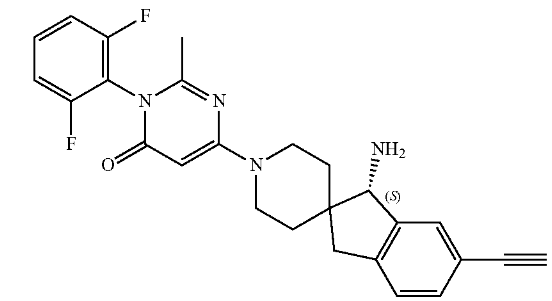 | 447.2 | $^1$H NMR (400 MHz, $CD_3OD$): δ 7.63-7.53 (m, 1H), 7.46 (s, 1H), 7.32-7.27 (m, 1H), 7.24-7.16 (m, 3H), 5.47 (s, 1H), 4.51-4.00 (m, 2H), 3.91 (s, 1H), 3.39 (s, 1H), 3.27-3.10 (m, 3H), 2.81-2.72 (m, 1H), 2.14 (s, 3H), 1.88-1.79 (m, 1H), 1.75-1.67 (m, 1H), 1.60-1.54 (m, 1H), 1.36-1.31 (m, 1H). | I-B12 I-C3 |
| 36 | 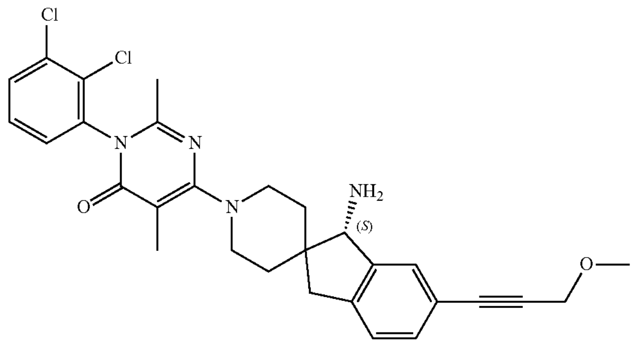 | 537.1 | $^1$H NMR (400 MHz, $CD_3OD$): δ 7.74-7.67 (m, 1H), 7.52-7.41 (m, 2H), 7.39-7.33 (m, 1H), 7.30-7.24 (m, 1H), 7.23-7.16 (m, 1H), 4.33-4.26 (m, 2H), 3.96-3.86 (m, 3H), 3.40 (s, 3H), 3.25-3.19 (m, 2H), 3.16-3.11 (m, 1H), 2.82-2.72 (m, 1H), 2.05 (s, 3H), 2.00 (s, 3H), 1.95-1.88 (m, 1H), 1.85-1.77 (m, 1H), 1.60-1.54 (m, 1H), 1.39-1.34 (m, 1H). | I-B13 I-C7 |
| 39 | 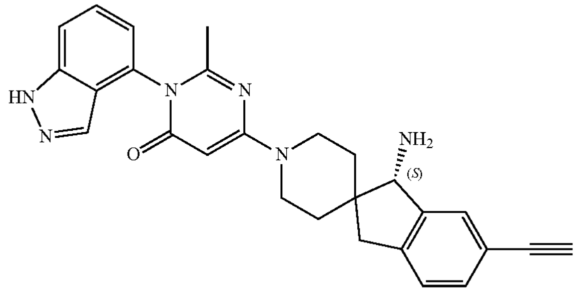 | 451.2 | $^1$H NMR (400 MHz, $CD_3OD$): δ 7.84 (s, 1H), 7.71-7.65 (m, 1H), 7.54-7.46 (m, 2H), 7.33-7.27 (m, 1H), 7.23-7.18 (m, 1H), 7.11-7.05 (m, 1H), 5.54 (s, 1H), 4.39-4.17 (m, 2H), 3.94 (s, 1H), 3.39 (s, 1H), 3.28-3.13 (m, 3H), 2.84-2.74 (m, 1H), 2.06 (s, 3H), 1.90-1.81 (m, 1H), 1.79-1.70 (m, 1H), 1.61-1.56 (m, 1H), 1.40-1.34 (m, 1H). | I-B14 I-C3 |

-continued
| Compounds | Structural formula | LC-MS $[M + H]^+$ | $^1$HNMR | Interme-diates |
|---|---|---|---|---|
| 41 | 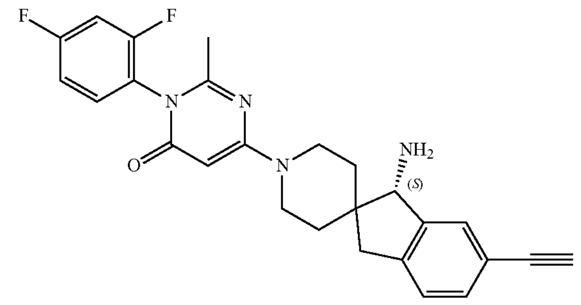 | 447.2 | $^1$H NMR (400 MHz, $CD_3OD$): δ 7.47-7.35 (m, 2H), 7.31-7.26 (m, 1H), 7.25-7.11 (m, 3H), 5.48-5.44 (m, 1H), 4.46-4.00 (m, 2H), 3.91 (s, 1H), 3.33 (s, 1H), 3.28-3.09 (m, 3H), 2.82-2.68 (m, 1H), 2.20-1.98 (m, 3H), 1.90-1.79 (m, 1H), 1.75-1.55 (m, 2H), 1.38-1.31 (m, 1H). | I-B15<br>I-C3 |
| 42 | 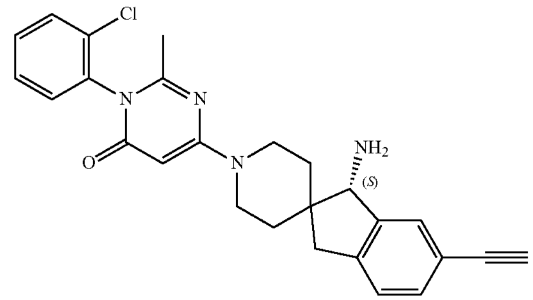 | 445.2 | $^1$H NMR (400 MHz, $CD_3OD$): δ 7.65-7.60 (m, 1H), 7.52-7.46 (m, 3H), 7.40-7.37 (m, 1H), 7.32-7.28 (m, 1H), 7.22-7.18 (m, 1H), 5.49-5.47 (m, 1H), 4.42-4.12 (m, 2H), 3.94-3.91 (m, 1H), 3.39 (s, 1H), 3.26-3.12 (m, 3H), 2.82-2.74 (m, 1H), 2.04 (s, 3H), 1.88-1.79 (m, 1H), 1.76-1.68 (m, 1H), 1.61-1.54 (m, 1H), 1.39-1.33 (m, 1H). | I-B16<br>I-C3 |
| 43 | 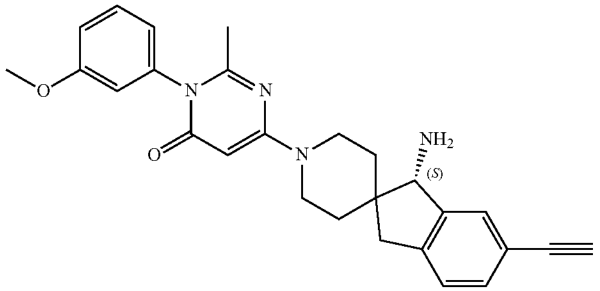 | 441.2 | $^1$H NMR (400 MHz, $CD_3OD$): δ 7.49-7.39 (m, 2H), 7.33-7.27 (m, 1H), 7.22-7.16 (m, 1H), 7.07-7.01 (m, 1H), 6.85-6.77 (m, 2H), 5.51-5.45 (m, 1H), 4.38-4.10 (m, 2H), 3.94-3.89 (m, 1H), 3.39 (s, 1H), 3.24-3.11 (m, 3H), 2.81-2.73 (m, 1H), 2.10 (s, 3H), 1.85-1.77 (m, 1H), 1.75-1.66 (m, 1H), 1.59-1.52 (m, 1H), 1.38-1.31 (m, 1H). | I-B17<br>I-C3 |

-continued
| Compounds | Structural formula | LC-MS [M + H]+ | $^1$HNMR | Interme-diates |
|---|---|---|---|---|
| 44 | 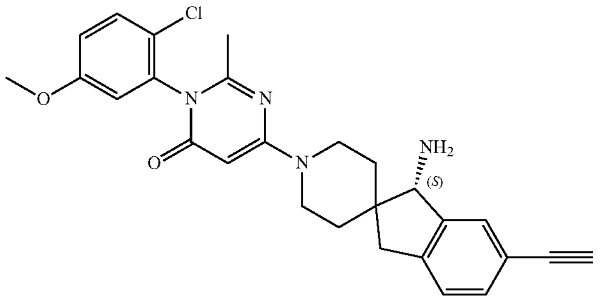 | 475.2 | $^1$H NMR (400 MHz, $CD_3OD$): δ 7.51-7.45 (m, 2H), 7.32-7.28 (m, 1H), 7.21-7.18 (m, 1H), 7.09-7.05 (m, 1H), 7.00-6.98 (m, 1H), 5.48-5.47 (m, 1H), 4.40-4.12 (m, 2H), 3.93-3.91 (m, 1H), 3.39 (s, 1H), 3.25-3.12 (m, 3H), 2.81-2.74 (m, 1H), 2.08 (s, 3H), 1.87-1.79 (m, 1H), 1.76-1.67 (m, 1H), 1.60-1.54 (m, 1H), 1.38-1.33 (m, 1H). | I-B18 I-C3 |
| 45 | 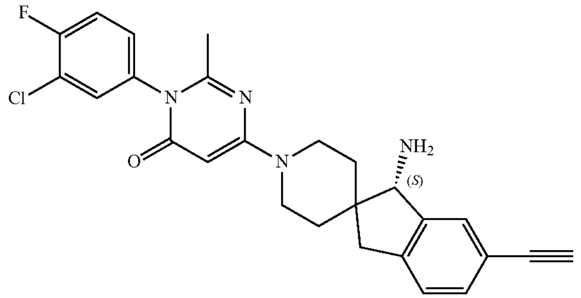 | 463.1 | $^1$H NMR (400 MHz, $CD_3OD$): δ 7.54-7.48 (m, 1H), 7.48-7.43 (m, 1H), 7.43-7.38 (m, 1H), 7.31-7.23 (m, 2H), 7.21-7.16 (m, 1H), 5.49-5.45 (m, 1H), 4.35-4.12 (m, 2H), 3.93-3.88 (m, 1H), 3.39 (s, 1H), 3.25-3.11 (m, 3H), 2.81-2.72 (m, 1H), 2.11 (s, 3H), 1.85-1.76 (m, 1H), 1.74-1.66 (m, 1H), 1.59-1.52 (m, 1H), 1.38-1.31 (m, 1H). | I-B19 I-C3 |
| 46 | 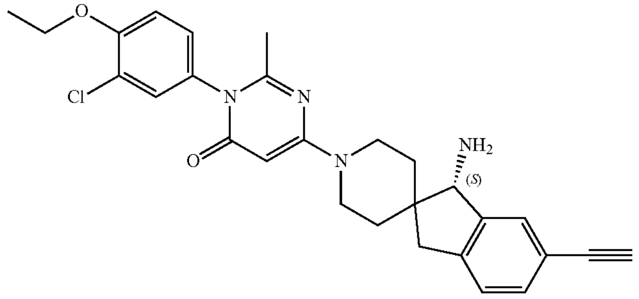 | 489.2 | $^1$H NMR (400 MHz, $CD_3OD$): δ 7.49-7.44 (m, 1H), 7.34-7.27 (m, 2H), 7.20-7.15 (m, 2H), 7.14-7.10 (m, 1H), 5.48-5.45 (m, 1H), 4.32-4.12 (m, 4H), 3.92-3.89 (m, 1H), 3.39 (s, 1H), 3.25-3.11 (m, 3H), 2.80-2.73 (m, 1H), 2.10 (s, 3H), 1.85-1.76 (m, 1H), 1.74-1.65 (m, 1H), 1.58-1.52 (m, 1H), 1.45 (t, J = 7.0 Hz, 3H), 1.36-1.30 (m, 1H). | I-B20 I-C3 |

-continued
| Compounds | Structural formula | LC-MS $[M + H]^+$ | $^1$HNMR | Interme-diates |
|---|---|---|---|---|
| 48 | 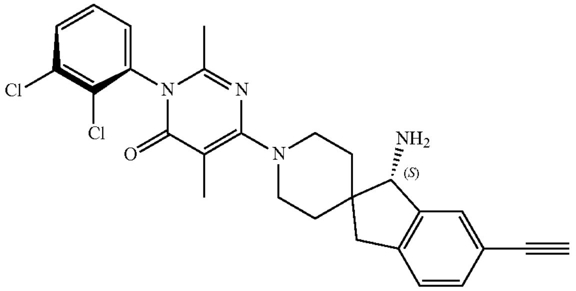 + | 493.2 | $^1$H NMR (400 MHz, $CD_3OD$): δ 7.73-7.67 (m, 1H), 7.51-7.45 (m, 2H), 7.39-7.33 (m, 1H), 7.32-7.27 (m, 1H), 7.21-7.16 (m, 1H), 3.96-3.85 (m, 3H), 3.39 (s, 1H), 3.28-3.17 (m, 2H), 3.17-3.09 (m, 1H), 2.80-2.71 (m, IH), 2.05 (s, 3H), 2.00 (s, 3H), 1.96-1.87 (m, 1H), 1.85-1.75 (m, 1H), 1.60-1.52 (m, 1H), 1.38-1.32 (m, 1H). | I-B21 I-C3 |
| 49 | 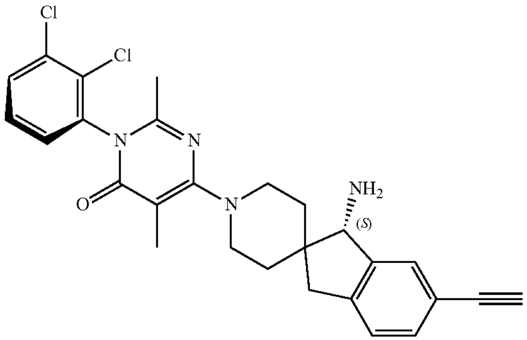 | 493.1 | $^1$H NMR (400 MHz, $CD_3OD$): δ 7.73-7.67 (m, 1H), 7.52-7.44 (m, 2H), 7.39-7.34 (m, 1H), 7.32-7.27 (m, 1H), 7.21-7.17 (m, 1H), 3.99-3.85 (m, 3H), 3.39 (s, 1H), 3.28-3.19 (m, 2H), 3.18-3.10 (m, 1H), 2.82-2.72 (m, 1H), 2.05 (s, 3H), 2.00 (s, 3H), 1.96-1.86 (m, 1H), 1.86-1.76 (m, 1H), 1.60-1.54 (m, 1H), 1.39-1.34 (m, 1H). | I-B22 I-C3 |
| 50 | 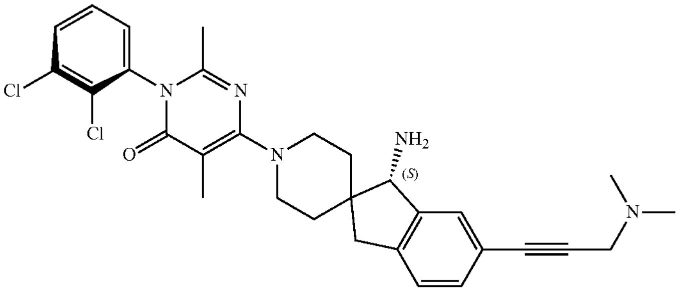 + | 550.2 | $^1$H NMR (400 MHz, $CD_3OD$): δ 7.74-7.68 (m, 1H), 7.51-7.46 (m, 1H), 7.44 (s, 1H), 7.40-7.33 (m, 1H), 7.29-7.24 (m, 1H), 7.21-7.15 (m, 1H), 3.97-3.85 (m, 3H), 3.49-3.41 (m, 2H), 3.28-3.18 (m, 2H), 3.17-3.09 (m, 1H), 2.82-2.72 (m, 1H), 2.36 (s, 6H), 2.05 (s, 3H), 2.00 (s, 3H), 1.97-1.86 (m, IH), 1.86-1.75 (m, 1H), 1.62-1.52 (m, 1H), 1.39-1.33 (m, 1H). | I-B21 I-C10 |

-continued
| Compounds | Structural formula | LC-MS $[M + H]^+$ | $^1$HNMR | Interme-diates |
|---|---|---|---|---|
| 51 | 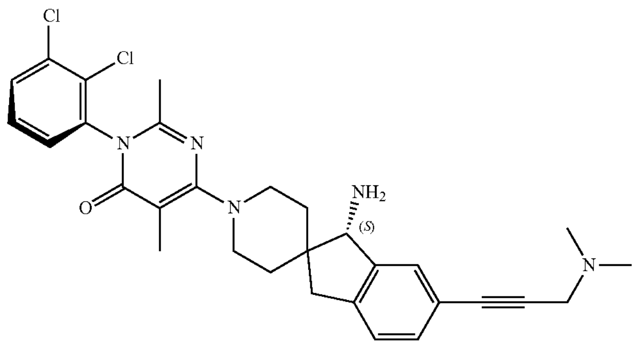 | 550.2 | $^1$H NMR (400 MHz, $CD_3OD$): δ 7.72-7.68 (m, 1H), 7.52-7.45 (m, 1H), 7.44 (s, 1H), 7.39-7.34 (m, 1H), 7.29-7.23 (m, 1H), 7.21-7.15 (m, 1H), 4.00-3.80 (m, 3H), 3.49-3.42 (m, 2H), 3.28-3.18 (m, 2H), 3.17-3.08 (m, 1H), 2.81-2.70 (m, 1H), 2.36 (s, 6H), 2.05 (s, 3H), 2.00 (s, 3H), 1.96-1.86 (m, 1H), 1.86-1.75 (m, 1H), 1.61-1.51 (m, 1H), 1.40-1.32 (m, 1H). | I-B22 I-C10 |
| 52 | 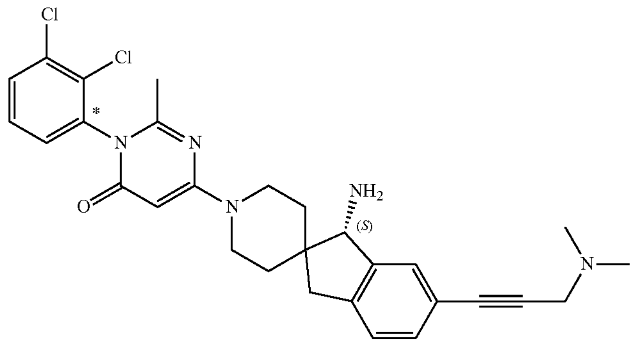 | 537.2 | $^1$H NMR (400 MHz, $CD_3OD$): δ 7.73-7.67 (m, 1H), 7.50-7.45 (m, 1H), 7.44 (s, 1H), 7.40-7.34 (m, 1H), 7.29-7.24 (m, 1H), 7.21-7.16 (m, 1H), 5.47 (s, 1H), 4.51-3.95 (m, 2H), 3.91 (s, 1H), 3.48-3.43 (m, 2H), 3.28-3.17 (m, 2H), 3.17-3.10 (m, 1H), 2.83-2.67 (m, 1H), 2.35 (s, 6H), 2.05 (s, 3H), 1.88-1.77 (m, 1H), 1.76-1.65 (m, 1H), 1.61-1.52 (m, 1H), 1.40-1.30 (m, 1H). | I-B1 I-C10 |
| 53 | 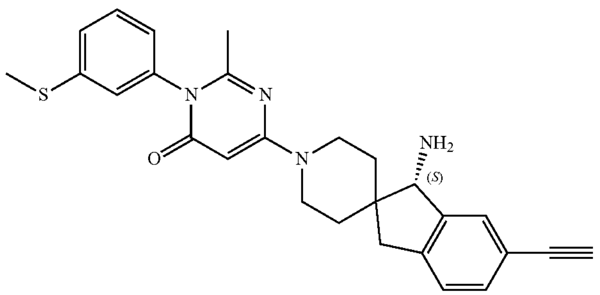 | 457.2 | $^1$H NMR (400 MHz, $CD_3OD$): δ 7.50-7.28 (m, 4H), 7.22-7.10 (m, 2H), 7.01-6.97 (m, 1H), 5.48 (s, 1H), 4.34-4.14 (m, 2H), 3.91 (s, 1H), 3.39 (s, 1H), 3.25 -3.09 (m, 3H), 2.79-2.75 (m, 1H), 2.49 (s, 3H), 2.09 (s, 3H), 1.86-1.64 (m, 2H), 1.57-1.53 (m, 1H), 1.36-1.32 (m, 1H). | I-B23 I-C3 |

-continued
| Compounds | Structural formula | LC-MS $[M + H]^+$ | $^1$HNMR | Interme-diates |
|---|---|---|---|---|
| 54 | 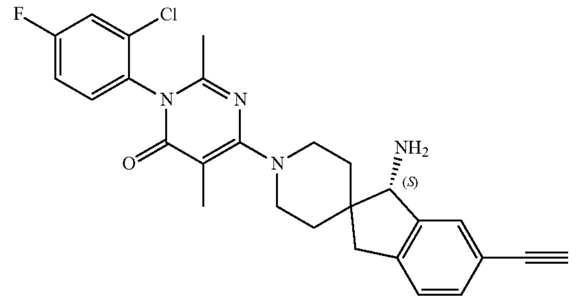 | 477.2 | $^1$H NMR (400 MHz, $CD_3OD$): δ 7.52-7.38 (m, 3H), 7.32-7.24 (m, 2H), 7.20-7.18 (m, 1H), 3.97-3.83 (m, 3H), 3.39 (s, 1H), 3.26-3.08 (m, 3H), 2.77-2.75 (m, 1H), 2.08-1.72 (m, 8H), 1.58-1.54 (m, 1H), 1.37-1.33 (m, 1H). | I-B24 I-C3 |
| 55 | 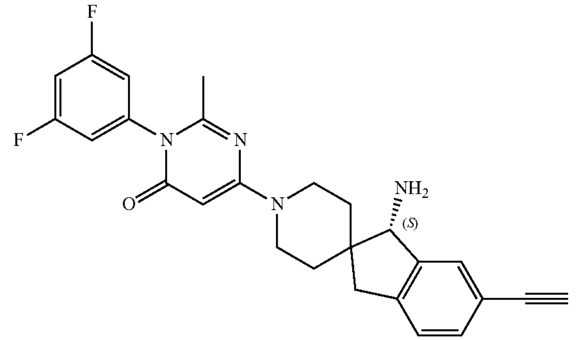 | 447.2 | $^1$H NMR (400 MHz, $CD_3OD$): δ 7.46 (s, 1H), 7.35-6.95 (m, 5H), 5.46 (s, 1H), 4.34-4.14 (m, 2H), 3.90 (s, 1H), 3.39 (s, 1H), 3.27-3.09 (m, 3H), 2.78-2.74 (m, 1H), 2.13 (s, 3H), 1.86-1.63 (m, 2H), 1.57-1.53 (m, 1H), 1.36-1.32 (m, 1H). | I-B25 I-C3 |
| 60 | 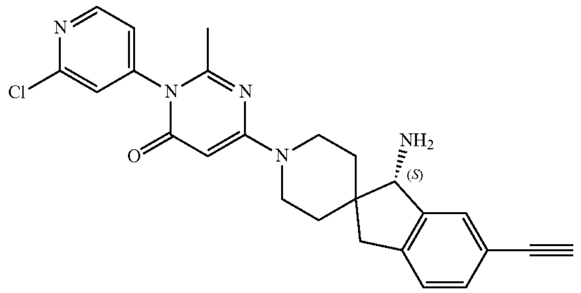 | 446.2 | $^1$H NMR (400 MHz, $CD_3OD$): δ 8.57-8.52 (m, 1H), 7.57-7.53 (m, 1H), 7.49-7.44 (m, 1H), 7.39-7.35 (m, 1H), 7.32-7.27 (m, 1H), 7.21-7.16 (m, 1H), 5.46 (s, 1H), 4.24 (br, 2H), 3.91 (s, 1H), 3.39 (s, 1H), 3.26-3.11 (m, 3H), 2.80-2.73 (m, 1H), 2.13 (s, 3H), 1.85-1.76 (m, 1H), 1.74-1.66 (m, 1H), 1.60-1.53 (m, 1H), 1.38-1.31 (m, 1H). | I-B26 I-C3 |

-continued
| Compounds | Structural formula | LC-MS [M + H]+ | $^1$HNMR | Interme-diates |
|---|---|---|---|---|
| 61 | 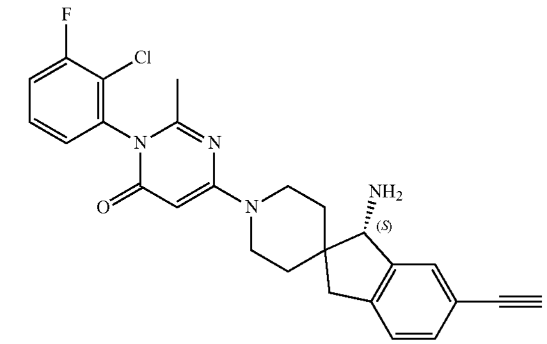 | 463.2 | $^1$H NMR (400 MHz, $CD_3OD$): δ 7.60-7.45 (m, 3H), 7.37-7.29 (m, 2H), 7.26-7.22 (m, 1H), 5.53 (s, 1H), 4.31 (s, 2H), 3.97 (s, 1H), 3.44 (s, 1H), 3.31-3.17 (m, 3H), 2.86-2.78 (m, 1H), 2.15-2.06 (m, 3H), 1.93-1.74 (m, 2H), 1.66-1.60 (m, 1H), 1.44-1.38 (m, 1H). | I-B27<br>I-C3 |
| 62 | 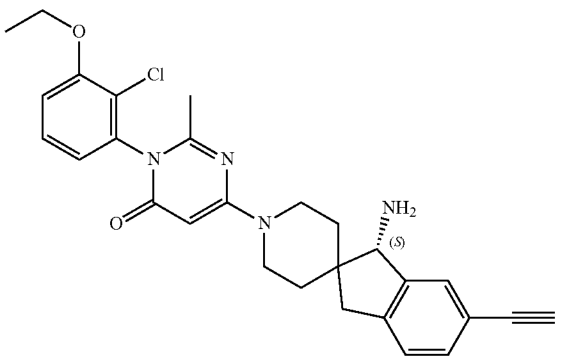 | 489.2 | $^1$H NMR (400 MHz, $CD_3OD$): δ 7.52 (s, 1H), 7.49-7.43 (m, 1H), 7.35 (d, J = 7.0 Hz, 1H), 7.28-7.20 (m, 2H), 6.99 (d, J = 7.0 Hz, 1H), 5.53 (s, 1H), 4.41-4.18 (m, 4H), 3.96 (s, 1H), 3.38 (s, 1H), 3.31-3.17 (m, 3H), 2.87-2.79 (m, 1H), 2.10 (s, 3H), 1.93-1.72 (m, 2H), 1.66-1.59 (m, 1H), 1.53-1.45 (m, 3H), 1.44-1.37 (m, 1H). | I-B28<br>I-C3 |
| 63 | 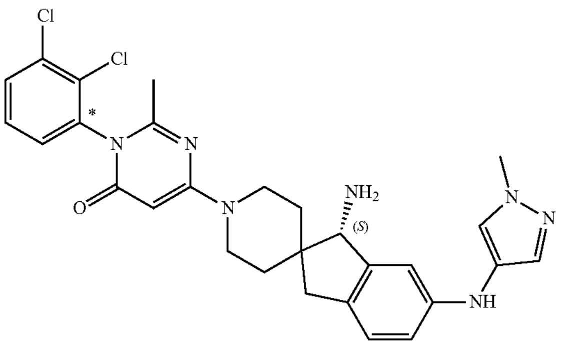 | 550.2 | $^1$H NMR (400 MHz, $CD_3OD$): δ 7.70 (dd, J = 8.1, 1.4 Hz, 1H), 7.52 (s, 1H), 7.47 (t, J = 8.0 Hz, 1H), 7.37 (dd, J = 7.9, 1.4 Hz, 1H), 7.32 (s, 1H), 6.98 (d, J = 8.1 Hz, 1H), 6.86 (d, J = 2.0 Hz, 1H), 6.65 (dd, J = 8.1, 2.3 Hz, 1H), 5.47 (s, 1H), 4.49-4.06 (m, 2H), 3.84-3.81 (m, 4H), 3.27-3.16 (m, 2H), 3.01 (d, J = 15.2 Hz, 1H), 2.66 (d, J = 15.1 Hz, 1H), 2.05 (s, 3H), 1.84-1.65 (m, 2H), 1.60-1.52 (m, 1H), 1.44-1.36 (m, 1H). | I-B1<br>I-C11 |

-continued
| Compounds | Structural formula | LC-MS $[M + H]^+$ | $^1$HNMR | Interme-diates |
|---|---|---|---|---|
| 64 | 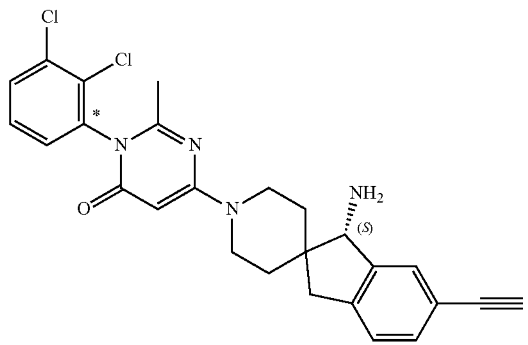 | 479.1 | $^1$H NMR (400 MHz, $CD_3OD$): δ 7.70 (dd, J = 8.2, 1.5 Hz, 1H), 7.52-7.45 (m, 2H), 7.38 (dd, J = 7.9, 1.5 Hz, 1H), 7.33-7.27 (m, 1H), 7.19 (d, J = 7.7 Hz, 1H), 5.48 (s, 1H), 4.51-4.05 (m, 2H), 3.92 (s, 1H), 3.39 (s, 1H), 3.26- 3.12 (m, 3H), 2.77 (d, J = 16.1 Hz, 1H), 2.06 (s, 3H), 1.89-1.67 (m, 2H), 1.63-1.54(m, 1H), 1.39-1.31 (m, 1H). | I-B2 I-C3 |
| 68 | 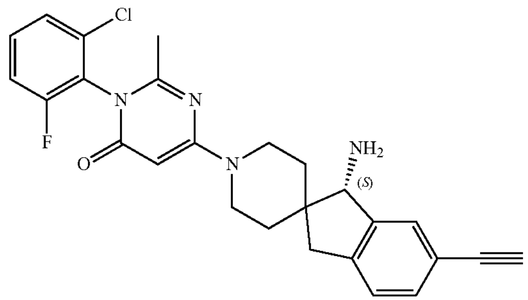 | 463.1 | $^1$H NMR (400 MHz, $CD_3OD$): δ 7.60-7.22 (m, 6H), 5.48 (s, 1H), 4.40-4.10 (m, 3H), 3.44 (s, 1H), 3.28-3.11 (m, 3H), 2.94-2.90 (m, 1H), 2.09 (s, 3H), 1.87-1.42 (m, 4H). | I-B29 I-C3 |
| 69 | 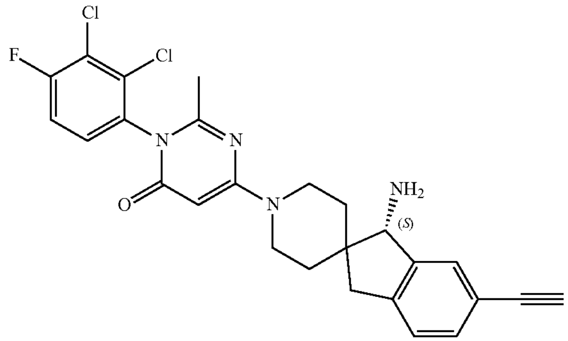 | 497.1 | $^1$H NMR (400 MHz, $CD_3OD$): δ 7.54-7.37 (m, 3H), 7.33-7.16 (m, 2H), 5.48 (s, 1H), 4.40-4.05 (m, 2H), 3.92 (s, 1H), 3.41 (s, 1H), 3.33-3.13 (m, 3H), 2.81-2.75 (m, 1H), 2.07 (s, 3H), 1.90-1.65 (m, 2H), 1.61-1.52 (m, 1H), 1.41-1.32 (m, 1H). | I-B30 I-C3 |

-continued
| Compounds | Structural formula | LC-MS $[M+H]^+$ | $^1$HNMR | Interme-diates |
|---|---|---|---|---|
| 70 | 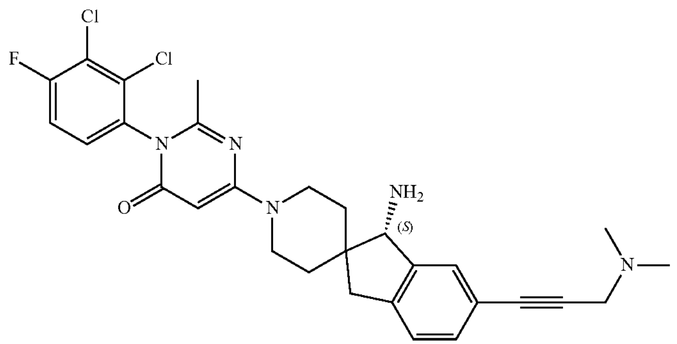 | 554.2 | $^1$H NMR (400 MHz, $CD_3OD$): δ 7.50-7.41 (m, 3H), 7.32-7.17 (m, 2H), 5.48 (s, 1H), 4.50-4.07 (m, 2H), 3.95 (s, 1H), 3.47 (s, 2H), 3.27-3.09 (m, 3H), 2.84-2.80 (m, 1H), 2.36 (s, 6H), 2.07 (s, 3H), 1.88-1.63 (m, 2H), 1.60-1.56 (m, 1H), 1.40-1.36 (m, 1H). | I-B30<br>I-C10 |
| 73 | 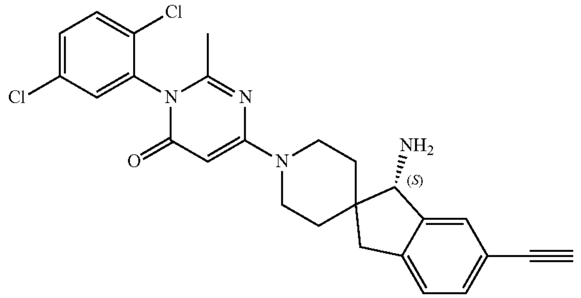 | 479.1 | $^1$H NMR (400 MHz, $CD_3OD$): δ 7.65-7.60 (m, 1H), 7.57-7.51 (m, 2H), 7.47 (s, 1H), 7.33-7.28 (m, 1H), 7.22-7.17 (m, 1H), 5.48 (s, 1H), 4.55-3.99 (m, 2H), 3.92 (s, 1H), 3.40 (s, 1H), 3.28-3.11 (m, 3H), 2.85-2.70 (m, 1H), 2.08 (s, 3H), 1.88-1.79 (m, 1H), 1.75-1.66 (m, 1H), 1.61-1.54 (m, 1H), 1.39-1.32 (m, 1H). | I-B31<br>I-C3 |
| 74 | 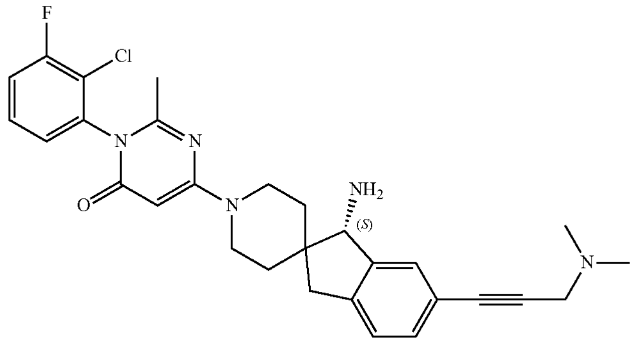 | 520.3 | $^1$H NMR (400 MHz, $CD_3OD$): δ 7.60-7.53 (m, 1H), 7.52-7.44 (m, 2H), 7.35-7.28 (m, 2H), 7.27-7.19 (m, 1H), 5.53 (s, 1H), 4.32 (s, 2H), 3.98 (s, 1H), 3.51 (s, 2H), 3.31-3.13 (m, 3H), 2.87-2.79 (m, 1H), 2.41 (s, 6H), 2.10 (s, 3H), 1.92-1.83 (m, 1H), 1.82-1.72 (m, 1H), 1.68-1.58 (m, 1H), 1.45-1.37 (m, 1H). | I-B27<br>I-C10 |

-continued
| Compounds | Structural formula | LC-MS $[M + H]^+$ | $^1$HNMR | Interme-diates |
|---|---|---|---|---|
| 77 | 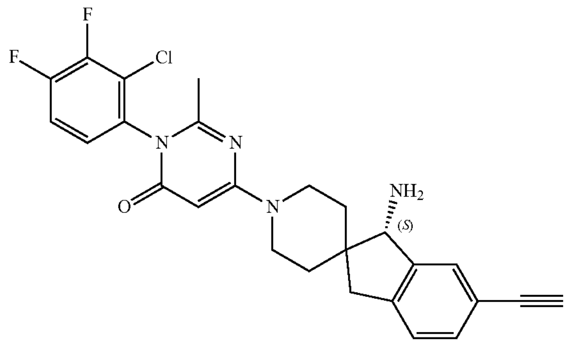 | 481.2 | $^1$H NMR (400 MHz, $CD_3OD$): δ 7.52-7.42 (m, 2H), 7.35-7.28 (m, 2H), 7.24-7.17 (m, 1H), 5.48 (s, 1H), 4.28 (br, 2H), 3.94 (s, 1H), 3.40 (s, 1H), 3.27-3.12 (m, 3H), 2.85-2.74 (m, 1H), 2.08 (s, 3H), 1.88-1.79 (m, 1H), 1.76-1.67 (m, 1H), 1.62-1.55 (m, 1H), 1.40-1.33 (m, 1H). | I-B32 I-C3 |
| 78 | 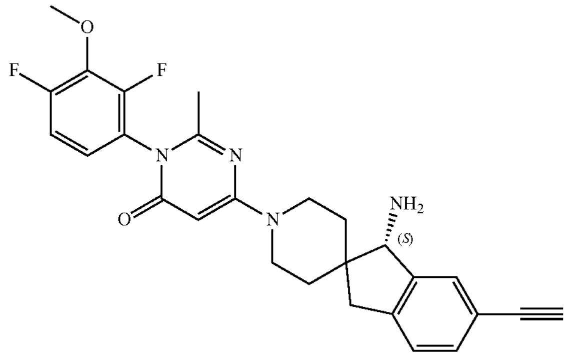 | 477.2 | $^1$H NMR (400 MHz, $CD_3OD$): δ 7.50-7.42 (m, 1H), 7.34-7.27 (m, 1H), 7.22-7.12 (m, 2H), 7.10-7.04 (m, 1H), 5.47 (s, 1H), 4.27 (br, 2H), 4.01 (s, 3H), 3.92 (s, 1H), 3.40 (s, 1H), 3.26-3.12 (m, 3H), 2.82-2.74 (m, 1H), 2.12 (s, 3H), 1.88-1.78 (m, 1H), 1.76-1.66 (m, 1H), 1.61-1.54 (m, 1H), 1.38-1.32 (m, 1H). | I-B33 I-C3 |

-continued
| Compounds | Structural formula | LC-MS $[M + H]^+$ | $^1$HNMR | Interme-diates |
|---|---|---|---|---|
| 80 | 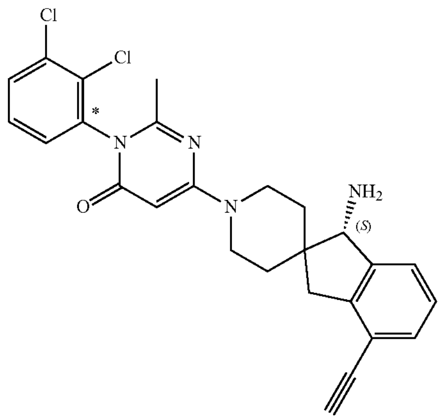 | 479.1 | $^1$H NMR (400 MHz, $CD_3OD$): δ 7.74-7.67 (m, 1H), 7.52-7.46 (m, 1H), 7.42-7.36 (m, 2H), 7.33-7.28 (m, 1H), 7.23-7.17 (m, 1H), 5.49 (s, 1H), 4.29 (br, 2H), 3.97 (s, 1H), 3.67 (s, 1H), 3.36-3.19 (m, 3H), 2.90-2.80 (m, 1H), 2.06 (s, 3H), 1.87-1.70 (m, 2H), 1.62-1.56 (m, 1H), 1.43-1.36 (m, 1H). | I-B1<br>I-C12 |
| 82 | 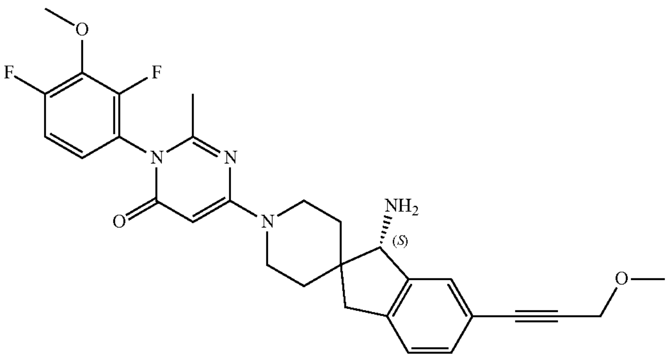 | 521.2 | $^1$H NMR (400 MHz, $CD_3OD$): δ 7.48-7.40 (m, 1H), 7.30-7.25 (m, 1H), 7.22-7.12 (m, 2H), 7.11-7.04 (m, 1H), 5.47 (s, 1H), 4.42-4.15 (m, 4H), 4.01 (s, 3H), 3.92 (s, 1H), 3.41 (s, 3H), 3.26-3.12 (m, 3H), 2.83-2.73 (m, 1H), 2.12 (s, 3H), 1.88-1.78 (m, 1H), 1.76-1.66 (m, 1H), 1.61-1.53 (m, 1H), 1.38-1.32 (m, 1H). | I-B33<br>I-C7 |

-continued
| Compounds | Structural formula | LC-MS $[M + H]^+$ | $^1$HNMR | Interme-diates |
|---|---|---|---|---|
| 83 | 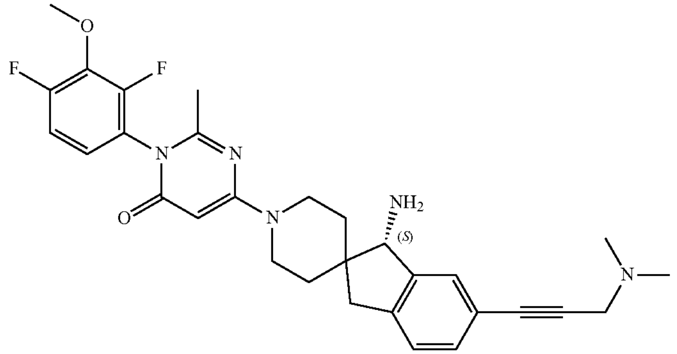 | 534.3 | $^1$H NMR (400 MHz, $CD_3OD$): δ 7.46-7.41 (m, 1H), 7.29-7.25 (m, 1H), 7.20-7.12 (m, 2H), 7.10-7.04 (m, 1H), 5.47 (s, 1H), 4.27 (br, 2H), 4.01 (s, 3H), 3.92 (s, 1H), 3.46 (s, 2H), 3.26-3.12 (m, 3H), 2.82-2.73 (m, 1H), 2.36 (s, 6H), 2.12 (s, 3H), 1.88-1.79 (m, 1H), 1.76-1.67 (m, 1H), 1.60-1.54 (m, 1H), 1.38-1.32 (m, 1H). | I-B33 I-C10 |
| 84 | 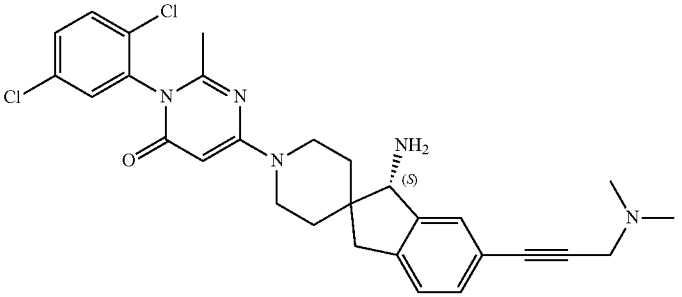 | 536.2 | $^1$H NMR (400 MHz, $CD_3OD$): δ 7.65-7.60 (m, 1H), 7.57-7.51 (m, 2H), 7.44 (s, 1H), 7.30-7.24 (m, 1H), 7.22-7.16 (m, 1H), 5.47 (s, 1H), 4.55-4.02 (m, 2H), 3.92 (s, 1H), 3.46 (s, 2H), 3.27-3.12 (m, 3H), 2.82-2.71 (m, 1H), 2.36 (s, 6H), 2.08 (s, 3H), 1.87-1.78 (m, 1H), 1.76-1.67 (m, 1H), 1.60-1.55 (m, 1H), 1.39-1.33 (m, 1H). | I-B31 I-C10 |
| 85 | 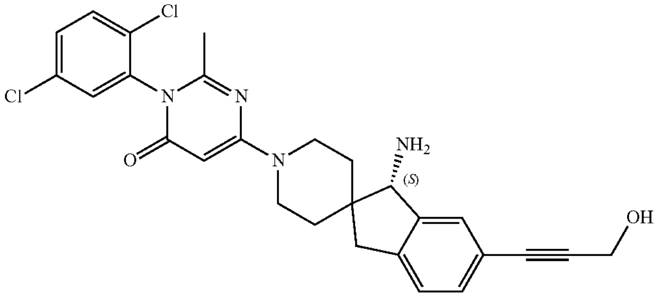 | 509.2 | $^1$H NMR (400 MHz, $CD_3OD$): δ 7.65-7.59 (m, 1H), 7.57-7.51 (m, 2H), 7.43 (s, 1H), 7.29-7.23 (m, 1H), 7.21-7.17 (m, 1H), 5.48 (s, 1H), 4.51-4.03 (m, 4H), 3.92 (s, 1H), 3.27-3.18 (m, 2H), 3.17-3.12 (m, 1H), 2.81-2.74 (m, 1H), 2.08 (s, 3H), 1.88-1.79 (m, 1H), 1.76-1.67 (m, 1H), 1.60-1.54 (m, 1H), 1.39-1.33 (m, 1H). | I-B31 I-C8 |

-continued
| Compounds | Structural formula | LC-MS $[M + H]^+$ | $^1$HNMR | Interme-diates |
| --- | --- | --- | --- | --- |
| 90 | 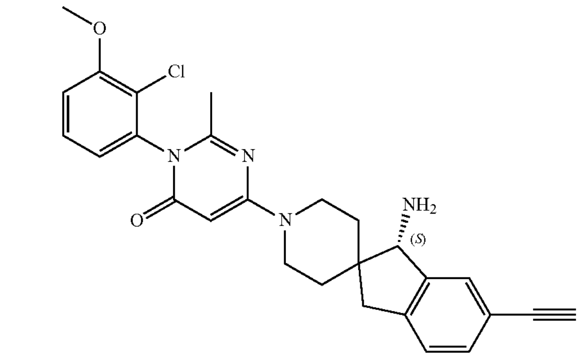 | 475.2 | $^1$H NMR (400 MHz, $CD_3OD$): δ 7.50-7.40 (m, 2H), 7.32-7.17 (m, 3H), 6.96 (d, J = 7.8 Hz, 1H), 5.48 (s, IH), 4.42-4.15 (m, 2H), 3.99-3.90 (m, 4H), 3.40 (s, 1H), 3.28-3.13 (m, 3H), 2.81-2.72 (m, 1H), 2.04 (s, 3H), 1.90-1.64 (m, 2H), 1.59-1.55 (m, 1H), 1.37-1.33 (m, 1H). | I-B34 I-C3 |
| 92 | 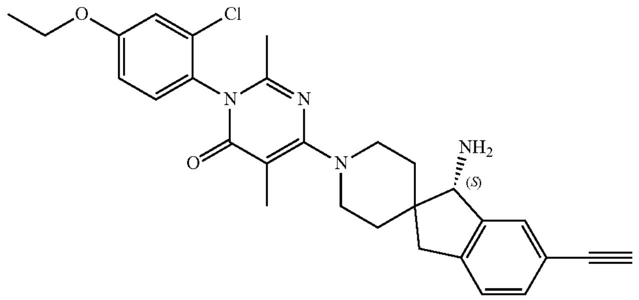 | 503.2 | $^1$H NMR (400 MHz, $CD_3OD$): δ 7.48 (s, 1H), 7.30 (d, J = 7.7 Hz, 1H), 7.25-7.14 (m, 3H), 7.03-6.99 (m, 1H), 4.09 (q, J = 6.9 Hz, 2H), 3.96-3.80 (m, 3H), 3.40 (s, 1H), 3.26-3.12 (m, 3H), 2.79-2.75 (m, 1H), 2.06-1.81 (m, 8H), 1.58-1.54 (m, 1H), 1.42-1.32 (m, 4H). | I-B35 I-C3 |
| 93 | 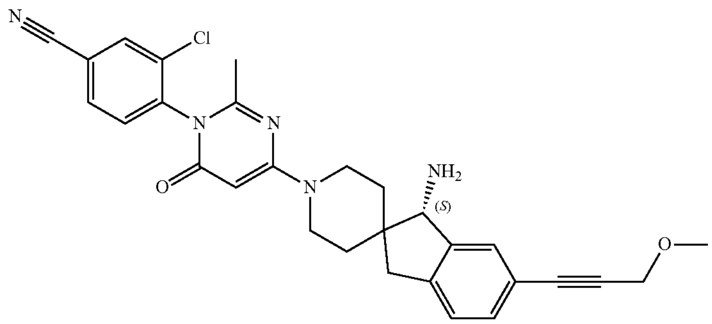 | 514.2 | $^1$H NMR (400 MHz, $CD_3OD$): δ 8.14-8.05 (m, 1H), 7.91-7.83 (m, 1H), 7.67-7.60 (m, 1H), 7.44 (s, 1H), 7.31-7.25 (m, 1H), 7.23-7.17 (m, 1H), 5.48 (s, 1H), 4.56-3.97 (m, 4H), 3.92 (s, 1H), 3.41 (s, 3H), 3.28-3.10 (m, 3H), 2.86-2.70 (m, 1H), 2.06 (s, 3H), 1.89-1.79 (m, 1H), 1.78-1.66 (m, 1H), 1.62-1.55 (m, 1H), 1.39-1.33 (m, 1H). | I-B36 I-C7 |

-continued
| Compounds | Structural formula | LC-MS $[M + H]^+$ | $^1$HNMR | Interme-diates |
|---|---|---|---|---|
| 94 | 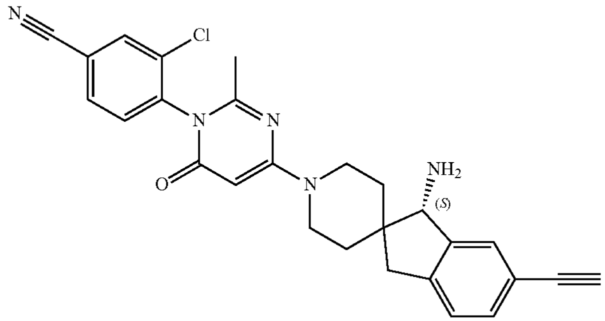 | 470.2 | $^1$H NMR (400 MHz, $CD_3OD$): δ 8.15-8.08 (m, 1H), 7.92-7.85 (m, 1H), 7.69-7.59 (m, 2H), 7.51-7.43 (m, 1H), 7.38-7.30 (m, 1H), 5.51 (s, 1H), 4.63-3.99 (m, 3H), 3.53 (s, 1H), 3.24-3.04 (m, 2H), 2.98 (s, 1H), 2.85 (s, 1H), 2.07 (s, 3H), 1.90-1.71 (m, 2H), 1.71-1.52 (m, 2H). | I-B36 I-C3 |
| 96 | 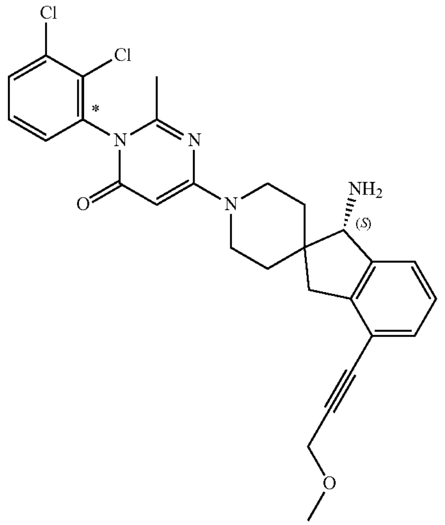 | 523.2 | $^1$H NMR (400 MHz, $CD_3OD$): δ 7.74-7.67 (m, 1H), 7.51-7.46 (m, 1H), 7.41-7.34 (m, 2H), 7.31-7.25 (m, 1H), 7.24-7.17 (m, 1H), 5.49 (s, 1H), 4.49-4.06 (m, 4H), 3.97 (s, 1H), 3.43 (s, 3H), 3.28-3.16 (m, 3H), 2.88-2.80 (m, 1H), 2.06 (s, 3H), 1.86-1.71 (m, 2H), 1.61-1.55 (m, 1H), 1.43-1.36 (m, 1H). | I-B1 I-C13 |

-continued
| Compounds | Structural formula | LC-MS $[M + H]^+$ | $^1$HNMR | Interme-diates |
|---|---|---|---|---|
| 99 | 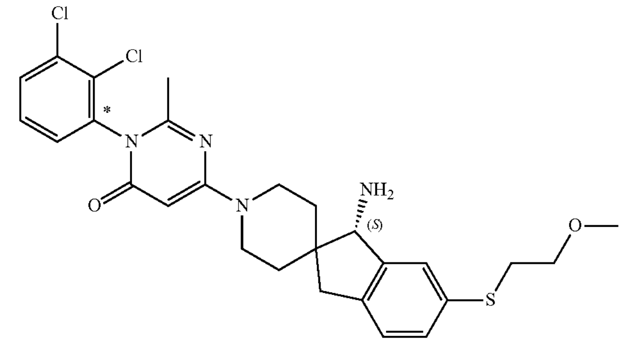 | 545.2 | $^1$H NMR (400 MHz, $CD_3OD$): δ 7.78-7.65 (m, 1H), 7.48 (t, J = 8.1 Hz, 1H), 7.43-7.35 (m, 2H), 7.22 (d, J = 7.9 Hz, 1H), 7.16 (d, J = 7.8 Hz, 1H), 5.48 (s, 1H), 4.48-4.05 (m, 2H), 3.91 (s, 1H), 3.61-3.50 (m, 2H); 3.31 (s, 3H), 3.26-3.17 (m, 2H), 3.15-3.03 (m, 3H), 2.74 (d, J = 15.8 Hz, 1H), 2.06 (s, 3H), 1.84 (t, J = 10.4 Hz, 1H), 1.72 (t, J = 10.5 Hz, 1H), 1.58 (d, J = 13.3 Hz, 1H), 1.37 (d, J = 13.5 Hz, 1H). | I-B1 I-C14 |
| 101 | 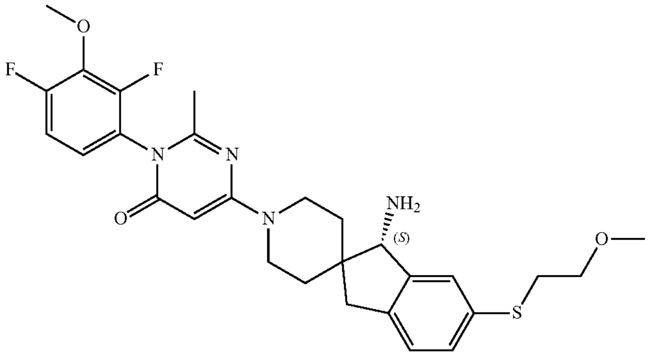 | 543.4 | $^1$H NMR (400 MHz, $CD_3OD$): 7.41 (s, 1H), 7.25-7.20 (m, 1H), 7.20-7.11 (m, 2H), 7.12-7.02 (m, 1H), 5.47 (s, 1H), 4.52-4.06 (m, 2H), 4.01 (s, 3H), 3.91 (s, 1H), 3.58-3.49 (m, 2H), 3.31 (s, 3H), 3.27-3.17 (m, 2H), 3.14-3.03 (m, 3H), 2.77-2.71 (m, 1H), 2.12 (s, 3H), 1.89-1.77 (m, 1H), 1.77-1.64 (m, 1H), 1.62-1.52 (m, 1H), 1.41-1.32 (m, 1H). | I-B33 I-C14 |

-continued
| Compounds | Structural formula | LC-MS $[M + H]^+$ | $^1$HNMR | Interme-diates |
| --- | --- | --- | --- | --- |
| 104 | 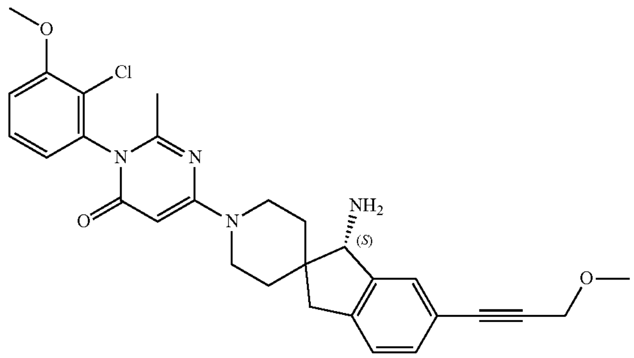 | 519.2 | $^1$H NMR (400 MHz, $CD_3OD$): δ 7.48-7.40 (m, 2H), 7.30-7.18 (m, 3H), 6.98-6.94 (m, 1H), 5.48 (s, 1H), 4.40-4.20 (m, 4H), 3.98-3.90 (m, 4H), 3.41 (s, 3H), 3.27-3.09 (m, 3H), 2.82-2.72 (m, 1H), 2.05 (s, 3H), 1.90-1.64 (m, 2H), 1.60-1.56 (m, 1H), 1.38-1.34 (m, 1H). | I-B34 I-C7 |
| 106 | 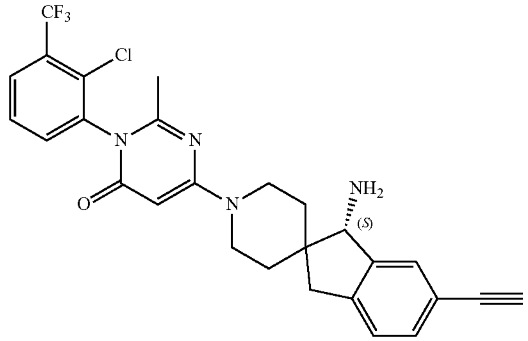 | 513.2 | $^1$H NMR (400 MHz, $CD_3OD$): δ 8.04-7.96 (m, 1H), 7.80-7.69 (m, 2H), 7.52 (s, 1H), 7.35 (d, J = 7.6 Hz, 1H), 7.24 (d, J = 7.6 Hz, 1H), 5.54 (s, 1H), 4.33 (s, 2H), 3.97 (s, 1H), 3.44 (s, 1H), 3.32-3.16 (m, 3H), 2.87-2.79 (m, 1H), 2.10 (s, 3H), 1.95-1.71 (m, 2H), 1.63 (d, J = 13.6 Hz, 1H), 1.41 (d, J = 13.6 Hz, 1H). | I-B37 I-C3 |
| 107 | 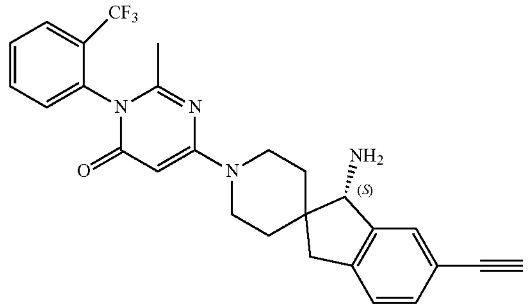 | 479.2 | $^1$H NMR (400 MHz, $CD_3OD$): δ 7.99-7.91 (m, 1H), 7.91-7.81 (m, 1H), 7.80-7.72 (m, 1H), 7.55-7.45 (m, 2H), 7.35 (d, J = 7.5 Hz, 1H), 7.24 (d, J = 7.5 Hz, 1H), 5.51 (s, 1H), 4.32 (s, 2H), 3.97 (s, 1H), 3.34 (s, 1H), 3.31-3.11 (m, 3H), 2.87-2.75 (m, 1H), 2.08 (s, 3H), 1.95-1.71 (m, 2H), 1.63 (d, J = 12.9 Hz, 1H), 1.40 (d, J = 12.9 Hz, 1H). | I-B38 I-C3 |

-continued
| Compounds | Structural formula | LC-MS $[M+H]^+$ | $^1$HNMR | Interme-diates |
| --- | --- | --- | --- | --- |
| 115 | 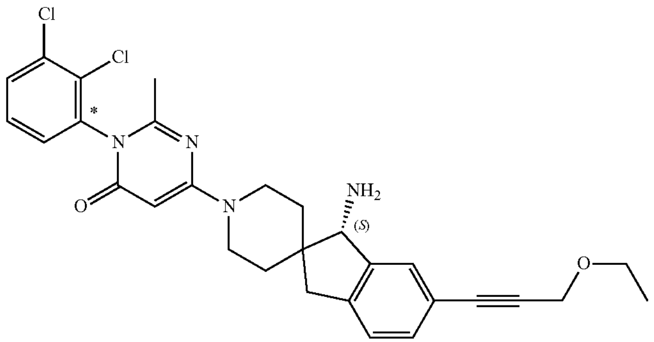 | 537.2 | $^1$H NMR (400 MHz, $CD_3OD$): δ 7.74-7.66 (m, 1H), 7.52-7.42 (m, 2H), 7.40-7.35 (m, 1H), 7.34-7.25 (m, 1H), 7.21-7.12 (m, 1H), 5.48 (s, 1H), 4.49-4.70 (m, 4H), 3.91 (s, 1H), 3.71-3.53 (m, 2H), 3.26-3.10 (m, 3H), 2.82-2.71 (m, 1H), 2.06 (s, 3H), 1.87-1.79 (m, 1H), 1.75-1.66 (m, 1H), 1.60-1.53 (m, 1H), 1.38-1.32 (m, 1H), 1.26-1.16 (m, 3H). | I-B1 I-C15 |
| 121 | 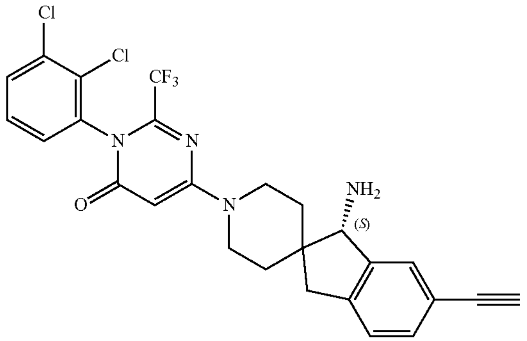 | 533.1 | $^1$H NMR (400 MHz, $CD_3OD$): δ 7.77-7.70 (m, 1H), 7.51-7.41 (m, 3H), 7.31 (d, J = 7.5 Hz, 1H), 7.20 (d, J = 7.8 Hz, 1H), 5.67 (s, 1H), 4.76-4.04 (m, 2H), 3.94 (s, 1H), 3.40 (s, 1H), 3.37-3.31 (m, 2H), 3.18 (d, J = 16.1 Hz, 1H), 2.80 (d, J = 16.2 Hz, 1H), 1.95-1.83 (m, 1H), 1.81-1.69 (mz, 1H), 1.67-1.58 (m, 1H), 1.44-1.34 ( m, 1H). | I-B39 I-C3 |
| 127 | 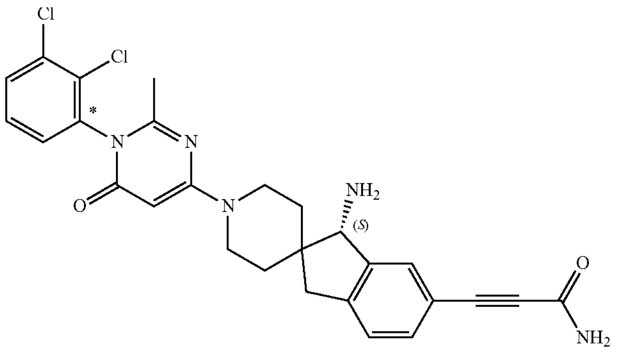 | 522.1 | $^1$H NMR (400 MHz, $CD_3OD$): δ 7.73-7.69 (m, 1H), 7.58-7.55 (m, 1H), 7.51-7.46 (m, 1H), 7.45-7.41 (m, 1H), 7.40-7.37 (m, 1H), 7.30-7.26 (m, 1H), 5.49 (s, 1H), 4.28 (br, 2H), 3.95 (s, 1H), 3.29-3.16 (m, 3H), 2.85-2.78 (m, 1H), 2.07 (s, 3H), 1.90-1.81 (m, 1H), 1.78-1.68 (m, 1H), 1.63-1.56 (m, 1H), 1.38-1.32 (m, 1H). | I-B1 I-C16 |

-continued
| Compounds | Structural formula | LC-MS $[M + H]^+$ | $^1$HNMR | Interme-diates |
|---|---|---|---|---|
| 130 | 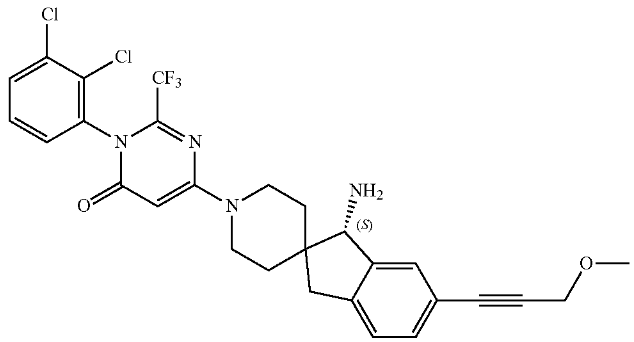 | 577.2 | $^1$H NMR (400 MHz, $CD_3OD$): δ 7.76-7.71 (m, 1H), 7.49-7.44 (m, 3H), 7.30-7.19 (m, 2H), 5.67 (s, 1H), 4.51-4.02 (m, 4H), 3.94 (s, 1H), 3.41 (s, 3H), 3.37-3.30 (m, 2H), 3.18 (d, J = 16.1 Hz, 1H), 2.79 (d, J = 16.1 Hz, 1H), 1.95-1.82 (m, 1H), 1.81-1.69 (m, 1H), 1.63 (d, J = 13.7 Hz, 1H), 1.39 (d, J = 13.5 Hz, 1H). | I-B39<br>I-C7 |
| 133 | 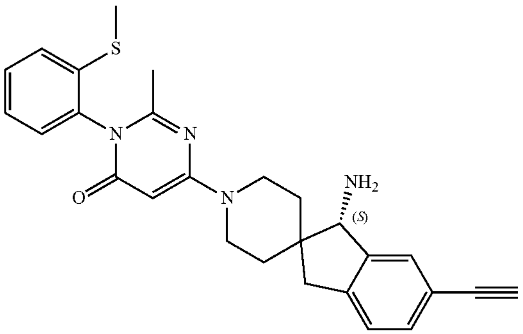 | 457.2 | $^1$H NMR (400 MHz, $CD_3OD$) δ 7.52-7.41 (m, 3H), 7.35-7.27 (m, 2H), 7.22-7.15 (m, 2H), 5.48 (s, 1H), 4.39-4.11 (m, 2H), 3.91 (s, 1H), 3.40 (s, 1H), 3.26-3.10 (m, 3H), 2.80-2.70 (m, 1H), 2.45 (s, 3H), 2.03 (s, 3H), 1.88-1.79 (m, 1H), 1.76-1.67 (m, 1H), 1.60-1.53 (m, 1H), 1.38-1.32 (m, 1H). | I-B40<br>I-C3 |

-continued
| Compounds | Structural formula | LC-MS $[M + H]^+$ | $^1$HNMR | Interme-diates |
|---|---|---|---|---|
| 135 | 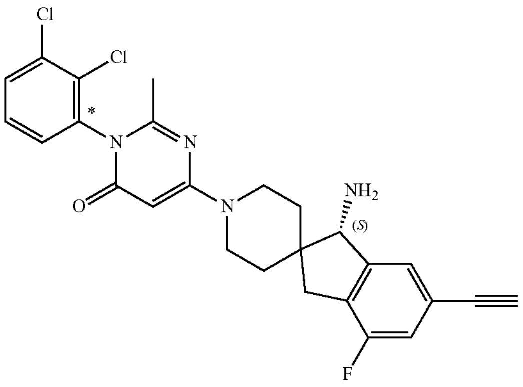 | 497.2 | $^1$H NMR (400 MHz, $CD_3OD$): δ 7.71 (d, J = 8.4 Hz, 1H), 7.49 (t, J = 7.7 Hz, 1H), 7.39 (d, J = 7.3 Hz, 1H), 7.32 (s, 1H), 7.04 (d, J = 8.9 Hz, 1H), 5.49 (s, 1H), 4.53-4.07 (m, 2H), 3.95 (s, 1H), 3.51 (s, 1H), 3.27-3.16 (m, 3H), 2.78 (d, J = 16.0 Hz, 1H), 2.07 (s, 3H), 1.91-1.70 (m, 2H), 1.61 (d, J = 13.0 Hz, 1H), 1.37 (d, J = 12.8 Hz, 1H). | I-B1<br>I-C19 |
| 157 | 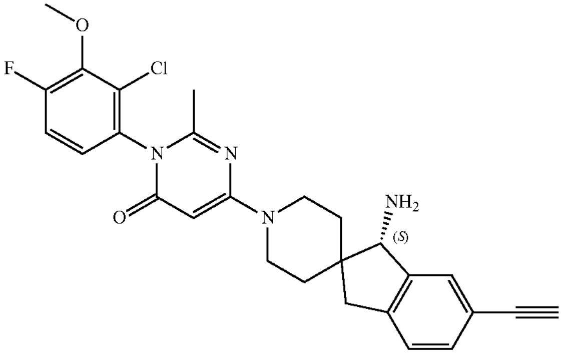 | 493.2 | $^1$H NMR (400 MHz, $CD_3OD$): δ 7.51-7.44 (m, 1H), 7.36-7.28 (m, 2H), 7.22-7.14 (m, 2H), 5.48 (s, 1H), 4.28 (br, 2H), 4.00 (d, J = 1.1 Hz, 3H), 3.94 (s, 1H), 3.40 (s, 1H), 3.26-3.14 (m, 3H), 2.84 -.74 (m, 1H), 2.06 (S, 3H), 1.89-1.79 (m, 1H), 1.77-1.67 (m, 1H), 1.62-1.55 (m, 1H), 1.40-1.34 (m, 1H). | I-B41<br>I-C2 |

-continued
| Compounds | Structural formula | LC-MS $[M + H]^+$ | $^1$HNMR | Interme-diates |
|---|---|---|---|---|
| 158 | 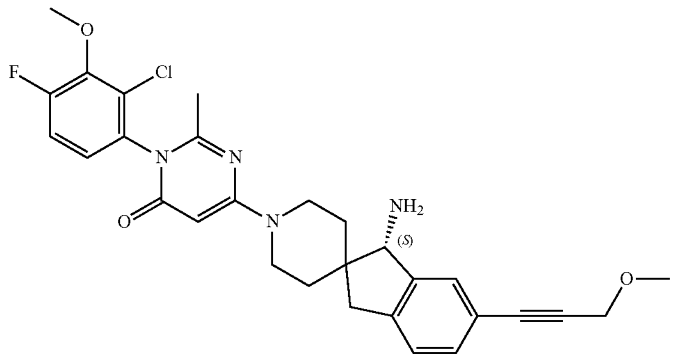 | 537.2 | $^1$H NMR (400 MHz, $CD_3OD$): δ 7.49-7.41 (m, 1H), 7.35-7.27 (m, 2H), 7.23-7.14 (m, 2H), 5.53-5.44 (m, 1H), 4.40-4.15 (m, 4H), 4.00 (s, 3H), 3.95 (s, 1H), 3.41 (s, 3H), 3.26-3.13 (m, 3H), 2.85-2.76 (m, 1H), 2.06 (s, 3H), 1.88-1.79 (m, 1H), 1.77-1.68 (m, 1H), 1.62-1.55 (m, 1H), 1.41-1.34 (m, 1H). | I-B41 I-C7 |
| 160 | 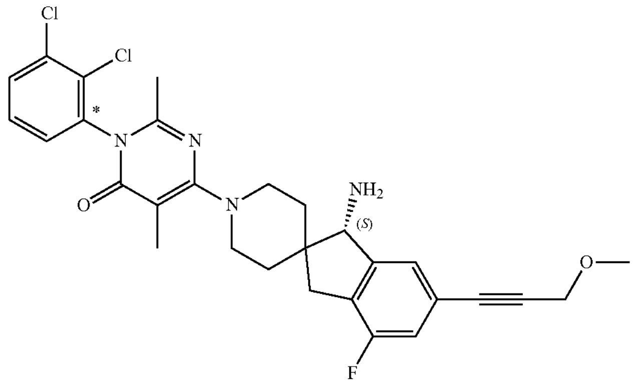 | 555.2 | $^1$H NMR (400 MHz, $CD_3OD$): δ 7.73-7.69 (m, 1H), 7.51-7.47 (m, 1H), 7.39-7.35 (m, 1H), 7.29 (s, 1H), 7.04-7.00 (m, 1H), 4.30 (s, 2H), 4.00-3.86 (m, 3H), 3.41 (s, 3H), 3.27-3.12 (m, 3H), 2.78-2.74 (m, 1H), 2.08-1.82 (m, 8H), 1.60-1.58 (m, 1H), 1.38-1.36 (m, 1H). | I-B22 I-C18 |

-continued
| Compounds | Structural formula | LC-MS $[M + H]^+$ | $^1$HNMR | Interme-diates |
| --- | --- | --- | --- | --- |
| 165 | 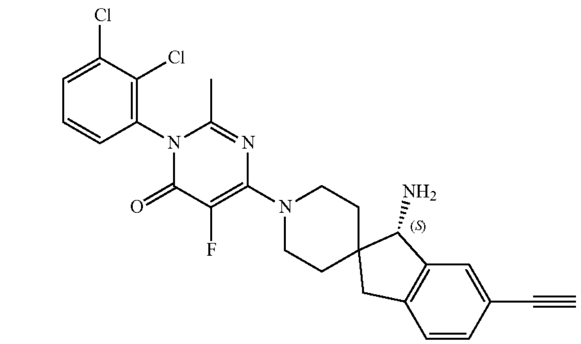 | 497.1 | $^1$H NMR (400 MHz, $CD_3OD$): δ 7.75 (dd, J = 8.1, 1.2 Hz, 1H), 7.54-7.41 (m, 3H), 7.31 (d, J = 7.9 Hz, 1H), 7.20 (d, J = 7.7 Hz, 1H), 4.50-4.41 (m, 2H), 3.92 (s, 1H), 3.43-3.35 (m, 3H), 3.18 (d, J = 16.0 Hz, 1H), 2.79 (d, J = 16.2 Hz, 1H), 2.04 (s, 3H), 1.96-1.73 (m, 2H), 1.60 (d, J = 13.5 Hz, 1H), 1.36 (d, J = 13.4 Hz, 1H). | I-B42<br>I-C3 |
| 166 | 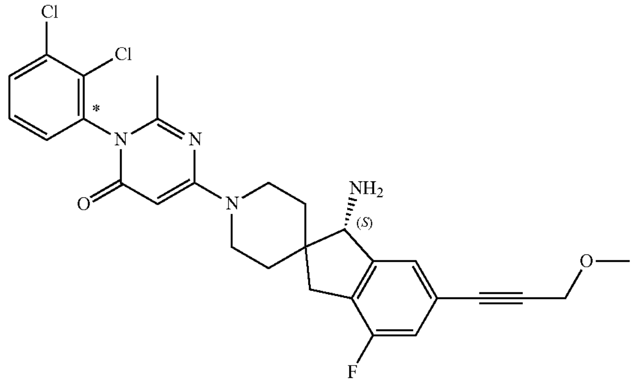 | 541.2 | $^1$H NMR (400 MHz, $CD_3OD$): δ 7.71 (dd, J = 8.2, 1.4 Hz, 1H), 7.49 (t, J = 8.0 Hz, 1H), 7.39 (dd, J = 7.9, 1.4 Hz, 1H), 7.29 (s, 1H), 7.02 (d, J = 9.3 Hz, 1H), 5.49 (s, 1H), 4.51-4.14 (m, 4H), 3.95 (s, 1H), 3.41 (s, 3H), 3.27-3.15 (m, 3H), 2.78 (d, J = 16.4 Hz, 1H), 2.07 (s, 3H), 1.90-1.70 (m, 2H), 1.61 (d, J = 13.0 Hz, 1H), 1.37 (d, J = 12.8 Hz, 1H). | I-B1<br>I-C18 |

-continued
| Compounds | Structural formula | LC-MS $[M + H]^+$ | $^1$HNMR | Interme-diates |
|---|---|---|---|---|
| 167 | 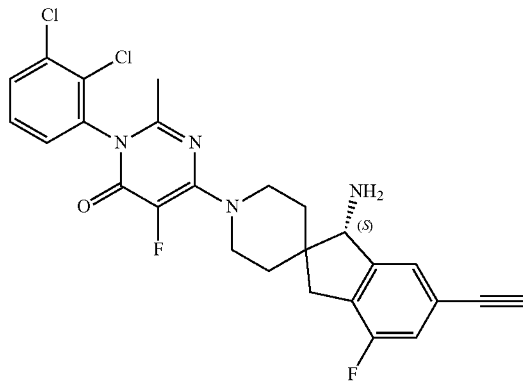 | 515.1 | $^1$H NMR (400 MHz, $CD_3OD$): δ 7.75 (dd, J = 8.1, 1.5 Hz, 1H), 7.51 (t, J = 8.0 Hz, 1H), 7.43 (dd, J = 8.0, 1.5 Hz, 1H), 7.32 (s, 1H), 7.04 (d, J = 9.3 Hz, 1H), 4.51-4.39 (m, 2H), 3.95 (s, 1H), 3.51 (s, 1H), 3.44-3.33 (dd, m, 2H), 3.22 (d, J = 16.3 Hz, 1H), 2.79 (d, J = 16.2 Hz, 1H), 2.04 (s, 3H), 1.95-1.77 (m, 2H), 1.62 (d, J = 13.4 Hz, 1H), 1.37 (d, J = 13.1 Hz, 1H). | I-B42 I-C19 |
| 168 | 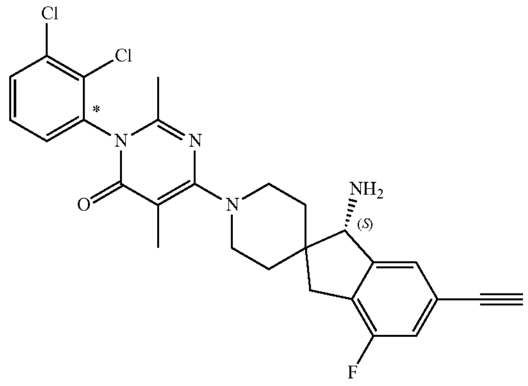 | 511.2 | $^1$H NMR (400 MHz, $CD_3OD$): δ 7.75-7.68 (m, 1H), 7.52-7.46 (m, 1H), 7.41-7.35 (m, 1H), 7.32 (s, 1H), 7.08-7.00 (m, 1H), 4.01-3.86 (m, 3H), 3.52 (s, 1H), 3.28-3.15 (m, 3H), 2.82-2.70 (m, 1H), 2.06 (s, 3H), 2.01 (s, 3H), 1.97-1.89 (m, 1H), 1.89-1.80 (m, 1H), 1.63-1.56 (m, 1H), 1.40-1.34 (m, 1H). | I-B22 I-C19 |

-continued
| Compounds | Structural formula | LC-MS $[M + H]^+$ | $^1$HNMR | Interme-diates |
|---|---|---|---|---|
| 169 | 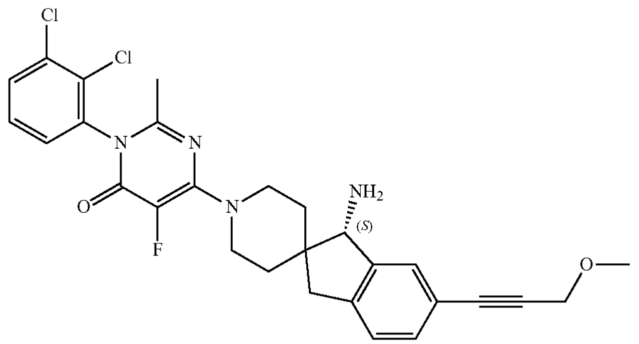 | 541.2 | $^1$H NMR (400 MHz, $CD_3OD$): δ 7.74 (dd, J = 8.1, 1.4 Hz, 1H), 7.51 (t, J = 8.0 Hz, 1H), 7.46-7.41 (m, 2H), 7.28 (d, J = 8.8 Hz, 1H), 7.20 (d, J = 7.7 Hz, 1H), 4.50-4.39 (m, 2H), 4.30 (s, 2H), 3.92 (s, 1H), 3.41 (s, 3H), 3.39-3.32 (m, 2H), 3.18 (d, J = 16.1 Hz, 1H), 2.79 (d, J = 16.1 Hz, 1H), 2.04 (s, 3H), 1.96-1.75 (m, 2H), 1.59 (d, J = 13.9 Hz, 1H), 1.36 (d, J = 12.5 Hz, 1H). | I-B42 I-C7 |
| 170 | 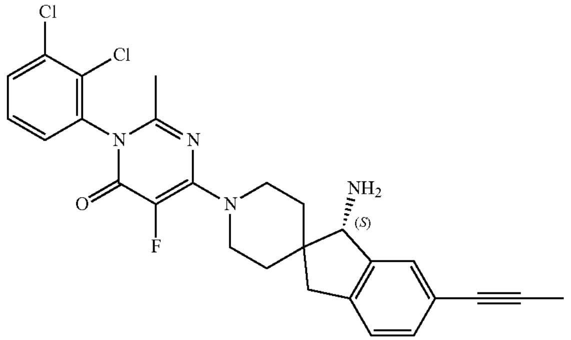 | 511.1 | $^1$H NMR (400 MHz, $CD_3OD$): δ 7.74 (dd, J = 8.1, 1.5 Hz, 1H), 7.51 (t, J = 8.0 Hz, 1H), 7.43 (dd, J = 7.9, 1.5 Hz, 1H), 7.36 (s, 1H), 7.21-7.11 (m, 2H), 4.49-4.39 (m, 2H), 3.90 (s, 1H), 3.42-3.34 (m, 2H), 3.15 (d, J = 15.9 Hz, 1H), 2.77 (d, J = 15.8 Hz, 1H), 2.04 (s, 3H), 1.99 (s, 3H), 1.93-1.75 (m, 2H), 1.58 (d, J = 14.1 Hz, 1H), 1.37 (d, J = 13.0 Hz, 1H). | I-B42 I-C17 |
| 173 | 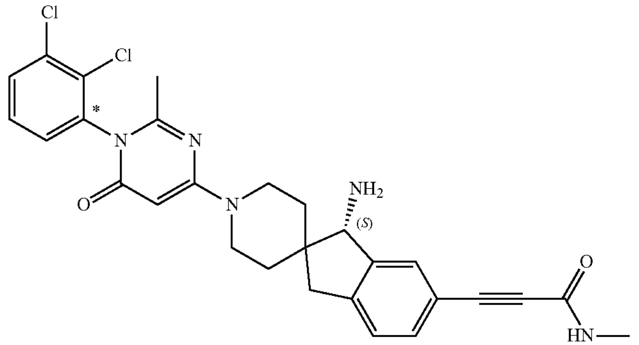 | 536.2 | $^1$H NMR (400 MHz, DMSO-$d_6$): δ 8.66 (s, 1H), 7.79 (s, 1H), 7.59-7.43 (m, 3H), 7.40-7.32 (m, 1H), 7.30-7.23 (m, 1H), 5.40 (s, 1H), 4.16 (s, 1H), 3.84 (s, 1H), 3.17-3.02 (m, 4H), 2.69-2.63 (m, 3H), 1.98 (s, 1H), 1.91-1.69 (m, 3H), 1.63-1.48 (m, 2H), 1.23 (s, 3H), 1.08-0.96 (m, 1H). | I-B1 I-C20 |

-continued
| Compounds | Structural formula | LC-MS $[M + H]^+$ | $^1$HNMR | Interme-diates |
|---|---|---|---|---|
| 174 | 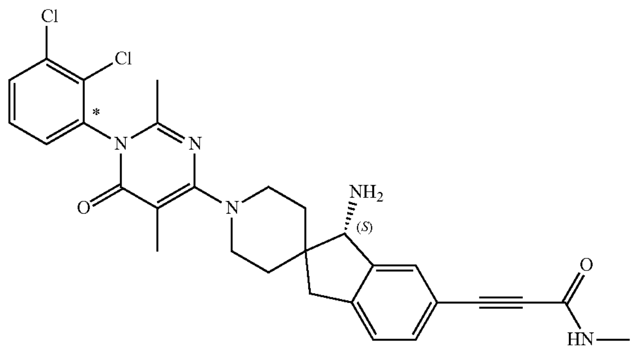 | 550.2 | $^1$H NMR (400 MHz, $CD_3OD$): δ 7.74-7.70 (m, 1H), 7.57 (s, 1H), 7.52-7.47 (m, 1H), 7.43-7.40 (m, 1H), 7.39-7.36 (m, 1H), 7.30-7.27 (m, 1H), 4.00-3.88 (m, 3H), 3.27-3.16 (m, 3H), 2.84-2.75 (m, 4H), 2.07 (s, 3H), 2.01 (s, 3H), 1.99-1.89 (m, 1H), 1.87-1.79 (m, 1H), 1.62-1.56 (m, 1H), 1.38-1.34 (m, 1H). | I-B22 I-C20 |
| 183 | 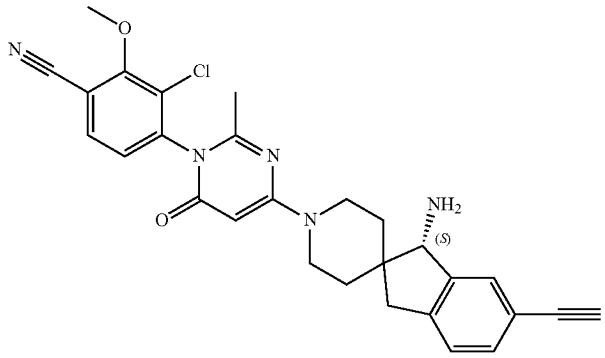 | 500.2 | $^1$H NMR (400 MHz, $CD_3OD$): δ 7.85-7.79 (m, 1H), 7.48 (s, 1H), 7.40-7.34 (m, 1H), 7.33-7.28 (m, 1H), 7.23-7.18 (m, 1H), 5.49 (s, 1H), 4.55-4.14 (m, 2H), 4.11 (s, 3H), 3.92 (s, 1H), 3.42 (s, 1H), 3.29-3.12 (m, 3H), 2.84-2.72 (m, 1H), 2.08 (s, 3H), 1.88-1.78 (m, 1H), 1.77-1.66 (m, 1H), 1.63-1.53 (m, 1H), 1.40-1.32 (m, 1H). | I-B43 I-C3 by-product |

-continued
| Compounds | Structural formula | LC-MS $[M + H]^+$ | $^1$HNMR | Interme-diates |
|---|---|---|---|---|
| 184 | 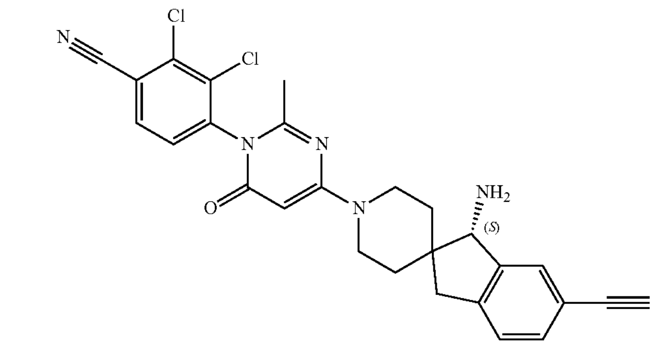 | 504.2 | $^1$H NMR (400 MHz, $CD_3OD$): δ 8.01-7.95 (m, 1H), 7.66-7.61 (m, 1H), 7.48 (s, 1H), 7.34-7.29 (m, 1H), 7.24-7.17 (m, 1H), 5.49 (s, 1H), 4.53-4.06 (m, 2H), 3.93 (s, 1H), 3.41 (s, 1H), 3.29-3.11 (m, 3H), 2.84-2.73 (m, 1H), 2.09 (s, 3H), 1.90-1.79 (m, 1H), 1.78-1.67 (m, 1H), 1.64-1.55 (m, 1H), 1.40-1.34 (m, 1H). | I-B44 I-C3 |
| 185 | 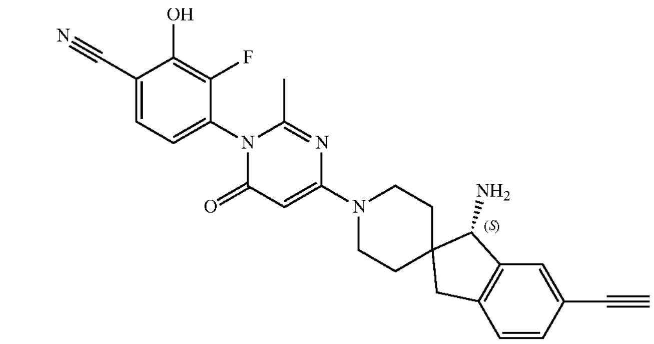 | 470.2 | $^1$H NMR (400 MHz, $CD_3OD$): δ 7.48 (s, 1H), 7.35-7.27 (m, 1H), 7.24-7.18 (m, 1H), 7.17-7.11 (m, 1H), 6.22-6.12 (m, 1H), 5.46 (s, 1H), 4.43-4.06 (m, 2H), 3.93 (s, 1H), 3.40 (s, 1H), 3.28-3.11 (m, 3H), 2.84-2.72 (m, 1H), 2.16 (s, 3H), 1.88-1.78 (m, 1H), 1.76-1.66 (m, 1H), 1.62-1.51 (m, 1H), 1.40-1.33 (m, 1H). | I-B45 I-C3 by-product |
| 186 | 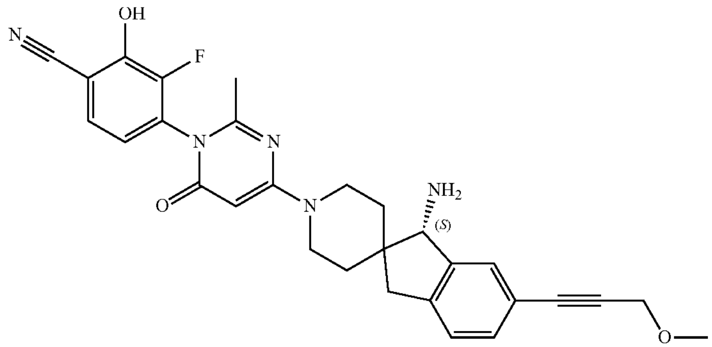 | 514.2 | $^1$H NMR (400 MHz, $CD_3OD$): δ 7.45 (s, 1H), 7.31-7.26 (m, 1H), 7.24-7.18 (m, 1H), 7.17-7.11 (m, 1H), 6.21-6.12 (m, 1H), 5.46 (s, 1H), 4.44-4.07 (m, 4H), 3.93 (s, 1H), 3.42 (s, 3H), 3.27-3.12 (m, 3H), 2.83-2.74 (m, 1H), 2.16 (s, 3H), 1.88-1.78 (m, 1H), 1.77-1.66 (m, 1H), 1.61-1.53 (m, 1H), 1.39-1.33 (m, 1H). | I-B45 I-C7 by-product |

-continued
| Compounds | Structural formula | LC-MS $[M + H]^+$ | $^1$HNMR | Interme-diates |
|---|---|---|---|---|
| 194 | 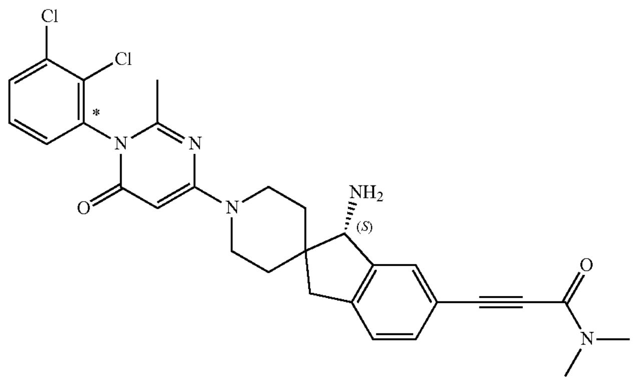 | 550.2 | $^1$H NMR (400 MHz, $CD_3OD$): δ 7.73-7.71 (m, 1H), 7.60 (s, 1H), 7.50-7.45 (m, 2H), 7.40-7.38 (m, 1H), 7.32-7.30 (m, 1H), 5.49 (s, 1H), 4.28 (br, 2H), 3.97 (s, 1H), 3.33 (s, 3H), 3.26-3.20 (m, 3H), 3.01 (s, 3H), 2.84-2.82 (m, 1H), 2.07 (s, 3H), 1.91-1.68 (m, 2H), 1.65-1.55 (m, 1H), 1.41-1.31 (m, 1H), | I-B1<br>I-C21 |
| 195 | 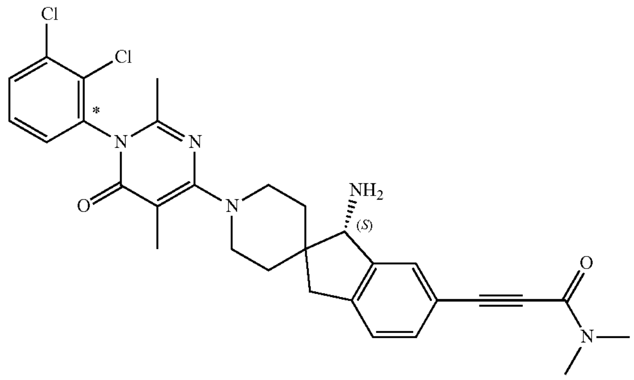 | 564.2 | $^1$H NMR (400 MHz, $CD_3OD$): δ 7.74-7.70 (m, 1H), 7.60 (s, 1H), 7.53-7.43 (m, 2H), 7.40-7.36 (m, 1H), 7.32-7.28 (m, 1H), 4.01-3.86 (m, 3H), 3.33 (s, 3H), 3.27-3.18 (m, 3H), 3.02 (s, 3H), 2.85-2.81 (m, 1H), 2.10-1.85 (m, 8H), 1.61-1.57 (m, 1H), 1.38-1.34 (m, 1H). | I-B22<br>I-C21 |

-continued
| Compounds | Structural formula | LC-MS [M + H]$^+$ | $^1$HNMR | Interme-diates |
| --- | --- | --- | --- | --- |
| 197 | 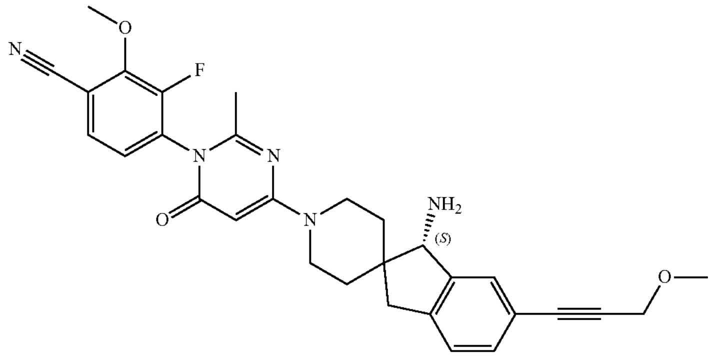 | 528.2 | $^1$H NMR (400 MHz, $CD_3OD$): δ 7.64-7.61 (m, 1H), 7.45 (s, 1H), 7.30-7.27 (m, 1H), 7.24-7.20 (m, 2H), 5.48 (s, 1H), 4.43-4.19 (m, 4H), 4.18-4.17 (m, 3H), 3.93 (s, 1H), 3.43-3.40 (m, 3H), 3.28-3.20 (m, 2H), 3.19-3.14 (m, 1H), 2.81-2.76 (m, 1H), 2.23-2.06 (m, 3H), 1.88-1.80 (m, 1H), 1.76-1.69 (m, 1H), 1.61-1.55 (m, 1H), 1.39-1.34 (m, 1H). | I-B45 I-C7 |
| 198 | 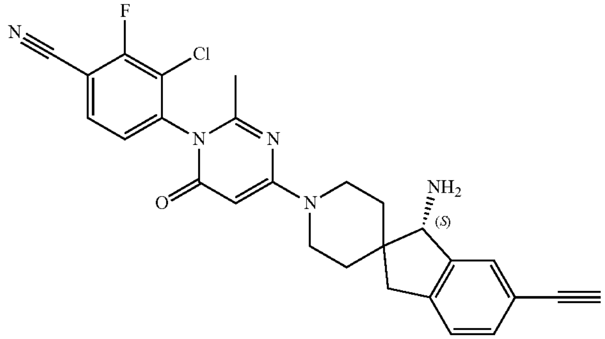 | 488.2 | $^1$H NMR (400 MHz, $CD_3OD$): δ 7.96-7.89 (m, 1H), 7.55-7.45 (m, 2H), 7.34-7.29 (m, 1H), 7.24-7.18 (m, 1H), 5.49 (s, 1H), 4.54-3.97 (m, 2H), 3.93 (s, 1H), 3.41 (s, 1H), 3.30-3.11 (m, 3H), 2.85-2.71 (m, 1H), 2.10 (s, 3H), 1.89-1.80 (m, 1H), 1.78-1.68 (m, 1H), 1.63-1.55 (m, 1H), 1.42-1.33 (m, 1H). | I-B43 I-C22 |
| 202 | 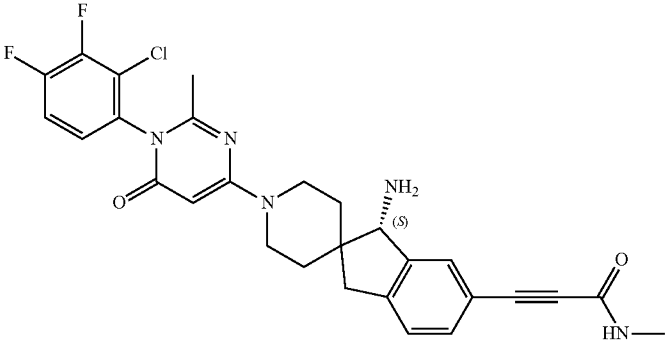 | 538.2 | $^1$H NMR (400 MHz, $CD_3OD$): δ 7.56-7.53 (m, 1H), 7.49-7.42 (m, 1H), 7.42-7.38 (m, 1H), 7.33-7.28 (m, 1H), 7.28-7.25 (m, 1H), 5.47 (s, 1H), 4.27 (br, 2H), 3.94 (s, 1H), 3.26-3.15 (m, 3H), 2.84-2.76 (m, 4H), 2.07 (s, 3H), 1.88-1.79 (m, 1H), 1.77-1.67 (m, 1H), 1.61-1.55 (m, 1H), 1.37-1.31 (m, 1H). | I-B32 I-C20 |

-continued
| Compounds | Structural formula | LC-MS $[M + H]^+$ | $^1$HNMR | Interme-diates |
|---|---|---|---|---|
| 206 | 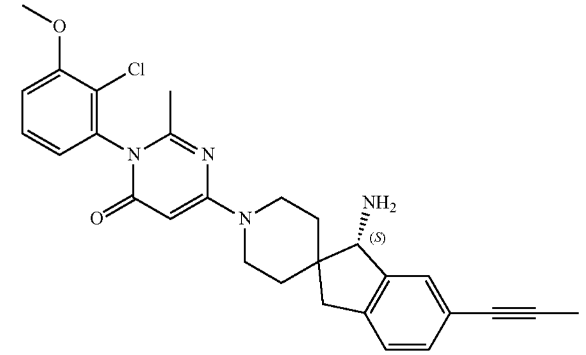 | 489.2 | $^1$H NMR (400 MHz, $CD_3OD$): δ 7.45-7.39 (m, 2H), 7.28-7.16 (m, 3H), 6.95 (d, J = 7.8 Hz, 1H), 5.47 (s, 1H), 4.26 (br, 2H), 4.04 (s, 1H), 3.94 (s, 3H), 3.27-3.10 (m, 3H), 2.89-2.85 (m, 1H), 2.06-1.98 (m, 6H), 1.83-1.69 (m, 2H), 1.61-1.41 (m, 2H). | I-B34 I-C17 |
| 211 | 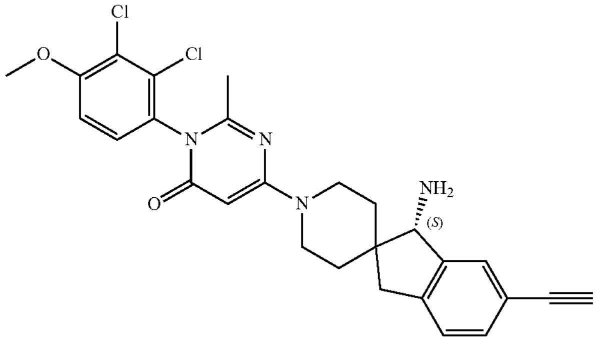 | 509.1 | $^1$H NMR (400 MHz, $CD_3OD$): δ 7.49-7.45 (m, 1H), 7.33-7.29 (m, 2H), 7.22-7.18 (m, 2H), 5.47 (s, 1H), 4.27 (br, 2H), 3.97 (s, 3H), 3.93 (s, 1H), 3.39 (s, 1H), 3.27-3.12 (m, 3H), 2.83-2.75 (m, 1H), 2.05 (s, 3H), 1.87-1.78 (m, 1H), 1.76-1.68 (m, 1H), 1.60-1.55 (m, 1H), 1.39-1.34 (m, 1H). | I-B46 I-C3 |

-continued
| Compounds | Structural formula | LC-MS $[M + H]^+$ | $^1$HNMR | Interme-diates |
|---|---|---|---|---|
| 212 | 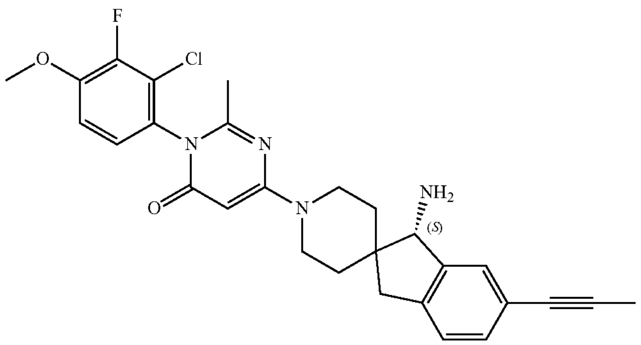 | 493.2 | $_1$H NMR (400 MHz, $CD_3OD$): δ 7.49-7.45 (s, 1H), 7.32-7.28 (m, 1H), 7.24-7.15 (m, 3H), 5.47 (s, 1H), 4.26 (br, 2H), 3.95 (s, 3H), 3.93 (s, 1H), 3.39 (s, 1H), 3.25-3.13 (m, 3H), 2.82-2.75 (m, 1H), 2.06 (s, 3H), 1.87-1.78 (m, 1H), 1.76-1.67 (m, 1H), 1.60-1.54 (m, 1H), 1.39-1.34 (m, 1H). | I-B47 I-C3 |
| 214 | 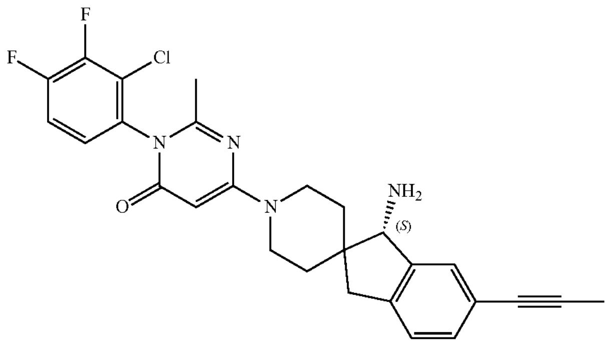 | 495.2 | $^1$H NMR (400 MHz, $CD_3OD$): δ 7.49-7.42 (m, 1H), 7.37-7.33 (m, 1H), 7.33-7.28 (m, 1H), 7.20-7.11 (m, 2H), 5.47 (s, 1H), 4.26 (br, 2H), 3.89 (s, 1H), 3.27-3.17 (m, 2H), 3.15-3.09 (m, 1H), 2.79-2.72 (m, 1H), 2.07 (s, 3H), 1.98 (s, 3H), 1.86-1.77 (m, 1H), 1.76-1.65 (m, 1H), 1.60-1.53 (m, 1H), 1.40-1.33 (m, 1H). | I-B32 I-C17 |

-continued
| Compounds | Structural formula | LC-MS $[M+H]^+$ | $^1$HNMR | Interme-diates |
|---|---|---|---|---|
| 228 | 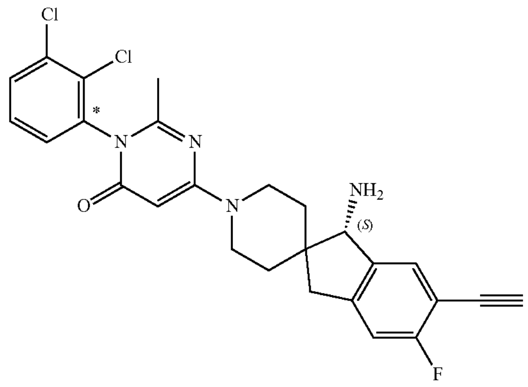 | 497.1 | $^1$H NMR (400 MHz, $CD_3OD$): δ 7.72-7.68 (m, 1H), 7.50-7.43 (m, 2H), 7.39-7.35 (m, 1H), 7.00 (d, J = 9.3 Hz, 1H), 5.47 (s, 1H), 4.25 (br, 2H), 3.88 (s, 1H), 3.66 (s, 1H), 3.25-3.10 (m, 3H), 2.79-2.77 (m, 1H), 2.05 (s, 3H), 1.85-1.67 (m, 2H), 1.58-1.54 (m, 1H), 1.38-1.34 (m, 1H). | I-B1<br>I-C26 |
| 245 | 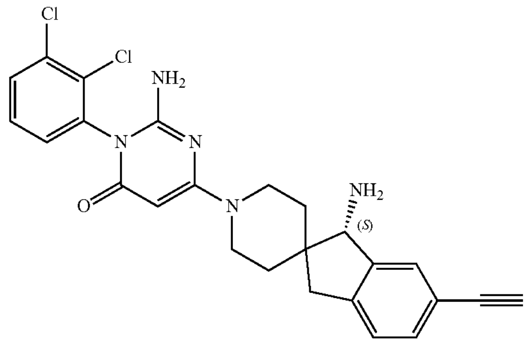 | 480.1 | $^1$H NMR (400 MHz, $CD_3OD$): δ 7.75-7.68 (m, 1H), 7.55-7.45 (m, 2H), 7.38-7.31 (m, 2H), 7.27-7.21 (m, 1H), 5.20 (s, 1H), 4.28 (s, 2H), 3.96 (s, 1H), 3.44 (s, 1H), 3.28-3.15 (m, 3H), 2.86-2.77 (m, 1H), 1.91-1.69 (m, 2H), 1.62-1.54 (m, 1H), 1.41-1.36 (m, 1H). | I-B48<br>I-C3 |

The optically pure diastereomers in the table are subjected to chiral HPLC under the following conditions (flow rate: 15 mL/minute; detector: UV 254 nm):

| Compounds | Column | Mobile phase | RT/minute | de % |
|---|---|---|---|---|
| 20 | IG (2 × 25 cm) | Acetonitrile/ | 26.084 | 100% |
| 24 | | ethanol = 10/90 | 17.095 | 100% |
| 11 | IG (2 × 25 cm) | Acetonitrile/ | 16.291 | 100% |
| 28 | | ethanol = 10/90 | 14.413 | 100% |
| 12 | IG (2 × 25 cm) | Acetonitrile/ | 16.514 | 100% |
| 64 | | ethanol = 10/90 | 11.431 | 100% |
| 48 | IG (2 × 25 cm) | Acetonitrile/ | 5.640 | 100% |

-continued

| Compounds | Column | Mobile phase | RT/minute | de % |
|---|---|---|---|---|
| 49 | | ethanol = 10/90 | 6.740 | 100% |
| 50 | IG (2 × 25 cm) | Acetonitrile/ | 8.240 | 100% |
| 51 | | ethanol = 10/90 | 10.836 | 100% |

Compound 81

(S)-6-(1-amino-6-(oxetan-3-ylthio)-1,3-dihydrospiro[indene-2,4'-piperidin]-1'-yl)-3-(2,3-dichlorophenyl)-2-methylpyrimidin-4(3H)-one

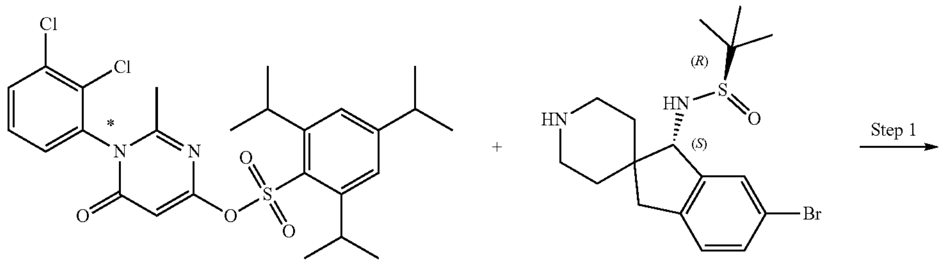

I-B1 I-C4

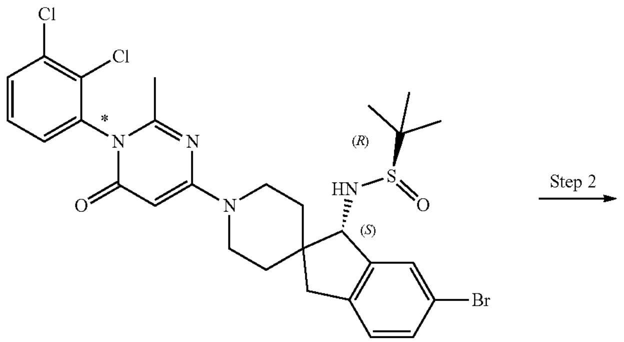

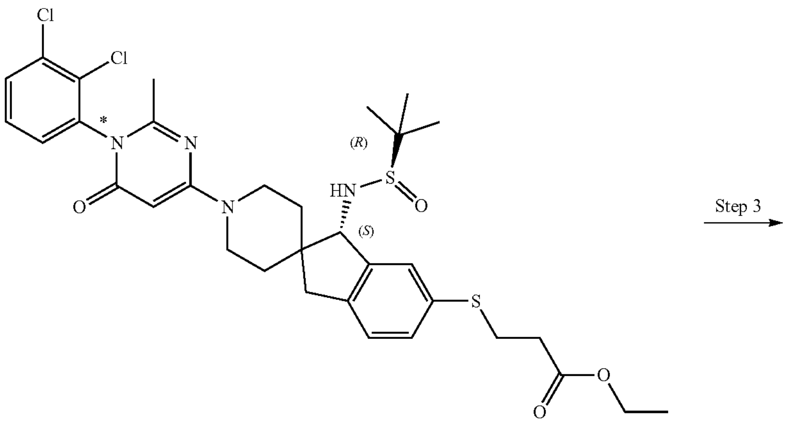

-continued

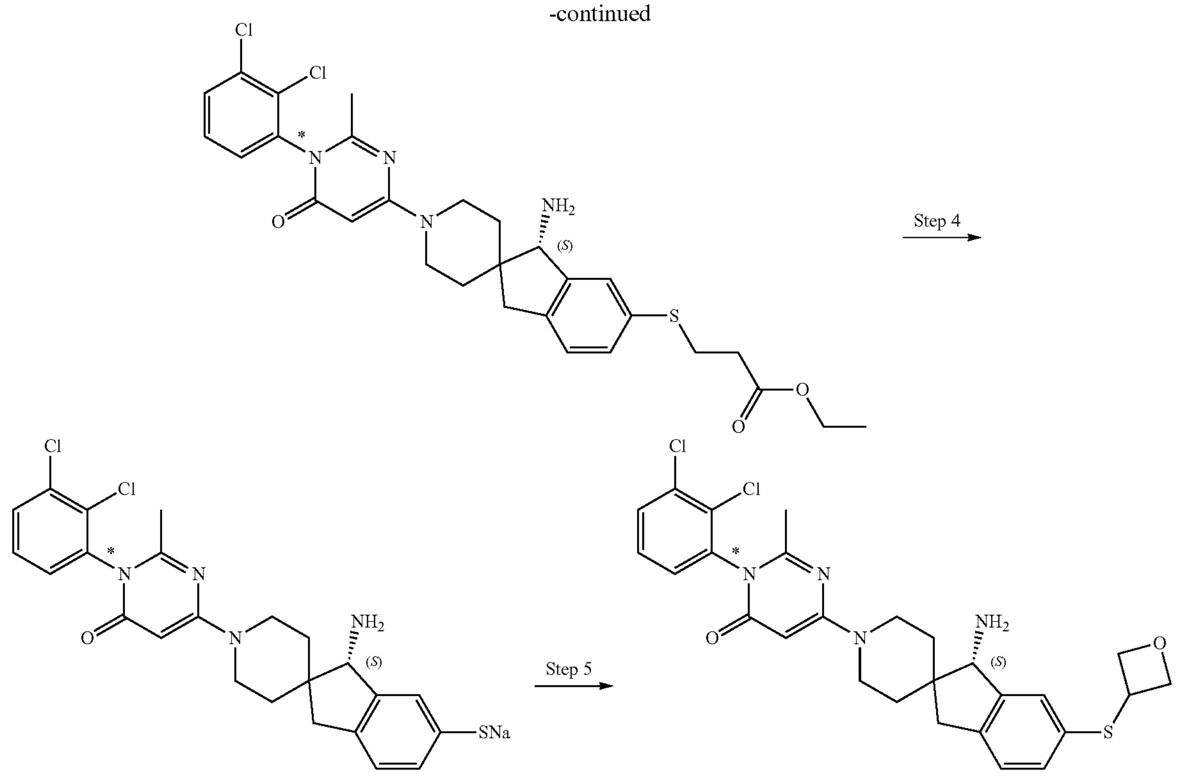

81

Step 1: (R)—N—((S)-5-bromo-1'-(1-(2,3-dichlorophenyl)-2-methyl-6-oxo-1,6-dihydropyrimidin-4-yl)-1,3-dihydrospiro[indene-2,4'-piperidin]-3-yl)-2-methylpropane-2-sulfinamde The target product was prepared by following the step 1 for preparing compound 12 from corresponding starting materials and reagents. $[M+H]^+$ 639.1

Step 2: Ethyl 3-(((S)-1-(((R)-tert-butylsulfinyl)amino)-1'-(1-(2,3-dichlorophenyl)-2-methyl-6-oxo-1,6-dihydropyrimidin-4-yl)-1,3-dihydrospiro[indene-2,4'-piperidin]-6-yl)thio)propanoate The target product was prepared by following the step 1 for preparing intermediate I-A1 from corresponding starting materials and reagents. $[M+H]^+$ 691.1

Step 3: Ethyl (S)-3-((1-amino-1'-(1-(2,3-dichlorophenyl)-2-methyl-6-oxo-1,6-dihydropyrimidin-4-yl)-1,3-dihydrospiro[indene-2,4'-piperidin]-6-yl)thio)propanoate The target product was prepared by following the step 2 for preparing compound 12 from corresponding starting materials and reagents. $[M+H]^+$ 587.2

Step 4: Sodium (S)-1-amino-1'-(1-(2,3-dichlorophenyl)-2-methyl-6-oxo-1,6-dihydropyrimidin-4-yl)-1,3-dihydrospiro[indene-2,4'-piperidine]-6-thiolate The target product was prepared by following the step 2 for preparing intermediate I-A1 from corresponding starting materials and reagents.

Step 5: (S)-6-(1-amino-6-(oxetan-3-ylthio)-1,3-dihydrospiro[indene-2,4'-piperidin]-1'-yl)-3-(2,3-dichlorophenyl)-2-methylpyrimidin-4(3H)-one Sodium (S)-1-amino-1'-(1-(2,3-dichlorophenyl)-2-methyl-6-oxo-1,6-dihydropyrimidin-4-yl)-1,3-dihydrospiro[indene-2,4'-piperidine]-6-thiolate was dissolved in N,N-dimethylformamide (3 mL), and 3-bromooxetane (93 mg, 0.68 mmoL) was added thereto. The reaction was stirred at room temperature for 30 minutes, and water (10 mL) was added thereto. The mixture was extracted with dichloromethane. The organic phases were collected and combined, and concentrated in vacuum under reduced pressure, and the residue was purified with silica gel column chromatography (dichloromethane/methanol) to give the target product (13 mg, yield 7.0%). $[M+H]^+$ 543.2. $^1H$ NMR (400 MHz, $CD_3OD$): δ 7.71 (dd, J=8.1, 1.4 Hz, 1H), 7.48 (t, J=8.0 Hz, 1H), 7.38 (dd, J=7.9, 1.4 Hz, 1H), 7.29 (s, 1H), 7.21-7.10 (m, 2H), 5.48 (s, 1H), 5.04 (t, J=6.8 Hz, 2H), 4.58-4.47 (m, 3H), 4.44-4.10 (m, 2H), 3.91 (s, 1H), 3.25-3.20 (m, 2H), 3.13 (d, J=15.9 Hz, 1H), 2.75 (d, J=15.9 Hz, 1H), 2.06 (s, 3H), 1.90-1.79 (m, 1H), 1.77-1.67 (m, 1H), 1.62-1.54 (m, 1H), 1.39-1.32 (m, 1H).

The compounds in the table below were prepared by following the steps for preparing compound 81 from corresponding intermediates and reagents:

| Compounds | Structural formula | LC-MS $[M + H]^+$ | $^1$HNMR | Intermediates |
|---|---|---|---|---|
| 37 | 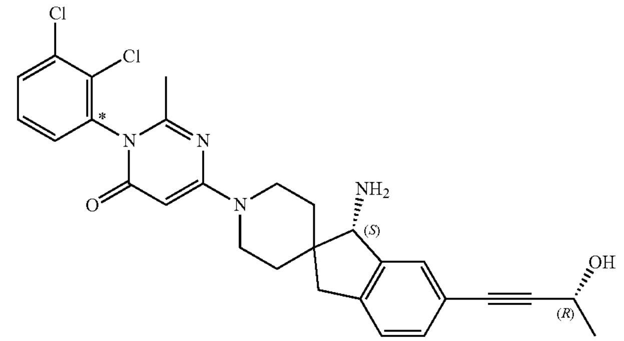 | 523.2 | $^1$H NMR (400 MHz, $CD_3OD$): δ 7.70 (dd, J = 8.1, 1.5 Hz, 1H), 7.48 (t, J = 8.0 Hz, 1H), 7.42-7.36 (m, 2H), 7.25 (d, J = 7.6 Hz, 1H), 7.18 (d, J = 7.7 Hz, 1H), 5.48 (s, 1H), 4.65 (q, J = 6.5 Hz, 1H), 4.44-4.10 (s, 2H), 3.91 (s, 1H), 3.25-3.24 (m, 1H), 3.23-3.21 (m, 1H), 3.17-3.12 (m, 1H), 2.80-2.74 (m, 1H), 2.06 (s, 3H), 1.86-1.68 (m, 2H), 1.61-1.53 (m, 1H), 1.45 (d, J = 6.6 Hz, 3H), 1.39-1.33 (m, 1H). | I-B1 I-C4 |
| 38 | 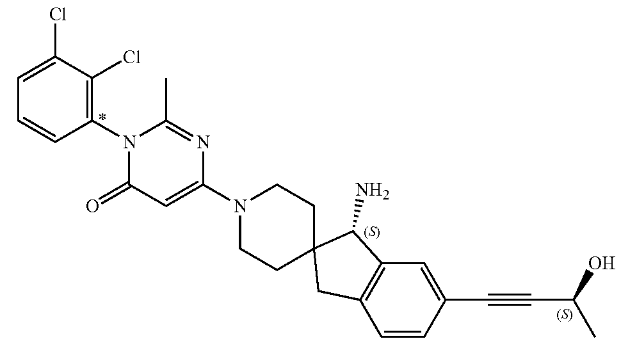 | 523.2 | $^1$H NMR (400 MHz, $CD_3OD$): δ 7.70 (dd, J = 8.1, 1.5 Hz, 1H), 7.48 (t, J = 8.0 Hz, 1H), 7.42-7.36 (m, 2H), 7.24 (dd, J = 7.7,1H), 7.18 (d, J = 7.8 Hz, 1H), 5.46 (d, J = 9.9 Hz, 1H), 4.65 (q, J = 6.6 Hz, 1H), 4.41-4.10 (m, 2H), 3.90 (s, 1H), 3.26-3.17 (m, 2H), 3.14 (d, J = 16.1 Hz, 1H), 2.76 (d, J = 16.0 Hz, 1H), 2.05 (s, 3H), 1.86-1.68 (m, 2H), 1.60-1.54 (m, 1H), 1.45 (dd, J = 6.6, 3H), 1.38-1.32 (m, 1H). | I-B1 I-C4 |
| 47 | 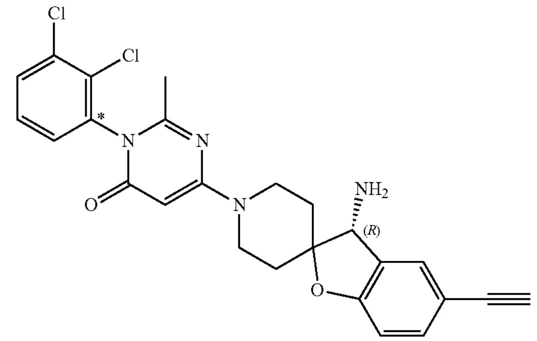 | 481.1 | $^1$H NMR (400 MHz, $CD_3OD$): δ 7.71 (dd, J = 8.1, 1.5 Hz, 1H), 7.53-7.43 (m, 2H), 7.39 (dd, J = 7.9, 1.5 Hz, 1H), 7.31 (dd, J = 8.3, 1.8 Hz, 1H), 6.76 (d, J = 8.3 Hz, 1H), 5.54 (s, 1H), 4.58-4.19 (m, 2H), 4.10 (s, 1H), 3.48-3.35 (m, 2H), 3.30 (s, 1H), 1.97-1.87 (m, 2H), 1.84-1.77 (m, 2H). | I-B1 I-C9 |
| 67 | 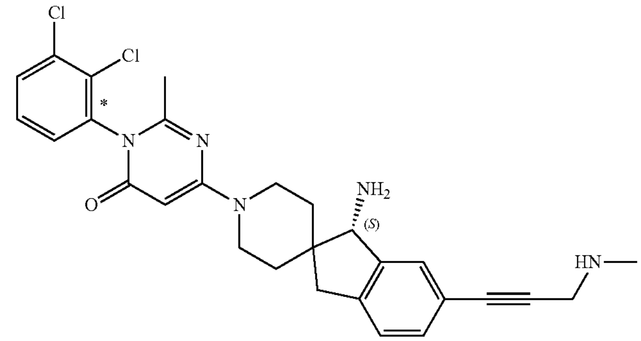 | 522.2 | $^1$H NMR (400 MHz, $CD_3OD$): δ 7.73-7.71 (m, 1H), 7.63 (s, 1H), 7.51-7.45 (m, 2H), 7.40-7.36 (m, 2H), 5.51 (s, 1H), 4.44-4.30 (m, 3H), 4.07 (s, 2H), 3.27-3.08 (m, 4H), 2.75 (s, 3H), 2.07 (s, 3H), 1.82-1.56 (m, 4H). | I-B1 I-C4 |

-continued

| Compounds | Structural formula | LC-MS [M + H]$^+$ | $^1$HNMR | Intermediates |
|---|---|---|---|---|
| 79 | 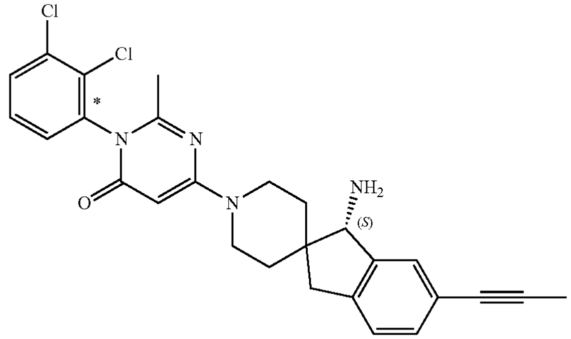 | 493.2 | $^1$H NMR (400 MHz, $CD_3OD$): δ 7.74-7.68 (m, 1H), 7.51-7.45 (m, 1H), 7.41-7.37 (m, 1H), 7.36 (s, 1H), 7.21-7.16 (m, 1H), 7.16-7.12 (m, 1H), 5.48 (s, 1H), 4.52-4.01 (m, 2H), 3.90 (s, 1H), 3.28-3.17 (m, 2H), 3.16-3.10 (m, 1H), 2.81-2.72 (m, 1H), 2.06 (s, 3H), 1.99 (s, 3H), 1.86-1.78 (m, 1H), 1.76-1.67 (m, 1H), 1.60-1.54 (m, 1H), 1.39-1.34 (m, 1H). | I-B1 I-C4 |
| 91 | 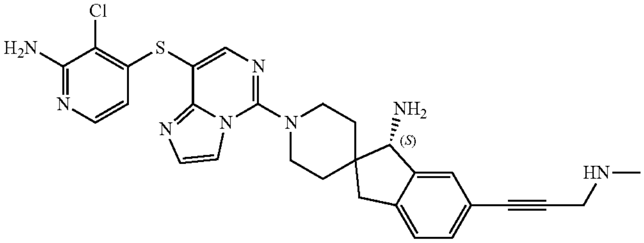 | 545,2 | $^1$H NMR (400 MHz, $CD_3OD$): δ 8.03 (s, 1H), 7.83 (d, J = 1.6 Hz, 1H), 7.54 (d, J = 1.6 Hz, 1H), 7.51-7.44 (m, 2H), 7.31-7.19 (m, 2H), 5.87 (d, J = 5.6 Hz, 1H), 4.06-3.95 (m, 3H), 3.61 (s, 2H), 3.45-3.31 (m, 3H), 3.22-3.15 (m, 1H), 2.49 (s, 3H), 2.14-1.96 (m, 2H), 1.72-1.68 (m, 1H), 1.52-1.48 (m, 1H). | I-A1 I-C4 |

Compound 87

(S)-(3-(1-amino-6-(3-methoxyprop-1-yn-1-yl)-1,3-dihydrospiro[indene-2,4'-piperidin]-1'-yl)-6-((2-aminopyrimidin-4-yl)thio)pyrazin-2-yl)methanol

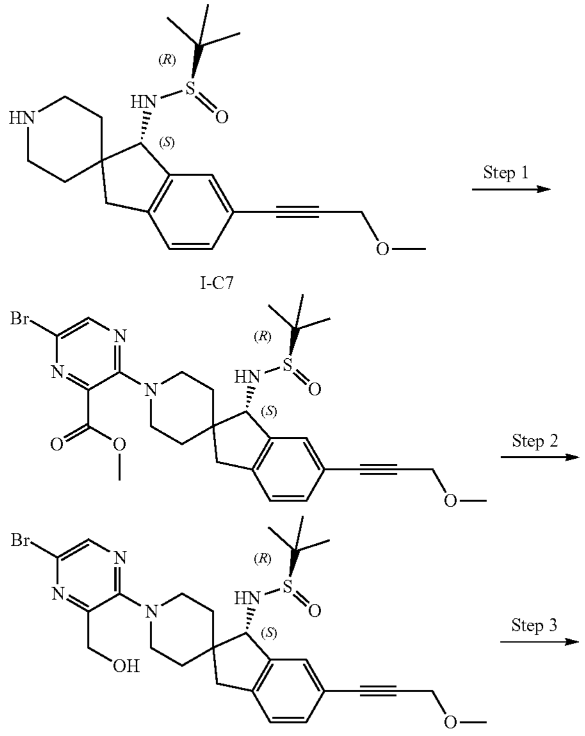

-continued

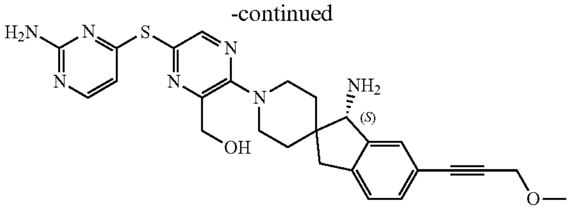

87

Step 1: Methyl 6-bromo-3-((S)-1-(((R)-tert-butylsulfinyl)amino)-6-(3-methoxyprop-1-yn-1-yl)-1,3-dihydrospiro[indene-2,4'-piperidin]-1'-yl)pyrazine-2-carboxylate The target product was prepared by following the step 1 for preparing compound 1 from corresponding starting materials and reagents. [M+H]$^+$ 589.1

Step 2: (R)—N—((S)-1'-(5-bromo-3-(hydroxymethyl)pyrazin-2-yl)-5-(3-methoxyprop-1-yn-1-yl)-1,3-dihydrospiro[indene-2,4'-piperidin]-3-yl)-2-methylpropane-2-sulfinamide Under nitrogen, at −78° C., to a solution of methyl 6-bromo-3-((S)-1-(((R)-tert-butylsulfinyl)amino)-6-(3-methoxyprop-1-yn-1-yl)-1,3-dihydrospiro[indene-2,4'-piperidin]-1'-yl)pyrazine-2-carboxylate (380 mg, 0.64 mmol) in anhydrous THF (15 mL) was added dropwise 1.0 M DIBAL-H solution (3.2 mL, 3.2 mmol). The reaction mixture was stirred at −78° C. for 2 hours, warmed to room temperature and stirred for 20 minutes. $Na_2SO_4\cdot 10H_2O$ and water (20 mL) were added thereto, and the mixture was filtered. The aqueous layer was extracted with dichloromethane. The organic phases were collected and combined, washed with saturated brine, dried over anhydrous $Na_2SO_4$, and concentrated in vacuum under reduced pressure. The residue was purified with silica gel column chromatography (water/methanol) to give the target product (186 mg, yield 52%). $[M+H]^+$ 561.2

Step 3: (S)-(3-(1-amino-6-(3-methoxyprop-1-yn-1-yl)-1,3-dihydrospiro[indene-2,4'-piperidin]-1'-yl)-6-((2-aminopyrimidin-4-yl)thio)pyrazin-2-yl)methanol The target product was prepared by following the steps 2-3 for preparing compound 1 from corresponding starting materials and reagents. $[M+H]^+$ 504.2. $^1H$ NMR (400 MHz, $CD_3OD$): δ 8.31 (s, 1H), 7.90 (d, J=5.5 Hz, 1H), 7.45 (s, 1H), 7.27 (d, J=7.7 Hz, 1H), 7.19 (d, J=7.8 Hz, 1H), 6.28 (d, J=5.5, 1H), 4.66 (s, 2H), 4.30 (s, 2H), 3.93 (s, 1H), 3.84-3.75 (m, 2H), 3.41 (s, 3H), 3.26-3.17 (m, 2H), 3.13 (d, J=16.0 Hz, 1H), 2.76 (d, J=16.1 Hz, 1H), 2.03-1.83 (m, 2H), 1.61 (d, J=12.2 Hz, 1H), 1.39 (d, J=12.6 Hz, 1H).

The compounds in the table below were prepared by following the steps for preparing compound 87 from corresponding intermediates and reagents:

| Compounds | Structural formula | LC-MS $[M + H]^+$ | $^1$HNMR | Intermediates |
|---|---|---|---|---|
| 116 | 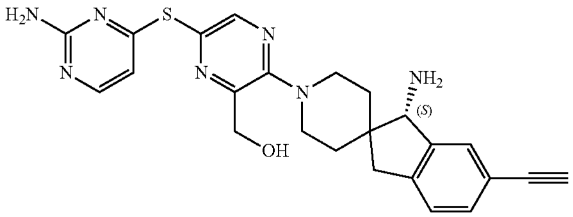 | 460.2 | $^1H$ NMR (400 MHz, $CD_3OD$): δ 8.31 (s, 1H), 7.90 (d, J = 5,5 Hz, 1H), 7.48 (s, 1H), 7.30 (d, J = 7.7 Hz, 1H), 7.19 (d, J = 7.7 Hz, 1H), 6.28 (d, J = 5.5 Hz, 1H), 4.66 (s, 2H), 3.93 (s, 1H), 3.85-3.76 (m, 2H), 3.39 (s, 1H), 3.26-3.18 (m, 2H), 3.14 (d, J = 16.1 Hz, 1H), 2.76 (d, J = 16.1 Hz, 1H), 2.03-1.94 (m, 1H), 1.93-1.82 (m, 1H), 1.61 (d, J = 12.6 Hz, 1H), 1.39 (d, J = 13.4 Hz, 1H). | I-A6<br>I-C3 |
| 122 | 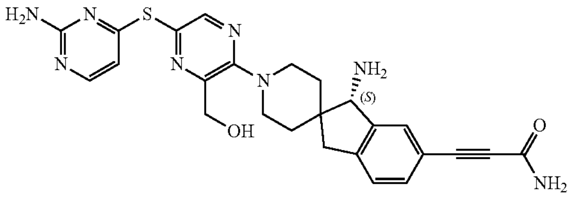 | 503.2 | $^1H$ NMR (400 MHz, $CD_3OD$): δ 8.33-8.29 (m, 1H), 7.91-7.89 (m, 1H), 7.59-7.55 (m, 1H), 7.44-7.40 (m, 1H), 7.29-7.26 (m, 1H), 6.29-6.27 (m, 1H), 4.67 (s, 2H), 3.96 (s, 1H), 3.81 (br, 2H), 3.25-3.15 (m, 3H), 2.84-2.75 (m, 1H), 2.03-1.98 (m, 1H), 1.94-1.84 (m, 1H), 1.65-1.59 (m, 1H), 1.41-1.35 (m, 1H). | I-A6<br>I-C16 |
| 123 | 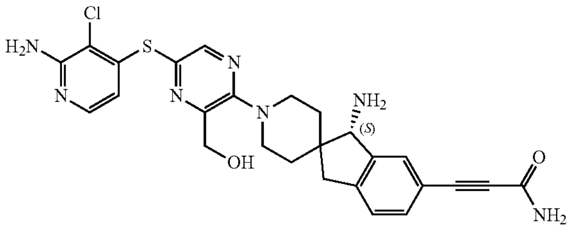 | 536.2 | $^1H$ NMR (400 MHz, $CD_3OD$): δ 8.28-8.27 (m, 1H), 7.61-7.59 (m, 1H), 7.58-7.56 (m, 1H), 7.44-7.40 (m, 1H), 7.29-7.26 (m, 1H), 6.05-6.02 (m, 1H), 4.67 (s, 2H), 3.97 (s, 1H), 3.84 (br, 2H), 3.26-3.15 (m, 3H), 2.83-2.77 (m, 1H), 2.04-1.97 (m, 1H), 1.92-1.84 (m, 1H), 1.65-1.59 (m, 1H), 1.41-1.35 (m, 1H). | I-A1<br>I-C16 |
| 199 | 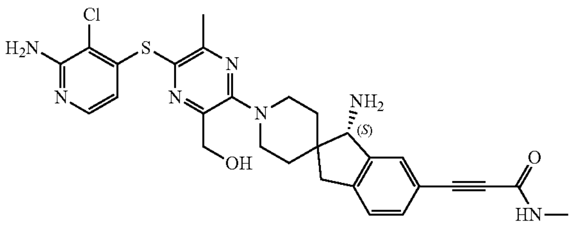 | 564.2 | $^1H$ NMR (400 MHz, $CD_3OD$): δ 7.62-7.54 (m, 2H), 7.41 (d, J = 7.7 Hz, 1H), 7.28 (d, J = 7.8 Hz, 1H), 5.88 (d, J = 5.6 Hz, 1H), 4.64 (s, 2H), 3.96 (s, 1H), 3.93-2.84 (m, 2H), 3.28-3.15 (m, 3H), 2.84-2.77 (m, 4H), 2.48 (s, 3H), 2.04-1.84 (m, 2H), 1.61 (d, J = 12.3 Hz, 1H), 1.38 (d, J = 12.9 Hz, 1H). | I-A1<br>I-C20 |

Compound 159
(S)-1-(3-(1-amino-1'-(6-amino-5-((2-amino-3-chloropyridin-4-yl)thio)pyrazin-2-yl)-1,3-dihydrospiro[indene-2,4'-piperidin]-6-yl)prop-2-yn-1-yl)urea
Step 1: N,N-bis(4-methoxybenzyl)prop-2-yn-1-amine
To the solution of propargylamine (550 mg, 10 mmol) in MeCN (30 mL) was added p-methoxybenzyl chloride (3.4 g,
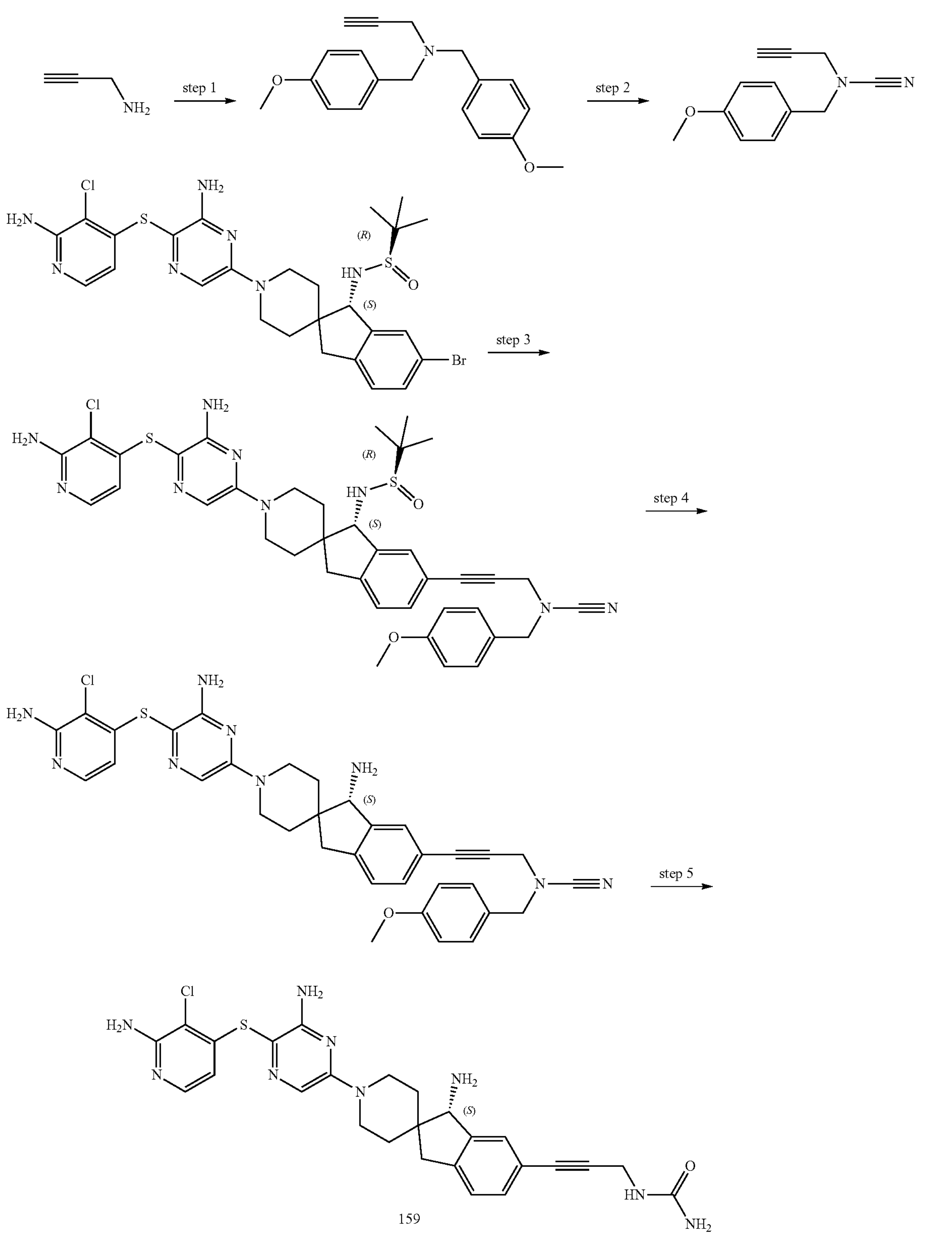
159

22 mmol) and $K_2CO_3$ (4.1 g, 30 mmol). The reaction solution was heated to 60° C. and stirred for 16 hours. After cooling to room temperature, added water (100 mL), extracted with EA (100 mL×2). The organic layer was collected, combined, and concentrated in vacuum under reduced pressure. The residue was purified by silica gel column chromatography (eluting with PE/EA) to give target product (2.1 g, 71% yield). $[M+H]^+$ 296.1

Step 2: N-(4-methoxybenzyl)-N-(prop-2-yn-1-yl) cyanamide

N,N-bis(4-methoxybenzyl)prop-2-yn-1-amine (2.1 g, 7.1 mmol), BrCN (1.5 g, 14.2 mmol) and $K_2CO_3$ (2.2 g, 16.3 mmol) were placed in 1,4-dioxane (70 mL), stirred at room temperature for 20 hours, added water (50 mL), extracted with EA (50 mL×2). The organic layer was collected, combined, and concentrated in vacuum under reduced pressure. The residue was purified by silica gel column chromatography (eluting with PE/EA) to give target product (750 mg, 50% yield). $[M+Na]^+$ 223.2

Step 3: (R)—N—((S)-1'-(6-amino-5-((2-amino-3-chloropyridin-4-yl)thio)pyrazin-2-yl)-5-(3-(N-(4-methoxybenzyl)cyanamido)prop-1-yn-1-yl)-1,3-dihydrospiro[indene-2,4'-piperidin]-3-yl)-2-methylpropane-2-sulfinamide Under $N_2$, (R)—N—((S)-1'-(6-amino-5-((2-amino-3-chloropyridin-4-yl)thio)pyrazin-2-yl)-5-bromo-1,3-dihydrospiro[indene-2,4'-piperidin]-3-yl)-2-methylpropane-2-sulfinamide (424 mg, 0.67 mmol; prepared by following the step 1 for preparing compound 1 from intermediates I-A2 and I-C4), N-(4-methoxybenzyl)-N-(prop-2-yn-1-yl)cyanamide (200 mg, 1 mmol), $Pd(PPh_3)_2Cl_2$ (94 mg, 0.13 mmol), CuI (25 mg, 0.13 mmol) and DIEA (1 mL) were placed in DMF (3 mL). The reaction solution was heated to 90° C. and stirred for 20 hours. The mixture was concentrated in vacuum under reduced pressure. The residue was purified by silica gel column chromatography (eluting with water/MeOH) to give target product (70 mg, 14% yield). $[M+H]^+$ 756.3

Step 4: (S)—N-(3-(1-amino-1'-(6-amino-5-((2-amino-3-chloropyridin-4-yl)thio)pyrazin-2-yl)-1,3-dihydrospiro[indene-2,4'-piperidin]-6-yl)prop-2-yn-1-yl)-N-(4-methoxybenzyl)cyanamide (R)—N—((S)-1'-(6-amino-5-((2-amino-3-chloropyridin-4-yl)thio)pyrazin-2-yl)-5-(3-(N-(4-methoxybenzyl)cyanamido)prop-1-yn-1-yl)-1,3-dihydrospiro[indene-2,4'-piperidin]-3-yl)-2-methylpropane-2-sulfinamide (70 mg, 0.09 mmol) was dissolved in 2 M HCl/MeOH solution (1 mL) and stirred at room temperature for 10 minutes. The mixture was adjusted to pH=9 with aqueous ammonia, added water (10 mL), extracted with DCM (10 mL×2). The organic layer was collected, combined, and concentrated in vacuum under reduced pressure to give target product (50 mg, 85% yield). $[M+H]^+$ 652.2

Step 5: (S)-1-(3-(1-amino-1'-(6-amino-5-((2-amino-3-chloropyridin-4-yl)thio)pyrazin-2-yl)-1,3-dihydrospiro[indene-2,4'-piperidin]-6-yl)prop-2-yn-1-yl) urea To (S)—N-(3-(1-amino-1'-(6-amino-5-((2-amino-3-chloropyridin-4-yl)thio)pyrazin-2-yl)-1,3-dihydrospiro[indene-2,4'-piperidin]-6-yl)prop-2-yn-1-yl)-N-(4-methoxybenzyl) cyanamide (50 mg, 0.07 mmol) was added TFA (2 mL) and stirred at 50° C. for 1 hour. After cooling to room temperature, the mixture was concentrated in vacuum under reduced pressure, added saturated $NaHCO_3$ aqueous solution (10 mL), extracted with DCM (10 mL×2). The organic layer was collected, combined, and concentrated in vacuum under reduced pressure. The residue was purified by thin layer chromatography (eluting with DCM/MeOH) to give target product (10 mg, 25% yield). $[M+H]^+$ 550.2. $^1H$ NMR (400 MHz, $CD_3OD$): δ 7.59-7.56 (m, 2H), 7.42 (s, 1H), 7.30-7.25 (m, 1H), 7.22-7.18 (m, 1H), 5.94-5.86 (m, 1H), 4.33-4.24 (m, 2H), 4.09 (s, 2H), 3.96 (s, 1H), 3.25-3.13 (m, 3H), 2.84-2.80 (m, 1H), 1.88-1.67 (m, 2H), 1.58-1.56 (m, 1H), 1.40-1.38 (m, 1H).

Compound 222

(S)-3-(1-amino-1'-(6-amino-5-((2-amino-3-chloropyridin-4-yl)thio)-3-chloropyrazin-2-yl)-1,3-dihydrospiro[indene-2,4'-piperidin]-6-yl)-N-methylpropiolamide

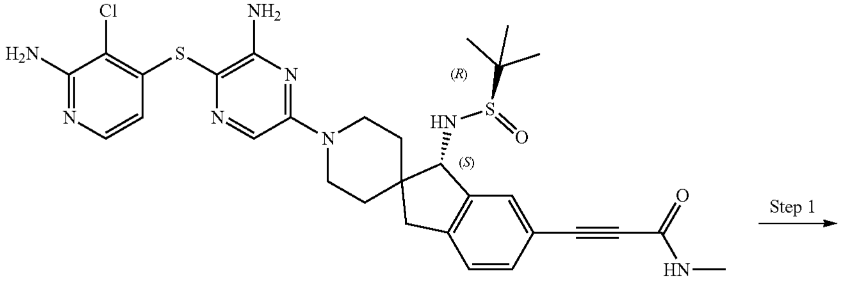

-continued

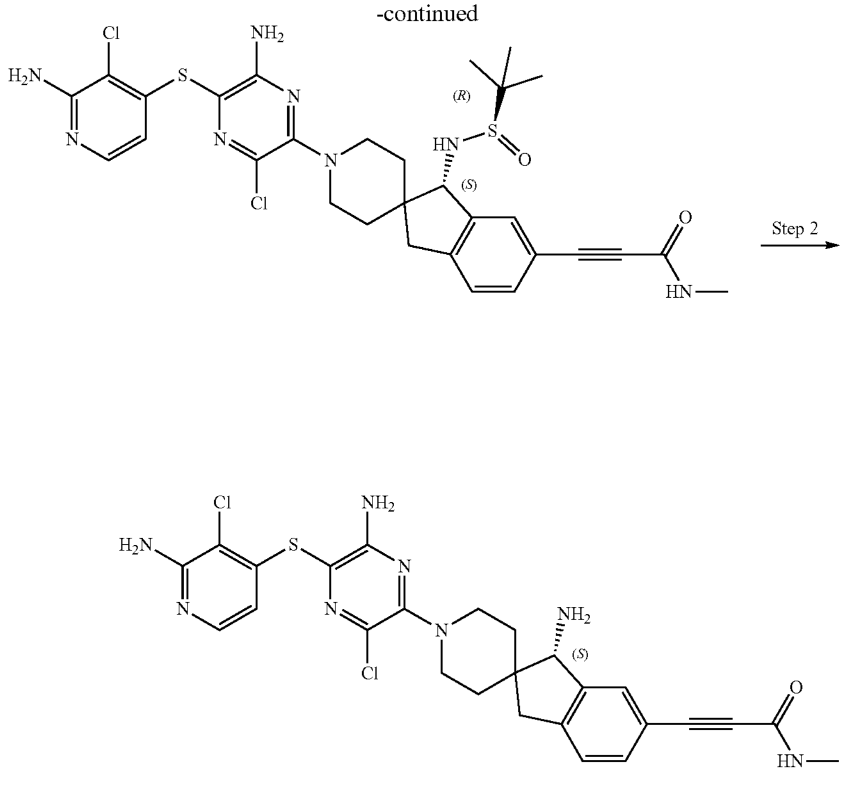

222

Step 1: 3-((S)-1'-(6-amino-5-((2-amino-3-chloropyridin-4-yl)thio)-3-chloropyrazin-2-yl)-1-(((R)-tert-butylsulfinyl)amino)-1,3-dihydrospiro[indene-2,4'-piperidin]-6-yl)-N-methylpropiolamide To the solution of 3-((S)-1'-(6-amino-5-((2-amino-3-chloropyridin-4-yl)thio)pyrazin-2-yl)-1-(((R)-tert-butylsulfinyl)amino)-1,3-dihydrospiro[indene-2,4'-piperidin]-6-yl)-N-methylpropiolamide (96 mg, 0.15 mmol; prepared by following the step 1 for preparing compound 1 from intermediates I-A2 and I-C20) in DMF (3 mL) was added NCS (40 mg, 0.30 mmol) and stirred at room temperature for 30 minutes. The reaction solution was purified by silica gel column chromatography (eluting with water/MeOH) to give target product.

Step 2: (S)-3-(1-amino-1'-(6-amino-5-((2-amino-3-chloropyridin-4-yl)thio)-3-chloropyrazin-2-yl)-1,3-dihydrospiro[indene-2,4'-piperidin]-6-yl)-N-methylpropiolamide The target product was prepared by following the step 3 for preparing compound 1 from corresponding starting materials and reagents (26 mg, 31% yield of two steps). $[M+H]^+$ 569.2. $^1H$ NMR (400 MHz, $CD_3OD$): δ 7.60 (d, J=5.5 Hz, 1H), 7.55 (s, 1H), 7.40 (d, J=7.7 Hz, 1H), 7.26 (d, J=7.8 Hz, 1H), 5.94 (d, J=5.5 Hz, 1H), 4.08-4.01 (m, 2H), 3.94 (s, 1H), 3.22-3.12 (m, 3H), 2.81-2.74 (m, 4H), 1.99-1.82 (m, 2H), 1.58 (d, J=13.4 Hz, 1H), 1.36 (d, J=13.2 Hz, 1H).

The compounds in the table below were prepared by following the steps for preparing compound 222 from corresponding intermediates and reagents:

| Compounds | Structural formula | LC-MS $[M + H]^+$ | $^1$HNMR | Intermediates |
|---|---|---|---|---|
| 223 | 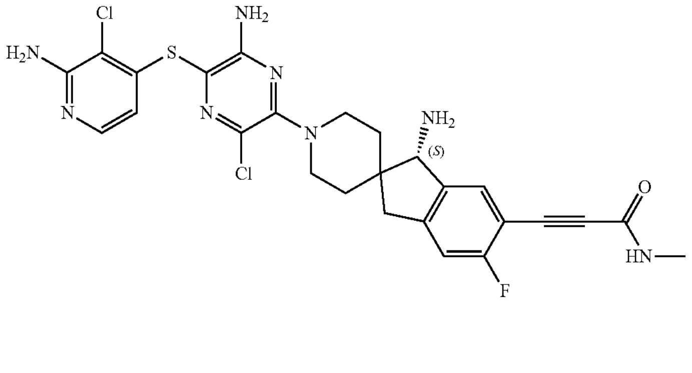 | 587.2 | $^1H$ NMR (400 MHz, $CD_3OD$) δ 7.62-7.51 (m, 2H), 7.07 (d, J = 9.3 Hz, 1H), 5.94 (d, J = 5.5 Hz, 1H), 4.06-4.02 (m, 2H), 3.92 (s, 1H), 3.21-3.11 (m, 3H), 2.84-2.80 (m, 1H), 2.78 (s, 3H), 1.96-1.81 (m, 2H), 1.59-1.55 (m, 1H), 1.40-1.36 (m, 1H). | I-A2 I-C24 |

-continued

| Compounds | Structural formula | LC-MS $[M + H]^+$ | $^1$HNMR | Intermediates |
|---|---|---|---|---|
| 224 | 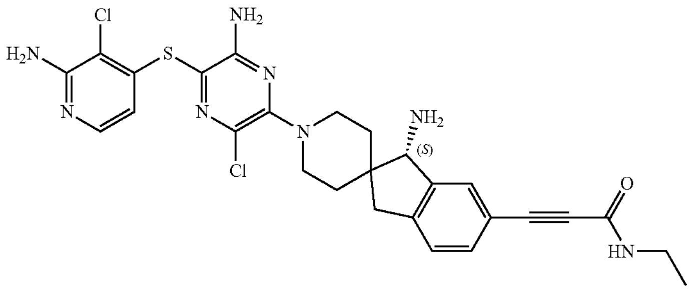 | 583.1 | $^1$H NMR (400 MHz, $CD_3OD$): δ 7.61 (d, J = 5.5 Hz, 1H), 7.55 (s, 1H), 7.40 (d, J = 7.9 Hz, 1H), 7.26 (d, J = 7.7 Hz, 1H), 5.95 (d, J = 5.5 Hz, 1H), 4.08-4.02 (m, 2H), 3.94 (s, 1H), 3.26-3.10 (m, 5H), 2.78 (d, J = 16.0 Hz, 1H), 2.03-1.82 (m, 2H), 1.58 (d, J = 15.0 Hz, 1H), 1.36 (d, J = 15.3 Hz, 1H), 1.15 (t, J = 7.3 Hz, 3H). | I-A2 I-C23 |
| 230 | 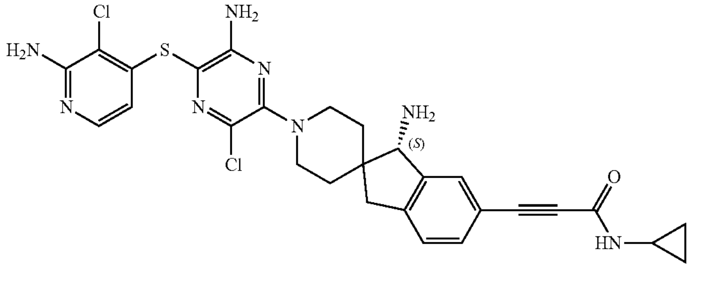 | 595.2 | $^1$H NMR (400 MHz, $CD_3OD/CDCl_3$): δ 7.60-7.58 (m, 1H), 7.53 (s, 1H), 7.41-7.35 (m, 1H), 7.27-7.22 (m, 1H), 5.96-5.92 (m, 1H), 4.07-4.00 (m, 2H), 3.93 (s, 1H), 3.21-3.11 (m, 3H), 2.81-2.70 (m, 2H), 1.98-1.82 (m, 2H), 1.59-1.53 (m, 1H), 1.37-1.32 (m, 1H), 0.78-0.72 (m, 2H), 0.60-0.52 (m, 2H). | I-A2 I-C25 |

Compound 239

(S)-3-(1-amino-1'-(6-amino-5-((2-amino-3-chloropyridin-4-yl)thio)-3-fluoropyrazin-2-yl)-1,3-dihydrospiro[indene-2,4'-piperidin]-6-yl)-N-methylpropiolamide

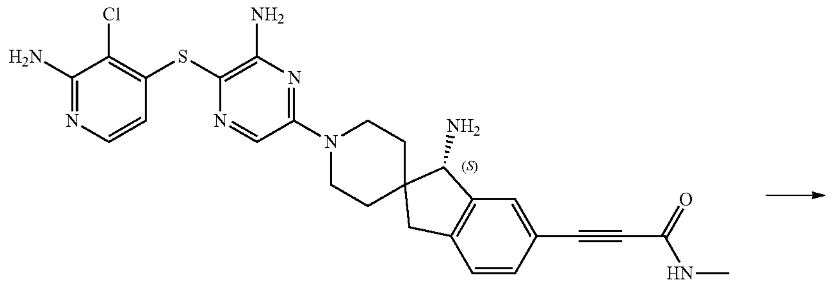

229

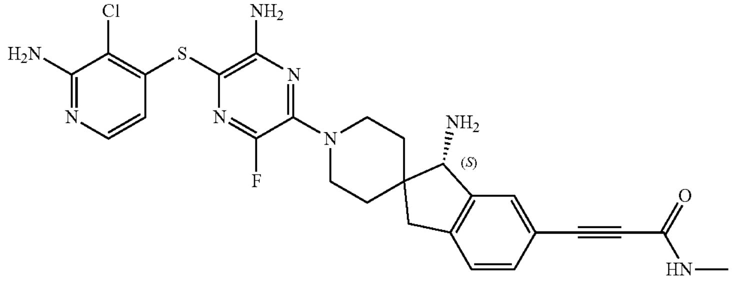

239

At 0° C., to the solution of (S)-3-(1-amino-1'-(6-amino-5-((2-amino-3-chloropyridin-4-yl)thio)pyrazin-2-yl)-1,3-dihydrospiro[indene-2,4'-piperidin]-6-yl)-N-methylpropiolamide (compound 229; 165 mg, 0.31 mmol) in DMF (2 mL) and MeCN (3 mL) was added NFSI (97 mg, 0.31 mmol) and stirred at room temperature for 3 hours. The reaction solution was purified by silica gel column chromatography (eluting with water/MeOH) and thin layer chromatography (eluting with DCM/MeOH) to give target product (28 mg, 16% yield). $[M+H]^+$ 553.2. $^1$H NMR (400 MHz, $CD_3OD$): δ 7.63-7.57 (m, 1H), 7.54 (s, 1H), 7.42-7.38 (m, 1H), 7.26 (d, J=7.7 Hz, 1H), 5.99 (d, J=5.5 Hz, 1H), 4.30-4.26 (m, 2H), 3.94 (s, 1H), 3.34-3.32 (m, 1H), 3.26-3.01 (m, 2H), 2.82-2.78 (m, 4H), 1.95-1.72 (m, 2H), 1.59-1.55 (m, 1H), 1.35-1.31 (m, 1H).

Compound 240

(S)-3-(1-amino-1'-(6-amino-5-((2-amino-3-chloropyridin-4-yl)thio)-3-bromopyrazin-2-yl)-1,3-dihydrospiro[indene-2,4'-piperidin]-6-yl)-N-methylpropiolamide

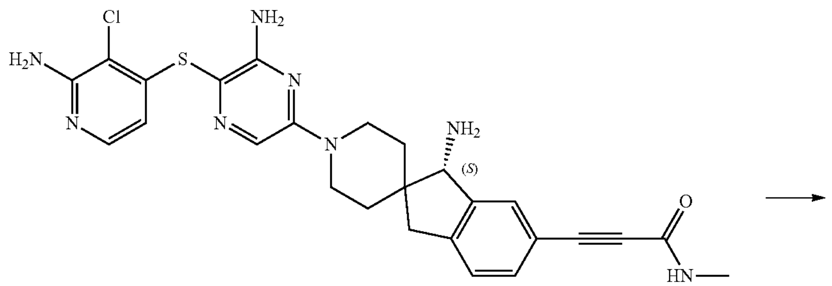

229

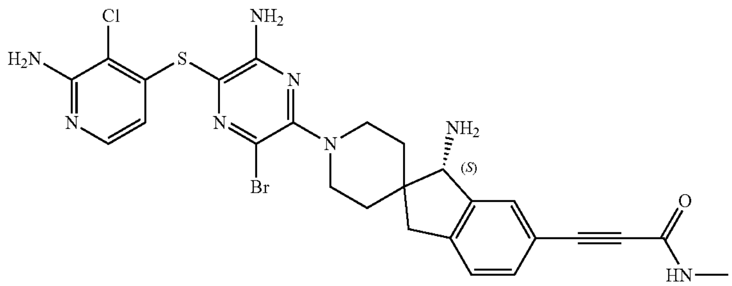

240

To the solution of (S)-3-(1-amino-1'-(6-amino-5-((2-amino-3-chloropyridin-4-yl)thio)pyrazin-2-yl)-1,3-dihydrospiro[indene-2,4'-piperidin]-6-yl)-N-methylpropiolamide (compound 229; 60 mg, 0.093 mmol) in DMF (1.5 mL) was added NBS (33 mg, 0.188 mmol) and stirred at room temperature for 1 hour. The reaction solution was purified by silica gel column chromatography (eluting with water/MeOH) and thin layer chromatography (eluting with DCM/MeOH) to give target product (15 mg, 26% yield). $[M+H]^+$ 613.1. $^1H$ NMR (400 MHz, $CD_3OD$): δ 7.62 (d, J=5.5 Hz, 1H), 7.57 (s, 1H), 7.41 (d, J=7.7 Hz, 1H), 7.27 (d, J=7.8 Hz, 1H), 5.96 (d, J=5.6 Hz, 1H), 4.09-3.91 (m, 3H), 3.24-3.09 (m, 3H), 2.87-2.73 (m, 4H), 2.04-1.80 (m, 2H), 1.62-1.58 (m, 1H), 1.41-1.37 (m, 1H).

Compound 243

(S)-3-(1-amino-1'-(5-(3,4-dihydro-1,5-naphthyridin-1(2H)-yl)pyrazin-2-yl)-1,3-dihydrospiro[indene-2,4'-piperidin]-6-yl)-N-ethylpropiolamide

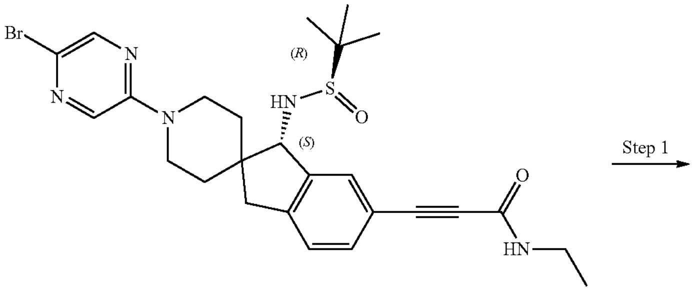

-continued

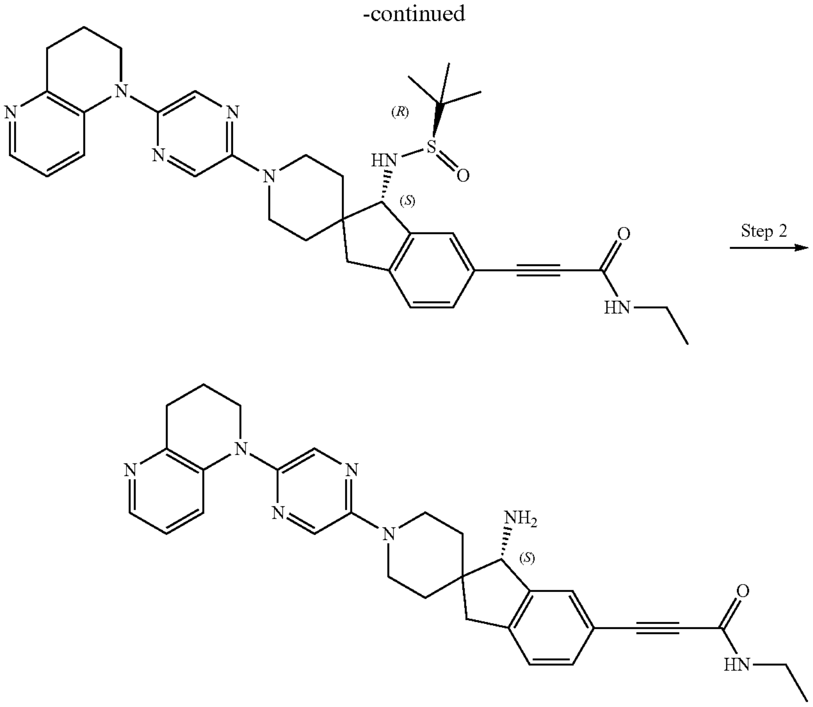

243

Step 1: 3-((S)-1-(((R)-tert-butylsulfinyl)amino)-1'-(5-(3,4-dihydro-1,5-naphthyridin-1(2H)-yl)pyrazin-2-yl)-1,3-dihydrospiro[indene-2,4'-piperidin]-6-yl)-N-ethylpropiolamide Under $N_2$, 3-((S)-1'-(5-bromopyrazin-2-yl)-1-(((R)-tert-butylsulfinyl)amino)-1,3-dihydrospiro[indene-2,4'-piperidin]-6-yl)-N-ethylpropiolamide (80 mg, 0.14 mmol; prepared by following the step 1 for preparing compound 1 from 2,5-dibromopyrazine and intermediate I-C23), 1,2,3,4-tetrahydro-1,5-naphthyridine (37 mg, 0.28 mmol), $Pd_2(dba)_3$ (9 mg, 0.01 mmol), Xant-phos (12 mg, 0.02 mmol) and $Cs_2CO_3$ (91 mg, 0.28 mmol) were placed in 1,4-dioxane (10 mL). The reaction mixture was heated to 100° C. and stirred for 16 hours. After concentration in vacuum under reduced pressure, the residue was purified by silica gel column chromatography (eluting with water/MeOH, 0.05% formic acid) to give target product.

Step 2: (S)-3-(1-amino-1'-(5-(3,4-dihydro-1,5-naphthyridin-1(2H)-yl)pyrazin-2-yl)-1,3-dihydrospiro[indene-2,4'-piperidin]-6-yl)-N-ethylpropiolamide The target product was prepared by following the step 3 for preparing compound 1 from corresponding starting materials and reagents (25 mg, 35% yield). $[M+H]^+$ 508.3. $^1H$ NMR (400 MHz, $CD_3OD$): δ 8.06 (d, J=2.4 Hz, 2H), 7.83 (dd, J=4.7, 1.3 Hz, 1H), 7.56 (s, 1H), 7.42 (d, J=7.6 Hz, 1H), 7.28 (d, J=7.8 Hz, 1H), 7.08 (dd, J=8.4, 1.2 Hz, 1H), 7.03-6.95 (m, 1H), 4.25-4.12 (m, 2H), 3.95 (s, 1H), 3.72-3.65 (m, 2H), 3.29-3.14 (m, 5H), 2.99 (t, J=6.5 Hz, 2H), 2.81 (d, J=16.3 Hz, 1H), 2.18-2.09 (m, 2H), 1.96-1.75 (m, 2H), 1.60 (d, J=12.5 Hz, 1H), 1.37 (d, J=12.7 Hz, 1H), 1.16 (t, J=7.3 Hz, 3H).

The compounds in the table below were prepared by following the steps for preparing compound 243 from corresponding intermediates and reagents:

| Compounds | Structural formula | LC-MS $[M + H]^+$ | $^1$HNMR | Intermediates |
|---|---|---|---|---|
| 244 | 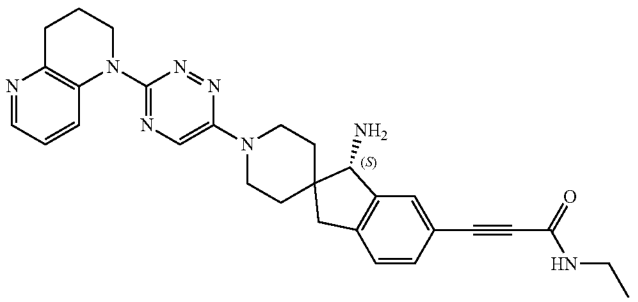 | 509.3 | $^1H$ NMR (400 MHz, $CD_3OD$): δ 8.37 (s, 1H), 7.94 (d, J = 4.6 Hz, 1H), 7.55 (s, 1H), 7.41 (d, J = 7.5 Hz, 1H), 7.28 (t, J = 8.8 Hz, 2H), 7.10-7.02 (m, 1H), 4.58-4.46 (m, 2H), 3.93 (s, 1H), 3.85-3.77 (m, 2H), 3.28-3.18 (m, 5H), 2.99 (t, J = 6.6 Hz, 2H), 2.81 (d, J = 16.4 Hz, 1H), 2.19-2.09 (m, 2H), 1.93-1.70 (m, 2H), 1.58 (d, J = 12.1 Hz, 1H), 1.34 (d, J = 12.1 Hz, 1H), 1.15 (t, J = 7.3 Hz, 3H). | I-C23 |

-continued

| Compounds | Structural formula | LC-MS $[M + H]^+$ | $^1$HNMR | Intermediates |
|---|---|---|---|---|
| 251 | 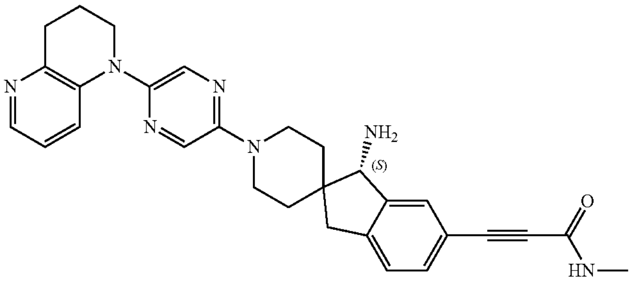 | 494.3 | $^1$H NMR (400 MHz,$CD_3OD$): δ 8.11-8.06 (m, 2H), 7.88-7.85 (m, 1H), 7.60 (s, 1H), 7.47-7.42 (m, 1H), 7.33-7.28 (m, 1H), 7.14-7.09 (m, 1H), 7.05-6.99 (m. 1H), 4.27-4.14 (m, 2H), 3.98 (s, 1H), 3.76-3.67 (m, 2H), 3.29-3.16 (m, 3H), 3.05-2.98 (m, 2H), 2.88-2.79 (m, 4H), 2.21-2.12 (m, 2H), 1.99-1.87 (m, 1H), 1.86-1.75 (m, 1H), 1.67-1.58 (m, 1H), 1.43-1.37 (m, 1H). | I-C20 |
| 258 | 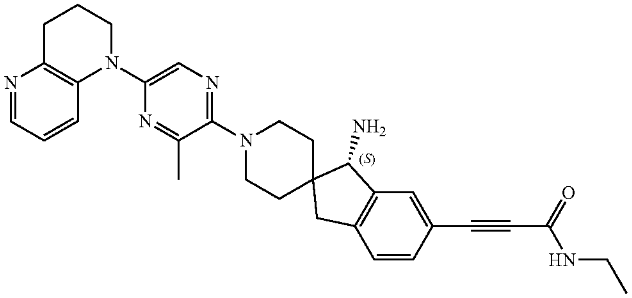 | 522.2 | $^1$H NMR (400 MHz, $CD_3OD$): δ 8.00 (s, 1H), 7.96-7.89 (m, 1H), 7.57 (s, 1H), 7.49-7.37 (m, 2H), 7.30-7.23 (m, 1H), 7.09-7.02 (m, 1H), 3.97 (s, 1H), 3.81-3.74 (m, 2H), 3.37-3.32 (m, 2H), 3.30-3.25 (m, 2H), 3.18-3.11 (m, 1H), 3.06-2.94 (m, 4H), 2.82-2.72 (m, 1H), 2.47 (s, 3H), 2.14-2.07 (m, 2H), 2.06-1.99 (m, 1H), 1.96-1.86 (m, 1H), 1.66-1.58 (m, 1H), 1.44-1.36 (m, 1H), 1.25-1.11 (m, 3H). | I-C23 |
| 263 | 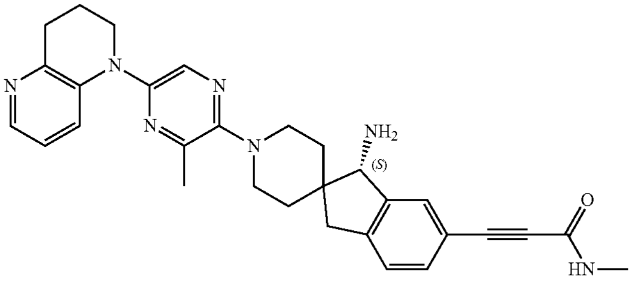 | 508.2 | $^1$H NMR (400 MHz, $CD_3OD$): δ 8.02-7.96 (m, 1H), 7.95-7.89 (m, 1H), 7.57 (s, 1H), 7.47-7.37 (m, 2H), 7.29-7.24 (m, 1H), 7.09-7.01 (m, 1H), 3.96 (s, 1H), 3.80-3.74 (m, 2H), 3.37-3.31 (m, 2H), 3.17-3.11 (m, 1H), 3.06-2.95 (m, 4H), 2.86-2.69 (m, 4H), 2.47 (s, 3H), 2.13-2.07 (m, 2H), 2.06-1.98 (m, 1H), 1.95-1.86 (m, 1H), 1.65-1.57 (m, 1H), 1.42-1.34 (m, 1H). | I-C20 |
| 287 | 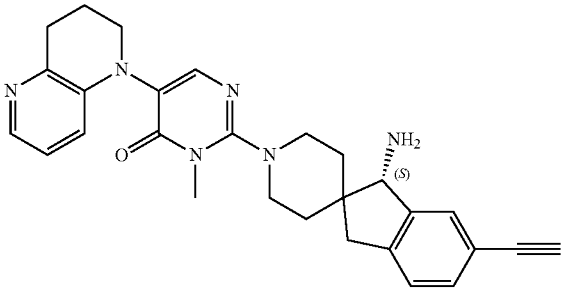 | 467.2 | $^1$H NMR (400 MHz, $CD_3OD$): δ 7.87 (s, 1H), 7.70 (dd, J = 4.7, 1.2 Hz, 1H), 7.48 (s, 1H), 7.36-7.26 (m, 1H), 7.19 (d, J = 7.7 Hz, 1H), 6.92 (dd, J = 8.3, 4.8 Hz, 1H), 6.67 (dd, J = 8.4, 1.2 Hz, 1H), 3.95 (s, 1H), 3.57-3.46 (m, 7H), 3.39 (s, 1H), 3.19-3.07 (m, 3H), 2.96 (t, J = 6.5 Hz, 2H), 2.75 (d, J = 16.0 Hz, 1H), 2.18-2.09 (m, 2H), 2.06-1.97 (m, 1H), 1.94-1.84 (m, 1H), 1.66-1.58 (m, 1H), 1.42-1.36 (m, 1H). | I-C3 |

Compound 279

(S)-3-(1-amino-1'-(5-((2-amino-3-chloropyridin-4-yl)thio)pyrazin-2-yl)-1,3-dihydrospiro[indene-2,4'-piperidin]-6-yl)propiolic acid

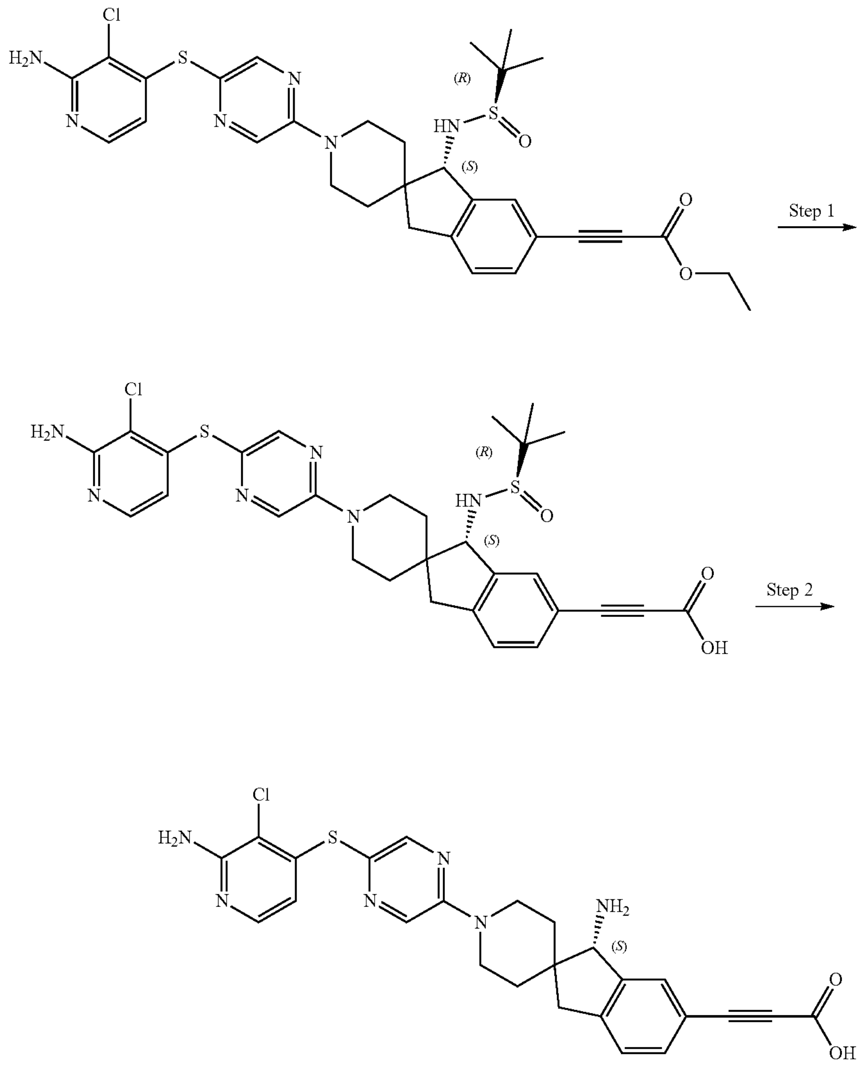

279

Step 1: 3-((S)-1'-(5-((2-amino-3-chloropyridin-4-yl)thio)pyrazin-2-yl)-1-(((R)-tert-butylsulfinyl)amino)-1,3-dihydrospiro[indene-2,4'-piperidin]-6-yl)propiolic acid To the solution of ethyl 3-((S)-1'-(5-((2-amino-3-chloropyridin-4-yl)thio)pyrazin-2-yl)-1-(((R)-tert-butylsulfinyl)amino)-1,3-dihydrospiro[indene-2,4'-piperidin]-6-yl)propiolate (320 mg, 0.5 mmol; prepared by following the step 1 for preparing compound 1 from intermediates I-A15 and I-C30) in EtOH/water was added LiOH (120 mg, 5.0 mmol). The reaction solution was stirred at 70° C. for 1 hour, adjusted pH to 5 with $MeSO_3H$. After concentration in vacuum under reduced pressure, the residue was purified by silica gel column chromatography (eluting with DCM/MeOH) to give target product (80 mg, 26% yield).

Step 2: (S)-3-(1-amino-1'-(5-((2-amino-3-chloropyridin-4-yl)thio)pyrazin-2-yl)-1,3-dihydrospiro[indene-2,4'-piperidin]-6-yl)propiolic acid The target product was prepared by following the step 3 for preparing compound 1 from corresponding starting materials and reagents (30 mg, 45% yield). $[M+H]^+$ 507.2. $^1H$ NMR (400 MHz, $CD_3OD$): δ 8.45-8.30 (m, 2H), 7.73-7.54 (m, 3H), 7.49-7.38 (m, 1H), 6.00-5.91 (m, 1H), 4.55-4.46 (m, 2H), 4.41-4.34 (m, 1H), 3.46-3.38 (m, 2H), 3.27-3.21 (m, 2H), 1.91-1.67 (m, 4H).

The compounds in the table below were prepared by following the steps for preparing compound 279 from corresponding intermediates and reagents:

| Compounds | Structural formula | LC-MS $[M + H]^+$ | $^1$HNMR | Intermediates |
|---|---|---|---|---|
| 283 | 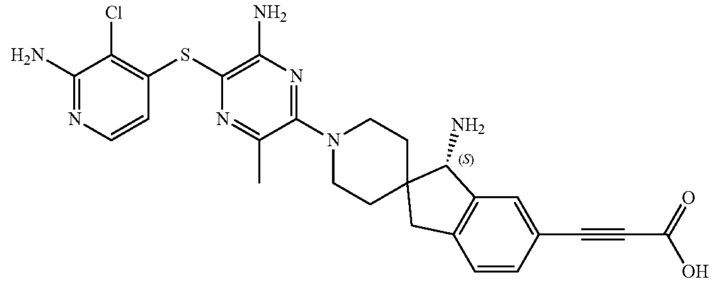 | 536.2 | $^1$H NMR (400 MHz, $CD_3OD$): δ 7.66 (s, 1H), 7.62 (d, J = 5.6 Hz, 1H), 7.57-7.54 (m, 1H), 7.41-7.38 (m. 1H), 5.90 (d, J = 5.6 Hz, 1H), 4.41 (s, 1H), 3.83-3.68 (m, 2H), 3.25-3.10 (m, 4H), 2.42 (s, 3H), 2.04-1.91 (m, 2H), 1.74-1.63 (m, 2H). | I-A11 I-C31 |

Compounds 56 and 57

Diastereomers of (S)-6-(1-amino-6-ethynyl-1,3-dihydrospiro[indene-2,4'-piperidin]-1'-yl)-3-(2-chlorophenyl)-2-methylpyrimidin-4(3H)-one

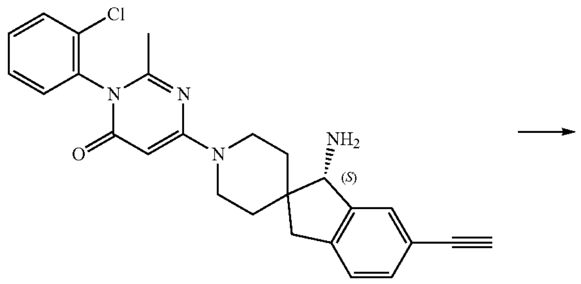

42

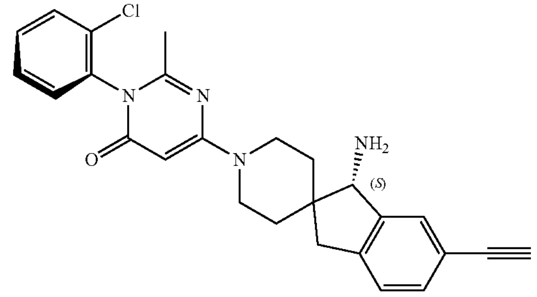

+

-continued

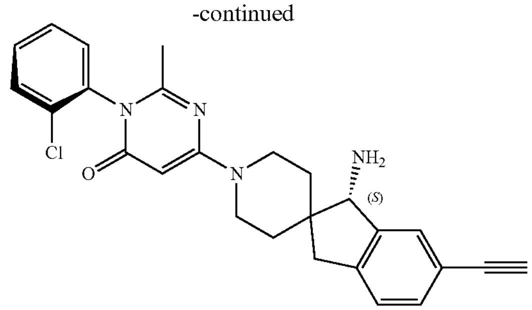

56 + 57

(S)-6-(1-amino-6-ethynyl-1,3-dihydrospiro[indene-2,4'-piperidin]-1'-yl)-3-(2-chlorophenyl)-2-methylpyrimidin-4(3H)-one (compound 42) was resolved by chiral HPLC to obtain a pair of diastereomers. Chiral HPLC conditions: column: IC (2x25 cm); mobile phase: acetonitrile/ethanol=10:90; flow rate: 15 mL/minute; detector: UV 254 nm.

First eluent (compound 56, RT=6.942 minutes), de %=100%, $[M+H]^+$ 445.2. $^1$H NMR (400 MHz, $CD_3OD$): δ 7.65-7.59 (m, 1H), 7.53-7.46 (m, 3H), 7.41-7.36 (m, 1H), 7.33-7.28 (m, 1H), 7.22-7.17 (m, 1H), 5.48 (s, 1H), 4.27 (br, 2H), 3.92 (s, 1H), 3.39 (s, 1H), 3.27-3.13 (m, 3H), 2.82-2.74 (m, 1H), 2.04 (s, 3H), 1.88-1.79 (m, 1H), 1.77-1.67 (m, 1H), 1.61-1.54 (m, 1H), 1.39-1.32 (m, 1H).

Second eluent (compound 57, RT=9.352 minutes), de %=100%, $[M+H]^+$ 445.2. $^1$H NMR (400 MHz, $CD_3OD$): δ 7.66-7.60 (m, 1H), 7.54-7.45 (m, 3H), 7.41-7.36 (m, 1H), 7.33-7.27 (m, 1H), 7.22-7.17 (m, 1H), 5.48 (s, 1H), 4.27 (br, 2H), 3.93 (s, 1H), 3.39 (s, 1H), 3.27-3.12 (m, 3H), 2.83-2.74 (m, 1H), 2.04 (s, 3H), 1.88-1.78 (m, 1H), 1.77-1.68 (m, 1H), 1.61-1.54 (m, 1H), 1.40-1.33 (m, 1H).

The compounds in the table below were prepared by following the chiral resolution conditions of compounds 56 and 57:

| Compounds | Structural formula | LC-MS $[M + H]^+$ | $^1$HNMR | |
|---|---|---|---|---|
| 58 | 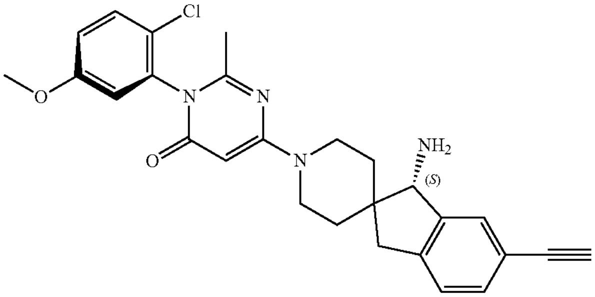 | 475.2 | $^1$H NMR (400 MHz, $CD_3OD$): δ 7.52-7.45 (m, 2H), 7.33-7.27 (m, 1H), 7.21-7.19 (m, 1H), 7.10-7.04 (m, 1H), 7.01-6.97 (m, 1H), 5.48 (s, 1H), 4.26 (br, 2H), 3.92 (s, 1H), 3.82 (s, 3H), 3.39 (s, 1H), 3.26-3.11 (m, 3H), 2.81-2.74 (m, 1H), 2.08 (s, 3H), 1.88-1.79 (m, 1H), 1.76-1.67 (m, 1H), 1.60-1.54 (m, 1H), 1.39-1.33 (m, 1H). | Obtained by resolution of compound 44 |
| | + | | | |
| 59 | 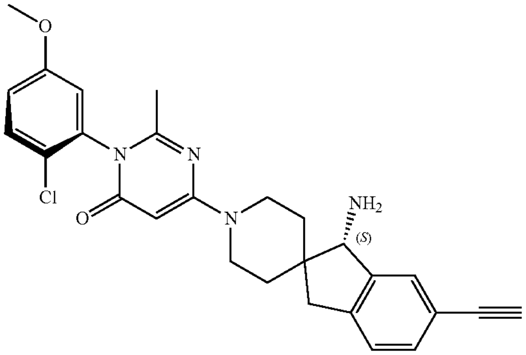 | 475.2 | $^1$H NMR (400 MHz, $CD_3OD$): δ 7.52-7.45 (m, 2H), 7.32-7.28 (m, 1H), 7.21-7.17 (m, 1H), 7.09-7.05 (m, 1H), 7.01-6.97 (m, 1H), 5.48 (s, 1H), 4.26 (br, 2H), 3.92 (s, 1H), 3.82 (s, 3H), 3.39 (s, 1H), 3.26-3.12 (m, 3H), 2.81-2.74 (m, 1H), 2.08 (s, 3H), 1.87-1.78 (m, 1H), 1.76-1.68 (m, 1H), 1.61-1.54 (m, 1H), 1.39-1.33 (m, 1H). | |
| 65 | 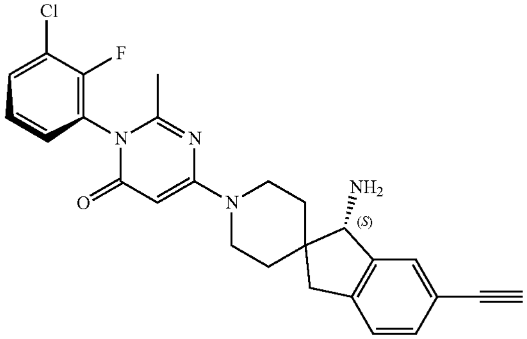 | 463.1 | $^1$H NMR (400 MHz, $CD_3OD$): δ 7.66-7.63 (m, 1H), 7.49 (s, 1H), 7.40-7.26 (m, 3H), 7.24-7.20 (m, 1H), 5.48 (s, 1H), 4.30-4.26 (m, 2H), 4.00 (s, 1H), 3.41 (s, 1H), 3.26-3.13 (m, 3H), 2.86-2.82 (m, 1H), 2.12 (s, 3H), 1.89-1.65 (m, 2H), 1.60-1.56 (m, 1H), 1.42-1.36 (m, 1H). | Obtained by resolution of compound 16 |
| | + | | | |
| 66 | 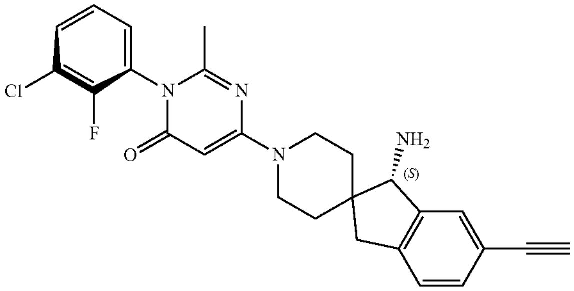 | 463.2 | $^1$H NMR (400 MHz, $CD_3OD$): δ 7.68-7.62 (m, 1H), 7.55 (s, 1H), 7.44-7.40 (m, 1H), 7.37-7.26 (m, 3H), 5.50 (s, 1H), 4.40-4.16 (m, 3H), 3.48 (s, 1H), 3.27-2.96 (m, 4H), 2.12 (s, 3H), 1.80-1.74 (m, 2H), 1.61-1.53 (m, 2H). | |

-continued
| Compounds | Structural formula | LC-MS $[M + H]^+$ | $^1$HNMR | |
|---|---|---|---|---|
| 88 | 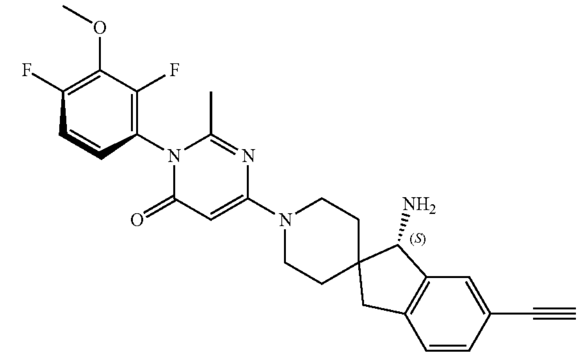 | 477.2 | $^1$H NMR (400 MHz, $CD_3OD$): δ 7.49-7.44 (m, 1H), 7.33-7.27 (m, 1H), 7.21-7.12 (m, 2H), 7.10-7.04 (m, 1H), 5.47 (s, 1H), 4.26 (br, 2H), 4.01 (s, 3H), 3.92 (s, 1H), 3.39 (s, 1H), 3.26-3.13 (m, 3H), 2.81-2.75 (m, 1H), 2.12 (s, 3H), 1.88-1.79 (m, 1H), 1.76-1.67 (m, 1H), 1.60-1.54 (m, 1H), 1.38-1.32 (m, 1H). | Obtained by resolution of compound 78 |
| | + | | | |
| 89 | 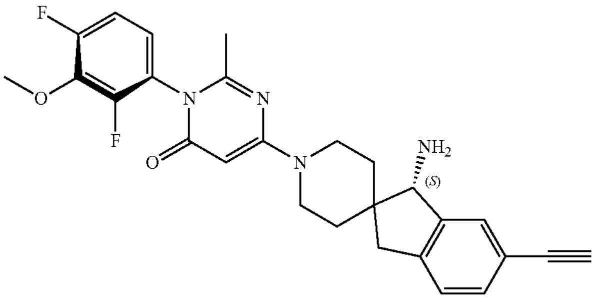 | 477.2 | $^1$H NMR (400 MHz, $CD_3OD$): δ 7.51-7.44 (m, 1H), 7.34-7.27 (m, 1H), 7.22-7.12 (m, 2H), 7.10-7.03 (m, 1H), 5.48 (s, 1H), 4.27 (br, 2H), 4.01 (s, 3H), 3.94 (s, 1H), 3.40 (s, 1H), 3.24-3.13 (m, 3H), 2.84-2.75 (m, 1H), 2.12 (s, 3H), 1.88-1.78 (m, 1H), 1.76-1.66 (m, 1H), 1.61-1.53 (m, 1H), 1.39-1.32 (m, 1H). | |
| 102 | 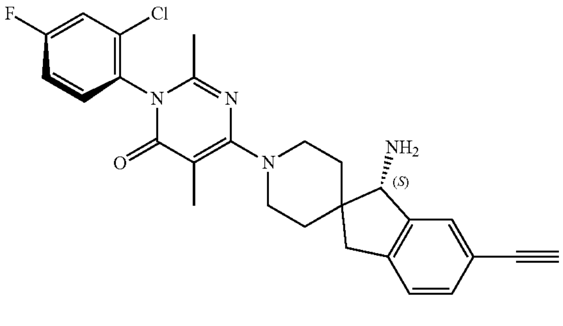 | 477.2 | $^1$H NMR (400 MHz, $CD_3OD$): δ 7.53-7.36 (m, 3H), 7.34-7.23 (m, 2H), 7.20-7.18 (m, 1H), 3.95-3.85 (m, 3H), 3.40 (s, 1H), 3.26-3.07 (m, 3H), 2.79-2.75 (m, 1H), 2.08-1.74 (m, 8H), 1.59-1.55 (m, 1H), 1.38-1.34 (m, 1H). | Obtained by resolution of compound 54 |
| | + | | | |
| 103 | 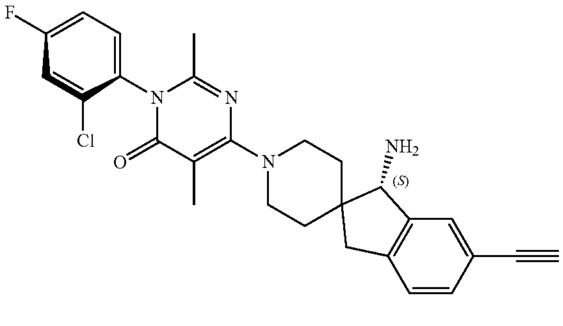 | 477.2 | $^1$H NMR (400 MHz, $CD_3OD$): δ 7.62-7.39 (m, 3H), 7.36-7.24 (m, 2H), 7.22-7.18 (m, 1H), 3.98-3.81 (m, 3H), 3.41 (s, 1H), 3.27-3.08 (m, 3H), 2.79-2.75 (m, 1H), 2.09-1.74 (m, 8H), 1.58-1.54 (m, 1H), 1.38-1.34 (m, 1H). | |

-continued
| Compounds | Structural formula | LC-MS [M + H]+ | 1HNMR | |
|---|---|---|---|---|
| 108 | 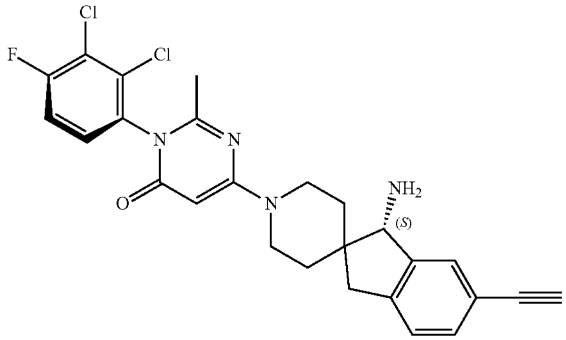 | 497.2 | 1H NMR (400 MHz, $CD_3OD$) δ 7.53-7.38 (m, 3H), 7.31 (d, J = 7.4 Hz, 1H), 7.20 (d, J = 7.5 Hz, 1H), 5.48 (s, 1H), 4.27 (br, 2H), 3.94 (s, 1H), 3.40 (s, 1H), 3.30-3.10 (m, 3H), 2.81-2.77 (m, 1H), 2.07 (s, 3H), 1.90-1.67 (m, 2H), 1.60-1.56 (m, 1H), 1.39-1.35 (m, 1H). | Obtained by resolution of compound 69 |
| | + | | | |
| 109 | 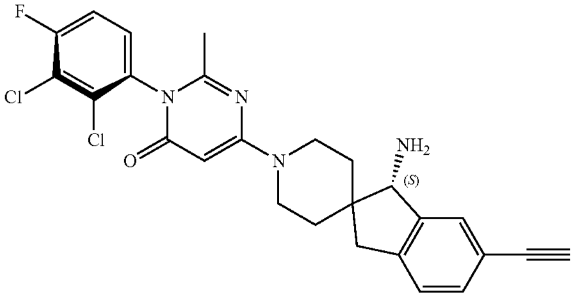 | 497.2 | 1H NMR (400 MHz, $CD_3OD$) δ 7.55-7.41 (m, 3H), 7.32 (d, J = 7.5 Hz, 1H), 7.21 (d, J = 7.5 Hz, 1H), 5.48 (s, 1H), 4.28 (br, 2H), 3.95 (s, 1H), 3.41 (s, 1H), 3.27-3.09 (m, 3H), 2.87-2.76 (m, 1H), 2.07 (s, 3H), 1.90-1.63 (m, 2H), 1.60-1.56 (m, 1H), 1.40-1.36 (m, 1H). | |
| 110 | 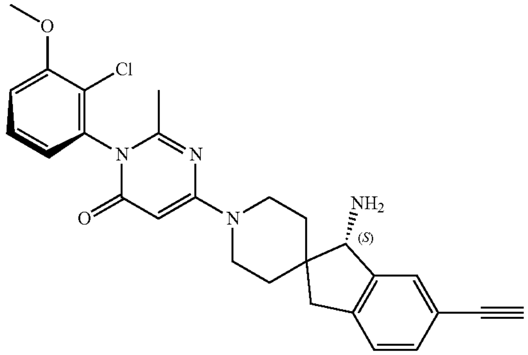 | 475.2 | 1H NMR (400 MHz, $CD_3OD$) δ 7.55-7.20 (m, 5H), 6.98-6.94 (m, 1H), 5.48 (s, 1H), 4.27 (br, 2H), 4.02-3.94 (m, 4H), 3.42 (s, 1H), 3.26-3.12 (m, 3H), 2.87-2.83 (m, 1H), 2.05 (s, 3H), 1.90-1.63 (m, 2H), 1.60-1.56 (m, 1H), 1.43-1.39 (m, 1H). | Obtained by resolution of compound 90 |
| | + | | | |
| 111 | 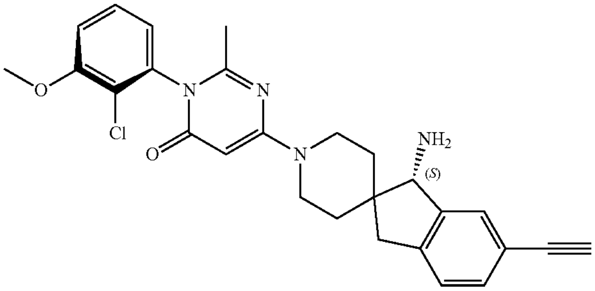 | 475.2 | 1H NMR (400 MHz, $CD_3OD$) δ 7.52-7.18 (m, 5H), 6.98-6.94 (m, 1H), 5.48 (s, 1H), 4.20 (br, 2H), 3.99-3.93 (m, 4H), 3.42 (s, 1H), 3.26-3.16 (m, 3H), 2.84-2.80 (m, 1H), 2.05 (s, 3H), 1.90-1.63 (m, 2H), 1.60-1.56 (m, 1H), 1.41-1.37 (m, 1H). | |

-continued

| Com-pounds | Structural formula | LC-MS $[M + H]^+$ | $^1$HNMR | |
|---|---|---|---|---|
| 113 | 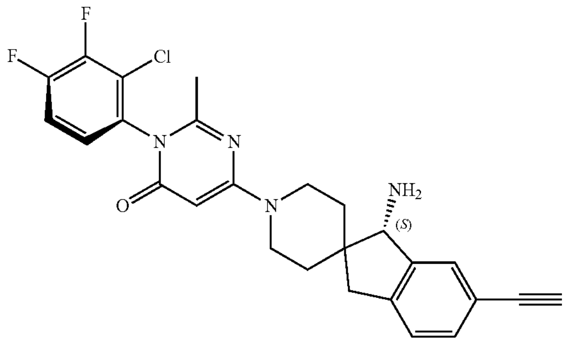 | 481.1 | $^1$H NMR (400 MHz, $CD_3OD$): δ 7.51-7.42 (m, 2H), 7.34-7.28 (m, 2H), 7.22-7.17 (m, 1H), 5.48 (s, 1H), 4.28 (s, 2H), 3.92 (s, 1H), 3.40 (s, 1H), 3.27-3.12 (m, 3H), 2.83-2.74 (m, 1H), 2.08 (s, 3H), 1.90-1.80 (m, 1H), 1.77-1.66 (m, 1H), 1.62-1.54 (m, 1H), 1.40-1.33 (m, 1H). | Obtained by resolution of compound 77 |
| | + | | | |
| 114 | 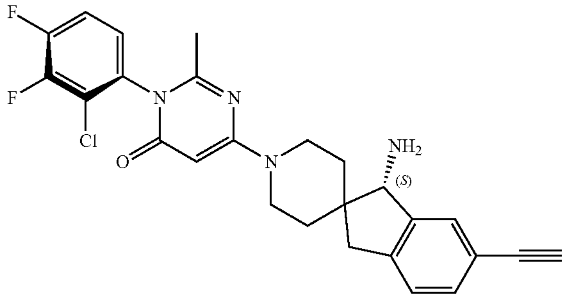 | 481.2 | $^1$H NMR (400 MHz, $CD_3OD$): δ 7.53-7.39 (m, 2H), 7.34-7.27 (m, 2H), 7.22-7.17 (m, 1H), 5.48 (s, 1H), 4.27 (br, 2H), 3.92 (s, 1H), 3.40 (s, 1H), 3.26-3.12 (m, 3H), 2.83-2.74 (m, 1H), 2.08 (s, 3H), 1.88-1.78 (m, 1H), 1.76-1.67 (m, 1H), 1.61-1.54 (m, 1H), 1.39-1.33 (m, 1H). | |
| 118 | 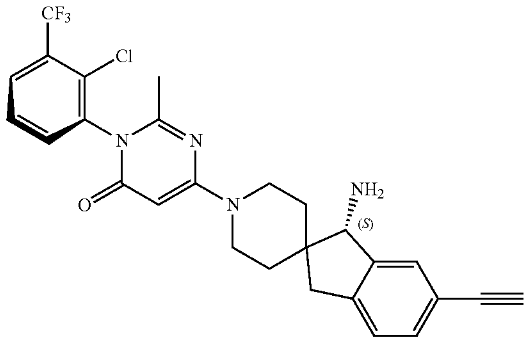 | 513.2 | $^1$H NMR (400 MHz, $CD_3OD$): δ 8.08-7.93 (m, 1H), 7.83-7.64 (m, 2H), 7.52 (s, 1H), 7.36 (d, J = 7.6 Hz, 1H), 7.25 (d, J = 7.6 Hz, 1H), 5.54 (s, 1H), 4.35 (s, 2H), 3.98 (s, 1H), 3.45 (s, 1H), 3.32-3.17 (m, 3H), 2.88-2.75 (m, 1H), 2.10 (s, 3H), 1.95-1.71 (m, 2H), 1.68-1.58 (m, 1H), 1.46-1.37 (m, 1H). | Obtained by esolution of compound 106 |
| | + | | | |
| 119 | 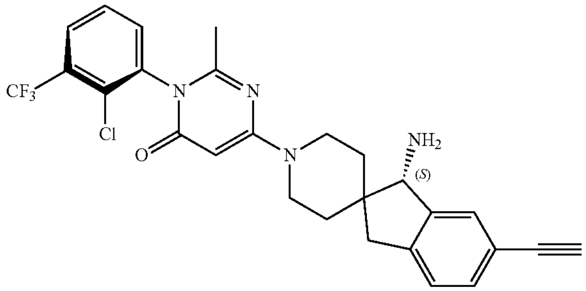 | 513.2 | $^1$H NMR (400 MHz, $CD_3OD$): δ 8.05-7.98 (m, 1H), 7.79-7.69 (m, 2H), 7.53 (s, 1H), 7.36 (d, J = 7.8 Hz, 1H), 7.25 (d, J = 7.8 Hz, 1H), 5.55 (s, 1H), 4.34 (s, 2H), 3.99 (s, 1H), 3.46 (s, 1H), 3.32-3.16 (m, 3H), 2.89-2.78 (m, 1H), 2.10 (s, 3H), 1.94-1.72 (m, 2H), 1.68-1.60 (m, 1H), 1.47-1.39 (m, 1H). | |

-continued

| Com-pounds | Structural formula | LC-MS [M + H]$^+$ | $^1$HNMR | |
|---|---|---|---|---|
| 124 | 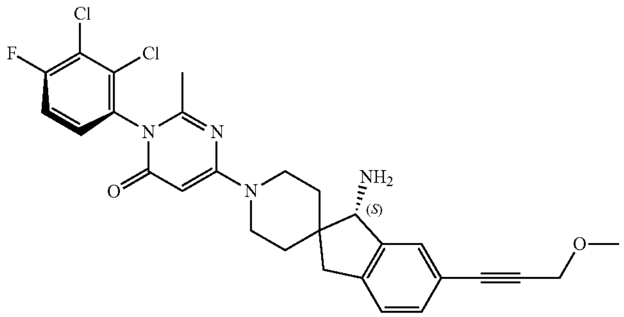 | 541.1 | $^1$H NMR (400 MHz, $CD_3OD$): δ 7.53-7.42 (m, 3H), 7.32-7.18 (m, 2H), 5.48 (s, 1H), 4.50-4.10 (m, 4H), 3.93 (s, 1H), 3.41 (s, 3H), 3.26-3.13 (m, 3H), 2.81-2.75 (m, 1H), 2.07 (s, 3H), 1.90-1.65 (m, 2H), 1.60-1.56 (m, 1H), 1.38-1.34 (m, 1H). | Prepared from I-B30 and I-C7 by following the steps for preparing compound 12, and obtained by further resolution |
| | + | | | |
| 125 | 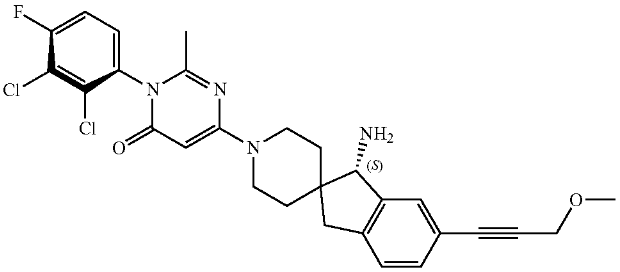 | 541.2 | $^1$H NMR (400 MHz, $CD_3OD$): o 7.51-7.42 (m, 3H), 7.31-7.18 (m, 2H), 5.48 (s, 1H), 4.40-4.20 (m, 4H), 3.93 (s, 1H), 3.41 (s, 3H), 3.26-3.09 (m, 3H), 2.81-2.77 (m, 1H), 2.07 (s, 3H), 1.86-1.65 (m, 2H), 1.60-1.56 (m, 1H), 1.39-1.35 (m, 1H). | |
| 161 | 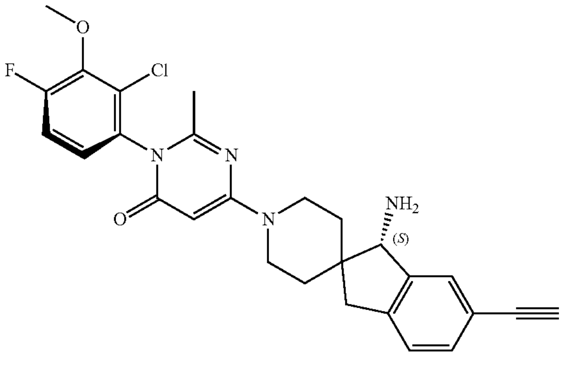 | 493.2 | $^1$H NMR (400 MHz, $CD_3OD$): δ 7.51-7.45 (m, 1H), 7.36-7.29 (m, 2H), 7.22-7.14 (m, 2H), 5.48 (s, 1H), 4.28 (br, 2H), 4.00 (s, 3H), 3.94 (s, 1H), 3.41 (s, 1H), 3.26-3.13 (m, 3H), 2.83-2.75 (m, 1H), 2.06 (s, 3H), 1.88-1.79 (m, 1H), 1.77-1.70 (m, 1H), 1.61-1.55 (m, 1H), 1.40-1.34 (m, 1H). | Obtained by resolution of compound 157 |
| | + | | | |
| 162 | 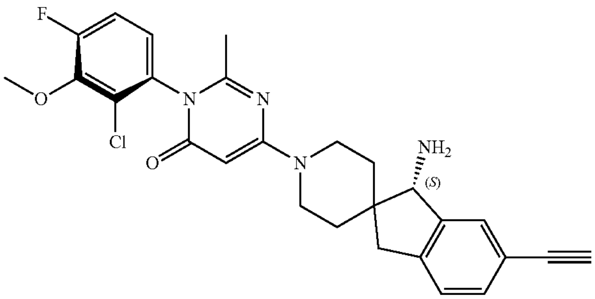 | 493.2 | $^1$H NMR (400 MHz, $CD_3OD$): δ 7.50-7.45 (m, 1H), 7.35-7.29 (m, 2H), 7.22-7.14 (m, 2H), 5.48 (s, 1H), 4.28 (br, 2H), 4.00 (s, 3H), 3.92 (s, 1H), 3.40 (s, 1H), 3.25-3.14 (m, 3H), 2.82-2.75 (m, 1H), 2.06 (s, 3H), 1.89-1.79 (m, 1H), 1.77-1.68 (m, 1H), 1.61-1.55 (m, 1H), 1.39-1.33 (m, 1H). | |

-continued

| Com-pounds | Structural formula | LC-MS [M + H]$^+$ | $^1$HNMR | |
|---|---|---|---|---|
| 163 | 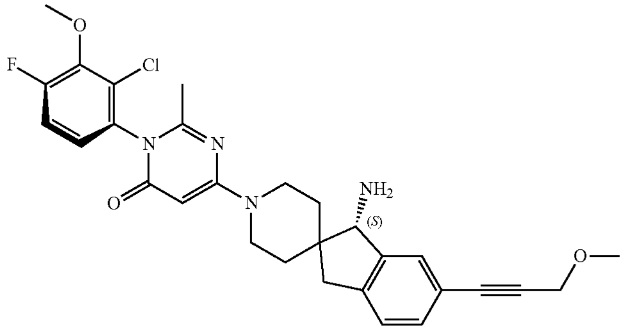 | 537.2 | $^1$H NMR (400 MHz, $CD_3OD$): δ 7.48-7.41 (m, 1H), 7.35-7.26 (m, 2H), 7.22-7.14 (m, 2H), 5.48 (s, 1H), 4.30 (br, 4H), 4.03-3.97 (m, 3H), 3.92 (s, 1H), 3.41 (s, 3H), 3.27-3.13 (m, 3H), 2.83-2.74 (m, 1H), 2.06 (s, 3H), 1.88-1.79 (m, 1H), 1.76-1.67 (m, 1H), 1.61-1.55 (m, 1H), 1.39-1.33 (m, 1H). | Obtained by resolution of compound 158 |
| | + | | | |
| 164 | 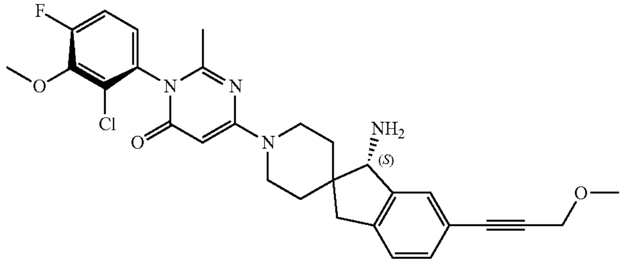 | 537.2 | $^1$H NMR (400 MHz, $CD_3OD$): δ 7.49-7.41 (m, 1H), 7.35-7.26 (m, 2H), 7.22-7.14 (m, 2H), 5.48 (s, 1H), 4.30 (br, 4H), 4.03-3.97 (m, 3H), 3.93 (s, 1H), 3.41 (s, 3H), 3.26-3.13 (m, 3H), 2.82-2.76 (m, 1H), 2.06 (s, 3H), 1.87-1.79 (m, 1H), 1.76-1.68 (m, 1H), 1.61-1.55 (m, 1H), 1.40-1.33 (m, 1H). | |
| 181 | 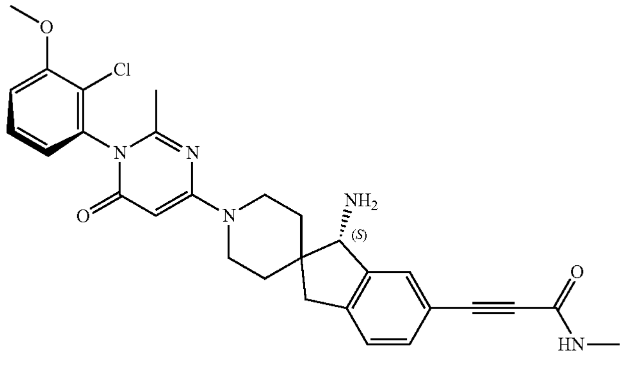 | 532.2 | $^1$H NMR (400 MHz, $CD_3OD$): δ 7.69 (s, 1H), 7.60-7.58 (m, 1H), 7.48-7.44 (m, 2H), 7.27-7.25 (m, 1H), 6.98-6.96 (m, 1H), 5.52 (s, 1H), 4.48-4.20 (m, 3H), 3.96 (s, 3H), 3.30-3.14 (m, 4H), 2.81 (s, 3H), 2.07 (s, 3H), 1.90-1.54 (m, 4H). | Prepared from I-B34 and I-C20 by following the steps for preparing compound 12, and obtained by further resolution |
| | + | | | |
| 182 | 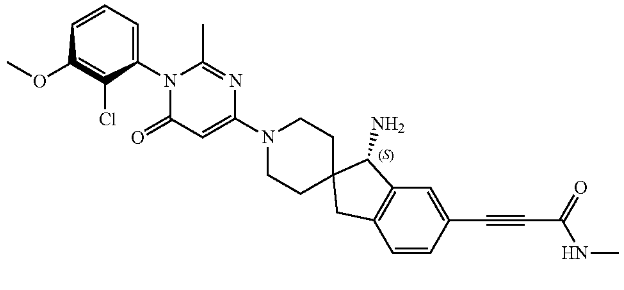 | 532.2 | $^1$H NMR (400 MHz, $CD_3OD$): δ 7.64 (s, 1H), 7.57-7.34 (m, 3H), 7.26-7.24 (m, 1H), 6.98-6.96 (m, 1H), 5.51 (s, 1H), 4.48-4.20 (m, 3H), 3.96 (s, 3H), 3.29-2.99 (m, 4H), 2.80 (s, 3H), 2.06 (s, 3H), 1.83-1.50 (m, 4H). | |

-continued

| Com-pounds | Structural formula | LC-MS $[M + H]^+$ | $^1$HNMR | |
|---|---|---|---|---|
| 190 | 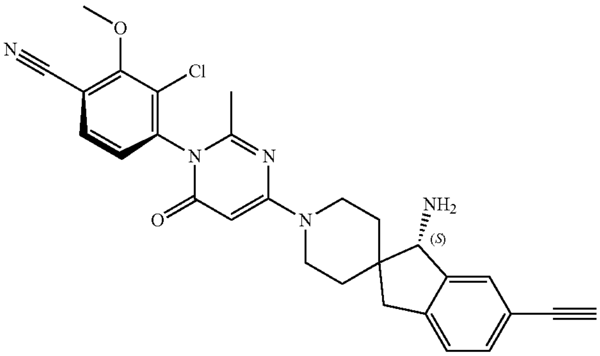 | 500.2 | $^1$H NMR (400 MHz, $CD_3OD$): δ 7.86 (d, J = 8.3 Hz, 1H), 7.52 (s, 1H), 7.41 (d, J = 8.3 Hz, 1H), 7.35 (d, J = 7.6 Hz, 1H), 7.25 (d, J = 7.6 Hz, 1H), 5.53 (s, 1H), 4.34 (s, 2H), 4.16 (s, 3H), 3.98 (s, 1H), 3.45 (s, 1H), 3.32-3.17 (m, 3H), 2.87-2.78 (m, 1H), 2.12 (s, 3H), 1.93-1.72 (m, 2H), 1.63 (d, J = 12.1 Hz, 1H), 1.41 (d, J = 12,1 Hz, 1H). | Obtained by resolution of compound 183 |
| | + | | | |
| 191 | 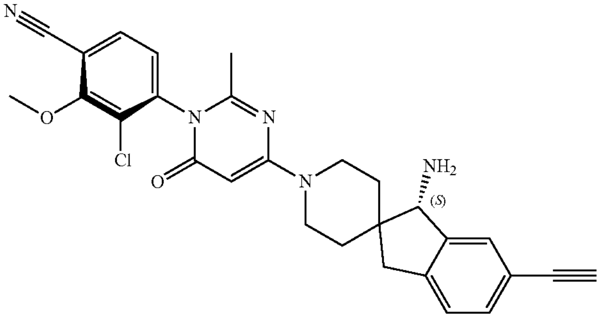 | 500.2 | $^1$H NMR (400 MHz, $CD_3OD$): δ 7.86 (d, J = 8.4 Hz, 1H), 7.52 (s, 1H), 7.41 (d, J = 8.4 Hz, 1H), 7.36 (d, J = 7.7 Hz, 1H), 7.25 (d, J = 7.7 Hz, 1H), 5.53 (s, 1H), 4.34 (s, 2H), 4.16 (s, 3H), 3.98 (s, 1H), 3.45 (s, 1H), 3.33-3.14 (m, 3H), 2.87-2.78 (m, 1H), 2.12 (s, 3H), 1.93-1.71 (m, 2H), 1.63 (d, J = 13.6 Hz, 1H), 1.42 (d, J = 13.6 Hz, 1H). | |
| 192 | 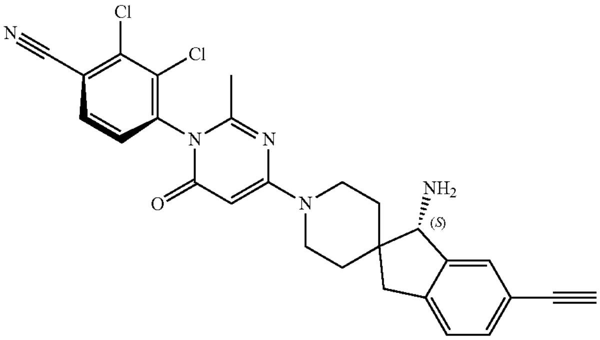 | 504.1 | $^1$H NMR (400 MHz, $CD_3OD$): δ 8.01 (d, J = 8.2 Hz, 1H), 7.67 (d, J = 8.2 Hz, 1H), 7.52 (s, 1H), 7.35 (d, J = 7.7 Hz, 1H), 7.24 (d, J = 7.7 Hz, 1H), 5.53 (s, 1H), 4.33 (s, 2H), 3.97 (s, 1H), 3.44 (s, 1H), 3.32-3.11 (m, 3H), 2.87-2.79 (m, 1H), 2.13 (s, 3H), 1.94-1.72 (m, 2H), 1.63 (d, J = 12.8 Hz, 1H), 1.41 (d, J = 12.8 Hz, 1H). | Obtained by resolution of compound 184 |
| | + | | | |
| 193 | 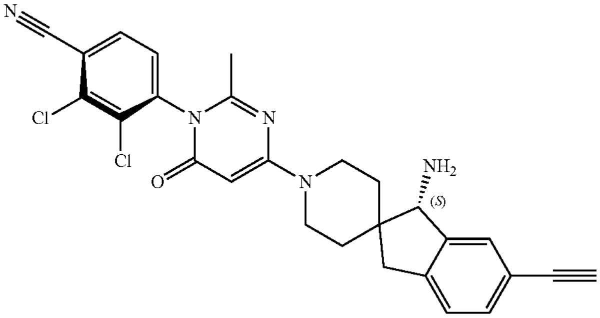 | 504.1 | $^1$H NMR (400 MHz, $CD_3OD$): δ 8.01 (d, J = 8.3 Hz, 1H), 7.67 (d, J = 8.3 Hz, 1H), 7.52 (s, 1H), 7.35 (d, J = 7.8 Hz, 1H), 7.25 (d, J = 7.8 Hz, 1H), 5.53 (s, 1H), 4.32 (s, 2H), 3.98 (s, 1H), 3.45 (s, 1H), 3.32-3.16 (m, 3H), 2.87-2.78 (m, 1H), 2.13 (s, 3H), 1.94-1.70 (m, 2H), 1.63 (d, J = 13.3 Hz, 1H), 1.41 (d, J = 13.3 Hz, 1H). | |

-continued

| Compounds | Structural formula | LC-MS $[M + H]^+$ | $^1$HNMR | |
|---|---|---|---|---|
| 200 | 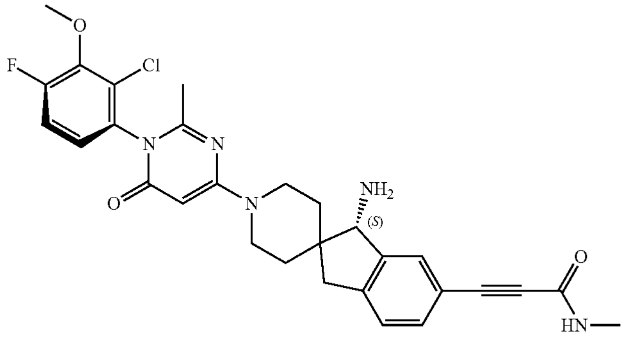 | 550.2 | $^1$H NMR (400 MHz, $CD_3OD$): δ 7.56 (s, 1H), 7.42 (d, J = 7.7 Hz, 1H), 7.36-7.26 (m, 2H), 7.20-7.14 (m, 1H), 5.49 (s, 1H), 4.45-4.10 (m, 2H), 4.01 (d, J = 1.2 Hz, 3H), 3.95 (s, 1H), 3.28-3.15 (m, 3H), 2.86-2.73 (m, 4H), 2.07 (s, 3H), 1.90-1.69 (m, 2H), 1.59 (d, J = 13.3 Hz, 1H), 1.35 (d, J = 12.3 Hz, 1H). | Prepared from I-B41 and I-C20 by following the steps for preparing compound 12, and obtained by further resolution |
| | + | | | |
| 201 | 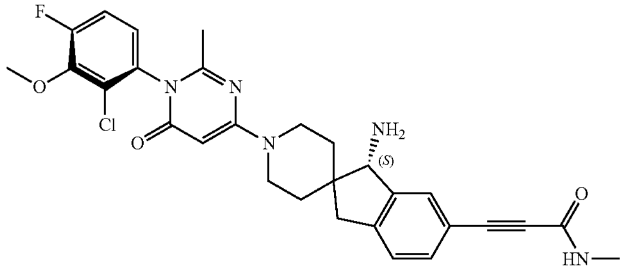 | 550.2 | $^1$H NMR (400 MHz, $CD_3OD$): δ 7.56 (s, 1H), 7.42 (d, J = 7.7 Hz, 1H), 7.36-7.26 (m, 2H), 7.20-7.14 (m, 1H), 5.49 (s, 1H), 4.45-4.10 (m, 2H), 4.01 (d, J = 1.2 Hz, 3H), 3.95 (s, 1H), 3.28-3.15 (m, 3H), 2.86-2.73 (m, 4H), 2.07 (s, 3H), 1.90-1.69 (m, 2H), 1.59 (d, J = 13.3 Hz, 1H), 1.35 (d, J = 12.3 Hz, IH). | |
| 207 | 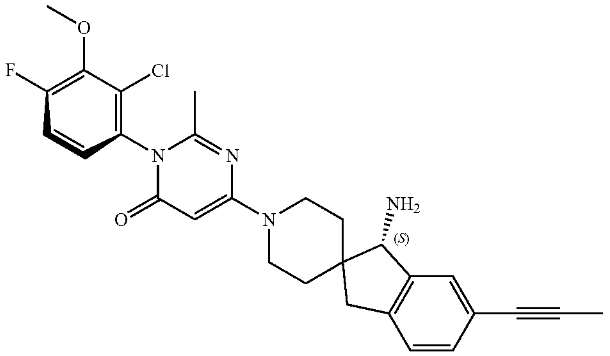 | 507.2 | $^1$H NMR (400 MHz, CDCI3): δ 7.33 (s, 1H), 7.23-7.08 (m, 3H), 6.99-6.95 (m, 1H), 5.44 (s, 1H), 4.15 (br, 2H), 4.02 (s, 3H), 3.92 (s, 1H), 3.17-3.10 (m, 2H), 3.06-3.02 (m, 1H), 2.67-2.63 (m, 1H), 2.04-2.02 (m, 6H), 1.87-1.67 (m, 2H), 1.32-1.26 (m, 2H). | Prepared from I-B41 and I-C17 by following the steps for preparing compound 12, and obtained by further resolution |
| | + | | | |
| 208 | 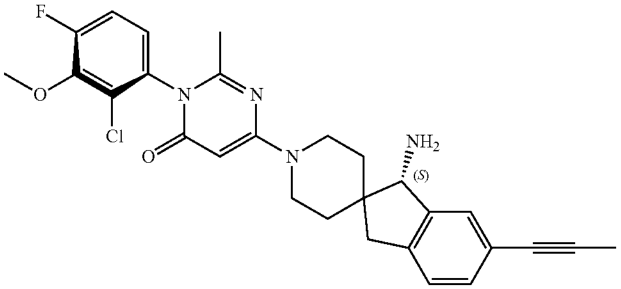 | 507.2 | $^1$H NMR (400 MHz, $CD_3OD$): δ 7.38-7.27 (m, 2H), 7.20-7.10 (m, 3H), 5.46 (s, 1H), 4.21 (br, 2H), 3.99 (s, 3H), 3.88 (s, 1H), 3.24-3.05 (m, 3H), 2.76-2.72 (m, 1H), 2.09-1.93 (m, 6H), 1.84-1.64 (m, 2H), 1.58-1.54 (m, 1H), 1.37-1.33 (m, 1H). | |

-continued
| Compounds | Structural formula | LC-MS [M + H]+ | 1HNMR | |
|---|---|---|---|---|
| 209 | 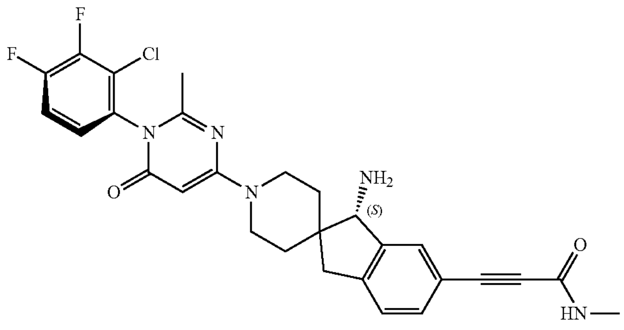 | 538.2 | 1H NMR (400 MHz, $CD_3OD$): δ 7.56-7.53 (s, 1H), 7.49-7.39 (m, 2H), 7.33-7.25 (m, 2H), 5.47 (s, 1H), 4.27 (br, 2H), 3.95 (s, 1H), 3.27-3.15 (m, 3H), 2.85-2.74 (m, 4H), 2.07 (s, 3H), 1.89-1.79 (m, 1H), 1.77-1.67 (m, 1H), 1.62-1.55 (m, 1H), 1.38-1.31 (m, 1H). | Obtained by resolution of compound 202 |
| | + | | | |
| 210 | 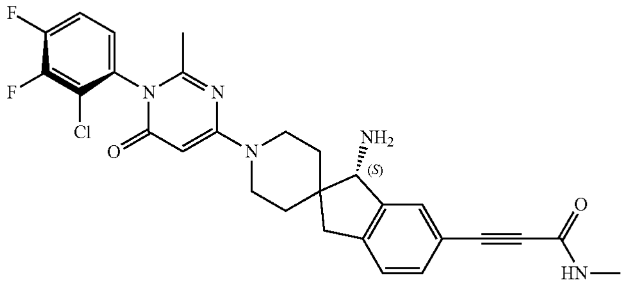 | 538.2 | 1H NMR (400 MHz, $CD_3OD$): δ 7.57-7.53 (m, 1H), 7.50-7.39 (m, 2H), 7.33-7.26 (m, 2H), 5.47 (s, 1H), 4.25 (br, 2H), 3.96 (s, 1H), 3.27-3.15 (m, 3H), 2.86-2.76 (m, 4H), 2.07 (s, 3H), 1.87-1.79 (m, 1H), 1.77-1.68 (m, 1H), 1.61-1.55 (m, 1H), 1.39-1.33 (m, 1H). | |
| 217 | 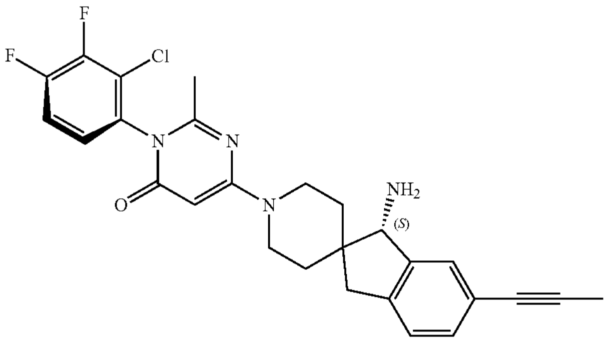 | 495.2 | 1H NMR (400 MHz, $CD_3OD$): δ 7.49-7.42 (m, 1H), 7.37-7.33 (m, 1H), 7.32-7.27 (m, 1H), 7.21-7.17 (m, 1H), 7.15-7.11 (m, 1H), 5.47 (s, 1H), 4.26 (br, 2H), 3.90 (s, 1H), 3.26-3.17 (m, 2H), 3.15-3.09 (m, 1H), 2.79-2.72 (m, 1H), 2.07 (s, 3H), 1.98 (s, 3H), 1.85-1.77 (m, 1H), 1.75-1.67 (m, 1H), 1.59-1.53 (m, 1H), 1.40-1.34 (m, 1H). | Obtained by resolution of compound 214 |
| | + | | | |
| 218 | 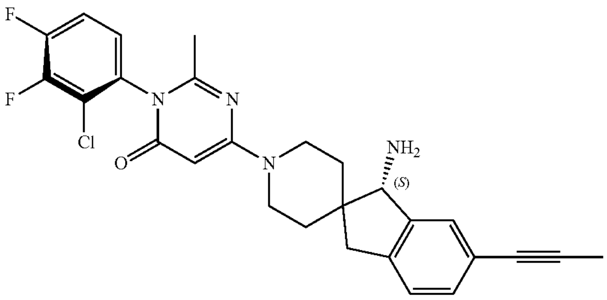 | 495.1 | 1H NMR (400 MHz, $CD_3OD$): δ 7.49-7.42 (m, 1H), 7.37-7.33 (m, 1H), 7.32-7.27 (m, 1H), 7.22-7.17 (m, 1H), 7.17-7.11 (m, 1H), 5,47 (s, 1H), 4.26 (br, 2H), 3.91 (s, 1H), 3.27-3.18 (m, 2H), 3.15-3.09 (m, 1H), 2.81-2.72 (m, 1H), 2.07 (s, 3H), 1.98 (s, 3H), 1.85-1.77 (m, 1H), 1.75-1.67 (m, 1H), 1.60-1.53 (m, 1H), 1.41-1.33 (m, 1H). | |

-continued

| Compounds | Structural formula | LC-MS [M + H]+ | 1HNMR | |
|---|---|---|---|---|
| 220 | 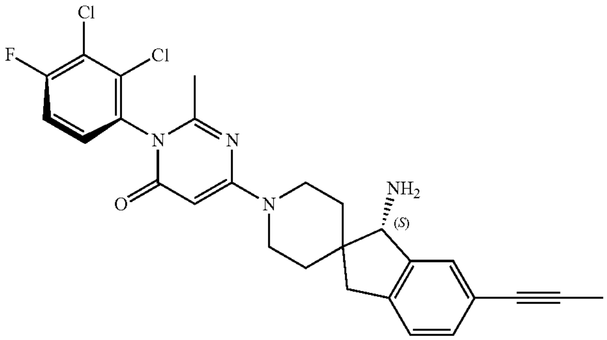 | 511.2 | 1H NMR (400 MHz, $CD_3OD$): δ 7.59-7.33 (m, 3H), 7.20-7.16 (m, 2H), 5.47 (s, 1H), 4.25 (br, 2H), 3.95 (s, 1H), 3.27-3.05 (m, 3H), 2.82-2.78 (m, 1H), 2.18-1.92 (m, 6H), 1.82-1.68 (m, 2H), 1.60-1.52 (m, 1H), 1.44-1.36 (m, 1H). | Prepared from I-B30 and I-C17 by following the steps for preparing compound 12, and obtained by further resolution |
| | + | | | |
| 221 | 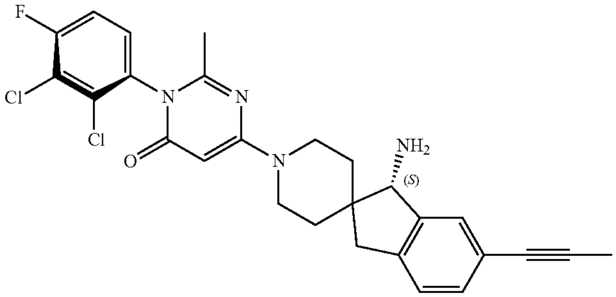 | 511.2 | 1H NMR (400 MHz, $CD_3OD$): $ 7.54-7.28 (m, 3H), 7.18-7.12 (m, 2H), 5.47 (s, 1H), 4.24 (br, 2H), 3.89 (s, 1H), 3.26-3.06 (m, 3H), 2.76-2.72 (m, 1H), 2.20-1.90 (m, 6H), 1.82-1.64 (m, 2H), 1.58-1.52 (m, 1H), 1.38-1.32 (m, 1H). | |
| 267 | 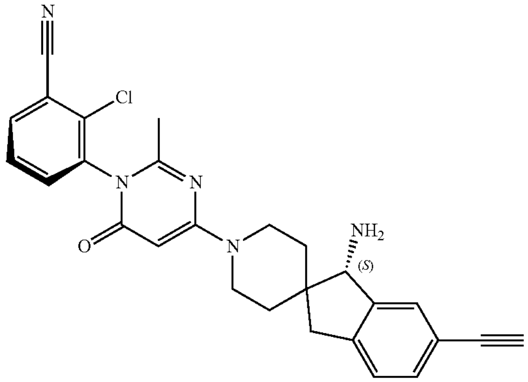 | 470.2 | 1H NMR (400 MHz, $CD_3OD$): & 8.00-7.94 (m, 1H), 7.77-7.73 (m, 1H), 7.69-7.64 (m, 1H), 7.47 (s, 1H), 7.34-7.27 (m, 1H), 7.22-7.18 (m, 1H), 5.49 (s, 1H), 4.50-3.98 (m, 2H), 3.92 (s, 1H), 3.39 (s, 1H), 3.28-3.20 (m, 2H), 3.19-3.11 (m, 1H), 2.84-2.72 (m, 1H), 2.06 (s, 3H), 1.89-1.78 (m, 1H), 1.78-1.67 (m, 1H), 1.61-1.56 (m, 1H), 1.39-1.34 (m, 1H). | Obtained by resolution of compound 34 |
| | + | | | |
| 268 | 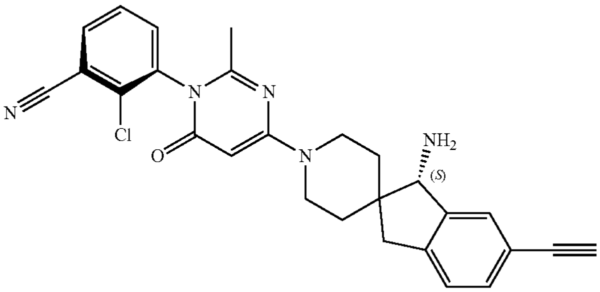 | 470.2 | 1H NMR (400 MHz, $CD_3OD$): δ 8.01-7.94 (m, 1H), 7.78-7.72 (m, 1H), 7.70-7.62 (m, 1H), 7.47 (s, 1H), 7.33-7.27 (m, 1H), 7.23-7.16 (m, 1H), 5.49 (s, 1H), 4.47-4.02 (m, 2H), 3.92 (s, 1H), 3.39 (s, 1H), 3.28-3.19 (m, 2H), 3.19-3.12 (m, 1H), 2.83-2.71 (m, 1H), 2.06 (s, 3H), 1.89-1.78 (m, 1H), 1.77-1.67 (m, 1H), 1.61-1.55 (m, 1H), 1.40-1.33 (m, 1H). | |

The diastereomers in the table are subjected to chiral HPLC under the following conditions (flow rate: 15 mL/minute; detector: UV 254 nm):

| Compounds | Column | Mobile phase | RT/minute | de % |
|---|---|---|---|---|
| 58 | IC (2 × 25 cm) | Acetonitrile/ | 7.180 | 100% |
| 59 | | ethanol = 10:90 | 9.684 | 100% |
| 65 | IC (2 × 25 cm) | Acetonitrile/ | 6.427 | 100% |
| 66 | | ethanol = 10:90 | 7.045 | 100% |
| 88 | IC (2 × 25 cm) | Acetonitrile/ | 6.136 | 93.39% |
| 89 | | ethanol = 10:90 | 6.832 | 93.92% |
| 102 | ODH (2 × 25 cm) | n-Heptane/ | 10.838 | 100% |
| 103 | | ethanol = 50:50 | 12.127 | 99.30% |
| 108 | IC (2 × 25 cm) | Acetonitrile/ | 6.311 | 96.97% |
| 109 | | ethanol = 10:90 | 7.702 | 97.01% |
| 110 | ODH (2 × 25 cm) | Acetonitrile/ | 14.376 | 100% |
| 111 | | ethanol = 10:90 | 23.609 | 100% |
| 113 | IC (2 × 25 cm) | Acetonitrile/ | 5.515 | 100% |
| 114 | | ethanol = 10:90 | 6.581 | 100% |
| 118 | IC (2 × 25 cm) | Acetonitrile/ | 4.193 | 97.78% |
| 119 | | ethanol = 40:60 | 4.660 | 97.17% |
| 124 | IC (2 × 25 cm) | Acetonitrile/ | 8.555 | 100% |
| 125 | | ethanol = 10:90 | 10.658 | 96.90% |
| 161 | IC (2 × 25 cm) | Acetonitrile/ | 6.693 | 99.01% |
| 162 | | ethanol = 10:90 | 8.071 | 95.18% |

-continued

| Compounds | Column | Mobile phase | RT/minute | de % |
|---|---|---|---|---|
| 163 | IC (2 × 25 cm) | Acetonitrile/ | 9.344 | 100% |
| 164 | | ethanol = 10:90 | 11.191 | 93.96% |
| 181 | ODH (2 × 25 cm) | Acetonitrile/ | 5.810 | 100% |
| 182 | | ethanol = 50:50 | 7.066 | 100% |
| 190 | IA (2 × 25 cm) | Acetonitrile/ | 12.754 | 100% |
| 191 | | ethanol = 10:90 | 19.343 | 100% |
| 192 | ADH (2 × 25 cm) | Acetonitrile/ | 5.340 | 100% |
| 193 | | ethanol = 10:90 | 14.222 | 100% |
| 200 | IA (2 × 25 cm) | Acetonitrile/ | 5.599 | 100% |
| 201 | | ethanol = 10:90 | 10.573 | 100% |
| 207 | IC (2 × 25 cm) | Ethanol | 18.586 | 99.815 |
| 208 | | | 25.797 | 99.57% |
| 209 | IC (2 × 25 cm) | Ethanol | 10.679 | 100% |
| 210 | | | 14.798 | 100% |
| 217 | IC (2 × 25 cm) | Ethanol | 10.544 | 100% |
| 218 | | | 15.425 | 100% |
| 220 | IA (2 × 25 cm) | Acetonitrile/ | 6.682 | 100% |
| 221 | | ethanol = 10:90 | 13.507 | 100% |
| 267 | ODH (2 × 25 cm) | Acetonitrile/ | 7.894 | 100% |
| 268 | | ethanol = 10:90 | 14.016 | 100% |

The compounds in the table below were prepared by following the steps for preparing the above compounds from corresponding intermediates and reagents:

| Compounds | Structural formula | Molecular weight |
|---|---|---|
| 136 | 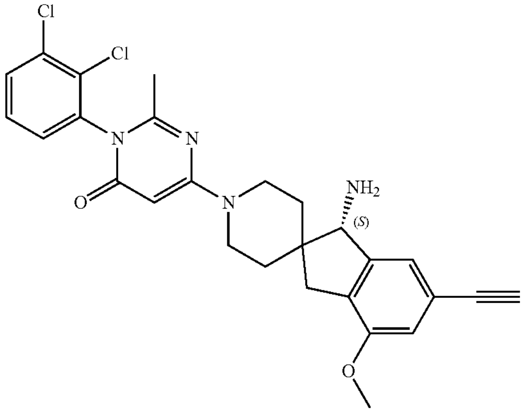 | 509.43 |
| 137 | 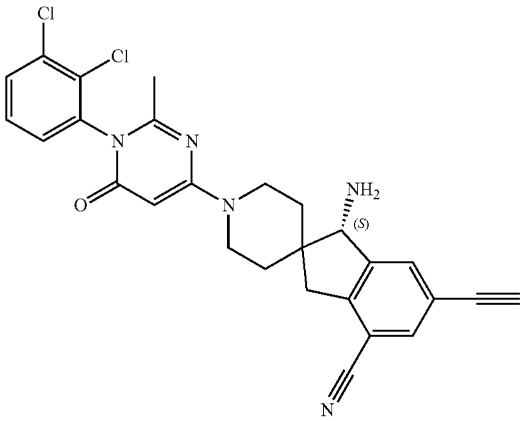 | 504.42 |

-continued
| Com-pounds | Structural formula | Molecular weight |
|---|---|---|
| 138 | 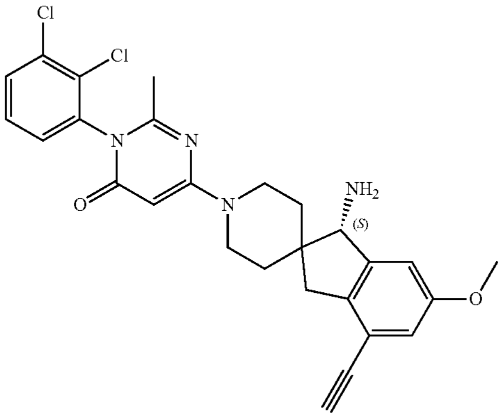 | 509.43 |
| 139 | 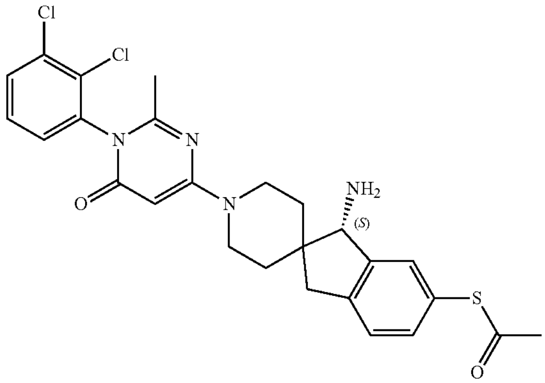 | 529.48 |
| 140 | 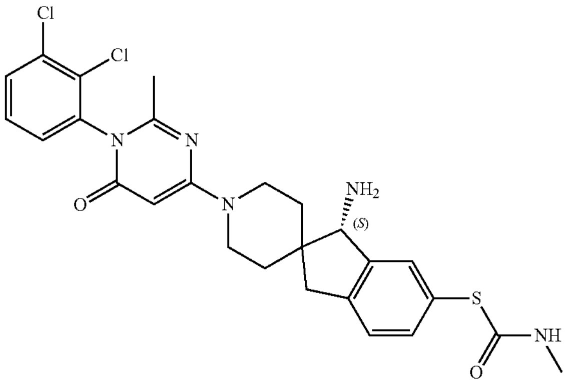 | 544.50 |
| 141 | 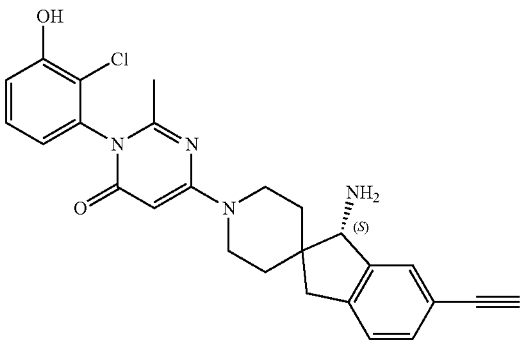 | 460.96 |

-continued
| Compounds | Structural formula | Molecular weight |
|---|---|---|
| 142 | 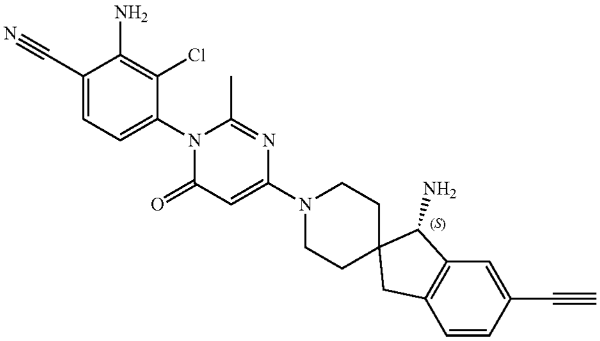 | 484.99 |
| 143 | 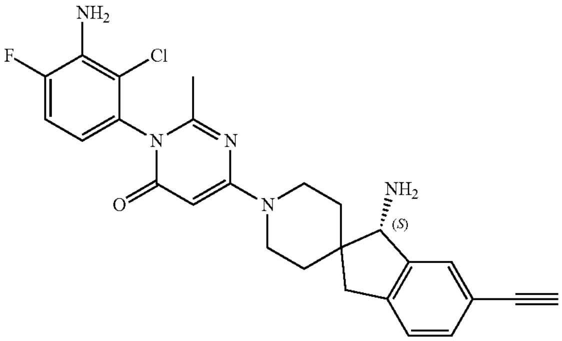 | 477.97 |
| 144 | 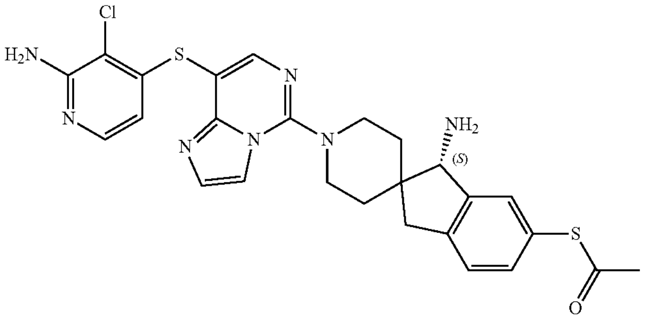 | 552.11 |
| 145 | 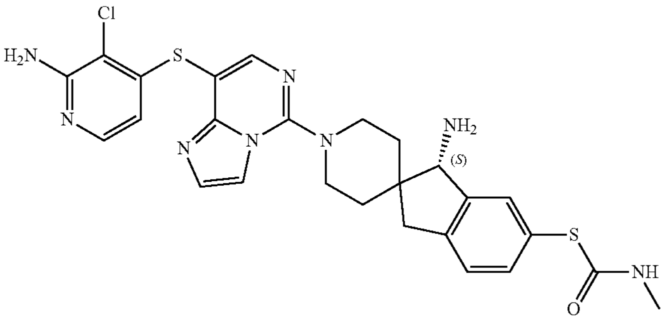 | 567.13 |

-continued
| Compounds | Structural formula | Molecular weight |
|---|---|---|
| 146 | 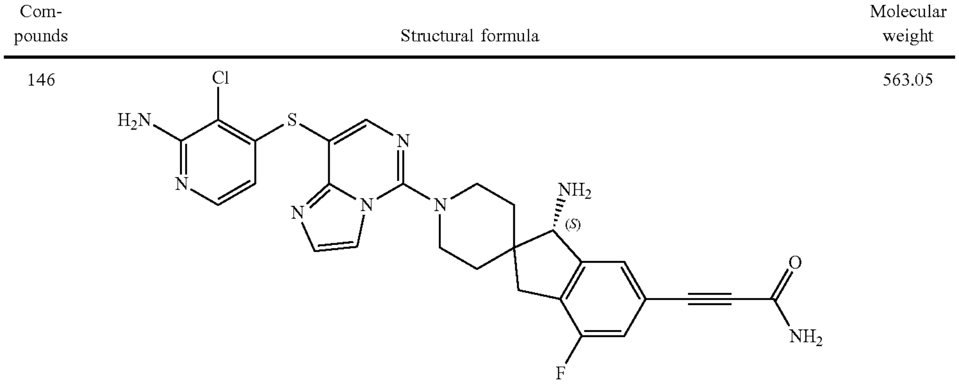 | 563.05 |
| 149 | 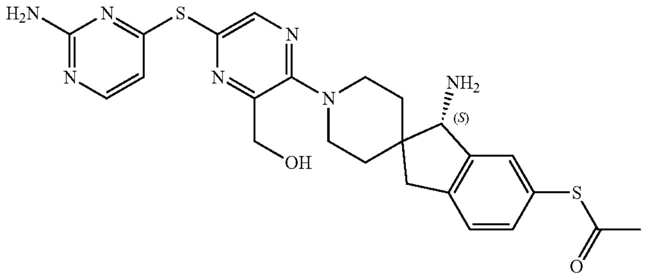 | 509.65 |
| 150 | 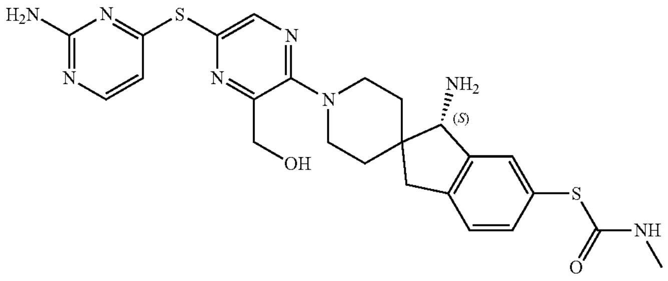 | 524.66 |
| 151 | 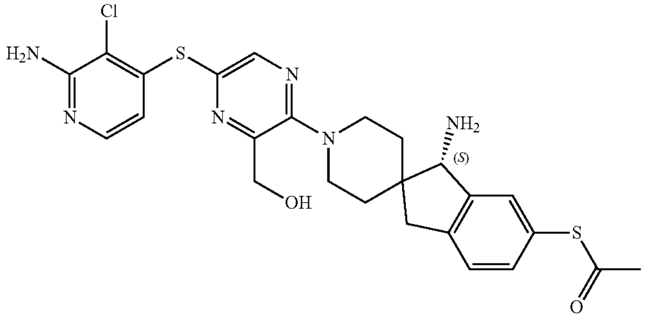 | 543.10 |
| 152 | 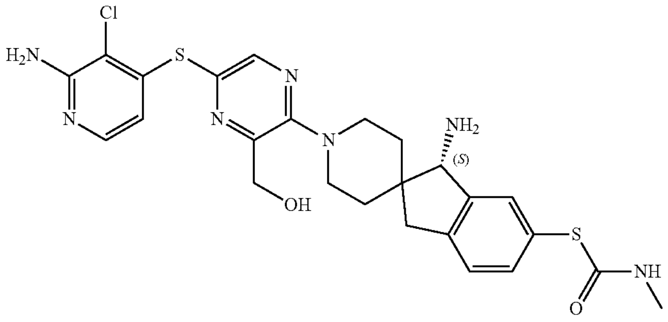 | 558.12 |

-continued

| Compounds | Structural formula | Molecular weight |
|---|---|---|
| 153 | 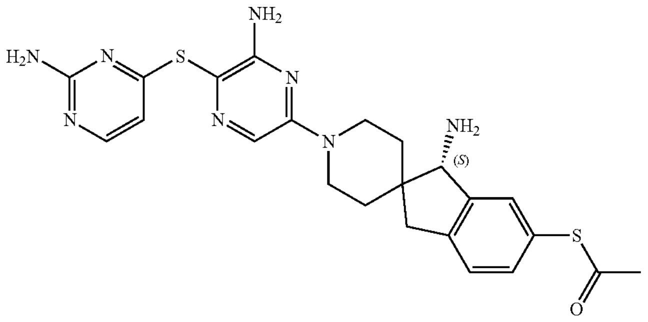 | 494.64 |
| 154 | 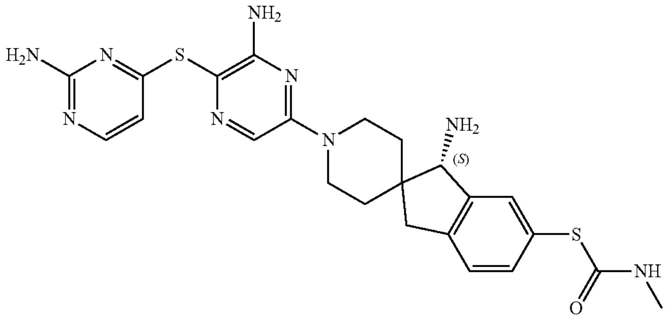 | 509.65 |
| 304 | 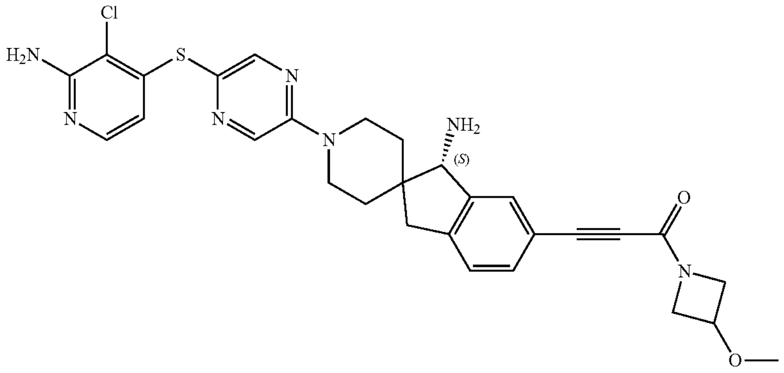 | 576.12 |
| 305 | 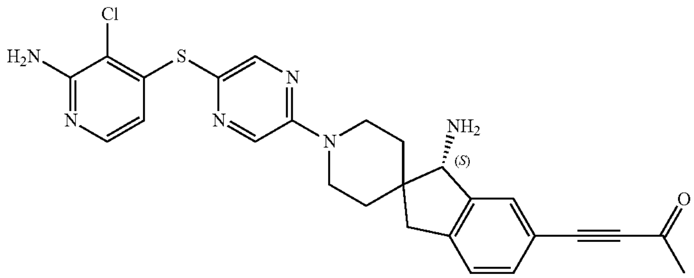 | 505.04 |

Example 2 Assay of Full-Length SHP2 Phosphatase Activity

1. Reagents and Materials
   - Human full-length SHP2 recombinant protein: BPS Bioscience, Cat #79018;
   - SHP2 substrate DiFMUP (1 mM): BPS Bioscience, Cat #79769;
   - SHP2 activating peptide (100 μM): BPS Bioscience, Cat #79319-2;
   - DTT: Merck, Cat #DTT-RO;
   - 384-well plate: Corning, Cat #3575;
   - 96-well plate: Thermo Fisher Scientific, Cat #249952;
   - Instrument: EnVision 2104, PerkinElmer.
2. Preparation of Reaction Solutions
   - The test compound was dissolved in DMSO and diluted with DMSO to 100.0 μM, and the compound was further 3-fold diluted with DMSO to: 100.00, 33.33, 11.11, 3.70, 1.23, 0.41, 0.14 and 0.05 μM. Then 4 μL of the compound at different dilution concentrations was added to 96 μL of an enzymatic reaction buffer to prepare a 4× test compound, wherein DMSO was at the concentration of 4% (DMSO was at the final concentration of 1%).

Preparation of 1× enzymatic reaction buffer: the 5× reaction buffer (250 mM HEPES, 500 mM NaCl, 2.5 mM EDTA, 0.005% Brij-35 and 0.01% BSA, pH 7.2) was diluted 5-fold with deionized water, and then DTT was added thereto so that the 1× enzymatic reaction buffer contained 5 mM DTT.

Preparation of 4× mixed solution of SHP2 enzyme/activating peptide: the SHP2 enzyme (75.5 nM) and activating peptide (100 μM) were diluted with the enzymatic reaction buffer to prepare a 4× mixed solution of SHP2 enzyme/activating peptide (0.12 nM SHP2 and 2 μM activating peptide), so that the SHP2 enzyme and activating peptide were at the final concentrations of 0.03 nM and 0.5 μM in the enzymatic reaction system, respectively.

Preparation of 2×DiFMUP substrate: 1 mM DiFMUP was diluted 100-fold with the enzymatic reaction buffer to prepare a 2× substrate (10 μM), so that the substrate DiFMUP was at the final concentration of 5 μM in the enzymatic reaction system.

3. Experimental Steps

To the corresponding wells of the 384-well plate was added 2.5 μL of 4× test compound or 2.5 μL of 4% DMSO solution, and centrifugation was carried out at 1000 rpm for 30 seconds.

To the test compound well and positive control well was added 2.5 μL of 4× mixed solution of SHP2 enzyme/activating peptide while to the negative control well was added 2.5 μL of 1× enzymatic reaction buffer; centrifugation was carried out at 1000 rpm for 30 seconds and incubation was carried out at room temperature for 30 minutes.

To each well was added 5 μL of 2×DiFMUP substrate to initiate the enzymatic reaction, then the plate was transiently oscillated and centrifuged at 1000 rpm for 30 seconds, and the 384-well plate was sealed with a sealing membrane and incubated at 25° C. on a low-speed shaker (100 rpm) in the dark for 60 minutes.

The fluorescence value (relative fluorescence units, RFU) of each well was detected on EnVision2104 (excitation: 355 nm, emission: 460 nm).

4. Data Analysis $$\text{Inhibition rate (\%)} = 100 - \frac{RFU \text{ of compound well} - RFU \text{ of negative control well}}{RFU \text{ of positive control well} - RFU \text{ of negative control well}} \times 100$$

wherein the RFU of compound well refers to the fluorescence reading at 460 nm of the well containing the test compounds;

the RFU of negative control well refers to the fluorescence reading at 460 nm of the background well containing 1% DMSO and the enzymatic reaction buffer;

the RFU of positive control well refers to the fluorescence reading at 460 nm of the well containing 1% DMSO and the mixed solution of SHP2 enzyme/activating peptide.

$IC_{50}$ values were calculated following formula 205: y=A+((B−A)/(1+((C/X)^D))), by using the XL-Fit 5.0 software.

5. Test Results

| Compound no. | $IC_{50}$ (μM) | Compound no. | $IC_{50}$ (μM) | Compound no. | $IC_{50}$ (μM) | Compound no. | $IC_{50}$ (μM) |
|---|---|---|---|---|---|---|---|
| 1 | 0.002 | 23 | 0.757 | 45 | 0.011 | 67 | 0.001 |
| 2 | 0.005 | 24 | 0.412 | 46 | 0.096 | 68 | 0.130 |
| 3 | 0.009 | 25 | 0.012 | 47 | 0.011 | 69 | 0.005 |
| 4 | 0.004 | 26 | 0.158 | 48 | 0.063 | 70 | 0.002 |
| 5 | 0.002 | 27 | 0.001 | 49 | 0.003 | 71 | 0.001 |
| 6 | 0.420 | 28 | >1 | 50 | 0.015 | 72 | 0.978 |
| 7 | 0.010 | 29 | 0.025 | 51 | 0.001 | 73 | 0.253 |
| 8 | 0.003 | 30 | 0.002 | 52 | <0.0005 | 74 | 0.004 |
| 9 | 0.004 | 31 | 0.005 | 53 | 0.018 | 75 | 0.002 |
| 10 | 0.035 | 32 | 0.001 | 54 | 0.003 | 76 | 0.002 |
| 11 | 0.097 | 33 | 0.310 | 55 | 0.026 | 77 | 0.005 |
| 12 | 0.001 | 34 | 0.004 | 56 | 0.002 | 78 | 0.003 |
| 13 | >1 | 35 | 0.017 | 57 | 0.028 | 79 | 0.001 |
| 14 | >1 | 36 | 0.006 | 58 | 0.013 | 80 | 0.004 |
| 15 | 0.008 | 37 | 0.044 | 59 | 0.248 | 81 | 0.002 |
| 16 | 0.004 | 38 | 0.046 | 60 | 0.013 | 82 | 0.002 |
| 17 | 0.018 | 39 | 0.021 | 61 | 0.003 | 83 | 0.001 |
| 18 | >1 | 40 | 0.002 | 62 | 0.005 | 84 | 0.067 |
| 19 | >1 | 41 | 0.021 | 63 | 0.004 | 85 | 0.050 |
| 20 | 0.012 | 42 | 0.006 | 64 | 0.184 | 86 | 0.002 |
| 21 | 0.541 | 43 | 0.006 | 65 | 0.002 | 87 | 0.001 |
| 22 | 0.348 | 44 | 0.060 | 66 | 0.024 | 88 | 0.0008 |
| 89 | 0.015 | 101 | 0.012 | 114 | 0.053 | 126 | 0.002 |
| 90 | 0.0011 | 102 | 0.002 | 115 | 0.002 | 127 | 0.0006 |
| 91 | 0.0007 | 103 | 0.017 | 116 | 0.0005 | 128 | 0.0009 |
| 92 | 0.011 | 104 | 0.004 | 117 | 0.002 | 129 | 0.0006 |
| 93 | 0.016 | 106 | 0.009 | 118 | 0.003 | 130 | >1.0 |
| 94 | 0.007 | 107 | 0.739 | 119 | 0.178 | 131 | 0.003 |
| 95 | 0.003 | 108 | 0.001 | 120 | 0.045 | 132 | 0.003 |
| 96 | 0.005 | 109 | 0.118 | 121 | >1.0 | 133 | 0.029 |
| 97 | 0.002 | 110 | 0.249 | 122 | 0.0006 | 134 | 0.0014 |
| 98 | 0.003 | 111 | 0.002 | 123 | 0.0006 | 135 | 0.005 |
| 99 | 0.002 | 112 | 0.002 | 124 | 0.0013 | 147 | 0.003 |
| 100 | 0.002 | 113 | 0.002 | 125 | 0.096 | 148 | 0.004 |

-continued

| Compound no. | $IC_{50}$ (μM) | Compound no. | $IC_{50}$ (μM) | Compound no. | $IC_{50}$ (μM) | Compound no. | $IC_{50}$ (μM) |
|---|---|---|---|---|---|---|---|
| 155 | 0.001 | 193 | 0.001 | 231 | <0.0005 | 269 | 0.0009 |
| 156 | 0.006 | 194 | 0.001 | 232 | 0.002 | 270 | 0.0004 |
| 157 | 0.002 | 195 | 0.001 | 233 | 0.0011 | 271 | 0.001 |
| 158 | 0.003 | 196 | 0.003 | 234 | 0.0028 | 272 | 0.017 |
| 159 | 0.001 | 197 | 0.003 | 235 | 0.0017 | 273 | 0.001 |
| 160 | 0.013 | 198 | 0.016 | 236 | 0.0013 | 274 | 0.001 |
| 161 | 0.001 | 199 | 0.001 | 237 | 0.0039 | 275 | 0.0005 |
| 162 | 0.034 | 200 | 0.025 | 238 | 0.0013 | 276 | 0.002 |
| 163 | 0.001 | 201 | 0.001 | 239 | 0.003 | 277 | 0.001 |
| 164 | 0.042 | 202 | 0.001 | 240 | 0.0015 | 278 | 0.005 |
| 165 | 0.006 | 203 | 0.002 | 241 | 0.0012 | 279 | 0.0004 |
| 166 | 0.006 | 204 | 0.006 | 242 | 0.0007 | 280 | 0.011 |
| 167 | 0.025 | 205 | 0.012 | 243 | 0.0007 | 281 | 0.010 |
| 168 | 0.010 | 206 | 0.003 | 244 | 0.011 | 282 | 0.001 |
| 169 | 0.006 | 207 | 0.002 | 245 | <0.0005 | 283 | 0.001 |
| 170 | 0.009 | 208 | 0.058 | 246 | 0.133 | 284 | 0.002 |
| 171 | 0.006 | 209 | 0.001 | 247 | 0.001 | 285 | 0.085 |
| 172 | 0.001 | 210 | 0.052 | 248 | <0.0005 | 286 | 0.002 |
| 173 | 0.001 | 211 | 0.017 | 249 | 0.001 | 287 | 0.012 |
| 174 | 0.006 | 212 | 0.023 | 250 | 0.001 | 288 | 0.002 |
| 175 | 0.014 | 213 | 0.068 | 251 | 0.001 | 289 | 0.002 |
| 176 | 0.038 | 214 | 0.004 | 252 | 0.001 | 290 | 0.001 |
| 177 | 0.002 | 215 | 0.025 | 253 | 0.001 | 291 | 0.001 |
| 178 | 0.002 | 216 | 0.001 | 254 | 0.003 | 292 | 0.0009 |
| 179 | 0.004 | 217 | 0.001 | 255 | 0.003 | 293 | 0.001 |
| 180 | 0.013 | 218 | 0.104 | 256 | 0.004 | 294 | 0.001 |
| 181 | 0.044 | 219 | 0.003 | 257 | <0.0005 | 295 | 0.002 |
| 182 | 0.001 | 220 | 0.317 | 258 | 0.010 | 296 | 0.0003 |
| 183 | 0.002 | 221 | 0.001 | 259 | 0.004 | 297 | 0.0003 |
| 184 | 0.003 | 222 | 0.004 | 260 | 0.001 | 298 | 0.0003 |
| 185 | 0.014 | 223 | 0.004 | 261 | 0.0009 | 299 | 0.001 |
| 186 | 0.042 | 224 | 0.009 | 262 | 0.0003 | 300 | 0.001 |
| 187 | 0.001 | 225 | 0.002 | 263 | 0.009 | 301 | 0.0004 |
| 188 | 0.005 | 226 | 0.001 | 264 | 0.0006 | 302 | 0.0004 |
| 189 | 0.001 | 227 | 0.001 | 265 | 0.0004 | 303 | 0.0005 |
| 190 | 0.253 | 228 | 0.203 | 266 | 0.005 | | |
| 191 | 0.001 | 229 | 0.001 | 267 | >0.1 | | |
| 192 | >1.0 | 230 | 0.010 | 268 | 0.001 | | |

Example 3 Assay of Intracellular pERK1/2 (Thr202/Tyr204) Phosphorylation

1. Reagents and Materials
   - pERK1/2 (Thr202/Tyr204) HTRF kit: Cisbio, Cat #64ERKPEH;
   - Cell line: Miapaca2, ATCC, CRL-1420;
   - OptiPlate™-384-well plate: PerkinElmer, Cat #6007299;
   - 96-well plate: Corning, Cat #353072;
   - Instrument: EnVision2104, PerkinElmer.
2. Preparation of Reaction Solutions
   - The test compound was dissolved in DMSO and diluted with DMSO to 600.0 μM, and the compound was further 3-fold diluted with DMSO to: 600.0, 200.0, 66.7, 22.2, 7.4, 2.5, 0.82 and 0.27 μM. Then 10 μL of the compound at different dilution concentrations was added to 190 μL of a DMEM medium to prepare a 10× test compound, wherein DMSO was at the concentration of 5% (DMSO was at the final concentration of 0.5%).
   - 1× cell lysis buffer: 4× cell lysis stock solution (provided by the kit) was diluted 4-fold with deionized water, and then 1% 100× blocking stock solution (provided by the kit) was added thereto.
   - pERK1/2 detection solution (prepared just before use): the pERK1/2 d2 antibody (provided by the kit) and pERK1/2 Cryptate antibody (provided by the kit) were diluted with the detection solution (provided by the kit) at a ratio of 1:1:38.
3. Experimental Steps
   - Miapaca2 cells were inoculated into a 96-well plate at a density of 10000 cells/well at 90 μL/well and cultured in a cell incubator at 5% $CO_2$ and 37° C. overnight.
   - 10 μL of 10× test compound was added to the 90 μL cell culture 96-well plate; to the cell positive control well was added 10 μL of 5% DMSO culture solution; and the plate was cultured in a cell incubator at 5% $CO_2$ and 37° C. for 2 hours.
   - The medium in the 96-well plate was removed; 50 μL of 1× cell lysis buffer was added to each well; the plate was placed in a microplate shaker; and lysis under shaking was carried out at 900 rpm at room temperature for 1 hour.
   - 16 μL of the lysis buffer in the 96-well plate was taken and transferred to a 384-well plate, and centrifugation was carried out at 1000 rpm for 30 seconds; then 4 μL of pERK1/2 detection solution was added to each well and centrifugation was carried out at 1000 rpm for 30 seconds; and the 384-well plate was sealed with a sealing membrane and incubated at 25° C. on a low-speed shaker (100 rpm) in the dark for 2 hours.
   - The fluorescence value (relative fluorescence units, RFU) of each well was detected on EnVision2104 (emission 1: 665 nm, emission 2: 615 nm).

4. Data Analysis $$\text{Fluorescence ratio} = \frac{RFU_{665\,nm}}{RFU_{615\,nm}}$$

$$\text{Inhibition rate (\%)} = 100 - \frac{\text{Fluorescence ratio of compound well} - \text{fluorescence ratio of negative control well}}{\text{Fluorescence ratio of positive control well} - \text{fluorescence ratio of negative control well}} \times 100$$

wherein the fluorescence ratio of compound well refers to the fluorescence ratio of the well containing the test compounds;

the fluorescence ratio of negative control well refers to the fluorescence ratio of the background containing the cell lysis buffer and no Miapaca2 cells;

the fluorescence ratio of positive control well refers to the fluorescence ratio of the well containing 0.5% DMSO and Miapaca2 cells.

$IC_{50}$ values were calculated following formula 205: y=A+((B−A)/(1+((C/X)^D))), by using the XL-Fit 5.0 software.

5. Test Results

| Compound no. | $IC_{50}$ (μM) | Compound no. | $IC_{50}$ (μM) | Compound no. | $IC_{50}$ (μM) | Compound no. | $IC_{50}$ (μM) |
|---|---|---|---|---|---|---|---|
| 1 | 0.018 | 32 | 0.006 | 55 | 0.388 | 78 | 0.043 |
| 2 | 0.023 | 34 | 0.244 | 56 | 0.085 | 79 | 0.060 |
| 3 | 0.081 | 35 | 0.274 | 57 | 0.526 | 80 | 0.125 |
| 4 | 0.160 | 36 | 0.033 | 58 | 0.260 | 81 | 0.089 |
| 5 | 0.023 | 37 | 0.599 | 60 | >1.0 | 82 | 0.043 |
| 6 | >3 | 38 | 0.343 | 61 | 0.078 | 83 | 0.057 |
| 7 | 0.028 | 39 | 0.294 | 62 | 0.105 | 84 | >1 |
| 8 | 0.008 | 40 | 0.006 | 63 | 0.177 | 85 | 0.785 |
| 9 | 0.038 | 41 | 0.115 | 64 | 0.891 | 86 | 0.006 |
| 10 | 0.220 | 42 | 0.133 | 65 | 0.060 | 87 | 0.002 |
| 11 | 1.148 | 43 | 0.117 | 66 | 0.271 | 88 | 0.026 |
| 12 | 0.007 | 44 | 0.415 | 67 | 0.039 | 89 | 0.153 |
| 15 | 0.087 | 45 | 0.261 | 68 | 0.510 | 90 | 0.053 |
| 16 | 0.034 | 46 | 0.648 | 69 | 0.066 | 91 | 0.017 |
| 17 | 0.203 | 47 | 0.115 | 70 | 0.141 | 92 | 0.117 |
| 20 | 0.052 | 48 | 0.231 | 71 | 0.022 | 93 | 0.301 |
| 25 | 0.151 | 49 | 0.018 | 72 | >1.0 | 94 | 0.155 |
| 26 | >3 | 50 | 0.318 | 73 | >1.0 | 95 | 0.002 |
| 27 | 0.011 | 51 | 0.021 | 74 | 0.223 | 96 | 0.055 |
| 29 | 0.489 | 52 | 0.037 | 75 | 0.046 | 97 | 0.011 |
| 30 | 0.008 | 53 | 0.364 | 76 | 0.004 | 98 | 0.020 |
| 31 | 0.037 | 54 | 0.036 | 77 | 0.056 | 99 | 0.040 |
| 100 | 0.012 | 108 | 0.007 | 115 | 0.026 | 122 | 0.007 |
| 101 | 0.096 | 109 | 0.259 | 116 | 0.001 | 123 | 0.004 |
| 102 | 0.012 | 110 | 0.959 | 117 | 0.024 | 124 | 0.015 |
| 103 | 0.080 | 111 | 0.015 | 118 | 0.040 | 125 | 0.175 |
| 104 | 0.040 | 112 | 0.006 | 119 | 0.698 | 126 | 0.042 |
| 106 | 0.084 | 113 | 0.014 | 120 | 0.385 | 127 | 0.013 |
| 107 | >1.0 | 114 | 0.284 | 121 | >1.0 | 128 | 0.015 |
| 129 | 0.003 | 131 | 0.004 | 132 | 0.009 | 133 | 0.147 |
| 134 | 0.005 | 135 | 0.056 | 147 | 0.010 | 148 | 0.013 |
| 155 | 0.002 | 193 | 0.024 | 231 | 0.007 | 269 | 0.007 |
| 156 | 0.010 | 194 | 0.018 | 232 | 0.008 | 270 | 0.002 |
| 157 | 0.025 | 195 | 0.011 | 233 | 0.014 | 271 | 0.004 |
| 158 | 0.031 | 196 | 0.008 | 234 | 0.153 | 272 | 0.252 |
| 159 | 0.005 | 197 | 0.029 | 235 | 0.009 | 273 | 0.005 |
| 160 | 0.056 | 198 | 0.191 | 236 | 0.003 | 274 | 0.006 |
| 161 | 0.013 | 199 | 0.005 | 237 | 0.004 | 275 | 0.002 |
| 162 | 0.155 | 200 | 0.512 | 238 | 0.004 | 276 | 0.004 |
| 163 | 0.014 | 201 | 0.006 | 239 | 0.015 | 277 | 0.011 |
| 164 | 0.154 | 202 | 0.040 | 240 | 0.018 | 278 | 0.034 |
| 165 | 0.039 | 203 | 0.007 | 241 | 0.010 | 279 | 0.183 |
| 166 | 0.038 | 204 | 0.054 | 242 | 0.013 | 280 | 0.035 |
| 167 | 0.124 | 205 | 0.029 | 243 | 0.019 | 281 | 0.167 |
| 168 | 0.034 | 206 | 0.069 | 244 | 0.139 | 282 | 0.003 |
| 169 | 0.125 | 207 | 0.009 | 245 | 0.012 | 283 | 0.737 |
| 170 | 0.143 | 208 | 0.187 | 246 | 0.688 | 284 | 0.005 |
| 171 | 0.038 | 209 | 0.019 | 247 | 0.003 | 285 | 0.962 |
| 172 | 0.008 | 210 | 0.527 | 248 | 0.002 | 286 | 0.010 |
| 173 | 0.018 | 211 | 0.161 | 249 | 0.031 | 287 | 0.140 |
| 174 | 0.033 | 212 | 0.223 | 250 | 0.072 | 288 | 0.004 |
| 175 | 0.122 | 213 | 0.447 | 251 | 0.024 | 289 | 0.004 |
| 176 | 0.041 | 214 | 0.100 | 252 | 0.003 | 290 | 0.004 |
| 177 | 0.007 | 215 | 0.167 | 253 | 0.010 | 291 | 0.009 |
| 178 | 0.048 | 216 | 0.045 | 254 | 0.011 | 292 | 0.006 |
| 179 | 0.112 | 217 | 0.049 | 255 | 0.008 | 293 | 0.005 |
| 180 | 0.251 | 218 | 0.944 | 256 | 0.012 | 294 | 0.018 |
| 181 | 0.447 | 219 | 0.007 | 257 | 0.001 | 295 | 0.022 |
| 182 | 0.023 | 220 | >1 | 258 | 0.188 | 296 | 0.002 |
| 183 | 0.050 | 221 | 0.015 | 259 | 0.023 | 297 | 0.001 |
| 184 | 0.067 | 222 | 0.006 | 260 | 0.005 | 298 | 0.001 |

-continued

| Compound no. | $IC_{50}$ (μM) | Compound no. | $IC_{50}$ (μM) | Compound no. | $IC_{50}$ (μM) | Compound no. | $IC_{50}$ (μM) |
|---|---|---|---|---|---|---|---|
| 185 | >1.0 | 223 | 0.023 | 261 | 0.007 | 299 | 0.002 |
| 186 | >1.0 | 224 | 0.020 | 262 | 0.007 | 300 | 0.013 |
| 187 | 0.003 | 225 | 0.006 | 263 | 0.204 | 301 | 0.005 |
| 188 | 0.014 | 226 | 0.002 | 264 | 0.002 | 302 | 0.005 |
| 189 | 0.007 | 227 | 0.002 | 265 | 0.0009 | 303 | 0.009 |
| 190 | 0.672 | 228 | >1 | 266 | 0.026 | | |
| 191 | 0.021 | 229 | 0.002 | 267 | >1 | | |
| 192 | >1.0 | 230 | 0.031 | 268 | 0.063 | | |

Example 4 Assay of Cell Proliferation on Miapaca2 3D Spheroids

1. Reagents and Materials

CellTiter-Glo® 3D Cell Viability Assay Kit: Promega, Cat #G9683;

CellCarrier Spheroid ULA 96-well plate: Corning, Cat #4515;

Instrument: Envision, Perkinelmer;

Cell line: Miapaca2, ATCC, Cat #CRL-1420.

2. Preparation of Reaction Solutions

The test compound was dissolved in DMSO and diluted with DMSO to 3000.0 μM, and the compound was further 3-fold diluted with DMSO to: 1000.0, 333.3, 111.1, 37.0, 12.3, 4.1, and 1.4 μM. Then 2 μL of the compound at different dilution concentrations was added to 198 μL of a 1640 medium to prepare a 10× test compound, wherein DMSO was at the concentration of 1% (DMSO was at the final concentration of 0.1%).

3. Experimental Methods

Day0: Digest cells and count cell numbers. Miapaca2 cells were inoculated into a spheroid ULA 96-well plate at a density of 300 cells/well at 100 μL/well and cultured in a cell incubator at 5% $CO_2$ and 37° C.

Day2: The cell spheroids formed at day2. Add 10 μL of 10× test compounds to the 96-well plate. To the cell positive control well was added 10 μL of 1% DMSO 1640 medium. Incubate the cell spheroids in a cell incubator at 5% $CO_2$ and 37° C. for additional 5 days.

Cell viability assay: Add 50 μL of CellTiter-Glo reagent to each well, place the plate in a microplate shaker, and lysis under shaking at 900 rpm at room temperature for 5 minutes. Then incubate the plate at room temperature in the dark for 30 minutes.

The luminescene of each well was detected on Envision2104.

4. Data Analysis $$\text{Cell Survial }\%=(Lum(d7\text{ treatment})-Lum(d2\text{ cell}))/(Lum(d7\text{ cell})-Lum(d2\text{ cell}))\times 100$$

Wherein:

Lum(d7 treatment) refers to the luminescene of the test compound treated cells on day7;

Lum(d2 cell) refers to the luminescene of the 0.1% DMSO treated Miapaca2 cells on day2;

Lum(d7 cell) refers to the luminescene of the 0.1% DMSO treated Miapaca2 cells on day7.

$IC_{50}$ values were calculated following formula 205: y=A+((B−A)/(1+((C/X)^D))), by using the XL-Fit 5.0 software.

5. Test Results

| Compound no. | $IC_{50}$ (μM) |
|---|---|
| 135 | 0.095 |
| 147 | 0.048 |
| 148 | 0.047 |
| 155 | 0.0009 |
| 156 | 0.031 |
| 157 | 0.028 |
| 158 | 0.032 |
| 159 | 0.006 |
| 160 | 0.041 |
| 161 | 0.008 |
| 163 | 0.020 |
| 165 | 0.071 |
| 166 | 0.110 |
| 168 | 0.077 |
| 170 | 0.162 |
| 171 | 0.039 |
| 172 | 0.009 |
| 173 | 0.024 |
| 174 | 0.053 |
| 175 | 0.100 |
| 176 | 0.097 |
| 177 | 0.004 |
| 178 | 0.041 |
| 179 | 0.065 |
| 182 | 0.018 |
| 183 | 0.068 |
| 184 | 0.096 |
| 187 | 0.003 |
| 188 | 0.047 |
| 189 | 0.015 |
| 191 | 0.058 |
| 193 | 0.090 |
| 194 | 0.036 |
| 195 | 0.030 |
| 196 | 0.021 |
| 197 | 0.038 |
| 199 | 0.012 |
| 201 | 0.018 |
| 202 | 0.046 |
| 203 | 0.016 |
| 204 | 0.121 |
| 205 | 0.068 |
| 206 | 0.078 |
| 207 | 0.035 |
| 209 | 0.038 |
| 216 | 0.028 |
| 217 | 0.062 |
| 219 | 0.006 |
| 221 | 0.063 |
| 222 | 0.015 |
| 225 | 0.002 |
| 226 | 0.0004 |
| 227 | 0.0004 |
| 229 | 0.0005 |
| 230 | 0.0074 |
| 231 | 0.0008 |
| 232 | 0.0009 |
| 233 | 0.0032 |
| 235 | 0.0009 |
| 236 | 0.001 |

-continued

| Compound no. | $IC_{50}$ (μM) |
|---|---|
| 237 | 0.0024 |
| 238 | 0.001 |
| 239 | 0.0021 |
| 240 | 0.005 |
| 241 | 0.0038 |
| 242 | 0.002 |
| 243 | 0.015 |
| 244 | 0.041 |
| 245 | 0.017 |
| 247 | 0.001 |
| 248 | 0.0004 |
| 249 | 0.019 |
| 250 | 0.014 |
| 251 | 0.029 |
| 252 | 0.001 |
| 253 | 0.002 |
| 254 | 0.010 |
| 255 | 0.003 |
| 256 | 0.006 |
| 257 | 0.0003 |
| 259 | 0.005 |
| 260 | 0.002 |
| 261 | 0.002 |
| 262 | 0.001 |
| 264 | 0.0004 |
| 265 | 0.0004 |
| 266 | 0.010 |
| 268 | 0.017 |
| 269 | 0.003 |
| 270 | 0.0006 |
| 271 | 0.002 |
| 273 | 0.002 |
| 274 | 0.003 |
| 275 | 0.002 |
| 276 | 0.003 |
| 277 | 0.005 |
| 278 | 0.016 |
| 279 | 0.042 |
| 280 | 0.035 |
| 281 | 0.024 |
| 282 | 0.002 |
| 283 | 0.243 |
| 284 | 0.004 |
| 286 | 0.009 |
| 288 | 0.002 |
| 289 | 0.002 |
| 290 | 0.0003 |
| 291 | 0.0003 |
| 292 | 0.001 |
| 293 | 0.0009 |
| 294 | 0.009 |
| 295 | 0.004 |
| 296 | 0.0007 |
| 297 | 0.0003 |
| 298 | 0.0003 |
| 299 | 0.001 |
| 300 | 0.016 |
| 301 | 0.001 |
| 302 | 0.001 |

The invention claimed is:

1. A compound of formula (V):

(V)

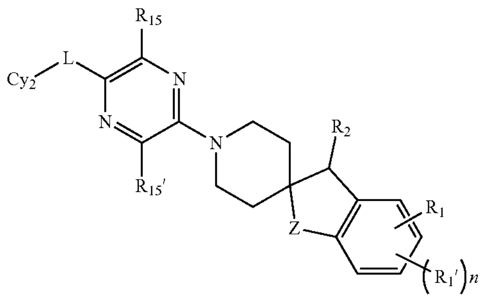

or a pharmaceutically acceptable salt thereof, or a solvate, a racemic mixture, an enantiomer, a diastereomer or a tautomer thereof, wherein:

Z is $CH_2$ or O;

$R_1$ is $C_{2-6}$ alkynyl, wherein the $C_{2-6}$ alkynyl is optionally substituted with one or more groups independently chosen from: —O($C_{1-6}$ alkyl), —$NHCONH_2$, —CON$R_aR_b$, —$COOR_c$ and —$COR_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), —($C_{1-6}$ alkyl)-OH, $C_{3-8}$ cycloalkyl and 4-8 membered heterocyclyl; and the above-mentioned 4-8 membered heterocyclyl is each optionally substituted with —O($C_{1-6}$ alkyl);

$R_1'$ is halogen, and n is 0 or 1;

$R_2$ is —$NH_2$;

$R_{15}$ and $R_{15}'$ are each independently chosen from hydrogen, —$NH_2$, —CN, halogen, $C_{1-6}$ alkyl, and —($C_{1-6}$ alkyl)-OH;

$Cy_2$ is pyridyl, pyrimidyl, or 1,2,3,4-tetrahydro-1,5-naphthyridinyl, each of which is optionally substituted with one or more groups independently chosen from: halogen, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are hydrogen; and L is absent, or L is S.

2. The compound or the pharmaceutically acceptable salt thereof, or the solvate, the racemic mixture, the enantiomer, the diastereomer or the tautomer thereof according to claim 1, wherein $Cy_2$ is chosen from

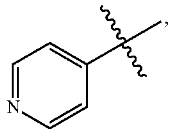,
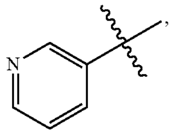,
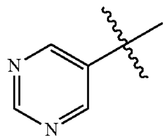
and
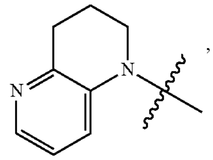, each of which is optionally substituted with one or more groups independently chosen from: halogen, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are hydrogen.

3. The compound or the pharmaceutically acceptable salt thereof, or the solvate, the racemic mixture, the enantiomer, the diastereomer or the tautomer thereof according to claim 2, wherein $Cy_2$ is

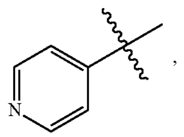

which is optionally substituted with one or more groups independently chosen from: halogen, $C_{1-6}$ alkyl, —O($C_{1-6}$ alkyl) and —$NR_7R_8$, wherein both $R_7$ and $R_8$ are hydrogen; or $Cy_2$ is

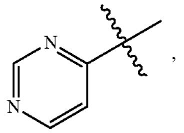 [SMILES: *c1ccncn1]

which is optionally substituted with one or more groups independently chosen from: $C_{1-6}$ alkyl and —$NR_7R_8$, wherein both $R_7$ and $R_8$ are hydrogen.

4. The compound or the pharmaceutically acceptable salt thereof, or the solvate, the racemic mixture, the enantiomer, the diastereomer or the tautomer thereof according to claim 1, which is chosen from:

| No. | Structural formula |
|---|---|
| 28 | 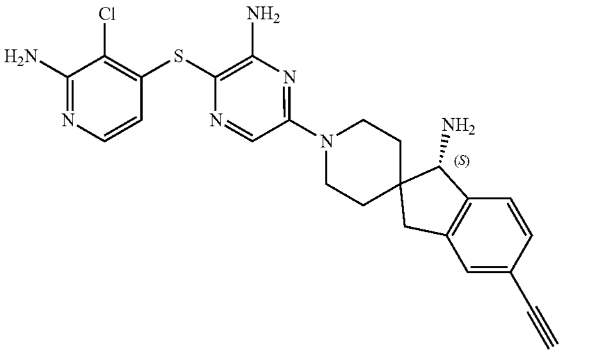 |
| 6 | 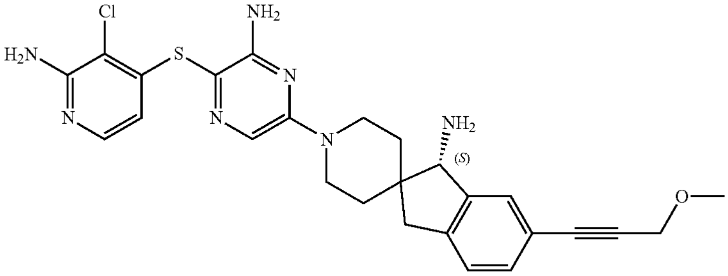 |
| 87 | 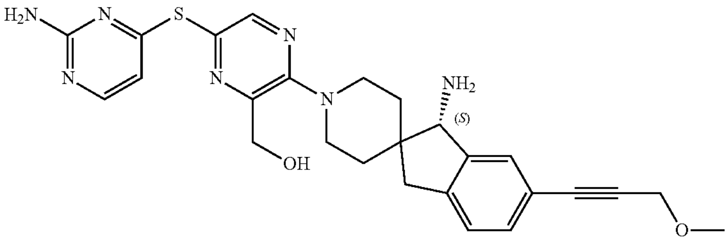 |
| 95 | 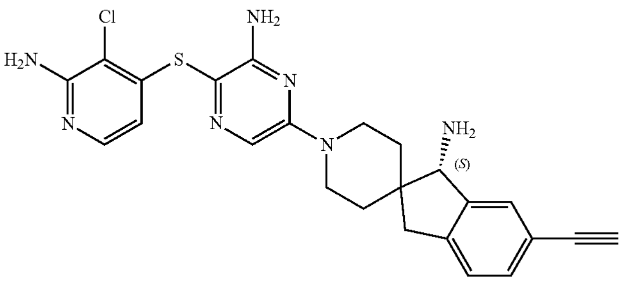 |

-continued
| No. | Structural formula |
|---|---|
| 112 | 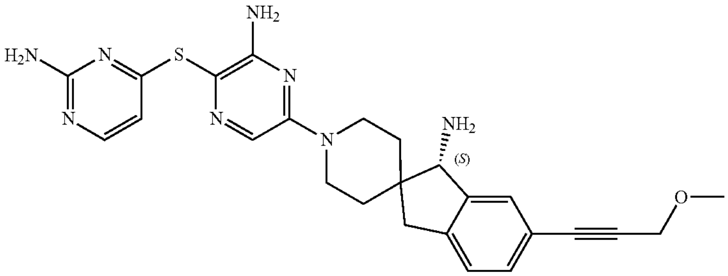 |
| 116 | 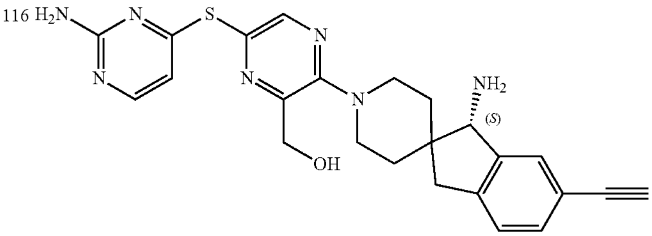 |
| 122 | 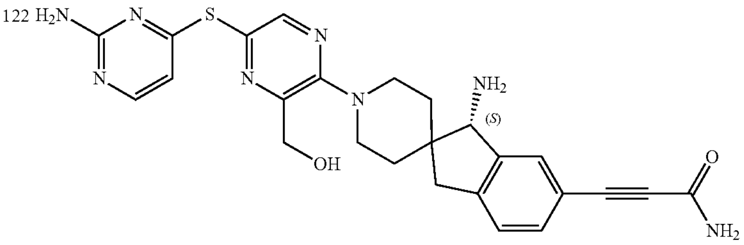 |
| 123 | 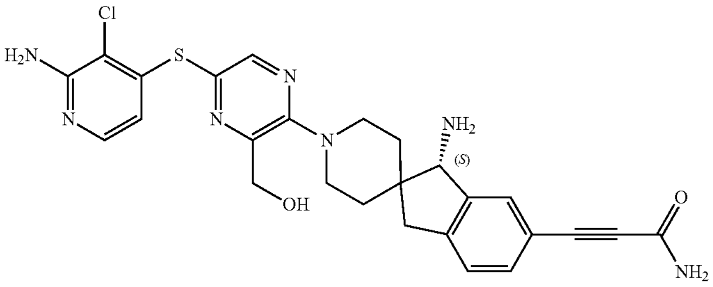 |
| 126 | 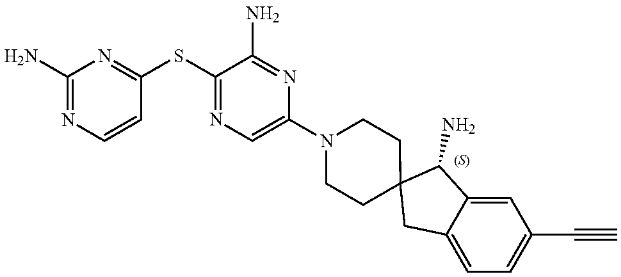 |

-continued
| No. | Structural formula |
|---|---|
| 129 | 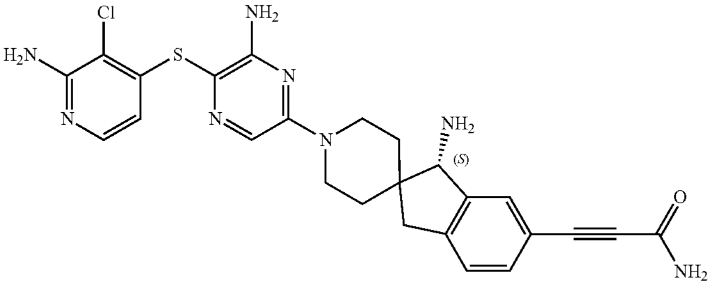 |
| 131 | 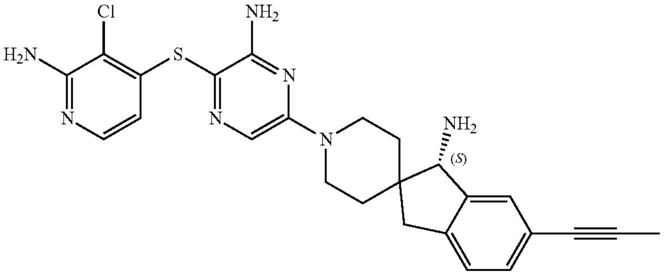 |
| 134 | 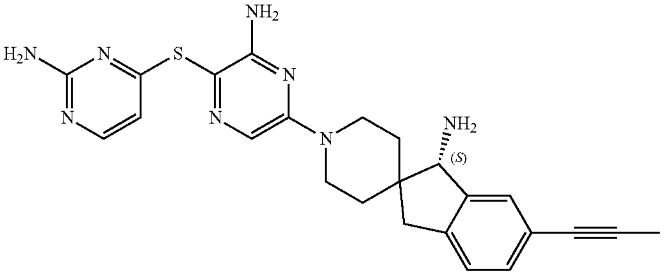 |
| 155 | 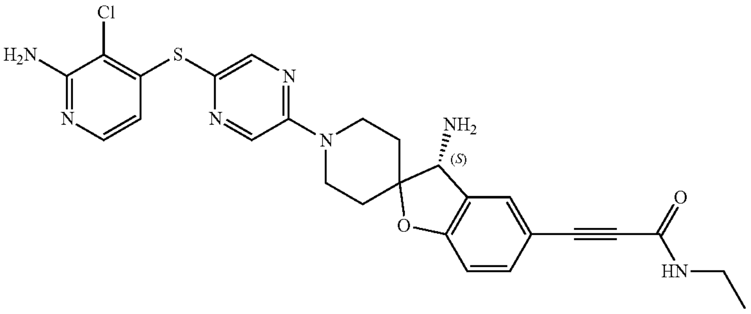 |
| 159 | 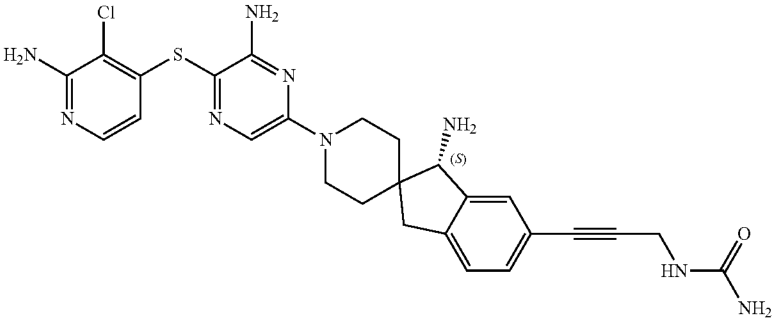 |

-continued
| No. Structural formula |
|---|
| 187 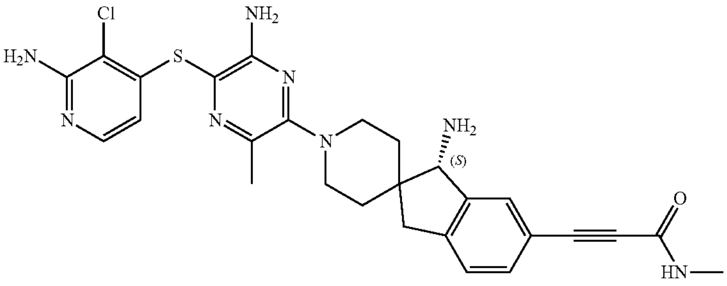 |
| 188 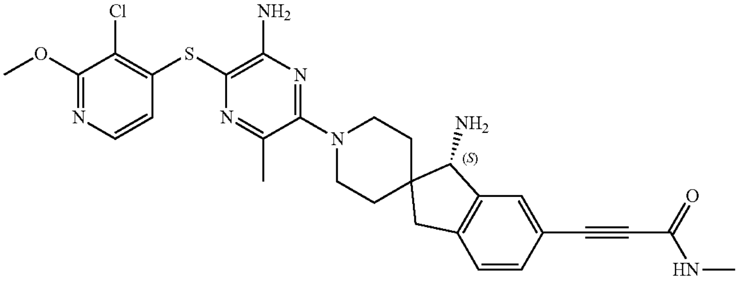 |
| 189 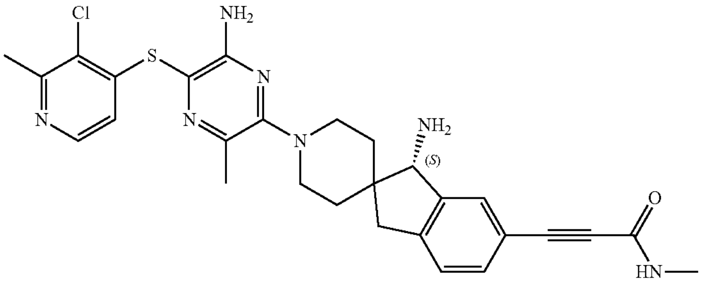 |
| 199 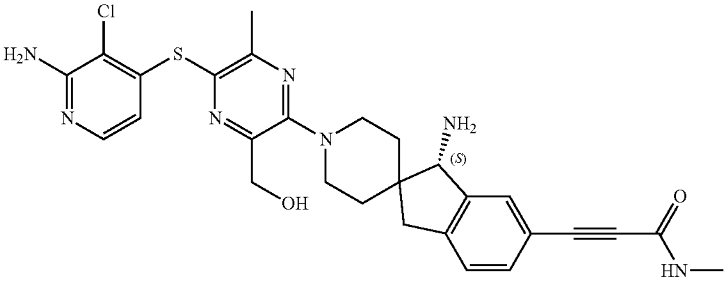 |
| 203 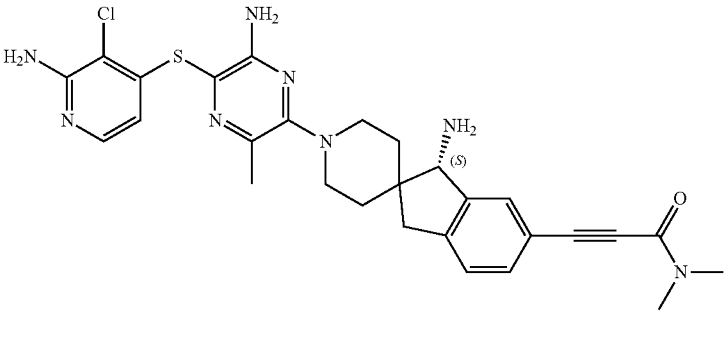 |

-continued
| No. | Structural formula |
| --- | --- |
| 204 | 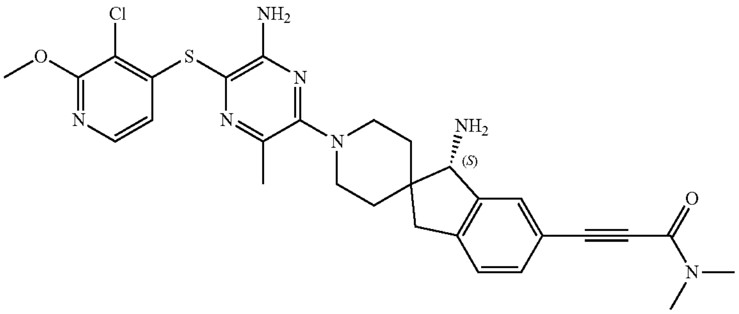 |
| 216 | 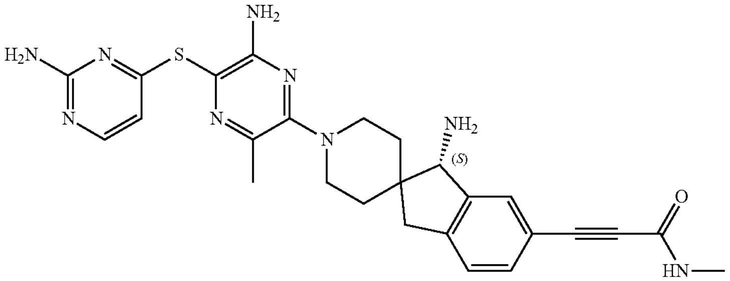 |
| 219 | 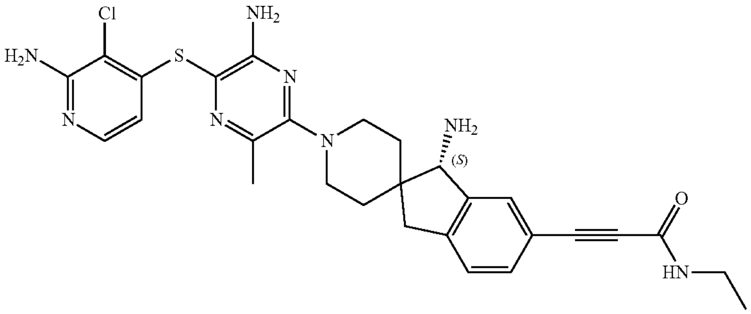 |
| 222 | 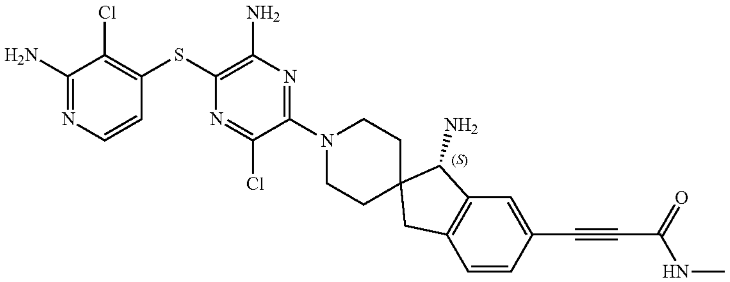 |
| 223 | 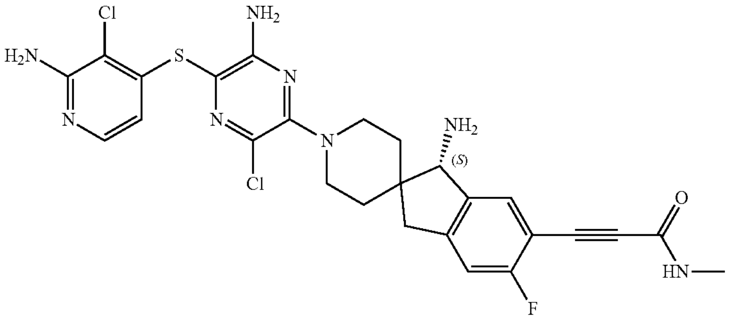 |

-continued
| No. | Structural formula |
|---|---|
| 224 | 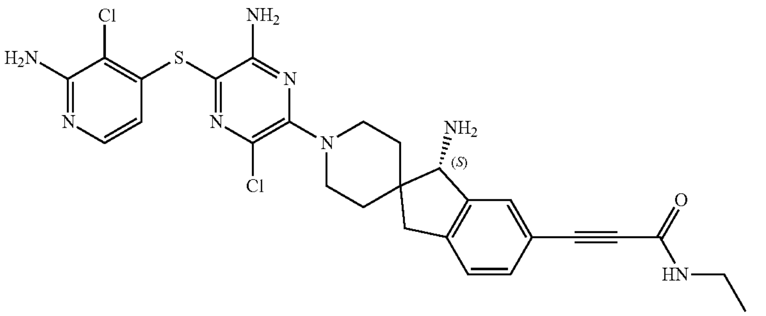 |
| 225 | 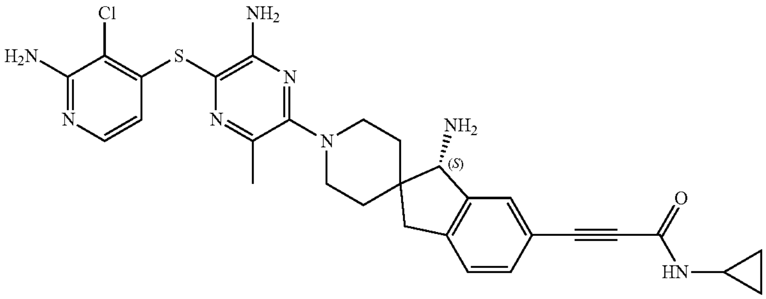 |
| 226 | 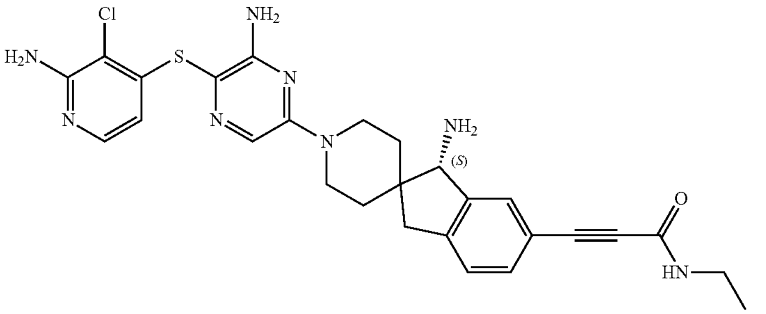 |
| 227 | 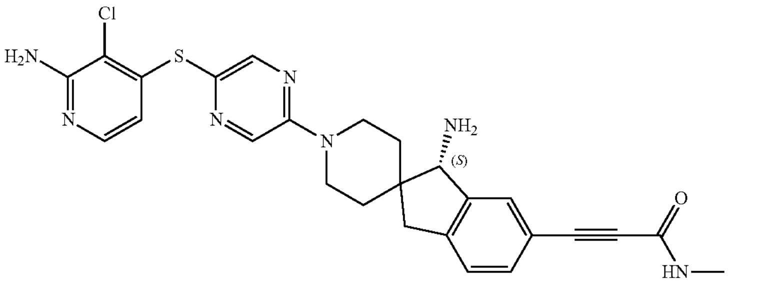 |
| 229 | 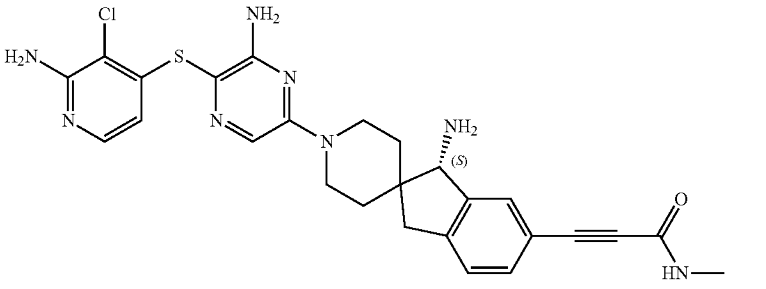 |

-continued
| No. | Structural formula |
|---|---|
| 230 | 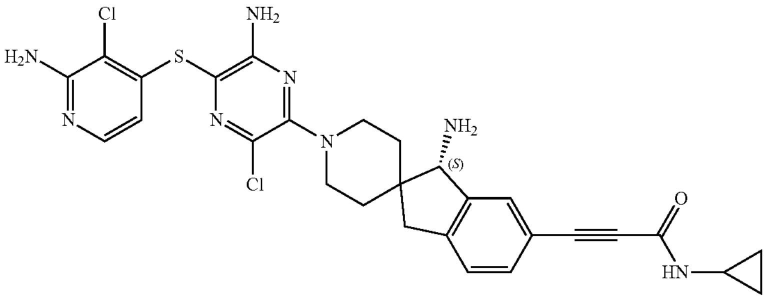 |
| 231 | 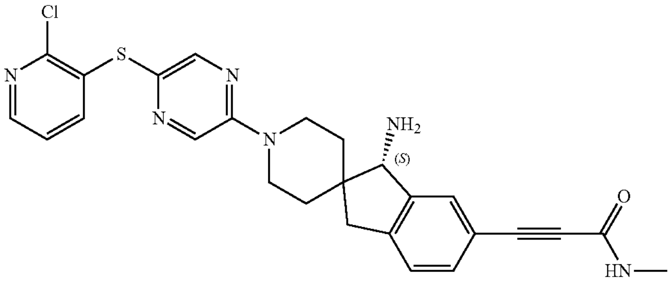 |
| 232 | 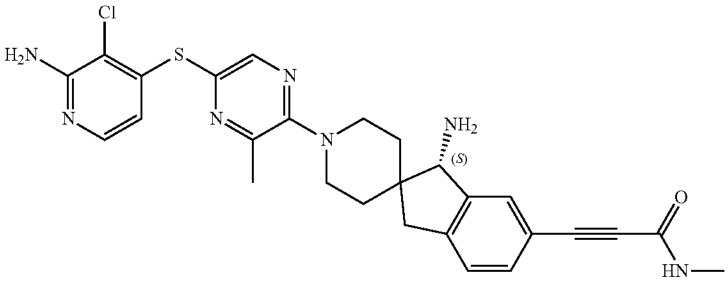 |
| 233 | 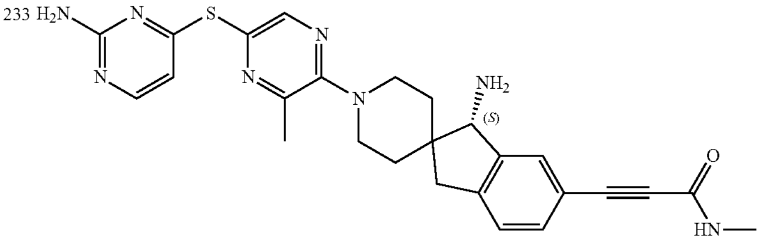 |
| 236 | 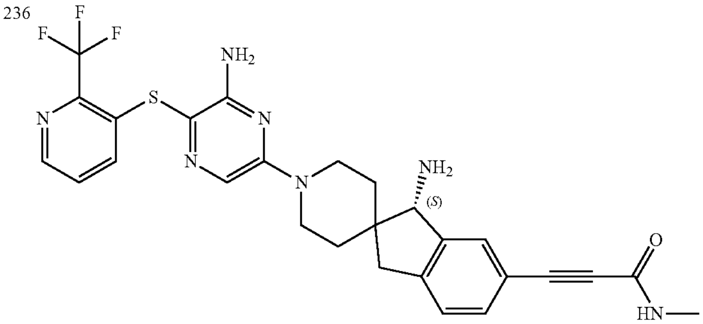 |

-continued
No. Structural formula
235
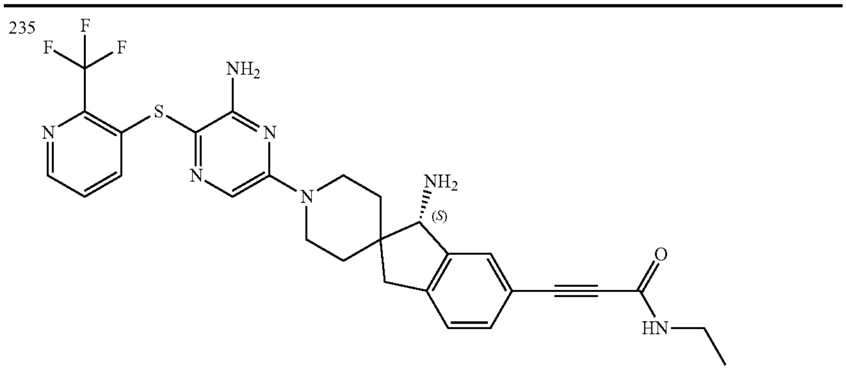
238
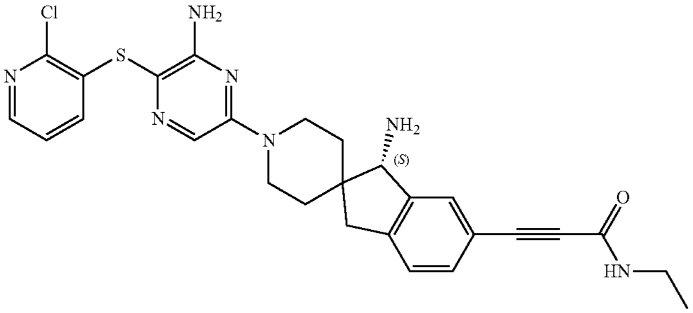
237
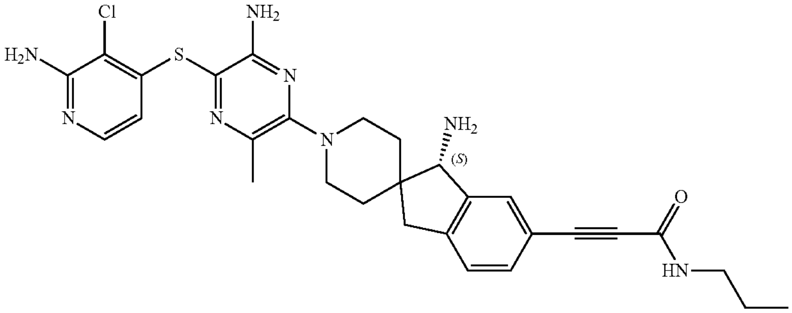
240
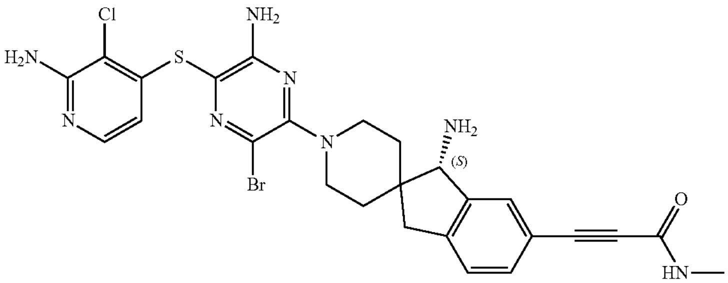
239
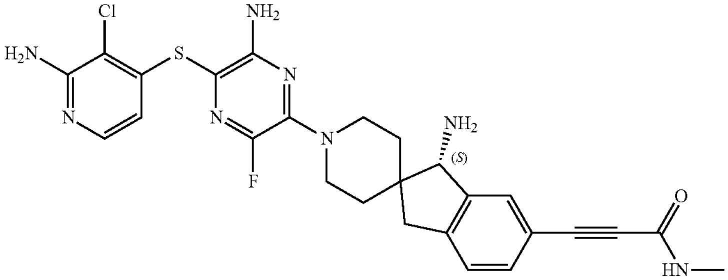

-continued
No. Structural formula
242
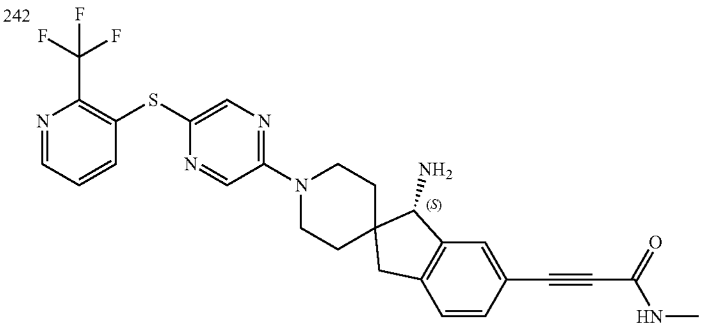
241
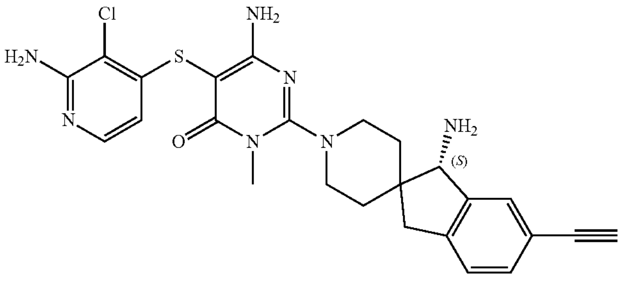
243
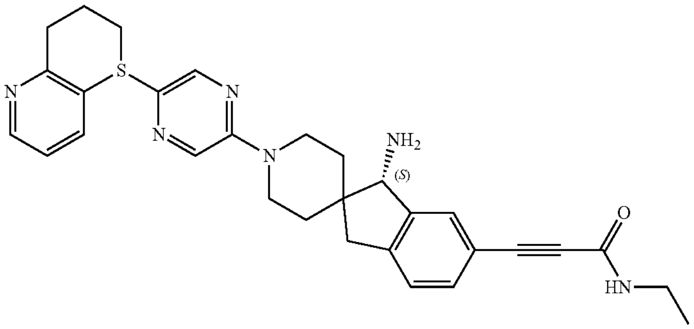
247
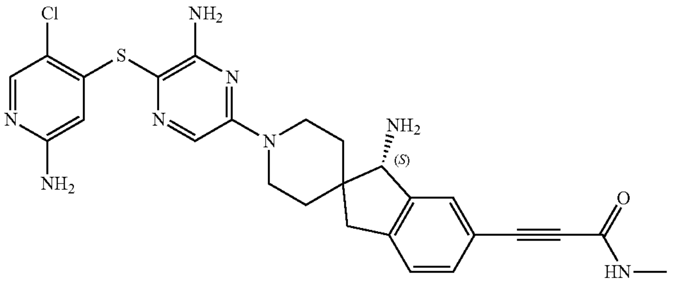
248
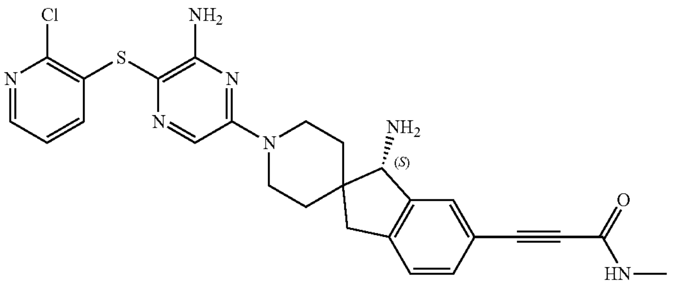

-continued
| No. | Structural formula |
|---|---|
| 251 | 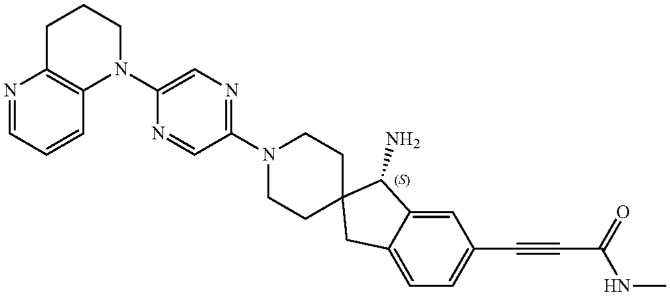 |
| 252 | 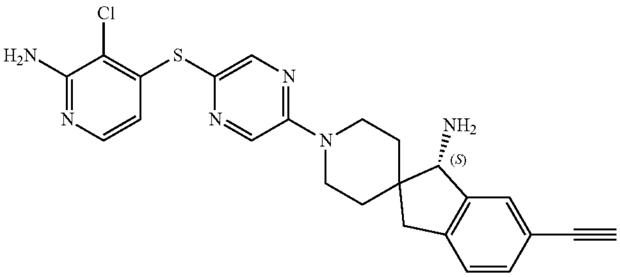 |
| 253 | 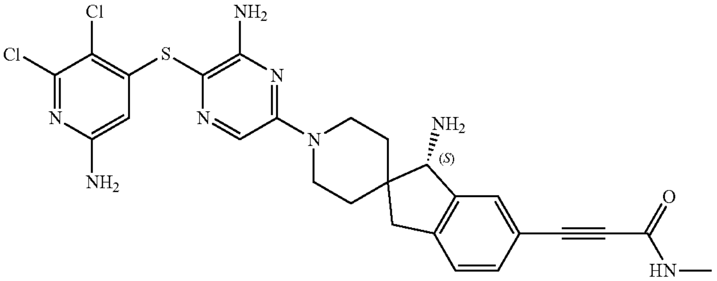 |
| 254 | 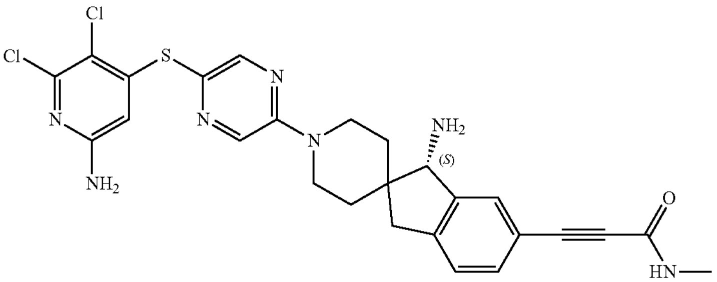 |
| 255 | 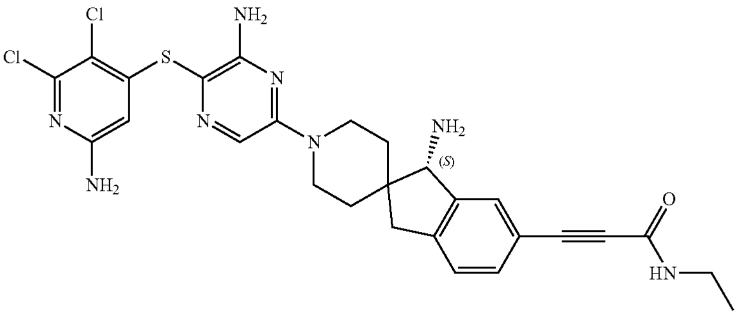 |

-continued
| No. | Structural formula |
|---|---|
| 256 | 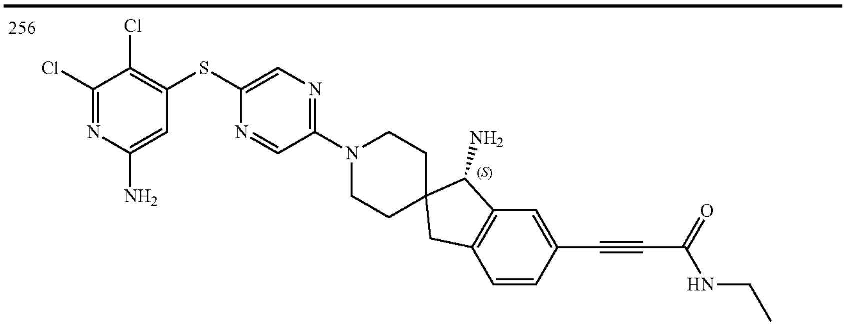 |
| 257 | 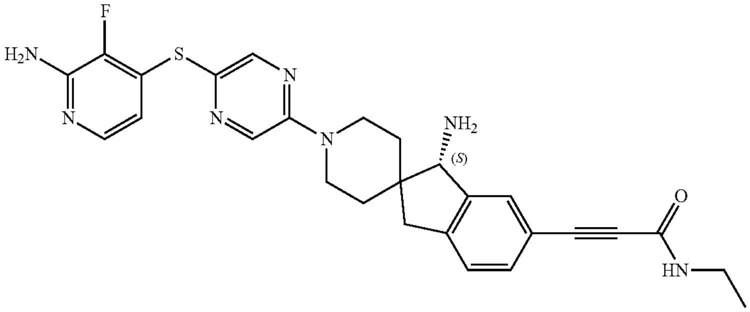 |
| 258 | 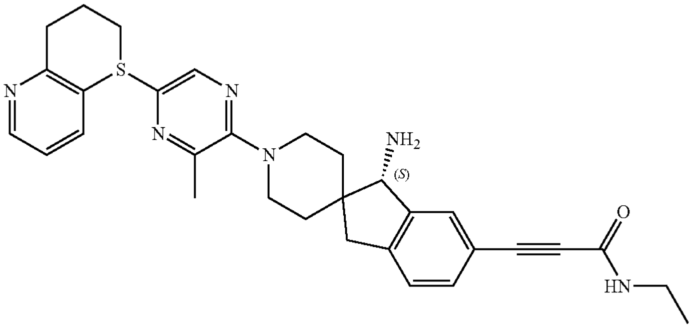 |
| 259 | 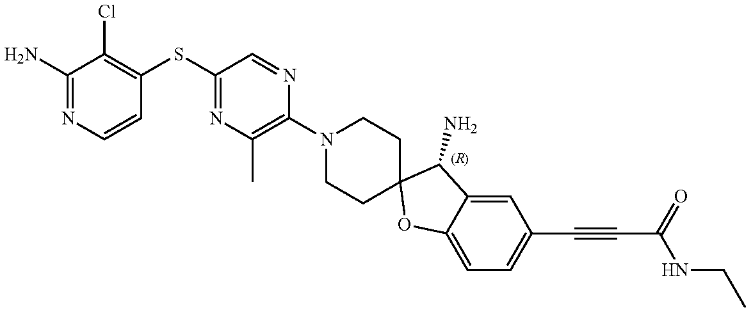 |
| 260 | 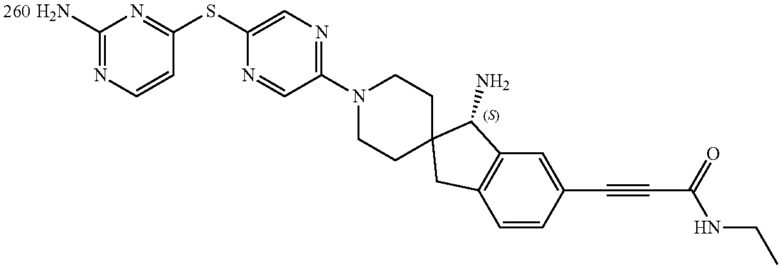 |

-continued
No. Structural formula
261 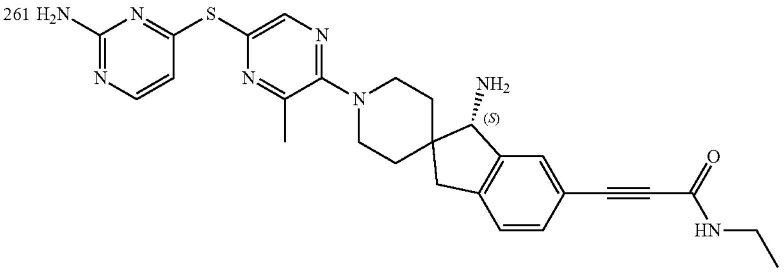
262 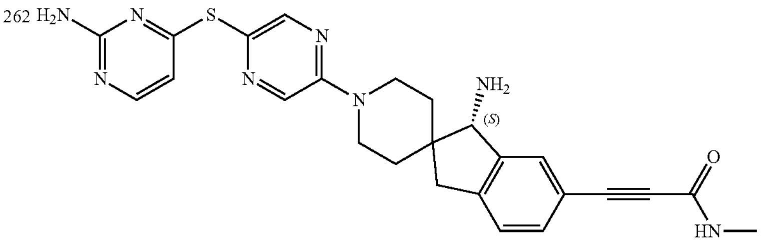
263 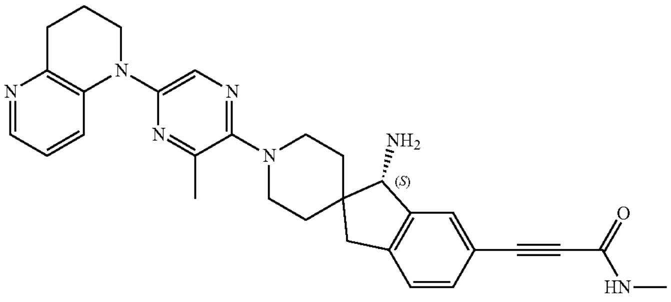
264 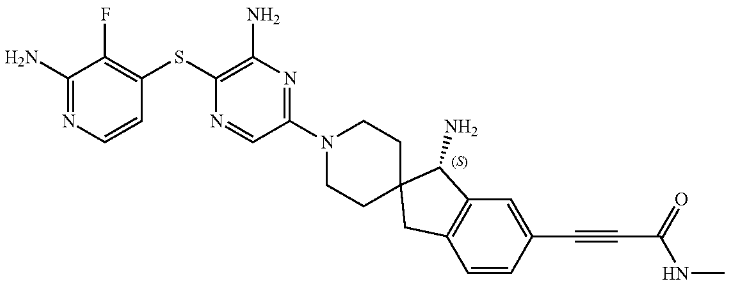
265 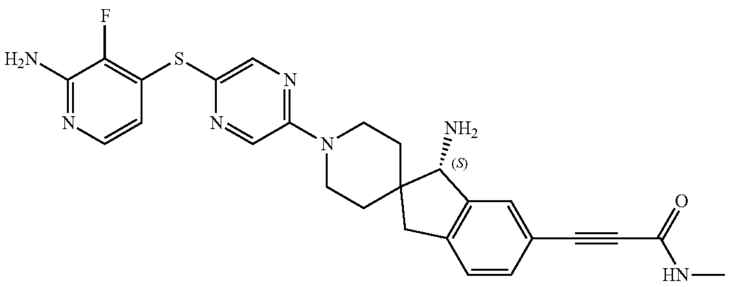

-continued
| No. | Structural formula |
| --- | --- |
| 266 | 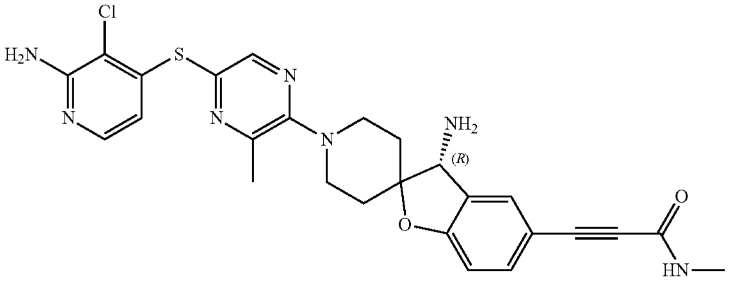 |
| 269 | 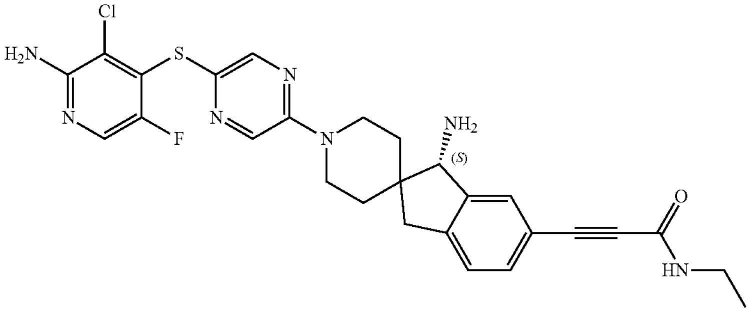 |
| 270 | 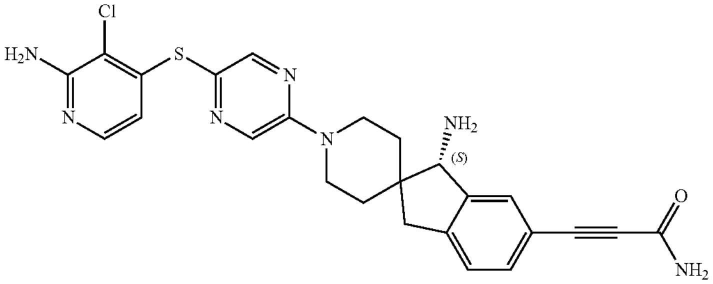 |
| 271 | 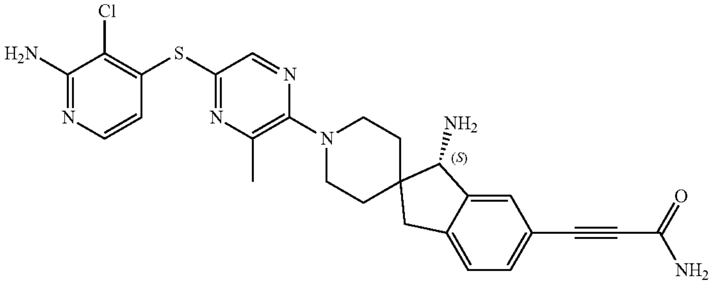 |
| 272 | 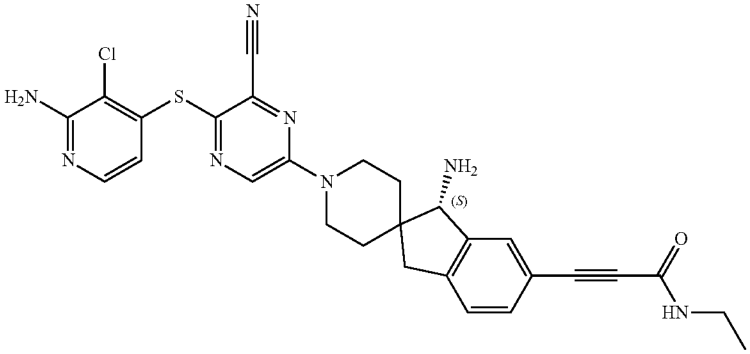 |

-continued
| No. | Structural formula |
|---|---|
| 273 | 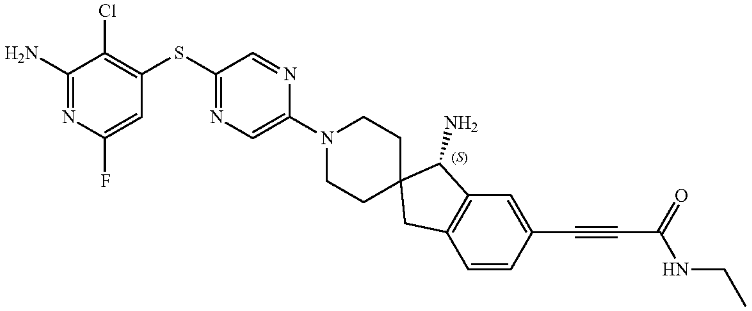 |
| 274 | 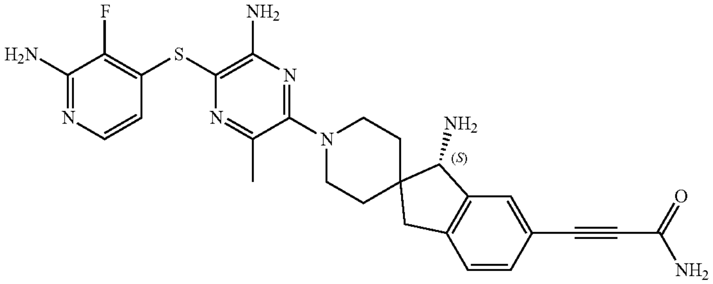 |
| 275 | 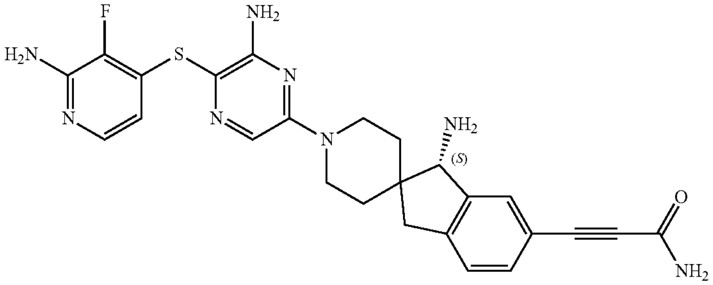 |
| 276 | 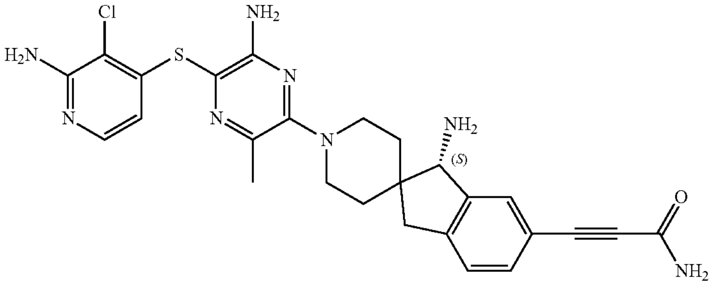 |
| 277 | 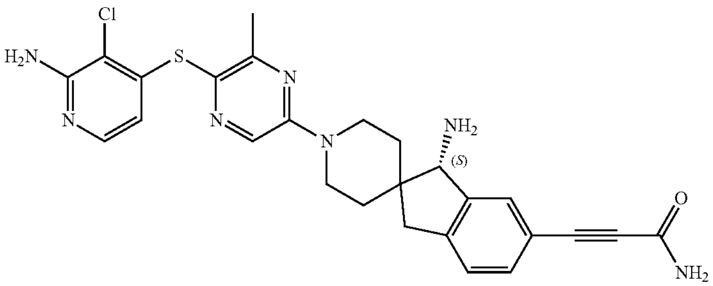 |

-continued
| No. Structural formula |
|---|
| 278 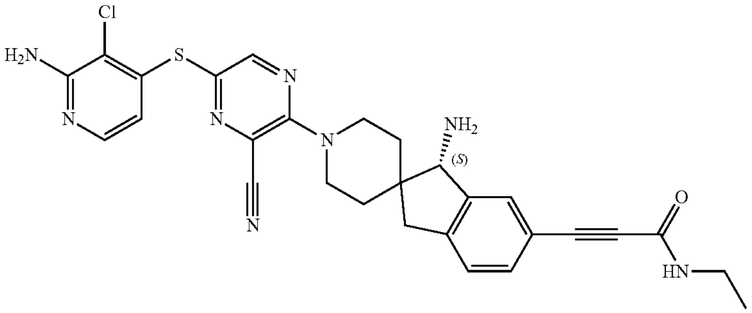 |
| 279 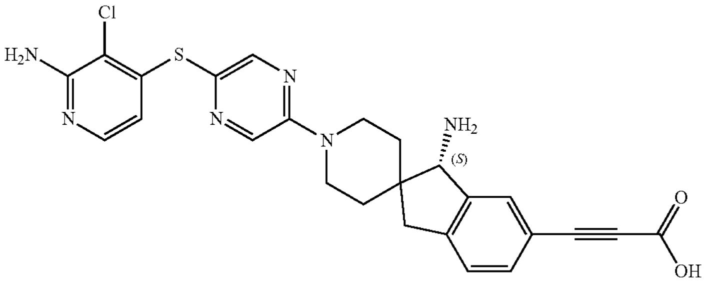 |
| 280 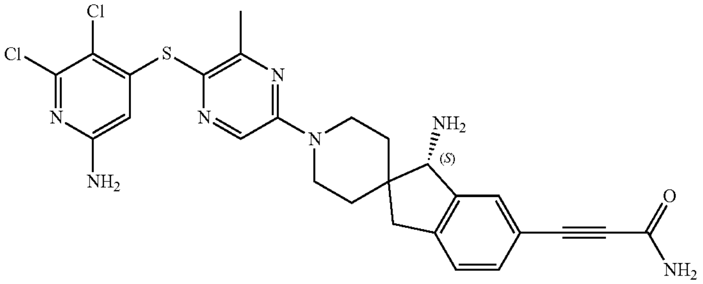 |
| 281 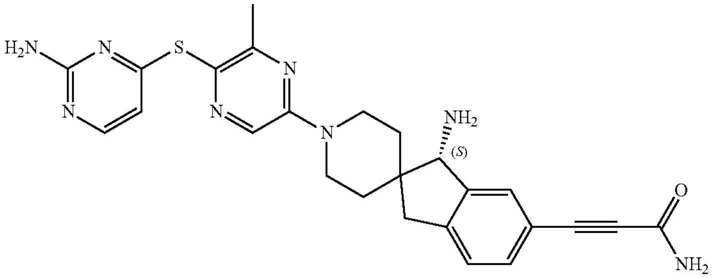 |
| 283 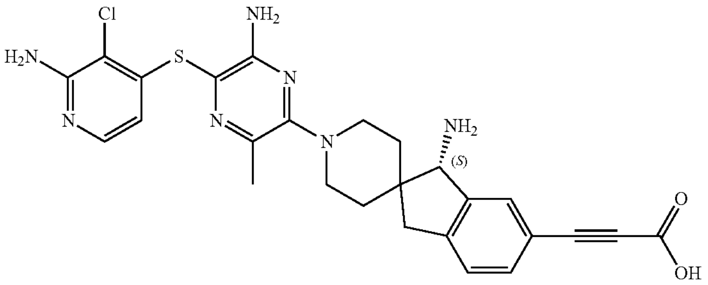 |

-continued
| No. | Structural formula |
| --- | --- |
| 290 | 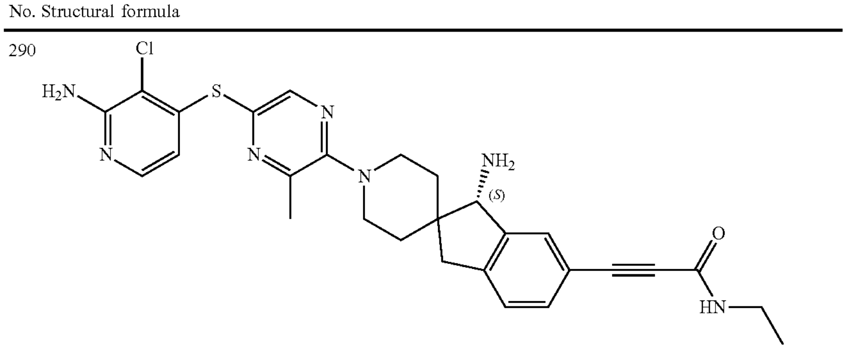 |
| 292 | 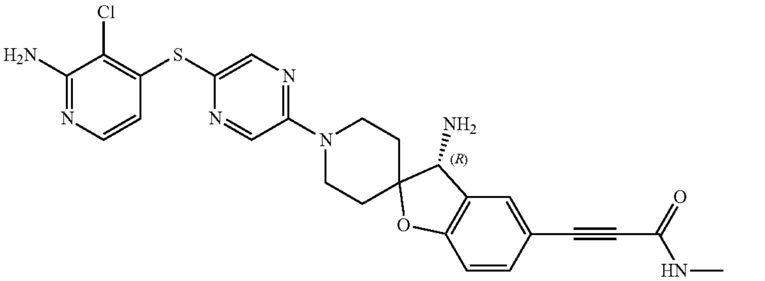 |
| 293 | 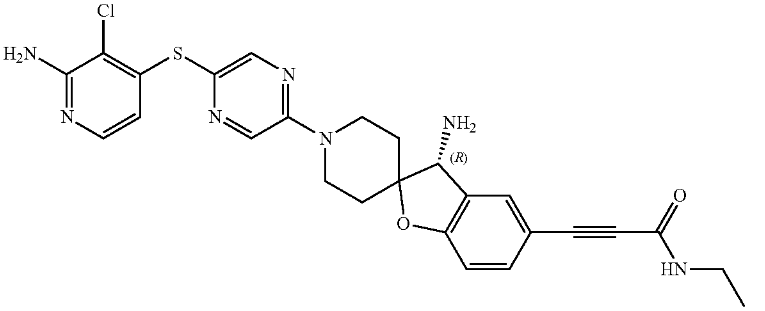 |
| 296 | 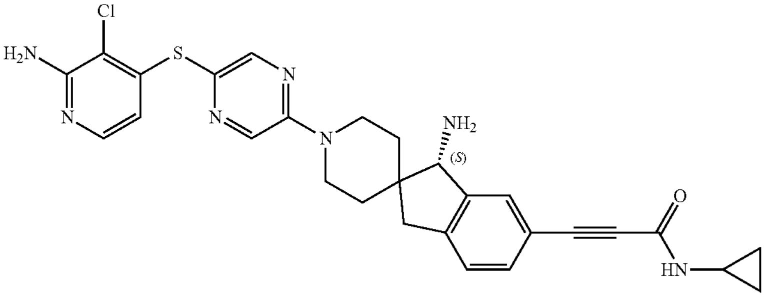 |
| 297 | 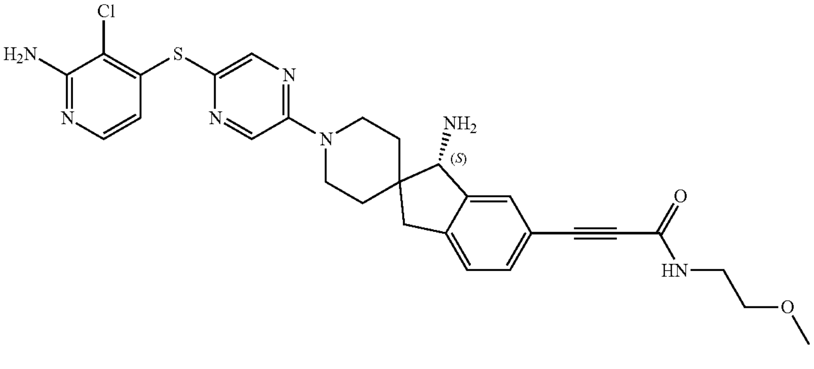 |

-continued
| No. | Structural formula |
|---|---|
| 298 | 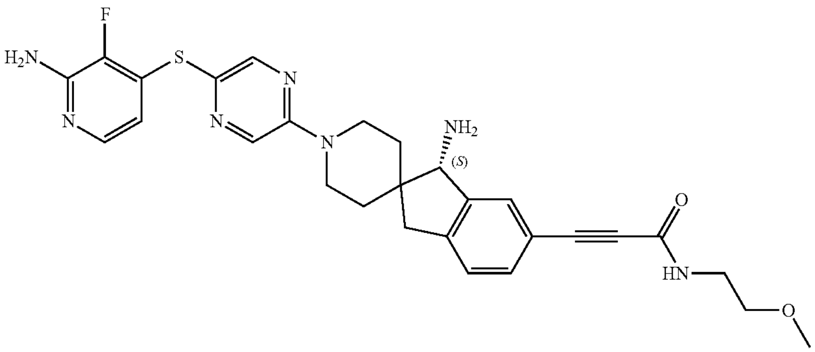 |
| 301 | 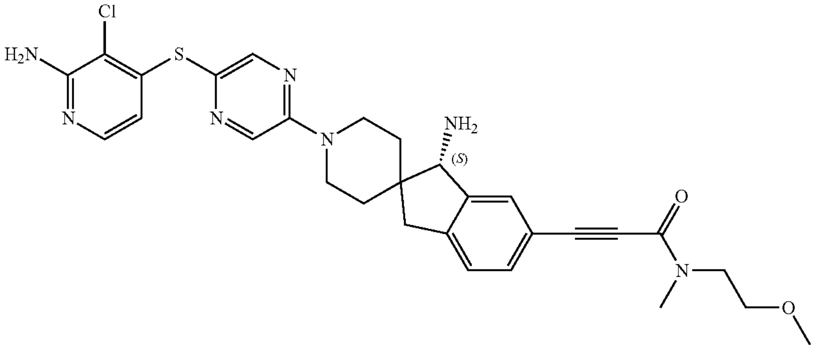 |
| 300 | 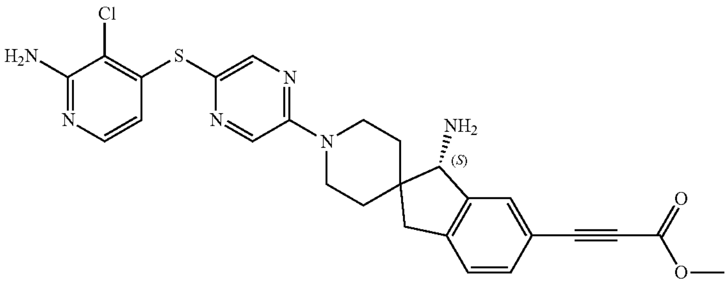 |
| 303 | 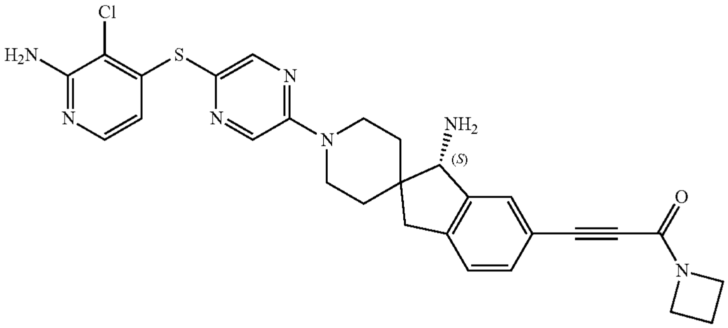 |

-continued

| No. | Structural formula |
|---|---|
| 302 | 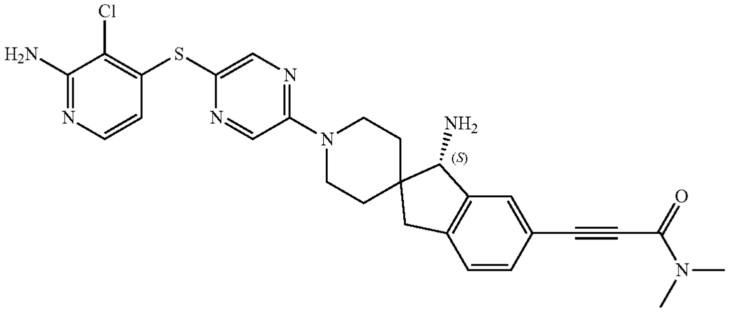 |
| 305 | 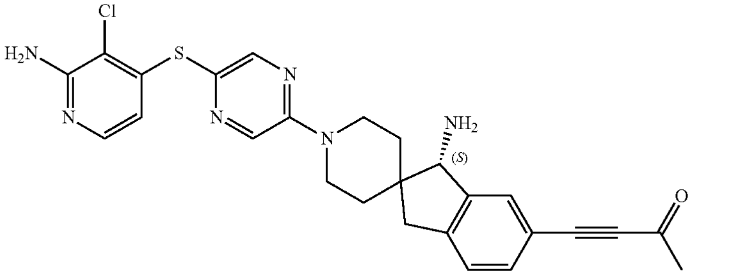 |
| 304 | 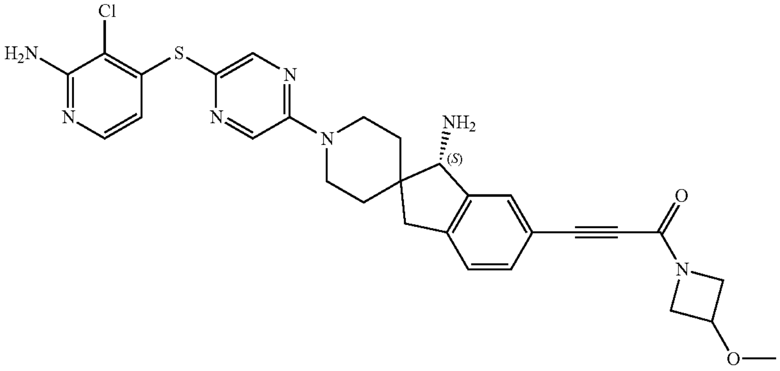 |

5. A pharmaceutical composition, comprising the compound and/or the pharmaceutically acceptable salt thereof according to claim 1 and a pharmaceutically acceptable excipient.

6. A method of in vivo or in vitro inhibiting SHP2 activity in vitro, comprising contacting SHP2 with an effective amount of the compound and/or the pharmaceutically acceptable salt thereof according to claim 1.

7. A method of treating a disease in a subject, comprising administering to the subject in need thereof an effective amount of the compound and/or the pharmaceutically acceptable salt thereof according to claim 1, wherein the disease is a disease mediated by SHP2 or at least in part by SHP2, and the disease is cancer, Noonan Syndrome or LEOPARD Syndrome.

8. A pharmaceutical combination, comprising the compound and/or the pharmaceutically acceptable salt thereof according to claim 1, and at least one additional therapeutic agent, wherein the additional therapeutic agent is chosen from: an anti-neoplastic active agent, an anti-inflammatory agent or an immunomodulator, wherein the anti-neoplastic active agent includes a chemotherapeutic agent, an immune checkpoint inhibitor or agonist, and a targeted therapeutic agent.

9. The compound or the pharmaceutically acceptable salt thereof, or the solvate, the racemic mixture, the enantiomer, the diastereomer or the tautomer thereof according to claim 1, wherein Z is $CH_2$.

10. The compound or the pharmaceutically acceptable salt thereof, or the solvate, the racemic mixture, the enantiomer, the diastereomer or the tautomer thereof according to claim 1, wherein $R_1$ is $C_{2-6}$ alkynyl, wherein the $C_{2-6}$ alkynyl is optionally substituted with one or more groups independently chosen from: —O($C_{1-6}$ alkyl), —$NHCONH_2$, —$CONR_aR_b$, —$COOR_c$ and —$COR_d$, wherein $R_a$, $R_b$, $R_c$ and $R_d$ are each independently chosen from hydrogen, $C_{1-6}$ alkyl, —($C_{1-6}$ alkyl)-O—($C_{1-6}$ alkyl), $C_{3-8}$ cycloalkyl and 4-8 membered heterocyclyl, wherein the 4-8 membered heterocyclyl is optionally substituted with —O($C_{1-6}$ alkyl).

11. The compound or the pharmaceutically acceptable salt thereof, or the solvate, the racemic mixture, the enantiomer, the diastereomer or the tautomer thereof according to claim 1, wherein $R_1$ is $C_{2-6}$ alkynyl, wherein the $C_{2-6}$ alkynyl is optionally substituted with one or more groups independently chosen from: —$CONH_2$, —O($C_{1-6}$ alkyl), —$NHCONH_2$, —CONH($C_{1-6}$ alkyl), —CONH($C_{1-6}$ alkyl)-O—($C_{1-6}$ alkyl), —CON($C_{1-6}$ alkyl)$_2$, —CON($C_{1-6}$ alkyl)

($C_{1-6}$ alkyl-O—$C_{1-6}$ alkyl), —CONH($C_{3-8}$ cycloalkyl), —COOH, —COO($C_{1-6}$ alkyl), —CO($C_{1-6}$ alkyl), —CO(4-8 membered heterocyclyl) and —CO(4-8 membered heterocyclyl)-O—($C_{1-6}$ alkyl).

12. The compound or the pharmaceutically acceptable salt thereof, or the solvate, the racemic mixture, the enantiomer, the diastereomer or the tautomer thereof according to claim 1, wherein $R_1$ is ethynyl, propynyl or butynyl, each of which is unsubstituted or substituted with —$CONH_2$, —$OCH_3$, —$NHCONH_2$, —CONH($C_{1-3}$ alkyl), —CONH($CH_2CH_2$)—O—($CH_3$), —CON$(CH_3)_2$, —CON($CH_3$)($CH_2CH_2$—O—$CH_3$), —CONH(cyclopropyl), —COOH, —COO($CH_3$), —CO($CH_3$), —CO(azetidinyl) or —CO(azetidinyl)-O—($CH_3$).

13. The compound or the pharmaceutically acceptable salt thereof, or the solvate, the racemic mixture, the enantiomer, the diastereomer or the tautomer thereof according to claim 1, wherein $R_1$ is ethynyl substituted with —CONH($CH_3$), —CONH($CH_2CH_3$) or —CONH($CH_2CH_2$)—O—($CH_3$).

14. The compound or the pharmaceutically acceptable salt thereof, or the solvate, the racemic mixture, the enantiomer, the diastereomer or the tautomer thereof according to claim 1, wherein n is 0.

15. The compound or the pharmaceutically acceptable salt thereof, or the solvate, the racemic mixture, the enantiomer, the diastereomer or the tautomer thereof according to claim 1, wherein $R_{15}$ and $R_{15}'$ are each independently chosen from hydrogen, —$NH_2$, $C_{1-6}$ alkyl and —($C_{1-6}$ alkyl)-OH.

16. The compound or the pharmaceutically acceptable salt thereof, or the solvate, the racemic mixture, the enantiomer, the diastereomer or the tautomer thereof according to claim 1, wherein $R_{15}$ and $R_{15}'$ are hydrogen.

17. The compound or the pharmaceutically acceptable salt thereof, or the solvate, the racemic mixture, the enantiomer, the diastereomer or the tautomer thereof according to claim 1, wherein L is S.

18. The compound or the pharmaceutically acceptable salt thereof, or the solvate, the racemic mixture, the enantiomer, the diastereomer or the tautomer thereof according to claim 1, wherein $Cy_2$ is chosen from

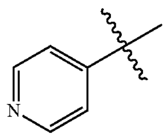

, and

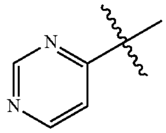

, each of which is optionally substituted with one or more groups independently chosen from: halogen, —OH, $C_{1-6}$ alkyl, $C_{1-6}$ haloalkyl, —O($C_{1-6}$ alkyl), —S($C_{1-6}$ alkyl) and —$NR_7R_8$, wherein $R_7$ and $R_8$ are hydrogen.

19. The method according to claim 7, wherein the cancer is a solid tumor or hematologic malignancy.

20. The method according to claim 7, wherein the cancer is chosen from breast cancer, melanoma, glioblastoma, esophageal cancer, gastric cancer, colon cancer, colorectal cancer, pancreatic cancer, lung cancer, head and neck cancer, liver cancer, renal cancer, ovarian cancer, cervical cancer, prostate cancer, endometrial cancer, thyroid carcinoma, sarcoma, adrenal carcinoma, acute myelogenous leukemia (AML), juvenile acute myelogenous leukemia, chronic myelogenous leukemia (CML), acute lymphocytic leukemia (ALL), B-cell acute lymphocytic leukemia (B-ALL), acute lymphoblastic leukemia, chronic lymphocytic leukemia (CLL), diffuse large B-cell lymphoma (DLBCL), large B-cell lymphoma (LBCL), B-cell lymphoma, T-cell lymphoma, mantle cell lymphoma, follicular lymphoma, non-Hodgkin's lymphoma, Hodgkin's lymphoma, myelodysplastic syndrome, and myeloma.

* * * * *